United States Patent [19]
Fujimoto et al.

[11] Patent Number: 5,556,864
[45] Date of Patent: Sep. 17, 1996

[54] α-ω-DIARYLALKANE COMPOUNDS SEROTONIN-2 RECEPTOR AGONISTS

[75] Inventors: Koichi Fujimoto; Naoki Tanaka; Fumitoshi Asai; Tomiyoshi Ito; Hiroyuki Koike, all of Tokyo, Japan

[73] Assignee: Sankyo Company, Limited, Tokyo, Japan

[21] Appl. No.: 369,255

[22] Filed: Jan. 5, 1995

Related U.S. Application Data

[63] Continuation of Ser. No. 159,744, Nov. 30, 1993, abandoned.

[30] Foreign Application Priority Data

Nov. 30, 1992 [JP] Japan ..................................... 4-320609
Dec. 18, 1992 [JP] Japan ..................................... 4-338307

[51] Int. Cl.$^6$ ........................ C07C 37/055; C07C 39/17; A61K 31/205; A61K 31/135
[52] U.S. Cl. .................... 514/315; 514/237.8; 514/238.2; 514/238.8; 514/239.2; 514/239.5; 514/331; 514/427; 514/428; 514/415; 514/650; 514/651; 544/386; 544/391; 544/162; 544/170; 546/192; 546/201; 546/225; 548/570; 548/578; 560/123; 560/127; 560/129; 562/444; 562/471; 564/337; 564/347; 564/348; 564/349; 564/353; 564/362
[58] Field of Search ..................................... 514/415, 651, 514/650, 315, 331, 427, 428, 238.8, 237.2, 238.8, 239.2, 239.5; 564/337, 347, 340, 349, 353, 362; 562/444, 471; 560/123, 127, 193; 548/570, 578; 546/192, 201, 225; 544/386, 391, 162, 170

[56] References Cited

U.S. PATENT DOCUMENTS

| | | | |
|---|---|---|---|
| 4,485,258 | 11/1984 | Kikumoto et al. | 562/471 |
| 4,792,570 | 12/1988 | Nelson et al. | 514/651 |
| 4,853,408 | 8/1989 | Clemence et al. | 514/415 |
| 4,892,671 | 1/1990 | O'Neil et al. | 252/51.5 R |

FOREIGN PATENT DOCUMENTS

| | | |
|---|---|---|
| 0001759 | 5/1979 | European Pat. Off. . |
| 0072942 | 3/1983 | European Pat. Off. . |
| 0201400 | 12/1986 | European Pat. Off. . |
| 0216127 | 4/1987 | European Pat. Off. . |
| 0241918 | 10/1987 | European Pat. Off. . |
| 0398326 | 11/1990 | European Pat. Off. . |
| 2518992 | 7/1983 | France . |
| 2856793 | 8/1977 | Germany ..................... 564/347 |
| 1111338 | 4/1968 | United Kingdom . |
| WO89/04303 | 5/1989 | WIPO . |
| WO92/22527 | 12/1992 | WIPO . |
| WO93/15073 | 8/1993 | WIPO . |

OTHER PUBLICATIONS

Chemical Abstracts, vol. 116, No. 1, 6 Jan. 1992, Columbus, Ohio, Hara et al., "Antithrombotic effect of MCI–9042, a new antiplatelet agent on experimental thrombosis models". Abstract No. 454q.

Journal of Medicinal Chemistry, vol. 33, No. 4, 1990, Washington, US, pp. 1818–1823, Kikumoto et al., III, "Syntheses and platelet aggregation inhibitory and antithrombotic properties of [2–(ω–Aminoalkoxy)phenyl]ethyl benzenes".

Journal of Medicinal Chemistry, vol. 33, No. 4, 1990, Washington US, pp. 1194–1200, Huang et al. II, "Development of a novel series of (2–quinolinylmthoxy)phenyl–containing compounds as high-affinity leukotriene D4 receptor antagonists. 2. Effects of an additional phenyl ring on receptor affinity".

Journal of Medicinal Chemistry, vol. 35, No. 1, 1992, Washington US, pp. 189–194, Y. Watanabe et al, "Synthesis and 5–HT2 Antagonist Activity of Bicyclic 1,2, 4–Trizol–3(2H)–one and 1,3,5–Triazine–2,4(3H)–dione Derivatives".

Primary Examiner—Floyd D. Higel
Attorney, Agent, or Firm—Frishauf, Holtz, Goodman, Langer & Chick, P.C.

[57] ABSTRACT

Compounds of formula (I):

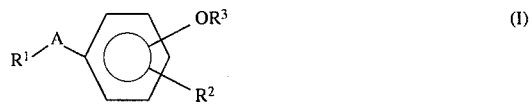

[wherein: $R^1$ is aryl; $R^2$ is hydrogen, alkyl, alkoxy, halogen or cyano; $R^3$ is a group of formula —B—$NR^4R^5$, where $R^4$ and $R^5$ are independently hydrogen, alkyl or substituted alkyl or $R^4$ and $R^5$, together with the nitrogen to which they are attached, form a heterocycle, and B is alkylene or a group of formula —$CH_2CH(OR^6)CH_2$—, where $R^6$ is hydrogen, alkanoyl, substituted alkanoyl or arylcarbonyl, or a group of formula —D—$R^7$, where D is a single bond or alkylene and $R^7$ is a heterocycle; and A is alkylene; and pharmaceutically acceptable salts and esters thereof] are useful for the treatment and prevention of circulatory diseases and psychosis.

75 Claims, No Drawings

α-ω-DIARYLALKANE COMPOUNDS SEROTONIN-2 RECEPTOR AGONISTS

This application is a Continuation, of application Ser. No. 08/159,744, filed Nov. 30, 1993 (now abandoned).

BACKGROUND OF THE INVENTION

The present invention relates to a series of new α,ω-diarylalkane derivatives which are serotonin-2 receptor antagonists and which, therefore, are useful for the treatment and prevention of circulatory (cardiovascular) diseases and psychosis. The invention also provides methods and compositions using these novel compounds, as well as processes for their preparation.

Classically, serotonin has been grouped with the autacoids. A known neurotransmitter, serotonin exhibits many physiological actions in vivo which are mediated through diverse receptors. It is known that there are many subtypes of serotonin receptors. In the circulatory system, receptors classified as serotonin-2 receptors are distributed in the blood vessel endothelial cells and platelets, and these receptors are strongly implicated in vasoconstriction and platelet agglutination [e.g. S. J. Peroutka et al., Fed. Proc., 42, 213 (1983)]. Antagonists to these receptors are useful in preventing vasoconstriction and blocking platelet agglutination.

Recent reports have suggested the use of MCI-9042, which is a {2-[ω-aminoalkoxy)phenyl]ethyl}benzene, to block platelet agglutination based on its serotonin-2 receptor antagonist action [e.g. J. Med. Chem., 35, 189 (1992)].

Although these compounds do not exhibit any antagonistic effect on adrenaline-$\alpha_1$, their antagonistic effect on serotonin-2 receptors and/or their platelet agglutination blocking effect is also insufficiently strong. Therefore, in order to achieve results at the clinical level, the development of a drug which had both a potent and selective antagonistic effect on serotonin-2 receptors was needed.

A number of compounds having generally a α,ω-diarylalkane structure has been proposed for the treatment of circulatory diseases, based on their platelet agglutination effects. Examples of such compounds are disclosed in European Patent Publications No. 1 759, 72 942 and 398 326, as well as in J. Med. Chem., 33, 1818 (1990) and the aforesaid J. Med. Chem., 35, 189 (1992).

We have surprisingly found that certain compounds of this type, as well as having unexpectedly improved serotonin-2 receptor antagonist activity leading to their use in the treatment and prophylaxis of circulatory diseases, also has unexpected dopamine-2 receptor antagonist activity, leading to their use in the treatment and prophylaxis of psychiatric conditions, notably psychosis.

BRIEF SUMMARY OF INVENTION

It is, therefore, an object of the present invention to provide a series of new α,ω-diarylalkane derivatives.

It is a further, and more specific, object of the present invention to provide such compounds which are antagonists of the serotonin-2 receptor.

Other objects and advantages of the present invention will become apparent as the description proceeds.

The compounds of the present invention are those α,ω-diarylalkane compounds of formula (I):

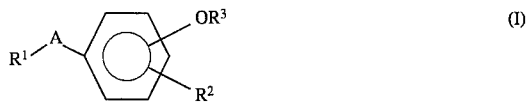

wherein:
- $R^1$ represents an aryl group;
- $R^2$ represents a hydrogen atom, an alkyl group, an alkoxy group, a halogen atom or a cyano group;
- $R^3$ represents
  a group of formula —B—$NR^4R^5$,
    where $R^4$ and $R^5$ are independently selected from the group consisting of hydrogen atoms, alkyl groups and substituted alkyl groups or $R^4$ and $R^5$ together with the nitrogen atom to which they are attached, represent a heterocyclic group having from 3 to 6 ring atoms, and B represents an alkylene group having from 2 to 6 carbon atoms or a group of formula —$CH_2CH(OR^6)CH_2$—, where $R^6$ represents a hydrogen atom, an alkanoyl group, a substituted alkanoyl group or an arylcarbonyl group,
  or a group of formula —D—$R^7$ where D represents a carbon-carbon single bond or an alkylene group having from 1 to 4 carbon atoms and $R^7$ represents a heterocyclic group having 5 or 6 ring atoms bonded to D via a carbon atom in the heterocyclic group;
- A represents an alkylene group having from 2 to 8 carbon atoms;

and pharmaceutically acceptable salts and esters thereof;
  PROVIDED THAT, where A represents an ethylene group, $R^3$ represents a group of formula —D—$R^7$;
  said alkyl, substituted alkyl and alkoxy groups have from 1 to 6 carbon atoms;
  said substituted alkyl groups are substituted by at least one of substituents ζ, defined below;
  said substituents ζ are selected from the group consisting of hydroxy groups, dialkylamino groups in which the or each alkyl part has from 1 to 6 carbon atoms and aryl groups which have from 6 to 10 ring carbon atoms and which are unsubstituted or are substituted by at least one substituent selected from the group consisting of substituents β, defined below;
  said alkanoyl and substituted alkanoyl groups have no more than 6 carbon atoms, and, in the case of the substituted groups are substituted by at least one carboxy group;
  aryl groups have from 6 to 10 ring carbon atoms and are unsubstituted or are substituted by at least one substituent selected from the group consisting of substituents α, defined below;
  the aryl parts of said arylcarbonyl groups have from 6 to 10 ring carbon atoms and are unsubstituted or are substituted by at least one substituent selected from the group consisting of substituents α, defined below;
  said substituents α are selected from the group consisting of
    alkyl groups having from 1 to 6 carbon atoms,
    alkenyl groups having from 2 to 6 carbon atoms,
    alkynyl groups having from 2 to 6 carbon atoms,
    hydroxy groups,
    alkoxy groups having from 1 to 6 carbon atoms,
    haloalkoxy groups having from 1 to 6 carbon atoms, halogen atoms, cyano groups, carbamoyl groups, mono- and di- alkylcarbamoyl groups in which the or each alkyl part has from 1 to 6 carbon atoms, and aryl groups which have from 6 to 10 ring carbon atoms and which are unsubstituted or are substituted by at least one substituent selected from the group consisting of substituents β;

said substituents β are selected from the group consisting of alkyl groups having from 1 to 6 carbon atoms, alkoxy groups having from 1 to 6 carbon atoms, and halogen atoms, said heterocyclic groups have at least one carbon atom and at least one hetero-atom selected from the group consisting of nitrogen, oxygen and sulfur hetero-atoms and are unsubstituted or substituted; in the case of substituents on a nitrogen atom, said substituents are selected from the group consisting of substituents γ; in the case of substituents on a carbon atom of the heterocyclic group represented by $R^4$ and $R^5$ together, said substituents are selected from the group consisting of substituents δ; in the case of substituents on a carbon atom of the heterocyclic group represented by $R^7$, said substituents are selected from the group consisting of substituents ε;

said substituents γ are selected from the group consisting of alkyl groups having from 1 to 6 carbon atoms and aryl groups which have from 6 to 10 ring carbon atoms and which are unsubstituted or are substituted by at least one substituent selected from the group consisting of substituents β;

said substituents δ are selected from the group consisting of:

alkyl groups having from 1 to 6 carbon atoms;

hydroxy groups; and aryl groups which have from 6 to 10 ring carbon atoms and which are unsubstituted or are substituted by at least one substituent selected from the group consisting of substituents β;

said substituents ε are selected from the group consisting of:

alkyl groups having from 1 to 6 carbon atoms;

alkenyl groups having from 2 to 6 carbon atoms;

alkynyl groups having from 2 to 6 carbon atoms;

hydroxy groups;

alkoxy groups having from 1 to 6 carbon atoms;

alkoxycarbonyloxy groups having from 2 to 7 carbon atoms;

alkanoyloxy groups which have from 1 to 20 carbon atoms;

substituted alkanoyloxy groups which have from 2 to 5 carbon atoms and which are substituted by at least one carboxy group;

carbamoyloxy groups;

mono- and di- alkylcarbamoyloxy groups in which the or each alkyl part has from 1 to 6 carbon atoms;

halogen atoms;

cyano groups; and aryl groups which have from 6 to 10 ring carbon atoms and which are unsubstituted or are substituted by at least one substituent selected from the group consisting of substituents β.

The invention further provides a pharmaceutical composition comprising a compound of formula (I) or a pharmaceutically acceptable salt or ester thereof in admixture with a pharmaceutically acceptable carrier or diluent.

The invention still further provides a method for the treatment or prophylaxis of circulatory diseases in a mammal, by the administration to said mammal of an effective amount of an active compound, wherein the active compound is at least one compound of formula (I) or a pharmaceutically acceptable salt or ester thereof.

The invention still further provides a method for the treatment or prophylaxis of psychosis in a mammal, by the administration to said mammal of an effective amount of an active compound, wherein the active compound is at least one compound of formula (I) or a pharmaceutically acceptable salt or ester thereof.

The invention also provides processes for preparing the compounds of the present invention, which processes are described in more detail hereafter.

DETAILED DESCRIPTION OF INVENTION

In the compounds of the present invention, $R^1$ represents an aryl group which has from 6 to 10 ring carbon atoms and which is unsubstituted or is substituted by at least one substituent selected from the group consisting of substituents α, defined above and exemplified below. We particularly prefer that the aryl group should contain 6 or 10 ring carbon atoms, and the phenyl, α-naphthyl and β-naphthyl groups are more preferred of the unsubstituted aryl groups, the phenyl group being most preferred. In the case of the substituted aryl groups, there is no particular restriction on the number of substituents, except such as may be imposed by the number of substitutable carbon atoms in the aromatic ring (5 in the case of the phenyl group or 7 in the case of the naphthyl groups) and possibly by steric constraints. In general, however, we prefer 1, 2 or 3 such substituents, 1 or 2 being more preferred. Examples of groups and atoms which may be included in substituents α are:

alkyl groups having from 1 to 6 carbon atoms, which may be straight or branched chain groups, such as the methyl, ethyl, propyl, isopropyl, butyl, isobutyl, sec-butyl, t-butyl, pentyl, isopentyl, 2-methylbutyl, neopentyl, 1-ethylpropyl, hexyl, 4-methylpentyl, 3-methylpentyl, 2-methylpentyl, 1-methylpentyl, 3,3-dimethylbutyl, 2,2-dimethylbutyl, butyl, 1,1-dimethylbutyl, 1,2-dimethylbutyl, 1,3-dimethylbutyl, 2,3-dimethylbutyl and 2-ethylbutyl groups, of which we prefer those alkyl groups having from 1 to 4 carbon atoms, the methyl, ethyl, propyl, isopropyl, butyl, isobutyl, sec-butyl and t-butyl groups being more preferred, and the methyl and ethyl groups being still more preferred; the methyl group is the most preferred such alkyl group; alkenyl groups having from 2 to 6 carbon atoms, which may be straight or branched chain groups, such as the vinyl, 1-propenyl, allyl, 1-methyl-1-propenyl, 1-methyl-2-propenyl, 2-methyl-1-propenyl, 2-methyl-2-propenyl, 2-ethyl-2-propenyl, 1-butenyl, 2-butenyl, 1-methyl-1-butenyl, 1-methyl-2-butenyl, 2-methyl-2-butenyl, 3-methyl-2-butenyl, 1-ethyl-2-butenyl, 3-butenyl, 1-methyl-3-butenyl, 2-methyl-3-butenyl, 1-ethyl-3-butenyl, 1-pentenyl, 2-pentenyl, 1-methyl-2-pentenyl, 2-methyl-2-pentenyl, 3-pentenyl, 1-methyl-3-pentenyl, 2-menthyl-3-pentenyl, 4-pentenyl, 1-methyl-4-pentenyl, 2-methyl-4-pentenyl, 1-hexenyl, 2-hexenyl, 3-hexenyl, 4-hexenyl and 5-hexenyl groups, of which we prefer those alkenyl groups having from 3 to 5 carbon atoms, the allyl, 1-propenyl, 1-methyl-2-propenyl, 1-butenyl, 2-butenyl and 1-methyl-1- butenyl groups being more preferred and the allyl group being most preferred;

alkynyl groups having from 2 to 6 carbon atoms, which may be straight or branched chain groups, such as the ethynyl, 2-propynyl, 1-methyl-2-propynyl, 2-butynyl, 1-methyl-2-butynyl, 1-ethyl-2-butynyl, 3-butynyl, 1-methyl-3-butynyl, 2-methyl-3-butynyl, 1-ethyl-3-butynyl, 2-pentynyl, 1-methyl-2-pentynyl, 3-pentynyl, 1-methyl-3-pentynyl, 2-methyl-3-pentynyl, 4-pentynyl, 1-methyl-4-pentynyl, 2-methyl-4-pentynyl, 2-hexynyl, 3-hexynyl, 4-hexynyl and 5-hexynyl groups, of which we prefer those alkynyl groups having from 3 to 5 carbon atoms, the ethynyl, 2-propynyl and 1-methyl-2-butynyl groups being more preferred and the 2-propynyl group being most preferred;

hydroxy groups;

alkoxy groups having from 1 to 6 carbon atoms, which may be straight or branched chain groups, such as the methoxy, ethoxy, propoxy, isopropoxy, butoxy, isobutoxy, sec-butoxy, t-butoxy, pentyloxy, isopentyloxy, 2-methylbutoxy, neopentyloxy, 1-ethylpropoxy, hexyloxy, 4-methylpentyloxy, 3-methylpentyloxy, 2-methylpentyloxy, 1-methylpentyloxy, 3,3-dimethylbutoxy, 2,2-dimethylbutoxy, 1,1-dimethylbutoxy, 1,2-dimethylbutoxy, 1,3-dimethylbutoxy, 2,3-dimethylbutoxy and 2-ethylbutoxy groups, of which we prefer those alkoxy groups having from 1 to 4 carbon atoms, the methoxy, ethoxy, propoxy, isopropoxy, butoxy, isobutoxy, sec-butoxy and t-butoxy groups being more preferred, and the methoxy and ethoxy groups being still more preferred; the methoxy group is the most preferred such alkoxy group;

haloalkoxy groups having from 1 to 6, more preferably from 1 to 4 and most preferably 1 or 2, carbon atoms, in which the alkoxy part may be as defined and exemplified above and is substituted by one or more halogen atoms as exemplified below; examples of such groups include the fluoromethoxy, difluoromethoxy, trifluoromethoxy, 2-fluoroethoxy, 2-chloroethoxy, 2-bromoethoxy, 2-iodoethoxy, 3-fluoropropoxy, 4-fluorobutoxy, 5-fluoropentyloxy and 6-fluorohexyloxy groups, of which we prefer the fluoromethoxy, difluoromethoxy, trifluoromethoxy and 2-fluoroethoxy groups, the fluoromethoxy, difluoromethoxy and 2-fluoroethoxy groups being more preferred, and the difluoromethoxy group being most preferred;

halogen atoms, such as the fluorine, chlorine, bromine and iodine atoms, preferably a fluorine, chlorine or bromine atom;

cyano groups;

carbamoyl groups;

mono- and di- alkylcarbamoyl groups in which the or each alkyl part has from 1 to 6 carbon atoms, such as the alkyl groups examplified above; examples of such mono- and di- alkylcarbamoyl groups include the methylcarbamoyl, ethylcarbamoyl, propylcarbamoyl, isopropylcarbamoyl, butylcarbamoyl, isobutylcarbamoyl, sec-butylcarbamoyl, t-butylcarbamoyl, N,N-dimethylcarbamoyl, N,N-diethylcarbamoyl, N,N-dipropylcarbamoyl, N,N-diisopropylcarbamoyl, N,N-dibutylcarbamoyl, N,N-diisobutylcarbamoyl, N-methyl-N-ethylcarbamoyl, N-ethyl-N-propylcarbamoyl, N-methyl-N-propylcarbamoyl, N-methyl-N-isopropylcarbamoyl and N-methyl-N-butylcarbamoyl groups, of which the mono- and di- alkylcarbamoyl groups in which the or each alkyl part has from 1 to 4 carbon atoms are preferred and the methylcarbamoyl, ethylcarbamoyl, N,N-dimethylcarbamoyl and N,N-diethylcarbamoyl groups are more preferred; and aryl groups which have from 6 to 10 ring carbon atoms and which are unsubstituted or are substituted by at least one substituent selected from the group consisting of substituents β; we particularly prefer that the group should contain 6 or 10 ring carbon atoms, of which the phenyl, α-naphthyl and β-naphthyl groups are more preferred of the unsubstituted groups, the phenyl group being most preferred; in the case of the substituted groups, there is no particular restriction on the number of substituents, except such as may be imposed by the number of substitutable carbon atoms (5 in the case of the phenyl group or 7 in the case of the naphthyl groups) and possibly by steric constraints. In general, however, we prefer 1, 2 or 3 such substituents, 1 or 2 being more preferred and 1 being most preferred; examples of groups and atoms which may be included in substituents β are: alkyl groups having from 1 to 6 carbon atoms, alkoxy groups having from 1 to 6 carbon atoms, and halogen atoms, all as defined and exemplified in relation to the similar groups and atoms which may be included in substituents α; specific examples of substituted and unsubstituted aryl groups which may be included in substituents α are the phenyl, α-naphthyl, β-naphthyl, 3-methoxyphenyl, 2-methylphenyl, 3-methylphenyl, 4-methylphenyl and 3-chlorophenyl groups, of which the unsubstituted groups are preferred, the phenyl group being most preferred.

Of these substituents, we prefer alkyl groups having from 1 to 4 carbon atoms, hydroxy groups, alkoxy groups having from 1 to 4 carbon atoms, haloalkoxy groups having from 1 to 4 carbon atoms, halogen atoms, cyano groups, and carbamoyl groups, the methyl, ethyl, hydroxy, methoxy, ethoxy, fluoromethoxy, difluoromethoxy, 2-fluoroethoxy and cyano groups and the fluorine, chlorine and bromine atoms being more preferred.

Specific examples of preferred substituted and unsubstituted aryl groups which may be represented by $R^1$ include the phenyl, α-naphthyl, β-naphthyl, 2-methoxyphenyl, 3-methoxyphenyl, 4-methoxyphenyl, 2-ethoxyphenyl, 3-ethoxyphenyl, 4-ethoxyphenyl, 2-fluoromethoxyphenyl, 3-fluoromethoxyphenyl, 4-fluoromethoxyphenyl, 2-difluoromethoxyphenyl, 3-difluoromethoxyphenyl, 4-difluoromethoxyphenyl, 2-(2-fluoroethoxy)phenyl, 3-(2-fluoroethoxy)phenyl, 4-(2-fluoroethoxy)phenyl, 2-methylphenyl, 3-methylphenyl, 4-methylphenyl, 2-ethylphenyl, 3-ethylphenyl, 4-ethylphenyl, 2-fluorophenyl, 3-fluorophenyl, 4-fluorophenyl, 2-chlorophenyl, 3-chlorophenyl, 4-chlorophenyl, 2-bromophenyl, 3-bromophenyl, 4-bromophenyl, 2-hydroxyphenyl, 3-hydroxyphenyl, 4-hydroxyphenyl, 2-cyanophenyl, 3-cyanophenyl, 4-cyanophenyl, 2-carbamoylphenyl, 3-carbamoylphenyl, 4-carbamoylphenyl, 2-isopropylphenyl, 3-isopropylphenyl, 4-isopropylphenyl, 3,4-dimethoxyphenyl, 3,5-dimethoxyphenyl, biphenylyl, 3,5-dimethylphenyl, 3-ethoxy-5-methoxyphenyl, 3-hydroxy-5-methoxyphenyl, 2,3-dichlorophenyl, 3,4-dichlorophenyl, 3,5-dichlorophenyl, 3,4,5-trimethoxyphenyl, 2,4,6-trimethoxyphenyl, 3,4,5-trichlorophenyl and 2,4,6-trichlorophenyl groups.

In general, of the substituted and unsubstituted aryl groups, we prefer the unsubstituted phenyl groups, the substituted phenyl groups and the unsubstituted naphthyl groups, the unsubstituted and substituted phenyl groups being most preferred.

Where $R^2$ represents an alkyl group, this may be a straight or branched chain group having from 1 to 6, preferably from 1 to 4, carbon atoms, and examples include the methyl, ethyl, propyl, isopropyl, butyl, isobutyl, sec-butyl, t-butyl, pentyl, isopentyl, neopentyl, 2-methylbutyl, 1-ethylpropyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, 2-ethylbutyl, hexyl and isohexyl groups. Of these, we prefer those alkyl groups having from 1 to 4 carbon atoms, preferably the methyl, ethyl, propyl, isopropyl, butyl, isobutyl, sec-butyl and t-butyl groups, more preferably the methyl and ethyl groups, and most preferably the methyl group.

Where $R^2$ represents an alkoxy group, this may be a straight or branched chain group having from 1 to 6, preferably from 1 to 4, carbon atoms, and examples include the methoxy, ethoxy, propoxy, isopropoxy, butoxy, isobutoxy, sec-butoxy, t-butoxy, pentyloxy, isopentyloxy, 2-methylbutoxy, neopentyloxy, 1-ethylpropoxy, hexyloxy, 4-methylpentyloxy, 3-methylpentyloxy, 2-methylpentyloxy, 1-methylpentyloxy, 3,3-dimethylbutoxy, 2,2-dimethylbutoxy, 1,1-dimethylbutoxy, 1,2-dimethylbutoxy, 1,3-dimethylbutoxy, 2,3-dimethylbutoxy and 2-ethylbutoxy groups, of which we prefer those alkoxy groups having from 1 to 4 carbon atoms, the methoxy, ethoxy, propoxy, isopropoxy, butoxy, isobutoxy, sec-butoxy and t-butoxy groups being more preferred, and the methoxy and ethoxy groups being still more preferred; the methoxy group is the most preferred such alkoxy group.

Where $R^2$ represents a halogen atom, this may be, for example, a fluorine, chlorine, bromine or iodine atom, preferably a fluorine or chlorine atom.

$R^2$ preferably represents a hydrogen atom, a methyl group, an ethyl group, a methoxy group, an ethoxy group, a fluorine atom or a chlorine atom.

Where $R^3$ represents a group of formula —B—NR$^4$R$^5$, R$^4$ and R$^5$ may be the same or different from each other, and each may represent a hydrogen atom, an alkyl group or a substituted alkyl group or R$^4$ and R$^5$, together with the nitrogen atom to which they are attached, may represent a heterocyclic group having from 3 to 6 ring atoms.

Where R$^4$ or R$^5$ represents an alkyl group, this may be a straight or branched chain group having from 1 to 6, preferably from 1 to 4, carbon atoms, and examples include the methyl, ethyl, propyl, isopropyl, butyl, isobutyl, sec-butyl, t-butyl, pentyl, isopentyl, neopentyl, 2-methylbutyl, 1-ethylpropyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, 2-ethylbutyl, hexyl and isohexyl groups. Of these, we prefer those alkyl groups having from 1 to 4 carbon atoms, preferably the methyl, ethyl, propyl, isopropyl, butyl, isobutyl, sec-butyl and t-butyl groups, more preferably the methyl and ethyl groups, and most preferably the methyl group.

Where R$^4$ or R$^5$ represents a substituted alkyl group, this may be any of the unsubstituted groups listed above but which is substituted by at least one of substituents ζ, defined above and exemplified below. Examples of the groups which may be included in substituents ζ are:

hydroxy groups;

dialkylamino groups in which each alkyl part has from 1 to 6 carbon atoms, such as the alkyl groups exampified above; examples of such dialkylamino groups include the N,N-dimethylamino, N,N-diethylamino, N,N-dipropylamino, N,N-diisopropylamino, N,N-dibutylamino, N,N-diisobutylamino, N-methyl-N-ethylamino, N-ethyl-N-propylamino, N-methyl-N-propylamino, N-methyl-N-isopropylamino and N-methyl-N-butylamino groups, of which the N,N-dimethylamino and N,N-diethylamino groups are preferred; and aryl groups which have from 6 to 10 ring carbon atoms and which are unsubstituted or are substituted by at least one substituent selected from the group consisting of substituents β; we particularly prefer that the group should contain 6 or 10 ring carbon atoms, of which the phenyl, α-naphthyl and β-naphthyl groups are more preferred of the unsubstituted groups, the phenyl group being most preferred; in the case of the substituted groups, there is no particular restriction on the number of substituents, except such as may be imposed by the number of substitutable carbon atoms (5 in the case of the phenyl group or 7 in the case of the naphthyl groups) and possibly by steric constraints. In general, however, we prefer 1, 2 or 3 such substituents, 1 or 2 being more preferred and 1 being most preferred; examples of groups and atoms which may be included in substituents β are: alkyl groups having from 1 to 6 carbon atoms, alkoxy groups having from 1 to 6 carbon atoms, and halogen atoms, all as defined and exemplified in relation to the similar groups and atoms which may be included in substituents α; specific examples of substituted and unsubstituted aryl groups which may be included in substituents α are the phenyl, α-naphthyl, β-naphthyl, 3-methoxyphenyl, 2-methylphenyl, 3-methylphenyl, 4-methylphenyl and 3-chlorophenyl groups, of which the unsubstituted groups are preferred, the phenyl group being most preferred.

Alternatively, R$^4$ and R$^5$, together with the nitrogen atom to which they are attached, may represent a heterocyclic group having from 3 to 6 ring atoms. Of these ring atoms, at least one is a carbon atom and at least one is a hetero-atom selected from the group consisting of nitrogen, oxygen and sulfur hetero-atoms. Necessarily, at least one of the ring atoms is a nitrogen atom, provided by the nitrogen atom to which R$^4$ and R$^5$ are attached. More preferably, from 1 to 4 of the ring atoms are hetero-atoms selected from the group consisting of nitrogen, oxygen and sulfur hetero-atoms. In the case of those groups having 4 hetero-atoms in a ring, we prefer that 3 or 4 of them should be nitrogen atoms and 1 or 0 should be an oxygen or sulfur atom. In the case of those groups having 3 hetero-atoms in a ring, we prefer that 1, 2 or 3 should be nitrogen atoms and, correspondingly, 2, 1 or 0 should be oxygen and/or sulfur atoms. In the case of those groups having 1 or 2 hetero-atoms in a ring, the hetero-atoms may be freely chosen from nitrogen, oxygen and sulfur atoms. The group may be saturated, partly saturated or fully unsaturated, but is preferably saturated. The group may be substituted or unsubstituted and, if substituted, the substituents on the nitrogen atom are selected from the group consisting of substituents y, as defined above and exemplified below, and the substituents on carbon atoms are selected from the group consisting of substituents δ, as defined above and exemplified below.

Examples of the unsubstituted groups include the 1-aziridinyl, 1-azetidinyl, 1-pyrrolidinyl, piperidino, 1-piperazinyl, morpholino, 4-thiomorpholinyl, 1-imidazolidinyl, 1-pyrazolidinyl, 1-triazinyl and 1-tetrazolidinyl groups; preferably a 1-azetidinyl, 1-pyrrolidinyl, 1-piperidinyl, 1-piperazinyl, 4-morpholinyl, 4-thiomorpholinyl, 1-imidazolidinyl or 1-pyrazolidinyl group; and more preferably a 1-pyrrolidinyl, 1-piperidinyl, 1-piperazinyl, 4-morpholinyl or 1-imidazolidinyl group. One or more carbon atoms of the heterocyclic ring or, in the case of those groups containing a nitrogen atom in addition to the nitrogen atom to which R$^4$ and R$^5$ are attached, this additional nitrogen atom, e.g. a nitrogen atom at the 4-position of a piperazinyl group, may optionally have one or more substituents. In the case of substituents on a carbon atom, the substituents may be selected from the group consisting of substituents δ, and examples of such substituents include: hydroxy groups; alkyl groups having from 1 to 6 carbon atoms, such as those defined and exemplified above in relation to substituents α; and aryl groups, such as those defined and exemplified above in relation to substituents α. In the case of substituents on a nitrogen atom, the substituents may be selected from the group consisting of substituents γ, and examples of such substituents include: alkyl groups having from 1 to 6 carbon atoms, such as those defined and exemplified above in relation to substituents α; and aryl groups, such as those defined and exemplified above in relation to substituents α.

Of these substituents, we prefer the hydroxy groups (on the carbon atom or atoms of a heterocyclic ring alone), and the methyl, ethyl and phenyl groups. Examples of substituted heterocyclyl groups include, for example, the 4-phenyl-1-piperazinyl, 4-methyl-1-piperazinyl, 4-phenylpiperidino, 4-methylpiperidino and 4-hydroxypiperidino groups.

Where $R^3$ represents a group of formula —B—$NR^4R^5$, B may represent an alkylene group having from 2 to 6 carbon atoms or a group of formula —$CH_2CH(OR^6)CH_2$—, where $R^6$ represents a hydrogen atom, an alkanoyl group, a substituted alkanoyl group or an arylcarbonyl group, Where B represents an alkylene group, this may contain from 2 to 6, preferably from 2 to 5, carbon atoms, and may be a straight or branched chain group. In the case of those groups where the two "free" valencies are attached to the same carbon atom, these groups are sometimes referred to as alkylidene groups. However, in the present invention, we prefer that the two "free" valencies are attached to different carbon atoms, and more prefer those compounds in which the group is a straight chain group where the two "free" valencies are attached to different carbon atoms. The preferred alkylene groups represented by B are the ethylene, propylene, trimethylene, tetramethylene, pentamethylene and hexamethylene groups, of which the ethylene, propylene, trimethylene, tetramethylene and pentamethylene groups are preferred, the ethylene, trimethylene and tetramethylene groups are more preferred, and the ethylene and trimethylene groups are most preferred.

Where $R^6$ represents an alkanoyl group, this may be a straight or branched chain group having from 1 to 6, preferably from 2 to 5 and more preferably from 2 to 4, carbon atoms, and examples include the formyl, acetyl, propionyl, butyryl, isobutyryl, valeryl, isovaleryl, pivaloyl and hexanoyl groups, of which we prefer the acetyl, propionyl, butyryl, isobutyryl, valeryl and pivaloyl groups, the acetyl and propionyl groups being most preferred.

Where $R^6$ represents a substituted alkanoyl group, this has from 3 to 6 carbon atoms and may be any of those alkanoyl groups exemplified above (other than the formyl and acetyl groups). The group is substituted by at least one, and preferably only one, carboxy group. Examples of such groups include the succinyl, glutaryl, adipoyl and pimeloyl groups, of which we prefer the succinyl and glutaryl groups.

Where $R^6$ represents an arylcarbonyl group, the aryl part may be as defined and exemplified above in relation to substituents α. Specific examples of such groups include the benzoyl, α-naphthoyl, β-naphthoyl, 3-methoxybenzoyl, 2-methylbenzoyl, 3-methylbenzoyl, 4-methylbenzoyl and 3-chlorobenzoyl groups, of which the unsubstituted groups are preferred, the benzoyl group being most preferred.

Alternatively, $R^3$ may represent a group of formula —D—$R^7$, where D represents a carbon-carbon single bond or an alkylene group having from 1 to 4 carbon atoms and $R^7$ represents a heterocyclic group having 5 or 6 ring atoms bonded to D via a carbon atom in the heterocyclic group;

Where D represents an alkylene group, this may contain from 1 to 4, preferably 1 or 2, carbon atoms, and may be a straight or branched chain group. In the present invention, we prefer that the two "free" valencies are attached to different carbon atoms, and more prefer those compounds in which the group is a straight chain group where the two "free" valencies are attached to different carbon atoms. The preferred alkylene groups represented by D are the methylene, ethylene, trimethylene and tetramethylene groups, of which the methylene and ethylene groups are preferred.

Where $R^7$ represents a heterocyclic group, this has 5 or 6 ring atoms. Of these ring atoms, at least one is a carbon atom and at least one is a hetero-atom selected from the group consisting of nitrogen, oxygen and sulfur hetero-atoms. Preferably, at least one of the ring atoms is a nitrogen atom. More preferably, from 1 to 4 of the ring atoms are hetero-atoms selected from the group consisting of nitrogen, oxygen and sulfur hetero-atoms. In the case of those groups having 4 hetero-atoms in a ring, we prefer that 3 or 4 of them should be nitrogen atoms and 1 or 0 should be an oxygen or sulfur atom. In the case of those groups having 3 hetero-atoms in a ring, we prefer that 1, 2 or 3 should be nitrogen atoms and, correspondingly, 2, 1 or 0 should be oxygen and/or sulfur atoms. In the case of those groups having 1 or 2 hetero-atoms in a ring, the hetero-atoms may be freely chosen from nitrogen, oxygen and sulfur atoms. The group may be saturated, partly saturated or fully unsaturated, but is preferably saturated. The group may be substituted or unsubstituted and, if substituted, the substituents on the nitrogen atom are selected from the group consisting of substituents γ, as defined exemplified above, and the substituents on carbon atoms are selected from the group consisting of substituents ε, as defined above and exemplified below.

Examples of the groups and atoms which may be included in substituents ε are:

alkyl groups having from 1 to 6 carbon atoms, alkenyl groups having from 2 to 6 carbon atoms, alkynyl groups having from 2 to 6 carbon atoms and alkoxy groups having from 1 to 6 carbon atoms, all as defined and exemplified above in relation to substituents α;

hydroxy groups;

alkoxycarbonyloxy groups having from 2 to 7 carbon atoms (i.e. the alkoxy part has from 1 to 6 carbon atoms, which may be straight or branched chain groups, such as the methoxycarbonyloxy, ethoxycarbonyloxy, propoxycarbonyloxy, isopropoxycarbonyloxy, butoxycarbonyloxy, isobutoxycarbonyloxy, sec-butoxycarbonyloxy, t-butoxycarbonyloxy, pentyloxycarbonyloxy, isopentyloxycarbonyloxy, 2-methylbutoxycarbonyloxy, neopentyloxycarbonyloxy, 1-ethylpropoxycarbonyloxy, hexyloxycarbonyloxy, 4-methylpentyloxycarbonyloxy, 3-methylpentyloxycarbonyloxy, 2-methylpentyloxycarbonyloxy, 1-methylpentyloxycarbonyloxy, 3,3-dimethylbutoxycarbonyloxy, 2,2-dimethylbutoxycarbonyloxy, 1,1-dimethylbutoxycarbonyloxy, 1,2-dimethylbutoxycarbonyloxy, 1,3-dimethylbutoxycarbonyloxy, 2,3-dimethylbutoxycarbonyloxy and 2-ethylbutoxycarbonyloxy groups, of which we prefer those alkoxycarbonyloxy groups having from 1 to 4 carbon atoms, the methoxycarbonyloxy, ethoxycarbonyloxy, propoxycarbonyloxy, isopropoxycarbonyloxy, butoxycarbonyloxy, isobutoxycarbonyloxy, sec-butoxycarbonyloxy and t-butoxycarbonyloxy groups being more preferred, and the ethoxycarbonyloxy, isopropoxycarbonyloxy and t-butoxycarbonyloxy groups being most preferred;

alkanoyloxy groups which have from 1 to 20 carbon atoms, such as the formyloxy, acetoxy, propionyloxy, butyryloxy, isobutyryloxy, pivaloyloxy, valeryloxy, isovaleryloxy, hexanoyloxy, heptanoyloxy, octanoyloxy, lauroyloxy, myristoyloxy, tridecanoyloxy, pentadecanoyloxy, palmitoyloxy, heptadecanoyloxy, stearoyloxy, nonadecanoyloxy and icosanoyloxy groups; we prefer those groups which have from 2 to 6 or from 12 to 20 carbon atoms and more prefer the acetoxy and pivaloyloxy groups and those alkanoyloxy groups having from 14 to 20 carbon atoms, of which the acetoxy, pivaloyloxy, palmitoyloxy and stearoyloxy groups are preferred, and the acetoxy group is most preferred;

substituted alkanoyloxy groups which have from 3 to 6 carbon atoms and which are substituted by at least one carboxy group; examples of such groups include the succinyloxy, glutaryloxy, adipoyloxy and pimeloyloxy groups, of which we prefer the succinyloxy, glutaryloxy, adipoyloxy and pimeloyloxy groups, the succinyloxy and glutaryloxy groups being most preferred;

carbamoyloxy groups;

mono- and di- alkylcarbamoyloxy groups in which the or each alkyl part has from 1 to 6 carbon atoms, such as the alkyl groups exemplified above; examples of such mono- and di- alkylcarbamoyloxy groups include the methylcarbamoyloxy, ethylcarbamoyloxy, propylcarbamoyloxy, isopropylcarbamoyloxy, butylcarbamoyloxy, isobutylcarbamoyloxy, sec-butylcarbamoyloxy, t-butylcarbamoyloxy, N,N-dimethylcarbamoyloxy, N,N-diethylcarbamoyloxy, N,N-dipropylcarbamoyloxy, N,N-diisopropylcarbamoyloxy, N,N-dibutylcarbamoyloxy, N,N-diisobutylcarbamoyloxy, N-methyl-N-ethylcarbamoyloxy, N-ethyl-N-propylcarbamoyloxy, N-methyl-N-propylcarbamoyloxy, N-methyl-N-isopropylcarbamoyloxy and N-methyl-N-butylcarbamoyloxy groups, of which the methylcarbamoyloxy, ethylcarbamoyloxy, N,N-dimethylcarbamoyloxy and N,N-diethylcarbamoyloxy groups are preferred;

cyano groups; and halogen atoms and aryl groups which have from 6 to 10 ring carbon atoms and which are unsubstituted or are substituted by at least one substituent selected from the group consisting of substituents β, both of which are as defined and exemplified above in relation to substituents α.

Specific preferred substituents ε are the methyl, ethyl, hydroxy, methoxy, ethoxy, ethoxycarbonyl, isopropoxycarbonyl, t-butoxycarbonyl, acetoxy, propionyloxy, pivaloyloxy, lauroyloxy, myristoyloxy, tridecanoyloxy, pentadecanoyloxy, palmitoyloxy, heptadecanoyloxy, stearoyloxy, nonadecanoyloxy, icosanoyloxy, succinyloxy, glutaryloxy, carbamoyloxy, N-methylcarbamoyloxy, N-ethylcarbamoyloxy, N,N-dimethylcarbamoyloxy and N,N-diethylcarbamoyloxy groups, of which the methyl, hydroxy, ethoxycarbonyloxy, isopropoxycarbonyloxy, t-butoxycarbonyloxy, acetoxy, pivaloyloxy, palmitoyloxy, stearoyloxy, succinyloxy, carbamoyloxy and N,N-dimethylcarbamoyloxy groups are most preferred.

Where a nitrogen atom of the heterocyclic group is substituted, it is substituted by one or more of substituents γ, defined above and which may be exemplified by the corresponding groups included in substituents α. Examples of preferred such substituents on a nitrogen atom include alkyl groups having from 1 to 4 carbon atoms, preferably a methyl or ethyl group.

There is no particular restriction on the number of substituents, except such as may be imposed by the number of substitutable carbon or nitrogen atoms in the heterocyclic ring and possibly by steric constraints. In general, however, we prefer 1, 2 or 3 such substituents, 1 or 2 being more preferred and 1 being most preferred, only for the heterocyclic groups represented by $R^4$ and $R^5$. Examples of groups and atoms which may be included in substituents α are:

The heterocyclic group represented by $R^7$ is attached to the single bond or alkylene group represented by D by a carbon atom in the heterocyclic group.

Examples of unsubstituted heterocyclic groups which may be represented by $R^7$ include: the pyrrolidinyl, piperidyl, piperazinyl, morpholinyl and thiomorpholinyl groups, any of which may be substituted by any one or more of the substituents ε and γ. Specific examples of preferred substituted and unsubstituted heterocyclic groups which may be represented by $R^7$ include: the pyrrolidinyl, methylpyrrolidinyl, ethylpyrrolidinyl, propylpyrrolidinyl, isopropylpyrrolidinyl, butylpyrrolidinyl, hydroxypyrrolidinyl, methoxypyrrolidinyl, ethoxypyrrolidinyl, propoxypyrrolidinyl, isopropoxypyrrolidinyl, butoxypyrrolidinyl, methoxycarbonyloxypyrrolidinyl, ethoxycarbonyloxypyrrolidinyl, propoxycarbonyloxypyrrolidinyl, isopropoxycarbonyloxypyrrolidinyl, butoxycarbonyloxypyrrolidinyl, t-butoxycarbonyloxypyrrolidinyl, formyloxypyrrolidinyl, acetoxypyrrolidinyl, propionyloxypyrrolidinyl, butyryloxypyrrolidinyl, pivaloyloxypyrrolidinyl, valeryloxypyrrolidinyl, lauroyloxypyrrolidinyl, myristoyloxypyrrolidinyl, tridecanoyloxypyrrolidinyl, pentadecanoyloxypyrrolidinyl, palmitoyloxypyrrolidinyl, heptadecanoyloxypyrrolidinyl, stearoyloxypyrrolidinyl, nonadecanoyloxypyrrolidinyl, icosanoyloxypyrrolidinyl, (succinoyloxy)pyrrolidinyl, (glutaroyloxy)pyrrolidinyl, (carbamoyloxy)pyrrolidinyl, (N-methylcarbamoyloxy)pyrrolidinyl, (N-ethylcarbamoyloxy)pyrrolidinyl, (N,N-dimethylcarbamoyloxy)pyrrolidinyl, (N,N-diethylcarbamoyloxy)pyrrolidinyl, (N-methyl-N-ethylcarbamoyloxy)pyrrolidinyl, 1-methyl-hydroxypyrrolidinyl, 1-methyl-methoxypyrrolidinyl, 1-methyl-ethoxypyrrolidinyl, 1-methyl-methoxycarbonyloxypyrrolidinyl, 1-methyl-ethoxycarbonyloxypyrrolidinyl, 1-methyl-propoxycarbonyloxypyrrolidinyl, 1-methyl-isopropoxycarbonyloxypyrrolidinyl, 1-methyl-butoxycarbonyloxypyrrolidinyl, 1-methyl-t-butoxycarbonyloxypyrrolidinyl, 1-methyl-acetoxypyrrolidinyl, 1-methyl-propionyloxypyrrolidinyl, 1-methyl-pivaloyloxypyrrolidinyl, 1-methyl-lauroyloxypyrrolidinyl, 1-methyl-myristoyloxypyrrolidinyl, 1-methyl-tridecanoyloxypyrrolidinyl, 1-methyl-pentadecanoyloxypyrrolidinyl, 1-methyl-palmitoyloxypyrrolidinyl, 1-methyl-heptadecanoyloxypyrrolidinyl, 1-methyl-stearoyloxypyrrolidinyl, 1-methyl-nonadecanoyloxypyrrolidinyl, 1-methyl-icosanoyloxypyrrolidinyl, 1-methyl-(succinoyloxy)pyrrolidinyl, 1-methyl-(glutaroyloxy)pyrrolidinyl, 1-methyl-(carbamoyloxy)pyrrolidinyl, 1-methyl-(N-methylcarbamoyloxy)pyrrolidinyl, 1-methyl-(N-ethylcarbamoyloxy)pyrrolidinyl, 1-methyl-(N,N-dimethylcarbamoyloxy)pyrrolidinyl, 1-methyl-(N,N-diethylcarbamoyloxy)pyrrolidinyl, 1-methyl-(N-methyl-N-ethylcarbamoyloxy)pyrrolidinyl, 1-ethylhydroxypyrrolidinyl, 1-ethyl-methoxypyrrolidinyl, 1-ethyl-methoxycarbonyloxypyrrolidinyl, 1-ethyl-ethoxycarbonyloxypyrrolidinyl, 1-ethyl-propoxycarbonyloxypyrrolidinyl, 1-ethyl-isopropoxycarbonyloxypyrrolidinyl, 1-ethyl-butoxycarbonyloxypyrrolidinyl, 1-ethyl-t-butoxycarbonyloxypyrrolidinyl, 1-ethyl-acetoxypyrrolidinyl, 1-ethyl-pivaloyloxypyrrolidinyl, 1-ethyl-lauroyloxypyrrolidinyl, 1-ethyl-myristoyloxypyrrolidinyl, 1-ethyl-tridecanoyloxypyrrolidinyl, 1-ethyl-pentadecanoyloxypyrrolidinyl, 1-ethyl-palmitoyloxypyrrolidinyl, 1-ethyl-heptadecanoyloxypyrrolidinyl, 1-ethyl-stearoyloxypyrrolidinyl, 1-ethyl-nonadecanoyloxypyrrolidinyl, 1-ethyl-icosanoyloxypyrrolidinyl, 1-ethyl-(succinoyloxy)pyrrolidinyl, piperidyl, methylpiperidyl, ethylpiperidyl, propylpiperidyl, isopropylpiperidyl, butylpiperidyl, hydroxypiperidyl, methoxypiperidyl, ethoxypiperidyl, methoxycarbonyloxypiperidyl, ethoxycarbonyloxypiperidyl, propoxycarbonyloxypiperidyl, isopropoxycarbonyloxypiperidyl, butoxycarbonyloxypiperidyl, t-butoxycarbonyloxypiperidyl, acetoxypiperidyl, propionyloxypiperidyl, pivaloyloxypiperidyl, lauroyloxypiperidyl, myristoyloxypiperidyl, tridecanoyloxypiperidyl, pentadecanoyloxypiperidyl, palmitoyloxypiperidyl, heptadecanoyloxypiperidyl, stearoyloxypiperidyl, nonadecanoyloxypiperidyl, icosanoyloxypiperidyl, succinoyloxypiperidyl, glutaroyloxypiperidyl, carbamoyloxypiperidyl, (N-methylcarbamoyloxy)piperidyl, (N-ethylcarbamoyloxy)piperidyl, (N,N-dimethylcarbamoyloxy)piperidyl, 1-methyl-(N-methyl-N-ethylcarbamoyloxy)piperidyl, 1-methyl-hydroxypiperidyl, 1-methyl-methoxypiperidyl, 1-methyl-ethoxypiperidyl, 1-methyl-methoxycarbonyloxypiperidyl, 1-methyl-ethoxycarbonyloxypiperidyl, 1-methyl-propoxycarbonyloxypiperidyl, 1methyl-isopropoxycarbonyloxypiperidyl, 1-methyl-butoxycarbonyloxypiperidyl, 1-methyl-t-butoxycarbonyloxypiperidyl, 1-methyl-acetoxypiperidyl, 1-methyl-propionyloxypiperidyl, 1-methyl-pivaloyloxypiperidyl, 1-methyl-lauroyloxypiperidyl, 1-methyl-myristoyloxypiperidyl, 1-methyl-tridecanoyloxypiperidyl, 1-methyl-pentadecanoyloxypiperidyl, 1-methyl-palmitoyloxypiperidyl, 1-methyl-heptadecanoyloxypiperidyl, 1-methyl-stearoyloxypiperidyl, 1-methyl-nonadecanoyloxypiperidyl, 1-methyl-icosanoyloxypiperidyl, 1-methyl-(succinoyloxy)piperidyl, 1-methyl-(N-methylcarbamoyloxy)piperidyl, 1-methyl-carbamoyloxypiperidyl, 1-methyl-(N-ethyl-carbamoyloxy)piperidyl, 1-methyl-(N,N-dimethylcarbamoyloxy)piperidyl, 1-methyl-(N-methyl-N-ethylcarbamoyloxy)piperidyl, 1-ethyl-hydroxypiperidyl, 1-ethyl-methoxypiperidyl, 1-ethyl-ethoxypiperidyl, 1-ethyl-methoxycarbonyloxypiperidyl, 1-ethyl-ethoxycarbonyloxypiperidyl, 1-ethyl-propoxycarbonyloxypiperidyl, 1-ethyl-isopropoxycarbonyloxypiperidyl, 1-ethyl-t-butoxycarbonyloxypiperidyl, 1-ethyl-acetoxypiperidyl, 1-ethyl-pivaloyloxypiperidyl, 1-ethyl-myristoyloxypiperidyl, 1-ethyl-tridecanoyloxypiperidyl, 1-ethyl-pentadecanoyloxypiperidyl, 1-ethyl-palmitoyloxypiperidyl, 1-ethyl-heptadecanoyloxypiperidyl, 1-ethyl-stearoyloxypiperidyl, 1-ethyl-nonadecanoyloxypiperidyl, 1-ethyl-icosanoyloxypiperidyl, 1-ethyl-succinoyloxypiperidyl, piperazinyl, 1,4-dimethylpiperazinyl, morpholinyl, 4-methylmorpholinyl, 4-ethylmorpholinyl, 4-propylmorpholinyl, 4-isopropylmorpholinyl, 4-butylmorpholinyl, thiomorpholinyl, 4-methylthiomorpholinyl, 4-ethylthiomorpholinyl, 4-propylthiomorpholinyl, 4-isopropylthiomorpholinyl and 4-butylthiomorpholinyl groups. Of these, we prefer the pyrrolidinyl, 1-methylpyrrolidinyl, 1-ethylpyrrolidinyl, 4-hydroxy-2-pyrrolidinyl, 4-methoxy-2-pyrrolidinyl, 4-ethoxycarbonyloxy-2-pyrrolidinyl, 4-isopropoxycarbonyloxy-2-pyrrolidinyl, 4-t-butoxycarbonyloxy-2-pyrrolidinyl, 4-formyloxy-2-pyrrolidinyl, 4-acetoxy-2-pyrrolidinyl, 4-pivaloyloxy-2-pyrrolidinyl, 4-valeryloxy-2-pyrrolidinyl, 4-myristoyloxy- 2-pyrrolidinyl, 4-tridecanoyloxy-2-pyrrolidinyl, 4-pentadecanoyloxy-2-pyrrolidinyl, 4-palmitoyloxy-2-pyrrolidinyl, 4-heptadecanoyloxy-2-pyrrolidinyl, 4-stearoyloxy-2-pyrrolidinyl, 4-nonadecanoyloxy-2-pyrrolidinyl, 4-icosanoyloxy-2-pyrrolidinyl, 4-(succinoyloxy)-2-pyrrolidinyl, 4-(glutaroyloxy)-2-pyrrolidinyl, 4-(carbamoyloxy)-2-pyrrolidinyl, 4-(N-methylcarbamoyloxy)-2-pyrrolidinyl, 4-(N,N-dimethylcarbamoyloxy)-2-pyrrolidinyl, 4-(N-methyl-N-ethylcarbamoyloxy)- 2-pyrrolidinyl, 1-methyl-4-hydroxy-2-pyrrolidinyl, 1-methyl-4-methoxy-2-pyrrolidinyl, 1-methyl-4-ethoxycarbonyloxy-2-pyrrolidinyl, 1-methyl-4-isopropoxycarbonyloxy-2-pyrrolidinyl, 1-methyl-4-t-butoxycarbonyloxy-2-pyrrolidinyl, 1-methyl-4-acetoxy-2-pyrrolidinyl, 1-methyl-4-myristoyloxy-2-pyrrolidinyl, 1-methyl-4-tridecanoyloxy-2-pyrrolidinyl, 1-methyl-4-pentadecanoyloxy-2-pyrrolidinyl, 1-methyl-4-palmitoyloxy- 2-pyrrolidinyl, 1-methyl-4-heptadecanoyloxy-2-pyrrolidinyl, 1-methyl-4-stearoyloxy-2-pyrrolidinyl, 1-methyl-4-nonadecanoyloxy-2-pyrrolidinyl, 1-methyl-4-icosanoyloxy-2-pyrrolidinyl, 1-methyl-4-succinoyloxy-2-pyrrolidinyl, 1-methyl-4- glutaroyloxy-2-pyrrolidinyl, 1-methyl-4-(carbamoyloxy)-2-pyrrolidinyl, 1-methyl-4-(N-methylcarbamoyloxy)-2-pyrrolidinyl, 1-methyl-4-(N,N-dimethylcarbamoyloxy)-2-pyrrolidinyl, 1-methyl-4-(N-methyl-N-ethylcarbamoyloxy)- 2-pyrrolidinyl, 1-ethyl-4-hydroxy- 2-pyrrolidinyl, 1-ethyl-4-methoxy-2-pyrrolidinyl, 1-ethyl-4-ethoxycarbonyloxy-2-pyrrolidinyl, 1-ethyl-4-isopropoxycarbonyloxy-2-pyrrolidinyl, 1-ethyl-4-t-butoxycarbonyloxy-2-pyrrolidinyl, 1-ethyl-4-acetoxy-2-pyrrolidinyl, 1-ethyl-4-myristoyloxy-2-pyrrolidinyl, 1-ethyl-4-tridecanoyloxy-2-pyrrolidinyl, 1-ethyl-4-pentadecanoyloxy-2-pyrrolidinyl, 1-ethyl-4-palmitoyloxy-2-pyrrolidinyl, 1-ethyl-4-heptadecanoyloxy-2-pyrrolidinyl, 1-ethyl-4-stearoyloxy-2-pyrrolidinyl, 1-ethyl-4-nonadecanoyloxy-2-pyrrolidinyl, 1-ethyl-4-icosanoyloxy-2-pyrrolidinyl, 1-ethyl-4-succinoyl- oxy-2-pyrrolidinyl, piperidyl, 1-methylpiperidyl, 1-ethylpiperidyl, hydroxypiperidyl, methoxypiperidyl, ethoxycarbonyloxypiperidyl, isopropoxycarbonyloxypiperidyl, t-butoxycarbonyloxypiperidyl, acetoxypiperidyl, myristoyloxypiperidyl, tridecanoyloxypiperidyl, pentadecanoyloxypiperidyl, palmitoyloxypiperidyl, heptadecanoyloxypiperidyl, stearoyloxypiperidyl, nonadecanoyloxypiperidyl, icosanoyloxypiperidyl, succinoyloxypiperidyl, glutaroyloxypiperidyl, carbamoyloxypiperidyl, (N-methylcarbamoyloxy)piperidyl, (N,N-dimethylcarbamoyloxy)piperidyl, (N-methyl-N-ethylcarbamoyloxy)piperidyl, 1-methyl-hydroxypiperidyl, 1-methyl-methoxypiperidyl, 1-methyl-ethoxycarbonyloxypiperidyl, 1-methyl-isopropoxycarbonyloxypiperidyl, 1-methyl-t-butoxycarbonyloxypiperidyl, 1-methylacetoxypiperidyl, 1-methyl-myristoyloxypiperidyl, 1-methyl-tridecanoyloxypiperidyl, 1-methyl-pentadecanoyloxypiperidyl, 1-methyl-palmitoyloxypiperidyl, 1-methyl-heptadecanoyloxypiperidyl, 1-methyl-stearoyloxypiperidyl, 1-methyl-nonadecanoyloxypiperidyl, 1-methyl-icosanoyloxypiperidyl, 1-methyl-(succinoyloxy)piperidyl, 1-methyl-carbamoyloxypiperidyl, 1-methyl-(N-methylcarbamoyloxy)piperidyl, 1-methyl-(N,N-dimethylcarbamoyloxy)piperidyl, 1-ethyl-hydroxypiperidyl, 1-ethyl-methoxypiperidyl, 1-ethylethoxycarbonyloxypiperidyl, 1-ethyl-isopropoxycarbonyloxypiperidyl, 1-ethyl-t-butoxycarbonyloxypiperidyl, 1-ethyl-acetoxypiperidyl, 1-ethyl-myristoyloxypiperidyl, 1-ethyl-tridecanoyloxypiperidyl, 1-ethyl-pentadecanoyloxypiperidyl, 1-ethyl-palmitoyloxypiperidyl, 1-ethyl-heptadecanoyloxypiperidyl, 1-ethyl-stearoyloxypiperidyl, 1-ethyl-nonadecanoyloxypiperidyl, 1-ethyl-icosanoyloxypiperidyl, 1-ethyl-succinoyloxypiperidyl, piperazinyl, 1,4-dimethylpiperazinyl, morpholinyl, 4-methylmorpholinyl, 4-ethylmorpholinyl, 4-propylmorpholinyl, 4-isopropylmorpholinyl, 4-butylmorpholinyl, thiomorpholinyl, 4-methylthiomorpholinyl, 4-ethylthiomorpholinyl, 4-propylthiomorpholinyl, 4-isopropylthiomorpholinyl and 4-butylthiomorpholinyl groups. Of these, the more preferred groups are the pyrrolidinyl, 1-methyl-2-pyrrolidinyl, 1-methyl-3-pyrrolidinyl, 4-hydroxy-2-pyrrolidinyl, 4-methoxy-2-pyrrolidinyl, 4-ethoxycarbonyloxy-2-pyrrolidinyl, 4-isopropoxycarbonyloxy-2-pyrrolidinyl, 4-t-butoxycarbonyloxy-2-pyrrolidinyl, 4-acetoxy-2-pyrrolidinyl, 4-myristoyloxy- 2-pyrrolidinyl, 4-palmitoyloxy-2-pyrrolidinyl, 4-stearoyloxy-2-pyrrolidinyl, 4-icosanoyloxy-2-pyrrolidinyl, 4-(succinoyloxy)-2-pyrrolidinyl, 4-(glutaroyloxy)-2-pyrrolidinyl, 4-(carbamoyloxy)-2-pyrrolidinyl, 4-(N-methylcarbamoyloxy)-2-pyrrolidinyl, 4-(N,N-dimethylcarbamoyloxy)-2-pyrrolidinyl, 1-methyl-4-hydroxy-2-pyrrolidinyl, 1-methyl-4-methoxy-2-pyrrolidinyl, 1-methyl-4-ethoxycarbonyloxy-2-pyrrolidinyl, 1-methyl-4-isopropoxy-2-carbonyloxypyrrolidinyl, 1-methyl-4-t-butoxycarbonyloxy-2-pyrrolidinyl, 1-methyl-4-acetoxy-2-pyrrolidinyl, 1-methyl-4-myristoyloxy-2-pyrrolidinyl, 1-methyl-4-palmitoyloxy-2-pyrrolidinyl, 1-methyl-4-stearoyloxy-2-pyrrolidinyl, 1-methyl-4-icosanoyloxy-2-pyrrolidinyl, 1-methyl-4-succinoyloxypyrrolidinyl, 1-methyl-4-glutaroyloxy-2-pyrrolidinyl, 1-methyl-4-carbamoyloxy-2-pyrrolidinyl, 1-methyl-4-(N-methylcarbamoyloxy)-2-pyrrolidinyl, 1-methyl-4-(N,N-dimethylcarbamoyloxy)-2-pyrrolidinyl, 1-ethyl-4-hydroxy-2-pyrrolidinyl, 1-ethyl- 4-ethoxycarbonyloxy-2-pyrrolidinyl, 1-ethyl-4-isopropoxycarbonyloxy-2-pyrrolidinyl, 1-ethyl-4-t-butoxycarbonyloxy- 2-pyrrolidinyl, 1-ethyl-4-acetoxy-2-pyrrolidinyl, 1-ethyl-4-myristoyloxy-2-pyrrolidinyl, 1-ethyl-4-palmitoyloxy-2-pyrrolidinyl, 1-ethyl-4-stearoyloxy-2-pyrrolidinyl, 1-ethyl-4-icosanoyloxy-2-pyrrolidinyl, 1-ethyl-4-succinoyloxy-2-pyrrolidinyl, 2-piperidyl, 3-piperidyl, 4-piperidyl, 1-methyl-2-piperidyl, 1-methyl-3-piperidyl, 1-methyl-4-piperidyl, piperazinyl, 1,4-dimethylpiperazinyl, 2-morpholinyl, 4-methyl-2-morpholinyl, 4-ethyl-2-morpholinyl, 2-thiomorpholinyl and 4-methyl-2-thiomorpholinyl groups. Still more preferred groups are the 2-pyrrolidinyl, 3-pyrrolidinyl, 1-methyl-2-pyrrolidinyl, 4-hydroxy-2-pyrrolidinyl, 4-methoxy-2-pyrrolidinyl, 4-ethoxycarbonyloxy-2-pyrrolidinyl, 4-isopropoxycarbonyloxy-2-pyrrolidinyl, 4-t-butoxycarbonyloxy-2-pyrrolidinyl, 4-acetoxy-2-pyrrolidinyl, 4-myristoyloxy-2-pyrrolidinyl, 4-palmitoyloxy-2-pyrrolidinyl, 4-stearoyloxy-2-pyrrolidinyl, 4-(succinoyloxy)-2-pyrrolidinyl, 4-(carbamoyloxy)-2-pyrrolidinyl, 4-(N,N-dimethylcarbamoyloxy)-2-pyrrolidinyl, 1-methyl-4-hydroxy-2-pyrrolidinyl, 1-methyl-4-methoxy-2-pyrrolidinyl, 1-methyl-4-ethoxycarbonyloxy-2-pyrrolidinyl, 1-methyl-4-isopropoxy-2-carbonyloxypyrrolidinyl, 1-methyl-4-t-butoxycarbonyloxy-2-pyrrolidinyl, 1-methyl-4-acetoxy-2-pyrrolidinyl, 1-methyl-4-myristoyloxy-2-pyrrolidinyl, 1-methyl-4-palmitoyloxy-2-pyrrolidinyl, 1-methyl-4-stearoyloxy-2-pyrrolidinyl, 1-methyl-4-succinoyloxy-2-pyrrolidinyl, 1-methyl-4-carbamoyloxy-2-pyrrolidinyl, 1-methyl-4-(N,N-dimethylcarbamoyloxy)-2-pyrrolidinyl, 2-piperidyl, 3-piperidyl, 4-piperidyl, 1-methyl-2-piperidyl, 1-methyl-3-piperidyl, 1-methyl-4-piperidyl, 2-morpholinyl, 4-methyl-2-morpholinyl and 2-thiomorpholinyl groups. The most preferred groups are the 2-pyrrolidinyl, 1-methyl-2-pyrrolidinyl, 4-hydroxy- 2-pyrrolidinyl, 4-methoxy-2-pyrrolidinyl, 4-acetoxy-2-pyrrolidinyl, 4-(succinoyloxy)-2-pyrrolidinyl, 4-(carbamoyloxy)-2-pyrrolidinyl, 1-methyl-4-hydroxy-2-pyrrolidinyl, 1-methyl-4-succinoyloxy-2-pyrrolidinyl, 2-piperidyl, 3-piperidyl, 4-piperidyl, 1-methyl-2-piperidyl, 1-methyl-3-piperidyl, 1-methyl-4-piperidyl, 2-morpholinyl and 4-methyl-2-morpholinyl groups.

Where A represents an alkylene group, this may contain from 2 to 8 carbon atoms, preferably from 2 to 7 carbon atoms, more preferably from 2 to 5 carbon atoms. In the case of compounds intended for the treatment or prophylaxis of circulatory diseases, A still more preferably represents an alkylene group having from 2 to 4, yet more preferably 2 or 4, and most preferably 2, carbon atoms. In the case of compounds intended for the treatment or prophylaxis of psychosis, A still more preferably represents an alkylene group having 4 or 5 carbon atoms. Examples of such alkylene groups which may be represented by A include the ethylene, propylene, trimethylene, tetramethylene, pentamethylene, hexamethylene, heptamethylene and octamethylene groups, of which we prefer the ethylene, trimethylene, tetramethylene, pentamethylene, hexamethylene and heptamethylene groups, the ethylene and tetramethylene groups being most preferred for the treatment or prophylaxis of circulatory diseases, and the tetramethylene and pentamethylene groups being most preferred for the treatment or prophylaxis of psychosis.

The compounds of the present invention can form salts. There is no restriction on the nature of such salts, provided that, where the compounds are to be used for therapeutic purposes, the salts are pharmaceutically acceptable, that is they are not less active or unacceptably less active or more toxic or unacceptably more toxic than the free acid. Where the compounds are to be used for non-therapeutic purposes, e.g. as intermediates in the preparation of other compounds, even this restriction does not apply. Where the compound contains a carboxy group, e.g. supplied by the carboxy group present as a substituent on an alkanoyl group represented by $R^6$ or an alkanoyloxy group included in substituents ε, examples of such salts include: salts with an alkali metal, such as sodium, potassium or lithium; salts with an alkaline earth metal, such as barium or calcium; salts with another metal, such as magnesium or aluminum; ammonium salts; organic base salts, such as a salt with triethylamine, diisopropyl- amine, cyclohexylamine or dicyclohexylamine; and salts with a basic amino acid, such as lysine or arginine. Also, where the compound of the present invention contains a basic group in its molecule, it can form acid addition salts. Examples of such acid addition salts include: salts with mineral acids, especially hydrohalic acids (such as hydrobromic acid, hydroiodic acid or hydrochloric acid), nitric acid, perchloric acid, carbonic acid, sulfuric acid or phosphoric acid; salts with lower alkylsulfonic acids, such as methanesulfonic acid, trifluoromethanesulfonic acid or ethanesulfonic acid; salts with arylsulfonic acids, such as benzenesulfonic acid or p-toluenesulfonic acid; salts with organic carboxylic acids, such as acetic acid, fumaric acid, tartaric acid, oxalic acid, maleic acid, malic acid, succinic acid, benzoic acid, mandelic acid, ascorbic acid, lactic acid, gluconic acid or citric acid; and salts with amino acids, such as glutamic acid or aspartic acid.

Where the compounds of the present invention contain a carboxy group, they may also form esters, as is well known in the art. There is also no particular restriction on the nature of such esters, although they are preferably pharmaceutically acceptable, and examples of esters are well known in the art. By way of example, preferred esters include alkyl esters, in which the alkyl group has from 1 to 6, preferably from 1 to 4 carbon atoms and may be as defined and exemplified above in relation to the alkyl groups which may be represented by $R^2$, or aralkyl esters in which the alkyl part preferably has from 1 to 4, more preferably 1 or 2, carbon atoms, and the aryl part is as defined and exemplified above in relation to the aryl groups which may be represented by $R^1$. Preferred examples of esters include the methyl, ethyl, propyl, isopropyl, butyl, t-butyl, benzyl, phenethyl and benzhydryl esters.

The group represented by —$OR^3$ is preferably present at the 2-position of the benzene ring (relative to the position of attachment of the group represented by A taken to be the 1-position).

The compounds of the present invention may contain one or more asymmetric carbon atoms in their molecules, and may thus form optical isomers. Although these are all represented herein by a single molecular formula, the present invention includes both the individual, isolated isomers and mixtures, including racemates thereof. Where stereospecific synthesis techniques are employed or optically active compounds are employed as starting materials, individual isomers may be prepared directly; on the other hand, if a mixture of isomers is prepared, the individual isomers may be obtained by conventional resolution techniques.

A preferred class of compounds of the present invention comprises those compounds of formula (I) in which:

$R^1$ represents a phenyl or naphthyl group which is unsubstituted or is substituted by at least one substituent selected from the group consisting of
  alkyl groups having from 1 to 4 carbon atoms,
  hydroxy groups,
  alkoxy groups having from 1 to 4 carbon atoms,
  haloalkoxy groups having from 1 to 4 carbon atoms,
  halogen atoms,
  cyano groups, and
  carbamoyl groups;

$R^2$ represents a hydrogen atom, a methyl group, an ethyl group, a methoxy group, an ethoxy group, a fluorine atom or a chlorine atom;

the group represented by —$OR^3$ is present at the 2-position of the benzene ring (relative to the position of attachment of the group represented by A taken to be the 1-position);

$R^3$ represents
  a group of formula —B—$NR^4R^5$,
    where $R^4$ and $R^5$ are independently selected from the group consisting of hydrogen atoms, alkyl groups having from 1 to 4 carbon atoms, substituted alkyl groups having from 1 to 4 carbon atoms and substituted by at least one phenyl group, and substituted alkyl groups having from 2 to 4 carbon atoms and substituted by at least one substituent selected from the group consisting of hydroxy groups and dialkylamino groups in which each alkyl part is a methyl or ethyl group, or
    $R^4$ and $R^5$ together with the nitrogen atom to which they are attached, represent a heterocyclic group having from 5 to 6 ring atoms, preferably a 1-pyrrolidinyl, 1-piperidyl, 4-morpholinyl, 4-thiomorpholinyl, 1-piperazinyl, 1-imidazolyl, 1-pyrazolyl or 1-triazolyl group, any of which may be substituted or unsubstituted, said substituted heterocyclic groups being substituted on at least one of a carbon atom and a nitrogen atom, the substituents being, in the case of substituents on a carbon atom, selected from the group consisting of
      alkyl groups having from 1 to 4 carbon atoms,
      hydroxy groups and phenyl groups which are unsubstituted or which have at least one substituent selected from the group consisting of methyl groups, methoxy groups, fluorine atoms and chlorine atoms, and B represents an alkylene group having from 2 to 4 carbon atoms or a group of formula —$CH_2CH(OR^6)CH_2$—, where $R^6$ represents a hydrogen atom, an alkanoyl group having from 2 to 4 carbon atoms, a substituted alkanoyl group having 2 or 3 carbon atoms and substituted by a carboxy group, or a benzoyl group which is unsubstituted or is substituted by at least one substituent selected from the group consisting of methyl groups, methoxy groups, fluorine atoms and chlorine atoms, or a group of formula —D—$R^7$, where D represents a carbon-carbon single bond or an alkylene group having from 1 to 3 carbon atoms and $R^7$ represents a heterocyclic group having 5 or 6 ring atoms bonded to D via a carbon atom in the heterocyclic group, said heterocyclic group being selected from the group consisting of pyrrolidinyl groups, piperidyl groups, morpholinyl groups, thiomorpholinyl groups and piperazinyl groups which are unsubstituted or are substituted on at least one of a carbon atom and a nitrogen atom by at least one substituent selected from the group consisting of in the case of substituents on a carbon atom, alkyl groups having from 1 to 4 carbon atoms, hydroxy groups, alkoxy groups having from 1 to 4 carbon atoms, alkoxycarbonyloxy groups having from 2 to 5 carbon atoms, alkanoyloxy groups having from 2 to 20 carbon atoms, carboxy-substituted alkanoyloxy groups having 3 or 4 carbon atoms in the alkanoyl part, carbamoyloxy groups, mono- and di- alkyl- carbamoyloxy groups in which the or each alkyl part is a methyl or ethyl group, fluorine atoms and chlorine atoms, in the case of substituents on a nitrogen atom, alkyl groups having from 1 to 4 carbon atoms, and phenyl groups which are unsubstituted or which have at least one substituent selected from the group consisting of methyl groups, methoxy groups, fluorine atoms and chlorine atoms;

A represents an alkylene group having from 2 to 7 carbon atoms;

and pharmaceutically acceptable salts and esters thereof.

A more preferred class of compounds of the present invention for the treatment of circulatory diseases comprises those compounds of formula (I) in which:

$R^1$ represents a phenyl group which is unsubstituted or is substituted by at least one substituent selected from the group consisting of methyl groups, ethyl groups, fluoromethoxy groups, difluoromethoxy groups, 2-fluoroethoxy groups, hydroxy groups, methoxy groups, ethoxy groups, fluorine atoms, chlorine atoms, bromine atoms and cyano groups;

$R^2$ represents a hydrogen atom; the group represented by —$OR^3$ is present at the 2-position of the benzene ring (relative to the position of attachment of the group represented by A taken to be the 1-position);

R³ represents
a group of formula —B—NR⁴R⁵,
where R⁴ and R⁵ are independently selected from the group consisting of hydrogen atoms, alkyl groups having from 1 to 4 carbon atoms, benzyl groups, phenethyl groups, 2-hydroxyethyl groups, 3-hydroxypropyl groups, 2-(N,N-dimethylamino)ethyl groups and 2-(N,N-dimethylamino)propyl groups, or R⁴ and R⁵, together with the nitrogen atom to which they are attached, represent a 1-pyrrolidinyl group, a 1-piperidyl group, a 4-hydroxy-1-piperidyl group, a 4-morpholinyl group, a 4-methyl-1-piperazinyl group, a 4-ethyl-1-piperazinyl group, a 4-phenyl-1-piperazinyl group, a 1-imidazolyl group or a 1-triazolyl group, and
B represents an alkylene group having 2 or 3 carbon atoms or a group of formula —CH₂CH(OR⁶)CH₂—, where R⁶ represents a hydrogen atom, an alkanoyl group having 2 or 3 carbon atoms, or a substituted alkanoyl group having 3 or 4 carbon atoms and substituted by a carboxy group,
or a group of formula —D—R⁷, where D represents a carbon-carbon single bond or an alkylene group having 1 or 2 carbon atoms and R⁷ represents a heterocyclic group having 5 or 6 ring atoms bonded to D via a carbon atom in the heterocyclic group, said heterocyclic group being selected from the group consisting of pyrrolidinyl groups, piperidyl groups, morpholinyl groups and thiomorpholinyl groups which are unsubstituted or are substituted on at least one of a carbon atom and a nitrogen atom by at least one substituent selected from the group consisting of in the case of substituents on a carbon atom, alkyl groups having from 1 to 4 carbon atoms, hydroxy groups, alkoxy groups having from 1 to 4 carbon atoms, alkoxycarbonyloxy groups having from 2 to 5 carbon atoms, alkanoyloxy groups having 2 or 3 carbon atoms, alkanoyloxy groups having from 12 to 20 carbon atoms, carboxy-substituted alkanoyloxy groups having 3 or 4 carbon atoms in the alkanoyl part, carbamoyloxy groups, and mono- and di- alkyl- carbamoyloxy groups in which the or each alkyl part is a methyl or ethyl group, in the case of substituents on a nitrogen atom, alkyl groups having from 1 to 4 carbon atoms;

A represents an alkylene group having from 2 to 5 carbon atoms;

and pharmaceutically acceptable salts and esters thereof.

A still more preferred class of compounds of the present invention for the treatment of circulatory diseases comprises those compounds of formula (I) in which:

R¹ represents a phenyl group which is unsubstituted or is substituted by at least one substituent selected from the group consisting of methyl groups, ethyl groups, fluoromethoxy groups, difluoromethoxy groups, 2-fluoroethoxy groups, hydroxy groups, methoxy groups, ethoxy groups, fluorine atoms, chlorine atoms, bromine atoms and cyano groups;

R² represents a hydrogen atom;

the group represented by —OR³ is present at the 2-position of the benzene ring (relative to the position of attachment of the group represented by A taken to be the 1-position);

R³ represents
a group of formula —B—NR⁴R⁵,
where R⁴ and R⁵ are independently selected from the group consisting of hydrogen atoms, methyl groups, ethyl groups, benzyl groups and 2-hydroxyethyl groups, or R⁴ and R⁵, together with the nitrogen atom to which they are attached, represent a 1-pyrrolidinyl group, a 1-piperidyl group, a 4-hydroxy-1-piperidyl group, a 4-morpholinyl group, a 4-methyl-1-piperazinyl group, a 4-phenyl-1-piperazinyl group or a 1-imidazolyl group, and
B represents an alkylene group having 2 or 3 carbon atoms or a group of formula —CH₂CH(OR⁶)CH₂—, where R⁶ represents a hydrogen atom, an acetyl group, a succinyl group or a glutaryl group,
or a group of formula —D—R⁷, where D represents a carbon-carbon single bond or an alkylene group having 1 or 2 carbon atoms and R⁷ represents a heterocyclic group having 5 or 6 ring atoms bonded to D via a carbon atom in the heterocyclic group, said heterocyclic group being selected from the group consisting of pyrrolidinyl groups, piperidyl groups, morpholinyl groups and thiomorpholinyl groups which are unsubstituted or are substituted on at least one of a carbon atom and a nitrogen atom by at least one substituent selected from the group consisting of in the case of substituents on a carbon atom, methyl groups, ethyl groups, hydroxy groups, methoxy groups, ethoxy groups, ethoxycarbonyloxy groups, isopropoxycarbonyloxy groups, t-butoxycarbonyloxy groups, alkanoyloxy groups having 2 or 3 carbon atoms, alkanoyloxy groups having from 14 to 20 carbon atoms, carboxy-substituted alkanoyloxy groups having 3 or 4 carbon atoms in the alkanoyl part, carbamoyloxy groups, and mono- and di- alkyl- carbamoyloxy groups in which the or each alkyl part is a methyl or ethyl group, in the case of substituents on a nitrogen atom, methyl groups and ethyl groups;

A represents an alkylene group having from 2 to 4 carbon atoms;

and pharmaceutically acceptable salts and esters thereof.

A yet more preferred class of compounds of the present invention for the treatment of circulatory diseases comprises those compounds of formula (I) in which:

R¹ represents a phenyl group which is unsubstituted or is substituted by at least one substituent selected from the group consisting of methyl groups, hydroxy groups, methoxy groups, ethoxy groups, fluoromethoxy groups, difluoromethoxy groups, fluorine atoms, chlorine atoms, bromine atoms and cyano groups;

R² represents a hydrogen atom; the group represented by —OR³ is present at the 2-position of the benzene ring (relative to the position of attachment of the group represented by A taken to be the 1-position);

R³ represents a group of formula —B—NR⁴R⁵,
where R⁴ and R⁵ are independently selected from the group consisting of methyl groups, ethyl groups and 2-hydroxyethyl groups, or R⁴ and R⁵, together with the nitrogen atom to which they are attached, represent a 1-pyrrolidinyl group, a 1-piperidyl group, a 4-hydroxy-1-piperidyl group or a 4-morpholinyl group, and
B represents an alkylene group having 2 or 3 carbon atoms or a group of formula —CH₂CH(OR⁶)CH₂—, where R⁶ represents a hydrogen atom, an acetyl group, a succinyl group or a glutaryl group, or a group of formula —D—R$^7$, where D represents a carbon-carbon single bond or an alkylene group having 1 or 2 carbon atoms and R$^7$ represents a heterocyclic group bonded to D via a carbon atom in the heterocyclic group, said heterocyclic group being selected from the group consisting of pyrrolidinyl groups, 1-methylpyrrolidinyl groups, 4-hydroxy-1-methylpyrrolidinyl groups, 4-ethoxycarbonyloxy-1-methylpyrrolidinyl groups, 4-isopropoxycarbonyloxy-1-methylpyrrolidinyl groups, 4-t-butoxycarbonyloxy-1-methylpyrrolidinyl groups, 4-palmitoyloxy-1-methylpyrrolidinyl groups, 4-stearoyloxy-1-methylpyrrolidinyl groups, piperidyl groups, 1-methylpiperidyl groups, morpholinyl groups and thiomorpholinyl groups;

A represents an ethylene group or a tetramethylene group; and pharmaceutically acceptable salts and esters thereof.

The most preferred class of compounds of the present invention for the treatment of circulatory diseases comprises those compounds of formula (I) in which:

R$^1$ represents a phenyl group which is unsubstituted or is substituted by at least one substituent selected from the group consisting of methyl groups, hydroxy groups, methoxy groups, ethoxy groups, difluoromethoxy groups, fluorine atoms, chlorine atoms, bromine atoms and cyano groups;

R$^2$ represents a hydrogen atom;

the group represented by —OR$^3$ is present at the 2-position of the benzene ring (relative to the position of attachment of the group represented by A taken to be the 1-position);

R$^3$ represents a group of formula —D—R$^7$, where D represents a carbon-carbon single bond or an alkylene group having 1 or 2 carbon atoms and R$^7$ represents a heterocyclic group bonded to D via a carbon atom in the heterocyclic group, said heterocyclic group being selected from the group consisting of pyrrolidinyl groups, 1-methylpyrrolidinyl groups, 4-hydroxy-1-methylpyrrolidinyl groups, piperidyl groups, 1-methylpiperidyl groups, morpholinyl groups and thiomorpholinyl groups;

A represents an ethylene group; and pharmaceutically acceptable salts and esters thereof.

A more preferred class of compounds of the present invention for the treatment of psychosis comprises those compounds of formula (I) in which:

R$^1$ represents a phenyl group which is unsubstituted or is substituted by at least one substituent selected from the group consisting of methyl groups, ethyl groups, hydroxy groups, methoxy groups, ethoxy groups, fluoromethoxy groups, difluoromethoxy groups, 2-fluoroethoxy groups, fluorine atoms, chlorine atoms, bromine atoms and cyano groups;

R$^2$ represents a hydrogen atom;

the group represented by —OR$^3$ is present at the 2-position of the benzene ring (relative to the position of attachment of the group represented by A taken to be the 1-position);

R$^3$ represents
a group of formula —B—NR$^4$R$^5$,
where R$^4$ and R$^5$ are independently selected from the group consisting of hydrogen atoms, alkyl groups having from 1 to 4 carbon atoms, benzyl groups, phenethyl groups, 2-hydroxyethyl groups, 3-hydroxypropyl groups, 2-(N,N-dimethylamino)ethyl groups and 3-(N,N-dimethylamino)propyl groups, or R$^4$ and R$^5$, together with the nitrogen atom to which they are attached, represent a 1-pyrrolidinyl group, a 1-piperidyl group, a 4-hydroxy-1-piperidyl group, a 4-morpholinyl group, a 4-methyl-1-piperazinyl group, a 4-ethyl-1-piperazinyl group, a 4-phenyl-1-piperazinyl group, a 1-imidazolyl group or a 1-triazolyl group, and B represents an alkylene group having 2 or 3 carbon atoms or a group of formula —CH$_2$CH(OR$^6$)CH$_2$—, where R$^6$ represents a hydrogen atom, an alkanoyl group having 2 or 3 carbon atoms, or a substituted alkanoyl group having 3 or 4 carbon atoms and substituted by a carboxy group, or a group of formula —D—R$^7$ where D represents a carbon-carbon single bond or an alkylene group having 1 or 2 carbon atoms and R$^7$ represents a heterocyclic group bonded to D via a carbon atom in the heterocyclic group, said heterocyclic group being selected from the group consisting of pyrrolidinyl groups, piperidyl groups, morpholinyl groups and thiomorpholinyl groups which are unsubstituted or are substituted on at least one of a carbon atom and a nitrogen atom by at least one substituent selected from the group consisting of in the case of substituents on a carbon atom, alkyl groups having from 1 to 4 carbon atoms, hydroxy groups, alkoxy groups having from 1 to 4 carbon atoms, alkoxycarbonyloxy groups having from 2 to 5 carbon atoms, alkanoyloxy groups having 2 or 3 carbon atoms, alkanoyloxy groups having from 12 to 20 carbon atoms, carboxy-substituted alkanoyloxy groups having 3 or 4 carbon atoms in the alkanoyl part, carbamoyloxy groups, and mono- and di- alkylcarbamoyloxy groups in which the or each alkyl part is a methyl or ethyl group, in the case of substituents on a nitrogen atom, alkyl groups having from 1 to 4 carbon atoms;

A represents an alkylene group having from 2 to 7 carbon atoms;

and pharmaceutically acceptable salts and esters thereof.

A still more preferred class of compounds of the present invention for the treatment of psychosis comprises those compounds of formula (I) in which:

R$^1$ represents a phenyl group which is unsubstituted or is substituted by at least one substituent selected from the group consisting of methyl groups, ethyl groups, hydroxy groups, methoxy groups, ethoxy groups, fluoromethoxy groups, difluoromethoxy groups, fluorine atoms, chlorine atoms, bromine atoms and cyano groups;

R$^2$ represents a hydrogen atom;

the group represented by —OR$^3$ is present at the 2position of the benzene ring (relative to the position of attachment of the group represented by A taken to be the 1-position);

R$^3$ represents
a group of formula —B—NR$^4$R$^5$,
where R$^4$ and R$^5$ are independently selected from the group consisting of hydrogen atoms, methyl groups, ethyl groups, benzyl groups and 2-hydroxyethyl groups, or R$^4$ and R$^5$, together with the nitrogen atom to which they are attached, represent a 1-pyrrolidinyl group, a 1-piperidyl group, a 4-hydroxy-1-piperidyl group, a 4-morpholinyl group, a 4-methyl-1-piperazinyl group, a 4-phenyl-1-piperazinyl group or a 1-imidazolyl group, and B represents an alkylene group having 2 or 3 carbon atoms or a group of formula —CH$_2$CH(OR$^6$)CH$_2$—, where R$^6$ represents a hydrogen atom, an acetyl group, a succinyl group or a glutaryl group, or a group of formula —D—R$^7$ where D represents a carbon-carbon single bond or an alkylene group having 1 or 2 carbon atoms and R$^7$ represents a heterocyclic group bonded to D via a carbon atom in the heterocyclic group, said heterocyclic group being selected from the group consisting of pyrrolidinyl groups, piperidyl groups, morpholinyl groups and thiomorpholinyl groups which are unsubstituted or are substituted on at least one of a carbon atom and a nitrogen atom by at least one substituent selected from the group consisting of in the case of substituents on a carbon atom, methyl groups, ethyl groups, hydroxy groups, methoxy groups, ethoxy groups, ethoxycarbonyloxy groups, isopropoxycarbonyloxy groups, t-butoxycarbonyloxy groups, alkanoyloxy groups having 2 or 3 carbon atoms, alkanoyloxy groups having from 14 to 20 carbon atoms, carboxy-substituted alkanoyloxy groups having 3 or 4 carbon atoms in the alkanoyl part, carbamoyloxy groups, and mono- and di- alkylcarbamoyloxy groups in which the or each alkyl part is a methyl or ethyl group, in the case of substituents on a nitrogen atom, methyl groups and ethyl groups;

A represents an alkylene group having from 2 to 5 carbon atoms;

and pharmaceutically acceptable salts and esters thereof.

A yet more preferred class of compounds of the present invention for the treatment of psychosis comprises those compounds of formula (I) in which:

R$^1$ represents a phenyl group which is unsubstituted or is substituted by at least one substituent selected from the group consisting of methyl groups, ethyl groups, hydroxy groups, methoxy groups, ethoxy groups, difluoromethoxy groups, fluorine atoms, chlorine atoms, bromine atoms and cyano groups;

R$^2$ represents a hydrogen atom;

the group represented by —OR$^3$ is present at the 2-position of the benzene ring (relative to the position of attachment of the group represented by A taken to be the 1-position);

R$^3$ represents a group of formula —B—NR$^4$R$^5$, where R$^4$ and R$^5$ are independently selected from the group consisting of hydrogen atoms, methyl groups, ethyl groups and 2-hydroxyethyl groups, or R$^4$ and R$^5$, together with the nitrogen atom to which they are attached, represent a 1-pyrrolidinyl group, a 1-piperidyl group, a 4-hydroxy-1-piperidyl group or a 4-morpholinyl group, and B represents an alkylene group having 2 or 3 carbon atoms or a group of formula —CH$_2$CH(OR$^6$)CH$_2$—, where R$^6$ represents a hydrogen atom, an acetyl group, a succinyl group or a glutaryl group, or a group of formula —D—R, where D represents a carbon-carbon single bond or an alkylene group having 1 or 2 carbon atoms and R$^7$ represents a heterocyclic group bonded to D via a carbon atom in the heterocyclic group, said heterocyclic group being selected from the group consisting of pyrrolidinyl groups, 1-methylpyrrolidinyl groups, 4-hydroxy-1-methylpyrrolidinyl groups, piperidyl groups, 1-methylpiperidyl groups, morpholinyl groups and 4-methylmorpholinyl groups;

A represents an alkylene group having from 2 to 5 carbon atoms;

and pharmaceutically acceptable salts and esters thereof.

The most preferred class of compounds of the present invention for the treatment of psychosis comprises those compounds of formula (I) in which:

R$^1$ represents a phenyl group which is unsubstituted or is substituted by at least one substituent selected from the group consisting of methyl groups, hydroxy groups, methoxy groups, ethoxy groups, difluoromethoxy groups, fluorine atoms, chlorine atoms, bromine atoms and cyano groups;

R$^2$ represents a hydrogen atom;

the group represented by —OR$^3$ is present at the 2-position of the benzene ring (relative to the position of attachment of the group represented by A taken to be the 1-position);

R$^3$ represents a group of formula —D—R$^7$, where D represents a carbon-carbon single bond or an alkylene group having 1 or 2 carbon atoms and R$^7$ represents a heterocyclic group bonded to D via a carbon atom in the heterocyclic group, said heterocyclic group being selected from the group consisting of pyrrolidinyl groups, 1-methylpyrrolidinyl groups, 4-hydroxy-1-methylpyrrolidinyl groups, piperidyl groups, 1-methylpiperidyl groups, morpholinyl groups and 4-methylmorpholinyl groups;

A represents a tetramethylene group or a pentamethylene group;

and pharmaceutically acceptable salts and esters thereof.

Specific examples of individual compounds of the present invention are given by the following formulae (I-1) to (I-3), in which the various symbols used are as defined in the corresponding one of Tables 1 to 3, that is Table 1 relates to formula (I-1), Table 2 relates to formula (I-2) and Table 3 relates to formula (I-3). In the Tables, the following abbreviations are used for certain groups:

| | |
|---|---|
| Ac | acetyl |
| Et | ethyl |
| Glu | glutaryl |
| Imi | imidazolyl |
| Me | methyl |
| Mor | morpholinyl |
| Np | naphthyl |
| Pal | palmitoyl |
| Ph | phenyl |
| Pip | piperidyl |
| Piz | piperazinyl |
| Pr | propyl |
| iPr | isopropyl |
| Pyrd | pyrrolidinyl |
| Ste | stearoyl |
| Suc | succinyl |
| Tmor | thiomorpholinyl |

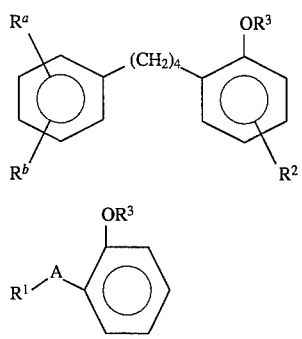

(I-1)

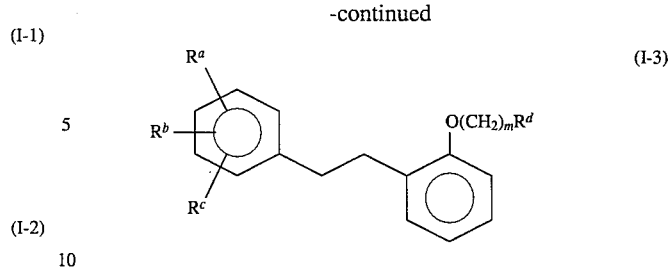

(I-3)

(I-2)

TABLE 1

| Cpd. No. | $R^a$ | $R^b$ | $R^2$ | $R^3$ |
|---|---|---|---|---|
| 1-1 | H | H | H | $CH_2CH(OH)CH_2NMe_2$ |
| 1-2 | H | H | H | $CH_2CH_2NMe_2$ |
| 1-3 | H | H | H | $CH_2CH_2CH_2NMe_2$ |
| 1-4 | H | H | H | $CH_2CH(OH)CH_2NEt_2$ |
| 1-5 | H | H | H | $CH_2CH_2NEt_2$ |
| 1-6 | H | H | H | $CH_2CH_2CH_2NEt_2$ |
| 1-7 | H | H | H | $CH_2CH(OH)CH_2N(CH_2CH_2OH)_2$ |
| 1-8 | H | H | H | $CH_2CH(OH)CH_2NHPh$ |
| 1-9 | H | H | H | $CH_2CH(OH)CH_2(1\text{-Pyrd})$ |
| 1-10 | H | H | H | $CH_2CH(OH)CH_2\text{-}1\text{-Pip}$ |
| 1-11 | H | H | H | $CH_2CH(OH)CH_2(4\text{-OH-}1\text{-Pip})$ |
| 1-12 | H | H | H | $CH_2CH(OH)CH_2\text{-}4\text{-Mor}$ |
| 1-13 | H | H | H | $CH_2CH(OH)CH_2(4\text{-Me-}1\text{-Piz})$ |
| 1-14 | H | H | H | $CH_2CH(OH)CH_2(4\text{-Ph-}1\text{-Piz})$ |
| 1-15 | H | H | H | $CH_2CH(OH)CH_2N(Me)(CH_2CH_2NMe_2)$ |
| 1-16 | H | H | H | $CH_2(2\text{-Mor})$ |
| 1-17 | H | H | H | $CH_2(4\text{-Me-}2\text{-Mor})$ |
| 1-18 | H | H | H | $CH_2CH_2(1\text{-Me-}2\text{-Pyrd})$ |
| 1-19 | H | H | H | $CH_2CH_2(2\text{-Pip})$ |
| 1-20 | H | H | H | $CH_2CH_2(1\text{-Me-}2\text{-Pip})$ |
| 1-21 | H | H | H | $CH_2(1\text{-Me-}3\text{-Pip})$ |
| 1-22 | H | H | H | $1\text{-Me-}4\text{-Pip}$ |
| 1-23 | H | H | H | $CH_2CH_2(1\text{-Me-}4\text{-Pip})$ |
| 1-24 | H | H | H | $CH_2(1\text{-Me-}2\text{-Pyrd})$ |
| 1-25 | H | H | H | $CH_2(1\text{-Me-}4\text{-OH-}2\text{-Pyrd})$ |
| 1-26 | H | H | H | $CH_2CH_2(4\text{-Tmor})$ |
| 1-27 | H | H | H | $CH_2(3\text{-Pip})$ |
| 1-28 | H | H | H | $3\text{-Pip}$ |
| 1-29 | H | H | H | $1\text{-Me-}3\text{-Pip}$ |
| 1-30 | 3-OMe | H | H | $CH_2CH(OH)CH_2NMe_2$ |
| 1-31 | 3-OMe | H | H | $CH_2CH_2NMe_2$ |
| 1-32 | 3-OMe | H | H | $CH_2CH_2CH_2NMe_2$ |
| 1-33 | 3-OMe | H | H | $CH_2CH(OH)CH_2(1\text{-Pip})$ |
| 1-34 | 3-OMe | H | H | $CH_2CH(OH)CH_2(4\text{-Mor})$ |
| 1-35 | 3-OMe | H | H | $CH_2CH(OH)CH_2(4\text{-Ph-}1\text{-Piz})$ |
| 1-36 | 3-OMe | H | H | $CH_2(2\text{-Mor})$ |
| 1-37 | 3-OMe | H | H | $CH_2(4\text{-Me-}2\text{-Mor})$ |
| 1-38 | 3-OMe | H | H | $CH_2CH_2(1\text{-Me-}2\text{-Pyrd})$ |
| 1-39 | 3-OMe | H | H | $CH_2CH(OH)CH_2(1\text{-Pyrd})$ |
| 1-40 | 3-OMe | H | H | $CH_2CH_2(2\text{-Pip})$ |
| 1-41 | 3-OMe | H | H | $CH_2CH_2(1\text{-Me-}2\text{-Pip})$ |
| 1-42 | 3-OMe | H | H | $1\text{-Me-}4\text{-Pip}$ |
| 1-43 | 3-OMe | H | H | $CH_2(1\text{-Me-}3\text{-Pip})$ |
| 1-44 | 3-OMe | H | H | $1\text{-Me-}3\text{-Pip}$ |
| 1-45 | 3-OMe | H | H | $CH_2(1\text{-Me-}4\text{-OH-}2\text{-Pyrd})$ |
| 1-46 | 3-OEt | H | H | $CH_2CH(OH)CH_2NMe_2$ |
| 1-47 | 3-OEt | H | H | $CH_2CH_2CH_2NMe_2$ |
| 1-48 | 3-OEt | H | H | $CH_2(4\text{-Me-}2\text{-Mor})$ |
| 1-49 | 3-OEt | H | H | $CH_2CH_2(1\text{-Me-}2\text{-Pyrd})$ |
| 1-50 | 3-OEt | H | H | $CH_2CH_2(1\text{-Me-}2\text{-Pip})$ |
| 1-51 | 3-Me | H | H | $CH_2CH(OH)CH_2NMe_2$ |
| 1-52 | 3-Me | H | H | $CH_2CH_2CH_2NMe_2$ |
| 1-53 | 3-Me | H | H | $CH_2CH(OH)CH_2(1\text{-Pip})$ |
| 1-54 | 3-Me | H | H | $CH_2CH(OH)CH_2(1\text{-Pyrd})$ |
| 1-55 | 3-Me | H | H | $CH_2CH(OH)CH_2(4\text{-Mor})$ |
| 1-56 | 3-Me | H | H | $CH_2(4\text{-Me-}2\text{-Mor})$ |
| 1-57 | 3-Me | H | H | $CH_2CH_2(1\text{-Me-}2\text{-Pyrd})$ |
| 1-58 | 3-Me | H | H | $CH_2CH_2(1\text{-Me-}2\text{-Pip})$ |

TABLE 1-continued

| Cpd. No. | $R^a$ | $R^b$ | $R^2$ | $R^3$ |
|---|---|---|---|---|
| 1-59 | 3-F | H | H | $CH_2CH(OH)CH_2NMe_2$ |
| 1-60 | 3-F | H | H | $CH_2$(4-Me-2-Mor) |
| 1-61 | 3-F | H | H | $CH_2CH_2$(1-Me-2-Pyrd) |
| 1-62 | 3-Cl | H | H | $CH_2CH_2(OH)CH_2NMe_2$ |
| 1-63 | 3-Cl | H | H | $CH_2CH_2NMe_2$ |
| 1-64 | 3-Cl | H | H | $CH_2CH_2CH_2NMe_2$ |
| 1-65 | 3-Cl | H | H | $CH_2CH(OH)CH_2N(CH_2CH_2OH)_2$ |
| 1-66 | 3-Cl | H | H | $CH_2CH(OH)CH_2$(1-Pyrd) |
| 1-67 | 3-Cl | H | H | $CH_2$(4-Me-2-Mor) |
| 1-68 | 3-Cl | H | H | $CH_2CH_2$(1-Me-2-Pyrd) |
| 1-69 | 3-Cl | H | H | $CH_2$(1-Me-3-Pip) |
| 1-70 | 3-OH | H | H | $CH_2CH(OH)CH_2NMe_2$ |
| 1-71 | 3-OH | H | H | $CH_2CH_2CH_2NMe_2$ |
| 1-72 | 3-OH | H | H | $CH_2CH(OH)CH_2$(1-Pip) |
| 1-73 | 3-OH | H | H | $CH_2$(4-Me-2-Mor) |
| 1-74 | 3-OH | H | H | $CH_2CH_2$(1-Me-2-Pyrd) |
| 1-75 | 3-OH | H | H | $CH_2CH_2$(1-Me-2-Pip) |
| 1-76 | 2-CN | H | H | $CH_2CH(OH)CH_2NMe_2$ |
| 1-77 | 2-$CONH_2$ | H | H | $CH_2CH(OH)CH_2NMe_2$ |
| 1-78 | 2-OMe | H | H | $CH_2CH(OH)CH_2NMe_2$ |
| 1-79 | 2-OMe | H | H | $CH_2CH_2CH_2NMe_2$ |
| 1-80 | 2-OMe | H | H | $CH_2$(4-Me-2-Mor) |
| 1-81 | 2-OMe | H | H | $CH_2CH_2$(1-Me-2-Pyrd) |
| 1-82 | 2-OMe | H | H | $CH_2CH_2$(1-Me-2-Pip) |
| 1-83 | 4-OMe | H | H | $CH_2CH(OH)CH_2NMe_2$ |
| 1-84 | 4-OMe | H | H | $CH_2$(4-Me-2-Mor) |
| 1-85 | 4-OMe | H | H | $CH_2CH_2$(1-Me-2-Pyrd) |
| 1-86 | 2-Me | H | H | $CH_2CH(OH)CH_2NMe_2$ |
| 1-87 | 4-Me | H | H | $CH_2CH(OH)CH_2NMe_2$ |
| 1-88 | 4-Me | H | H | $CH_2$(1-Me-2-Pyrd) |
| 1-89 | 4-iPr | H | H | $CH_2CH(OH)CH_2NMe_2$ |
| 1-90 | 3-OMe | 4-OMe | H | $CH_2CH(OH)CH_2NMe_2$ |
| 1-91 | 3-OMe | 4-OMe | H | $CH_2$(4-Me-2-Mor) |
| 1-92 | 3-OMe | 4-OMe | H | $CH_2CH_2$(1-Me-2-Pyrd) |
| 1-93 | 3-OMe | 5-OMe | H | $CH_2CH(OH)CH_2NMe_2$ |
| 1-94 | 3-OMe | 5-OMe | H | $CH_2CH(OH)CH_2$(4-Mor) |
| 1-95 | 3-OMe | 5-OMe | H | $CH_2$(4-Me-2-Mor) |
| 1-96 | 2-Cl | H | H | $CH_2CH(OH)CH_2NMe_2$ |
| 1-97 | H | H | H | $CH_2$(4-OH-2-Pyrd) |
| 1-98 | H | H | H | $CH_2CH_2$(4-Mor) |
| 1-99 | 3-OMe | 5-OMe | H | $CH_2CH(OH)CH_2N(CH_2CH_2OH)_2$ |
| 1-100 | 3-OMe | 5-OMe | H | $CH_2CH(OH)CH_2$(4-OH-1-Pip) |
| 1-101 | H | H | H | $CH_2CH(OH)CH_2$(1-Imi) |
| 1-102 | 2-OH | H | H | $CH_2CH(OH)CH_2NMe_2$ |
| 1-103 | 2-Cl | H | H | $CH_2CH(OH)CH_2NEt_2$ |
| 1-104 | 4-OMe | H | H | $CH_2CH(OH)CH_2$(4-Ph-1-Piz) |
| 1-105 | H | H | H | $CH_2CH(OCOCH_2CH_2CO_2H)CH_2NMe_2$ |
| 1-106 | 3-OMe | H | H | $CH_2CH(OCOCH_2CH_2CO_2H)CH_2NMe_2$ |
| 1-107 | H | H | H | $CH_2$(1-Me-4-$OCOCH_2CH_2CO_2H$-2-Pyrd) |
| 1-108 | 3-OMe | H | H | $CH_2$(1-Me-4-$OCOCH_2CH_2CO_2H$-2-Pyrd) |
| 1-109 | 3-OMe | 5-OMe | H | $CH_2CH(OCOCH_2CH_2CO_2H)CH_2NMe_2$ |
| 1-110 | 3-OMe | 5-OMe | H | $(CH_2)_2NMe_2$ |
| 1-111 | 3-OMe | 5-OMe | H | $(CH_2)_3NMe_2$ |
| 1-112 | 3-OMe | 5-OMe | H | $CH_2CH(OH)CH_2$(1-Pip) |
| 1-113 | 3-OMe | 5-OMe | H | $CH_2CH(OH)CH_2$(4-Me-1-Piz) |
| 1-114 | 3-OMe | 5-OMe | H | $CH_2CH(OH)CH_2$(4-Ph-1-Piz) |
| 1-115 | 3-OMe | 5-OMe | H | $CH_2$(2-Mor) |
| 1-116 | 3-OMe | 5-OMe | H | $CH_2CH_2$(1-Me-4-OH-2-Pyrd) |
| 1-117 | 3-OMe | 5-OMe | H | $(CH_2)_2$(1-Me-2-Pyrd) |
| 1-118 | 3-OMe | 5-OMe | H | $CH_2CH(OH)CH_2$(1-Pyrd) |
| 1-119 | 3-OMe | 5-OMe | H | $(CH_2)_2$(2-Pip) |
| 1-120 | 3-OMe | 5-OMe | H | $CH_2$(1-Me-2-Pip) |
| 1-121 | 3-OMe | 5-OMe | H | 1-Me-3-Pip |
| 1-122 | 3-OMe | 5-OMe | H | $CH_2$(1-Me-3-Pip) |
| 1-123 | 3-OMe | 5-OMe | H | $CH_2CH_2$[1-Me-4-($OCOCH_2CH_2CO_2H$)-2-Pyrd] |
| 1-124 | 3-OMe | 5-OMe | H | $CH_2$(1-Me-4-OH-2-Pyrd) |
| 1-125 | 3-OMe | 5-OMe | H | $CH_2$(3-Pip) |
| 1-126 | 3-OMe | H | H | $CH_2$(3-Pip) |
| 1-127 | H | H | H | $CH_2$(1-Et-3-Pip) |
| 1-128 | H | H | H | $CH_2CH_2$(2-Pyrd) |
| 1-129 | H | H | H | $CH_2CH_2$(1-Et-2-Pyrd) |
| 1-130 | H | H | H | $CH_2CH_2$(1-Me-4-OH-2-Pyrd) |
| 1-131 | H | H | H | $CH_2CH_2$[1-Me-4-($OCOCH_2CH_2CO_2H$)-2-Pyrd] |
| 1-132 | H | H | H | $CH_2CH_2$(1-Et-2-Pip) |
| 1-133 | 3-OMe | H | H | $CH_2$(1-Et-3-Pip) |
| 1-134 | 3-OMe | H | H | $CH_2CH_2$(2-Pyrd) |

TABLE 1-continued

| Cpd. No. | R$^a$ | R$^b$ | R$^2$ | R$^3$ |
|---|---|---|---|---|
| 1-135 | 3-OMe | H | H | CH$_2$CH$_2$(1-Et-2-Pyrd) |
| 1-136 | 3-OMe | H | 4-Me | CH$_2$CH$_2$(1-Me-2-Pip) |
| 1-137 | 3-OMe | H | H | CH$_2$CH$_2$(1-Et-2-Pip) |
| 1-138 | 2-OMe | H | H | CH$_2$(3-Pip) |
| 1-139 | 2-OMe | H | H | CH$_2$(1-Me-3-Pip) |
| 1-140 | 2-OMe | H | H | CH$_2$(1-Et-3-Pip) |
| 1-141 | 2-OMe | H | H | CH$_2$(2-Mor) |
| 1-142 | 2-OMe | H | H | CH$_2$CH$_2$(2-Pyrd) |
| 1-143 | 2-OMe | H | H | CH$_2$CH$_2$(1-Et-2-Pyrd) |
| 1-144 | 4-OMe | H | H | CH$_2$(3-Pip) |
| 1-145 | 4-OMe | H | H | CH$_2$(1-Me-3-Pip) |
| 1-146 | 4-OMe | H | H | CH$_2$(1-Et-3-Pip) |
| 1-147 | 4-OMe | H | H | CH$_2$(2-Mor) |
| 1-148 | 4-OMe | H | H | CH$_2$CH$_2$(2-Pyrd) |
| 1-149 | 4-OMe | H | H | CH$_2$CH$_2$(1-Et-2-Pyrd) |
| 1-150 | 3-OEt | H | H | CH$_2$(3-Pip) |
| 1-151 | 3-OEt | H | H | CH$_2$(1-Me-3-Pip) |
| 1-152 | 3-OEt | H | H | CH$_2$(1-Et-3-Pip) |
| 1-153 | 3-OEt | H | H | CH$_2$(2-Mor) |
| 1-154 | 3-OEt | H | H | CH$_2$CH$_2$(2-Pyrd) |
| 1-155 | 3-OEt | H | H | CH$_2$CH$_2$(1-Et-2-Pyrd) |
| 1-156 | 2-OEt | H | H | CH$_2$(3-Pip) |
| 1-157 | 2-OEt | H | H | CH$_2$(1-Me-3-Pip) |
| 1-158 | 2-OEt | H | H | CH$_2$(2-Mor) |
| 1-159 | 2-OEt | H | H | CH$_2$(4-Me-2-Mor) |
| 1-160 | 2-OEt | H | H | CH$_2$CH$_2$(2-Pyrd) |
| 1-161 | 2-OEt | H | H | CH$_2$CH$_2$(1-Me-2-Pyrd) |
| 1-162 | 4-OEt | H | H | CH$_2$(3-Pip) |
| 1-163 | 4-OEt | H | H | CH$_2$(1-Me-3-Pip) |
| 1-164 | 4-OEt | H | H | CH$_2$(2-Mor) |
| 1-165 | 4-OEt | H | H | CH$_2$(4-Me-2-Mor) |
| 1-166 | 4-OEt | H | H | CH$_2$CH$_2$(2-Pyrd) |
| 1-167 | 4-OEt | H | H | CH$_2$CH$_2$(1-Me-2-Pyrd) |
| 1-168 | 3-Me | H | H | CH$_2$(3-Pip) |
| 1-169 | 3-Me | H | H | CH$_2$(1-Me-3-Pip) |
| 1-170 | 3-Me | H | H | CH$_2$(1-Et-3-Pip) |
| 1-171 | 3-Me | H | H | CH$_2$(2-Mor) |
| 1-172 | 3-Me | H | H | CH$_2$CH$_2$(2-Pyrd) |
| 1-173 | 3-Me | H | H | CH$_2$CH$_2$(1-Et-2-Pyrd) |
| 1-174 | 2-Me | H | H | CH$_2$(3-Pip) |
| 1-175 | 2-Me | H | H | CH$_2$(1-Me-3-Pip) |
| 1-176 | 2-Me | H | H | CH$_2$(2-Mor) |
| 1-177 | 2-Me | H | H | CH$_2$(4-Et-2-Mor) |
| 1-178 | 2-Me | H | H | CH$_2$CH$_2$(2-Pyrd) |
| 1-179 | 2-Me | H | H | CH$_2$CH$_2$(1-Me-2-Pyrd) |
| 1-180 | 4-Me | H | H | CH$_2$(3-Pip) |
| 1-181 | 4-Me | H | H | CH$_2$(1-Me-3-Pip) |
| 1-182 | 4-Me | H | H | CH$_2$(2-Mor) |
| 1-183 | 4-Me | H | H | CH$_2$(4-Et-2-Mor) |
| 1-184 | 4-Me | H | H | CH$_2$CH$_2$(2-Pyrd) |
| 1-185 | 4-Me | H | H | CH$_2$CH$_2$(1-Me-2-Pyrd) |
| 1-186 | 3-F | H | H | CH$_2$(3-Pip) |
| 1-187 | 3-F | H | H | CH$_2$(1-Me-3-Pip) |
| 1-188 | 3-F | H | H | CH$_2$(1-Et-3-Pip) |
| 1-189 | 3-F | H | H | CH$_2$(2-Mor) |
| 1-190 | 3-F | H | H | CH$_2$CH$_2$(2-Pyrd) |
| 1-191 | 3-F | H | H | CH$_2$CH$_2$(1-Et-2-Pyrd) |
| 1-192 | 2-F | H | H | CH$_2$(3-Pip) |
| 1-193 | 2-F | H | H | CH$_2$(1-Me-3-Pip) |
| 1-194 | 2-F | H | H | CH$_2$(2-Mor) |
| 1-195 | 2-F | H | H | CH$_2$(4-Me-2-Mor) |
| 1-196 | 2-F | H | H | CH$_2$CH$_2$(2-Pyrd) |
| 1-197 | 2-F | H | H | CH$_2$CH$_2$(1-Me-2-Pyrd) |
| 1-198 | 4-F | H | H | CH$_2$(3-Pip) |
| 1-199 | 4-F | H | H | CH$_2$(1-Me-3-Pip) |
| 1-200 | 4-F | H | H | CH$_2$(2-Mor) |
| 1-201 | 4-F | H | H | CH$_2$(4-Me-2-Mor) |
| 1-202 | 4-F | H | H | CH$_2$CH$_2$(2-Pyrd) |
| 1-203 | 4-F | H | H | CH$_2$CH$_2$(1-Me-2-Pyrd) |
| 1-204 | 3-Cl | H | H | CH$_2$(3-Pip) |
| 1-205 | 3-Cl | H | H | CH$_2$(1-Et-3-Pip) |
| 1-206 | 3-Cl | H | H | CH$_2$(2-Mor) |
| 1-207 | 3-Cl | H | H | CH$_2$CH$_2$(2-Pyrd) |
| 1-208 | 3-Cl | H | H | CH$_2$CH$_2$(1-Et-2-Pyrd) |
| 1-209 | 2-Cl | H | H | CH$_2$(3-Pip) |
| 1-210 | 2-Cl | H | H | CH$_2$(1-Me-3-Pip) |

TABLE 1-continued

| Cpd. No. | $R^a$ | $R^b$ | $R^2$ | $R^3$ |
|---|---|---|---|---|
| 1-211 | 2-Cl | H | H | $CH_2$(2-Mor) |
| 1-212 | 2-Cl | H | H | $CH_2$(4-Me-2-Mor) |
| 1-213 | 2-Cl | H | H | $CH_2CH_2$(2-Pyrd) |
| 1-214 | 2-Cl | H | H | $CH_2CH_2$(1-Me-2-Pyrd) |
| 1-215 | 4-Cl | H | H | $CH_2$(3-Pip) |
| 1-216 | 4-Cl | H | H | $CH_2$(1-Me-3-Pip) |
| 1-217 | 4-Cl | H | H | $CH_2$(2-Mor) |
| 1-218 | 4-Cl | H | H | $CH_2$(4-Me-2-Mor) |
| 1-219 | 4-Cl | H | H | $CH_2CH_2$(2-Pyrd) |
| 1-220 | 4-Cl | H | H | $CH_2CH_2$(1-Me-2-Pyrd) |
| 1-221 | 3-OH | H | H | $CH_2$(3-Pip) |
| 1-222 | 3-OH | H | H | $CH_2$(1-Me-3-Pip) |
| 1-223 | 3-OH | H | H | $CH_2$(1-Et-3-Pip) |
| 1-224 | 3-OH | H | H | $CH_2$(2-Mor) |
| 1-225 | 3-OH | H | H | $CH_2CH_2$(2-Pyrd) |
| 1-226 | 3-OH | H | H | $CH_2CH_2$(1-Et-2-Pyrd) |
| 1-227 | 2-OH | H | H | $CH_2$(3-Pip) |
| 1-228 | 2-OH | H | H | $CH_2$(1-Me-3-Pip) |
| 1-229 | 2-OH | H | H | $CH_2$(2-Mor) |
| 1-230 | 2-OH | H | H | $CH_2$(4-Me-2-Mor) |
| 1-231 | 2-OH | H | H | $CH_2CH_2$(2-Pyrd) |
| 1-232 | 2-OH | H | H | $CH_2CH_2$(1-Me-2-Pyrd) |
| 1-233 | 4-OH | H | H | $CH_2$(3-Pip) |
| 1-234 | 4-OH | H | H | $CH_2$(1-Me-3-Pip) |
| 1-235 | 4-OH | H | H | $CH_2$(2-Mor) |
| 1-236 | 4-OH | H | H | $CH_2$(4-Me-2-Mor) |
| 1-237 | 4-OH | H | H | $CH_2CH_2$(2-Pyrd) |
| 1-238 | 4-OH | H | H | $CH_2CH_2$(1-Me-2-Pyrd) |
| 1-239 | 3-CN | H | H | $CH_2$(3-Pip) |
| 1-240 | 3-CN | H | H | $CH_2$(1-Me-3-Pip) |
| 1-241 | 3-CN | H | H | $CH_2$(1-Et-3-Pip) |
| 1-242 | 3-CN | H | H | $CH_2$(2-Mor) |
| 1-243 | 3-CN | H | H | $CH_2$(4-Me-2-Mor) |
| 1-244 | 3-CN | H | H | $CH_2CH_2$(2-Pyrd) |
| 1-245 | 3-CN | H | H | $CH_2CH_2$(1-Me-2-Pyrd) |
| 1-246 | 3-CN | H | H | $CH_2CH_2$(1-Et-2-Pyrd) |
| 1-247 | 2-CN | H | H | $CH_2$(3-Pip) |
| 1-248 | 2-CN | H | H | $CH_2$(1-Me-3-Pip) |
| 1-249 | 2-CN | H | H | $CH_2$(1-Et-3-Pip) |
| 1-250 | 2-CN | H | H | $CH_2$(2-Mor) |
| 1-251 | 2-CN | H | H | $CH_2$(4-Me-2-Mor) |
| 1-252 | 2-CN | H | H | $CH_2CH_2$(2-Pyrd) |
| 1-253 | 2-CN | H | H | $CH_2CH_2$(1-Me-2-Pyrd) |
| 1-254 | 2-CN | H | H | $CH_2CH_2$(1-Et-2-Pyrd) |
| 1-255 | 4-CN | H | H | $CH_2$(3-Pip) |
| 1-256 | 4-CN | H | H | $CH_2$(1-Me-3-Pip) |
| 1-257 | 4-CN | H | H | $CH_2$(1-Et-3-Pip) |
| 1-258 | 4-CN | H | H | $CH_2$(2-Mor) |
| 1-259 | 4-CN | H | H | $CH_2$(4-Me-2-Mor) |
| 1-260 | 4-CN | H | H | $CH_2CH_2$(2-Pyrd) |
| 1-261 | 4-CN | H | H | $CH_2CH_2$(1-Me-2-Pyrd) |
| 1-262 | 4-CN | H | H | $CH_2CH_2$(1-Et-2-Pyrd) |
| 1-263 | 3-$OCHF_2$ | H | H | $CH_2$(3-Pip) |
| 1-264 | 3-$OCHF_2$ | H | H | $CH_2$(1-Me-3-Pip) |
| 1-265 | 3-$OCHF_2$ | H | H | $CH_2$(1-Et-3-Pip) |
| 1-266 | 3-$OCHF_2$ | H | H | $CH_2$(2-Mor) |
| 1-267 | 3-$OCHF_2$ | H | H | $CH_2$(4-Me-2-Mor) |
| 1-268 | 3-$OCHF_2$ | H | H | $CH_2CH_2$(2-Pyrd) |
| 1-269 | 3-$OCHF_2$ | H | H | $CH_2CH_2$(1-Me-2-Pyrd) |
| 1-270 | 3-$OCHF_2$ | H | H | $CH_2CH_2$(1-Et-2-Pyrd) |
| 1-271 | 2-$OCHF_2$ | H | H | $CH_2$(3-Pip) |
| 1-272 | 2-$OCHF_2$ | H | H | $CH_2$(1-Me-3-Pip) |
| 1-273 | 2-$OCHF_2$ | H | H | $CH_2$(1-Et-3-Pip) |
| 1-274 | 2-$OCHF_2$ | H | H | $CH_2$(2-Mor) |
| 1-275 | 2-$OCHF_2$ | H | H | $CH_2$(4-Me-2-Mor) |
| 1-276 | 2-$OCHF_2$ | H | H | $CH_2CH_2$(2-Pyrd) |
| 1-277 | 2-$OCHF_2$ | H | H | $CH_2CH_2$(1-Me-2-Pyrd) |
| 1-278 | 2-$OCHF_2$ | H | H | $CH_2CH_2$(1-Et-2-Pyrd) |
| 1-279 | 4-$OCHF_2$ | H | H | $CH_2$(3-Pip) |
| 1-280 | 4-$OCHF_2$ | H | H | $CH_2$(1-Me-3-Pip) |
| 1-281 | 4-$OCHF_2$ | H | H | $CH_2$(1-Et-3-Pip) |
| 1-282 | 4-$OCHF_2$ | H | H | $CH_2$(2-Mor) |
| 1-283 | 4-$OCHF_2$ | H | H | $CH_2$(4-Me-2-Mor) |
| 1-284 | 4-$OCHF_2$ | H | H | $CH_2CH_2$(2-Pyrd) |
| 1-285 | 4-$OCHF_2$ | H | H | $CH_2CH_2$(1-Me-2-Pyrd) |
| 1-286 | 4-$OCHF_2$ | H | H | $CH_2CH_2$(1-Et-2-Pyrd) |

TABLE 1-continued

| Cpd. No. | $R^a$ | $R^b$ | $R^2$ | $R^3$ |
|---|---|---|---|---|
| 1-287 | 3-OCH$_2$F | H | H | CH$_2$(3-Pip) |
| 1-288 | 3-OCH$_2$F | H | H | CH$_2$(1-Me-3-Pip) |
| 1-289 | 3-OCH$_2$F | H | H | CH$_2$(2-Mor) |
| 1-290 | 3-OCH$_2$F | H | H | CH$_2$(4-Me-2-Mor) |
| 1-291 | 3-OCH$_2$F | H | H | CH$_2$CH$_2$(2-Pyrd) |
| 1-292 | 3-OCH$_2$F | H | H | CH$_2$CH$_2$(1-Me-2-Pyrd) |
| 1-293 | 2-OCH$_2$F | H | H | CH$_2$(3-Pip) |
| 1-294 | 2-OCH$_2$F | H | H | CH$_2$(1-Me-3-Pip) |
| 1-295 | 2-OCH$_2$F | H | H | CH$_2$(2-Mor) |
| 1-296 | 2-OCH$_2$F | H | H | CH$_2$(4-Me-2-Mor) |
| 1-297 | 2-OCH$_2$F | H | H | CH$_2$CH$_2$(2-Pyrd) |
| 1-298 | 2-OCH$_2$F | H | H | CH$_2$CH$_2$(1-Me-2-Pyrd) |
| 1-299 | 4-OCH$_2$F | H | H | CH$_2$(3-Pip) |
| 1-300 | 4-OCH$_2$F | H | H | CH$_2$(1-Me-3-Pip) |
| 1-301 | 4-OCH$_2$F | H | H | CH$_2$(2-Mor) |
| 1-302 | 4-OCH$_2$F | H | H | CH$_2$(4-Me-2-Mor) |
| 1-303 | 4-OCH$_2$F | H | H | CH$_2$CH$_2$(2-Pyrd) |
| 1-304 | 4-OCH$_2$F | H | H | CH$_2$CH$_2$(1-Me-2-Pyrd) |
| 1-305 | 3-Br | H | H | CH$_2$(3-Pip) |
| 1-306 | 3-Br | H | H | CH$_2$(1-Me-3-Pip) |
| 1-307 | 3-Br | H | H | CH$_2$(1-Et-3-Pip) |
| 1-308 | 3-Br | H | H | CH$_2$(2-Mor) |
| 1-309 | 3-Br | H | H | CH$_2$(4-Me-2-Mor) |
| 1-310 | 3-Br | H | H | CH$_2$(4-Et-2-Mor) |
| 1-311 | 3-Br | H | H | CH$_2$CH$_2$(2-Pyrd) |
| 1-312 | 3-Br | H | H | CH$_2$CH$_2$(1-Me-2-Pyrd) |
| 1-313 | 3-Br | H | H | CH$_2$CH$_2$(1-Et-2-Pyrd) |
| 1-314 | 2-Br | H | H | CH$_2$(3-Pip) |
| 1-315 | 2-Br | H | H | CH$_2$(1-Me-3-Pip) |
| 1-316 | 2-Br | H | H | CH$_2$(2-Mor) |
| 1-317 | 2-Br | H | H | CH$_2$(4-Me-2-Mor) |
| 1-318 | 2-Br | H | H | CH$_2$CH$_2$(2-Pyrd) |
| 1-319 | 2-Br | H | H | CH$_2$CH$_2$(1-Me-2-Pyrd) |
| 1-320 | 4-Br | H | H | CH$_2$(3-Pip) |
| 1-321 | 4-Br | H | H | CH$_2$(1-Me-3-Pip) |
| 1-322 | 4-Br | H | H | CH$_2$(2-Mor) |
| 1-323 | 4-Br | H | H | CH$_2$(4-Me-2-Mor) |
| 1-324 | 4-Br | H | H | CH$_2$CH$_2$(2-Pyrd) |
| 1-325 | 4-Br | H | H | CH$_2$CH$_2$(1-Me-2-Pyrd) |
| 1-326 | 3-OMe | 5-OMe | H | CH$_2$(1-Et-3-Pip) |
| 1-327 | 3-OMe | 5-OMe | H | CH$_2$(4-Et-2-Mor) |
| 1-328 | 3-OMe | 5-OMe | H | CH$_2$CH$_2$(2-Pyrd) |
| 1-329 | 3-OMe | 5-OMe | H | CH$_2$CH$_2$(1-Et-2-Pyrd) |
| 1-330 | 3-OMe | 4-OMe | H | CH$_2$CH$_2$(2-Pyrd) |
| 1-331 | 3-OMe | 4-OMe | H | CH$_2$CH$_2$(1-Et-2-Pyrd) |

TABLE 2

| Cpd. No. | $R^1$ | A | $R^3$ |
|---|---|---|---|
| 2-1 | Ph | CH$_2$CH(Me)(CH$_2$)$_2$ | CH$_2$CH(OH)CH$_2$NMe$_2$ |
| 2-2 | Ph | CH$_2$CH(Me)(CH$_2$)$_2$ | CH$_2$(4-Me-2-Mor) |
| 2-3 | Ph | CH$_2$CH(Me)(CH$_2$)$_2$ | CH$_2$CH$_2$(1-Me-2-Pyrd) |
| 2-4 | 2-Np | (CH$_2$)$_4$ | CH$_2$CH(OH)CH$_2$NMe$_2$ |
| 2-5 | 2-Np | (CH$_2$)$_4$ | CH$_2$(4-Me-2-Mor) |
| 2-6 | 2-Np | (CH$_2$)$_4$ | CH$_2$CH$_2$(1-Me-2-Pyrd) |
| 2-7 | 1-Np | (CH$_2$)$_4$ | CH$_2$CH(OH)CH$_2$NMe$_2$ |
| 2-8 | 1-Np | (CH$_2$)$_4$ | CH$_2$(4-Me-2-Mor) |
| 2-9 | 1-Np | (CH$_2$)$_4$ | CH$_2$CH$_2$(1-Me-2-Pyrd) |
| 2-10 | Ph | CH$_2$CH(Me)(CH$_2$)$_2$ | CH$_2$CH(OCOCH$_2$CH$_2$CO$_2$H)—CH$_2$NMe$_2$ |
| 2-11 | Ph | (CH$_2$)$_5$ | (CH$_2$)$_2$NMe$_2$ |
| 2-12 | Ph | (CH$_2$)$_5$ | (CH$_2$)$_2$NEt$_2$ |
| 2-13 | Ph | (CH$_2$)$_5$ | (CH$_2$)$_3$NMe$_2$ |
| 2-14 | Ph | (CH$_2$)$_5$ | CH$_2$CH(OH)CH$_2$NMe$_2$ |
| 2-15 | Ph | (CH$_2$)$_5$ | CH$_2$CH(OH)CH$_2$(1-Pip) |
| 2-16 | Ph | (CH$_2$)$_5$ | (CH$_2$)$_2$(2-Pyrd) |
| 2-17 | Ph | (CH$_2$)$_5$ | (CH$_2$)$_2$(1-Me-2-Pyrd) |
| 2-18 | Ph | (CH$_2$)$_5$ | (CH$_2$)$_2$(2-Pip) |
| 2-19 | Ph | (CH$_2$)$_5$ | (CH$_2$)$_2$(1-Me-2-Pip) |
| 2-20 | Ph | (CH$_2$)$_5$ | CH$_2$(3-Pip) |
| 2-21 | Ph | (CH$_2$)$_5$ | CH$_2$(1-Me-3-Pip) |
| 2-22 | Ph | (CH$_2$)$_5$ | CH$_2$(1-Et-3-Pip) |
| 2-23 | Ph | (CH$_2$)$_5$ | CH$_2$(2-Mor) |
| 2-24 | Ph | (CH$_2$)$_5$ | CH$_2$(4-Me-2-Mor) |

TABLE 2-continued

| Cpd. No. | R¹ | A | R³ |
|---|---|---|---|
| 2-25 | Ph | $(CH_2)_5$ | 4-Pip |
| 2-26 | Ph | $(CH_2)_5$ | 1-Me-4-Pip |
| 2-27 | 3-MeO—Ph | $(CH_2)_5$ | $(CH_2)_2NMe_2$ |
| 2-28 | 3-MeO—Ph | $(CH_2)_5$ | $(CH_2)_2NEt_2$ |
| 2-29 | 3-MeO—Ph | $(CH_2)_5$ | $(CH_2)_3NMe_2$ |
| 2-30 | 3-MeO—Ph | $(CH_2)_5$ | $CH_2CH(OH)CH_2NMe_2$ |
| 2-31 | 3-MeO—Ph | $(CH_2)_5$ | $CH_2CH(OH)CH_2(1\text{-Pip})$ |
| 2-32 | 3-MeO—Ph | $(CH_2)_5$ | $(CH_2)_2(2\text{-Pyrd})$ |
| 2-33 | 3-MeO—Ph | $(CH_2)_5$ | $(CH_2)_2(1\text{-Me-2-Pyrd})$ |
| 2-34 | 3-MeO—Ph | $(CH_2)_5$ | $(CH_2)_2(2\text{-Pip})$ |
| 2-35 | 3-MeO—Ph | $(CH_2)_5$ | $(CH_2)_2(1\text{-Me-2-Pip})$ |
| 2-36 | 3-MeO—Ph | $(CH_2)_5$ | $CH_2(3\text{-Pip})$ |
| 2-37 | 3-MeO—Ph | $(CH_2)_5$ | $CH_2(1\text{-Me-3-Pip})$ |
| 2-38 | 3-MeO—Ph | $(CH_2)_5$ | $CH_2(1\text{-Et-3-Pip})$ |
| 2-39 | 3-MeO—Ph | $(CH_2)_5$ | $CH_2(2\text{-Mor})$ |
| 2-40 | 3-MeO—Ph | $(CH_2)_5$ | $CH_2(4\text{-Me-2-Mor})$ |
| 2-41 | 3-MeO—Ph | $(CH_2)_5$ | 4-Pip |
| 2-42 | 3-MeO—Ph | $(CH_2)_5$ | 1-Me-4-Pip |
| 2-43 | 3-Me—Ph | $(CH_2)_5$ | $(CH_2)_2NMe_2$ |
| 2-44 | 3-Me—Ph | $(CH_2)_5$ | $CH_2CH(OH)CH_2NMe_2$ |
| 2-45 | 3-Me—Ph | $(CH_2)_5$ | $CH_2CH(OH)CH_2(1\text{-Pip})$ |
| 2-46 | 3-Me—Ph | $(CH_2)_5$ | $(CH_2)_2(2\text{-Pyrd})$ |
| 2-47 | 3-Me—Ph | $(CH_2)_5$ | $(CH_2)_2(1\text{-Me-2-Pyrd})$ |
| 2-48 | 3-Me—Ph | $(CH_2)_5$ | $(CH_2)_2(2\text{-Pip})$ |
| 2-49 | 3-Me—Ph | $(CH_2)_5$ | $(CH_2)_2(1\text{-Me-2-Pip})$ |
| 2-50 | 3-Me—Ph | $(CH_2)_5$ | $CH_2(3\text{-Pip})$ |
| 2-51 | 3-Me—Ph | $(CH_2)_5$ | $CH_2(1\text{-Me-3-Pip})$ |
| 2-52 | 3-Me—Ph | $(CH_2)_5$ | $CH_2(1\text{-Et-3-Pip})$ |
| 2-53 | 3-Me—Ph | $(CH_2)_5$ | $CH_2(2\text{-Mor})$ |
| 2-54 | 3-Me—Ph | $(CH_2)_5$ | $CH_2(4\text{-Me-2-Mor})$ |
| 2-55 | 3-Me—Ph | $(CH_2)_5$ | 4-Pip |
| 2-56 | 3-Me—Ph | $(CH_2)_5$ | 1-Me-4-Pip |
| 2-57 | 3-Cl—Ph | $(CH_2)_5$ | $CH_2CH(OH)CH_2NMe_2$ |
| 2-58 | 3-Cl—Ph | $(CH_2)_5$ | $CH_2CH(OH)CH_2(1\text{-Pip})$ |
| 2-59 | 3-Cl—Ph | $(CH_2)_5$ | $(CH_2)_2(2\text{-Pyrd})$ |
| 2-60 | 3-Cl—Ph | $(CH_2)_5$ | $(CH_2)_2(1\text{-Me-2-Pyrd})$ |
| 2-61 | 3-Cl—Ph | $(CH_2)_5$ | $(CH_2)_2(2\text{-Pip})$ |
| 2-62 | 3-Cl—Ph | $(CH_2)_5$ | $(CH_2)_2(1\text{-Me-2-Pip})$ |
| 2-63 | 3-Cl—Ph | $(CH_2)_5$ | $CH_2(3\text{-Pip})$ |
| 2-64 | 3-Cl—Ph | $(CH_2)_5$ | $CH_2(1\text{-Me-3-Pip})$ |
| 2-65 | 3-Cl—Ph | $(CH_2)_5$ | $CH_2(1\text{-Et-3-Pip})$ |
| 2-66 | 3-Cl—Ph | $(CH_2)_5$ | $CH_2(2\text{-Mor})$ |
| 2-67 | 3-Cl—Ph | $(CH_2)_5$ | $CH_2(4\text{-Me-2-Mor})$ |
| 2-68 | 3-Cl—Ph | $(CH_2)_5$ | 4-Pip |
| 2-69 | 3-Cl—Ph | $(CH_2)_5$ | 1-Me-4-Pip |
| 2-70 | 3-F—Ph | $(CH_2)_5$ | $CH_2CH(OH)CH_2NMe_2$ |
| 2-71 | 3-F—Ph | $(CH_2)_5$ | $CH_2CH(OH)CH_2(1\text{-pip})$ |
| 2-72 | 3-F—Ph | $(CH_2)_5$ | $(CH_2)_2(2\text{-Pyrd})$ |
| 2-73 | 3-F—Ph | $(CH_2)_5$ | $(CH_2)_2(1\text{-Me-2-Pyrd})$ |
| 2-74 | 3-F—Ph | $(CH_2)_5$ | $(CH_2)_2(2\text{-Pip})$ |
| 2-75 | 3-F—Ph | $(CH_2)_5$ | $(CH_2)_2(1\text{-Me-2-Pip})$ |
| 2-76 | 3-F—Ph | $(CH_2)_5$ | $CH_2(3\text{-Pip})$ |
| 2-77 | 3-F—Ph | $(CH_2)_5$ | $CH_2(1\text{-Me-3-Pip})$ |
| 2-78 | 3-F—Ph | $(CH_2)_5$ | $CH_2(1\text{-Et-3-Pip})$ |
| 2-79 | 3-F—Ph | $(CH_2)_5$ | $CH_2(2\text{-Mor})$ |
| 2-80 | 3-F—Ph | $(CH_2)_5$ | $CH_2(4\text{-Me-2-Mor})$ |
| 2-81 | 3-F—Ph | $(CH_2)_5$ | 4-Pip |
| 2-82 | 3-F—Ph | $(CH_2)_5$ | 1-Me-4-Pip |
| 2-83 | Ph | $(CH_2)_3$ | $(CH_2)_2NMe_2$ |
| 2-84 | Ph | $(CH_2)_3$ | $CH_2CH(OH)CH_2NMe_2$ |
| 2-85 | Ph | $(CH_2)_3$ | $CH_2CH(OH)CH_2(1\text{-Pip})$ |
| 2-86 | Ph | $(CH_2)_3$ | $(CH_2)_2(2\text{-Pyrd})$ |
| 2-87 | Ph | $(CH_2)_3$ | $(CH_2)_2(1\text{-Me-2-Pyrd})$ |
| 2-88 | Ph | $(CH_2)_3$ | $(CH_2)_2(2\text{-Pip})$ |
| 2-89 | Ph | $(CH_2)_3$ | $(CH_2)_2(1\text{-Me-2-Pip})$ |
| 2-90 | Ph | $(CH_2)_3$ | $CH_2(3\text{-Pip})$ |
| 2-91 | Ph | $(CH_2)_3$ | $CH_2(1\text{-Me-3-Pip})$ |
| 2-92 | Ph | $(CH_2)_3$ | $CH_2(1\text{-Et-3-Pip})$ |
| 2-93 | Ph | $(CH_2)_3$ | $CH_2(2\text{-Mor})$ |
| 2-94 | Ph | $(CH_2)_3$ | $CH_2(4\text{-Me-2-Mor})$ |
| 2-95 | Ph | $(CH_2)_3$ | 4-Pip |
| 2-96 | Ph | $(CH_2)_3$ | 1-Me-4-Pip |
| 2-97 | 3-MeO—Ph | $(CH_2)_3$ | $(CH_2)_2NMe_2$ |
| 2-98 | 3-MeO—Ph | $(CH_2)_3$ | $CH_2CH(OH)CH_2NMe_2$ |
| 2-99 | 3-MeO—Ph | $(CH_2)_3$ | $CH_2CH(OH)CH_2(1\text{-Pip})$ |
| 2-100 | 3-MeO—Ph | $(CH_2)_3$ | $(CH_2)_2(2\text{-Pyrd})$ |
| 2-101 | 3-MeO—Ph | $(CH_2)_3$ | $(CH_2)_2(1\text{-Me-2-Pyrd})$ |

TABLE 2-continued

| Cpd. No. | R¹ | A | R³ |
|---|---|---|---|
| 2-102 | 3-MeO—Ph | (CH$_2$)$_3$ | (CH$_2$)$_2$(2-Pip) |
| 2-103 | 3-MeO—Ph | (CH$_2$)$_3$ | (CH$_2$)$_2$(1-Me-2-Pip) |
| 2-104 | 3-MeO—Ph | (CH$_2$)$_3$ | CH$_2$(3-Pip) |
| 2-105 | 3-MeO—Ph | (CH$_2$)$_3$ | CH$_2$(1-Me-3-Pip) |
| 2-106 | 3-MeO—Ph | (CH$_2$)$_3$ | CH$_2$(1-Et-3-Pip) |
| 2-107 | 3-MeO—Ph | (CH$_2$)$_3$ | CH$_2$(2-Mor) |
| 2-108 | 3-MeO—Ph | (CH$_2$)$_3$ | CH$_2$(4-Me-2-Mor) |
| 2-109 | 3-MeO—Ph | (CH$_2$)$_3$ | 4-Pip |
| 2-110 | 3-MeO—Ph | (CH$_2$)$_3$ | 1-Me-4-Pip |
| 2-111 | 3-Me—Ph | (CH$_2$)$_3$ | CH$_2$CH(OH)CH$_2$NMe$_2$ |
| 2-112 | 3-Me—Ph | (CH$_2$)$_3$ | (CH$_2$)$_2$(2-Pyrd) |
| 2-113 | 3-Me—Ph | (CH$_2$)$_3$ | (CH$_2$)$_2$(1-Me-2-Pyrd) |
| 2-114 | 3-Me—Ph | (CH$_2$)$_3$ | (CH$_2$)$_2$(2-Pip) |
| 2-115 | 3-Me—Ph | (CH$_2$)$_3$ | (CH$_2$)$_2$(1-Me-2-Pip) |
| 2-116 | 3-Me—Ph | (CH$_2$)$_3$ | CH$_2$(3-Pip) |
| 2-117 | 3-Me—Ph | (CH$_2$)$_3$ | CH$_2$(1-Me-3-Pip) |
| 2-118 | 3-Me—Ph | (CH$_2$)$_3$ | CH$_2$(1-Et-3-Pip) |
| 2-119 | 3-Me—Ph | (CH$_2$)$_3$ | CH$_2$(2-Mor) |
| 2-120 | 3-Me—Ph | (CH$_2$)$_3$ | CH$_2$(4-Me-2-Mor) |
| 2-121 | 3-Me—Ph | (CH$_2$)$_3$ | 4-Pip |
| 2-122 | 3-Me—Ph | (CH$_2$)$_3$ | 1-Me-4-Pip |
| 2-123 | 3-Cl—Ph | (CH$_2$)$_3$ | CH$_2$CH(OH)CH$_2$NMe$_2$ |
| 2-124 | 3-Cl—Ph | (CH$_2$)$_3$ | (CH$_2$)$_2$(2-Pyrd) |
| 2-125 | 3-Cl—Ph | (CH$_2$)$_3$ | (CH$_2$)$_2$(1-Me-2-Pyrd) |
| 2-126 | 3-Cl—Ph | (CH$_2$)$_3$ | (CH$_2$)$_2$(2-Pip) |
| 2-127 | 3-Cl—Ph | (CH$_2$)$_3$ | (CH$_2$)$_2$(1-Me-2-Pip) |
| 2-128 | 3-Cl—Ph | (CH$_2$)$_3$ | CH$_2$(3-Pip) |
| 2-129 | 3-Cl—Ph | (CH$_2$)$_3$ | CH$_2$(1-Me-3-Pip) |
| 2-130 | 3-Cl—Ph | (CH$_2$)$_3$ | CH$_2$(1-Et-3-Pip) |
| 2-131 | 3-Cl—Ph | (CH$_2$)$_3$ | CH$_2$(2-Mor) |
| 2-132 | 3-Cl—Ph | (CH$_2$)$_3$ | CH$_2$(4-Me-2-Mor) |
| 2-133 | 3-Cl—Ph | (CH$_2$)$_3$ | 4-Pip |
| 2-134 | 3-Cl—Ph | (CH$_2$)$_3$ | 1-Me-4-Pip |
| 2-135 | 3-F—Ph | (CH$_2$)$_3$ | CH$_2$CH(OH)CH$_2$NMe$_2$ |
| 2-136 | 3-F—Ph | (CH$_2$)$_3$ | (CH$_2$)$_2$(2-Pyrd) |
| 2-137 | 3-F—Ph | (CH$_2$)$_3$ | (CH$_2$)$_2$(1-Me-2-Pyrd) |
| 2-138 | 3-F—Ph | (CH$_2$)$_3$ | (CH$_2$)$_2$(2-Pip) |
| 2-139 | 3-F—Ph | (CH$_2$)$_3$ | (CH$_2$)$_2$(1-Me-2-Pip) |
| 2-140 | 3-F—Ph | (CH$_2$)$_3$ | CH$_2$(3-Pip) |
| 2-141 | 3-F—Ph | (CH$_2$)$_3$ | CH$_2$(1-Me-3-Pip) |
| 2-142 | 3-F—Ph | (CH$_2$)$_3$ | CH$_2$(1-Et-3-Pip) |
| 2-143 | 3-F—Ph | (CH$_2$)$_3$ | CH$_2$(2-Mor) |
| 2-144 | 3-F—Ph | (CH$_2$)$_3$ | CH$_2$(4-Me-2-Mor) |
| 2-145 | 3-F—Ph | (CH$_2$)$_3$ | 4-Pip |
| 2-146 | 3-F—Ph | (CH$_2$)$_3$ | 1-Me-4-Pip |
| 2-147 | 3-F—Ph | (CH$_2$)$_3$ | 1-Et-4-Pip |
| 2-148 | Ph | (CH$_2$)$_6$ | (CH$_2$)$_2$NMe$_2$ |
| 2-149 | Ph | (CH$_2$)$_6$ | CH$_2$CH(OH)CH$_2$NMe$_2$ |
| 2-150 | Ph | (CH$_2$)$_6$ | CH$_2$CH(OH)CH$_2$(1-Pip) |
| 2-151 | Ph | (CH$_2$)$_6$ | (CH$_2$)$_2$(2-Pyrd) |
| 2-152 | Ph | (CH$_2$)$_6$ | (CH$_2$)$_2$(1-Me-2-Pyrd) |
| 2-153 | Ph | (CH$_2$)$_6$ | (CH$_2$)$_2$(2-Pip) |
| 2-154 | Ph | (CH$_2$)$_6$ | (CH$_2$)$_2$(1-Me-2-Pip) |
| 2-155 | Ph | (CH$_2$)$_6$ | CH$_2$(3-Pip) |
| 2-156 | Ph | (CH$_2$)$_6$ | CH$_2$(1-Me-3-Pip) |
| 2-157 | Ph | (CH$_2$)$_6$ | CH$_2$(1-Et-3-Pip) |
| 2-158 | Ph | (CH$_2$)$_6$ | CH$_2$(2-Mor) |
| 2-159 | Ph | (CH$_2$)$_6$ | CH$_2$(4-Me-2-Mor) |
| 2-160 | Ph | (CH$_2$)$_6$ | 4-Pip |
| 2-161 | Ph | (CH$_2$)$_6$ | 1-Me-4-Pip |
| 2-162 | 3-MeO—Ph | (CH$_2$)$_6$ | (CH$_2$)$_2$NMe$_2$ |
| 2-163 | 3-MeO—Ph | (CH$_2$)$_6$ | CH$_2$CH(OH)CH$_2$NMe$_2$ |
| 2-164 | 3-MeO—Ph | (CH$_2$)$_6$ | CH$_2$CH(OH)CH$_2$(1-Pip) |
| 2-165 | 3-MeO—Ph | (CH$_2$)$_6$ | (CH$_2$)$_2$(2-Pyrd) |
| 2-166 | 3-MeO—Ph | (CH$_2$)$_6$ | (CH$_2$)$_2$(1-Me-2-Pyrd) |
| 2-167 | 3-MeO—Ph | (CH$_2$)$_6$ | (CH$_2$)$_2$(2-Pip) |
| 2-168 | 3-MeO—Ph | (CH$_2$)$_6$ | (CH$_2$)$_2$(1-Me-2-Pip) |
| 2-169 | 3-MeO—Ph | (CH$_2$)$_6$ | CH$_2$(3-Pip) |
| 2-170 | 3-MeO—Ph | (CH$_2$)$_6$ | CH$_2$(1-Me-3-Pip) |
| 2-171 | 3-MeO—Ph | (CH$_2$)$_6$ | CH$_2$(1-Et-3-Pip) |
| 2-172 | 3-MeO—Ph | (CH$_2$)$_6$ | CH$_2$(2-Mor) |
| 2-173 | 3-MeO—Ph | (CH$_2$)$_6$ | CH$_2$(4-Me-2-Mor) |
| 2-174 | 3-MeO—Ph | (CH$_2$)$_6$ | 4-Pip |
| 2-175 | 3-MeO—Ph | (CH$_2$)$_6$ | 1-Me-4-Pip |
| 2-176 | 3-Me—Ph | (CH$_2$)$_6$ | CH$_2$CH(OH)CH$_2$NMe$_2$ |
| 2-177 | 3-Me—Ph | (CH$_2$)$_6$ | (CH$_2$)$_2$(2-Pyrd) |
| 2-178 | 3-Me—Ph | (CH$_2$)$_6$ | (CH$_2$)$_2$(1-Me-2-Pyrd) |

TABLE 2-continued

| Cpd. No. | R¹ | A | R³ |
|---|---|---|---|
| 2-179 | 3-Me—Ph | (CH$_2$)$_6$ | (CH$_2$)$_2$(2-Pip) |
| 2-180 | 3-Me—Ph | (CH$_2$)$_6$ | (CH$_2$)$_2$(1-Me-2-Pip) |
| 2-181 | 3-Me—Ph | (CH$_2$)$_6$ | CH$_2$(3-Pip) |
| 2-182 | 3-Me—Ph | (CH$_2$)$_6$ | CH$_2$(1-Me-3-Pip) |
| 2-183 | 3-Me—Ph | (CH$_2$)$_6$ | CH$_2$(1-Et-3-Pip) |
| 2-184 | 3-Me—Ph | (CH$_2$)$_6$ | CH$_2$(2-Mor) |
| 2-185 | 3-Me—Ph | (CH$_2$)$_6$ | CH$_2$(4-Me-2-Mor) |
| 2-186 | 3-Me—Ph | (CH$_2$)$_6$ | 4-Pip |
| 2-187 | 3-Me—Ph | (CH$_2$)$_6$ | 1-Me-4-Pip |
| 2-188 | 3-Cl—Ph | (CH$_2$)$_6$ | CH$_2$CH(OH)CH$_2$NMe$_2$ |
| 2-189 | 3-Cl—Ph | (CH$_2$)$_6$ | (CH$_2$)$_2$(2-Pyrd) |
| 2-190 | 3-Cl—Ph | (CH$_2$)$_6$ | (CH$_2$)$_2$(1-Me-2-Pyrd) |
| 2-191 | 3-Cl—Ph | (CH$_2$)$_6$ | (CH$_2$)$_2$(2-Pip) |
| 2-192 | 3-Cl—Ph | (CH$_2$)$_6$ | (CH$_2$)$_2$(1-Me-2-Pip) |
| 2-193 | 3-Cl—Ph | (CH$_2$)$_6$ | CH$_2$(3-Pip) |
| 2-194 | 3-Cl—Ph | (CH$_2$)$_6$ | CH$_2$(1-Me-3-Pip) |
| 2-195 | 3-Cl—Ph | (CH$_2$)$_6$ | CH$_2$(1-Et-3-Pip) |
| 2-196 | 3-Cl—Ph | (CH$_2$)$_6$ | CH$_2$(2-Mor) |
| 2-197 | 3-Cl—Ph | (CH$_2$)$_6$ | CH$_2$(4-Me-2-Mor) |
| 2-198 | 3-Cl—Ph | (CH$_2$)$_6$ | 4-Pip |
| 2-199 | 3-Cl—Ph | (CH$_2$)$_6$ | 1-Me-4-Pip |
| 2-200 | 3-F—Ph | (CH$_2$)$_6$ | CH$_2$CH(OH)CH$_2$NMe$_2$ |
| 2-201 | 3-F—Ph | (CH$_2$)$_6$ | (CH$_2$)$_2$(2-Pyrd) |
| 2-202 | 3-F—Ph | (CH$_2$)$_6$ | (CH$_2$)$_2$(1-Me-2-Pyrd) |
| 2-203 | 3-F—Ph | (CH$_2$)$_6$ | (CH$_2$)$_2$(2-Pip) |
| 2-204 | 3-F—Ph | (CH$_2$)$_6$ | (CH$_2$)$_2$(1-Me-2-Pip) |
| 2-205 | 3-F—Ph | (CH$_2$)$_6$ | CH$_2$(3-Pip) |
| 2-206 | 3-F—Ph | (CH$_2$)$_6$ | CH$_2$(1-Me-3-Pip) |
| 2-207 | 3-F—Ph | (CH$_2$)$_6$ | CH$_2$(1-Et-3-Pip) |
| 2-208 | 3-F—Ph | (CH$_2$)$_6$ | CH$_2$(2-Mor) |
| 2-209 | 3-F—Ph | (CH$_2$)$_6$ | CH$_2$(4-Me-2-Mor) |
| 2-210 | 3-F—Ph | (CH$_2$)$_6$ | 4-Pip |
| 2-211 | 3-F—Ph | (CH$_2$)$_6$ | 1-Me-4-Pip |
| 2-212 | Ph | (CH$_2$)$_7$ | (CH$_2$)$_2$NMe$_2$ |
| 2-213 | Ph | (CH$_2$)$_7$ | CH$_2$CH(OH)CH$_2$NMe$_2$ |
| 2-214 | Ph | (CH$_2$)$_7$ | (CH$_2$)$_2$(2-Pyrd) |
| 2-215 | Ph | (CH$_2$)$_7$ | (CH$_2$)$_2$(1-Me-2-Pyrd) |
| 2-216 | Ph | (CH$_2$)$_7$ | (CH$_2$)$_2$(2-Pip) |
| 2-217 | Ph | (CH$_2$)$_7$ | (CH$_2$)$_2$(1-Me-2-Pip) |
| 2-218 | Ph | (CH$_2$)$_7$ | CH$_2$(3-Pip) |
| 2-219 | Ph | (CH$_2$)$_7$ | CH$_2$(1-Me-3-Pip) |
| 2-220 | Ph | (CH$_2$)$_7$ | CH$_2$(1-Et-3-Pip) |
| 2-221 | Ph | (CH$_2$)$_7$ | CH$_2$(2-Mor) |
| 2-222 | Ph | (CH$_2$)$_7$ | CH$_2$(4-Me-2-Mor) |
| 2-223 | Ph | (CH$_2$)$_7$ | 4-Pip |
| 2-224 | Ph | (CH$_2$)$_7$ | 1-Me-4-Pip |
| 2-225 | 3-MeO—Ph | (CH$_2$)$_7$ | CH$_2$CH(OH)CH$_2$NMe$_2$ |
| 2-226 | 3-MeO—Ph | (CH$_2$)$_7$ | (CH$_2$)$_2$(2-Pyrd) |
| 2-227 | 3-MeO—Ph | (CH$_2$)$_7$ | (CH$_2$)$_2$(1-Me-2-Pyrd) |
| 2-228 | 3-MeO—Ph | (CH$_2$)$_7$ | (CH$_2$)$_2$(2-Pip) |
| 2-229 | 3-MeO—Ph | (CH$_2$)$_7$ | (CH$_2$)$_2$(1-Me-2-Pip) |
| 2-230 | 3-MeO—Ph | (CH$_2$)$_7$ | CH$_2$(3-Pip) |
| 2-231 | 3-MeO—Ph | (CH$_2$)$_7$ | CH$_2$(1-Me-3-Pip) |
| 2-232 | 3-MeO—Ph | (CH$_2$)$_7$ | CH$_2$(1-Et-3-Pip) |
| 2-233 | 3-MeO—Ph | (CH$_2$)$_7$ | CH$_2$(2-Mor) |
| 2-234 | 3-MeO—Ph | (CH$_2$)$_7$ | CH$_2$(4-Me-2-Mor) |
| 2-235 | 3-MeO—Ph | (CH$_2$)$_7$ | 4-Pip |
| 2-236 | 3-MeO—Ph | (CH$_2$)$_7$ | 1-Me-4-Pip |
| 2-237 | 3-Me—Ph | (CH$_2$)$_7$ | CH$_2$CH(OH)CH$_2$NMe$_2$ |
| 2-238 | 3-Me—Ph | (CH$_2$)$_7$ | (CH$_2$)$_2$(2-Pyrd) |
| 2-239 | 3-Me—Ph | (CH$_2$)$_7$ | (CH$_2$)$_2$(1-Me-2-Pyrd) |
| 2-240 | 3-Me—Ph | (CH$_2$)$_7$ | (CH$_2$)$_2$(2-Pip) |
| 2-241 | 3-Me—Ph | (CH$_2$)$_7$ | (CH$_2$)$_2$(1-Me-2-Pip) |
| 2-242 | 3-Me—Ph | (CH$_2$)$_7$ | CH$_2$(3-Pip) |
| 2-243 | 3-Me—Ph | (CH$_2$)$_7$ | CH$_2$(1-Me-3-Pip) |
| 2-244 | 3-Me—Ph | (CH$_2$)$_7$ | CH$_2$(1-Et-3-Pip) |
| 2-245 | 3-Me—Ph | (CH$_2$)$_7$ | CH$_2$(2-Mor) |
| 2-246 | 3-Me—Ph | (CH$_2$)$_7$ | CH$_2$(4-Me-2-Mor) |
| 2-247 | 3-Me—Ph | (CH$_2$)$_7$ | 4-Pip |
| 2-248 | 3-Me—Ph | (CH$_2$)$_7$ | 1-Me-4-Pip |
| 2-249 | 3-Cl—Ph | (CH$_2$)$_7$ | (CH$_2$)$_2$(2-Pyrd) |
| 2-250 | 3-Cl—Ph | (CH$_2$)$_7$ | (CH$_2$)$_2$(1-Me-2-Pyrd) |
| 2-251 | 3-Cl—Ph | (CH$_2$)$_7$ | (CH$_2$)$_2$(2-Pip) |
| 2-252 | 3-Cl—Ph | (CH$_2$)$_7$ | (CH$_2$)$_2$(1-Me-2-Pip) |
| 2-253 | 3-Cl—Ph | (CH$_2$)$_7$ | CH$_2$(3-Pip) |
| 2-254 | 3-Cl—Ph | (CH$_2$)$_7$ | CH$_2$(1-Me-3-Pip) |
| 2-255 | 3-Cl—Ph | (CH$_2$)$_7$ | CH$_2$(1-Et-3-Pip) |

TABLE 2-continued

| Cpd. No. | R¹ | A | R³ |
|---|---|---|---|
| 2-256 | 3-Cl—Ph | $(CH_2)_7$ | $CH_2$(2-Mor) |
| 2-257 | 3-Cl—Ph | $(CH_2)_7$ | $CH_2$(4-Me-2-Mor) |
| 2-258 | 3-Cl—Ph | $(CH_2)_7$ | 4-Pip |
| 2-259 | 3-Cl—Ph | $(CH_2)_7$ | 1-Me-4-Pip |
| 2-260 | 3-F—Ph | $(CH_2)_7$ | $(CH_2)_2$(2-Pyrd) |
| 2-261 | 3-F—Ph | $(CH_2)_7$ | $(CH_2)_2$(1-Me-2-Pyrd) |
| 2-262 | 3-F—Ph | $(CH_2)_7$ | $(CH_2)_2$(2-Pip) |
| 2-263 | 3-F—Ph | $(CH_2)_7$ | $(CH_2)_2$(1-Me-2-Pip) |
| 2-264 | 3-F—Ph | $(CH_2)_7$ | $CH_2$(3-Pip) |
| 2-265 | 3-F—Ph | $(CH_2)_7$ | $CH_2$(1-Me-3-Pip) |
| 2-266 | 3-F—Ph | $(CH_2)_7$ | $CH_2$(1-Et-3-Pip) |
| 2-267 | 3-F—Ph | $(CH_2)_7$ | $CH_2$(2-Mor) |
| 2-268 | 3-F—Ph | $(CH_2)_7$ | $CH_2$(4-Me-2-Mor) |
| 2-269 | 3-F—Ph | $(CH_2)_7$ | 4-Pip |
| 2-270 | 3-F—Ph | $(CH_2)_7$ | 1-Me-4-Pip |
| 2-271 | Ph | $(CH_2)_3$ | $(CH_2)_3NMe_2$ |
| 2-272 | 2-OMe—Ph | $(CH_2)_5$ | $CH_2$(3-Pip) |
| 2-273 | 2-OMe—Ph | $(CH_2)_5$ | $CH_2$(1-Me-3-Pip) |
| 2-274 | 2-OMe—Ph | $(CH_2)_5$ | $CH_2$(2-Mor) |
| 2-275 | 2-OMe—Ph | $(CH_2)_5$ | $CH_2$(4-Me-2-Mor) |
| 2-276 | 2-OMe—Ph | $(CH_2)_5$ | $CH_2CH_2$(2-Pyrd) |
| 2-277 | 2-OMe—Ph | $(CH_2)_5$ | $CH_2CH_2$(1-Me-2-Pyrd) |
| 2-278 | 4-OMe—Ph | $(CH_2)_5$ | $CH_2$(3-Pip) |
| 2-279 | 4-OMe—Ph | $(CH_2)_5$ | $CH_2$(1-Me-3-Pip) |
| 2-280 | 4-OMe—Ph | $(CH_2)_5$ | $CH_2$(2-Mor) |
| 2-281 | 4-OMe—Ph | $(CH_2)_5$ | $CH_2$(4-Me-2-Mor) |
| 2-282 | 4-OMe—Ph | $(CH_2)_5$ | $CH_2CH_2$(2-Pyrd) |
| 2-283 | 4-OMe—Ph | $(CH_2)_5$ | $CH_2CH_2$(1-Me-2-Pyrd) |
| 2-284 | 2-Me—Ph | $(CH_2)_5$ | $CH_2$(3-Pip) |
| 2-285 | 2-Me—Ph | $(CH_2)_5$ | $CH_2$(1-Me-3-Pip) |
| 2-286 | 2-Me—Ph | $(CH_2)_5$ | $CH_2$(2-Mor) |
| 2-287 | 2-Me—Ph | $(CH_2)_5$ | $CH_2$(4-Me-2-Mor) |
| 2-288 | 2-Me—Ph | $(CH_2)_5$ | $CH_2CH_2$(2-Pyrd) |
| 2-289 | 2-Me—Ph | $(CH_2)_5$ | $CH_2CH_2$(1-Me-2-Pyrd) |
| 2-290 | 4-Me—Ph | $(CH_2)_5$ | $CH_2$(3-Pip) |
| 2-291 | 4-Me—Ph | $(CH_2)_5$ | $CH_2$(1-Me-3-Pip) |
| 2-292 | 4-Me—Ph | $(CH_2)_5$ | $CH_2$(2-Mor) |
| 2-293 | 4-Me—Ph | $(CH_2)_5$ | $CH_2$(4-Me-2-Mor) |
| 2-294 | 4-Me—Ph | $(CH_2)_5$ | $CH_2CH_2$(2-Pyrd) |
| 2-295 | 4-Me—Ph | $(CH_2)_5$ | $CH_2CH_2$(1-Me-2-Pyrd) |
| 2-296 | 2-F—Ph | $(CH_2)_5$ | $CH_2$(3-Pip) |
| 2-297 | 2-F—Ph | $(CH_2)_5$ | $CH_2$(1-Me-3-Pip) |
| 2-298 | 2-F—Ph | $(CH_2)_5$ | $CH_2$(2-Mor) |
| 2-299 | 2-F—Ph | $(CH_2)_5$ | $CH_2$(4-Me-2-Mor) |
| 2-300 | 2-F—Ph | $(CH_2)_5$ | $CH_2CH_2$(2-Pyrd) |
| 2-301 | 2-F—Ph | $(CH_2)_5$ | $CH_2CH_2$(1-Me-2-Pyrd) |
| 2-302 | 4-F—Ph | $(CH_2)_5$ | $CH_2$(3-Pip) |
| 2-303 | 4-F—Ph | $(CH_2)_5$ | $CH_2$(1-Me-3-Pip) |
| 2-304 | 4-F—Ph | $(CH_2)_5$ | $CH_2$(2-Mor) |
| 2-305 | 4-F—Ph | $(CH_2)_5$ | $CH_2$(4-Me-2-Mor) |
| 2-306 | 4-F—Ph | $(CH_2)_5$ | $CH_2CH_2$(2-Pyrd) |
| 2-307 | 4-F—Ph | $(CH_2)_5$ | $CH_2CH_2$(1-Mc-2-Pyrd) |
| 2-308 | 2-Cl—Ph | $(CH_2)_5$ | $CH_2$(1-Me-3-Pip) |
| 2-309 | 2-Cl—Ph | $(CH_2)_5$ | $CH_2$(2-Mor) |
| 2-310 | 2-Cl—Ph | $(CH_2)_5$ | $CH_2$(4-Me-2-Mor) |
| 2-311 | 2-Cl—Ph | $(CH_2)_5$ | $CH_2CH_2$(2-Pyrd) |
| 2-312 | 2-Cl—Ph | $(CH_2)_5$ | $CH_2CH_2$(1-Me-2-Pyrd) |
| 2-313 | 4-Cl—Ph | $(CH_2)_5$ | $CH_2$(3-Pip) |
| 2-314 | 4-Cl—Ph | $(CH_2)_5$ | $CH_2$(1-Me-3-Pip) |
| 2-315 | 4-Cl—Ph | $(CH_2)_5$ | $CH_2$(2-Mor) |
| 2-316 | 4-Cl—Ph | $(CH_2)_5$ | $CH_2$(4-Me-2-Mor) |
| 2-317 | 4-Cl—Ph | $(CH_2)_5$ | $CH_2CH_2$(2-Pyrd) |
| 2-318 | 4-Cl—Ph | $(CH_2)_5$ | $CH_2CH_2$(1-Me-2-Pyrd) |
| 2-319 | 2-OEt—Ph | $(CH_2)_5$ | $CH_2$(3-Pip) |
| 2-320 | 2-OEt—Ph | $(CH_2)_5$ | $CH_2$(1-Me-3-Pip) |
| 2-321 | 2-OEt—Ph | $(CH_2)_5$ | $CH_2$(2-Mor) |
| 2-322 | 2-OEt—Ph | $(CH_2)_5$ | $CH_2$(4-Me-2-Mor) |
| 2-323 | 2-OEt—Ph | $(CH_2)_5$ | $CH_2CH_2$(2-Pyrd) |
| 2-324 | 2-OEt—Ph | $(CH_2)_5$ | $CH_2CH_2$(1-Me-2-Pyrd) |
| 2-325 | 3-OEt—Ph | $(CH_2)_5$ | $CH_2$(3-Pip) |
| 2-326 | 3-OEt—Ph | $(CH_2)_5$ | $CH_2$(1-Me-3-Pip) |
| 2-327 | 3-OEt—Ph | $(CH_2)_5$ | $CH_2$(2-Mor) |
| 2-328 | 3-OEt—Ph | $(CH_2)_5$ | $CH_2$(4-Me-2-Mor) |
| 2-329 | 3-OEt—Ph | $(CH_2)_5$ | $CH_2CH_2$(2-Pyrd) |
| 2-330 | 3-OEt—Ph | $(CH_2)_5$ | $CH_2CH_2$(1-Me-2-Pyrd) |
| 2-331 | 4-OEt—Ph | $(CH_2)_5$ | $CH_2$(3-Pip) |
| 2-332 | 4-OEt—Ph | $(CH_2)_5$ | $CH_2$(1-Me-3-Pip) |

TABLE 2-continued

| Cpd. No. | R¹ | A | R³ |
|---|---|---|---|
| 2-333 | 4-OEt—Ph | (CH$_2$)$_5$ | CH$_2$(2-Mor) |
| 2-334 | 4-OEt—Ph | (CH$_2$)$_5$ | CH$_2$(4-Me-2-Mor) |
| 2-335 | 4-OEt—Ph | (CH$_2$)$_5$ | CH$_2$CH$_2$(2-Pyrd) |
| 2-336 | 4-OEt—Ph | (CH$_2$)$_5$ | CH$_2$CH$_2$(1-Me-2-Pyrd) |
| 2-337 | 2-OH—Ph | (CH$_2$)$_5$ | CH$_2$(3-Pip) |
| 2-338 | 2-OH—Ph | (CH$_2$)$_5$ | CH$_2$(1-Me-3-Pip) |
| 2-339 | 2-OH—Ph | (CH$_2$)$_5$ | CH$_2$(2-Mor) |
| 2-340 | 2-OH—Ph | (CH$_2$)$_5$ | CH$_2$(4-Me-2-Mor) |
| 2-341 | 2-OH—Ph | (CH$_2$)$_5$ | CH$_2$CH$_2$(2-Pyrd) |
| 2-342 | 2-OH—Ph | (CH$_2$)$_5$ | CH$_2$CH$_2$(1-Me-2-Pyrd) |
| 2-343 | 3-OH—Ph | (CH$_2$)$_5$ | CH$_2$(3-Pip) |
| 2-344 | 3-OH—Ph | (CH$_2$)$_5$ | CH$_2$(1-Me-3-Pip) |
| 2-345 | 3-OH—Ph | (CH$_2$)$_5$ | CH$_2$(2-Mor) |
| 2-346 | 3-OH—Ph | (CH$_2$)$_5$ | CH$_2$(4-Me-2-Mor) |
| 2-347 | 3-OH—Ph | (CH$_2$)$_5$ | CH$_2$CH$_2$(2-Pyrd) |
| 2-348 | 3-OH—Ph | (CH$_2$)$_5$ | CH$_2$CH$_2$(1-Me-2-Pyrd) |
| 2-349 | 4-OH—Ph | (CH$_2$)$_5$ | CH$_2$(3-Pip) |
| 2-350 | 4-OH—Ph | (CH$_2$)$_5$ | CH$_2$(1-Me-3-Pip) |
| 2-351 | 4-OH—Ph | (CH$_2$)$_5$ | CH$_2$(2-Mor) |
| 2-352 | 4-OH—Ph | (CH$_2$)$_5$ | CH$_2$(4-Me-2-Mor) |
| 2-353 | 4-OH—Ph | (CH$_2$)$_5$ | CH$_2$CH$_2$(2-Pyrd) |
| 2-354 | 4-OH—Ph | (CH$_2$)$_5$ | CH$_2$CH$_2$(1-Me-2-Pyrd) |
| 2-355 | 2-CN—Ph | (CH$_2$)$_5$ | CH$_2$(3-Pip) |
| 2-356 | 2-CN—Ph | (CH$_2$)$_5$ | CH$_2$(1-Me-3-Pip) |
| 2-357 | 2-CN—Ph | (CH$_2$)$_5$ | CH$_2$(2-Mor) |
| 2-358 | 2-CN—Ph | (CH$_2$)$_5$ | CH$_2$(4-Me-2-Mor) |
| 2-359 | 2-CN—Ph | (CH$_2$)$_5$ | CH$_2$CH$_2$(2-Pyrd) |
| 2-360 | 2-CN—Ph | (CH$_2$)$_5$ | CH$_2$CH$_2$(1-Me-2-Pyrd) |
| 2-361 | 3-CN—Ph | (CH$_2$)$_5$ | CH$_2$(3-Pip) |
| 2-362 | 3-CN—Ph | (CH$_2$)$_5$ | CH$_2$(1-Me-3-Pip) |
| 2-363 | 3-CN—Ph | (CH$_2$)$_5$ | CH$_2$(2-Mor) |
| 2-364 | 3-CN—Ph | (CH$_2$)$_5$ | CH$_2$(4-Me-2-Mor) |
| 2-365 | 3-CN—Ph | (CH$_2$)$_5$ | CH$_2$CH$_2$(2-Pyrd) |
| 2-366 | 3-CN—Ph | (CH$_2$)$_5$ | CH$_2$CH$_2$(1-Me-2-Pyrd) |
| 2-367 | 4-CN—Ph | (CH$_2$)$_5$ | CH$_2$(3-Pip) |
| 2-368 | 4-CN—Ph | (CH$_2$)$_5$ | CH$_2$(1-Me-3-Pip) |
| 2-369 | 4-CN—Ph | (CH$_2$)$_5$ | CH$_2$(2-Mor) |
| 2-370 | 4-CN—Ph | (CH$_2$)$_5$ | CH$_2$(4-Me-2-Mor) |
| 2-371 | 4-CN—Ph | (CH$_2$)$_5$ | CH$_2$CH$_2$(2-Pyrd) |
| 2-372 | 4-CN—Ph | (CH$_2$)$_5$ | CH$_2$CH$_2$(1-Me-2-Pyrd) |
| 2-373 | 2-OCF$_2$H—Ph | (CH$_2$)$_5$ | CH$_2$(3-Pip) |
| 2-374 | 2-OCF$_2$H—Ph | (CH$_2$)$_5$ | CH$_2$(1-Me-3-Pip) |
| 2-375 | 2-OCF$_2$H—Ph | (CH$_2$)$_5$ | CH$_2$(2-Mor) |
| 2-376 | 2-OCF$_2$H—Ph | (CH$_2$)$_5$ | CH$_2$(4-Me-2-Mor) |
| 2-377 | 2-OCF$_2$H—Ph | (CH$_2$)$_5$ | CH$_2$CH$_2$(2-Pyrd) |
| 2-378 | 2-OCF$_2$H—Ph | (CH$_2$)$_5$ | CH$_2$CH$_2$(1-Me-2-Pyrd) |
| 2-379 | 3-OCF$_2$H—Ph | (CH$_2$)$_5$ | CH$_2$(3-Pip) |
| 2-380 | 3-OCF$_2$H—Ph | (CH$_2$)$_5$ | CH$_2$(1-Me-3-Pip) |
| 2-381 | 3-OCF$_2$H—Ph | (CH$_2$)$_5$ | CH$_2$(2-Mor) |
| 2-382 | 3-OCF$_2$H—Ph | (CH$_2$)$_5$ | CH$_2$(4-Me-2-Mor) |
| 2-383 | 3-OCF$_2$H—Ph | (CH$_2$)$_5$ | CH$_2$CH$_2$(2-Pyrd) |
| 2-384 | 3-OCF$_2$H—Ph | (CH$_2$)$_5$ | CH$_2$CH$_2$(1-Me-2-Pyrd) |
| 2-385 | 4-OCF$_2$H—Ph | (CH$_2$)$_5$ | CH$_2$(3-Pip) |
| 2-386 | 4-OCF$_2$H—Ph | (CH$_2$)$_5$ | CH$_2$(1-Me-3-Pip) |
| 2-387 | 4-OCF$_2$H—Ph | (CH$_2$)$_5$ | CH$_2$(2-Mor) |
| 2-388 | 4-OCF$_2$H—Ph | (CH$_2$)$_5$ | CH$_2$(4-Me-2-Mor) |
| 2-389 | 4-OCF$_2$H—Ph | (CH$_2$)$_5$ | CH$_2$CH$_2$(2-Pyrd) |
| 2-390 | 4-OCF$_2$H—Ph | (CH$_2$)$_5$ | CH$_2$CH$_2$(1-Me-2-Pyrd) |
| 2-391 | 2-OCFH$_2$—Ph | (CH$_2$)$_5$ | CH$_2$(3-Pip) |
| 2-392 | 2-OCFH$_2$—Ph | (CH$_2$)$_5$ | CH$_2$(1-Me-3-Pip) |
| 2-393 | 2-OCFH$_2$—Ph | (CH$_2$)$_5$ | CH$_2$(2-Mor) |
| 2-394 | 2-OCFH$_2$—Ph | (CH$_2$)$_5$ | CH$_2$(4-Me-2-Mor) |
| 2-395 | 2-OCFH$_2$—Ph | (CH$_2$)$_5$ | CH$_2$CH$_2$(2-Pyrd) |
| 2-396 | 2-OCFH$_2$—Ph | (CH$_2$)$_5$ | CH$_2$CH$_2$(1-Me-2-Pyrd) |
| 2-397 | 3-OCFH$_2$—Ph | (CH$_2$)$_5$ | CH$_2$(3-Pip) |
| 2-398 | 3-OCFH$_2$—Ph | (CH$_2$)$_5$ | CH$_2$(1-Me-3-Pip) |
| 2-399 | 3-OCFH$_2$—Ph | (CH$_2$)$_5$ | CH$_2$(2-Mor) |
| 2-400 | 3-OCFH$_2$—Ph | (CH$_2$)$_5$ | CH$_2$(4-Me-2-Mor) |
| 2-401 | 3-OCFH$_2$—Ph | (CH$_2$)$_5$ | CH$_2$CH$_2$(2-Pyrd) |
| 2-402 | 3-OCFH$_2$—Ph | (CH$_2$)$_5$ | CH$_2$CH$_2$(1-Me-2-Pyrd) |
| 2-403 | 4-OCFH$_2$—Ph | (CH$_2$)$_5$ | CH$_2$(3-Pip) |
| 2-404 | 4-OCFH$_2$—Ph | (CH$_2$)$_5$ | CH$_2$(1-Me-3-Pip) |
| 2-405 | 4-OCFH$_2$—Ph | (CH$_2$)$_5$ | CH$_2$(2-Mor) |
| 2-406 | 4-OCFH$_2$—Ph | (CH$_2$)$_5$ | CH$_2$(4-Me-2-Mor) |
| 2-407 | 4-OCFH$_2$—Ph | (CH$_2$)$_5$ | CH$_2$CH$_2$(2-Pyrd) |
| 2-408 | 4-OCFH$_2$—Ph | (CH$_2$)$_5$ | CH$_2$CH$_2$(1-Me-2-Pyrd) |
| 2-409 | 2-OCF$_3$—Ph | (CH$_2$)$_5$ | CH$_2$(3-Pip) |

TABLE 2-continued

| Cpd. No. | R¹ | A | R³ |
|---|---|---|---|
| 2-410 | 2-OCF₃—Ph | (CH₂)₅ | CH₂(1-Me-3-Pip) |
| 2-411 | 2-OCF₃—Ph | (CH₂)₅ | CH₂(2-Mor) |
| 2-412 | 2-OCF₃—Ph | (CH₂)₅ | CH₂(4-Me-2-Mor) |
| 2-413 | 2-OCF₃—Ph | (CH₂)₅ | CH₂CH₂(2-Pyrd) |
| 2-414 | 2-OCF₃—Ph | (CH₂)₅ | CH₂CH₂(1-Me-2-Pyrd) |
| 2-415 | 3-OCF₃—Ph | (CH₂)₅ | CH₂(3-Pip) |
| 2-416 | 3-OCF₃—Ph | (CH₂)₅ | CH₂(1-Me-3-Pip) |
| 2-417 | 3-OCF₃—Ph | (CH₂)₅ | CH₂(2-Mor) |
| 2-418 | 3-OCF₃—Ph | (CH₂)₅ | CH₂(4-Me-2-Mor) |
| 2-419 | 3-OCF₃—Ph | (CH₂)₅ | CH₂CH₂(2-Pyrd) |
| 2-420 | 3-OCF₃—Ph | (CH₂)₅ | CH₂CH₂(1-Me-2-Pyrd) |
| 2-421 | 4-OCF₃—Ph | (CH₂)₅ | CH₂(3-Pip) |
| 2-422 | 4-OCF₃—Ph | (CH₂)₅ | CH₂(1-Me-3-Pip) |
| 2-423 | 4-OCF₃—Ph | (CH₂)₅ | CH₂(2-Mor) |
| 2-424 | 4-OCF₃—Ph | (CH₂)₅ | CH₂(4-Me-2-Mor) |
| 2-425 | 4-OCF₃—Ph | (CH₂)₅ | CH₂CH₂(2-Pyrd) |
| 2-426 | 4-OCF₃—Ph | (CH₂)₅ | CH₂CH₂(1-Me-2-Pyrd) |
| 2-427 | 3,5-diOMe—Ph | (CH₂)₅ | CH₂(3-Pip) |
| 2-428 | 3,5-diOMe—Ph | (CH₂)₅ | CH₂(1-Me-3-Pip) |
| 2-429 | 3,5-diOMe—Ph | (CH₂)₅ | CH₂(2-Mor) |
| 2-430 | 3,5-diOMe—Ph | (CH₂)₅ | CH₂(4-Me-2-Mor) |
| 2-431 | 3,5-diOMe—Ph | (CH₂)₅ | CH₂CH₂(2-Pyrd) |
| 2-432 | 3,5-diOMe—Ph | (CH₂)₅ | CH₂CH₂(1-Me-2-Pyrd) |
| 2-433 | 2-Br—Ph | (CH₂)₅ | CH₂(3-Pip) |
| 2-434 | 2-Br—Ph | (CH₂)₅ | CH₂(1-Me-3-Pip) |
| 2-435 | 2-Br—Ph | (CH₂)₅ | CH₂(2-Mor) |
| 2-436 | 2-Br—Ph | (CH₂)₅ | CH₂(4-Me-2-Mor) |
| 2-437 | 2-Br—Ph | (CH₂)₅ | CH₂CH₂(2-Pyrd) |
| 2-438 | 2-Br—Ph | (CH₂)₅ | CH₂CH₂(1-Me-2-Pyrd) |
| 2-439 | 3-Br—Ph | (CH₂)₅ | CH₂(3-Pip) |
| 2-440 | 3-Br—Ph | (CH₂)₅ | CH₂(1-Me-3-Pip) |
| 2-441 | 3-Br—Ph | (CH₂)₅ | CH₂(2-Mor) |
| 2-442 | 3-Br—Ph | (CH₂)₅ | CH₂(4-Me-2-Mor) |
| 2-443 | 3-Br—Ph | (CH₂)₅ | CH₂CH₂(2-Pyrd) |
| 2-444 | 3-Br—Ph | (CH₂)₅ | CH₂CH₂(1-Me-2-Pyrd) |
| 2-445 | 4-Br—Ph | (CH₂)₅ | CH₂(3-Pip) |
| 2-446 | 4-Br—Ph | (CH₂)₅ | CH₂(1-Me-3-Pip) |
| 2-447 | 4-Br—Ph | (CH₂)₅ | CH₂(2-Mor) |
| 2-448 | 4-Br—Ph | (CH₂)₅ | CH₂(4-Me-2-Mor) |
| 2-449 | 4-Br—Ph | (CH₂)₅ | CH₂CH₂(2-Pyrd) |
| 2-450 | 4-Br—Ph | (CH₂)₅ | CH₂CH₂(1-Me-2-Pyrd) |

TABLE 3

| Cpd. No. | Rᵈ | Rᵃ | Rᵇ | Rᶜ | m |
|---|---|---|---|---|---|
| 3-1 | 1-Me-2-Pyrd | H | H | H | 2 |
| 3-2 | 1-Me-3-Pyrd | H | H | H | 2 |
| 3-3 | 2-Pyrd | H | H | H | 2 |
| 3-4 | 3-Pyrd | H | H | H | 2 |
| 3-5 | 1-Et-2-Pyrd | H | H | H | 2 |
| 3-6 | 1-Pr-2-Pyrd | H | H | H | 2 |
| 3-7 | 2-Pip | H | H | H | 2 |
| 3-8 | 3-Pip | H | H | H | 2 |
| 3-9 | 4-Pip | H | H | H | 2 |
| 3-10 | 1-Me-2-Pip | H | H | H | 2 |
| 3-11 | 1-Me-3-Pip | H | H | H | 2 |
| 3-12 | 1-Me-4-Pip | H | H | H | 2 |
| 3-13 | 1-Et-2-Pip | H | H | H | 2 |
| 3-14 | 1-Pr-2-Pip | H | H | H | 2 |
| 3-15 | 2-Pip | H | H | H | 1 |
| 3-16 | 3-Pip | H | H | H | 1 |
| 3-17 | 4-Pip | H | H | H | 1 |
| 3-18 | 1-Me-2-Pip | H | H | H | 1 |
| 3-19 | 1-Me-3-Pip | H | H | H | 1 |
| 3-20 | 1-Me-4-Pip | H | H | H | 1 |
| 3-21 | 1-Et-3-Pip | H | H | H | 1 |
| 3-22 | 1-Pr-3-Pip | H | H | H | 1 |
| 3-23 | 3-Pip | H | H | H | 0 |
| 3-24 | 4-Pip | H | H | H | 0 |
| 3-25 | 1-Me-3-Pip | H | H | H | 0 |
| 3-26 | 1-Me-4-Pip | H | H | H | 0 |
| 3-27 | 1-Et-4-Pip | H | H | H | 0 |
| 3-28 | 1-Pr-4-Pip | H | H | H | 0 |

TABLE 3-continued

| Cpd. No. | R$^d$ | R$^a$ | R$^b$ | R$^c$ | m |
|---|---|---|---|---|---|
| 3-29 | 2-Pyrd | H | H | H | 1 |
| 3-30 | 1-Me-2-Pyrd | H | H | H | 1 |
| 3-31 | 2-Mor | H | H | H | 1 |
| 3-32 | 1-Me-2-Mor | H | H | H | 1 |
| 3-33 | 1-Et-2-Mor | H | H | H | 1 |
| 3-34 | 2-Tmor | H | H | H | 1 |
| 3-35 | 1-Me-2-Tmor | H | H | H | 1 |
| 3-36 | 4-OH-1-Me-2-Pyrd | H | H | H | 1 |
| 3-37 | 4-OH-2-Pyrd | H | H | H | 1 |
| 3-38 | 4-OH-1-Me-2-Pyrd | H | H | H | 2 |
| 3-39 | 1-Me-2-Pyrd | 3-OH | H | H | 2 |
| 3-40 | 1-Me-2-Pip | 3-OH | H | H | 2 |
| 3-41 | 1-Me-2-Mor | 3-OH | H | H | 1 |
| 3-42 | 4-OH-1-Me-2-Pyrd | 3-OH | H | H | 1 |
| 3-43 | 1-Me-2-Pip | 2-OH | H | H | 2 |
| 3-44 | 1-Me-2-Pyrd | 2-OH | H | H | 2 |
| 3-45 | 1-Me-2-Mor | 2-OH | H | H | 1 |
| 3-46 | 1-Me-2-Pip | 4-OH | H | H | 2 |
| 3-47 | 1-Me-2-Pyrd | 4-OH | H | H | 2 |
| 3-48 | 1-Me-2-Mor | 4-OH | H | H | 1 |
| 3-49 | 2-Pyrd | 3-OH | H | H | 2 |
| 3-50 | 1-Me-2-Pyrd | 3-OMe | H | H | 2 |
| 3-51 | 2-Pip | 3-OMe | H | H | 2 |
| 3-52 | 1-Me-2-Pip | 3-OMe | H | H | 2 |
| 3-53 | 1-Me-3-Pip | 3-OMe | H | H | 2 |
| 3-54 | 1-Me-4-Pip | 3-OMe | H | H | 2 |
| 3-55 | 1-Et-2-Pip | 3-OMe | H | H | 2 |
| 3-56 | 1-Me-2-Pip | 3-OMe | H | H | 1 |
| 3-57 | 1-Me-3-Pip | 3-OMe | H | H | 1 |
| 3-58 | 1-Me-4-Pip | 3-OMe | H | H | 1 |
| 3-59 | 1-Me-3-Pip | 3-OMe | H | H | 0 |
| 3-60 | 1-Me-4-Pip | 3-OMe | H | H | 0 |
| 3-61 | 1-Me-2-Pyrd | 3-OMe | H | H | 1 |
| 3-62 | 4-OH-1-Me-2-Pyrd | 3-OMe | H | H | 1 |
| 3-63 | 4-Me-2-Mor | 3-OMe | H | H | 1 |
| 3-64 | 2-Mor | 3-OMe | H | H | 1 |
| 3-65 | 1-Me-2-Pyrd | 3-OMe | 4-OMe | H | 2 |
| 3-66 | 1-Me-2-Pip | 3-OMe | 4-OMe | H | 2 |
| 3-67 | 4-Me-2-Mor | 3-OMe | 4-OMe | H | 1 |
| 3-68 | 1-Me-2-Pip | 3-OMe | 4-OMe | H | 1 |
| 3-69 | 3-Pip | 3-OMe | 4-OMe | H | 1 |
| 3-70 | 1-Me-2-Pyrd | 3-OMe | 5-OMe | H | 2 |
| 3-71 | 1-Me-2-Pip | 3-OMe | 5-OMe | H | 2 |
| 3-72 | 4-Me-2-Mor | 3-OMe | 5-OMe | H | 1 |
| 3-73 | 3-Pip | 3-OMe | 5-OMe | H | 1 |
| 3-74 | 1-Me-3-Pip | 3-OMe | 5-OMe | H | 1 |
| 3-75 | 1-Me-4-Pip | 3-OMe | 5-OMe | H | 0 |
| 3-76 | 1-Me-2-Pyrd | 3-OMe | 5-OMe | H | 1 |
| 3-77 | 4-OMe-1-Me-2-Pyrd | 3-OMe | 5-OMe | H | 2 |
| 3-78 | 1-Me-2-Pyrd | 3-OMe | 4-OMe | 5-OMe | 2 |
| 3-79 | 1-Me-2-Pip | 3-OMe | 4-OMe | 5-OMe | 2 |
| 3-80 | 4-Me-2-Mor | 3-OMe | 4-OMe | 5-OMe | 1 |
| 3-81 | 1-Me-3-Pip | 3-OMe | 4-OMe | 5-OMe | 1 |
| 3-82 | 1-Me-4-Pip | 3-OMe | 4-OMe | 5-OMe | 0 |
| 3-83 | 1-Me-2-Pyrd | 3-OMe | 4-OMe | 5-OMe | 1 |
| 3-84 | 1-Me-2-Pyrd | 3-Me | H | H | 2 |
| 3-85 | 1-Me-2-Pip | 3-Me | H | H | 2 |
| 3-86 | 4-Me-2-Mor | 3-Me | H | H | 1 |
| 3-87 | 1-Me-3-Pip | 3-Me | H | H | 1 |
| 3-88 | 1-Me-4-Pip | 3-Me | H | H | 0 |
| 3-89 | 1-Me-2-Pyrd | 3-Me | H | H | 1 |
| 3-90 | 1-Me-2-Pyrd | 3-Cl | H | H | 2 |
| 3-91 | 1-Me-2-Pip | 3-Cl | H | H | 2 |
| 3-92 | 4-Me-2-Mor | 3-Cl | H | H | 1 |
| 3-93 | 1-Me-3-Pip | 3-Cl | H | H | 1 |
| 3-94 | 1-Me-4-Pip | 3-Cl | H | H | 0 |
| 3-95 | 1-Me-2-Pyrd | 3-F | H | H | 2 |
| 3-96 | 1-Me-2-Pip | 3-F | H | H | 2 |
| 3-97 | 4-Me-2-Mor | 3-F | H | H | 1 |
| 3-98 | 1-Me-3-Pip | 3-F | H | H | 1 |
| 3-99 | 1-Me-2-Pyrd | 3-F | H | H | 1 |
| 3-100 | 1-Me-2-Pyrd | 2-CN | H | H | 2 |
| 3-101 | 1-Me-3-Pip | 2-CN | H | H | 1 |
| 3-102 | 1-Me-2-Pip | 2-CN | H | H | 2 |
| 3-103 | 4-Me-2-Mor | 2-CN | H | H | 1 |
| 3-104 | 1-Me-4-Pip | 2-CN | H | H | 0 |

TABLE 3-continued

| Cpd. No. | $R^d$ | $R^a$ | $R^b$ | $R^c$ | m |
|---|---|---|---|---|---|
| 3-105 | 1-Me-2-Pyrd | 2-CONH$_2$ | H | H | 2 |
| 3-106 | 1-Me-3-Pip | 2-CONH$_2$ | H | H | 1 |
| 3-107 | 1-Me-2-Pip | 2-CONH$_2$ | H | H | 2 |
| 3-108 | 4-Me-2-Mor | 2-CONH$_2$ | H | H | 1 |
| 3-109 | 1-Me-2-Pyrd | 2-CONH$_2$ | H | H | 1 |
| 3-110 | 1-Me-2-Pyrd | 3-OEt | H | H | 2 |
| 3-111 | 1-Me-2-Pip | 3-OEt | H | H | 2 |
| 3-112 | 1-Me-3-Pip | 3-OEt | H | H | 1 |
| 3-113 | 4-Me-2-Mor | 3-OEt | H | H | 1 |
| 3-114 | 1-Me-4-Pip | 3-OEt | H | H | 0 |
| 3-115 | 1-Me-2-Pyrd | 2-OMe | H | H | 2 |
| 3-116 | 1-Me-2-Pip | 2-OMe | H | H | 2 |
| 3-117 | 4-Me-2-Mor | 2-OMe | H | H | 1 |
| 3-118 | 1-Me-3-Pip | 2-OMe | H | H | 1 |
| 3-119 | 1-Me-2-Pyrd | 2-OMe | H | H | 1 |
| 3-120 | 1-Me-2-Pyrd | 4-OMe | H | H | 2 |
| 3-121 | 1-Me-2-Pip | 4-OMe | H | H | 2 |
| 3-122 | 1-Me-3-Pip | 4-OMe | H | H | 1 |
| 3-123 | 4-Me-2-Mor | 4-OMe | H | H | 1 |
| 3-124 | 1-Me-4-Pip | 4-OMe | H | H | 0 |
| 3-125 | 1-Me-2-Pyrd | 3-Et | H | H | 2 |
| 3-126 | 1-Me-2-Pip | 3-Et | H | H | 2 |
| 3-127 | 1-Me-2-Pyrd | 4-Et | H | H | 2 |
| 3-128 | 1-Me-2-Pip | 3-Et | 5-OMe | H | 2 |
| 3-129 | 1-Me-2-Pyrd | 4-iPr | H | H | 2 |
| 3-130 | 1-Me-2-Pyrd | 4-Ph | H | H | 2 |
| 3-131 | 1-Me-2-Pip | 4-Ph | H | H | 2 |
| 3-132 | 1-Me-2-Pyrd | 3-Me | 5-Me | H | 2 |
| 3-133 | 1-Me-2-Pyrd | 3-OEt | 5-OEt | H | 2 |
| 3-134 | 1-Me-2-Pyrd | 3-OH | 5-OH | H | 2 |
| 3-135 | 1-Me-2-Pyrd | 4-Me | H | H | 2 |
| 3-136 | 1-Me-2-Pyrd | 2-Me | H | H | 2 |
| 3-137 | 1-Me-2-Pyrd | 3-Br | H | H | 2 |
| 3-138 | 1-Me-2-Pip | 3-Br | H | H | 2 |
| 3-139 | 1-Et-2-Pyrd | 2-Cl | H | H | 2 |
| 3-140 | 1-Me-2-Pip | 2-Cl | H | H | 2 |
| 3-141 | 1-Me-2-Pyrd | 4-Cl | H | H | 2 |
| 3-142 | 1-Me-2-Pyrd | 2-Cl | 3-Cl | H | 2 |
| 3-143 | 1-Me-2-Pyrd | 3-Cl | 4-Cl | H | 2 |
| 3-144 | 1-Me-2-Pyrd | 3-Cl | 5-Cl | H | 2 |
| 3-145 | 1-Me-4-SucO-2-Pyrd | H | H | H | 1 |
| 3-146 | 1-Me-4-AcO-2-Pyrd | H | H | H | 1 |
| 3-147 | 1-Me-4-SucO-2-Pyrd | 3-OMe | H | H | 1 |
| 3-148 | 1-Me-4-AcO-2-Pyrd | 3-OMe | H | H | 1 |
| 3-149 | 1-Me-4-SucO-2-Pyrd | H | H | H | 2 |
| 3-150 | 1-Me-4-AcO-2-Pyrd | H | H | H | 2 |
| 3-151 | 1-Me-3-Pip | 3-OH | H | H | 1 |
| 3-152 | 1-Me-4-Pip | 3-OH | H | H | 0 |
| 3-153 | 2-Pip | 3-OH | H | H | 2 |
| 3-154 | 1-Me-4-SucO-2-Pyrd | 3-OMe | 5-OMe | H | 1 |
| 3-155 | 1-Me-4-GluO-2-Pyrd | H | H | H | 1 |
| 3-156 | 1-Me-4-GluO-2-Pyrd | 3-OMe | H | H | 1 |
| 3-157 | 1-Me-4-OCONH$_2$-2-Pyrd | H | H | H | 1 |
| 3-158 | 1-Me-4-OCONH$_2$-2-Pyrd | 3-OMe | H | H | 1 |
| 3-159 | 1-Me-4-OCON(Me)$_2$-2-Pyrd | H | H | H | 1 |
| 3-160 | 1-Me-4-OCON(Me)$_2$-2-Pyrd | 3-OMe | H | H | 1 |
| 3-161 | 4-Pip | 3-OMe | H | H | 0 |
| 3-162 | 2-Pyrd | 3-OH | H | H | 1 |
| 3-163 | 1-Me-2-Pyrd | 3-OH | H | H | 1 |
| 3-164 | 3-Pip | 3-OMe | H | H | 1 |
| 3-165 | 3-Pip | 3-OMe | H | H | 0 |
| 3-166 | 4-Pip | 3-OMe | H | H | 2 |
| 3-167 | 4-Pip | 3-OH | H | H | 2 |
| 3-168 | 1-Me-4-Pip | 3-OH | H | H | 2 |
| 3-169 | 2-Pip | 3-OMe | H | H | 1 |
| 3-170 | 4-OH-2-Pyrd | 3-Me | H | H | 1 |
| 3-171 | 2-Pip | 4-Et | H | H | 2 |
| 3-172 | 1-Me-2-Pip | 4-Et | H | H | 2 |
| 3-173 | 2-Pyrd | 3-OMe | H | H | 1 |
| 3-174 | 1-Me-4-OMe-Pyrd | 3-OMe | 5-OMe | H | 1 |
| 3-175 | 4-OH-2-Pyrd | H | H | H | 2 |
| 3-176 | 4-EtOCOO-2-Pyrd | H | H | H | 2 |
| 3-177 | 4-iPrOCOO-2-Pyrd | H | H | H | 2 |
| 3-178 | 4-tBuOCOO-2-Pyrd | H | H | H | 2 |
| 3-179 | 4-AcO-2-Pyrd | H | H | H | 2 |
| 3-180 | 4-PalO-2-Pyrd | H | H | H | 2 |

TABLE 3-continued

| Cpd. No. | R$^d$ | R$^a$ | R$^b$ | R$^c$ | m |
|---|---|---|---|---|---|
| 3-181 | 4-SteO-2-Pyrd | H | H | H | 2 |
| 3-182 | 1-Et-4-OH-2-Pyrd | H | H | H | 2 |
| 3-183 | 1-Et-4-EtOCOO-2-Pyrd | H | H | H | 2 |
| 3-184 | 1-Et-4-iPrOCOO-2-Pyrd | H | H | H | 2 |
| 3-185 | 1-Et-4-tBuOCOO-2-Pyrd | H | H | H | 2 |
| 3-186 | 1-Et-4-AcO-2-Pyrd | H | H | H | 2 |
| 3-187 | 1-Et-4-PalO-2-Pyrd | H | H | H | 2 |
| 3-188 | 1-Et-4-SteO-2-Pyrd | H | H | H | 2 |
| 3-189 | 3-Pip | 3-OH | H | H | 1 |
| 3-190 | 1-Me-3-Pip | 3-OH | 5-OH | H | 1 |
| 3-191 | 2-Mor | 3-OH | H | H | 1 |
| 3-192 | 2-Pyrd | 3-OH | 5-OH | H | 2 |
| 3-193 | 1-Et-2-Pyrd | 3-OH | H | H | 2 |
| 3-194 | 4-OH-2-Pyrd | 3-OH | H | H | 2 |
| 3-195 | 1-Me-4-OH-2-Pyrd | 3-OH | H | H | 2 |
| 3-196 | 4-EtOCOO-2-Pyrd | 3-OH | H | H | 2 |
| 3-197 | 4-iPrOCOO-2-Pyrd | 3-OH | H | H | 2 |
| 3-198 | 4-tBuOCOO-2-Pyrd | 3-OH | H | H | 2 |
| 3-199 | 4-AcO-2-Pyrd | 3-OH | H | H | 2 |
| 3-200 | 4-PalO-2-Pyrd | 3-OH | H | H | 2 |
| 3-201 | 4-SteO-2-Pyrd | 3-OH | H | H | 2 |
| 3-202 | 1-Me-4-EtOCOO-2-Pyrd | 3-OH | H | H | 2 |
| 3-203 | 1-Me-4-iPrOCOO-2-Pyrd | 3-OH | H | H | 2 |
| 3-204 | 1-Me-4-tBuOCOO-2-Pyrd | 3-OH | H | H | 2 |
| 3-205 | 1-Me-4-AcO-2-Pyrd | 3-OH | H | H | 2 |
| 3-206 | 1-Me-4-PalO-2-Pyrd | 3-OH | H | H | 2 |
| 3-207 | 1-Me-4-SteO-2-Pyrd | 3-OH | H | H | 2 |
| 3-208 | 3-Pip | 2-OH | H | H | 1 |
| 3-209 | 1-Me-3-Pip | 2-OH | H | H | 1 |
| 3-210 | 2-Mor | 2-OH | H | H | 1 |
| 3-211 | 2-Pyrd | 2-OH | H | H | 2 |
| 3-212 | 4-OH-2-Pyrd | 2-OH | H | H | 2 |
| 3-213 | 1-Me-4-OH-2-Pyrd | 2-OH | H | H | 2 |
| 3-214 | 4-EtOCOO-2-Pyrd | 2-OH | H | H | 2 |
| 3-215 | 4-iPrOCOO-2-Pyrd | 2-OH | H | H | 2 |
| 3-216 | 4-tBuOCOO-2-Pyrd | 2-OH | H | H | 2 |
| 3-217 | 4-AcO-2-Pyrd | 2-OH | H | H | 2 |
| 3-218 | 4-PalO-2-Pyrd | 2-OH | H | H | 2 |
| 3-219 | 4-SteO-2-Pyrd | 2-OH | H | H | 2 |
| 3-220 | 1-Me-4-EtOCOO-2-Pyrd | 2-OH | H | H | 2 |
| 3-221 | 1-Me-4-iPrOCOO-2-Pyrd | 2-OH | H | H | 2 |
| 3-222 | 1-Me-4-tBuOCOO-2-Pyrd | 2-OH | H | H | 2 |
| 3-223 | 1-Me-4-AcO-2-Pyrd | 2-OH | H | H | 2 |
| 3-224 | 1-Me-4-PalO-2-Pyrd | 2-OH | H | H | 2 |
| 3-225 | 1-Me-4-SteO-2-Pyrd | 2-OH | H | H | 2 |
| 3-226 | 3-Pip | 4-OH | H | H | 1 |
| 3-227 | 1-Me-3-Pip | 4-OH | H | H | 1 |
| 3-228 | 2-Mor | 4-OH | H | H | 1 |
| 3-229 | 2-Pyrd | 4-OH | H | H | 2 |
| 3-230 | 4-OH-2-Pyrd | 4-OH | H | H | 2 |
| 3-231 | 1-Me-4-OH-2-Pyrd | 4-OH | H | H | 2 |
| 3-232 | 4-EtOCOO-2-Pyrd | 4-OH | H | H | 2 |
| 3-233 | 4-iPrOCOO-2-Pyrd | 4-OH | H | H | 2 |
| 3-234 | 4-tBuOCOO-2-Pyrd | 4-OH | H | H | 2 |
| 3-235 | 4-AcO-2-Pyrd | 4-OH | H | H | 2 |
| 3-236 | 4-PalO-2-Pyrd | 4-OH | H | H | 2 |
| 3-237 | 4-SteO-2-Pyrd | 4-OH | H | H | 2 |
| 3-238 | 1-Me-4-EtOCOO-2-Pyrd | 4-OH | H | H | 2 |
| 3-239 | 1-Me-4-iPrOCOO-2-Pyrd | 4-OH | H | H | 2 |
| 3-240 | 1-Me-4-tBuOCOO-2-Pyrd | 4-OH | H | H | 2 |
| 3-241 | 1-Me-4-AcO-2-Pyrd | 4-OH | H | H | 2 |
| 3-242 | 1-Me-4-PalO-2-Pyrd | 4-OH | H | H | 2 |
| 3-243 | 1-Me-4-SteO-2-Pyrd | 4-OH | H | H | 2 |
| 3-244 | 3-Pip | 3-OMe | 4-OMe | 5-OMe | 1 |
| 3-245 | 1-Et-3-Pip | 3-OMe | H | H | 1 |
| 3-246 | 1-Et-2-Pyrd | 3-OMe | H | H | 2 |
| 3-247 | 4-OH-2-Pyrd | 3-OMe | H | H | 2 |
| 3-248 | 1-Me-4-OH-2-Pyrd | 3-OMe | H | H | 2 |
| 3-249 | 1-Et-4-OH-2-Pyrd | 3-OMe | H | H | 2 |
| 3-250 | 4-EtOCOO-2-Pyrd | 3-OMe | H | H | 2 |
| 3-251 | 4-iPrOCOO-2-Pyrd | 3-OMe | H | H | 2 |
| 3-252 | 4-tBuOCOO-2-Pyrd | 3-OMe | H | H | 2 |
| 3-253 | 4-AcO-2-Pyrd | 3-OMe | H | H | 2 |
| 3-254 | 4-PalO-2-Pyrd | 3-OMe | H | H | 2 |
| 3-255 | 4-SteO-2-Pyrd | 3-OMe | H | H | 2 |
| 3-256 | 1-Me-4-EtOCOO-2-Pyrd | 3-OMe | H | H | 2 |

TABLE 3-continued

| Cpd. No. | $R^d$ | $R^a$ | $R^b$ | $R^c$ | m |
|---|---|---|---|---|---|
| 3-257 | 1-Me-4-iPrOCOO-2-Pyrd | 3-OMe | H | H | 2 |
| 3-258 | 1-Me-4-tBuOCOO-2-Pyrd | 3-OMe | H | H | 2 |
| 3-259 | 1-Me-4-AcO-2-Pyrd | 3-OMe | H | H | 2 |
| 3-260 | 1-Me-4-PalO-2-Pyrd | 3-OMe | H | H | 2 |
| 3-261 | 1-Me-4-SteO-2-Pyrd | 3-OMe | H | H | 2 |
| 3-262 | 3-Pip | 2-OMe | H | H | 1 |
| 3-263 | 1-Me-3-Pip | 2-OMe | 3-OMe | H | 1 |
| 3-264 | 2-Mor | 2-OMe | H | H | 1 |
| 3-265 | 4-Me-2-Mor | 2-OMe | 3-OMe | H | 1 |
| 3-266 | 2-Pyrd | 2-OMe | H | H | 2 |
| 3-267 | 1-Me-2-Pyrd | 2-OMe | 3-OMe | H | 2 |
| 3-268 | 4-OH-2-Pyrd | 2-OMe | H | H | 2 |
| 3-269 | 1-Me-4-OH-2-Pyrd | 2-OMe | H | H | 2 |
| 3-270 | 4-EtOCOO-2-Pyrd | 2-OMe | H | H | 2 |
| 3-271 | 4-iPrOCOO-2-Pyrd | 2-OMe | H | H | 2 |
| 3-272 | 4-tBuOCOO-2-Pyrd | 2-OMe | H | H | 2 |
| 3-273 | 4-AcO-2-Pyrd | 2-OMe | H | H | 2 |
| 3-274 | 4-PalO-2-Pyrd | 2-OMe | H | H | 2 |
| 3-275 | 4-SteO-2-Pyrd | 2-OMe | H | H | 2 |
| 3-276 | 1-Me-4-EtOCOO-2-Pyrd | 2-OMe | H | H | 2 |
| 3-277 | 1-Me-4-iPrOCOO-2-Pyrd | 2-OMe | H | H | 2 |
| 3-278 | 1-Me-4-tBuOCOO-2-Pyrd | 2-OMe | H | H | 2 |
| 3-279 | 1-Me-4-AcO-2-Pyrd | 2-OMe | H | H | 2 |
| 3-280 | 1-Me-4-PalO-2-Pyrd | 2-OMe | H | H | 2 |
| 3-281 | 1-Me-4-SteO-2-Pyrd | 2-OMe | H | H | 2 |
| 3-282 | 3-Pip | 4-OMe | H | H | 1 |
| 3-283 | 1-Me-3-Pip | 3-OMe | 4-OMe | H | 1 |
| 3-284 | 2-Mor | 4-OMe | H | H | 1 |
| 3-285 | 4-Me-2-Mor | 3-OMe | 4-OMe | H | 1 |
| 3-286 | 2-Pyrd | 4-OMe | H | H | 2 |
| 3-287 | 1-Me-2-Pyrd | 3-OMe | 4-OMe | H | 2 |
| 3-288 | 4-OH-2-Pyrd | 4-OMe | H | H | 2 |
| 3-289 | 1-Me-4-OH-2-Pyrd | 4-OMe | H | H | 2 |
| 3-290 | 4-EtOCOO-2-Pyrd | 4-OMe | H | H | 2 |
| 3-291 | 4-iPrOCOO-2-Pyrd | 4-OMe | H | H | 2 |
| 3-292 | 4-tBuOCOO-2-Pyrd | 4-OMe | H | H | 2 |
| 3-293 | 4-AcO-2-Pyrd | 4-OMe | H | H | 2 |
| 3-294 | 4-PalO-2-Pyrd | 4-OMe | H | H | 2 |
| 3-295 | 4-SteO-2-Pyrd | 4-OMe | H | H | 2 |
| 3-296 | 1-Me-4-EtOCOO-2-Pyrd | 4-OMe | H | H | 2 |
| 3-297 | 1-Me-4-iPrOCOO-2-Pyrd | 4-OMe | H | H | 2 |
| 3-298 | 1-Me-4-tBuOCOO-2-Pyrd | 4-OMe | H | H | 2 |
| 3-299 | 1-Me-4-AcO-2-Pyrd | 4-OMe | H | H | 2 |
| 3-300 | 1-Me-4-PalO-2-Pyrd | 4-OMe | H | H | 2 |
| 3-301 | 1-Me-4-SteO-2-Pyrd | 4-OMe | H | H | 2 |
| 3-302 | 3-Pip | 2-OMe | 3-OMe | H | 1 |
| 3-303 | 2-Mor | 2-OMe | 3-OMe | H | 1 |
| 3-304 | 2-Pyrd | 2-OMe | 3-OMe | H | 2 |
| 3-305 | 4-OH-2-Pyrd | 2-OMe | 3-OMe | H | 2 |
| 3-306 | 1-Me-4-OH-2-Pyrd | 2-OMe | 3-OMe | H | 2 |
| 3-307 | 4-EtOCOO-2-Pyrd | 2-OMe | 3-OMe | H | 2 |
| 3-308 | 4-iPrOCOO-2-Pyrd | 2-OMe | 3-OMe | H | 2 |
| 3-309 | 4-tBuOCOO-2-Pyrd | 2-OMe | 3-OMe | H | 2 |
| 3-310 | 4-AcO-2-Pyrd | 2-OMe | 3-OMe | H | 2 |
| 3-311 | 4-PalO-2-Pyrd | 2-OMe | 3-OMe | H | 2 |
| 3-312 | 4-SteO-2-Pyrd | 2-OMe | 3-OMe | H | 2 |
| 3-313 | 1-Me-4-EtOCOO-2-Pyrd | 2-OMe | 3-OMe | H | 2 |
| 3-314 | 1-Me-4-iPrOCOO-2-Pyrd | 2-OMe | 3-OMe | H | 2 |
| 3-315 | 1-Me-4-tBuOCOO-2-Pyrd | 2-OMe | 3-OMe | H | 2 |
| 3-316 | 3-Pip | 3-Me | H | H | 1 |
| 3-317 | 2-Mor | 3-Me | H | H | 1 |
| 3-318 | 2-Pyrd | 3-Me | H | H | 2 |
| 3-319 | 4-OH-2-Pyrd | 3-Me | H | H | 2 |
| 3-320 | 1-Me-4-OH-2-Pyrd | 3-Me | H | H | 2 |
| 3-321 | 4-EtOCOO-2-Pyrd | 3-Me | H | H | 2 |
| 3-322 | 4-iPrOCOO-2-Pyrd | 3-Me | H | H | 2 |
| 3-323 | 4-tBuOCOO-2-Pyrd | 3-Me | H | H | 2 |
| 3-324 | 4-AcO-2-Pyrd | 3-Me | H | H | 2 |
| 3-325 | 4-PalO-2-Pyrd | 3-Me | H | H | 2 |
| 3-326 | 4-SteO-2-Pyrd | 3-Me | H | H | 2 |
| 3-327 | 1-Me-4-EtOCOO-2-Pyrd | 3-Me | H | H | 2 |
| 3-328 | 1-Me-4-iPrOCOO-2-Pyrd | 3-Me | H | H | 2 |
| 3-329 | 1-Me-4-tBuOCOO-2-Pyrd | 3-Me | H | H | 2 |
| 3-330 | 3-Pip | 3-F | H | H | 1 |
| 3-331 | 2-Mor | 3-F | H | H | 1 |
| 3-332 | 2-Pyrd | 3-F | H | H | 2 |

TABLE 3-continued

| Cpd. No. | R$^d$ | R$^a$ | R$^b$ | R$^c$ | m |
|---|---|---|---|---|---|
| 3-333 | 4-OH-2-Pyrd | 3-F | H | H | 2 |
| 3-334 | 1-Me-4-OH-2-Pyrd | 3-F | H | H | 2 |
| 3-335 | 4-EtOCOO-2-Pyrd | 3-F | H | H | 2 |
| 3-336 | 4-iPrOCOO-2-Pyrd | 3-F | H | H | 2 |
| 3-337 | 4-tBuOCOO-2-Pyrd | 3-F | H | H | 2 |
| 3-338 | 4-AcO-2-Pyrd | 3-F | H | H | 2 |
| 3-339 | 4-PalO-2-Pyrd | 3-F | H | H | 2 |
| 3-340 | 4-SteO-2-Pyrd | 3-F | H | H | 2 |
| 3-341 | 1-Me-4-EtOCOO-2-Pyrd | 3-F | H | H | 2 |
| 3-342 | 1-Me-4-iPrOCOO-2-Pyrd | 3-F | H | H | 2 |
| 3-343 | 1-Me-4-tBuOCOO-2-Pyrd | 3-F | H | H | 2 |
| 3-344 | 3-Pip | 3-Cl | H | H | 1 |
| 3-345 | 2-Mor | 3-Cl | H | H | 1 |
| 3-346 | 2-Pyrd | 3-Cl | H | H | 2 |
| 3-347 | 4-OH-2-Pyrd | 3-Cl | H | H | 2 |
| 3-348 | 1-Me-4-OH-2-Pyrd | 3-Cl | H | H | 2 |
| 3-349 | 4-EtOCOO-2-Pyrd | 3-Cl | H | H | 2 |
| 3-350 | 4-iPrOCOO-2-Pyrd | 3-Cl | H | H | 2 |
| 3-351 | 4-tBuOCOO-2-Pyrd | 3-Cl | H | H | 2 |
| 3-352 | 4-AcO-2-Pyrd | 3-Cl | H | H | 2 |
| 3-353 | 4-PalO-2-Pyrd | 3-Cl | H | H | 2 |
| 3-354 | 4-SteO-2-Pyrd | 3-Cl | H | H | 2 |
| 3-355 | 1-Me-4-EtOCOO-2-Pyrd | 3-Cl | H | H | 2 |
| 3-356 | 1-Me-4-iPrOCOO-2-Pyrd | 3-Cl | H | H | 2 |
| 3-357 | 1-Me-4-tBuOCOO-2-Pyrd | 3-Cl | H | H | 2 |
| 3-358 | 3-Pip | 2-CN | H | H | 1 |
| 3-359 | 2-Mor | 2-CN | H | H | 1 |
| 3-360 | 2-Pyrd | 2-CN | H | H | 2 |
| 3-361 | 4-OH-2-Pyrd | 2-CN | H | H | 2 |
| 3-362 | 1-Me-4-OH-2-Pyrd | 2-CN | H | H | 2 |
| 3-363 | 4-EtOCOO-2-Pyrd | 2-CN | H | H | 2 |
| 3-364 | 4-iPrOCOO-2-Pyrd | 2-CN | H | H | 2 |
| 3-365 | 4-tBuOCOO-2-Pyrd | 2-CN | H | H | 2 |
| 3-366 | 4-AcO-2-Pyrd | 2-CN | H | H | 2 |
| 3-367 | 4-PalO-2-Pyrd | 2-CN | H | H | 2 |
| 3-368 | 4-SteO-2-Pyrd | 2-CN | H | H | 2 |
| 3-369 | 1-Me-4-EtOCOO-2-Pyrd | 2-CN | H | H | 2 |
| 3-370 | 1-Me-4-iPrOCOO-2-Pyrd | 2-CN | H | H | 2 |
| 3-371 | 1-Me-4-tBuOCOO-2-Pyrd | 2-CN | H | H | 2 |
| 3-372 | 3-Pip | 3-OEt | H | H | 1 |
| 3-373 | 2-Mor | 3-OEt | H | H | 1 |
| 3-374 | 2-Pyrd | 3-OEt | H | H | 2 |
| 3-375 | 4-OH-2-Pyrd | 3-OEt | H | H | 2 |
| 3-376 | 1-Me-4-OH-2-Pyrd | 3-OEt | H | H | 2 |
| 3-377 | 4-EtOCOO-2-Pyrd | 3-OEt | H | H | 2 |
| 3-378 | 4-iPrOCOO-2-Pyrd | 3-OEt | H | H | 2 |
| 3-379 | 4-tBuOCOO-2-Pyrd | 3-OEt | H | H | 2 |
| 3-380 | 4-AcO-2-Pyrd | 3-OEt | H | H | 2 |
| 3-381 | 4-PalO-2-Pyrd | 3-OEt | H | H | 2 |
| 3-382 | 4-SteO-2-Pyrd | 3-OEt | H | H | 2 |
| 3-383 | 1-Me-4-EtOCOO-2-Pyrd | 3-OEt | H | H | 2 |
| 3-384 | 1-Me-4-iPrOCOO-2-Pyrd | 3-OEt | H | H | 2 |
| 3-385 | 1-Me-4-tBuOCOO-2-Pyrd | 3-OEt | H | H | 2 |
| 3-386 | 3-Pip | 2-CONH$_2$ | H | H | 1 |
| 3-387 | 2-Mor | 2-CONH$_2$ | H | H | 1 |
| 3-388 | 2-Pyrd | 2-CONH$_2$ | H | H | 2 |
| 3-389 | 4-OH-2-Pyrd | 2-CONH$_2$ | H | H | 2 |
| 3-390 | 1-Me-4-OH-2-Pyrd | 2-CONH$_2$ | H | H | 2 |
| 3-391 | 4-EtOCOO-2-Pyrd | 2-CONH$_2$ | H | H | 2 |
| 3-392 | 4-i-PrOCOO-2-Pyrd | 2-CONH$_2$ | H | H | 2 |
| 3-393 | 4-tBuOCOO-2-Pyrd | 2-CONH$_2$ | H | H | 2 |
| 3-394 | 4-AcO-2-Pyrd | 2-CONH$_2$ | H | H | 2 |
| 3-395 | 4-PalO-2-Pyrd | 2-CONH$_2$ | H | H | 2 |
| 3-396 | 4-SteO-2-Pyrd | 2-CONH$_2$ | H | H | 2 |
| 3-397 | 1-Me-4-EtOCOO-2-Pyrd | 2-CONH$_2$ | H | H | 2 |
| 3-398 | 1-Me-4-iPrOCOO-2-Pyrd | 2-CONH$_2$ | H | H | 2 |
| 3-399 | 1-Me-4-tBuOCOO-2-Pyrd | 2-CONH$_2$ | H | H | 2 |
| 3-400 | 3-Pip | 3-OCF$_2$H | H | H | 1 |
| 3-401 | 1-Me-3-Pip | 3-OCF$_2$H | H | H | 1 |
| 3-402 | 2-Mor | 3-OCF$_2$H | H | H | 1 |
| 3-403 | 4-Me-2-Mor | 3-OCF$_2$H | H | H | 1 |
| 3-404 | 2-Pyrd | 3-OCF$_2$H | H | H | 2 |
| 3-405 | 1-Me-2-Pyrd | 3-OCF$_2$H | H | H | 2 |
| 3-406 | 1-Et-2-Pyrd | 3-OCF$_2$H | H | H | 2 |
| 3-407 | 4-OH-2-Pyrd | 3-OCF$_2$H | H | H | 2 |
| 3-408 | 1-Me-4-OH-2-Pyrd | 3-OCF$_2$H | H | H | 2 |

TABLE 3-continued

| Cpd. No. | $R^d$ | $R^a$ | $R^b$ | $R^c$ | m |
|---|---|---|---|---|---|
| 3-409 | 4-EtOCOO-2-Pyrd | 3-OCF$_2$H | H | H | 2 |
| 3-410 | 4-iPrOCOO-2-Pyrd | 3-OCF$_2$H | H | H | 2 |
| 3-411 | 4-tBuOCOO-2-Pyrd | 3-OCF$_2$H | H | H | 2 |
| 3-412 | 4-AcO-2-Pyrd | 3-OCF$_2$H | H | H | 2 |
| 3-413 | 4-PalO-2-Pyrd | 3-OCF$_2$H | H | H | 2 |
| 3-414 | 4-SteO-2-Pyrd | 3-OCF$_2$H | H | H | 2 |
| 3-415 | 1-Me-4-EtOCOO-2-Pyrd | 3-OCF$_2$H | H | H | 2 |
| 3-416 | 1-Me-4-iPrOCOO-2-Pyrd | 3-OCF$_2$H | H | H | 2 |
| 3-417 | 1-Me-4-tBuOCOO-2-Pyrd | 3-OCF$_2$H | H | H | 2 |
| 3-418 | 1-Me-4-AcO-2-Pyrd | 3-OCF$_2$H | H | H | 2 |
| 3-419 | 1-Me-4-PalO-2-Pyrd | 3-OCF$_2$H | H | H | 2 |
| 3-420 | 1-Me-4-SteO-2-Pyrd | 3-OCF$_2$H | H | H | 2 |
| 3-421 | 3-Pip | 2-OCF$_2$H | H | H | 1 |
| 3-422 | 1-Me-3-Pip | 2-OCF$_2$H | H | H | 1 |
| 3-423 | 2-Mor | 2-OCF$_2$H | H | H | 1 |
| 3-424 | 4-Me-2-Mor | 2-OCF$_2$H | H | H | 1 |
| 3-425 | 2-Pyrd | 2-OCF$_2$H | H | H | 2 |
| 3-426 | 1-Me-2-Pyrd | 2-OCF$_2$H | H | H | 2 |
| 3-427 | 4-OH-2-Pyrd | 2-OCF$_2$H | H | H | 2 |
| 3-428 | 1-Me-4-OH-2-Pyrd | 2-OCF$_2$H | H | H | 2 |
| 3-429 | 4-EtOCOO-2-Pyrd | 2-OCF$_2$H | H | H | 2 |
| 3-430 | 4-iPrOCOO-2-Pyrd | 2-OCF$_2$H | H | H | 2 |
| 3-431 | 4-tBuOCOO-2-Pyrd | 2-OCF$_2$H | H | H | 2 |
| 3-432 | 4-AcO-2-Pyrd | 2-OCF$_2$H | H | H | 2 |
| 3-433 | 4-PalO-2-Pyrd | 2-OCF$_2$H | H | H | 2 |
| 3-434 | 4-SteO-2-Pyrd | 2-OCF$_2$H | H | H | 2 |
| 3-435 | 1-Me-4-EtOCOO-2-Pyrd | 2-OCF$_2$H | H | H | 2 |
| 3-436 | 1-Me-4-iPrOCOO-2-Pyrd | 2-OCF$_2$H | H | H | 2 |
| 3-437 | 1-Me-4-tBuOCOO-2-Pyrd | 2-OCF$_2$H | H | H | 2 |
| 3-438 | 1-Me-4-AcO-2-Pyrd | 2-OCF$_2$H | H | H | 2 |
| 3-439 | 1-Me-4-PalO-2-Pyrd | 2-OCF$_2$H | H | H | 2 |
| 3-440 | 1-Me-4-SteO-2-Pyrd | 2-OCF$_2$H | H | H | 2 |
| 3-441 | 3-Pip | 4-OCF$_2$H | H | H | 1 |
| 3-442 | 1-Me-3-Pip | 4-OCF$_2$H | H | H | 1 |
| 3-443 | 2-Mor | 4-OCF$_2$H | H | H | 1 |
| 3-444 | 4-Me-2-Mor | 4-OCF$_2$H | H | H | 1 |
| 3-445 | 2-Pyrd | 4-OCF$_2$H | H | H | 2 |
| 3-446 | 1-Me-2-Pyrd | 4-OCF$_2$H | H | H | 2 |
| 3-447 | 4-OH-2-Pyrd | 4-OCF$_2$H | H | H | 2 |
| 3-448 | 1-Me-4-OH-2-Pyrd | 4-OCF$_2$H | H | H | 2 |
| 3-449 | 4-EtOCOO-2-Pyrd | 4-OCF$_2$H | H | H | 2 |
| 3-450 | 4-iPrOCOO-2-Pyrd | 4-OCF$_2$H | H | H | 2 |
| 3-451 | 4-tBuOCOO-2-Pyrd | 4-OCF$_2$H | H | H | 2 |
| 3-452 | 4-AcO-2-Pyrd | 4-OCF$_2$H | H | H | 2 |
| 3-453 | 4-PalO-2-Pyrd | 4-OCF$_2$H | H | H | 2 |
| 3-454 | 4-SteO-2-Pyrd | 4-OCF$_2$H | H | H | 2 |
| 3-455 | 1-Me-4-EtOCOO-2-Pyrd | 4-OCF$_2$H | H | H | 2 |
| 3-456 | 1-Me-4-iPrOCOO-2-Pyrd | 4-OCF$_2$H | H | H | 2 |
| 3-457 | 1-Me-4-tBuOCOO-2-Pyrd | 4-OCF$_2$H | H | H | 2 |
| 3-458 | 1-Me-4-AcO-2-Pyrd | 4-OCF$_2$H | H | H | 2 |
| 3-459 | 1-Me-4-PalO-2-Pyrd | 4-OCF$_2$H | H | H | 2 |
| 3-460 | 1-Me-4-SteO-2-Pyrd | 4-OCF$_2$H | H | H | 2 |
| 3-461 | 3-Pip | 3-OCFH$_2$ | H | H | 1 |
| 3-462 | 1-Me-3-Pip | 3-OCFH$_2$ | H | H | 1 |
| 3-463 | 2-Mor | 3-OCFH$_2$ | H | H | 1 |
| 3-464 | 4-Me-2-Mor | 3-OCFH$_2$ | H | H | 1 |
| 3-465 | 2-Pyrd | 3-OCFH$_2$ | H | H | 2 |
| 3-466 | 1-Me-2-Pyrd | 3-OCFH$_2$ | H | H | 2 |
| 3-467 | 1-Et-2-Pyrd | 3-OCFH$_2$ | H | H | 2 |
| 3-468 | 4-OH-2-Pyrd | 3-OCFH$_2$ | H | H | 2 |
| 3-469 | 1-Me-4-OH-2-Pyrd | 3-OCFH$_2$ | H | H | 2 |
| 3-470 | 4-EtOCOO-2-Pyrd | 3-OCFH$_2$ | H | H | 2 |
| 3-471 | 4-iPrOCOO-2-Pyrd | 3-OCFH$_2$ | H | H | 2 |
| 3-472 | 4-tBuOCOO-2-Pyrd | 3-OCFH$_2$ | H | H | 2 |
| 3-473 | 4-AcO-2-Pyrd | 3-OCFH$_2$ | H | H | 2 |
| 3-474 | 4-PalO-2-Pyrd | 3-OCFH$_2$ | H | H | 2 |
| 3-475 | 4-SteO-2-Pyrd | 3-OCFH$_2$ | H | H | 2 |
| 3-476 | 1-Me-4-EtOCOO-2-Pyrd | 3-OCFH$_2$ | H | H | 2 |
| 3-477 | 1-Me-4-iPrOCOO-2-Pyrd | 3-OCFH$_2$ | H | H | 2 |
| 3-478 | 1-Me-4-tBuOCOO-2-Pyrd | 3-OCFH$_2$ | H | H | 2 |
| 3-479 | 1-Me-4-AcO-2-Pyrd | 3-OCFH$_2$ | H | H | 2 |
| 3-480 | 1-Me-4-PalO-2-Pyrd | 3-OCFH$_2$ | H | H | 2 |
| 3-481 | 1-Me-4-SteO-2-Pyrd | 3-OCFH$_2$ | H | H | 2 |
| 3-482 | 3-Pip | 2-OCFH$_2$ | H | H | 1 |
| 3-483 | 1-Me-3-Pip | 2-OCFH$_2$ | H | H | 1 |
| 3-484 | 2-Mor | 2-OCFH$_2$ | H | H | 1 |

TABLE 3-continued

| Cpd. No. | R$^d$ | R$^a$ | R$^b$ | R$^c$ | m |
|---|---|---|---|---|---|
| 3-485 | 4-Me-2-Mor | 2-OCFH$_2$ | H | H | 1 |
| 3-486 | 2-Pyrd | 2-OCFH$_2$ | H | H | 2 |
| 3-487 | 1-Me-2-Pyrd | 2-OCFH$_2$ | H | H | 2 |
| 3-488 | 4-OH-2-Pyrd | 2-OCFH$_2$ | H | H | 2 |
| 3-489 | 1-Me-4-OH-2-Pyrd | 2-OCFH$_2$ | H | H | 2 |
| 3-490 | 4-EtOCOO-2-Pyrd | 2-OCFH$_2$ | H | H | 2 |
| 3-491 | 4-iPrOCOO-2-Pyrd | 2-OCFH$_2$ | H | H | 2 |
| 3-492 | 4-tBuOCOO-2-Pyrd | 2-OCFH$_2$ | H | H | 2 |
| 3-493 | 4-AcO-2-Pyrd | 2-OCFH$_2$ | H | H | 2 |
| 3-494 | 4-PalO-2-Pyrd | 2-OCFH$_2$ | H | H | 2 |
| 3-495 | 4-SteO-2-Pyrd | 2-OCFH$_2$ | H | H | 2 |
| 3-496 | 1-Me-4-EtOCOO-2-Pyrd | 2-OCFH$_2$ | H | H | 2 |
| 3-497 | 1-Me-4-iPrOCOO-2-Pyrd | 2-OCFH$_2$ | H | H | 2 |
| 3-498 | 1-Me-4-tBuOCOO-2-Pyrd | 2-OCFH$_2$ | H | H | 2 |
| 3-499 | 1-Me-4-AcO-2-Pyrd | 2-OCFH$_2$ | H | H | 2 |
| 3-500 | 1-Me-4-PalO-2-Pyrd | 2-OCFH$_2$ | H | H | 2 |
| 3-501 | 1-Me-4-SteO-2-Pyrd | 2-OCFH$_2$ | H | H | 2 |
| 3-502 | 3-Pip | 4-OCFH$_2$ | H | H | 1 |
| 3-503 | 1-Me-3-Pip | 4-OCFH$_2$ | H | H | 1 |
| 3-504 | 2-Mor | 4-OCFH$_2$ | H | H | 1 |
| 3-505 | 4-Me-2-Mor | 4-OCFH$_2$ | H | H | 1 |
| 3-506 | 2-Pyrd | 4-OCFH$_2$ | H | H | 2 |
| 3-507 | 1-Me-2-Pyrd | 4-OCFH$_2$ | H | H | 2 |
| 3-508 | 4-OH-2-Pyrd | 4-OCFH$_2$ | H | H | 2 |
| 3-509 | 1-Me-4-OH-2-Pyrd | 4-OCFH$_2$ | H | H | 2 |
| 3-510 | 4-EtOCOO-2-Pyrd | 4-OCFH$_2$ | H | H | 2 |
| 3-511 | 4-iPrOCOO-2-Pyrd | 4-OCFH$_2$ | H | H | 2 |
| 3-512 | 4-tBuOCOO-2-Pyrd | 4-OCFH$_2$ | H | H | 2 |
| 3-513 | 4-AcO-2-Pyrd | 4-OCFH$_2$ | H | H | 2 |
| 3-514 | 4-PalO-2-Pyrd | 4-OCFH$_2$ | H | H | 2 |
| 3-515 | 4-SteO-2-Pyrd | 4-OCFH$_2$ | H | H | 2 |
| 3-516 | 1-Me-4-EtOCOO-2-Pyrd | 4-OCFH$_2$ | H | H | 2 |
| 3-517 | 1-Me-4-iPrOCOO-2-Pyrd | 4-OCFH$_2$ | H | H | 2 |
| 3-518 | 1-Me-4-tBuOCOO-2-Pyrd | 4-OCFH$_2$ | H | H | 2 |
| 3-519 | 1-Me-4-AcO-2-Pyrd | 4-OCFH$_2$ | H | H | 2 |
| 3-520 | 1-Me-4-PalO-2-Pyrd | 4-OCFH$_2$ | H | H | 2 |
| 3-521 | 1-Me-4-SteO-2-Pyrd | 4-OCFH$_2$ | H | H | 2 |
| 3-522 | 3-Pip | 3-OCF$_3$ | H | H | 1 |
| 3-523 | 1-Me-3-Pip | 3-OCF$_3$ | H | H | 1 |
| 3-524 | 2-Mor | 3-OCF$_3$ | H | H | 1 |
| 3-525 | 4-Me-2-Mor | 3-OCF$_3$ | H | H | 1 |
| 3-526 | 2-Pyrd | 3-OCF$_3$ | H | H | 2 |
| 3-527 | 1-Me-2-Pyrd | 3-OCF$_3$ | H | H | 2 |
| 3-528 | 1-Et-2-Pyrd | 3-OCF$_3$ | H | H | 2 |
| 3-529 | 4-OH-2-Pyrd | 3-OCF$_3$ | H | H | 2 |
| 3-530 | 1-Me-4-OH-2-Pyrd | 3-OCF$_3$ | H | H | 2 |
| 3-531 | 4-EtOCOO-2-Pyrd | 3-OCF$_3$ | H | H | 2 |
| 3-532 | 4-iPrOCOO-2-Pyrd | 3-OCF$_3$ | H | H | 2 |
| 3-533 | 4-tBuOCOO-2-Pyrd | 3-OCF$_3$ | H | H | 2 |
| 3-534 | 4-AcO-2-Pyrd | 3-OCF$_3$ | H | H | 2 |
| 3-535 | 4-PalO-2-Pyrd | 3-OCF$_3$ | H | H | 2 |
| 3-536 | 4-SteO-2-Pyrd | 3-OCF$_3$ | H | H | 2 |
| 3-537 | 1-Me-4-EtOCOO-2-Pyrd | 3-OCF$_3$ | H | H | 2 |
| 3-538 | 1-Me-4-iPrOCOO-2-Pyrd | 3-OCF$_3$ | H | H | 2 |
| 3-539 | 1-Me-4-tBuOCOO-2-Pyrd | 3-OCF$_3$ | H | H | 2 |
| 3-540 | 1-Me-4-AcO-2-Pyrd | 3-OCF$_3$ | H | H | 2 |
| 3-541 | 1-Me-4-PalO-2-Pyrd | 3-OCF$_3$ | H | H | 2 |
| 3-542 | 1-Me-4-SteO-2-Pyrd | 3-OCF$_3$ | H | H | 2 |
| 3-543 | 1-Et-3-Pip | 3-OMe | 5-OMe | H | 1 |
| 3-544 | 2-Mor | 3-OMe | 5-OMe | H | 1 |
| 3-545 | 4-Et-2-Mor | 3-OMe | 5-OMe | H | 1 |
| 3-546 | 2-Pyrd | 3-OMe | 5-OMe | H | 2 |
| 3-547 | 1-Et-2-Pyrd | 3-OMe | 5-OMe | H | 2 |
| 3-548 | 4-OH-2-Pyrd | 3-OMe | 5-OMe | H | 2 |
| 3-549 | 1-Me-4-OH-2-Pyrd | 3-OMe | 5-OMe | H | 2 |
| 3-550 | 1-Et-4-OH-2-Pyrd | 3-OMe | 5-OMe | H | 2 |
| 3-551 | 4-EtOCOO-2-Pyrd | 3-OMe | 5-OMe | H | 2 |
| 3-552 | 4-iPrOCOO-2-Pyrd | 3-OMe | 5-OMe | H | 2 |
| 3-553 | 4-tBuOCOO-2-Pyrd | 3-OMe | 5-OMe | H | 2 |
| 3-554 | 4-AcO-2-Pyrd | 3-OMe | 5-OMe | H | 2 |
| 3-555 | 4-PalO-2-Pyrd | 3-OMe | 5-OMe | H | 2 |
| 3-556 | 4-SteO-2-Pyrd | 3-OMe | 5-OMe | H | 2 |
| 3-557 | 1-Me-4-EtOCOO-2-Pyrd | 3-OMe | 5-OMe | H | 2 |
| 3-558 | 1-Me-4-iPrOCOO-2-Pyrd | 3-OMe | 5-OMe | H | 2 |
| 3-559 | 1-Me-4-tBuOCOO-2-Pyrd | 3-OMe | 5-OMe | H | 2 |
| 3-560 | 1-Me-4-AcO-2-Pyrd | 3-OMe | 5-OMe | H | 2 |

TABLE 3-continued

| Cpd. No. | R$^d$ | R$^a$ | R$^b$ | R$^c$ | m |
|---|---|---|---|---|---|
| 3-561 | 1-Me-4-PalO-2-Pyrd | 3-OMe | 5-OMe | H | 2 |
| 3-562 | 1-Me-4-SteO-2-Pyrd | 3-OMe | 5-OMe | H | 2 |
| 3-563 | 1-Me-4-EtOCOO-2-Pyrd | H | H | H | 2 |
| 3-564 | 1-Me-4-iPrOCOO-2-Pyrd | H | H | H | 2 |
| 3-565 | 1-Me-4-tBuOCOO-2-Pyrd | H | H | H | 2 |
| 3-566 | 1-Me-4-PalO-2-Pyrd | H | H | H | 2 |
| 3-567 | 1-Me-4-SteO-2-Pyrd | H | H | H | 2 |
| 3-568 | 1-Me-4-SucO-2-Pyrd | 3-OMe | H | H | 2 |
| 3-569 | 2-Pyrd | 3-OMe | H | H | 2 |
| 3-570 | 1-Me-4-SucO-2-Pyrd | 3-OMe | 5-OMe | H | 2 |
| 3-571 | 1-Me-2-Pyrd | 2-F | H | H | 2 |
| 3-572 | 2-Pyrd | 2-F | H | H | 2 |
| 3-573 | 3-Pip | 2-F | H | H | 1 |
| 3-574 | 1-Me-3-Pip | 2-F | H | H | 1 |
| 3-575 | 4-Me-2-Mor | 2-F | H | H | 1 |
| 3-576 | 1-Me-4-OH-2-Pyrd | 2-F | H | H | 2 |
| 3-577 | 1-Me-4-SucO-2-Pyrd | 2-F | H | H | 2 |
| 3-578 | 1-Me-4-EtOCOO-2-Pyrd | 2-F | H | H | 2 |
| 3-579 | 1-Me-4-AcO-2-Pyrd | 2-F | H | H | 2 |
| 3-580 | 1-Me-4-PalO-2-Pyrd | 2-F | H | H | 2 |
| 3-581 | 1-Me-2-Pyrd | 4-F | H | H | 2 |
| 3-582 | 2-Pyrd | 4-F | H | H | 2 |
| 3-583 | 3-Pip | 4-F | H | H | 1 |
| 3-584 | 1-Me-3-Pip | 4-F | H | H | 1 |
| 3-585 | 4-Me-2-Mor | 4-F | H | H | 1 |
| 3-586 | 1-Me-4-OH-2-Pyrd | 4-F | H | H | 2 |
| 3-587 | 1-Me-4-SucO-2-Pyrd | 4-F | H | H | 2 |
| 3-588 | 1-Me-4-EtOCOO-2-Pyrd | 4-F | H | H | 2 |
| 3-589 | 1-Me-4-AcO-2-Pyrd | 4-F | H | H | 2 |
| 3-590 | 1-Me-4-PalO-2-Pyrd | 4-F | H | H | 2 |
| 3-591 | 1-Me-2-Pyrd | 2-Cl | H | H | 2 |
| 3-592 | 2-Pyrd | 2-Cl | H | H | 2 |
| 3-593 | 3-Pip | 2-Cl | H | H | 1 |
| 3-594 | 4-Me-2-Mor | 2-Cl | H | H | 1 |
| 3-595 | 1-Me-4-OH-2-Pyrd | 2-Cl | H | H | 2 |
| 3-596 | 1-Me-4-SucO-2-Pyrd | 2-Cl | H | H | 2 |
| 3-597 | 1-Me-4-EtOCOO-2-Pyrd | 2-Cl | H | H | 2 |
| 3-598 | 1-Me-4-AcO-2-Pyrd | 2-Cl | H | H | 2 |
| 3-599 | 1-Me-4-PalO-2-Pyrd | 2-Cl | H | H | 2 |
| 3-600 | 2-Pyrd | 4-Cl | H | H | 2 |
| 3-601 | 3-Pip | 4-Cl | H | H | 1 |
| 3-602 | 1-Me-3-Pip | 4-Cl | H | H | 1 |
| 3-603 | 4-Me-2-Mor | 4-Cl | H | H | 1 |
| 3-604 | 1-Me-4-OH-2-Pyrd | 4-Cl | H | H | 2 |
| 3-605 | 1-Me-4-SucO-2-Pyrd | 4-Cl | H | H | 2 |
| 3-606 | 1-Me-4-EtOCOO-2-Pyrd | 4-Cl | H | H | 2 |
| 3-607 | 1-Me-4-AcO-2-Pyrd | 4-Cl | H | H | 2 |
| 3-608 | 1-Me-4-PalO-2-Pyrd | 4-Cl | H | H | 2 |
| 3-609 | 1-Me-2-Pyrd | 4-CN | H | H | 2 |
| 3-610 | 2-Pyrd | 4-CN | H | H | 2 |
| 3-611 | 3-Pip | 4-CN | H | H | 1 |
| 3-612 | 1-Me-3-Pip | 4-CN | H | H | 1 |
| 3-613 | 4-Me-2-Mor | 4-CN | H | H | 1 |
| 3-614 | 1-Me-4-OH-2-Pyrd | 4-CN | H | H | 2 |
| 3-615 | 1-Me-4-SucO-2-Pyrd | 4-CN | H | H | 2 |
| 3-616 | 1-Me-4-EtOCOO-2-Pyrd | 4-CN | H | H | 2 |
| 3-617 | 1-Me-4-AcO-2-Pyrd | 4-CN | H | H | 2 |
| 3-618 | 1-Me-4-PalO-2-Pyrd | 4-CN | H | H | 2 |
| 3-619 | 1-Me-2-Pyrd | 3-CN | H | H | 2 |
| 3-620 | 2-Pyrd | 3-CN | H | H | 2 |
| 3-621 | 3-Pip | 3-CN | H | H | 1 |
| 3-622 | 1-Me-3-Pip | 3-CN | H | H | 1 |
| 3-623 | 4-Me-2-Mor | 3-CN | H | H | 1 |
| 3-624 | 1-Me-4-OH-2-Pyrd | 3-CN | H | H | 2 |
| 3-625 | 1-Me-4-SucO-2-Pyrd | 3-CN | H | H | 2 |
| 3-626 | 1-Me-4-EtOCOO-2-Pyrd | 3-CN | H | H | 2 |
| 3-627 | 1-Me-4-AcO-2-Pyrd | 3-CN | H | H | 2 |
| 3-628 | 1-Me-4-PalO-2-Pyrd | 3-CN | H | H | 2 |
| 3-629 | 4-Me-2-Mor | 3-Br | H | H | 1 |
| 3-630 | 1-Me-4-OH-2-Pyrd | 3-Br | H | H | 2 |
| 3-631 | 1-Me-4-SucO-2-Pyrd | 3-Br | H | H | 2 |
| 3-632 | 1-Me-4-EtOCOO-2-Pyrd | 3-Br | H | H | 2 |
| 3-633 | 1-Me-4-AcO-2-Pyrd | 3-Br | H | H | 2 |
| 3-634 | 1-Me-4-PalO-2-Pyrd | 3-Br | H | H | 2 |
| 3-635 | 1-Me-3-Pip | 2-Me | H | H | 1 |
| 3-636 | 4-Me-2-Mor | 2-Me | H | H | 1 |

TABLE 3-continued

| Cpd. No. | $R^d$ | $R^a$ | $R^b$ | $R^c$ | m |
|---|---|---|---|---|---|
| 3-637 | 1-Et-4-OH-2-Pyrd | 2-Me | H | H | 2 |
| 3-638 | 1-Me-4-SucO-2-Pyrd | 2-Me | H | H | 2 |
| 3-639 | 1-Me-4-EtCCOO-2-Pyrd | 2-Me | 3-OMe | H | 2 |
| 3-640 | 1-Me-4-AcO-2-Pyrd | 2-Me | H | H | 2 |
| 3-641 | 1-Me-4-PalO-2-Pyrd | 2-Me | H | H | 2 |
| 3-642 | 1-Me-3-Pip | 4-Me | H | H | 1 |
| 3-643 | 4-Me-2-Mor | 4-Me | H | H | 1 |
| 3-644 | 1-Me-4-OH-2-Pyrd | 4-Me | H | H | 2 |
| 3-645 | 1-Me-4-SucO-2-Pyrd | 4-Me | H | H | 2 |
| 3-364 | 1-Me-4-EtOCOO-2-Pyrd | 4-Me | H | H | 2 |
| 3-647 | 1-Me-4-AcO-2-Pyrd | 4-Me | H | H | 2 |
| 3-648 | 1-Me-4-PalO-2-Pyrd | 4-Me | H | H | 2 |
| 3-649 | 2-Pyrd | 3-Me | 5-Me | H | 2 |
| 3-650 | 3-Pip | 3-Me | 5-Me | H | 1 |
| 3-651 | 1-Me-3-Pip | 3-Me | 5-Me | H | 1 |
| 3-652 | 4-Me-2-Mor | 3-Me | 5-Me | H | 1 |
| 3-653 | 1-Me-4-OH-2-Pyrd | 3-Me | 5-Me | H | 2 |
| 3-654 | 1-Me-4-SucO-2-Pyrd | 3-Me | 5-Me | H | 2 |
| 3-655 | 1-Me-4-EtOCOO-2-Pyrd | 3-Me | 5-Me | H | 2 |
| 3-656 | 1-Me-4-iPrOCOO-2-Pyrd | 3-Me | 5-Me | H | 2 |
| 3-657 | 1-Me-4-tBuOCOO-2-Pyrd | 3-Me | 5-Me | H | 2 |
| 3-658 | 1-Me-4-AcO-2-Pyrd | 3-Me | 5-Me | H | 2 |
| 3-659 | 1-Me-4-PalO-2-Pyrd | 3-Me | 5-Me | H | 2 |
| 3-660 | 1-Me-4-SteO-2-Pyrd | 3-Me | 5-Me | H | 2 |
| 3-661 | 1-Me-3-Pip | 4-Et | H | H | 1 |
| 3-662 | 4-Me-2-Mor | 4-Et | H | H | 1 |
| 3-663 | 1-Me-4-OH-2-Pyrd | 4-Et | H | H | 2 |
| 3-664 | 1-Me-4-SucO-2-Pyrd | 4-Et | H | H | 2 |
| 3-665 | 1-Me-4-EtOCOO-2-Pyrd | 4-Et | H | H | 2 |
| 3-666 | 1-Me-3-Pip | 3-Et | H | H | 1 |
| 3-667 | 4-Me-2-Mor | 3-Et | H | H | 1 |
| 3-668 | 1-Me-4-OH-2-Pyrd | 3-Et | H | H | 2 |
| 3-669 | 1-Me-4-SucO-2-Pyrd | 3-Et | H | H | 2 |
| 3-670 | 1-Me-4-EtOCOO-2-Pyrd | 3-Et | H | H | 2 |
| 3-671 | 2-Pip | 3-OMe | H | H | 2 |
| 3-672 | 4-OH-2-Pyrd | 3-OMe | H | H | 1 |
| 3-673 | 1-Me-4-SucO-2-Pyrd | 2-OH | H | H | 2 |
| 3-674 | 1-Me-4-SucO-2-Pyrd | 4-OH | H | H | 2 |
| 3-675 | 1-Me-4-SucO-2-Pyrd | 3-OH | H | H | 2 |
| 3-676 | 1-Me-4-SucO-2-Pyrd | 3-Me | H | H | 2 |
| 3-677 | 1-Me-4-SucO-2-Pyrd | 3-Cl | H | H | 2 |
| 3-678 | 1-Me-4-SucO-2-Pyrd | 3-F | H | H | 2 |
| 3-679 | 1-Me-4-SucO-2-Pyrd | 2-CN | H | H | 2 |
| 3-680 | 1-Me-4-SucO-2-Pyrd | 3-Et | H | H | 2 |
| 3-681 | 1-Me-4-SucO-2-Pyrd | 2-OMe | H | H | 2 |
| 3-682 | 1-Me-4-SucO-2-Pyrd | 4-OMe | H | H | 2 |
| 3-683 | 1-Me-4-OH-2-Pyrd | 3-OH | 5-OH | H | 2 |
| 3-684 | 1-Me-4-SucO-2-Pyrd | 3-OH | 5-OH | H | 2 |
| 3-685 | 1-Me-3-Pip | 3-Br | H | H | 1 |
| 3-686 | 1-Me-3-Pip | 2-Cl | H | H | 1 |
| 3-687 | 1-Me-4-SucO-2-Pyrd | 2-OCHF$_2$ | H | H | 2 |
| 3-688 | 1-Me-4-SucO-2-Pyrd | 4-OCHF$_2$ | H | H | 2 |
| 3-689 | 1-Me-4-SucO-2-Pyrd | 3-OCHF$_2$ | H | H | 2 |
| 3-690 | 1-Me-4-SucO-2-Pyrd | 3-OCF$_3$ | H | H | 2 |
| 3-691 | 1-Me-2-Pyrd | 4-OEt | H | H | 2 |
| 3-692 | 1-Me-3-Pip | 4-OEt | H | H | 1 |
| 3-693 | 4-Me-2-Mor | 4-OEt | H | H | 1 |
| 3-694 | 1-Me-4-OH-2-Pyrd | 4-OEt | H | H | 2 |
| 3-695 | 1-Me-4-SucO-2-Pyrd | 4-OEt | H | H | 2 |
| 3-696 | 1-Me-2-Pyrd | 2-OEt | H | H | 2 |
| 3-697 | 1-Me-3-Pip | 2-OEt | H | H | 1 |
| 3-698 | 4-Me-2-Mor | 2-OEt | H | H | 1 |
| 3-699 | 1-Me-4-OH-2-Pyrd | 2-OEt | H | H | 2 |
| 3-700 | 1-Me-4-SucO-2-Pyrd | 2-OEt | H | H | 2 |

Of the compounds listed above, the following are preferred for the treatment of circulatory diseases, that is to say Compounds No.

1-1, 1-3, 1-9, 1-17, 1-18, 1-30, 1-32, 1-37, 1-38, 1-39, 1-49, 1-59, 1-61, 1-68, 1-78, 1-81, 1-83, 1-85, 1-93, 1-117, 1-130, 1-161, 1-197, 1-203, 3-1, 3-5, 3-10, 3-16, 3-18, 3-19, 3-24, 3-26, 3-30, 3-31, 3-32, 3-35, 3-36, 3-38, 3-39, 3-41, 3-44, 3-45, 3-50, 3-52, 3-57, 3-60, 3-62, 3-63, 3-64, 3-65, 3-66, 3-67, 3-70, 3-72, 3-73, 3-74, 3-75, 3-78, 3-81, 3-82, 3-84, 3-86, 3-87, 3-88, 3-90, 3-92, 3-93, 3-94, 3-95, 3-97, 3-98, 3-100, 3-101, 3-103, 3-104, 3-105, 3-106, 3-110, 3-111, 3-112, 3-113, 3-114, 3-115, 3-117, 3-118, 3-120, 3-121, 3-122, 3-123, 3-124, 3-125, 3-127, 3-130, 3-132, 3-133, 3-134, 3-135, 3-136, 3-137, 3-141, 3-149, 3-150, 3-151, 3-152, 3-161, 3-164, 3-175, 3-189, 3-190, 3-195, 3-202, 3-209, 3-213, 3-247, 3-248, 3-256, 3-257, 3-258, 3-259, 3-260, 3-261, 3-262, 3-263, 3-265, 3-267, 3-268, 3-269, 3-276, 3-277, 3-280, 3-282, 3-288, 3-289, 3-296, 3-299, 3-306, 3-320, 3-327, 3-330, 3-334, 3-341, 3-348, 3-355, 3-362, 3-369, 3-372, 3-373, 3-375, 3-376, 3-383, 3-384, 3-390, 3-400, 3-401, 3-402, 3-403, 3-404, 3-405, 3-408, 3-415, 3-416, 3-417, 3-418, 3-419, 3-420, 3-422, 3-424, 3-426, 3-428, 3-435, 3-439, 3-442, 3-444, 3-446, 3-448, 3-455, 3-458, 3-459, 3-461, 3-462, 3-464, 3-466, 3-469, 3-476, 3-479, 3-480, 3-483, 3-485, 3-487, 3-489, 3-496, 3-503, 3-505, 3-507, 3-509, 3-523, 3-525, 3-527, 3-530, 3-537, 3-538, 3-540, 3-541, 3-548, 3-549, 3-557, 3-558, 3-560, 3-561, 3-562, 3-563, 3-564, 3-565, 3-566, 3-567, 3-568, 3-569, 3-570, 3-571, 3-574, 3-575, 3-576, 3-577, 3-578, 3-580, 3-581, 3-584, 3-585, 3-586, 3-587, 3-588, 3-591, 3-593, 3-594, 3-595, 3-596, 3-597, 3-598, 3-599, 3-602, 3-603, 3-604, 3-605, 3-606, 3-607, 3-608, 3-609, 3-612, 3-613, 3-614, 3-615, 3-616, 3-619, 3-622, 3-623, 3-624, 3-625, 3-626, 3-628, 3-629, 3-630, 3-631, 3-633, 3-634, 3-635 3-636, 3-637, 3-642, 3-643, 3-644, 3-649, 3-650, 3-651, 3-652, 3-653, 3-661, 3-662, 3-663, 3-664, 3-665, 3-666, 3-667, 3-668, 3-669, 3-670, 3-675, 3-676, 3-677, 3-678, 3-679, 3-680, 3-681, 3-682, 3-683, 3-685, 3-686, 3-687, 3-688, 3-689, 3-690, 3-691, 3-694, 3-696 and 3-699.

More preferred compounds for the treatment of circulatory diseases are Compounds No.

1-1, 1-18, 1-30, 1-38, 1-59, 1-61, 1-68, 1-81, 1-83, 1-85, 1-117, 1-130, 1-197, 3-1, 3-16, 3-19, 3-26, 3-32, 3-38, 3-39, 3-44, 3-50, 3-57, 3-60, 3-63, 3-65, 3-70, 3-74, 3-75, 3-78, 3-84, 3-87, 3-90, 3-93, 3-95, 3-98, 3-100, 3-105, 3-110, 3-112, 3-113, 3-115, 3-118, 3-120, 3-122, 3-125, 3-127, 3-132, 3-133, 3-135, 3-136, 3-137, 1-141, 3-149, 3-150, 3-151, 3-152, 3-164, 3-195, 3-202, 3-213, 3-248, 3-256, 3-257, 3-259, 3-260, 3-261, 3-269, 3-289, 3-296, 3-320, 3-334, 3-348, 3-362, 3-376, 3-383, 3-400, 3-401, 3-403, 3-405, 3-408, 3-415, 3-416, 3-418, 3-419, 3-426, 3-428, 3-446, 3-448, 3-466, 3-469, 3-487, 3-489, 3-507, 3-509, 3-527, 3-530, 3-549, 3-557, 3-558, 3-560, 3-561, 3-562, 3-563, 3-564, 3-566, 3-568, 3-570, 3-571, 3-576, 3-577, 3-581, 3-586, 3-587, 3-591, 3-595, 3-596, 3-604, 3-605, 3-609, 3-614, 3-615, 3-619, 3-624, 3-625, 3-630, 3-631, 3-633, 3-634, 3-637, 3-644, 3-651, 3-663, 3-668, 3-675, 3-677, 3-678, 3-680, 3-681, 3-682, 3-687, 3-690, 3-691, 3-694, 3-696 and 3-699.

Still more preferred compounds for the treatment of circulatory diseases are Compounds No.

1-1, 1-18, 1-30, 1-38, 1-61, 1-68, 1-81, 1-83, 1-197, 3-1, 3-38, 3-50, 3-57, 3-60, 3-63, 3-70, 3-90, 3-95, 3-100, 3-110, 3-135, 3-137, 3-141, 3-149, 3-164, 3-248, 3-256, 3-257, 3-259, 3-260, 3-269, 3-334, 3-348, 3-376, 3-400, 3-401, 3-405, 3-408, 3-415, 3-418, 3-469, 3-549, 3-557, 3-560, 3-568, 3-570, 3-571, 3-576, 3-581, 3-586, 3-591, 3-595, 3-604, 3-609, 3-614, 3-619, 3-630, 3-631, 3-632, 3-680, 3-687, 3-691 and 3-696.

Yet more preferred compounds for the treatment of circulatory diseases are Compounds No.

1-1, 1-18, 1-30, 1-38, 3-1, 3-38, 3-50, 3-57, 3-60, 3-63, 3-70, 3-95, 3-100, 3-110, 3-135, 3-137, 3-248, 3-256, 3-259, 3-334, 3-401, 3-405, 3-408, 3-549, 3-568, 3-570, 3-571, 3-630, 3-687, 3-691 and 3-696.

The most preferred compounds for the treatment of circulatory diseases are Compounds No.

1-1. 3-Dimethylamino-1-[2-(4-phenylbutyl)phenoxy]-2-propanol;

1-18. 1-Methyl-2-{2-[2-(4-phenylbutyl)phenoxy]ethyl}pyrrolidine;

1-38. 1-Methyl-2-(2-{2-[4-(3-methoxyphenyl)butyl]phenoxy}ethyl)pyrrolidine;

3-1. 1-Methyl-2-{2-[2-(2-phenylethyl)phenoxy]ethyl}pyrrolidine;

3-38. 4-Hydroxy-1-methyl-2-{2-[2-(2-phenylethyl)phenoxy]ethyl}pyrrolidine;

3-50. 1-Methyl-2-(2-{2-[2-(3-methoxyphenyl)ethyl]phenoxy}ethyl)pyrrolidine;

3-70. 2-(2-{2-[2-(3,5-Dimethoxyphenyl)ethyl]phenoxy}ethyl)-1-methylpyrrolidine;

3-95. 2-(2-{2-[2-(3-Fluorophenyl)ethyl]phenoxy}ethyl)-1-methylpyrrolidine;

3-137. 2-(2-{2-[2-(3-Bromophenyl)ethyl]phenoxy}ethyl)-1-methylpyrrolidine;

3-248. 4-Hydroxy-1-methyl-2-(2-{2-[2-(3-methoxyphenyl) ethyl]phenoxy}ethyl)pyrrolidine;

3-334. 2-(2-{2-[2-(3-Fluorophenyl)ethyl]phenoxy}ethyl)-4-hydroxy-1-methylpyrrolidine;

3-405. 2-(2-{2-[2-(3-Difluoromethoxyphenyl)ethyl]phenoxy}ethyl)-1-methylpyrrolidine;

3-408. 2-(2-{2-[2-(3-Difluoromethoxyphenyl)ethyl]phenoxy}ethyl)-4-hydroxy-1-methylpyrrolidine;

3-549. 2-(2-{2-[2-(3,5-Dimethoxyphenyl)ethyl]phenoxy}ethyl)-4-hydroxy-1-methylpyrrolidine;

3-568. 1-Methyl-2-(2-{2-[2-(3-methoxyphenyl)ethyl]phenoxy}ethyl)-4-succinyloxypyrrolidine;

3-570. 2-(2-{2-[2-(3,5-Dimethoxyphenyl)ethyl]phenoxy}ethyl)-4-succinyloxy-1-methylpyrrolidine;

3-630. 2-(2-{2-[2-(3-Bromophenyl)ethyl]phenoxy}ethyl)-4-hydroxy-1-methylpyrrolidine; and 3-687. 2-(2-{2-[2-(2-Difluoromethoxyphenyl)ethyl]phenoxy}ethyl)-4-succinyloxy-1-methylpyrrolidine;

and pharmaceutically acceptable salts and esters thereof.

For the treatment of psychiatric conditions, preferred compounds are as follows, that is to say Compounds No.

1-2, 1-3, 1-5, 1-6, 1-17, 1-18, 1-19, 1-20, 1-21, 1-22, 1-26, 1-29, 1-32, 1-38, 1-41, 1-42, 1-43, 1-47, 1-49, 1-50, 1-52, 1-57, 1-58, 1-61, 1-64, 1-68, 1-75, 1-79, 1-81, 1-85, 1-117, 1-122, 1-126, 1-127, 1-129, 1-132, 1-133, 1-135, 1-137, 1-139, 1-140, 1-145, 1-146, 1-151, 1-152, 1-155, 1-157, 1-161, 1-163, 1-167, 1-169, 1-170, 1-173, 1-175, 1-181, 1-187, 1-188, 1-191, 1-193, 1-197, 1-199, 1-203, 1-205, 1-210, 1-214, 1-216, 1-223, 1-228, 1-249, 1-264, 1-265, 1-269, 1-270, 1-272, 1-273, 1-277, 1-278, 1-280, 1-281, 1-285, 1-286, 1-288, 1-294, 1-300, 1-306, 1-315, 1-321, 1-326, 2-13, 2-17, 2-21, 2-29, 2-33, 2-37, 2-47, 2-51, 2-60, 2-64, 2-73, 2-77, 2-87, 2-91, 2-101, 2-105, 2-113, 2-117, 2-125, 2-129, 2-137, 2-141, 2-148, 2-152, 2-156, 2-162, 2-166, 2-170, 2-178, 2-182, 2-190, 2-194, 2-202, 2-206, 2-219, 2-231, 2-243, 2-254, 2-265, 2-271, 2-277, 2-279, 2-283, 2-285, 2-289, 2-291, 2-295, 2-297, 2-301, 2-303, 2-307, 2-308, 2-312, 2-314, 2-318, 2-320, 2-324, 2-326, 2-332, 2-338, 2-344, 2-350, 2-356, 2-360, 2-362, 2-368, 2-374, 2-378, 2-380, 2-384, 2-386, 2-390, 2-392, 2-398, 2-404, 2-408, 2-410, 2-414, 2-416, 2-424, 2-428, 2-434, 2-440, 2-446, 2-450, 3-10, 3-19, 3-26, 3-44, 3-52, 3-54, 3-57, 3-60, 3-70, 3-74, 3-75, 3-78, 3-81, 3-82, 3-87, 3-88, 3-93, 3-94, 3-98, 3-112, 3-114, 3-128, 3-172, 3-401, 3-422, 3-442, 3-462, 3-483, 3-503, 3-523, 3-571, 3-649, 3-685 and 3-686.

More preferred compounds for the treatment of psychiatric conditions, are Compounds No.

1-2, 1-3, 1-6, 1-17, 1-18, 1-19, 1-20, 1-21, 1-22, 1-29, 1-32, 1-38, 1-41, 1-43, 1-47, 1-49, 1-57, 1-61, 1-68, 1-79, 1-81, 1-85, 1-117, 1-122, 1-126, 1-139, 1-145, 1-151, 1-157, 1-163, 1-169, 1-175, 1-187, 1-193, 1-199, 1-210, 1-228, 1-264, 1-270, 1-272, 1-280, 1-306, 1-315, 1-321, 2-13, 2-17, 2-21, 2-29, 2-33, 2-37, 2-51, 2-64, 2-77, 2-1.52, 2-156, 2-162, 1-166, 2-170, 2-182, 2-194, 2-206, 2-279, 2-285, 2-291, 2-297, 2-303, 2-308, 2-314, 2-326, 2-374, 2-378, 2-380, 2-384, 2-386, 2-392, 2-398, 2-404, 2-410, 2-416, 2-428, 2-440, 3-10, 3-19, 3-44, 3-52, 3-54, 3-57, 3-70, 3-74, 3-78, 3-81, 3-93, 3-112, 3-172, 3-401, 3-571 and 3-685.

Still more preferred compounds for the treatment of psychiatric conditions, are Compounds No.

1-3, 1-18, 1-21, 1-22, 1-32, 1-41, 1-43, 1-79, 1-81, 1-85, 1-117, 1-122, 1-126, 1-139, 1-145, 1-151, 1-169, 1-187, 1-264, 1-306, 1-315, 1-321, 2-17, 2-21, 2-37, 2-156, 2-170, 2-380, 2-428 and 3-52.

The most preferred compounds for the treatment of psychiatric conditions, are Compounds No.

1-3 N,N-Dimethyl-3-[2-(4-phenylbutyl)phenoxy]propylamine;

1-18. 1-Methyl-2-{2-[2-(4-phenylbutyl)phenoxy]ethyl}pyrrolidine;

1-21. 1-Methyl-3-[2-(4-phenylbutyl)phenoxymethyl]piperidine;

1-32. N,N-Dimethyl-3-{2-[4-(3-methoxyphenyl)butyl]phenoxy}propylamine;

1-43. 1-Methyl-3-{2-[4-(3-methoxyphenyl)butyl]phenoxymethyl}piperidine;

1-79. N,N-Dimethyl-3-{2-[4-(2-methoxyphenyl)butyl]phenoxy}propylamine;

1-81. 1-Methyl-2-(2-{2-[4-(2-methoxyphenyl)butyl]phenoxy}ethyl)pyrrolidine;

1-117. 2-(2-{2-[4-(3,5-Dimethoxyphenyl)butyl]phenoxy}ethyl)-1-methylpyrrolidine;

1-122. 3-{2-[4-(3,5-Dimethoxyphenyl)butyl]phenoxymethyl}-1-methylpiperidine;

1-139. 1-Methyl-3-{2-[4-(2-methoxyphenyl)butyl]phenoxymethyl}piperidine;

2-17. 1-Methyl-2-{2-[2-(5-phenylpentyl)phenoxy]ethyl}pyrrolidine;

2-21. 1-Methyl-3-[2-(5-phenylpentyl)phenoxymethyl]piperidine;

2-37. 1-Methyl-3-{2-[5-(3-methoxyphenyl)pentyl]phenoxymethyl}piperidine;

2-156. 1-Methyl-3-[2-(6-phenylhexyl)phenoxymethyl]piperidine;

2-170. 1-Methyl-3-{2-[6-(3-methoxyphenyl)hexyl]phenoymethyl}piperidine; and 2-428. 3-{2-[5-(3,5-Dimethoxyphenyl)pentyl]phenoxymethyl}-1-methylpiperidine;

and pharmaceutically acceptable salts and esters thereof.

The compounds of the present invention may be prepared by a variety of methods well known for the preparation of compounds of this type. For example, in general terms, they may be prepared by reacting a compound of formula (II):

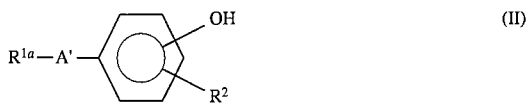

(in which:

R² is as defined above;

R¹ᵃ represents any of the groups represented by R¹, except that hydroxy groups (if any) are protected; and A' represents an alkylene group having from 2 to 8 carbon atoms or such a group in which at least one (and preferably only one) carbon-carbon single bond is replaced by a carbon-carbon double bond)

with a compound of formula (III), (IV) or (VII):

(in which:

D is as defined above;

B' represents an alkylene group having from 2 to 6 carbon atoms; and $R^{4a}$ and $R^{5a}$ represents any of the groups represented by $R^4$ and $R^5$, respectively and such groups in which hydroxy groups (if any) are protected or substituted;

$R^{7a}$ represents any of the groups represented by $R^7$, except that any hydroxy group is protected and any heterocylic nitrogen atom is protected; and Z represents a hydroxy group or a group or atom capable of leaving as a nucleophilic residue;

and, if necessary, removing protecting groups;

and, if necessary, any one or more of the following steps (i) to (viii):

(i) converting a group of formula >C=C< in the group represented by A' to a group of formula >CH—CH<;

(ii) converting a cyano group to a carbamoyl group;

(iii) converting a group of formula

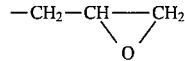

to a group of formula —CH₂CH(OH)CH₂NR⁴ᵃR⁵ᵃ, where $R^{4a}$ and $R^{5a}$ are as defined above;

(iv) converting a group of formula —CH₂CH(OH)CH₂NR⁴ᵃR⁵ᵃ to a group of formula —CH₂CH(OR⁶)CH₂NR⁴ᵃR⁵ᵃ, where $R^{4a}$, $R^{5a}$ and $R^6$ are as defined above;

(v) alkylating a group of formula >NH;
(vi) converting an alkoxycarbonyl group to a methyl group;
(vii) converting an alkanoyl group to an alkyl group; and
(viii) salifying or esterifying the product.

Examples of preferred groups and atoms, Z, capable of leaving as a nucleophilic residue include:

halogen atoms, such as the chlorine, bromine and iodine atoms; aliphatic acyloxy groups, including:
   alkylcarbonyloxy groups, such as the acetoxy and propionyloxy groups;
   halogenated alkylcarbonyloxy groups, such as the chloroacetoxy, dichloroacetoxy, trichloroacetoxy and trifluoroacetoxy groups;
   lower alkoxyalkylcarbonyloxy groups, such as the methoxyacetoxy group; and
   alkenylcarbonyloxy groups, such as the (E)-2-methyl-2-butenoyloxy group;

aromatic acyloxy groups, including:
   arylcarbonyloxy groups, such as the benzoyloxy group;
   halogenated arylcarbonyloxy groups, such as the 4-chlorobenzoyloxy group;
   lower alkylated arylcarbonyloxy groups, such as the 2,4,6-trimethylbenzoyloxy and 4-toluoyloxy groups;
   lower alkoxylated arylcarbonyloxy groups, such as the 4-anisoyloxy group; and
   nitrated arylcarbonyloxy groups, such as the 4-nitrobenzoyloxy and 2-nitrobenzoyloxy groups;

trihalomethoxy groups, such as the trichloromethoxy group;

lower alkanesulfonyloxy groups, such as the methanesulfonyloxy, ethanesulfonyloxy, propanesulfonyloxy and butanesulfonyloxy groups; halogenated lower alkanesulfonyloxy groups, such as the trifluoromethanesulfonyloxy and pentafluoroethanesulfonyloxy groups; and arylsulfonyloxy groups, such as the benzenesulfonyloxy, o-, m- or p-toluenesulfonyloxy, o-, m- or p-methoxybenzenesulfonyloxy, o-, m- or p- chlorobenzenesulfonyloxy, o-, m- or p- fluorobenzenesulfonyloxy, o-, m- or p-nitrobenzenesulfonyloxy and naphthalenesulfonyloxy groups.

Of these, we prefer the halogen atoms, the lower alkanesulfonyloxy groups, the halogenated lower alkanesulfonyloxy groups and the arylsulfonyloxy groups, of which the chlorine, bromine and iodine atoms and the methanesulfonyloxy, ethanesulfonyloxy, benzenesulfonyloxy, p-toluenesulfonyloxy and p-nitrobenzenesulfonyloxy groups are more preferred.

There is no particular restriction on the nature of the protecting group used to protect hydroxy groups in these reactions, and any group commonly used for this purpose may equally be used here. In particular, it is possible to use protecting groups capable of cleavage by chemical means, such as hydrogenolysis, hydrolysis, electrolysis or photolysis, and protecting groups capable of cleavage by biological means, such as by hydrolysis in vivo.

Examples of hydroxy-protecting group capable of cleavage by chemical means include:

aliphatic acyl groups, preferably:
   alkanoyl groups having from 1 to 25 carbon atoms, more preferably from 1 to 20 carbon atoms, still more preferably from 1 to 6 carbon atoms, and most preferably from 1 to 4 carbon atoms, (such as the formyl, acetyl, propionyl, butyryl, isobutyryl, pivaloyl, valeryl, isovaleryl, hexanoyl, heptanoyl, octanoyl, nonanoyl, decanoyl, lauroyl, myristoyl, tridecanoyl, palmitoyl, stearoyl, 3-methylnonanoyl, 8-methylnonanoyl, 3-ethyloctanoyl, 3,7-dimethyloctanoyl, undecanoyl, tridecanoyl, pentadecanoyl, 1-methylpentadecanoyl, 14-methylpentadecanoyl, 13,13-dimethyltetradecanoyl, heptadecanoyl, 15-methylhexadecanoyl, 1-methylheptadecanoyl, nonadecanoyl, icosanoyl and henicosanoyl groups, of which the acetyl group is most preferred);
   carboxylated alkylcarbonyl groups, such as the succinyl, glutaryl and adipoyl groups;
   halogenated alkanoyl groups having from 2 to 6 carbon atoms, especially halogenated acetyl groups (such as the chloroacetyl, dichloroacetyl, trichloroacetyl and trifluoroacetyl groups);
   lower alkoxyalkanoyl groups in which the alkoxy part has from 1 to 5, preferably from 1 to 3, carbon atoms and the alkanoyl part has from 2 to 6 carbon atoms and is preferably an acetyl group (such as the methoxyacetyl group); and
   unsaturated analogs of such groups, especially alkenoyl or alkynoyl groups having from 3 to 6 carbon atoms [such as the acryloyl, methacryloyl, propioloyl, crotonoyl, isocrotonoyl and (E)-2-methyl-2-butenoyl groups];

aromatic acyl groups, preferably arylcarbonyl groups, in which the aryl part has from 6 to 14, more preferably from 6 to 10, still more preferably 6 or 10, and most preferably 6, ring carbon atoms and is a carbocyclic group, which is unsubstituted or has from 1 to 5, preferably from 1 to 3 substituents, selected from the group consisting of substituents α, defined above and exemplified below, preferably:
   unsubstituted groups (such as the benzoyl, α-naphthoyl and β-naphthoyl groups);
   halogenated arylcarbonyl groups (such as the 2-bromobenzoyl and 4-chlorobenzoyl groups);
   lower alkyl-substituted arylcarbonyl groups, in which the or each alkyl substituent has from 1 to 5, preferably from 1 to 4, carbon atoms (such as the 2,4,6-trimethylbenzoyl and 4-toluoyl groups);
   lower alkoxy-substituted arylcarbonyl groups, in which the or each alkoxy substituent preferably has
   from 1 to 5, preferably from 1 to 4, carbon atoms (such as the 4-anisoyl group);
   carboxy-substituted arylcarbonyl groups, such as the 2-carboxybenzoyl, 3-carboxybenzoyl and 4-carboxybenzoyl groups;
   nitro-substituted arylcarbonyl groups (such as the 4-nitrobenzoyl and 2-nitro- benzoyl groups);
   lower alkoxycarbonyl-substituted arylcarbonyl groups, in which the or each alkoxycarbonyl substituent preferably has from 2 to 6 carbon atoms [such as the 2-(methoxycarbonyl)benzoyl group]; and
   aryl-substituted arylcarbonyl groups, in which the aryl substituent is as defined above, except that, if it is substituted by a further aryl group, that aryl group is not itself substituted by an aryl
   group (such as the 4-phenylbenzoyl group);

heterocyclic groups having 5 or 6 ring atoms, of which 1 or 2 are hetero-atoms selected from the group consisting of oxygen, sulfur and nitrogen atoms, preferably oxygen or sulfur atoms, which groups may be unsubstituted or may have at least one substituent selected from the group consisting of substituents α, defined and exemplified above, and oxygen atoms; examples include:

the tetrahydropyranyl groups, which may be substituted or unsubstituted, such as the tetrahydropyran-2-yl and 4-methoxytetrahydropyran-4-yl groups;

tetrahydrothiopyranyl groups, which may be substituted or unsubstituted, such as the tetrahydrothiopyran-2-yl and 4-methoxytetrahydrothiopyran-4-yl groups;

tetrahydrofuranyl groups, which may be substituted or unsubstituted, such as the tetrahydrofuran-2-yl group; and tetrahydrothienyl groups, which may be substituted or unsubstituted, such as the tetrahydrothien-2-yl group;

tri-substituted silyl groups, in which all three or two or one of the substituents are alkyl groups having from 1 to 5, preferably from 1 to 4, carbon atoms, and none, one or two of the substituents are aryl groups, as defined above, but preferably phenyl or substituted phenyl groups, preferably:

tri(lower alkyl)silyl groups (such as the trimethylsilyl, triethylsilyl, isopropyldimethylsilyl, t-butyldimethylsilyl, methyldiisopropylsilyl, methyldi-t-butylsilyl and triisopropylsilyl groups); and tri(lower alkyl)silyl groups in which one or two of the alkyl groups have been replaced by aryl groups (such as the diphenylmethylsilyl, diphenylbutylsilyl, diphenyl-t-butylsilyl, diphenylisopropylsilyl and phenyldiisopropylsilyl groups);

alkoxyalkyl groups, in which the alkoxy and alkyl parts each have from 1 to 5, preferably from 1 to 4, carbon atoms, especially alkoxymethyl groups, and such groups which have at least one, preferably from 1 to 5, more preferably from 1 to 3, and most preferably 1, substituents, preferably:

lower alkoxymethyl groups and other alkoxyalkyl groups (such as the methoxymethyl, 1,1-dimethyl-1-methoxymethyl, ethoxymethyl, propoxymethyl, isopropoxymethyl, butoxymethyl and t-butoxymethyl groups);

lower alkoxy-substituted lower alkoxymethyl groups (such as the methoxymethoxymethyl and 2-methoxyethoxymethyl groups);

halogenated lower alkoxymethyl groups [such as the 2,2,2-trichloroethoxymethyl and bis(2-chloroethoxy)methyl groups]; and lower alkoxy-substituted ethyl groups (such as the 1-ethoxyethyl, 1-methyl-1-methoxyethyl and 1-isopropoxyethyl groups);

other substituted ethyl groups, preferably:

halogenated ethyl groups (such as the 2,2,2-trichloroethyl group); and arylselenyl-substituted ethyl groups, in which the aryl part is as defined above [such as the 2-(phenylselenyl)ethyl group];

aralkyl groups, preferably alkyl groups having from 1 to 4, more preferably from 1 to 3 and most preferably 1 or 2, carbon atoms which are substituted with from 1 to 3 aryl groups, as defined and exemplified above, which may be unsubstituted (such as the benzyl, 1-phenylethyl, α-naphthylmethyl, β-naphthylmethyl, diphenylmethyl, triphenylmethyl, α-naphthyldiphenylmethyl and 9-anthrylmethyl groups) or substituted on the aryl part with a lower alkyl group, a lower alkoxy group, a nitro group, a halogen atom, a cyano group, or an alkylenedioxy group having from 1 to 3 carbon atoms, preferably a methylenedioxy group, [such as the 4-methylbenzyl, 2,4,6-trimethylbenzyl, 3,4,5-trimethylbenzyl, 4-methoxybenzyl, 4-methoxyphenyldiphenylmethyl, 2-nitrobenzyl, 4-nitrobenzyl, 4-chlorobenzoyl, 4-bromobenzyl, 4-cyanobenzyl, 4-cyanobenzyldiphenylmethyl, bis(2-nitrophenyl)methyl and piperonyl groups);

alkoxycarbonyl groups, especially such groups having from 2 to 7, more preferably 2 to 5, carbon atoms and which may be unsubstituted (such as the methoxycarbonyl, ethoxycarbonyl, t-butoxycarbonyl and isobutoxycarbonyl groups) or substituted with a halogen atom or a tri-substituted silyl group, e.g. a tri(lower alkylsilyl) group (such as the 2,2,2-trichloroethoxycarbonyl and 2-trimethylsilylethoxycarbonyl groups);

alkenyloxycarbonyl groups in which the alkenyl part has from 2 to 6, preferably from 2 to 4, carbon atoms (such as the vinyloxycarbonyl and allyloxycarbonyl groups); and aralkyloxycarbonyl groups, in which the aralkyl part is as defined and exemplified above, and in which the aryl ring, if substituted, preferably has one or two lower alkoxy or nitro substituents (such as the benzyloxycarbonyl, 4-methoxybenzyloxycarbonyl, 3,4-dimethoxybenzyloxycarbonyl, 4-bromobenzyloxycarbonyl, 2-nitrobenzyloxycarbonyl and 4-nitrobenzyloxycarbonyl groups.

Examples of protecting groups capable of cleavage by biological means such as hydrolysis in vivo include: for example, the foregoing carbonyloxyalkyl groups; the foregoing aliphatic acyl groups; the foregoing aromatic acyl groups; a salt residue of a carboxylated lower alkylcarbonyl group, such as a salt residue of a succinic acid monoester; a salt residue of a phosphate; an ester residue of an amino acid; a carbamoyl group; a substituted carbamoyl group, which is a carbamoyl group substituted by one or two alkyl groups each having from 1 to 6 carbon atoms, such as the methylcarbamoyl, dimethylcarbamoyl, ethylcarbamoyl, propylcarbamoyl, butylcarbamoyl, t-butylcarbamoyl, pentylcarbamoyl or hexylcarbamoyl groups; and a carbonyloxyalkyloxycarbonyl group, such as a pivaloyloxymethyloxycarbonyl group. It is simple to determine whether a protecting group is capable of cleavage by biological means such as hydrolysis in vivo, by administering a protected compound or pharmaceutically acceptable salt thereof by intravenous injection to a laboratory animal, such as a rat or mouse, and then determining the nature of the active compound recovered from the body fluids of the animal used.

Examples of preferred protecting groups for the protected hydroxy group include: the tetrahydrofuranyl, tetrahydropyranyl and tetrahydrothiopyranyl groups; the silyl groups; the alkoxymethyl groups; the methoxymethoxymethyl group; the aralkyl groups; and the aralkyloxycarbonyl groups; more preferably the tetrahydropyranyl, methoxymethyl, benzyl, p-methoxybenzyl, p-bromobenzyl, benzyloxycarbonyl, p-methoxybenzyloxycarbonyl and p-bromobenzyloxycarbonyl groups.

$R^{7a}$ represents any of the groups represented by $R^7$ but in which a ring nitrogen atom or atoms is or are substituted with an amino-protecting group or a lower alkyl group and one or more of the ring carbon atom or atoms may optionally be substituted with any of substituents ε, defined and exemplified above, except that any hydroxy group is protected.

There is no particular limitation upon the nature of the amino-protecting group which may be used, and any such group conventionally used for this purpose may equally be used here. Examples of preferred amino-protecting groups include: aliphatic acyl groups, aromatic acyl groups, alkoxycarbonyl groups alkenyloxycarbonyl groups, aralkyloxycarbonyl groups, silyl groups and aralkyl groups, all such as those defined above in relation to hydroxy-protecting groups. Of these, we prefer the t-butoxycarbonyl, benzyl, p-methoxybenzyl, p-bromobenzyl, benzyloxycarbonyl, p-methoxybenzyloxycarbonyl and p-bromobenzyloxycarbonyl groups.

In more detail, the compounds of the present invention may be prepared as illustrated in the following Reaction Schemes A, B and C.

Reaction Scheme A:

In Reaction Scheme A, a compound of formula (Ia), which is a compound of formula (I) in which B is replaced by B' (as defined above) is prepared:

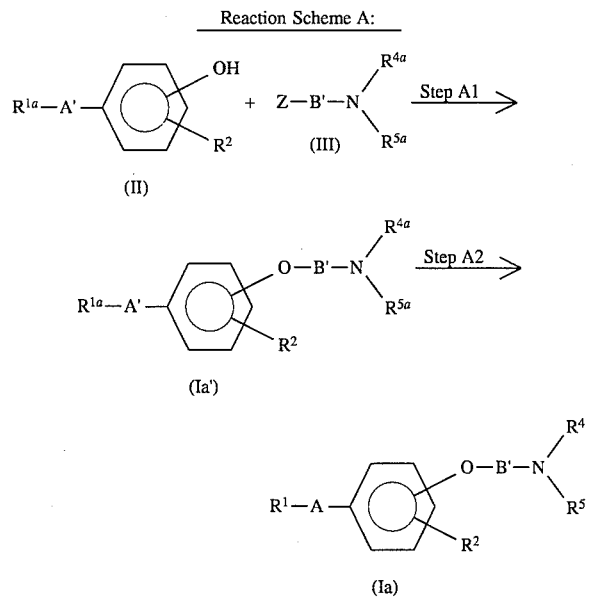

In the above formulae, $R^1$, $R^2$, $R^{1a}$, A, A', B', Z, $R^4$, $R^5$, $R^{4a}$ and $R^{5a}$ are as defined above.

Step A1:

Step A1 of this reaction scheme involves the preparation of a compound of formula (Ia') by reacting a compound of formula (II) with a compound of formula (III).

Where Z represents a group or atom capable of leaving in a nucleophilic reaction, such as a halogen atom, an alkanesulfonyloxy group or an arylsulfonyloxy group, the reaction is normally and preferably carried out in an inert solvent and in the presence of a base.

There is no particular restriction on the nature of the base employed, and any base commonly used in reactions of this type may equally be used here, provided that it has no adverse effect on any part of the molecule of the reagents. Examples of preferred bases include: alkali metal carbonates, such as sodium carbonate or potassium carbonate; alkali metal hydrogencarbonates, such as sodium hydrogencarbonate or potassium hydrogencarbonate; alkali metal fluorides, such as sodium fluoride or potassium fluoride; alkali metal hydrides, such as sodium hydride, potassium hydride or lithium hydride; alkali metal alkoxides, such as sodium methoxide, sodium ethoxide, potassium t-butoxide or lithium methoxide; and organic amines, such as pyridine, picoline, triethylamine, N-methylmorpholine or 4-dimethylaminopyridine. Of these, we prefer the alkali metal carbonates, alkali metal fluorides, alkali metal hydrides and alkali metal alkoxides.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: hydrocarbons, such as hexane, benzene or toluene; halogenated hydrocarbons, preferably halogenated aliphatic hydrocarbons, such as methylene chloride, chloroform or 1,2-dichloroethane; ethers, such as diethyl ether, tetrahydrofuran or dioxane; ketones, such as acetone or methyl ethyl ketone; nitriles, such as acetonitrile; amides, such as dimethylacetamide, dimethylformamide, N-methyl-2-pyrrolidinone or hexamethylphosphoric triamide; and sulfoxides, such as dimethyl sulfoxide. A single one of these solvents or a mixture of any two or more of them may be employed. Of these, we prefer the ethers, ketones, amides and sulfoxides.

In order that the reaction may proceed more effectively, it can be conducted in the presence of a quaternary ammonium salt, such as benzyltriethylammonium chloride or tetrabutylammonium chloride, or a crown ether, such as dibenzo-18-crown-6.

The reaction can take place over a wide range of temperatures, and the precise reaction temperature is not critical to the invention, although the preferred temperature may vary, depending upon the nature of the starting compounds (II) and (III) as well as the nature of the solvent and base. In general, we find it convenient to carry out the reaction at a temperature of from 0° C. to 100° C., more preferably from 10° C. to 80° C. The time required for the reaction may also vary widely, depending on many factors, notably the reaction temperature and the nature of the reagents and solvent employed. However, provided that the reaction is effected under the preferred conditions outlined above, a period of from 30 minutes to 48 hours, more preferably from 1 to 24 hours will usually suffice.

Where Z represents a hydroxy group, the reaction of this Step is normally and preferably carried out in an inert solvent in the presence of triphenylphosphine and azodicarboxylic acid esters, such as dimethyl azodicarboxylate or diethyl azodicarboxylate.

The inert solvents to be used are as exemplified above, preferably an aromatic hydrocarbons, a halogenated hydrocarbon or an ether.

The reaction can take place over a wide range of temperatures, and the precise reaction temperature is not critical to the invention, although the preferred temperature may vary, depending upon the nature of the starting compounds (II) and (III) as well as the nature of the solvent and base. In general, we find it convenient to carry out the reaction at a temperature of from −20° C. to 100° C., more preferably from 10° C. to 80° C. The time required for the reaction may also vary widely, depending on many factors, notably the reaction temperature and the nature of the reagents and solvent employed. However, provided that the reaction is effected under the preferred conditions outlined above, a period of from 30 minutes to 48 hours, more preferably from 1 to 24 hours will usually suffice.

After completion of the reaction, the desired compound of formula (Ia') can be recovered from the reaction mixture by conventional means. For example, in one suitable recovery procedure, insoluble materials, if any, are filtered off, and then the solvent is distilled off from the filtrate under reduced pressure, to give the desired compound. Alternatively, the solvent is distilled off under reduced pressure, the residue is diluted with water and extracted with a water-immiscible organic solvent, such as ethyl acetate, the extract is dried over a drying agent, such as anhydrous magnesium sulfate, and finally the solvent is distilled off. The resulting residue can, if necessary, be further purified by conventional means, for example, by recrystallization or the various chromatography techniques, notably column chromatography.

Step A2:

Step A2 is optional and may consist of one or more of the following reactions:

Reaction (a): elimination of the hydroxy-protecting group included in $R^{1a}$, $R^{4a}$ or $R^{5a}$;

Reaction (b): reduction of any carbon-carbon double bond included in A'; and

Reaction (c): conversion of a cyano group to a carbamoyl group.

These reactions may be conducted in any desired order.

Reaction (a):

In Reaction (a), the hydroxy-protecting group included in $R^{1a}$, $R^{4a}$ or $R^{5a}$ is eliminated. The nature of this reaction will, of course, depend upon the type of the protecting group, but the reactions involved are well-known in the field of organic synthetic chemistry.

For example, where the hydroxy-protecting group is an aralkyl or aralkyloxycarbonyl group, elimination may be carried out by reacting the protected compound with hydrogen (normally under a pressure of from 1 to 10 atmospheres, more preferably from 1 to 3 atmospheres).

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: alcohols, such as methanol, ethanol or isopropanol; ethers, such as diethyl ether, tetrahydrofuran or dioxane; aromatic hydrocarbons, such as toluene, benzene or xylene; aliphatic hydrocarbons, such as hexane or cyclohexane; esters, such as ethyl acetate or butyl acetate; and fatty acids, such as acetic acid. A mixture of any one or more of these organic solvents with water may also be used.

The reaction is carried out in the presence of a catalyst for catalytic reduction, preferably palladium on charcoal, Raney nickel, platinum oxide, platinum black, rhodium on alumina, triphenylphosphine-rhodium choride or palladium on barium sulfate.

The reaction can take place over a wide range of temperatures, and the precise reaction temperature is not critical to the invention. In general, we find it convenient to carry out the reaction at a temperature of from 0° C. to 100° C., more preferably from 20° C. to 80° C. The time required for the reaction may also vary widely, depending on many factors, notably the reaction temperature and the nature of the reagents and solvent employed. However, provided that the reaction is effected under the preferred conditions outlined above, a period of from 30 minutes to 48 hours, more preferably from 1 to 24 hours will usually suffice.

The reaction is accompanied by the reduction of any double bond include in A'.

Where the hydroxy-protecting group is an alkoxyalkyl group, such as a methoxymethyl or methoxymethoxymethyl group, or a heterocyclic group, such as a tetrahydropyranyl group, elimination may be effected by reacting the protected compound with an acid (for example: an inorganic acid, such as hydrogen chloride, nitric acid, hydrochloric acid or sulfuric acid; an organic acid, such as acetic acid, trifluoroacetic acid, methanesulfonic acid or R-toluenesulfonic acid; a Lewis acid, such as boron trifluoride; or a strongly acidic cation exchange resin, such as Dowex 50W (trade mark). Of these, we prefer the inorganic and organic acids, more preferably hydrochloric acid, sulfuric acid or trifluoroacetic acid.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: hydrocarbons, such as hexane or benzene; halogenated hydrocarbons, preferably halogenated aliphatic hydrocarbons, such as methylene chloride or chloroform; esters, such as ethyl acetate; ketones, such as acetone or methyl ethyl ketone; alcohols, such as methanol or ethanol; ethers, such as diethyl ether, tetrahydrofuran or dioxane; and mixtures of any one or more of these organic solvents with water. Of these, we prefer the esters, ethers and halogenated hydrocarbons.

The reaction can take place over a wide range of temperatures, and the precise reaction temperature is not critical to the invention. In general, we find it convenient to carry out the reaction at a temperature of from −10° C. to 100° C., more preferably from −5° C. to 50° C. The time required for the reaction may also vary widely, depending on many factors, notably the reaction temperature and the nature of the reagents and solvent employed. However, provided that the reaction is effected under the preferred conditions outlined above, a period of from 5 minutes to 48 hours, more preferably from 30 minutes to 10 hours will usually suffice.

After completion of the reaction, the desired compound can be recovered from the reaction mixture by conventional means. For example, the reaction mixture is neutralized, insoluble materials, if any, are filtered off, the filtrate is diluted with a water-immiscible organic solvent, such as ethyl acetate, the extract is washed with water and then the solvent is distilled off. The desired compound can, if necessary, be further purified by conventional means, for example, recrystallization, reprecipitation, or the various chromatography techniques, notably column chromatography.

Reaction (b):

In Reaction (b), a double bond represented by A' is reduced. The reaction conditions employed are similar to those employed in the foregoing elimination reaction (a) when the hydroxy-protecting group is an aralkyl group.

Reaction (c):

In Reaction (c), a cyano group is converted to a carbamoyl group, for example by reacting the cyano compound with a base. There is no particular restriction on the nature of the base employed, and any base commonly used in reactions of this type may equally be used here, provided that it has no adverse effect on any part of the molecule of the reagents. Examples of preferred bases include: alkali metal hydroxides, such as sodium hydroxide or potassium hydroxide; and alkali metal carbonates, such as sodium carbonate or potassium carbonate, of which the alkali metal hydroxides are preferred.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: water; aqueous alcohols, such as aqueous methanol or aqueous ethanol; and aqueous ethers, such as aqueous diethyl ether, aqueous tetrahydrofuran or aqueous dioxane, of which the aqueous alcohols are preferred.

The reaction can take place over a wide range of temperatures, and the precise reaction temperature is not critical to the invention. In general, we find it convenient to carry out the reaction at a temperature of from 10° C. to 200° C., more preferably from 50° C. to 150° C. The time required for the reaction may also vary widely, depending on many factors, notably the reaction temperature and the nature of the reagents and solvent employed. However, provided that the reaction is effected under the preferred conditions outlined above, a period of from 30 minutes to 48 hours, more preferably from 1 to 20 hours will usually suffice.

After completion of the reaction, the desired compound can be recovered from the reaction mixture by conventional means. For example, the reaction mixture is neutralized, or insoluble materials, if any, are filtered off, a water-immiscible organic solvent, such as ethyl acetate is added thereto, the extract is washed with water and then the solvent is distilled off. The desired compound thus obtained may, if desired, be further purified by conventional means, for example, recrystallization, reprecipitation, or the various chromatography techniques, notably column chromatography.

Reaction Scheme B:

In Reaction Scheme B, a compound of formula (Ib) is prepared, that is a compound of formula (I) wherein $R^3$ represents a group of formula:

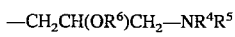
—$CH_2CH(OR^6)CH_2$—$NR^4R^5$ wherein $R^4$, $R^5$ and $R^6$ are as defined above.

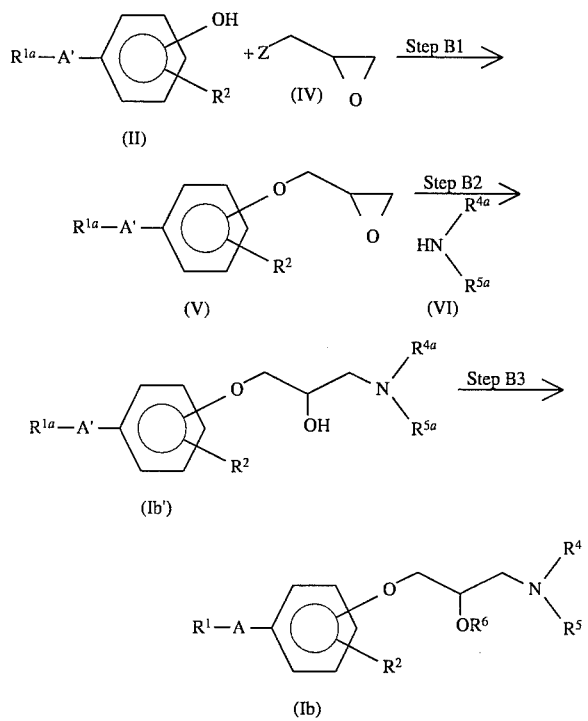

Step B1:

In Step B1, a compound of formula (V) is prepared by reacting a compound of formula (II) with a compound of formula (IV). This reaction is essentially the same as that described above in Step A1 of Method A, and may be carried out using the same reagents and reaction conditions.

Step B2:

In Step B2, a compound of formula (Ib') is prepared by reacting a compound of formula (V) with an amino compound of formula (VI).

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: hydrocarbons, such as hexane, benzene or toluene; halogenated hydrocarbons, preferably halogenated aliphatic hydrocarbons, such as methylene chloride, chloroform or 1,2-dichloroethane; ethers, such as diethyl ether, tetrahydrofuran or dioxane; ketones, such as acetone or methyl ethyl ketone; nitriles, such as acetonitrile; amides, such as dimethylacetamide, dimethylformamide, N-methyl-2-pyrrolidinone or hexamethylphosphoric triamide; sulfoxides, such as dimethyl sulfoxide; and water. If desired, a single one of these solvents or a mixture of any two or more of them may be used. Of these, we prefer the ethers, ketones, amides, sulfoxides and water or a mixture of any two or more of these solvents.

The reaction can take place over a wide range of temperatures, and the precise reaction temperature is not critical to the invention, although the preferred temperature may vary, depending upon the nature of the starting compounds (V) and (VI) as well as the nature of the solvent and base. In general, we find it convenient to carry out the reaction at a temperature of from 0° C. to 100° C., more preferably from 20° C. to 80° C. The time required for the reaction may also vary widely, depending on many factors, notably the reaction temperature and the nature of the reagents and solvent employed. However, provided that the reaction is effected under the preferred conditions outlined above, a period of from 30 minutes to 48 hours, more preferably from 1 to 24 hours will usually suffice.

After completion of the reaction the desired compound of formula (Ib') can be recovered from the reaction mixture by conventional means. For example, in one suitable recovery procedure, the solvent is simply distilled off under reduced pressure. Alternatively, the solvent is distilled off under reduced pressure, the residue is mixed with water and extracted with water-immiscible organic solvent and then the extract is dried over a drying agent, such as anhydrous magnesium sulfate, after which the solvent is distilled off to produce the desired compound. The product can, if necessary, be further purified by conventional means, for example, recrystallization, or the various chromatography techniques, notably column chromatography.

Step B3:

Step B3 is optional and may consist of any one or more of the following reactions:

Reaction (a): acylation of a hydroxy group produced by Step B2;

Reaction (b): elimination of a hydroxy-protecting group included in $R^{1a}$, $R^{4a}$ and/or $R^{5a}$;

Reaction (c): reduction of a double bond included in A'; and

Reaction (d): conversion of a cyano group to a carbamoyl group.

These reactions may be conducted in any desired order.

Reaction (a):

In Reaction (a) acylation of a hydroxy group may be carried out by procedures well-known in organic synthetic chemistry. For example, acylation may be carried out by reacting the starting compound with a $C_2$–$C_5$ alkanoyl halide, such as acetyl chloride, proionyl chloride, butyryl chloride, butyryl bromide, valeryl chloride or pivaloyl chloride; a $C_3$–$C_{10}$ aliphatic carboxylic anhydride, such as a mixed acid anhydride of formic acid and acetic acid, acetic anhydride, propionic anhydride, valeric anhydride or pivaloic anhydride; or a cyclic acid anhydride, such as succinic anhydride, glutaric anhydride or adipic anhydride.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aromatic hydrocarbons, such as benzene or toluene; halogenated hydrocarbons, preferably halogenated aliphatic hydrocarbons, such as methylene chloride or chloroform; esters, such as ethyl acetate; ethers, such as tetrahydrofuran or dioxane; ketones, such as acetone or methyl ethyl ketone; and amides, such as dimethylacetamide.

The reaction may be carried out in the presence or absence of a base, preferably an organic tertiary amine, such as triethylamine, pyridine, diethylisopropylamine or 4-dimethylaminopyridine.

The reaction can take place over a wide range of temperatures, and the precise reaction temperature is not critical to the invention. In general, we find it convenient to carry out the reaction at a temperature of from 0° C. to 120° C., more preferably from 0° C. to 80° C. The time required for the reaction may also vary widely, depending on many factors, notably the reaction temperature and the nature of the reagents and solvent employed. However, provided that the reaction is effected under the preferred conditions outlined above, a period of from 1 to 24 hours, more preferably from 1 to 16 hours will usually suffice.

After completion of the reaction, the reaction product can be recovered from the reaction mixture by conventional means. For example, recovery may be carried out in a similar manner to that described in Step A1 of Method A.

Reaction (b):

In Reaction (b) a hydroxy-protecting group is eliminated. This reaction is essentially the same as that described above in Reaction (a) of Step A2 of Method A, and may be carried out using the same reagents and reaction conditions. By selecting the type of protecting group and the conditions employed for its elimination, the protecting group included in $R^{1a}$, $R^{4a}$ and/or $R^{5a}$ can be selectively eliminated.

Reaction (c):

In Reaction (c) reduction of a double bond included in A' is carried out. This reaction is essentially the same as that described above in Reaction (a) of Step A2 of Method A, in which the hydroxy-protecting group is an aralkyl group, and may be carried out using the same reagents and reaction conditions.

Reaction (d):

In Reaction (d) conversion of a cyano group to a carbamoyl group is carried out. This reaction is essentially the same as that described above in Reaction (c) of Step A2 of Method A, and may be carried out using the same reagents and reaction conditions.

Reaction Scheme C:

In Reaction Scheme C, a compound of formula (Ic) is prepared, that is a compound of formula (I) wherein $R^3$ represents a group of formula —D—$R^7$ (wherein $R^7$ and D are as defined above).

Reaction Scheme C:

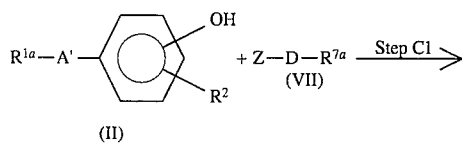

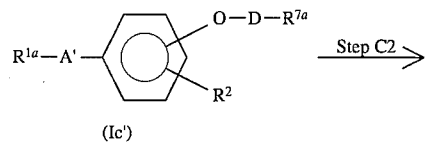

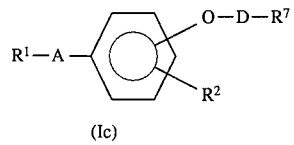

Step C1:

In Step C1, a compound of formula (I'c) is prepared by reacting a compound of formula (II) with a compound of formula (VII). This reaction is essentially the same as that described above in Step A1 of Method A, and may be carried out using the same reagents and reaction conditions.

Step C1:

Step C2 is optional and may consist of any one or more of the following reactions:

Reaction (a): elimination of a hydroxy-protecting group included in $R^{1a}$ and $R^{7a}$;

Reaction (b): alkylation, acylation or carbamoylation of a hydroxy group produced by Reaction (a);

Reaction (c): elimination of a nitrogen-protecting group included in $R^{7a}$;

Reaction (d): conversion of an alkoxycarbonyl group included in $R^{7a}$ to a methyl group or of an alkanoyl group included in $R^{7a}$ to alkyl group;

Reaction (e): alkylation of a =NH group produced by reaction (c);

Reaction (f): reduction of a double bond included in A'; and

Reaction (g): conversion of a cyano group to a carbamoyl group.

These reactions may be conducted in any desired order.

Reaction (a):

In Reaction (a) a hydroxy-protecting group is eliminated. This reaction is essentially the same as that described above in Reaction (a) of Step A2 of Method A, and may be carried out using the same reagents and reaction conditions. By selecting the type of protecting group and the conditions employed for its elimination, the protecting group included in $R^{7a}$ alone can be eliminated.

Reaction (b):

In Reaction (b) alkylation, acylation or carbamoylation of a hydroxy group is conducted by using an alkylating, acylating or carbamoylating agent in the presence of a base. This reaction is essentially the same as that described above in Reaction (a) of Step B3 of Method B, and may be carried out using the same reagents and reaction conditions.

Examples of suitable alkylating, acylating or carbamoylating agents to be used include: $C_1$–$C_6$ alkyl halides, such as methyl iodide, ethyl iodide, propyl iodide, butyl iodide, pentyl iodide or hexyl iodide; $C_1$–$C_6$ alkyl haloformates, such as methyl chloroformate, methyl bromoformate, ethyl chloroformate, propyl chloroformate, isopropyl chloroformate, butyl chloroformate, t-butyl chloroformate, pentyl chloroformate or hexyl chloroformate; $C_2$–$C_{20}$ alkanoyl halides, such as acetyl chloride, propionyl chloride, butyryl bromide, valeryl chloride, pivaloyl chloride, hexanoyl chloride, heptanoyl chloride, octanoyl chloride, lauroyl chloride, myristoyl chloride, tridecanoyl chloride, pentadecanoyl chloride, palmitoyl chloride, heptadecanoyl chloride, stearoyl chloride, nonadecanoyl chloride or icosanoyl chloride; $C_3$–$C_{10}$ aliphatic carboxylic acid anhydrides, such as a mixed acid anhydride of formic acid and acetic acid, acetic anhydride, propionic anhydride, valeric anhydride or pivalic anhydride; cyclic acid anhydrides, such as succinic anhydride, glutaric anhydride or adipic anhydride; isocyanic acid; $C_1$–$C_6$ alkyl isocyanates, such as methyl isocyanate, ethyl isocyanate, propyl isocyanate, butyl isocyanate, pentyl isocyanate or hexyl isocyanate; and dialkylcarbamoyl halides, in which each alkyl group has from 1 to 6 carbon atoms, such as N,N-dimethylcarbamoyl chloride, N,N-diethylcarbamoyl chloride, N,N-dipropylcarbamoyl chloride, N,N-dibutylcarbamoyl chloride, N,N-dipentylcarbamoyl chloride or N,N-dihexylcarbamoyl chloride.

Examples of suitable bases which may be used in this reaction include: alkali metal carbonates, such as sodium carbonate or potassium carbonate; alkali metal fluorides, such as sodium fluoride or potassium fluoride; alkali metal hydrides, such as sodium hydride; and organic tertiary amines, such as triethylamine, pyridine, diethylisopropylamine or 4-dimethylaminopyridine. Reaction (c):

In Reaction (c) elimination of a nitrogen-protecting group included in $R^{7a}$ is effected. The nature of the elimination reaction depends upon the type of protecting group, but the reaction may be conducted by means well-known in organic synthetic chemistry.

For example, where the nitrogen-protecting group is an aralkyl or aralkyloxycarbonyl group, elimination may be carried out in a similar manner to that described in Reaction (a) of Step B3, in which the hydroxy-protecting group is an aralkyl group.

Where the nitrogen-protecting group is a t-butoxycarbonyl group, elimination is carried out in a similar manner to that described in Reaction (a) of Step A3, in which the hydroxy-protecting group is an alkoxyalkyl group.

Where the nitrogen-protecting group is an alkoxycarbonyl residue, the corresponding protecting group can be eliminated by subjecting the protected compound to hydrolysis using a base, preferably an alkali metal hydroxide, such as lithium hydroxide, sodium hydroxide or potassium hydroxide; or an alkali metal carbonate, such as sodium carbonate or potassium carbonate. The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: alcohols, such as methanol or ethanol; ethers, such as tetrahydrofuran or dioxane; water; and a mixture of one or more of these organic solvents with water.

The reaction can take place over a wide range of temperatures, and the precise reaction temperature is not critical to the invention. In general, we find it convenient to carry out the reaction at a temperature of from 0° C. to 100° C., more preferably from about room temperature to 60° C. The time required for the reaction may also vary widely, depending on many factors, notably the reaction temperature and the nature of the reagents and solvent employed. However, provided that the reaction is effected under the preferred conditions outlined above, a period of from 1 to 24 hours, more preferably from 1 to 16 hours, will usually suffice.

After completion of the reaction, the reaction product can be recovered from the reaction mixture by similar means to that described in Step A1 of Method A.

Reaction (d):

In Reaction (d) conversion of an alkoxycarbonyl group included in $R^{7a}$ to a methyl group or of an alkanoyl group included in $R^{7a}$ to an alkyl group is conducted by using a reducing agent, preferably an alkali metal aluminum hydride, such as lithium aluminum hydride. The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: ethers, such as diethyl ether, tetrahydrofuran or dioxane.

The reaction can take place over a wide range of temperatures, and the precise reaction temperature is not critical to the invention. In general, we find it convenient to carry out the reaction at a temperature of from 0° C. to 100° C., more preferably from about room temperature to 80° C. The time required for the reaction may also vary widely, depending on many factors, notably the reaction temperature and the nature of the reagents and solvent employed. However, provided that the reaction is effected under the preferred conditions outlined above, a period of from 30 minutes to 24 hours, more preferably from 1 to 16 hours, will usually suffice.

After completion of the reaction, the reaction product can be recovered from the reaction mixture by similar means to that described in Step A1 of Method A.

Reaction (e):

In Reaction (e), alkylation of a =NH group produced by Reaction (c) is conducted by using a $C_1$–$C_6$ alkyl halide, such as methyl iodide, ethyl iodide, propyl iodide, butyl iodide, pentyl iodide or hexyl iodide, as an alkylating agent in the presence of a base, for example, an alkali metal carbonate, such as potassium carbonate or sodium carbonate, or an alkali metal hydride, such as sodium hydride. This reaction is essentially the same as that described above in Reaction (a) of Step B3, and may be carried out using the same reagents and reaction conditions.

Reaction (f):

In Reaction (f), conditions for reducing a double bond included in A' are similar to those described in Reaction (a) of Step A2 of Method A in relation to the elimination of a hydroxy-protecting group, which is an aralkyl group.

Reaction (g):

In Reaction (g), conversion of a cyano group to a carbamoyl group is carried out. This reaction is essentially the same as that described above in Reaction (c) of Step A2 of Method A, and may be carried out using the same reagents and reaction conditions.

The compounds of formula (I) can be converted to pharmaceutically acceptable salts by treatment with an acid by conventional means. For example, salts can be prepared by reacting the base with the corresponding acid. The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: ethers, such as diethyl ether, tetrahydrofuran or dioxane; alcohols, such as methanol or ethanol; and halogenated hydrocarbons, preferably halogenated aliphatic hydrocarbons, such as methylene chloride or chloroform. The reaction can take place over a wide range of temperatures, and the precise reaction temperature is not critical to the invention. In general, we find it convenient to carry out the reaction at a temperature of about room temperature. The time required for the reaction may also vary widely, depending on many factors, notably the reaction temperature and the nature of the reagents and solvent employed. However, provided that the reaction is effected under the preferred conditions outlined above, a period of from 5 minutes to 1 hours will usually suffice. The solvent may then be removed by distillation under reduced pressure. Alternatively the compound of formula (I) or its acid addition salt is absorbed on a column packed with an acidic resin (for example, CM Sephadex C-25—trade mark) and the adsorbate is eluted with dilute hydrochloric acid to produce the hydrochloride.

The starting compounds used in Methods A to C are known or can be prepared by known methods (for example, Japanese Patent Kokai Application No. Sho 55-20740, No. Hei 2-304022 and the like). Some compounds of formula (II) can also be prepared by the procedure summarized in the following Reaction Schemes D and E:

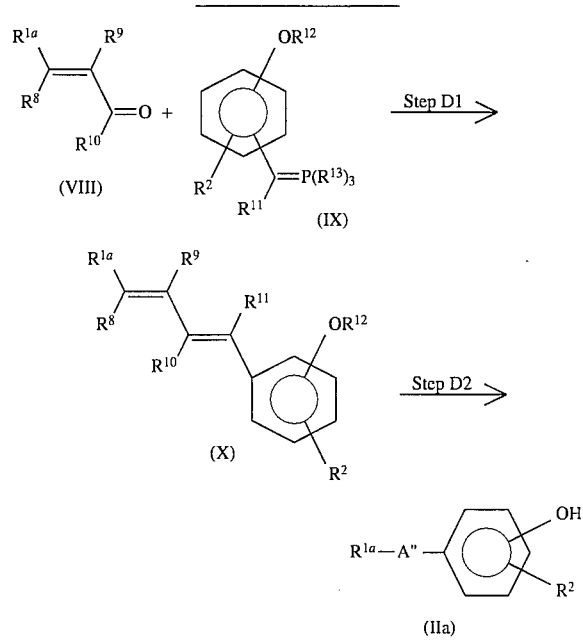

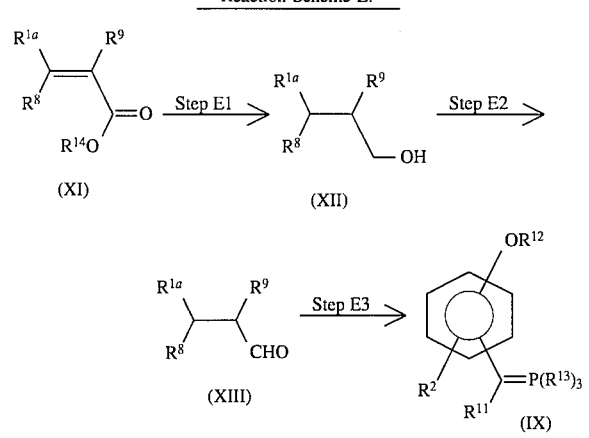

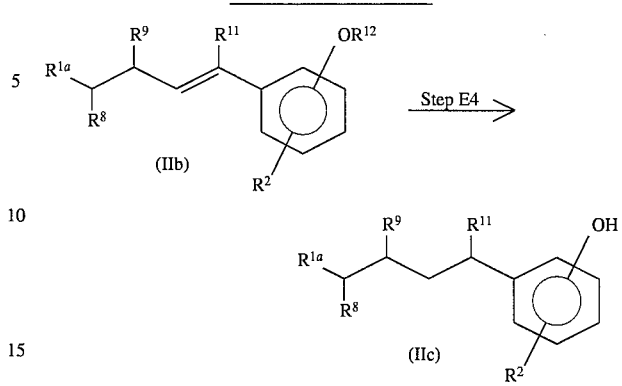

In the above formulae:

$R^{1a}$ and $R^2$ are as defined above;

A" represents a tetramethylene group which is unsubstituted or is substituted by an alkyl group having from 1 to 4 carbon atoms;

$R^8$, $R^9$, $R^{10}$ and $R^{11}$ are the same or different and each represents a hydrogen atom or an alkyl group having from 1 to 4 carbon atoms;

$R^{12}$ represents a hydroxy-protecting group;

$R^{13}$ represents a $C_6$–$C_{10}$ aryl group; and $R^{14}$ represents an alkyl group having from 1 to 6 carbon atoms.

Reaction Scheme D:

In Reaction Scheme D, a compound of formula (IIa) is prepared, that is a compound of formula (II) wherein A' is a group of formula A", wherein A" is as defined above.

Step D1:

In Step D1 a compound of formula (X) is prepared by reacting a compound of formula (VIII) with a compound of formula (IX). The reaction can take place over a wide range of temperatures, and the precise reaction temperature is not critical to the invention. In general, we find it convenient to carry out the reaction at a temperature of from 0° C. to 200° C., more preferably from 20° C. to 150° C. The time required for the reaction may also vary widely, depending on many factors, notably the reaction temperature and the nature of the reagents and solvent employed. However, provided that the reaction is effected under the preferred conditions outlined above, a period of from 30 minutes to 24 hours, more preferably from 1 to 10 hours will usually suffice. The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: nitriles, such as acetonitrile; aromatic hydrocarbons, such as benzene, toluene or xylene; amides, such as dimethylacetamide, N-methyl-2-pyrrolidinone or hexamethylphosphoric triamide; and ethers, such as diethyl ether, tetrahydrofuran or dioxane. The compound of formula (IX) is readily prepared by a synthetic method via an ylide, which is well-known in the field of organic chemistry. For example, it can be synthesized by reacting a compound of formula (IX'):

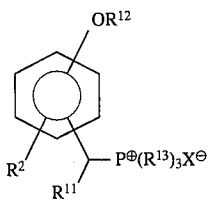

(wherein $R^2$, $R^{11}$, $R^{12}$ and $R^{13}$ are as defined above, and X represents a halogen atom) with a base, for example, an amine, such as 1,8-diazabicyclo[5,4,0]undec-7-ene or 1,5-diazabicyclo[4,3,0]non-5-ene; an alkali metal hydroxide, such as sodium hydroxide or potassium hydroxide; an alkali metal hydride, such as lithium hydride, sodium hydride or potassium hydride; an alkali metal amide, such as sodium amide or potassium amide; or an alkali metal alkoxide, such as sodium methoxide, sodium ethoxide or potassium t-butoxide. The reaction can take place over a wide range of temperatures, and the precise reaction temperature is not critical to the invention. In general, we find it convenient to carry out the reaction at a temperature of from 0° C. to 100° C., more preferably from 10° C. to 60° C. The time required for the reaction may also vary widely, depending on many factors, notably the reaction temperature and the nature of the reagents and solvent employed. However, provided that the reaction is effected under the preferred conditions outlined above, a period of from 10 minutes to 10 hours, more preferably from 30 minutes to 5 hours, will usually suffice. The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: nitriles, such as acetonitrile; hydrocarbons, such as hexane, benzene or toluene; amides, such as dimethylacetamide, N-methyl-2-pyrrolidinone or hexamethylphosphoric triamide; ethers, such as diethyl ether, tetrahydrofuran or dioxane; alcohols, such as methanol, ethanol, propanol or isopropanol; halogenated hydrocarbons, preferably halogenated aliphatic hydrocarbons, such as methylene chloride, chloroform or dichloroethane; water; or a mixture of one or more of these organic solvents with water.

Step D2:

In Step D2, a compound of formula (IIa) is prepared from the compound of formula (X) by reduction of the double bond and subsequent elimination of the hydroxy-protecting group represented by $R^{12}$. This reaction is essentially the same as that described above in Step A2 of Method A, and may be carried out using the same reagents and reaction conditions.

Reaction Scheme E:

In Reaction Scheme E a compound of formula (IIb), that is a compound of formula (II) wherein A' represents a group of formula:

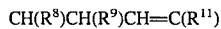

(wherein $R^8$, $R^9$ and $R^{11}$ are as defined above) or a compound of formula (IIc), that is a compound of formula (II) wherein A' represents a group of formula:

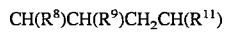

(wherein $R^8$, $R^9$ and $R^{11}$ are as defined above) is prepared.

Step E1:

In Step E1 a compound of formula (XII) is prepared from a compound of formula (XI) by reduction of the double bond and alkoxycarbonyl group. This reaction is essentially the same as that described above in Reaction (b) of Step A2 of Method A, and may be carried out using the same reagents and reaction conditions.

Step E2:

In Step E2 a compound of formula (XIII) is prepared by reacting a compound of formula (XII) with an oxidizing agent (for example, oxalyl chloride-dimethyl sulfoxide-triethylamine, sulfur trioxide-pyridine complex, pyridinium chlorochromate, pyridinium dichromate, or activated manganese dioxide). The reaction can take place over a wide range of temperatures, and the precise reaction temperature is not critical to the invention. In general, we find it convenient to carry out the reaction at a temperature of from 0° C. to 100° C., more preferably from 10° C. to 60° C. The time required for the reaction may also vary widely, depending on many factors, notably the reaction temperature and the nature of the reagents and solvent employed. However, provided that the reaction is effected under the preferred conditions outlined above, a period of from 10 minutes to 10 hours, more preferably from 20 minutes to 3 hours will usually suffice. The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: halogenated hydrocarbons, preferably halogenated aliphatic hydrocarbons, such as methylene chloride or chloroform; ethers, such as diethyl ether, tetrahydrofuran or dioxane; and esters, such as ethyl acetate.

Step E3:

In Step E3 a compound of formula (IIb) is prepared by reacting a compound of formula (XIII) with a compound of formula (IX). This reaction is essentially the same as that described above in Step D1 of Method D, and may be carried out using the same reagents and reaction conditions.

Step E4:

In Step E4 a compound of formula (IIc) is prepared from a compound of formula (IIb) by reduction of the double bond and subsequent elimination of the hydroxy-protecting group represented by $R^{12}$. This reaction is essentially the same as that described above in Step A2 of Method A, and may be carried out using the same reagents and reaction conditions.

BIOLOGICAL ACTIVITY

Test Example 1

Vasoconstriction Experiment

Contractions of the rat caudal ateries were investigated by the method of Van Neuten et al. (J. Pharmacol. Exp. Ther., 218, 217–230, 1981).

Male Sprague-Dawley rats, each weighing approximately 500 g, were sacrificed by rapid exsanguination. The caudal arteries were dissected free from connective tissue and cut into spiral strips (2×20 mm). The resulting preparations were mounted in organ baths, each containing 10 ml of Tyrode solution maintained at 37° C., and then gassed with a mixture of 95% by volume $O_2$ and 5% $CO_2$. The preparations were allowed to equilibrate for 1 hour before being used in the experiment.

An initial optimum resting tension of 0.5 g was applied to the preparations, and isometric contractions were recorded with force-displacement transducers. The relaxant effects of the test compounds were determined on preparations which had been precontracted with 5-HT (5-hydroxytryptamine) ($3\times10^{-6}$M), which is an agonist of the 5-HT$_2$ receptors, or phenylephrine ($10^{-6}$M), which is an agonist of the adrenaline-$\alpha_1$ receptors. After the constractile response to the 5-HT or the phenylephrine had reached a steady state, the test compound was added cumulatively to the bathing medium. At the end of the experiments, papaverine ($10^{-4}$M) was added to produce the maximum relaxation.

The relaxation induced by each test compound was calculated as a percentage of the maximum relaxation induced by $10^{-4}$M of papaverine. The concentrations causing one half of the maximum relaxation (IC$_{50}$) were calculated by the method of least squares. The results are shown in Table 4.

TABLE 4

| Cpd. of Ex. No. | IC$_{50}$ (nM) | |
| --- | --- | --- |
| | 5-HT$_2$ | adrenalin-$\alpha_1$ |
| 1 | 6.0 | 6800 |
| 2 | 4.7 | 3600 |
| 14 | 6.9 | 5600 |
| 48 | 3.7 | 2500 |
| 50 | 4.3 | 3700 |
| 58 | 5.0 | 4900 |
| 97 | 6.5 | 860 |
| 98 | 5.4 | 2200 |
| 99 | 6.1 | 1300 |
| 101 | 3.7 | 3700 |
| 108 | 2.2 | 1700 |
| 113 | 2.2 | 1200 |
| 114 | 5.7 | 1100 |
| 115 | 3.3 | 2300 |
| 116 | 2.2 | — |
| 117 | 1.8 | 5900 |
| 118 | 2.6 | 5400 |
| 120 | 4.2 | — |
| 121 | 2.2 | — |
| 123 | 5.7 | — |
| 124 | 4.6 | — |
| MCI-9042 | 72.0 | 50000 |

Test Example 2

Receptor Binding Experiment

Cerebral membrane fractions were prepared according to method of Leyson et al. (Mol. Pharmacol., 21, 301–314, 1982). Male Wistar rats, each weighing between 280 and 320 g, were used as the test animals.

The rats were killed by decapitation, and then the brains were immediately removed from the skulls. The cortex and the striatium were separated, frozen, and then stored at −80° C. until needed.

The frozen cerebral tissues were placed in 50 mM of a Tris-HCl buffer solution (pH 7.7) and homogenized using a Polytron PT-20; they were then centrifuged at 49,000 g for 10 minutes. [Tris is tris(hydroxymethyl)aminomethane]. The resulting pellet was again suspended in the same Tris buffer solution and centrifugation was repeated. Finally, the resulting pellet was again suspended in the same Tris buffer solution, adjusting the protein content to 0.57 mg of protein per ml, and the suspension was stored at −80° C.

The receptor binding assay was started by adding 440 µl of the membrane suspension to a tube containing 50 µl of $^3$H-ligand and 10 µl of the test compound (dissolved in dimethyl sulfoxide). The mixture was incubated for 1 hour at 30° C., and then the reaction was stopped by filtration under vacuum through a Whatman GF/B glass The filter was rinsed twice, each time with 4 ml of an ice-cold Tris buffer solution, and then ACS-II was added and the radioactivity on the filter was measured using a liquid scintillation counter.

Non-specific binding was assayed in the additional presence of 20 µM of atropine.

The inhibition of binding by the test compound was analysed to estimate the IC$_{50}$ (the concentration of the test compound causing 50% inhibition of binding) using the method of least squares. The results are shown in Table 5.

TABLE 5

| Cpd. of Ex. No. | IC$_{50}$ (ng/ml) | |
| --- | --- | --- |
| | serotonin-2 | dopamine-2 |
| 1 | 8.9 | 118 |
| 2 | 4.0 | 6.2 |
| 5 | 11.5 | 10.5 |
| 14 | 1.7 | 87.1 |
| 20 | 54 | 8 |
| 78 | 0.5 | 17 |
| 79 | 8.7 | 16 |
| 80 | 2.3 | 22 |
| 81 | 3.0 | 22 |
| 82 | 1.7 | 17 |
| 83 | 0.9 | 3.7 |
| 85 | 5.4 | 8.8 |
| 86 | 1.7 | 168 |
| 90 | 5.5 | 168 |

As the results in Table 4 clearly illustrate, the compounds of the present invention bind strongly and selectively to the serotonin-2 receptor.

In conclusion, the compounds of the present invention potently and selectively block the serotonin-2 receptor found in blood vessel endothelial cells and platelets. As a result, they are extremely useful in blocking the vasoconstriction and blood platelet agglutination mediated through serotonin-2 receptors. Consequently, these compounds are useful for treating and preventing recurrence of circulatory organ disorders, for example, such ischemic diseases as arrhythmia, angina pectoris, and myocardial infraction, cerebrovascular diseases such as vasospasm subsequent to subarachnoid hemorrhage, and peripheral circulatory diseases such as Raynaud disease and Buerger disease.

As the results in Table 5 clearly illustrate, the compounds of the present invention bind strongly to the serotonin-2 receptors and to the dopamine-2 receptors.

In conclusion, the compounds of the present invention potently block the serotonin-2 receptors and the dopamine-2 receptors, and they are thus extremely useful for treating and preventing psychotropic diseases, such as psychophrenia without extrapyramidal syndrome.

For these purposes, the compounds of the present invention can be administered orally in any suitable form, for example in the form of tablets, capsules, granules, powders or syrups, or parenterally by injection, suppositories or the like. These pharmaceutical preparations can be prepared by mixing the compound of the present invention with one or more adjuvants such as excipients (e.g. organic excipients including sugar derivatives such as lactose, sucrose, glucose, mannitol or sorbitol; starch derivatives such as corn starch, potato starch, α-starch, dextrine or carboxymethyl starch; cellulose derivatives such as crystalline cellulose, low hydroxypropyl-substituted cellulose, hydroxypropylmethyl cellulose, carboxymethyl cellulose, carboxymethyl cellulose calcium or internally bridged carboxymethyl cellulose sodium; gum arabic; dextran; and Pullulan; inorganic excipients including silicates such as light silicic acid anhydride (colloidal silicon dioxide), synthetic aluminium silicate or magnesium meta-silicic acid aluminate; phosphates such as calcium phosphate; carbonates such as calcium carbonate; and sulfates such as calcium sulfate); lubricants (e.g. metal stearates such as stearic acid, calcium stearate or magnesium stearate; talc; colloidal silica; waxes such as bee gum or spermaceti; boric acid; adipic acid; sulfates such as sodium sulfate; glycol; fumaric acid; sodium benzoate; DL-leucine; sodium salts of aliphatic acids; laurylsulfates such as sodium laurylsulfate or magnesium laurylsulfate; silicates such as silicic acid anhydride or silicic acid hydrate; and the foregoing starch derivatives); binders [e.g. polyvinyl pyrrolidone, Macrogol (polymer of glycols); and similar compounds to the excipients described above]; disintegrators (e.g. similar compounds to the excipients described above; and chemically modified starch-celluloses such as Crosscarmelose sodium (cross-linked sodium carboxymethylcellulose), sodium carboxymethyl starch or bridged polyvinyl pyrrolidone); stabilizers (e.g. p-hydroxybenzoates such as methylparaben or propylparaben; alcohols such as chlorobutanol, benzyl alcohol or phenylethyl alcohol; benzalkonium chloride; phenols such as phenol or cresol; thimerosal; dehydroacetic acid; and sorbic acid); corrigent (e.g. sweeteners, vinegar or perfums, which are conventionally used); diluents and the like.

The dose will vary depending upon the condition and age of the patient and upon the route and type of administration but, for example, the compounds of the present invention can be administered at a daily dose of from 1 to 1000 mg (preferably from 10 to 500 mg) in the case of oral administration, or at a daily dose of from 0.1 to 500 mg (from preferably 1 to 300 mg) in the case of intravenous injection to an adult human patient, which may be administered in single dose or in divided doses.

The invention is further illustrated by the following non-limiting Examples, which demonstrate the preparation of compounds of the present invention, and the subsequent Preparations, which show the preparation of certain of the starting materials used in these Examples.

EXAMPLE 1

3-Dimethylamino-1-[2-(4-phenylbutyl)phenoxy]-2-propanol hydrochloride

1(a) 2-[2-(4-Phenylbutyl)phenoxymethyl]oxirane 7.84 g of potassium t-butoxide were added at room temperature to a solution of 15.81 g of 2-(4-phenylbutyl)phenol (prepared as described in Preparation 3) in 350 ml of dimethylacetamide, and the resulting mixture was stirred at the same temperature for 20 minutes, after which 11.46 ml of epibromohydrin were added to it. The mixture was then stirred at room temperature overnight, after which the reaction mixture was partitioned between water and ethyl acetate. The organic layer was then washed with a saturated aqueous solution of sodium chloride, dried over anhydrous magnesium sulfate, and concentrated by evaporation under reduced pressure. The resulting residue was purified by column chromatography through silica gel, using a 7:1 by volume mixture of hexane and ethyl acetate as the eluent, to give 19.68 g (yield 99.8%) of the title compound as a colorless oil.

Nuclear Magnetic Resonance Spectrum ($CDCl_3$, 270 MHz), δ ppm: 1.5–1.8 (4H, multiplet); 2.6–2.9 (6H, multiplet); 3.2–3.4 (1H, multiplet); 3.97 (1H, doublet of doublets, J=5 & 11 Hz); 4.19 (1H, doublet of doublets, J=3 & 11 Hz); 6.8–6.9 (2H, multiplet); 7.1–7.35 (7H, multiplet).

1(b) 3-Dimethylamino-1-[2-(4-phenylbutyl)phenoxy]-2-propanol 30 ml of 50% by volume aqueous dimethylamine were added to a solution of 19.68 g of 2-[2-(4-phenylbutyl)phenoxymethyl]oxirane [prepared as described in step (a) above] in 300 ml of tetrahydrofuran, and the resulting mixture was stirred at room temperature overnight. At the end of this time, the solvent was removed by distillation under reduced pressure, and the pale yellow oily residue was purified by column chromatography through silica gel, using a 10:1 by volume mixture of methylene chloride and methanol as the eluent, to give 20.6 g (yield 90.4%) of the title compound as a colorless oil.

Nuclear Magnetic Resonance Spectrum ($CDCl_3$, 270 MHz), δ ppm: 1.5–1.8 (4H, multiplet); 2.34 (6H, singlet); 2.3–2.8 (6H, multiplet); 3.9–4.2 (3H, multiplet); 6.8–7.3 (9H, multiplet).

1(c) 3-Dimmethylamino-1-[2-(4-phenylbutyl)phenoxy]-2-propanol hydrochloride 23.5 ml of a 4N solution of hydrogen chloride in dioxane were added to a solution of 20.5 g of 3-dimethylamino-1-[2-(4-phenylbutyl)phenoxy]-2-propanol [prepared as described in step (b) above] in 200 ml of dioxane, and the resulting mixture was stirred at room temperature for 10 minutes. At the end of this time, it was concentrated by evaporation under reduced pressure. The oily residue thus obtained was dissolved in 50 ml of ethyl acetate, and the solution was allowed to stand at room temperature. The crystals which precipitated were collected by filtration and dried, to give 22.1 g (yield 97%) of the title compound as colorless needles, melting at 120°–122° C.

Nuclear Magnetic Resonance Spectrum ($CDCl_3+D_2O$, 270 MHz), δ ppm: 1.5–1.8 (4H, multiplet); 2.5–2.7 (4H, multiplet); 2.89 (6H, singlet); 3.1–3.4 (2H, multiplet); 3.8–4.2 (2H, multiplet); 4.4–4.6 (1H, multiplet); 6.83 (1H, doublet, J=8.3 Hz); 6.91 (1H, triplet, J=7.3 Hz); 7.1–7.3 (7H, multiplet).

Infrared Absorption Spectrum ($CHCl_3$), $\nu_{max}$ cm$^{-1}$: 1600, 1585, 1493, 1474, 1450, 1225.

EXAMPLE 2

N,N-Dimethyl-3-[2-(4-phenylbutyl)phenoxy]propylamine hydrochloride

2(a) N,N-Dimethyl-3-[2-(4-phenylbutyl)phenoxy]propylamine 96 mg of sodium hydride (as a 55% w/w dispersion in mineral oil) were added, whilst ice-cooling and stirring, to a solution of 226 mg of 2-(4-phenylbutyl)phenol (prepared as described in Preparation 3) in 10 ml of dimethylacetamide, and the resulting mixture was stirred at the same temperature for 30 minutes. At the end of this time, 174 mg of 3-dimethylaminopropyl chloride hydrochloride were added, and the reaction mixture was stirred at 70° C. for 14 hours. It was then poured into ice-water, and the aqueous mixture was extracted with ethyl acetate. The extract was washed with a saturated aqueous solution of sodium chloride, dried over anhydrous sodium sulfate and concentrated by evaporation under reduced pressure. The oily residue was purified by column chromatography through silica gel, using a 10:1 by volume mixture of methylene chloride and methanol as the eluent, to give 210 mg (yield 67%) of the title compound as a pale yellow oil.

Nuclear Magnetic Resonance Spectrum ($CDCl_3$, 270 MHz), δ ppm: 1.5–1.8 (4H, multiplet); 1.9–2.1 (2H, multiplet); 2.29 (6H, singlet); 2.51 (2H, triplet, J=7.3 Hz); 2.55–2.7 (4H, multiplet); 4.00 (2H, triplet, J=5.9 Hz); 6.8–6.95 (2H, multiplet); 7.1–7.3 (7H, multiplet).

2(b) N,N-Dimethyl-3-[2-(4-phenylbutyl)phenoxy]propylamine hydrochloride 0.18 ml of a 4N solution of hydrogen chloride in dioxane was added to a solution of 210 mg of N,N-dimethyl-3-[2-(4-phenylbutyl)phenoxy]propylamine [prepared as described in step (a) above] in 5 ml of ethyl acetate, and the resulting mixture was concentrated by distillation under reduced pressure. The resulting residue was dissolved in a small amount of ethyl acetate, and the resulting solution was allowed to stand at room temperature. The crystals which precipitated were collected by filtration to give 210 mg (yield 89%) of the title compound as colorless crystals, melting at 104°–106° C.

Nuclear Magnetic Resonance Spectrum (CDCl$_3$, 270 MHz), δ ppm: 1.55–1.8 (4H, multiplet); 2.3–2.45 (2H, multiplet); 2.55–2.8 (4H, multiplet); 2.76 (6H, singlet); 3.1–3.2 (2H, multiplet); 4.06 (2H, triplet, J=5.6 Hz); 6.80 (1H, doublet, J=7.8 Hz); 6.91 (1H, triplet, J=7.3 Hz); 7.1–7.3 (7H, multiplet).

Infrared Absorption Spectrum (KBr), ν$_{max}$ cm$^{-1}$: 1600, 1586, 1494, 1472, 1452, 1241.

EXAMPLE 3

N,N-Dimethyl-2-[2-(4-phenylbutyl)phenoxy]-ethylamine hydrochloride

3(a) N,N-Dimethyl-2-[2-(4-phenylbutyl)phenoxy] ethylamine

Following a procedure similar to that described in Example 2, 226 mg of 2-(4-phenylbutyl)phenol (prepared as described in Preparation 3), 96 mg of sodium hydride (as a 55% w/w dispersion in mineral oil) and 173 mg of dimethylaminoethyl chloride hydrochloride were reacted in dimethylacetamide. The crude product extracted was purified by column chromatography through silica gel, using a 20:1 by volume mixture of methylene chloride and methanol as the eluent, to give 230 mg (yield 77%) of the title compound as an oil.

Nuclear Magnetic Resonance Spectrum (CDCl$_3$, 270 MHz), δ ppm: 1.5–1.8 (4H, multiplet); 2.35 (6H, singlet); 2.55–2.7 (4H, multiplet); 2.74 (2H, triplet, J=5.9 Hz); 4.07 (2H, triplet, J=5.9 Hz); 6.8–6.95 (2H, multiplet); 7.1–7.3 (7H, multiplet).

3(b) N,N-Dimethyl-2-[2-(4-phenylbutyl)phenoxy]ethylamine hydrochloride 0.39 ml of a 4N solution of hydrogen chloride in dioxane was added to a solution of 230 mg of N,N-dimethyl-2-[2-(4-phenylbutyl)phenoxy]ethylamine [prepared as described in step (a) above] in 5 ml of ethyl acetate, and the resulting mixture was allowed to stand at room temperature. The crystals which precipitated were collected by filtration, washed with ethyl acetate and dried in vacuo, to give 241 mg (yield 93%) of the title compound as colorless crystals, melting at 170°–173° C.

Nuclear Magnetic Resonance Spectrum (CDCl$_3$, 270 MHz), δ ppm: 1.5–1.8 (4H, multiplet); 2.55–2.8 (4H, multiplet); 2.83 (6H, singlet); 3.37 (2H, triplet, J=4.4 Hz); 4.46 (2H, triplet, J=4.4 Hz); 6.83 (1H, doublet, J=7.8 Hz); 6.94 (1H, triplet, J=7.3 Hz); 7.1–7.3 (7H, multiplet).

Infrared Absorption Spectrum (KBr), ν$_{max}$ cm$^{-1}$: 1602, 1588, 1497, 1473, 1454, 1244.

EXAMPLE 4

N,N-Diethyl-2-[2-(4-phenylbutyl)phenoxy]ethylamine hydrochloride

4(a) N,N-Diethyl-2-[2-(4-phenylbutyl)phenoxy]ethylamine

Following a procedure similar to that described in Example 2, 340 mg of 2-(4-phenylbutyl)phenol (prepared as described in Preparation 3), 140 mg of sodium hydride (as a 55% w/w dispersion in mineral oil) and 310 mg of 2-diethylaminoethyl chloride hydrochloride were reacted in 20 ml of dimethylacetamide. The crude product, extracted following the procedure of Example 2, was purified by column chromatography through silica gel, using a 30:1 by volume mixture of methylene chloride and methanol as the eluent, to give 480 mg (yield 98%) of the title compound as an oil.

Nuclear Magnetic Resonance Spectrum (CDCl$_3$, 270 MHz), δ ppm: 1.08 (6H, triplet, J=7.3 Hz); 1.55–1.8 (4H, multiplet); 2.6–2.75 (8H, multiplet); 2.89 (2H, triplet, J=6.3 Hz); 4.04 (2H, triplet, J=6.3 Hz); 6.8–6.95 (2H, multiplet); 7.1–7.35 (7H, multiplet).

4(b) N,N-Diethyl-2-[2-(4- phenylbutyl)phenoxy]ethylamine hydrochloride 0.59 ml of a 4N solution of hydrogen chloride in dioxane was added to a solution of 490 mg of N,N-diethyl-2-[2-(4-phenylbutyl)phenoxy]ethylamine [prepared as described in step (a) above] in 5 ml of ethyl acetate, and the crystals which precipitated were collected by filtration, washed with ethyl acetate and dried in vacuo, to give 216 mg (yield 40%) of the title compound as colorless crystals, melting at 135°–138° C.

Nuclear Magnetic Resonance Spectrum (CDCl$_3$, 270 MHz), δ ppm: 1.42 (6H, triplet, J=7.3 Hz); 1.5–1.8 (4H, multiplet); 2.5–2.7 (4H, multiplet); 3.05–3.35 (4H, multiplet); 3.35–3.5 (2H, multiplet); 4.45–4.55 (2H, multiplet); 6.86 (1H, doublet, J=8.3 Hz); 6.94 (1H, triplet, J=7.3 Hz); 7.1–7.3 (7H, multiplet).

Infrared Absorption Spectrum (KBr), ν$_{max}$ cm$^{-1}$: 1602, 1588, 1497, 1456, 1246.

EXAMPLE 5

1-Methyl-2-{2-[2-(4-phenylbutyl)phenoxy]ethyl} pyrrolidine hydrochloride

5(a) 1-Methyl-2-{2-[2-(4-phenylbutyl)phenoxy] ethyl}pyrrolidine 522 mg of diethyl azodicarboxylate were added, whilst ice-cooling and stirring, to a solution of 226 mg of 2-(4-phenylbutyl)phenol (prepared as described in Preparation 3), 390 mg of 2-(2-hydroxyethyl)-1-methylpyrrolidine and 790 mg of triphenylphosphine in 40 ml of methylene chloride, and the resulting mixture was stirred at room temperature for 14 hours. At the end of this time, the reaction mixture was concentrated by evaporation under reduced pressure, and the resulting residue was partitioned between ethyl acetate and water. The organic layer was washed with a saturated aqueous solution of sodium chloride, dried over anhydrous sodium sulfate and concentrated by evaporation under reduced pressure. The resulting yellow oily concentrate was purified by column chromatography through silica gel, using a 10:1 by volume mixture of methylene chloride and methanol as the eluent, to give 130 mg (yield 38%) of the title compound as an oil.

Nuclear Magnetic Resonance Spectrum (CDCl$_3$, 270 MHz), δ ppm: 1.6–2.6 (12H, multiplet); 2.44 (3H, singlet); 2.6–2.75 (4H, multiplet); 3.2–3.3 (1H, multiplet); 3.95–4.15 (2H, multiplet); 6.85 (1H, doublet, J=8.6 Hz); 6.89 (1H, triplet, J=7.3 Hz); 7.1–7.4 (7H, multiplet).

5(b) 1-Methyl-2-{2-[2-(4-phenylbutyl)phenoxy] ethyl}pyrrolidine hydrochloride 0.2 ml of a 4N solution of hydrogen chloride in dioxane was added to a solution of 130 mg of 1-methyl-2-{2-[2-(4-phenylbutyl)phenoxy]ethyl}pyrrolidine [prepared as described in step (a) above] in 5 ml of ethyl acetate, and the resulting mixture was worked up in a similar manner to the procedure described in Example 1(c). The solvent was removed by distillation under reduced pressure, and the residue was dried in vacuo, to give 144 mg of the title compound as a colorless oil.

Nuclear Magnetic Resonance Spectrum (CDCl$_3$+D$_2$O, 270 MHz), δ ppm: 1.55–1.8 (4H, multiplet); 1.9–2.15 (2H, multiplet); 2.15–2.35 (2H, multiplet); 2.35–2.85 (7H, multiplet); 2.75 (3H, singlet); 3.2–3.4 (1H, multiplet); 3.8–4.3 (3H, multiplet); 6.82 (1H, doublet, J=8.3 Hz); 6.91 (1H, triplet, J=7.3 Hz); 7.1–7.3 (7H, multiplet).

Infrared Absorption Spectrum (CHCl$_3$), $v_{max}$ cm$^{-1}$: 1602, 1588, 1497, 1475, 1452, 1235.

EXAMPLE 6

4-{2-[2-(4-Phenylbutyl)phenoxy]ethyl}morpholine hydrochloride

6(a) 4-{2-[2-(4-Phenylbutyl)phenoxy]ethyl}morpholine

Following a procedure similar to that described in Example 2, 340 mg of 2-(4-phenylbutyl)phenol (prepared as described in Preparation 3), 330 mg of 4-(2-chloroethyl)morpholine hydrochloride and 140 mg of sodium hydride (as a 55% w/w dispersion in mineral oil) were reacted in 20 ml of dimethylacetamide. The crude product, extracted as described in Example 2, was purified by column chromatography through silica gel, using a 3:2 by volume mixture of ethyl acetate and hexane as the eluent, to give 390 mg (yield 76%) of the title compound as a colorless oil.

Nuclear Magnetic Resonance Spectrum (CDCl$_3$, 270 MHz), δ ppm: 1.55–1.8 (4H, multiplet); 2.55–2.7 (8H, multiplet); 2.79 (2H, triplet, J=5.9 Hz); 3.72 (4H, triplet, J=4.6 Hz); 4.10 (2H, triplet, J=5.9 Hz); 6.81 (1H, doublet, J=7.9 Hz); 6.87 (1H, triplet, J=7.3 Hz); 7.05–7.3 (7H, multiplet).

6(b) 4-{2-[2-(4-Phenylbutyl)phenoxy]ethyl}morpholine hydrochloride 0.57 ml of a 4N solution of hydrogen chloride in dioxane was added to a solution of 390 mg of 4-{2-[2-(4-phenylbutyl)phenoxy]ethyl}morpholine [prepared as described in step (a) above] in 5 ml of ethyl acetate, and the resulting mixture was concentrated by evaporation under reduced pressure. The oily residue was dissolved in ethyl acetate, and the resulting solution was allowed to stand at room temperature. The crystals which precipitated were collected by filtration and dried in vacuo, to give 400 mg (yield 92%) of the title compound as colorless needles, melting at 129°–131° C.

Nuclear Magnetic Resonance Spectrum (CDCl$_3$+D$_2$O, 270 MHz), δ ppm: 1.5–1.8 (4H, multiplet); 2.55–2.7 (4H, multiplet); 2.8–3.7 (4H, multiplet); 3.33 (2H, triplet, J=4.4 Hz); 3.8–4.3 (4H, multiplet); 4.51 (2H, triplet, J=4.4 Hz); 6.84 (1H, doublet, J=7.8 Hz); 6.94 (1H, triplet, J=7.3 Hz); 7.1–7.3 (7H, multiplet).

Infrared Absorption Spectrum (KBr), $v_{max}$ cm$^{-1}$: 1602, 1587, 1496, 1471, 1452, 1241.

EXAMPLE 7

2-[2-(4-Phenylbutyl)phenoxymethyl]morpholine hydrochloride

7(a) 4-t-Butoxycarbonyl-2-[2-(4-phenylbutyl)phenoxymethyl]morpholine 218 mg of sodium hydride (as a 55% w/w dispersion in mineral oil) were added, whilst ice-cooling and stirring, to a solution of 1.13 g of 2-(4-phenylbutyl)phenol (prepared as described in Preparation 3) in 20 ml of dimethylacetamide, and the resulting mixture was stirred at room temperature for 30 minutes. At the end of this time, 2.04 g of 4-t-butoxycarbonyl-2-(p-toluenesulfonyloxymethyl)morpholine were added, and the reaction mixture was stirred at 60° C. for 6 hours. The mixture was then partitioned between ethyl acetate and water. The organic layer was washed with a saturated aqueous solution of sodium chloride, dried over anhydrous magnesium sulfate and concentrated by evaporation under reduced pressure. The oily residue thus obtained was purified by column chromatography through silica gel, using a 20:1 by volume mixture of benzene and acetonitrile as the eluent, to give 671 mg of the title compound as an oil.

Nuclear Magnetic Resonance Spectrum (CDCl$_3$, 270 MHz), δ ppm: 1.47 (9H, singlet); 1.6–1.8 (4H, multiplet); 2.6–2.75 (4H, multiplet); 2.75–3.1 (2H, multiplet); 3.5–4.2 (7H, multiplet); 6.81 (1H, doublet, J=7.9 Hz); 6.89 (1H, triplet, J=7.3 Hz); 7.1–7.3 (7H, multiplet).

7(b) 2-[2-(4-phenylbutyl)phenoxymethyl]morpholine hydrochloride 671 mg of 4-t-butoxycarbonyl-2-[2-(4-phenylbutyl)phenoxymethyl]morpholine [prepared as described in step (a) above] was dissolved in 10 ml of a 4N solution of hydrogen chloride in dioxane, whilst ice-cooling, and the resulting solution was allowed to stand at room temperature for 30 minutes. At the end of this time, the solvent was removed by distillation under reduced pressure, and the resulting oily residue was dissolved in 20 ml of ethyl acetate. The solution thus obtained was then allowed to stand at room temperature. The crystals which precipitated were collected by filtration and dried in vacuo, to give 494 mg (yield 86%) of the title compound as colorless crystals, melting at 131°–132° C.

Nuclear Magnetic Resonance Spectrum (CDCl$_3$, 270 MHz), δ ppm: 1.55–1.8 (4H, multiplet); 2.6–2.8 (4H, multiplet); 3.0–3.2 (2H, multiplet); 3.33 (1H, doublet, J=12.5 Hz); 3.46 (1H, doublet, J=12.5 Hz); 3.95–4.2 (4H, multiplet); 4.25–4.4 (1H, multiplet); 6.78 (1H, doublet, J=7.9 Hz); 6.91 (1H, triplet, J=7.3 Hz); 7.1–7.4 (7H, multiplet).

Infrared Absorption Spectrum (KBr), $v_{max}$ cm$^{-1}$: 1602, 1589, 1497, 1483, 1455, 1248.

EXAMPLE 8

4-Methyl-2-[2-(4-phenylbutyl)phenoxymethyl]morpholine hydrochloride

8(a) 4-Methyl-2-[2-(4-phenylbutyl)phenoxymethyl]morpholine 115 mg of potassium carbonate and 118 mg of methyl iodide were added to a solution of 300 mg of 2-[2-(4-phenylbutyl)phenoxymethyl]morpholine hydrochloride (prepared as described in Example 7) in 6 ml of dimethylacetamide, and the resulting mixture was allowed to react at room temperature for 3 hours. At the end of this time, the reaction mixture was partitioned between ethyl acetate and water. The organic layer was washed with a saturated aqueous solution of sodium chloride, dried over anhydrous magnesium sulfate and concentrated by evaporation under reduced pressure. The resulting yellow oily residue was purified by column chromatography through silica gel, using ethyl acetate as the eluent, to give 183 mg (yield 65%) of the title compound as a colorless oil.

Nuclear Magnetic Resonance Spectrum (CDCl$_3$, 270 MHz), δ ppm: 1.6–1.8 (4H, multiplet); 2.0–2.25 (2H, multiplet); 2.32 (3H, singlet); 2.6–2.75 (5H, multiplet); 2.92 (1H, doublet, J=11.9 Hz); 3.65–3.8 (1H, multiplet); 3.85–4.1 (4H, multiplet); 6.81 (1H, doublet, J=7.9 Hz); 6.87 (1H, doublet, J=7.3 Hz); 7.1–7.3 (7H, multiplet).

8(b) 4-Methyl-2-[2-(4 -phenylbutyl)phenoxymethyl]morpholine hydrochloride 0.26 ml of a 4N solution of hydrogen chloride in dioxane was added to a solution of 183 mg of 4-methyl- 2-[2-(4-phenylbutyl)phenoxymethyl]morpholine [prepared as described in step (a) above] in 5 ml of ethyl acetate, and the resulting mixture was allowed to stand at room temperature. The crystals which precipitated were collected by filtration and dried in vacuo, to give 175 mg (yield 86%) of the title compound as colorless needles, melting at 135°–136° C.

Nuclear Magnetic Resonance Spectrum (CDCl$_3$, 270 MHz), δ ppm: 1.55–1.8 (4H, multiplet); 2.6–2.75 (4H, multiplet); 2.76 (3H, singlet); 2.8–3.0 (2H, multiplet); 3.3–3.55 (2H, multiplet); 3.95–4.2 (3H, multiplet); 4.36 (1H, triplet, J=12.2 Hz); 4.55 (1H, doublet, J=8.6 Hz); 6.81 (1H, doublet, J=8.6 Hz); 6.93 (1H, triplet, J=7.3 Hz); 7.1–7.35 (7H, multiplet).

Infrared Absorption Spectrum (KBr), $v_{max}$ cm$^{-1}$: 1601, 1586, 1493, 1453, 1242.

EXAMPLE 9

1-{2-[4-(2-Cyanophenyl)butyl]phenoxy}-3-dimethylamino-2-propanol hydrochloride

9(a)  2-{2-[4-(2-Cyanophenyl)butyl]phenoxymethyl}oxirane

Following a procedure similar to that described in Example 1(a), 634 mg of 2-[4-(2-cyanophenyl)butyl]phenol (prepared as described in Preparation 11), 283 mg of potassium t-butoxide and 345 mg of epibromohydrin were reacted in 6 ml of dimethylacetamide. The crude product, extracted as described in Example 1, was purified as described in Example 1, to give 690 mg (yield 89%) of the title compound as an oil.

Nuclear Magnetic Resonance Spectrum (CDCl$_3$, 60 MHz), δ ppm: 1.5–2.0 (4H, multiplet); 2.5–3.1 (6H, multiplet); 3.1–3.4 (1H, multiplet); 3.7–4.3 (2H, multiplet); 6.6–7.6 (8H, multiplet).

9(b) 1-{2-[4-(2-Cyanophenyl)butyl]phenoxy}-3-dimethylamino-2-propanol 2 ml of 50% by volume aqueous dimethylamine were added to a solution of 319 mg of 2-{2-[4-(2-cyanophenyl)butyl]phenoxymethyl}oxirane [prepared as described in step (a) above] in 10 ml of tetrahydrofuran, and the resulting mixture was reacted and worked-up in a similar manner to that described in Example 1(b). The resulting crude product was then purified by column chromatography through silica gel, using a 10:1 by volume mixture of methylene chloride and methanol as the eluent, to give 267 mg (yield 73%) of the title compound as a colorless oil.

Nuclear Magnetic Resonance Spectrum (CDCl$_3$, 270 MHz), δ ppm: 1.6–1.8 (4H, multiplet); 2.35 (6H, singlet); 2.46 (1H, doublet of doublets, J=3.6 & 11.9 Hz); 2.59 (1H, doublet of doublets, J=9.2 & 11.9 Hz); 2.68 (2H, triplet, J=7.2 Hz); 2.88 (2H, triplet, J=7.2 Hz); 3.9–4.15 (3H, multiplet); 6.8–6.95 (2H, multiplet); 7.1–7.35 (4H, multiplet); 7.49 (1H, triplet, J=8.6 Hz); 7.59 (1H, doublet, J=9.2 Hz).

9(c) 1-{2-[4-(2-Cyanophenyl)butyl]phenoxy}-3-dimethylamino-2-propanol hydrochloride Following a procedure similar to that described in Example 1(c), a solution of 267 mg of 1-{2-[4-(2-cyanophenyl) butyl]phenoxy}-3-dimethylamino-2-propanol [prepared as described in step (b) above] in a suitable amount of ethyl acetate was treated with 0.5 ml of a 4N solution of hydrogen chloride in dioxane. The solvent was then removed by distillation under reduced pressure, and the residue was dried in vacuo, to give 294 mg of the title compound as a colorless oil.

Nuclear Magnetic Resonance Spectrum (CDCl$_3$, 270 MHz), δ ppm: 1.6–1.8 (4H, multiplet); 2.64 (2H, triplet, J=7.3 Hz); 2.85 (2H, triplet, J=7.3 Hz); 2.9–3.1 (6H, multiplet); 3.3–3.55 (2H, multiplet); 3.96 (1H, triplet, J=9.2 Hz); 4.18 (1H, doublet of doublets, J 32 4.6 & 9.2 Hz); 4.55–4.7 (1H, multiplet); 6.84 (1H, doublet, J=8.6 Hz); 6.91 (1H, triplet, J=7.3 Hz); 7.1–7.3 (4H, multiplet); 7.53 (1H, triplet, J=7.3 Hz); 7.60 (1H, doublet, J=7.3 Hz).

Infrared Absorption Spectrum (liquid film) $v_{max}$ cm$^{-1}$: 2225, 1595, 1585, 1490, 1450, 1240.

EXAMPLE 10

2-{4-[2-(3-Dimethylamino-2-hydroxypropoxy)phenyl] butyl}benzamide 2 ml of an aqueous solution containing 1 g of sodium hydroxide were added to a solution of 430 mg of 1-{2-[4-(2-cyanophenyl)butyl]phenoxy}-3-dimethylamino-2-propanol [prepared as described in Example 9(b)] in 5 ml of ethanol, and the resulting mixture was heated under reflux for 15 hours. At the end of this time, the reaction mixture was neutralized by the addition of aqueous hydrochloric acid, after which it was concentrated by evaporation under reduced pressure. The resulting residue was mixed with ethanol, and insoluble materials were filtered off. The filtrate was concentrated by evaporation under reduced pressure, and the residue was purified by column chromatography through silica gel, using a 3:1 by volume mixture of methylene chloride and methanol as the eluent, to give a colorless oily material, which was dissolved in a small amount of methylene chloride and then allowed to stand at room temperature. The crystals which precipitated were collected by filtration and dried in vacuo, to give 238 mg (yield 62%) of the title compound as colorless crystals, melting at 149°–151° C.

Nuclear Magnetic Resonance Spectrum (hexadeuterated dimethyl sulfoxide+D$_2$O, 270 MHz) δ ppm: 1.5–1.7 (4H, multiplet); 2.60 (2H, triplet, J=6.6 Hz); 2.7–2.85 (2H, multiplet); 2.77 (6H, singlet); 3.0–3.3 (2H, multiplet); 3.9–4.05 (2H, multiplet); 4.2–4.3 (1H, multiplet); 6.8–7.0 (2H, multiplet); 7.1–7.4 (6H, multiplet).

Infrared Absorption Spectrum (KBr), $v_{max}$ cm$^{-1}$: 1652, 1615, 1492, 1451, 1373, 1243.

EXAMPLE 11

1-{2-[4-(3,5-Dimethoxyphenyl)butyl]phenoxy}-3-dimethylamino- 2-propanol hydrochloride 11(a)  2-{2-[4-(3,5-Dimethoxyphenyl)butyl]phenoxymethyl}oxirane Following a procedure similar to that described in Example 1(a), 1.9 g of 2-[4-(3,5-dimethoxyphenyl)butyl]phenol (prepared as described in Preparation 9), 0.75 g of potassium t-butoxide and 0.91 g of epichlorohydrin were reacted in 20 ml of dimethylacetamide. The crude product, extracted as described in Example 1(a), was purified to give 1.81 g (yield 80%) of the title compound as a colorless oil.

Nuclear Magnetic Resonance Spectrum (CDCl$_3$, 60 MHz) δ ppm: 1.5–1.9 (4H, multiplet); 2.4–3.0 (6H, multiplet); 3.1–3.6 (1H, multiplet); 3.76 (6H, singlet); 3.8–4.6 (2H, multiplet); 6.34 (3H, broad singlet); 6.7–7.4 (4H, multiplet).

11(b) 1-{2-[4-(3,5-Dimethoxyphenyl)butyl]phenoxy}-3-dimethylamino-2-propanol

Following a procedure similar to that described in Example 1(b), a solution of 0.42 g of 2-{2-[4-(3,5-dimethoxyphenyl)butyl]phenoxymethyl}oxirane [prepared as described in step (a) above] in 10 ml of tetrahydrofuran was treated with 2 ml of 50% by volume aqueous dimethylamine. After purification, 0.29 g (yield 62%) of the title compound was obtained as a colorless oil.

Nuclear Magnetic Resonance Spectrum (CDCl$_3$, 270 MHz), δ ppm: 1.6–1.7 (4H, multiplet); 2.33 (6H, singlet); 2.44 (1H, doublet of doublets, J=3.3 & 11.9 Hz); 2.5–2.7 (5H, multiplet); 3.77 (6H, singlet); 3.9–4.15 (3H, multiplet); 6.25–6.4 (3H, multiplet); 6.8–6.95 (2H, multiplet); 7.1–7.2 (2H, multiplet).

11(c) 1-{2-[4-(3,5 -Dimethoxyphenyl)butyl]phenoxy}-3-dimethylamino-2-propanol hydrochloride Following a procedure similar to that described in Example 1(c), 2 ml of a 4N solution of hydrogen chloride in dioxane were added to a solution of 0.29 g of 1-{2-[4-(3,5-dimethoxyphenyl)butyl]phenoxy}-3-dimethylamino-2-propanol [prepared as described in step (b) above] in ethyl acetate. The solvent was then removed by distillation under reduced pressure, and the resulting residue was dried in vacuo, to give 320 mg of the title compound as a colorless oil.

Nuclear Magnetic Resonance Spectrum (CDCl$_3$, 270 MHz), δ ppm: 1.55–1.7 (4H, multiplet); 2.5–2.7 (4H, multiplet); 2.88 (6H, singlet); 3.1–3.3 (2H, multiplet); 3.77 (6H, singlet); 3.85–4.0 (1H, multiplet); 4.1–4.2 (1H, multiplet); 4.45–4.65 (1H, multiplet); 6.30 (3H, singlet); 6.82 (1H, doublet, J=8.6 Hz); 6.91 (1H, triplet, J=7.6 Hz); 7.1–7.2 (2H, multiplet).

Infrared Absorption Spectrum (liquid film) ν$_{max}$ cm$^{-1}$: 1596, 1494, 1463, 1429, 1242, 1204, 1150.

EXAMPLE 12

3-[N,N-Bis(2-hydroxyethyl)amino]-1-{2-[4-(3,5-dimethoxyphenyl) butyl]phenoxy}-2-propanol hydrochloride 12(a) 3-[N,N-Bis(2-hydroxyethyl)amino]-1-{2-[4-(3,5-dimethoxyphenyl) butyl]phenoxy}-2-propanol 530 mg of diethanolamine were added to a solution of 345 mg of 2-{2-[4-(3,5-dimethoxyphenyl)butyl]phenoxymethyl}oxirane [prepared as described in Example 11(a)] in 10 ml of tetrahydrofuran, and the resulting mixture was stirred at 50° C. for 24 hours. At the end of this time, the solvent was removed by distillation under reduced pressure, and the resulting residue was purified by column chromatography through silica gel, using a 7:1 by volume mixture of methylene chloride and methanol as the eluent, to give 333 mg of the title compound as a colorless oil.

Nuclear Magnetic Resonance Spectrum (CDCl$_3$, 270 MHz), δ ppm: 1.55–1.7 (4H, multiplet); 2.5–2.9 (10H, multiplet); 3.55–3.8 (4H, multiplet); 3.76 (6H, singlet); 3.9–4.05 (2H, multiplet); 4.05–4.2 (1H, multiplet); 6.25–6.35 (3H, multiplet); 6.81 (1H, doublet, J=7.9 Hz); 6.88 (1H, triplet, J=7.3 Hz); 7.1–7.2 (2H, multiplet).

12(b) 3-[N,N-Bis(2-hydroxethyl)amino]-1-(2-[4-(3,5-dimethoxyphenyl) butyl]phenoxy}-2-propanol hydrochloride 0.37 ml of a 4N solution of hydrogen chloride in dioxane was added to a solution of 333 mg of 3-[N,N-bis(2-hydroxyethyl)amino]-1-{2-[4-(3,5-dimethoxyphenyl)butyl]phenoxy]-2-propanol [prepared as described in step (a) above] in 5 ml of ethyl acetate, and the resulting mixture was concentrated by distillation under reduced pressure. The oily residue thus obtained was then dissolved in a small amount of ethyl acetate and the solution was allowed to stand at room temperature. The crystals which precipitated were collected by filtration and dried in vacuo, to give 270 mg (yield 75%) of the title compound as colorless crystals, melting at 78°–80° C.

Nuclear Magnetic Resonance Spectrum (CDCl$_3$, 270 MHz), δ ppm: 1.5–1.7 (4H, multiplet); 2.5–2.7 (4H, multiplet); 3.2–3.7 (6H, multiplet); 3.74 (6H, singlet); 3.9–4.2 (6H, multiplet); 4.5–4.65 (1H, multiplet); 6.26 (1H, singlet); 6.29 (2H, singlet); 6.80 (1H, doublet, J=8.6 Hz); 6.87 (1H, triplet, J=7.3 Hz); 7.05–7.2 (2H, multiplet).

Infrared Absorption Spectrum (KBr) ν$_{max}$ cm$^{-1}$: 1596, 1495, 1460, 1428, 1246, 1205, 1150.

EXAMPLE 13

1-{-2-[4-(3,5-Dimethoxyphenyl)butyl]phenoxy}-3-(4-hydroxypiperidino)-2-propanol hydrochloride 13(a) 1-{2-[4-(3,5-Dimethoxyphenyl)butyl]phenoxy}-3-(4-hydroxypiperidino)-2-propanol 561 mg of potassium t-butoxide were added, whilst ice-cooling, to a solution of 688 mg of 4-hydroxypiperidine hydrochloride in methanol, and the resulting mixture was stirred at the same temperature for 30 minutes. At the end of this time, the solvent was removed by distillation under reduced pressure, the residue was mixed with tetrahydrofuran, and insoluble materials were filtered off. The filtrate was concentrated by evaporation under reduced pressure, to give a colorless oil, which was dissolved in 20 ml of tetrahydrofuran. 1.02 g of 2-{2-[4-(3,5-dimethoxyphenyl)butyl] phenoxymethyl}oxirane [prepared as described in Example 11(a)] were added to the resulting solution, and the mixture was stirred at 60° C. for 5 hours. At the end of this time, the solvent was removed by distillation under reduced pressure, and the residue was partitioned between ethyl acetate and water. The organic layer was dried over anhydrous magnesium sulfate, and concentrated by evaporation under reduced pressure. The resulting residue was purified by column chromatography through silica gel, using a 5:1 by volume mixture of methylene chloride and methanol as the eluent, to give 1.26 g (yield 95%) of the title compound as a colorless oil.

Nuclear Magnetic Resonance Spectrum (CDCl$_3$, 270 MHz), δ ppm: 1.55–1.75 (6H, multiplet); 1.8–2.0 (2H, multiplet); 2.2–2.35 (1H, multiplet); 2.45–2.7 (7H, multiplet); 2.7–2.85 (1H, multiplet); 2.9–3.0 (1H, multiplet); 3.7–3.85 (1H, multiplet); 3.77 (6H, singlet); 3.9–4.2 (3H, multiplet); 6.25–6.4 (3H, multiplet); 6.8–6.95 (2H, multiplet); 7.1–7.2 (2H, multiplet).

13(b) 1-{2-[4-(3,5-Dimethoxyphenyl)butyl]phenoxy}-3-(4-hydroxypiperidino)-2-propanol hydrochloride Following a procedure similar to that described in Example 11(c), a solution of 810 mg of 1-{2-[4-(3,5-dimethoxyphenyl) butyl]phenoxy}-3-(4-hydroxypiperido)-2-propanol [prepared as described in step (a) above] in ethyl acetate was treated with 1.4 ml of a 4N solution of hydrogen chloride in dioxane. The solvent was removed by distillation under reduced pressure, and the residue was dried in vacuo, to give 876 mg of the title compound as a colorless amorphous solid.

Nuclear Magnetic Resonance Spectrum (CDCl$_3$, 270 MHz), δ ppm: 1.55–1.7 (4H, multiplet); 1.8–2.0 (2H, multiplet); 2.4–2.7 (6H, multiplet); 3.0–3.6 (6H, multiplet); 3.77 (6H, singlet); 3.87 (1H, triplet, J=8.2 Hz); 4.05–4.3 (2H, multiplet); 4.5–4.7 (1H, multiplet); 6.31 (3H, singlet); 6.80 (1H, doublet, J=7.9 Hz); 6.91 (1H, triplet, J=7.3 Hz); 7.1–7.25 (2H, multiplet).

Infrared Absorption Spectrum (molten film) ν$_{max}$ cm$^{-1}$: 1596, 1495, 1455, 1429, 1242, 1205, 1151, 1053.

EXAMPLE 14

3-Dimethylamino-1-{2-[4-(3-methoxyphenyl) butyl]phenoxy}-2-propanol hydrochloride 14(a) 2-{2-[4-(3-Methoxyphenyl)butyl] phenoxymethyl}oxirane Following a procedure similar to that described in Example 1(a), 3.40 g of 2-[4-(3-methoxyphenyl)butyl]phenol (prepared as described in Preparation 7), 1.5 g of potassium t-butoxide and 3.63 9 of epibromohydrin were reacted in 70 ml of dimethylacetamide. The crude product, extracted as described in Example 1(a), was purified as described in Example 1(a), to give 3.73 g (yield 90%) of the title compound as a colorless oil.

Nuclear Magnetic Resonance Spectrum (CDCl$_3$, 270 MHz), δ ppm: 1.6–1.8 (4H, multiplet); 2.55–2.7 (4H, multiplet); 2.74 (1H, doublet of doublets, J=2.6 & 4.6 Hz); 2.88 (1H, triplet, J=4.6 Hz); 3.25–3.4 (1H, multiplet); 3.79 (3H, singlet); 3.98 (1H, doublet of doublets, J=5.3 & 11.2 Hz); 4.20 (1H, doublet of doublets, J=3.3 & 11.2 Hz); 6.7–6.95 (5H, multiplet); 7.1–7.2 (3H, multiplet).

14(b) 3-Dimethylamino-1-{2-[4-(3-methoxyphenyl)butyl] phenoxy}-2-propanol

Following a procedure similar to that described in Example 1(b), a solution of 300 mg of 2-{2-[4-(3-methoxyphenyl) butyl]phenoxymethyl}oxirane [prepared as described in step (a) above] in tetrahydrofuran was reacted with 50% by volume aqueous dimethylamine. After purification as described in Example 1(b), 335 mg (yield 97%) of the title compound were obtained as a colorless oil.

Nuclear Magnetic Resonance Spectrum (CDCl$_3$, 270 MHz), δ ppm: 1.55–1.75 (4H, multiplet); 2.34 (6H, singlet); 2.45 (1H, doublet of doublets, J=4 & 12.5 Hz); 2.5–2.7 (5H, multiplet); 3.79 (3H, singlet); 3.9–4.15 (3H, multiplet); 6.7–6.95 (5H, multiplet); 7.1–7.2 (3H, multiplet).

14(c) 3-Dimethylamino-1-{2-[4-(3-methoxyphenyl)butyl] phenoxy}-2-propanol hydrochloride 0.71 ml of a 4N solution of hydrogen chloride in dioxane was added to a solution of 335 mg of 3-dimethyl-amino-1-{2-[4-(3-methoxyphenyl)butyl]phenoxy}-2-propanol [prepared as described in step (a) above] in 5 ml of ethyl acetate, and the resulting mixture was concentrated by evaporation under reduced pressure. The resulting oily residue was dissolved in a small amount of ethyl acetate, and the solution was allowed to stand at room temperature. The crystals which precipitated were collected by filtration and dried in vacuo, to give 295 mg (yield 80%) of the title compound as colorless crystals, melting at 102°–104° C.

Nuclear Magnetic Resonance Spectrum (CDCl$_3$, 270 MHz), δ ppm: 1.55–1.75 (4H, multiplet); 2.55–2.7 (4H, multiplet); 2.87 (6H, singlet); 3.1–3.3 (2H, multiplet); 3.89 (3H, singlet); 3.92 (1H, doublet of doublets, J=7.6 & 9.9 Hz); 4.14 (1H, doublet of doublets, J=4.6 & 9.9 Hz); 4.45–4.6 (1H, multiplet); 6.7–7.0 (5H, multiplet); 7.1–7.25 (3H, multiplet).

Infrared Absorption Spectrum (KBr), ν$_{max}$ cm$^{-1}$: 1611, 1602, 1584, 1492, 1478, 1456, 1281, 1259, 1239.

EXAMPLE 15

3-Dimethylamino-1-{2-[4-(2-methoxyphenyl) butyl]phenoxy}-2-propanol hydrochloride 15(a) 2-{2-[4-(2-Methoxyphenyl)butyl] phenoxymethyl}oxirane Following a procedure similar to that described in Example 1(a), 230 mg of 2-[4-(2-methoxyphenyl)butyl]phenol (prepared as described in Preparation 4), 101 mg of potassium t-butoxide and 246 mg of epibromohydrin were reacted in 15 ml of dimethylacetamide. The crude product, extracted as described in Example 1(a), was purified as described in Example 1(a), to give 260 mg (yield 93%) of the title compound as an oil.

Nuclear Magnetic Resonance Spectrum (CDCl$_3$, 270 MHz), δ ppm: 1.55–1.75 (4H, multiplet); 2.55–2.75 (4H, multiplet); 2.76 (1H, doublet of doublets, J=2.6 & 5.3 Hz); 2.85–2.95 (1H, multiplet); 3.3–3.4 (1H, multiplet); 3.81 (3H, singlet); 4.00 (1H, doublet of doublets, J=5.3 & 11.2 Hz); 4.19 (1H, doublet of doublets, J=2.6 & 11.2 Hz); 6.7–6.95 (4H, multiplet); 7.0–7.2 (4H, multiplet).

15(b) 3-Dimethylamino-1-{2-[4-(2-methoxyphenyl)butyl] phenoxy}-2-propanol

Following a procedure similar to that described in Example 1(b), a solution of 260 mg of 2-{2-[4-(2-methoxyphenyl)butyl]phenoxymethyl}oxirane [prepared as described in step (a) above] in 10 ml of tetrahydrofuran was treated with 2 ml of 50% by volume aqueous dimethylamine and then worked up. The resulting crude product was purified by column chromatography through silica gel, using a 10:1 by volume mixture of methylene chloride and methanol as the eluent, to give 250 mg (yield 84%) of the title compound as a colorless oil.

Nuclear Magnetic Resonance Spectrum (CDCl$_3$, 270 MHz), δ ppm: 1.6–1.7 (4H, multiplet); 2.35 (6H, singlet); 2.48 (1H, doublet of doublets, J=4.0 & 12.5 Hz); 2.55–2.7 (5H, multiplet); 3.81 (3H, singlet); 3.94 (1H, doublet of doublets, J=5.3 & 9.2 Hz); 4.0–4.3 (2H, multiplet); 6.8–6.95 (4H, multiplet); 7.1–7.25 (4H, multiplet).

15(c) 3-Dimethylamino-1-{2-[4-(2-methoxyphenyl)butyl] phenoxy}-2-propanol hydrochloride Following a procedure similar to that described in Example 1(c), a solution of 250 mg of 3-dimethylamino-1-{2-[4-(2-methoxyphenyl)butyl]phenoxy}-2-propanol [prepared as described in step (b) above] in 5 ml of ethyl acetate was treated with 0.35 ml of a 4N solution of hydrogen chloride in dioxane. The solvent was then removed by distillation under reduced pressure, and the residue was dried in vacuo, to give 275 mg (a quantitative yield) of the title compound as a colorless oil.

Nuclear Magnetic Resonance Spectrum (CDCl$_3$+D$_2$O, 270 MHz), δ ppm: 1.55–1.75 (4H, multiplet); 2.55–2.7 (4H, multiplet); 2.89 (6H, singlet); 3.15–3.4 (2H, multiplet); 3.80 (3H, singlet); 3.93 (1H, doublet of doublets, J=7.8 & 9.8 Hz); 4.15 (1H, doublet of doublets, J=4.4 & 9.8 Hz); 4.5–4.6 (1H, multiplet); 6.8–7.0 (4H, multiplet); 7.1–7.25 (4H, multiplet).

Infrared Absorption Spectrum (CHCl$_3$) ν$_{max}$ cm$^{-1}$: 1600, 1585, 1490, 1465, 1450, 1240.

EXAMPLE 16

3-Dimethylamino-1-{2-[4-(4-isopropylphenyl)butyl]phenoxy}-2-propanol hydrochloride 16(a) 2-{2-[4-(4-Isopropylphenyl)butyl]phenoxymethyl}oxirane Following a procedure similar to that described in Example 1(a), 3.04 g of 2-[4-(4-isopropylphenyl)butyl]phenol (prepared as described in Preparation 8), 1.27 g of potassium t-butoxide and 3.11 g of epibromohydrin were reacted in 60 ml of dimethylacetamide. The crude product, extracted as described in Example 1(a), was purified as described in Example 1(a), to give 3.23 g (yield 88%) of the title compound as a colorless oil.

Nuclear Magnetic Resonance Spectrum (CDCl$_3$, 270 MHz), δ ppm: 1.23 (6H, doublet, J=6.6 Hz); 1.6–1.75 (4H, multiplet); 2.55–3.0 (7H, multiplet); 3.3–3.4 (1H, multiplet); 3.98 (1H, doublet of doublets, J=5.3 & 10.6 Hz); 4.19 (1H, doublet of doublets, J=3.3 & 10.6 Hz); 6.81 (1H, doublet, J=7.9 Hz); 6.89 (1H, triplet, J=7.3 Hz); 7.05–7.2 (6H, multiplet).

16(b) 3-Dimethylamino-1-{2-[4-(4-isopropylphenyl)butyl]phenoxy}-2-propanol

Following a procedure similar to that described in Example 1(b), a solution of 648 mg of 2-{2-[4-(4-isopropylphenyl)butyl]phenoxymethyl}oxirane [prepared as described in step (a) above] in 13 ml of tetrahydrofuran was treated with 2.6 ml of 50% by volume aqueous dimethylamine. The reaction mixture was worked up and purified as described in Example 1(b), to give 703 mg (yield 95%) the title compound as a colorless oil.

Nuclear Magnetic Resonance Spectrum (CDCl$_3$, 270 MHz), δ ppm: 1.23 (6H, doublet, J=7.3 Hz); 1.6–1.75 (4H, multiplet); 2.33 (6H, singlet); 2.44 (1H, doublet of doublets, J=4 & 11.9 Hz); 2.5–2.7 (5H, multiplet); 2.8–3.0 (1H, multiplet); 3.9–4.15 (3H, multiplet); 6.8–6.95 (2H, multiplet); 7.1–7.2 (6H, multiplet).

16(c) 3-Dimethyamino-1-{2-[4-(4-isopropylphenyl)butyl]phenoxy}-2-propanol hydrochloride Following a procedure similar to that described in Example 1(c), 1 ml of a 4N solution of hydrogen chloride in dioxane was added to a solution of 703 mg of 3-dimethylamino-1-{2-[4-(4-isopropylphenyl)butYl]phenoxy}-2-propanol [prepared as described in step (b) above] in 7 ml of ethyl acetate. The resulting mixture was concentrated by evaporation under reduced pressure, and the resulting oily residue was dissolved in ethyl acetate and allowed to stand. The crystals which precipitated were collected by filtration and dried in vacuo, to give 665 mg (yield 82%) of the title compound as colorless crystals, melting at 76°–77° C.

Nuclear Magnetic Resonance Spectrum (CDCl$_3$, 270 MHz), δ ppm: 1.23 (6H, doublet, J=7.3 Hz); 1.55–1.7 (4H, multiplet); 2.55–2.7 (4H, multiplet); 2.88 (6H, singlet); 2.8–3.0 (1H, multiplet); 3.15–3.35 (2H, multiplet); 3.93 (1H, doublet of doublets, J=7.9 & 9.2 Hz); 4.16 (1H, doublet of doublets, J=4.6 & 9.2 Hz); 4.5–4.65 (1H, multiplet); 6.83 (1H, doublet, J=8.6 Hz); 6.91 (1H, triplet, J=7.3 Hz); 7.05–7.2 (6H, multiplet).

Infrared Absorption Spectrum (KBr), ν$_{max}$ cm$^{-1}$: 1602, 1588, 1496, 1464, 1454, 1247.

EXAMPLE 17

3-Dimethylamino-1-{2-[4-(3-methylphenyl)butyl]phenoxy}-2-proanol hydrochloride

17(a) 2-{2-[4-(3-Methylphenyl)butyl]phenoxymethyl}oxirane

Following a procedure similar to that described in Example 1(a), 1.90 g of 2-[4-(3-methylphenyl)butyl]phenol (prepared as described in Preparation 10), 0.89 g of potassium t-butoxide and 1.08 g of epibromohydrin were reacted in 20 ml of dimethylacetamide. The crude product, extracted as described in Example 1(a), was purified as described in Example 1(a), to give 1.83 g (yield 78%) of the title compound as a colorless oil.

Nuclear Magnetic Resonance Spectrum (CDCl$_3$, 270 MHz), δ ppm: 1.6–1.75 (4H, multiplet); 2.32 (3H, singlet); 2.5–2.7 (4H, multiplet); 2.74 (1H, doublet of doublets, J=2.6 & 5.3 Hz); 2.88 (1H, doublet of doublets, J=4.0 & 5.3 Hz); 3.25–3.4 (1H, multiplet); 3.98 (1H, doublet of doublets, J=5.3 & 11.2 Hz); 4.20 (1H, doublet of doublets, J=3.3 & 11.2 Hz); 6.8–7.2 (8H, multiplet).

17(b) 3-Dimethylamino-1-{2-[4-(3-methylphenyl)butyl]phenoxy}-2-propanol

Following a procedure similar to that described in Example 1(b), 1.83 g of 2-{2-[4-(3-methylphenyl)butyl]phenoxymethyl}oxirane [prepared as described in step (a) above] dissolved in 20 ml of tetrahydrofuran were treated with 4 ml of 50% by volume aqueous dimethylamine. The crude product thus obtained was purified as described in Example 1(b), to give 1.25 g (yield 59%) of the title compound as a colorless oil.

Nuclear Magnetic Resonance Spectrum (CDCl$_3$, 270 MHz), δ ppm: 1.55–1.7 (4H, multiplet); 2.32 (9H, singlet); 2.4–2.8 (6H, multiplet); 3.8–4.1 (3H, multiplet); 6.7–7.2 (8H, multiplet).

17(c) 3-Dimethylamino-1-{2-[4-(3-methylphenyl)butyl]phenoxy}-2-propanol hydrochloride 1.25 g of 3-dimethylamino-1-{2-[4-(3-methylphenyl)butyl]phenoxy}-2-propanol [prepared as described in step (b) above] was adsorbed on a column packed with CM Sephadex (trade mark) C-25 (H$^+$ type), using methanol as a solvent, and then the absorbate was eluted with a 0.1N solution of hydrogen chloride in methanol. The eluate was concentrated by evaporation under reduced pressure and dried in vacuo, to give 0.93 g (yield 67%) of the title compound as a colorless oil.

Nuclear Magnetic Resonance Spectrum (CDCl$_3$, 270 MHz), δ ppm: 1.6–1.75 (4H, multiplet); 2.32 (3H, singlet); 2.55–2.7 (4H, multiplet); 2.85 (6H, singlet); 3.1–3.3 (2H, multiplet); 3.92 (1H, doublet of doublets, J=7.9 & 9.2 Hz); 4.14 (1H, doublet of doublets, J=4.6 & 9.2 Hz); 4.5–4.65 (1H, multiplet); 6.82 (1H, doublet, J=7.9 Hz); 6.85–7.05 (4H, multiplet); 7.1–7.25 (3H, multiplet).

Infrared Absorption Spectrum (liquid film) ν$_{max}$ cm$^{-1}$: 1601, 1588, 1494, 1453, 1243.

EXAMPLE 18

1-[2-(4-Phenylbutyl)phenoxy]-3-(4-phenylpiperazin-1-yl)-2-propanol dihydrochloride 18(a) 1-[2-(4-phenylbutyl)phenoxy]-3-(4-phenylpiperazin-1-yl)-2-propanol 3.89 g of N-phenylpiperazine were added to a solution of 1.69 g of 2-[2-(4-phenylbutyl)phenoxymethyl]oxirane [prepared as described in Example 1(a)] in 30 ml of acetonitrile, and the resulting mixture was stirred at 50° C. for 3 hours. At the end of this time, the solvent was removed by distillation under reduced pressure, and the resulting residue was purified by column chromatography through silica gel, using a 2:3 by volume mixture of ethyl acetate and hexane as the eluent, to give 920 mg (yield 34%) of the title compound as a colorless oil.

Nuclear Magnetic Resonance Spectrum (CDCl$_3$, 270 MHz), δ ppm: 1.5–1.8 (4H, multiplet); 2.5–2.7 (8H, multiplet); 2.75–2.9 (2H, multiplet); 3.15–3.3 (4H, multiplet); 3.9–4.2 (3H, multiplet); 6.8–7.4 (14H, multiplet).

18(b) 1-[2-(4-Phenylbutyl)phenoxy]-3-(4-phenylpiperazin-1-yl)-2-propanol dihydrochloride 1.55 ml of a 4N solution of hydrogen chloride in dioxane were added to a solution of 920 mg of 1-[2-(4-phenylbutyl)phenoxy]-3-(4-phenylpiperazin-1-yl)-2-propanol [prepared as described in step (a) above] in 20 ml of ethyl acetate, and the resulting mixture was allowed to stand at room temperature for 1 hour. The crystals which precipitated were collected by filtration and dried in vacuo, to give 990 mg (yield 92%) of the title compound as a colorless powder, melting at 102°–104° C.

Nuclear Magnetic Resonance Spectrum (CDCl$_3$, 270 MHz), δ ppm: 1.55–1.8 (4H, multiplet); 2.55–2.7 (4H, multiplet); 3.3–4.8 (13H, multiplet); 6.81 (1H, doublet, J=7.8 Hz); 6.92 (1H, triplet, J=7.3 Hz); 7.1–7.3 (7H, multiplet); 7.4–7.6 (3H, multiplet); 7.82 (2H, doublet, J=7.3 Hz).

Infrared Absorption Spectrum (KBr), $\nu_{max}$ cm$^{-1}$: 1599, 1587, 1493, 1453, 1442, 1245.

EXAMPLE 19

3-(Imidazol-1-yl)-1-[2-(4-phenylbutyl)phenoxy]-2-propanol hydrochloride

19(a) 3-(Imidazol-1-yl)-1-[2-(4-phenylbutyl)phenoxy]-2-propanol 940 mg of imidazole were added to a solution of 780 mg of 2-[2-(4-phenylbutyl)phenoxymethyl]oxirane [prepared as described in Example 1(a)] in 25 ml of acetonitrile, and the resulting mixture was heated under reflux for 24 hours. At the end of this time, the reaction mixture was freed from the solvent by distillation under reduced pressure. The resulting residue was purified by column chromatography through silica gel, using a 20:1 by volume mixture of methylene chloride and methanol as the eluent, to give 798 mg (yield 82%) of the title compound as a pale yellow oil.

Nuclear Magnetic Resonance Spectrum (CDCl$_3$, 270 MHz), δ ppm: 1.55–1.8 (4H, multiplet); 2.6–2.75 (4H, multiplet); 3.8–4.3 (5H, multiplet); 6.78 (1H, doublet, J=8.6 Hz); 6.9–6.95 (2H, multiplet); 7.01 (1H, singlet); 7.1–7.3 (7H, multiplet); 7.46 (1H, singlet).

19(b) 3-(Imidazol-1-yl)-1-[2-(4-phenylbutyl)phenoxy]-2-propanol hydrochloride.

1.7 ml of a 4N solution of hydrogen chloride in dioxane were added to a solution of 790 mg of 3-(imidazol-1-yl)-1-[2-(4-phenylbutyl)phenoxy]-2-propanol [prepared as described in step (a) above] in ethyl acetate, and the resulting mixture was allowed to stand at room temperature for 3 hours. The crystals which precipitated were collected by filtration and dried in vacuo, to give 810 mg (yield 92%) of the title compound as colorless crystals, melting at 128°–130° C.

Nuclear Magnetic Resonance Spectrum (CDCl$_3$, 270 MHz), δ ppm: 1.65–1.8 (4H, multiplet); 2.6–2.7 (4H, multiplet); 3.72 (1H, triplet, J=8.8 Hz); 4.12 (1H, doublet of doublets, J=4.4 & 9.5 Hz); 4.3–4.45 (2H, multiplet); 4.55 (1H, doublet, J=12.5 Hz); 6.80 (1H, doublet, J=8.1 Hz); 6.91 (1H, triplet, J=7.3 Hz); 6.95 (1H, singlet); 7.1–7.3 (8H, multiplet); 9.26 (1H, singlet).

Infrared Absorption Spectrum (KBr) $\nu_{max}$ cm$^{-1}$: 1601, 1574, 1494, 1476, 1452, 1240.

EXAMPLE 20

N,N-Dimethyl-3-{2-[4-(2-methoxyphenyl)butyl]phenoxy}propylamine hydrochloride

20(a) N,N-Dimethyl-3-{2-[4-(2-methoxyphenyl)butyl]phenoxy}propylamine

Following a procedure similar to that described in Example 2(a), 200 mg of 2-[4-(2-methoxyphenyl)butyl]phenol (prepared as described in Preparation 4), 75 mg of sodium hydride (as a 55% w/w dispersion in mineral oil) and 0.14 g of 3-dimethylaminopropyl chloride hydrochloride were reacted in 20 ml of dimethylacetamide. The crude product, extracted as described in Example 2(a), was purified by column chromatography through silica gel, using a 10:1 by volume mixture of methylene chloride and methanol as the eluent, to give 227 mg (yield 85%) of the title compound as pale yellow solid.

Nuclear Magnetic Resonance Spectrum (CDCl$_3$, 270 MHz), δ ppm: 1.6–1.75 (4H, multiplet); 1.9–2.1 (2H, multiplet); 2.32 (6H, singlet); 2.57 (2H, triplet, J=7.6 Hz); 2.6–2.7 (4H, multiplet); 3.81 (3H, singlet); 4.01 (2H, triplet, J=5.9 Hz); 6.75–6.95 (4H, multiplet); 7.1–7.3 (4H, multiplet).

20(b) N,N-Dimethyl-3-{2-[4-(2-methoxyphenyl)butyl]phenoxy}propylamine hydrochloride Following a procedure similar to that described in Example 1(c), 0.24 ml of a 4N solution of hydrogen chloride in dioxane was added to a solution of 227 mg of N,N-dimethyl-3-{2-[4-(2-methoxyphenyl)butyl]phenoxy}propylamine [prepared as described in step (a) above] in 5 ml of ethyl acetate. The crystals which precipitated were collected by filtration and dried in vacuo, to give 120 mg (yield 48%) of the title compound as colorless crystals, melting at 130°14 133° C.

Nuclear Magnetic Resonance Spectrum (CDCl$_3$, 270 MHz), δ ppm: 1.55–1.75 (4H, multiplet); 2.3–2.5 (2H, multiplet); 2.6–2.7 (4H, multiplet); 2.77 (6H, singlet); 3.17 (2H, triplet, J=8 Hz); 3.80 (3H, singlet); 4.01 (2H, triplet, J=5.4 Hz); 6.75–6.95 (4H, multiplet); 7.05–7.25 (4H, multiplet).

Infrared Absorption Spectrum (KBr), $\nu_{max}$ cm$^{-1}$: 1600, 1588, 1497, 1472, 1242.

EXAMPLE 21

3-Dimethylamino-1-{2-[4-(4-methylphenyl)butyl]phenoxy}-2-propanol hydrochloride

21(a) 2-{2-[4-(4-Methylphenyl)butyl]phenoxymethyl}-oxirane

Following a procedure similar to that described in Example 1(a), 0.70 g of 2-[4-(4-methylphenyl)butyl]phenol (prepared as described in Preparation 6), 0.33 g of potassium t-butoxide and 0.8 g of epibromohydrin were reacted in 40 ml of dimethylacetamide. The crude product, extracted as described in Example 1(a), was purified as described in Example 1(a), to give 0.63 g (yield 73%) of the title compound as a colorless oil.

Nuclear Magnetic Resonance Spectrum (CDCl$_3$, 270 MHz), δ ppm: 1.55–1.75 (4H, multiplet); 2.31 (3H, singlet); 2.55–2.7 (4H, multiplet); 2.74 (1H, doublet of doublets, J=2.6 & 5.3 Hz); 2.85–2.95 (1H, multiplet); 3.3–3.4 (1H, multiplet); 3.98 (1H, doublet of doublets, J=5.3 & 11.2 Hz); 4.19 (1H, doublet of doublets, J=3.3 & 11.2 Hz); 6.81 (1H, doublet, J=7.9 Hz) ; 6.89 (1H, triplet, J=6.9 Hz); 7.07 (4H, singlet); 7.1–7.2 (2H, multiplet).

21(b) 3-Dimethylamino-1-{2-[4-(4-methylphenyl)butyl]phenoxy}-2-propanol

Following a procedure similar to that described in Example 1(b), a solution of 0.63 g of 2-{2-[4-(4-methylphenyl)butyl]phenoxymethyl}oxirane [prepared as described in step (a) above] in 10 ml of tetrahydrofuran was treated with 2 ml of 50% by volume aqueous dimethylamine. The crude product thus obtained was purified by column chromatography through silica gel, using a 10:1 by volume mixture of methylene chloride and methanol as the eluent, to give 0.65 g (yield 89%) of the title compound as a colorless oil.

Nuclear Magnetic Resonance Spectrum (CDCl$_3$, 270 MHz), δ ppm: 1.65–1.8 (4H, multiplet); 2.31 (3H, singlet); 2.33 (6H, singlet); 2.35–2.7 (6H, multiplet); 3.9–4.15 (3H, multiplet); 6.8–6.9 (2H, multiplet); 7.0–7.2 (2H, multiplet); 7.07 (4H, singlet).

21(c) 3-Dimethylamino-1-{2-[4-(4-methylphenyl)butyl]phenoxy}-2-propanol hydrochloride 0.95 ml of a 4N solution of hydrogen chloride in dioxane was added to a solution of 640 mg of 3-dimethylamino-1-{2-[4-(4-methylphenyl)butyl]phenoxy}-2-propanol [prepared as described in step (b) above] in a suitable amount of ethyl acetate, and the resulting solution was concentrated by evaporation under reduced pressure. The resulting residue was then dried in vacuo, to give 708 mg (a quantitative yield) of the title compound as a colorless oil.

Nuclear Magnetic Resonance Spectrum (CDCl$_3$, 270 MHz), δ ppm: 1.55–1.7 (4H, multiplet); 2.31 (3H, singlet); 2.5–2.7 (4H, multiplet); 2.87 (6H, singlet); 3.1–3.4 (2H, multiplet); 3.92 (1H, doublet of doublets, J=7.8 & 9.3 Hz); 4.15 (1H, doublet of doublets, J=4.6 & 9.3 Hz); 4.5–4.65 (1H, multiplet); 6.82 (1H, doublet, J=8.3 Hz); 6.91 (1H, triplet, J=7.1 Hz); 7.0–7.2 (6H, multiplet).

Infrared Absorption Spectrum (CHCl$_3$), ν$_{max}$ cm$^{-1}$: 1600, 1585, 1525, 1495, 1475, 1455, 1235.

EXAMPLE 22

3-Dimethylamino-1-{2-[4-(2-hydroxyphenyl)butyl]phenoxy}-2-propanol hydrochloride 22(a) 2-{2-[4-(2-Benzyloxyphenyl)-1-buten-1-yl]phenoxymethyl}oxirane Following a procedure similar to that described in Example 1(a), 330 mg of 2-[4-(2-benzyloxyphenyl)-1-buten-1-yl]phenol (prepared as described in Preparation 14), 124 mg of potassium t-butoxide and 151 mg of epibromohydrin were reacted in 10 ml of dimethylacetamide. The crude product, extracted as described in Example 1(a), was purified as described in Example 1(a), to give 328 mg (yield 85%) of the title compound as a colorless oil.

Nuclear Magnetic Resonance Spectrum (CDCl$_3$, 270 MHz; cis-trans mixture) δ ppm: 2.5–2.95 (6H, multiplet); 3.3–3.4 (1H, multiplet); 3.9–4.05 (1H, multiplet); 4.15–4.25 (1H, multiplet); 5.10 & 5.11 (together 2H, each singlet); 5.7–7.5 (15H, multiplet).

22(b) 3-Dimethylamino-1-{2-[4-(2-hydroxyphenyl)butyl]phenoxy}-2-propanol

Following a procedure similar to that described in Example 1(b), a solution of 328 mg of 2-{2-[4-(2-benzyloxyphenyl)-1-buten-1-yl]phenoxymethyl}oxirane [prepared as described in step (a) above] dissolved in 5 ml of tetrahydrofuran was treated with 3 ml of 50% by volume aqueous dimethylamine. The crude product was purified as described in Example 1(b), to give 3-dimethylamino-1-{2-[4-(2-benzyloxyphenyl)-1-buten-1-yl]phenoxy}-2-propanol as a colorless oil.

The whole of this colorless oil was dissolved in 20 ml of ethanol. The resulting solution was stirred at 50° C. for 1.5 hours in an atmosphere of hydrogen at atmospheric pressure and in the presence of 20 mg of 5% w/w palladium-on-charcoal. At the end of this time, the catalyst was removed by filtration, and the filtrate was concentrated by evaporation under reduced pressure. The resulting residue was purified by column chromatography through silica gel, using a 9:1 by volume mixture of methylene chloride and methanol as the eluent, to give 281 mg (yield 96%) of the title compound as a colorless oil.

Nuclear Magnetic Resonance Spectrum (CDCl$_3$, 270 MHz), δ ppm: 1.6–1.8 (4H, multiplet); 2.35 (6H, singlet); 2.42 (1H, doublet of doublets, J=4.0 & 12.5 Hz); 2.55–2.8 (5H, multiplet); 3.9–4.2 (3H, multiplet); 6.7–7.2 (8H, multiplet).

22(c) 3-Dimethylamino-1-{2-[4-(2-hydroxyphenyl)butyl]phenoxy}-2-propanol hydrochloride Following a procedure similar to that described in Example 1(c), 0.5 ml of a 4N solution of hydrogen chloride in dioxane was added to a solution of 281 mg of 3-dimethylamino-1-{2-[4-(2-hydroxyphenyl)butyl]phenoxy}-2-propanol [prepared as described in step (b) above] in ethyl acetate. The reaction mixture was then concentrated by evaporation under reduced pressure and the resulting oily residue was dissolved in ethyl acetate; the solution was then cooled. The crystals which precipitated were collected by filtration and dried in vacuo, to give 156 mg (yield 50%) of the title compound as colorless crystals, melting at 122°–124° C.

Nuclear Magnetic Resonance Spectrum (hexadeuterated dimethyl sulfoxide, 270 MHz) δ ppm: 1.5–1.65 (4H, multiplet); 2.5–2.7 (4H, multiplet); 2.83 (6H, singlet); 3.15–3.4 (2H, multiplet); 3.85–4.05 (2H, multiplet); 4.2–4.4 (1H, multiplet); 6.65–7.2 (8H, multiplet); 9.21 (1H, singlet).

Infrared Absorption Spectrum (KBr) ν$_{max}$ cm$^{-1}$: 1604, 1591, 1494, 1454, 1243.

EXAMPLE 23

3-Dimethylamino-1-{2-[4-(3-hydroxyphenyl)butyl]phenoxy}-2-propanol hydrochloride 23(a) 2-{2-[4-(3-Methoxymethoxyphenyl)butyl]phenoxymethyl}oxirane Following a procedure similar to that described in Example 1(a), 2.87 g of 2-[4-(3-methoxymethoxyphenyl)butyl]phenol (prepared as described in Preparation 5), 1.18 g of potassium t-butoxide and 1.67 g of epibromohydrin were reacted in 30 ml of dimethylacetamide. The crude product, extracted as described in Example 1(a), was purified as described in Example 1(a), to give 2.05 g (yield 60%) of the title compound as a colorless oil.

Nuclear Magnetic Resonance Spectrum (CDCl$_3$, 60 MHz) δ ppm: 1.5–1.9 (4H, multiplet); 2.4–3.0 (6H, multiplet); 3.1–3.6 (1H, multiplet); 3.47 (3H, singlet); 3.8–4.6 (2H, multiplet); 5.14 (2H, singlet); 6.7–7.4 (8H, multiplet).

23(b) 3-Dimethylamino-1-{2-[4-(3-methoxymethoxyphenyl) butyl]phenoxy}-2-propanol Following a procedure similar to that described in Example 1(b), 1.40 g of 2-{2-[4-(3-methoxymethoxyphenyl)butyl]phenoxymethyl}oxirane [prepared as described in step (a) above] dissolved in 14 ml of tetrahydrofuran were treated with 2.8 ml of 50% by volume aqueous dimethylamine. The crude product was purified as described in Example 1(b), to give 1.51 g (yield 95%) of the title compound as a colorless oil.

Nuclear Magnetic Resonance Spectrum (CDCl$_3$, 60 MHz) δ ppm: 1.5–1.9 (4H, multiplet); 2.30 (6H, singlet); 2.3–3.0 (6H, multiplet); 3.46 (3H, singlet); 3.8–4.3 (3H, multiplet); 5.15 (2H, singlet); 6.7–7.3 (8H, multiplet).

23(c) 3-Dimethylamino-1-{2-[4-(3-hydroxyphenyl)butyl]phenoxy}-2-propanol hydrochloride 5 ml of a 4N solution of hydrogen chloride in dioxane were added to a solution of 1.00 g of 3-dimethylamino-1-{2-[4-(3-methoxymethoxyphenyl)butyl]phenoxy}-2-propanol [prepared as described in step (b) above] in 10 ml of methylene chloride, and the resulting mixture was allowed to stand at room temperature for 15 minutes. At the end of this time, the reaction mixture was concentrated by evaporation under reduced pressure, and the resulting residue was dissolved in ethyl acetate and then allowed to stand. The crystals which precipitated were collected by filtration and dried in vacuo, to give 0.87 g (yield 89%) of the title compound as colorless crystals, melting at 124°–125° C.

Nuclear Magnetic Resonance Spectrum (hexadeuterated dimethyl sulfoxide, 270 MHz) δ ppm: 1.45–1.7 (4H, multiplet); 2.4–2.65 (4H, multiplet); 2.84 (6H, singlet); 3.1–3.3 (2H, multiplet); 3.9–4.1 (2H, multiplet); 4.2–4.4 (1H, multiplet); 6.5–6.65 (3H, multiplet); 6.8–7.2 (5H, multiplet); 9.19 (1H, singlet).

Infrared Absorption Spectrum (KBr), $v_{max}$ cm$^{-1}$: 1600, 1586, 1494, 1484, 1475, 1453, 1242.

EXAMPLE 24

1-{2-[4-(2-Chlorophenyl)butyl]phenoxy}-3-dimethylamino-2-propanol hydrochloride

24(a) 2-{2-[4-(2-Chlorophenyl)butyl]phenoxymethyl}oxirane

Following a procedure similar to that described in Example 1(a), 800 mg of 2-[4-(2-chlorophenyl)butyl]phenol (prepared as described in Preparation 18), 344 mg of potassium t-butoxide and 835 mg of epibromohydrin were reacted in 20 ml of dimethylacetamide. The crude product, extracted as described in Example 1(a), was purified as described in Example 1(a), to give 860 mg (yield 88%) of the title compound as a colorless oil.

Nuclear Magnetic Resonance Spectrum (CDCl$_3$, 270 MHz), δ ppm: 1.6–1.8 (4H, multiplet); 2.68 (2H, triplet, J=7.3 Hz); 2.7–2.85 (3H, multiplet); 2.89 (1H, doublet of doublets, J=4.0 & 5.0 Hz); 3.3–3.4 (1H, multiplet); 3.99 (1H, doublet of doublets, J=5.3 & 11.2 Hz); 4.20 (1H, doublet of doublets, J=3.3 & 11.2 Hz); 6.82 (1H, doublet, J=8.6 Hz); 6.90 (1H, triplet, J=7.9 Hz); 7.05–7.4 (6H, multiplet).

24(b) 1-{2-[4-(2-Chlorophenyl)butyl]phenoxy}-3-dimethylamino-2-propanol

Following a procedure similar to that described in Example 1(b), 860 mg of 2-{2-[4-(2-chlorophenyl)butyl]phenoxymethyl}oxirane [prepared as described in step (a) above] dissolved in 20 ml of tetrahydrofuran were treated with 4 ml of 50% by volume aqueous dimethylamine. The crude product thus obtained was purified as described in Example 1(b), to give 790 mg (yield 80%) of the title compound as a colorless oil.

Nuclear Magnetic Resonance Spectrum (CDCl$_3$, 270 MHz), δ ppm: 1.6–1.8 (4H, multiplet); 2.33 (6H, singlet); 2.44 (1H, doublet of doublets, J=4.0 & 11.9 Hz); 2.5–2.8 (5H, multiplet); 3.9–4.15 (3H, multiplet); 6.8–6.95 (2H, multiplet); 7.1–7.4 (6H, multiplet).

24(c) 1-{2-[4-(2-Chlorophenyl)butyl]phenoxy}-3-dimethylamino-2-propanol hydrochloride Following a procedure similar to that described in Example 17(c), 500 mg of 1-{2-[4-(2-chlorophenyl)butyl]phenoxy}-3-dimethylamino-2-propanol [prepared as described in step (b) above] were converted to the hydrochloride by passing it through a column packed with CM Sephadex C-25 (H$^+$ type). The crude product was purified as described in Example 17(c), to give 398 mg (yield 72%) of the title compound as a colorless oil.

Nuclear Magnetic Resonance Spectrum (CDCl$_3$, 270 MHz), δ ppm: 1.55–1.75 (4H, multiplet); 2.62 (2H, triplet, J=6.6 Hz); 2.75 (2H, triplet, J=7.3 Hz); 2.85–3.0 (6H, multiplet); 3.2–3.35 (2H, multiplet); 3.93 (1H, doublet of doublets, J=8.0 & 9.2 Hz); 4.16 (1H, doublet of doublets, J=4.0 & 9.2 Hz); 4.5–4.65 (1H, multiplet); 6.82 (1H, doublet, J=7.9 Hz); 6.91 (1H, triplet, J=7.9 Hz); 7.1–7.4 (6H, multiplet).

Infrared Absorption Spectrum (liquid film) $v_{max}$ cm$^{-1}$: 1601, 1588, 1494, 1475, 1453, 1243.

EXAMPLE 25

1-{2-[4-(3-Chlorophenyl)butyl]phenoxy}-3-dimethylamino-2-propanol hydrochloride

25(a) 2-{2-[4-(3-Chlorophenyl)butyl]phenoxymethyl}oxirane

Following a procedure similar to that described in Example 1(a), 800 mg of 2-[4-(3-chlorophenyl)butyl]phenol (prepared as described in Preparation 17), 344 mg of potassium t-butoxide and 835 mg of epibromohydrin were reacted in 20 ml of dimethylacetamide. The crude product, extracted as described in Example 1(a), was purified as described in Example 1(a), to give 840 mg (yield 86%) of the title compound as a colorless oil.

Nuclear Magnetic Resonance Spectrum (CDCl$_3$, 270 MHz), δ ppm: 1.55–1.75 (4H, multiplet); 2.55–1.75 (4H, multiplet); 2.74 (1H, doublet of doublets, J=2.6 & 5.3 Hz); 2.89 (1H, doublet of doublets, J=4.0 & 5.3 Hz); 3.25–3.4 (1H, multiplet); 3.97 (1H, doublet of doublets, J=5.3 & 11.2 Hz); 4.21 (1H, doublet of doublets, J=2.6 & 11.2 Hz); 6.82 (1H, doublet, J=7.9 Hz); 6.90 (1H, triplet, J=7.3 Hz); 7.0–7.25 (6H, multiplet).

25(b) 1-{2-[4-(3-Chlorophenyl)butyl]phenoxy}-3-dimethylamino-2-propanol

Following a procedure similar to that described in Example 1(b), 840 mg of 2-{2-[4-(3-chlorophenyl)butyl]phenoxymethyl}oxirane [prepared as described in step (a) above] dissolved in 20 ml of tetrahydrofuran were treated with 4 ml of 50% by volume aqueous dimethylamine. The crude product was purified by column chromatography through silica gel, using a 10:1 by volume mixture of methylene chloride and methanol as the eluent, to give 789 mg (yield 82%) of the title compound as a colorless oil.

Nuclear Magnetic Resonance Spectrum (CDCl$_3$, 270 MHz), δ ppm: 1.55–1.75 (4H, multiplet); 2.33 (6H, singlet); 2.42 (1H, doublet of doublets, J=4.0 & 12.5 Hz); 2.5–2.7 (5H, multiplet); 3.9–4.15 (3H, multiplet); 6.8–6.95 (2H, multiplet); 7.0–7.25 (6H, multiplet).

25(c) 1-{2-[4-(3-Chlorophenyl)butyl]phenoxy}-3-dimethylamino-2-propanol hydrochloride Following a procedure similar to that described in Example 17(c), 760 mg of 1-{2-[4-(3-chlorophenyl)butyl]phenoxy}-3-dimethylamino-2-propanol [prepared as described in step (b) above] were converted to the hydrochloride by passing it through a column packed with CM Sephadex C-25 (H$^+$ type), and recrystallizing it from ethyl acetate, to give 571 mg (yield 68%) of the title compound as colorless crystals, melting at 83°–85° C.

Nuclear Magnetic Resonance Spectrum (CDCl$_3$, 270 MHz), δ ppm: 1.5–1.8 (4H, multiplet); 2.12 (4H, triplet, J=6.6 Hz); 2.90 (6H, singlet); 3.15–3.35 (2H, multiplet); 3.94 (1H, doublet of doublets, J=7.9 & 9.2 Hz); 4.15 (1H, doublet of doublets, J=4.6 & 9.2 Hz); 4.5–4.7 (1H, multiplet); 6.84 (1H, doublet, J=7.9 Hz); 6.94 (1H, triplet, J=7.6 Hz); 7.04 (1H, doublet, J=6.6 Hz); 7.1–7.3 (5H, multiplet).

Infrared Absorption Spectrum (KBr), ν$_{max}$ cm$^{-1}$: 1598, 1459, 1477, 1455, 1251.

EXAMPLE 26

3-Dimethylamino-1-{2-[4-(4-methoxyphenyl)butyl]phenoxy}-2-propanol hydrochloride 26(a) 2-{2-[4-(4-Methoxyphenyl)butyl]phenoxymethyl}oxirane A solution of 1.53 g of diethyl azodicarboxylate in 2 ml of methylene chloride was added dropwise, whilst ice-cooling and stirring, to a solution of 1.5 g of 2-[4-(4-methoxyphenyl)butyl]phenol (prepared as described in Preparation 12), 0.65 g of glycidol and 2.3 g of triphenylphosphine in 25 ml of methylene chloride, and the resulting mixture was stirred at room temperature for 1.5 hours. At the end of this time, the reaction mixture was mixed with water, and the methylene chloride layer which separated was dried over anhydrous sodium sulfate and then concentrated by evaporation under reduced pressure. The resulting residue was purified by column chromatography through silica gel, using a 4:1 by volume mixture of hexane and ethyl acetate as the eluent, to give 0.54 g (yield 29%) of the title compound as a colorless oil.

Nuclear Magnetic Resonance Spectrum (CDCl$_3$, 270 MHz), δ ppm: 1.55–1.75 (4H, multiplet); 2.55–2.7 (4H, multiplet); 2.74 (1H, doublet of doublets, J=2.6 & 5.3 Hz); 2.88 (1H, doublet of doublets, J=4.0 & 5.3 Hz); 3.3–3.4 (1H, multiplet); 3.78 (3H, singlet); 3.97 (1H, doublet of doublets, J=5.3 & 11.2 Hz); 4.20 (1H, doublet of doublets, J=3.3 & 11.2 Hz); 6.75–6.95 (4H, multiplet); 7.05–7.2 (4H, multiplet).

26(b) 3-Dimethylamino-1-{2-[4-(4-methoxyphenyl)butyl]phenoxy}-2-propanol

Following a procedure similar to that described in Example 1(b), 208 mg of 2-{2-[4-(4-methoxyphenyl)butyl]phenoxymethyl}oxirane [prepared as described in step (a) above] dissolved in 5 ml of tetrahydrofuran were treated with 1 ml of 50% by volume aqueous dimethylamine. The crude product was purified as described in Example 1(b), to give 223 mg (yield 93%) of the title compound as a colorless oil.

Nuclear Magnetic Resonance Spectrum (CDCl$_3$, 270 MHz), δ ppm: 1.55–1.75 (4H, multiplet); 2.33 (6H, singlet); 2.43 (1H, doublet of doublets, J=4.0 & 12.5 Hz); 2.5–2.75 (5H, multiplet); 3.78 (3H, singlet); 3.9–4.15 (3H, multiplet); 6.8–6.95 (4H, multiplet); 7.05–7.2 (4H, multiplet).

26(c) 3-Dimethylamino-1-{2-[4-(4-methoxyphenyl)butyl]phenoxy}-2-propanol hydrochloride Following a procedure similar to that described in Example 1(c), 0.23 ml of a 4N solution of hydrogen chloride in dioxane was added to a solution of 216 mg of 3-dimethylamino-1-{2-[4-(4-methoxyphenyl ) butyl]phenoxy}-2-propanol [prepared as described in step (b) above] in 10 ml of ethyl acetate. The reaction mixture was then concentrated by evaporation under reduced pressure, and the resulting residue was dissolved in 10 ml of ethyl acetate and then allowed to stand. The crystals which precipitated were collected by filtration, to give 191 mg (yield 80%) of the title compound as colorless crystals, melting at 97°–98° C.

Nuclear Magnetic Resonance Spectrum (CDCl$_3$, 270 MHz), δ ppm: 1.5–1.7 (4H, multiplet); 2.5–2.65 (4H, multiplet); 2.87 (6H, singlet); 3.1–3.35 (2H, multiplet); 3.78 (3H, singlet); 3.93 (1H, doublet of doublets, J=7.9 & 9.2 Hz); 4.14 (1H, doublet of doublets, J=4.6 & 9.2 Hz); 4.5–4.6 (1H, multiplet); 6.8–7.0 (4H, multiplet); 7.05–7.2 (4H, multiplet).

Infrared Absorption Spectrum (KBr), ν$_{max}$ cm$^{-1}$: 1610, 1584, 1513, 1496, 1473, 1465, 1452, 1243.

EXAMPLE 27

2-Dimethylamino-1-[2-(4-phenylbutyl)phenoxymethyl]ethyl hydrogen succinate hydrochloride 0.57 g of succinic anhydride was added to a solution of 1.79 g of 3-dimethylamino-1-[2-(4-phenylbutyl)phenoxy]-2-propanol [prepared as described in Example 1(b)] in 50 ml of acetone, and the resulting mixture was heated under reflux for 2 hours. At the end of this time, the reaction mixture was cooled, and 1.5 ml of a 4N solution of hydrogen chloride in dioxane were added, and the mixture was allowed to stand at room temperature. The crystals which precipitated were collected by filtration and dried in vacuo, to give 2.20 g (yield 93%) of the title compound as colorless crystals, melting at 123°–125° C.

Nuclear Magnetic Resonance Spectrum (CDCl$_3$, 270 MHz), δ ppm: 1.55–1.75 (4H, multiplet); 2.5–2.9 (8H, multiplet); 2.85 (6H, singlet); 3.3–3.55 (2H, multiplet); 4.10 (1H, doublet of doublets, J=5.3 & 10.6 Hz); 4.20 (1H, doublet of doublets, J=4.0 & 10.6 Hz); 5.6–5.8 (1H, multiplet); 6.80 (1H, doublet, J=7.9 Hz); 6.92 (1H, triplet, J=7.3 Hz); 7.1–7.35 (7H, multiplet).

Infrared Absorption Spectrum (KBr), ν$_{max}$ cm$^{-1}$: 1736, 1718, 1599, 1493, 1461, 1452, 1402, 1379, 1249, 1209, 1166.

EXAMPLE 28

3-Dimethylamino-1-{2-[4-(2-naphthyl)butyl]phenoxy}-2-propanol hydrochloride

28(a) 2-{2-[4-(2-Naphthyl)butyl]phenoxymethyl}oxirane

Following a procedure similar to that described in Example 1(a), 300 mg of 2-[4-(2-naphthyl)butyl]phenol (prepared as described in Preparation 15), 122 mg of potassium t-butoxide and 301 mg of epibromohydrin were reacted in 15 ml of dimethylacetamide. The crude product, extracted as described in Example 1(a), was purified as described in Example 1(a), to give 303 mg (yield 84%) of the title compound as a colorless oil.

Nuclear Magnetic Resonance Spectrum (CDCl$_3$, 270 MHz), δ ppm: 1.6–1.9 (4H, multiplet); 2.6–2.9 (6H, multiplet); 3.2–3.3 (1H, multiplet); 3.94 (1H, doublet of doublets, J=5.9 & 11.2 Hz); 4.17 (1H, doublet of doublets, J=3.3 & 11.2 Hz); 6.7–7.9 (11H, multiplet).

28(b) 3-Dimethylamino-1-{2-[4-(2-naphthyl)butyl]phenoxy}-2-propanol

Following a procedure similar to that described in Example 1(b), 291 mg of 2-{2-[4-(2-naphthyl)butyl]phenoxymethyl}oxirane [prepared as described in step (a) above] dissolved in 5 ml of tetrahydrofuran were treated with 1 ml of 50% by volume aqueous dimethylamine. The crude product thus obtained was purified by column chromatography through silica gel, using a 10:1 by volume mixture of methylene chloride and methanol as the eluent, to give 279 mg (yield 84%) of the title compound.

Nuclear Magnetic Resonance Spectrum (CDCl$_3$, 270 MHz), δ ppm: 1.6–1.85 (4H, multiplet); 2.29 (6H, singlet); 2.35–2.6 (2H, multiplet); 2.67 (2H, triplet, J=7.3 Hz); 2.80 (2H, triplet, J=7.3 Hz); 3.9–4.1 (3H, multiplet); 6.8–7.9 (11H, multiplet).

28(c) 3-Dimethylamino-1-{2-[4-(2-naphthyl)butyl]-phenoxy}-2-propanol hydrochloride Following a procedure similar to that described in Example 17(c), 279 mg of 3-dimethylamino-1-{2-[4-(2-naphthyl)butyl]phenoxy}-2-propanol [prepared as described in step (b) above] were converted to the hydrochloride by passing it through a column packed with CM Sephadex C-25 (H$^+$ type), to give 270 mg (yield 88%) of the title compound as a colorless oil.

Nuclear Magnetic Resonance Spectrum (CDCl$_3$, 270 MHz), δ ppm: 1.55–1.8 (4H, multiplet); 2.55–2.7 (2H, multiplet); 2.62 (3H, singlet); 2.63 (3H, singlet); 2.79 (2H, triplet, J=7.3 Hz); 2.9–3.2 (2H, multiplet); 3.88 (1H, triplet, J=8.6 Hz); 4.0–4.15 (1H, multiplet); 4.4–4.55 (1H, multiplet); 6.81 (1H, doublet, J=7.9 Hz); 6.91 (1H, triplet, J=7.3 Hz); 7.1–7.5 (5H, multiplet); 7.57 (1H, singlet); 7.7–7.85 (3H, multiplet).

EXAMPLE 29

3-Dimethylamino-1-{2-[4-(1-naphthyl)butyl] phenoxy}-2-propanol hydrochloride

29(a) 2-{2-[4-(1-Naphthyl)butyl]phenoxymethyl}oxirane

Following a procedure similar to that described in Example 1(a), 329 mg of 2-[4-(1-naphthyl)butyl]phenol (prepared as described in Preparation 16), 134 mg of potassium t-butoxide and 334 mg of epibromohydrin were reacted in 15 ml of dimethylacetamide. The crude product, extracted as described in Example 1(a), was purified as described in Example 1(a), to give 316 mg (yield 80%) of the title compound as a colorless oil.

Nuclear Magnetic Resonance Spectrum (CDCl$_3$, 270 MHz), δ ppm: 1.65–1.9 (4H, multiplet); 2.65–2.8 (3H, multiplet); 2.83 (1H, doublet of doublets, J=4.0 & 5.3 Hz); 3.11 (2H, triplet, J=7.3 Hz); 3.25–3.35 (1H, multiplet); 3.97 (1H, doublet of doublets, J=5.3 & 11.2 Hz); 4.19 (1H, doublet of doublets, J=3.3 & 11.2 Hz); 6.81 (1H, doublet, J=8.6 Hz); 6.89 (1H, triplet, J=7.3 Hz); 7.1–7.55 (6H, multiplet); 7.69 (1H, doublet, J=7.9 Hz); 7.84 (1H, doublet, J=7.3 Hz); 8.03 (1H, doublet, J=7.3 Hz).

29(b) 3-Dimethylamino-1-{2-[4-(1-naphthyl)butyl]phenoxy}-2-propanol

Following a procedure similar to that described in Example 1(b), 300 mg of 2-{2-[4-(1-naphthyl)butyl] phenoxymethyl}oxirane [prepared as described in step (a) above] dissolved in 6 ml of tetrahydrofuran were treated with 1.2 ml of 50% by volume aqueous dimethylamine. The crude product was purified as described in Example 1(b), to give 265 mg (yield 77%) of the title compound as a colorless oil.

Nuclear Magnetic Resonance Spectrum (CDCl$_3$, 270 MHz), δ ppm: 1.7–1.9 (4H, multiplet); 2.29 (6H, singlet); 2.41 (1H, doublet of doublets, J=4.0 & 12.5 Hz); 2.56 (1H, doublet of doublets, J=9.5 & 12.5 Hz); 2.69 (2H, triplet, J=7.3 Hz); 3.10 (2H, triplet, J=7.3 Hz); 3.9–4.1 (3H, multiplet); 6.8–8.1 (11H, multiplet).

29(c) 3-Dimethylamino-1-{2-[4-(1-naphthyl)butyl]phenoxy}-2-propanol hydrochloride Following a procedure similar to that described in Example 17(c), 265 mg of 3-dimethylamino-1-{2-[4-(1-naphthyl) butyl]phenoxy}-2-propanol [prepared as described in step (b) above] were converted the hydrochloride by passing it through a column packed with CM Sephadex C-25 (H$^+$ type), to give 200 mg (yield 60%) of the title compound as a colorless oil.

Nuclear Magnetic Resonance Spectrum (CDCl$_3$, 270 MHz), δ ppm: 1.65–1.9 (4H, multiplet); 2.5–2.7 (2H, multiplet); 2.62 (3H, singlet); 2.66 (3H, singlet); 2.9–3.2 (4H, multiplet); 3.8–3.95 (1H, multiplet); 4.0–4.2 (1H, multiplet); 4.4–4.6 (1H, multiplet); 6.81 (1H, doublet, J=7.9 Hz); 6.92 (1H, triplet, J=7.3 Hz); 7.1–7.5 (6H, multiplet); 7.71 (1H, doublet, J=7.9 Hz); 7.85 (1H, doublet, J=9.2 Hz); 8.01 (1H, doublet, J-8.6 Hz).

Infrared Absorption Spectrum (liquid film) ν$_{max}$ cm$^{-1}$: 1598, 1588, 1494, 1453, 1242.

EXAMPLE 30

3-Dimethylamino-1-[2-(3-methyl -4-phenylbutyl)phenoxy]-2-propanol hydrochloride

30(a) 2-[2-(3-Methyl -4-phenylbutyl)phenoxymethyl]oxirane

Following a procedure similar to that described in Example 1(a), 0.98 g of 2-(3-methyl-4-phenylbutyl)phenol (prepared as described in Preparation 13), 0.46 of potassium t-butoxide and 0.56 g of epibromohydrin were reacted in 10 ml of dimethylacetamide. The crude product, extracted as described in Example 1(a), was purified as described in Example 1(a), to give 1.0 g (yield 83%) of the title compound as a colorless oil.

Nuclear Magnetic Resonance Spectrum (CDCl$_3$, 270 MHz), δ ppm: 0.94 (3H, doublet, J=6.8 Hz); 1.4–1.9 (3H, multiplet); 2.42 (1H, doublet of doublets, J=7.9 & 13.9 Hz); 2.5–3.0 (5H, multiplet); 3.25–3.35 (1H, multiplet); 3.9–4.0 (1H, multiplet); 4.1–4.25 (1H, multiplet); 6.7–7.3 (9H, multiplet).

30(b) 3-Dimethylamino-1-[2-(3-methyl-4-phenylbutyl)phenoxy]-2-propanol

Following a procedure similar to that described in Example 1(b), 1.0 g of 2-[2-(3-methyl-4-phenylbutyl)phenoxymethyl]oxirane [prepared as described in step (a) above] dissolved in 20 ml of tetrahydrofuran was treated with 4 ml of 50% by volume aqueous dimethylamine. The crude product was purified as described in Example 1(b), to give 0.99 g (yield 86%) of the title compound as a colorless oil.

Nuclear Magnetic Resonance Spectrum (CDCl$_3$, 270 MHz), δ ppm: 0.93 (3H, doublet, J=5.9 Hz); 1.4–1.9 (3H, multiplet); 2.33 (6H, singlet); 2.4–2.8 (6H, multiplet); 3.8–4.15 (3H, multiplet); 6.8–6.95 (2H, multiplet); 7.1–7.35 (7H, multiplet).

30(c) 3-Dimethylamino-1-[2-(3-methyl-4-phenylbutyl)phenoxy]-2-propanol hydrochloride Following a procedure similar to that described in Example 1(c), 987 mg of 3-dimethylamino-1-[2-(3-methyl-4phenylbutyl)phenoxy]-2-propanol [prepared as described in step (b) above] dissolved in 20 ml of ethyl acetate were converted to the hydrochloride by treating it with 0.9 ml of a 4N solution of hydrogen chloride in dioxane. The solvent was then removed by distillation under reduced pressure, and the resulting residue was dried in vacuo, to give 1.09 g (a quantitative yield) of the title compound as a colorless oil.

Nuclear Magnetic Resonance Spectrum (CDCl$_3$, 270 MHz), δ ppm: 0.94 (3H, doublet, J=5.9 Hz); 1.3–1.9 (3H, multiplet); 2.4–2.8 (4H, multiplet); 2.85 (3H, singlet); 2.87 (3H, singlet); 3.15–3.3 (2H, multiplet); 3.85–4.0 (1H, multiplet); 4.1–4.2 (1H, multiplet); 4.45–4.6 (1H, multiplet); 6.82 (1H, doublet, J=8.6 Hz); 6.90 (1H, triplet, J=7.3 Hz); 7.1–7.35 (7H, multiplet).

Infrared Absorption Spectrum (liquid film) $v_{max}$ cm$^{-1}$: 1601, 1588, 1494, 1453, 1243.

EXAMPLE 31

2-{2-[2-(4-Phenylbutyl)phenoxy]ethyl}piperidine hydrochloride

31(a) 1-t-Butoxycarbonyl-2-{2-[2-(4-phenylbutyl)-phenoxy]ethyl}piperidine

Following a procedure similar to that described in Example 5(a), 1.69 g of 2-(4-phenylbutyl)phenol (prepared as described in Preparation 3), 1.72 g of 1-t-butoxycarbonyl-2-(2-hydroxyethyl)piperidine, 5.9 g of triphenylphosphine and 3.92 g of diethyl azodicarboxylate were reacted in 75 ml of methylene chloride. The crude oily product, extracted as described in Example 5(a), was purified by column chromatography through silica gel, using a 5:1 by volume mixture of hexane and ethyl acetate as the eluent, to give 1.13 g (yield 34%) of the title compound as an oil.

Nuclear Magnetic Resonance Spectrum (CDCl$_3$, 270 MHz), δ ppm: 1.39 (9H, singlet); 1.3–1.75 (10H, multiplet); 1.8–2.0 (1H, multiplet); 2.1–2.3 (1H, multiplet); 2.6–2.7 (4H, triplet, J=7.3 Hz); 2.82 (1H, triplet, J=13.1 Hz); 3.85–4.1 (3H, multiplet); 4.4–4.55 (1H, multiplet); 6.77 (1H, doublet, J=7.9 Hz); 6.84 (1H, triplet, J=6.6 Hz); 7.05–7.3 (7H, multiplet).

31(b) 2-{2-[2-(4-Phenylbutyl)phenoxy]ethyl}piperidine hydrochloride 10 ml of a 4N solution of hydrogen chloride in dioxane were added to a solution of 1.13 g of 1-t-butoxycarbonyl-2-{2-[2-(4-phenylbutyl)phenoxy]ethyl}piperidine [prepared as described in step (b) above] in 10 ml of dioxane, and the resulting mixture was stirred at room temperature for 30 minutes. At the end of this time, the reaction mixture was freed from the solvent by distillation under reduced pressure. The resulting residue was washed with hexane and dried in vacuo, to give 0.94 g (yield 97%) of the title compound as a colorless oil.

Nuclear Magnetic Resonance Spectrum (CDCl$_3$, 270 MHz), δ ppm: 1.2–2.3 (11H, multiplet); 2.4–2.7 (5H, multiplet); 2.75–2.9 (1H, multiplet); 3.15–3.3 (1H, multiplet); 3.45 (1H, doublet, J=12.5 Hz); 4.0–4.2 (2H, multiplet); 6.8–6.95 (2H, multiplet); 7.05–7.3 (7H, multiplet).

Infrared Absorption Spectrum (CHCl$_3$), $v_{max}$ cm$^{-1}$: 1600, 1585, 1495, 1475, 1450, 1235.

EXAMPLE 32

1-Methyl-2-{-2-[2-(4-phenylbutyl)phenoxy]ethyl}piperidine hydrochloride

32(a) 1-Methyl-2-{2-[2-(4-phenylbutyl)phenoxy]ethyl}piperidine

A solution of 820 mg of 1-t-butoxycarbonyl-2-{2-[2-(4-phenylbutyl)phenoxy]ethyl}piperidine [prepared as described in Example 31(a)] in 4 ml of tetrahydrofuran was added dropwise to a dispersion of 140 mg of lithium aluminum hydride in 4 ml of tetrahydrofuran, whilst ice-cooling. After the addition was complete, the reaction mixture was heated under reflux for 2 hours and then cooled. Sodium sulfate decahydrate was carefully added to the mixture in order to decompose any excess of the hydride. Insoluble materials were then filtered off, and the filtrate was concentrated by evaporation under reduced pressure. The resulting oily residue was purified by column chromatography through silica gel, using a 20:1 by volume mixture of methylene chloride and methanol as the eluent, to give 455 mg (yield 69%) of the title compound as a colorless oil.

Nuclear Magnetic Resonance Spectrum (CDCl$_3$, 270 MHz), δ ppm: 1.15–1.5 (2H, multiplet); 1.6–1.95 (9H, multiplet); 2.1–2.3 (3H, multiplet); 2.35 (3H, singlet); 2.64 (4H, triplet, J=6.9 Hz); 2.85–3.0 (1H, multiplet); 3.95–4.1 (2H, multiplet); 6.8–6.95 (2H, multiplet); 7.1–7.3 (7H, multiplet).

32(b) 1-Methyl-2-{2-[2-(4-phenylbutyl)phenoxy]ethyl}piperidine hydrochloride

Following a procedure similar to that described in Example 1(c), 450 mg of 1-methyl-2-{2-[2-(4-phenylbutyl)phenoxy]ethyl}piperidine [prepared as described in step (a) above] dissolved in 5 ml of ethyl acetate were converted to the hydrdochloride by treating it with 0.4 ml of a 4N solution of hydrogen chloride in dioxane. The reaction mixture was then concentrated by evaporation under reduced pressure and dried in vacuo, to give 496 mg of the title compound as a colorless oil.

Nuclear Magnetic Resonance Spectrum (CDCl$_3$+D$_2$O, 270 MHz), δ ppm: 1.2–1.5 (1H, multiplet); 1.55–2.45 (11H, multiplet); 2.45–2.9 (5H, multiplet); 2.76 (3H, singlet); 2.9–3.7 (2H, multiplet); 3.95–4.2 (2H, multiplet); 6.81 (1H, doublet, J=8.6 Hz); 6.91 (1H, triplet, J=6.9 Hz); 7.1–7.3 (7H, multiplet).

Infrared Absorption Spectrum (CHCl$_3$), $v_{max}$ cm$^{-1}$: 1600, 1585, 1495, 1470, 1450, 1230.

EXAMPLE 33

1-{2-[4-(4-Methoxyphenyl)butyl]phenoxy}-3-(4-phenylpiperazin-1-yl)-2-propanol dihydrochloride 33(a) 1-{2-[4-(4-Methoxyphenyl)butyl]phenoxy}-3-(4-phenylpiperazin-1-yl)-2-propanol A solution of 185 mg of 2-{2-[4-(4-methoxyphenyl)butyl]phenoxymethyl}oxirane [prepared as described in Example 26(a)] and 96 mg of 1-phenylpiperazine in 5 ml of tetrahydrofuran was stirred at 60° C. for 24 hours. At the end of this time, the reaction mixture was concentrated by evaporation under reduced pressure. The oily residue thus obtained was purified by column chromatography through silica gel, using a 20:1 by volume mixture of methylene chloride and methanol as the eluent, to give 296 mg (yield 96%) of the title compound as a colorless oil.

Nuclear Magnetic Resonance Spectrum (CDCl$_3$, 270 MHz), δ ppm: 1.5–1.75 (4H, multiplet); 2.5–2.9 (10H, multiplet); 3.1–3.3 (4H, multiplet); 3.77 (3H, singlet); 3.9–4.2 (3H, multiplet); 6.7–7.3 (13H, multiplet).

33(b) 1-{2-[4-(4-Methoxyphenyl)butyl]phenoxy}-3-(4-piperazin-1-yl)-2-propanol dihydrochloride 0.23 ml of a 4N solution of hydrogen chloride in dioxane was added to a solution of 286 mg of 1-{2-[4-(4-methoxyphenyl)butyl]phenoxy}-3-(4-phenylpiperazin-1-yl)-2-propanol [prepared as described in step (a) above] in 5 ml of dioxane, and the resulting solution was concentrated by evaporation under reduced pressure. The resulting oily residue was dissolved in ethyl acetate and then allowed to stand. The crystals which precipitated were collected by filtration and dried in vacuo, to give 223 mg (yield 72%) of the title compound as colorless crystals, melting at 147°–149° C.

Nuclear Magnetic Resonance Spectrum (CDCl$_3$+D$_2$O, 270 MHz), δ ppm: 1.5–1.7 (4H, multiplet); 2.5–2.7 (4H, multiplet); 3.1–3.8 (10H, multiplet); 3.74 (3H, singlet); 3.93 (1H, doublet of doublets, J=7.6 & 9.5 Hz); 4.14 (1H, doublet of doublets, J=4.6 & 9.5 Hz); 4.6–4.8 (1H, multiplet ); 6.75–7.4 (13H, multiplet).

Infrared Absorption Spectrum (KBr), $v_{max}$ cm$^{-1}$: 1610, 1599, 1587, 1511, 1495, 1453, 1253, 1238.

EXAMPLE 34

(4R)-4-Hydroxy-2-[2-(4-phenylbutyl)phenoxymethyl]pyrrolidine hydrochloride

34(a) (4R)-4-Benzyloxy-1-t-butoxycarbonyl-2-[2-(4-phenylbutyl) phenoxymethyl]pyrrolidine 441 mg of 2-(4-phenylbutyl)phenol (prepared as described in Preparation 3) and 241 mg of potassium t-butoxide were dissolved, with ice-cooling and stirring, in 20 ml of dimethylacetamide. 900 mg of (4R)-4-benzyloxy-1-t-butoxycarbonyl-2-(p-toluenesulfonyloxymethyl)pyrrolidine were then added to the solution thus obtained, and the resulting mixture was stirred at 40° C. for 5 hours. At the end of this time, the reaction mixture was cooled and partitioned between ethyl acetate and water. The organic layer was dried over anhydrous sodium sulfate, and concentrated by evaporation under reduced pressure. The residue was purified by column chromatography through silica gel, using a 4:1 by volume mixture of hexane and ethyl acetate as the eluent, to give 242 mg (yield 24%) of the title compound as a colorless oil.

Nuclear Magnetic Resonance Spectrum (CDCl$_3$, 270 MHz), δ ppm: 1.45 (9H, singlet); 1.5–1.75 (4H, multiplet); 2.1–2.3 (2H, multiplet); 2.5–2.7 (4H, multiplet); 3.4–4.6 (8H, multiplet); 6.7–6.95 (2H, multiplet); 7.05–7.4 (12H, multiplet).

34(b) (4R)-1-Butoxycarbonyl-4-hydroxy-2-[2-(4-phenylbutyl) phenoxymethyl]pyrrolidine A solution of 238 mg of (4R)-4-benzyloxy-1-t-butoxycarbonyl-2-[2-(4-phenylbutyl)phenoxymethyl]pyrrolidine [prepared as described in step (a) above] in 10 ml of ethanol was stirred at 55° C. for 6 hours in an atmosphere of hydrogen at atmospheric pressure and in the presence of 20 mg of 5% w/w palladium-on-charcoal. The mixture was cooled, and then the catalyst was filtered off, and the filtrate was concentrated by evaporation under reduced pressure. The residue was purified by column chromatography through silica gel, using a 1:1 by volume mixture of hexane and ethyl acetate as the eluent, to give 177 mg (yield 90%) of the title compound as a colorless oil.

Nuclear Magnetic Resonance Spectrum (CDCl$_3$, 270 MHz), δ ppm: 1.46 (9H, singlet); 1.5–1.8 (4H, multiplet); 2.0–2.3 (2H, multiplet); 2.5–2.7 (4H, multiplet); 3.4–4.6 (6H, multiplet); 6.75–6.95 (2H, multiplet); 7.05–7.35 (7H, multiplet).

34(c) (4R)-4-Hydroxy-2-[2-(4-phenylbutyl)phenoxymethyl]pyrrolidine hydrochloride 3 ml of a 4N solution of hydrogen chloride in dioxane were added to a solution of 173 mg of (4R)-1-t-butoxycarbonyl-4-hydroxy-2-[2-(4-phenylbutyl)phenoxymethyl]pyrrolidine [prepared as described in step (b) above] in 3 ml of dioxane, and the resulting mixture was allowed to stand at room temperature for 2 hours. At the end of this time, the reaction mixture was concentrated by evaporation under reduced pressure, and the residue was dissolved in methylene chloride. Ethyl acetate was added to the resulting solution and the mixture was allowed to stand. The crystals which precipitated were collected by filtration, to give mg (yield 74%) of the title compound as colorless crystals, melting at 135°–137° C.

Nuclear Magnetic Resonance Spectrum (CDCl$_3$, 270 MHz), δ ppm: 1.6–1.85 (4H, multiplet); 1.9–2.05 (1H, multiplet); 2.14 (1H, doublet of doublets, J=6.6 & 13.2 Hz); 2.5–2.7 (4H, multiplet); 3.25 (1H, doublet of doublets, J=3.3 & 12.5 Hz); 3.56 (1H, doublet, J=12.5 Hz); 4.05 (1H, doublet of doublets, J=4.6 & 10.6 Hz); 4.23 (1H, doublet of doublets, J=4.0 & 10.6 Hz); 4.2–4.4 (1H, multiplet); 4.4–4.55 (1H, multiplet); 6.82 (1H, doublet, J=7.9 Hz); 6.88 (1H, triplet, J=7.6 Hz); 7.05–7.3 (7H, multiplet).

Infrared Absorption Spectrum (KBr), $v_{max}$ cm$^{-1}$: 1602, 1588, 1495, 1465, 1451, 1237.

EXAMPLE 35

2-(2-{2-[2-(3-Methoxyphenyl)ethyl]phenoxy}ethyl]-1-methylpyrrolidine hydrochloride 35(a) 2-(2-{2-[2-(3-Methoxyphenyl)ethyl]phenoxy}ethyl)-1-methylpyrrolidine 9.83 g of potassium t-butoxide were added, whilst ice-cooling and stirring, to a solution of 20.0 g of 2-[2-(3-methoxyphenyl)ethyl]phenol (prepared as described in Preparation 20) in 50 ml of dimethylacetamide, and the resulting mixture was stirred at the same temperature for 30 minutes, to give potassium 2-[2-(3-methoxyphenyl)ethyl]phenolate.

Meanwhile, 9.83 g of potassium t-butoxide were added to a solution of 16.1 g of 2-(2-chloroethyl)-1-methylpyrrolidine hydrochloride in 80 ml of dimethylacetamide, whilst ice-cooling and stirring, to produce the free amine compound, which was then added, at room temperature and with stirring, to the solution of potassium 2-[2-(3-methoxyphenyl)ethyl]phenolate produced as described above. The resulting mixture was then stirred at 70° C. for 20 hours, after which it was cooled and diluted with 500 ml of ethyl acetate. The diluted solution was washed with water and with a saturated aqueous solution of sodium chloride, in that order, after which it was dried over anhydrous magnesium sulfate. The solvent was then removed by distillation under reduced pressure, and the resulting residue was purified by column chromatography through silica gel, using a 10:1 by volume mixture of methylene chloride and methanol as the eluent, to give 14.6 g (yield 49%) of the title compound as a colorless oil.

Nuclear Magnetic Resonance Spectrum (CDCl$_3$, 270 MHz), δ ppm: 1.55–2.6 (8H, multiplet); 2.42 (3H, singlet); 2.8–3.0 (4H, multiplet); 3.1–3.3 (1H, multiplet); 3.78 (3H, singlet); 3.9–4.15 (2H, multiplet); 6.7–6.95 (5H, multiplet); 7.1–7.3 (3H, multiplet).

35(b) 2-(2-{2-[2-(3-Methoxyphenyl)ethyl]phenoxy}-ethyl]-1-methylpyrrolidine hydrochloride 11 ml of a 4N solution of hydrogen chloride in ethyl acetate were added, whilst ice-cooling, to a solution of 14.5 g of 2-(2-{2-[2-(3-methoxyphenyl)ethyl]phenoxy}ethyl)-1-methylpyrrolidine [prepared as described in step (a) above] in 100 ml of ethyl acetate, and the resulting mixture was allowed to stand at room temperature. The crystals which precipitated were collected by filtration and dried in vacuo, to give 3.0 g (yield 81%) of the title compound as colorless crystals, melting at 109°–110° C.

Nuclear Magnetic Resonance Spectrum (CDCl₃, 270 MHz), δ ppm: 1.9–2.15 (2H, multiplet); 2.15–2.4 (2H, multiplet); 2.4–2.65 (2H, multiplet); 2.77 (3H, singlet); 2.7–3.0 (5H, multiplet); 3.2–3.4 (1H, multiplet); 3.78 (3H, singlet); 3.8–4.1 (2H, multiplet); 4.15–4.3 (1H, multiplet); 6.7–7.0 (5H, multiplet); 7.15–7.3 (3H, multiplet).

EXAMPLE 36

2-(2-{2-[2-(3-Methoxyphenyl)ethyl]phenoxy}ethyl)-1-methylpyrrolidine hydrochloride 36(a) 2-(2-{2-[2-(3-Methoxyphenyl)ethyl]phenoxy}ethyl)-1-methylpyrrolidine 11.3 g of diethyl azodicarboxylate were added dropwise, whilst ice-cooling and stirring, to a solution of 10.6 g of 2-[2-(3-methoxyphenyl)ethyl]phenol (prepared as described in Preparation 20), 8.4 g of 1-methyl-2-pyrrolidylethanol and 17 g of triphenylphosphine in 200 ml of methylene chloride, and the resulting mixture was stirred at room temperature for 15 hours. At the end of this time, the reaction mixture was concentrated by evaporation under reduced pressure, and the resulting residue was partitioned between ethyl acetate and water. The organic layer was dried over anhydrous magnesium sulfate, and the solvent was distilled off under reduced pressure. The resulting residue was purified by column chromatography through silica gel, using a 10:1 by volume mixture of methylene chloride and methanol as the eluent, to give 5.70 g (yield 36%) of the title compound as a colorless oil.

The nuclear magnetic resonance spectrum of this product was identical with that of the compound prepared as described in Example 35(a).

36(b) 2-(2-{2-[2-(3-Methoxyphenyl)ethyl]phenoxy}ethyl)-1-methylpyrrolidine hydrochloride Following a procedure similar to that described in Example 35(a), 5.70 g of 2-(2-{2-[2-(3-methoxyphenyl)ethyl]phenoxy}ethyl)-1-methylpyrrolidine [prepared as described in step (a) above] were converted to the hydrochloride, to give 4.89 g (yield 36%) of the title compound as colorless crystals.

The melting point and nuclear magnetic resonance spectrum of this product were identical with those of the compound prepared as described in Example 35(b).

EXAMPLE 37

4-{2-[2-(3-Methoxyphenyl)ethyl]phenoxy}piperidine hydrochloride

37(a) 1-t-Butoxycarbonyl-4-{2-[2-(3-methoxyphenyl)ethyl]phenoxy}piperidine

Following a procedure similar to that described in Example 36(a), 456 mg of 2-[2-(3-methoxyphenyl)ethyl]phenol (prepared as described in Preparation 20), 600 mg of 1-t-butoxycarbonyl-4-hydroxypiperidine and 865 mg of triphenylphosphine were reacted with 575 mg of diethyl azodicarboxylate in 30 ml of methylene chloride. The reaction mixture was worked up as described in Example 6(a), and the crude product thus obtained was purified by column chromatography through silica gel, using a 4:1 by volume mixture of hexane and ethyl acetate as the eluent, to give 379 mg (yield 46%) of the title compound as a colorless oil.

Nuclear Magnetic Resonance Spectrum (CDCl₃, 270 MHz), δ ppm: 1.47 (9H, singlet); 1.7–2.0 (4H, multiplet); 2.8–3.0 (4H, multiplet); 3.35–3.55 (2H, multiplet); 3.6–3.75 (2H, multiplet); 3.78 (3H, singlet); 4.55–4.6 (1H, multiplet); 6.7–6.9 (5H, multiplet); 7.1–7.3 (3H, multiplet).

37(b) 4-{2-[2-(3-Methoxyphenyl)ethyl]phenoxy}piperidine hydrochloride 379 mg of 1-t-butoxycarbonyl-4-{2-[2-(3-methoxyphenyl)ethyl]phenoxy}piperidine [prepared as described in step (a) above] were dissolved in 5 ml of a 4N solution of hydrogen chloride in dioxane, and the solution was allowed to stand at room temperature for 1 hour. The reaction mixture was then concentrated by distillation under reduced pressure, and the resulting oily residue was dissolved in 10 ml of ethyl acetate, after which it was allowed to stand at room temperature. The crystals which precipitated were collected by filtration and dried in vacuo, to give 290 mg (yield 90%) of the title compound as colorless crystals, melting at 121°–122° C.

Nuclear Magnetic Resonance Spectrum (CDCl₃, 270 MHz), δ ppm: 2.05–2.2 (2H, multiplet); 2.25–2.4 (2H, multiplet); 2.8–3.0 (4H, multiplet); 3.2–3.4 (4H, multiplet); 3.76 (3H, singlet); 4.55–4.6 (1H, multiplet); 6.6–6.8 (4H, multiplet); 6.92 (1H, triplet, J=7.3 Hz); 7.1–7.3 (3H, multiplet).

EXAMPLE 38

4-{2-[2-(3-Methoxyphenyl)ethyl]phenoxy}-1-methypiperidine hydrochloride

38(a) 4-{2-[2-(3-Methoxyphenyl)ethyl]phenoxy}-1-methylpiperidine

A solution of 482 mg of 1-t-butoxycarbonyl-4-{2-[2-(3-methoxylphenyl)ethyl]phenoxy}piperidine (prepared in a similar manner to that described in Example 37) in 5 ml of tetrahydrofuran was added dropwise to a dispersion of 44.5 mg of lithium aluminum hydride in 5 ml of tetrahydrofuran, whilst stirring. After the addition was complete, the reaction mixture was heated under reflux for 1 hour and then cooled. Sufficient sodium sulfate decahydrate was then added to the reaction mixture, in order to decompose any excess of the hydride, after which the mixture was stirred for about 30 minutes. Insoluble materials were filtered off, and then the filtrate was freed from the solvent by distillation under reduced pressure. The resulting oily residue was purified by column chromatography through silica gel, using a 10:1 by volume mixture of methylene chloride and methanol as the eluent, to give 220 mg (yield 57%) of the title compound as a colorless oil.

Nuclear Magnetic Resonance Spectrum (CDCl₃, 270 MHz), δ ppm: 1.85–2.15 (4H, multiplet); 2.3–2.5 (2H, multiplet); 2.33 (3H, singlet); 2.6–2.75 (2H, multiplet); 2.8–3.0 (4H, multiplet); 3.79 (3H, singlet); 4.35–4.5 (1H, multiplet); 6.7–6.9 (5H, multiplet); 7.1–7.3 (3H, multiplet).

38(b) 4-{2-[2-(3-Methoxyphenyl)ethyl]phenoxy}-1-methylpiperidine hydrochloride 0.2 ml of a 4N solution of hydrogen chloride in dioxane was added dropwise to a solution of 220 mg of 4-{2-[2-(3-methoxyphenyl)ethyl]phenoxy}-1-methylpiperidine [prepared as described in step (a) above] in 20 ml of ethyl acetate, and the mixture was allowed to stand at room temperature. The crystals which precipitated were collected by filtration and dried in vacuo, to give 170 mg (yield 69%) of the title compound as colorless crystals, melting at 147°–148° C.

Nuclear Magnetic Resonance Spectrum (CDCl₃, 270 MHz), δ ppm: 2.0–2.25 (2H, multiplet); 2.5–2.8 (2H, multiplet); 2.73 (3H, singlet); 2.8–3.1 (6H, multiplet); 3.2–3.4 (2H, multiplet); 3.76 (3H, singlet); 3.6–3.8 (1H, multiplet);

6.65–6.85 (4H, multiplet); 6.95 (1H, triplet, J=7.3 Hz); 7.15–7.3 (3H, multiplet).

EXAMPLE 39

2-(2-{2-[2-(3-Hydroxyphenyl)ethyl]phenoxy}ethyl) -1-methylpyrrolidine hydrochloride 39(a) 2-(2-{2-[2-(3-Methoxymethoxyphenyl)ethyl] phenoxy}ethyl]-1-methylpyrrolidine Following a procedure similar to that described in Example 35(a), 2.37 g of 2-[2-(3-methoxymethoxyphenyl)ethyl]phenol (prepared as described in Preparation 21), 1.03 g of potassium t-butoxide and 1.69 g of 2-(2-chloroethyl)-1-methylpyrrolidine hydrochloride were reacted in 50 ml of dimethylacetamide. The reaction mixture was then worked up as described in Example 35(a), and the crude product was purified by column chromatography through silica gel, using a 20:1 by volume mixture of methylene chloride and methanol as the eluent, to give 1.87 g (yield 62%) of the title compound as a colorless oil.

Nuclear Magnetic Resonance Spectrum (CDCl$_3$, 270 MHz), δ ppm: 1.5–2.4 (8H, multiplet); 2.39 (3H, singlet); 2.8–3.0 (4H, multiplet); 3.05–3.2 (1H, multiplet); 3.48 (3H, singlet); 3.95–4.15 (2H, multiplet); 5.15 (2H, singlet); 6.8–6.95 (5H, multiplet); 7.1–7.3 (3H, multiplet).

39(b) 2-(2-{2-[2-(3-Hydroxyphenyl)ethyl]phenoxy}ethyl)-1-methylpyrrolidine hydrochloride 1.80 g of 2-(2-{2-[2-(3-methoxymethoxyphenyl)ethyl]phenoxy}ethyl]-1-methylpyrrolidine [prepared as described in step (a) above] were dissolved in 20 ml of a 4N solution of hydrogen chloride in dioxane, and the solution was allowed to stand at room temperature for 30 minutes. At the end of this time, the mixture was concentrated by distillation under reduced pressure, and the resulting oily residue was dissolved in 20 ml of methylene chloride. Ethyl acetate was slowly added to the solution until it just began to show signs of turbidity. The mixture was then allowed to stand overnight at room temperature. The crystals which precipitated were collected by filtration and dried in vacuo, to give 1.25 g (yield 71%) of the title compound as colorless crystals, melting at 68°–70° C.

Nuclear Magnetic Resonance Spectrum (CDCl$_3$, 270 MHz), δ ppm: 1.9–2.6 (6H, multiplet); 2.65–3.1 (5H, multiplet); 2.83 (3H, singlet); 3.15–3.45 (1H, multiplet); 3.6–4.1 (3H, multiplet); 6.57 (1H, doublet, J=7.3 Hz); 6.7–6.8 (2H, multiplet); 6.92 (1H, triplet, J=7.3 Hz); 7.00 (1H, singlet); 7.05 (1H, triplet, J=7.9 Hz); 7.1–7.25 (2H, multiplet).

EXAMPLE 40

(S)-2-{2-[2-(3-Hydroxyphenyl)ethyl]phenoxymethyl} pyrrolidine hydrochloride

40(a) (S)-1-t-Butoxycarbonyl-2-{2-[2-(3-methoxymethoxyphenyl) ethyl]phenoxymethyl}pyrrolidine 0.721 g of potassium t-butoxide was added, whilst ice-cooling, to a solution of 1.66 g of 2-[2-(3-methoxymethoxyphenyl)ethyl]phenol (prepared as described in Preparation 21) in 5 ml of dimethylacetamide, and the resulting mixture was stirred for 15 minutes. At the end of this time, 2.28 g of ([)-1-t-butoxycarbonyl-2-(p-toluenesulfonyloxymethyl)pyrrolidine were added to the mixture, and the mixture was stirred at 50° C. for 2 hours. The reaction mixture was then cooled and partitioned between ethyl acetate and water. The ethyl acetate layer was washed with a saturated aqueous solution of sodium chloride and dried over anhydrous magnesium sulfate. The solvent was removed by distillation under reduced pressure, and the resulting residue was purified by column chromatography through silica gel, using a 4:1 by volume mixture of hexane and ethyl acetate as the eluent, to give 1.70 g (yield 60%) of the title compound as a colorless oil.

Nuclear Magnetic Resonance Spectrum (CDCl$_3$, 270 MHz), δ ppm: 1.47 (9H, singlet); 1.75–2.2 (4H, multiplet); 2.8–3.0 (4H, multiplet); 3.25–3.55 (2H, multiplet); 3.48 (3H, singlet); 3.75–4.3 (3H, multiplet); 5.15 (2H, singlet); 6.8–7.0 (5H, multiplet); 7.05–7.3 (3H, multiplet).

40(b) (S)-2-{2-[2-(3-Hydroxyphenyl)ethyl] phenoxymethyl}pyrrolidine hydrochloride 630 mg of (S)-1-t-butoxycarbonyl-2-{2-[2-(3-methoxymethoxyphenyl) ethyl]phenoxymethyl }pyrrolidine [prepared as described in step (a) above] were dissolved in 10 ml of a 4N solution of hydrogen chloride in dioxane, whilst ice-cooling, and the solution was allowed to stand at room temperature for 3 hours. At the end of this time, the mixture was concentrated by distillation under reduced pressure, and the resulting oily residue was dissolved in a small amount of isopropyl alcohol; the solution was then allowed to stand, whilst ice-cooling. The crystals which precipitated were collected by filtration and dried in vacuo, to give 318 mg (yield 66%) of the title compound as colorless crystals, melting at 127°–129° C.

[α]$_D^{25}$: +10.5° (c=1.0, methanol).

Nuclear Magnetic Resonance Spectrum (hexadeuterated dimethyl sulfoxide, 270 MHz) δ ppm: 1.8–2.0 (1H, multiplet); 2.05–2.2 (2H, multiplet); 2.2–2.35 (1H, multiplet); 2.7–3.1 (4H, multiplet); 3.2–3.35 (1H, multiplet); 3.4–3.55 (1H, multiplet); 4.05–4.25 (3H, multiplet); 6.61 (1H, doublet, J=7.9 Hz); 6.66 (1H, doublet of doublets, J=1.3 & 7.9 Hz); 6.84 (1H, doublet, J=7.9 Hz); 6.94 (1H, triplet, J=7.3 Hz); 7.0–7.25 (4H, multiplet).

EXAMPLE 41

2-{2-[2-(3-Hydroxyphenyl)ethyl]phenoxymethyl}- 1-methylpyrrolidine hydrochloride 41(a) 2-{2-[2-(3-Methoxymethoxyphenyl)ethyl]phenoxymethyl}-1-methylpyrrolidine Following a procedure similar to that described in Example 38, 1.00 g of 1-t-butoxycarbonyl-2-{2-[2-(3-methoxymethoxyphenyl)ethyl]phenoxymethyl}pyrrolidine [prepared in a similar manner to that described in Example 40(a)] was reacted with a dispersion of 88.1 mg of lithium aluminum hydride in 10 ml of tetrahydrofuran. The mixture was then worked up as described in Example 38, and the crude product thus obtained was purified by column chromatography through silica gel, using a 10:1 by volume mixture of methylene chloride and methanol as the eluent, to give 68 mg (yield 83%) of the title compound as a colorless oil.

Nuclear Magnetic Resonance Spectrum (CDCl$_3$, 270 MHz), δ ppm: 1.7–2.0 (3H, multiplet); 2.0–2.2 (1H, multiplet); 2.3–2.45 (1H, multiplet); 2.53 (3H, singlet); 2.7–3.0 (5H, multiplet); 3.1–3.2 (1H, multiplet); 3.48 (3H, singlet); 3.85 (1H, doublet of doublets, J=6.6 & 9.2 Hz); 4.08 (1H, doublet of doublets, J=5.3 & 9.2 Hz); 5.15 (2H, singlet); 6.8–6.9 (5H, multiplet); 7.1–7.3 (3H, multiplet).

41(b) 2-{2-[2-(3-Hydroxyphenyl)ethyl]phenoxymethyl}-1-methylpyrrolidine hydrochloride 660 mg of 2-{2-[2-(3-methoxymethoxyphenyl)ethyl]phenoxymethyl}-1-methylpyrrolidine [prepared as described in step (a) above] were dissolved in 5 ml of a 4N solution of hydrogen chloride in dioxane, and the solution was allowed to stand at room temperature for 30 minutes. At the end of this time, the solvent was removed by distillation under reduced pressure, and the resulting solid residue was recrystallized from isopropyl alcohol, to give 529 mg (yield 82%) of the title compound as colorless needles, melting at 232°–233° C. (with decomposition).

Nuclear Magnetic Resonance Spectrum (hexadeuterated dimethyl sulfoxide, 270 MHz) δ ppm: 1.8–2.2 (3H, multiplet); 2.2–2.4 (1H, multiplet); 2.7–2.95 (4H, multiplet); 2.97 (3H, singlet); 3.05–3.25 (1H, multiplet); 3.5–3.7 (1H, multiplet); 3.8–3.95 (1H, multiplet); 4.28 (1H, doublet of doublets, J=4.0 & 10.6 Hz); 4.40 (1H, doublet of doublets, J=7.9 & 10.6 Hz); 6.55–6.7 (3H, multiplet); 6.75–7.1 (3H, multiplet); 7.15 7.3 (2H, multiplet).

EXAMPLE 42

(R)-2-{2-[2-(3-Methoxyphenyl)ethyl]phenoxymethyl} morpholine hydrochloride

42(a) (R)-4-t-butoxycarbonyl-2-{2-[2-(3-methoxyphenyl) ethyl]phenoxymethyl}morpholine Following a procedure similar to that described in Example 40(a), 1.14 g of 2-[2-(3-methoxyphenyl)ethyl] phenol prepared as described in Preparation 20), 0.560 g of potassium t-butoxide and 1.86 9 of (R)-4-t-butoxycarbonyl-2-(p-toluenesulfonyloxymethyl)morpholine were reacted in 20 ml of dimethylacetamide. The mixture was then worked up as described in Example 40(a), and the crude product thus obtained was purified by column chromatography through silica gel, using a 4:1 by volume mixture of hexane and ethyl acetate as the eluent, to give 1.68 9 (yield 79%) of the title compound as an oil.

Nuclear Magnetic Resonance Spectrum (CDCl$_3$, 270 MHz), δ ppm: 1.44 (9H, singlet); 2.8–3.1 (6H, multiplet); 3.5–3.7 (1H, multiplet); 3.7–4.2 (6H, multiplet); 3.77 (3H, singlet); 6.7–6.95 (5H, multiplet); 7.1–7.3 (3H, multiplet).

42(b) (R)-2-{2-[2-(3-Methoxyphenyl)ethyl] phenoxymethyl}morpholine hydrochloride 10 ml of a 4N solution of hydrogen chloride in dioxane were added to a solution of 1.68 g of (R)-4-t-butoxycarbonyl-2-{2-[2-(3-methoxyphenyl)ethyl] phenoxymethyl}morpholine [prepared as described in step (a) above] in 10 ml of dioxane, and the resulting mixture was allowed to stand at room temperature for 30 minutes. At the end of this time, the solvent was removed by distillation under reduced pressure, and the resulting residue was dissolved in a small amount of methylene chloride. Ethyl acetate was added to the mixture, which was then allowed to stand at room temperature. The crystals which precipitated were collected by filtration and dried in vacuo, to give 1.24 g (yield 86%) of the title compound as colorless crystals, melting at 112°–113° C.

[α]$_D^{25}$: −7.4° (c=1.0, water).

Nuclear Magnetic Resonance Spectrum (CDCl$_3$, 270 MHz), δ ppm: 2.75–2.95 (4H, multiplet); 3.0–3.2 (2H, multiplet); 3.35 (1H, doublet, J=13.2 Hz); 3.46 (1H, doublet, J=11.2 Hz); 3.75 (3H, singlet); 3.95–4.2 (4H, multiplet); 4.3–4.4 (1H, multiplet); 6.65–6.95 (5H, multiplet); 7.05–7.3 (3H, multiplet).

EXAMPLE 43

(R)-2-{2-[2-(3-Methoxyphenyl)ethyl]phenoxymethyl}-4-methylmorpholine hydrochloride 43(a) (R)-2-{2-[2-(3-Methoxyphenyl)ethyl]phenoxymethyl}-4-methylmorpholine 152 mg of potassium carbonate were added to a solution of 404 mg of (E)-2-{2-[2-(3-methoxyphenyl)ethyl] phenoxymethyl}morpholine hydrochloride (prepared as described in Example 42) in 10 ml of dimethylacetamide, and the resulting mixture was stirred at room temperature for 1 hour. At the end of this time, 157 mg of methyl iodide were added, and the mixture was stirred at room temperature for 14 hours. The reaction mixture was then diluted with ethyl acetate. The diluted solution was washed with water and with a saturated aqueous solution of sodium chloride, in that order, after which it was dried over anhydrous magnesium sulfate. The solvent was then removed by distillation under reduced pressure, and the resulting oily residue was purified by column chromatography through silica gel, using a 20:1 by volume mixture of methylene chloride and methanol as the eluent, to give 310 mg (yield 82%) of the title compound as a colorless oil.

Nuclear Magnetic Resonance Spectrum (CDCl$_3$, 270 MHz), δ ppm: 2.0–2.25 (2H, multiplet); 2.32 (3H, singlet); 2.65–2.75 (1H, multiplet); 2.8–3.05 (5H, multiplet); 3.7–3.85 (1H, multiplet); 3.78 (3H, singlet); 3.9–4.1 (4H, multiplet); 6.7–6.95 (5H, multiplet); 7.1–7.3 (3H, multiplet).

43(b) (R)-2-{2-[2-(3-Methoxyphenyl)ethyl]phenoxymethyl}-4-methylmorpholine hydrochloride 0.25 ml of a 4N solution of hydrogen chloride in dioxane was added to a solution of 310 mg of (R)-2-{2-[2-(3-methoxyphenyl)ethyl]phenoxymethyl}-4-methylmorpholine [prepared as described in step (a) above] in a small amount of ethyl acetate, and the resulting mixture was allowed to stand at room temperature. The crystals which precipitated were collected by filtration and dried invacuo, to give 323 mg (yield 94%) of the title compound as colorless needles, melting at 184°–185° C.

[α]$_D^{25}$: −5.5° (c=1.0, ethanol).

Nuclear Magnetic Resonance Spectrum (CDCl$_3$, 270 MHz), δ ppm: 2.75 (3H, singlet); 2.75–3.05 (6H, multiplet); 3.38 (2H, triplet, J=13.2 Hz); 3.78 (3H, singlet); 4.0–4.2 (3H, multiplet); 4.3–4.45 (1H, multiplet); 4.5–4.6 (1H, multiplet); 6.7–6.9 (4H, multiplet); 6.94 (1H, triplet, J=7.3 Hz); 7.1–7.3 (3H, multiplet).

EXAMPLE 44

2-(2-{2-[2-(3,4-Dimethoxyphenyl)ethyl]phenoxy}] ethyl]-1-methylpyrrolidine hydrochloride 44(a) 2-(2-{2-[2-(3,4-Dimethoxyphenyl) ethyl]phenoxy}]ethyl]-1-methylpyrrolidine Following a procedure similar to that described in Example 35(a), 1.30 g of 2-[2-(3,4-dimethoxyphenyl)ethyl] phenol (prepared as described in Preparation 27), 1.69 g of potassium t-butoxide and 1.39 g of 2-(2-chloroethyl)-1-methylpyrrolidine were reacted in 30 ml of dimethylacetamide. The mixture was then worked up as described in Example 35(a), and the crude product thus obtained was purified by column chromatography through silica gel, using a 10:1 by volume mixture of methylene chloride and methanol as the eluent, to give 1.50 g (yield 80%) of the title compound as a colorless oil.

Nuclear Magnetic Resonance Spectrum (CDCl$_3$, 270 MHz), δ ppm: 1.55–2.5 (8H, multiplet); 2.41 (3H, singlet); 2.8–3.0 (4H, multiplet); 3.15–3.25 (1H, multiplet); 3.83 (3H, singlet); 3.86 (3H, singlet); 3.9–4.15 (2H, multiplet); 6.6–6.9 (5H, multiplet); 7.05–7.25 (2H, multiplet).

44(b) 2-(2-{2-[2-(3,4-Dimethoxyphenyl)ethyl]phenoxy}] ethyl-1-methylpyrrolidine hydrochloride 2 ml of a 4N solution of hydrogen chloride in dioxane were added to a solution of 1.50 g of 2-(2-{2-[2-(3,4-dimethoxyphenyl)ethyl]phenoxy}ethyl)-1-methylpyrrolidine [prepared as described in step (a) above] in 20 ml of methylene chloride, and the mixture was concentrated by distillation under reduced pressure. The resulting residue was dissolved in ethyl acetate and the solution was allowed to stand at room temperature. The crystals which precipitated were collected by filtration and dried in vacuo, to give 1.10 g (yield 67%) of the title compound as colorless crystals, melting at 147°–148° C.

Nuclear Magnetic Resonance Spectrum (CDCl$_3$, 270 MHz), δ ppm: 1.95–2.15 (2H, multiplet); 2.2–2.4 (2H, multiplet); 2.4–2.6 (2H, multiplet); 2.76 & 2.78 (together 3H, each singlet); 2.75–3.0 (5H, multiplet); 3.15–3.55 (1H, multiplet); 3.80 (3H, singlet); 3.86 (3H, singlet); 3.8–4.1 (2H, multiplet); 4.15–4.3 (1H, multiplet); 6.6–7.0 (5H, multiplet); 7.1–7.3 (2H, multiplet).

EXAMPLE 45

2-{2-[2-(3-Methoxyphenyl)ethyl]phenoxymethyl}morpholine hydrochliorode

45(a)  4-t-Butoxycarbonyl-2-{2-[2-(3-methoxyphenyl)ethyl]phenoxymethyl}morpholine Following a procedure similar to that described in Example 40, 1.00 g of 2-[2-(3-methoxyphenyl)ethyl]phenol (prepared as described in Preparation 20), 1.63 g of 4-t-butoxycarbonyl-2-(p-toluenesulfonyloxymethyl)morpholine and 0.490 g of potassium t-butoxide were reacted in 20 ml of dimethylacetamide. The mixture was then worked up as described in Example 40, and the crude product thus obtained was purified by column chromatography through silica gel, using a 4:1 by volume mixture of hexane and ethyl acetate as the eluent, to give 1.87 g (yield 94.5%) of the title compound as a colorless oil.

Nuclear Magnetic Resonance Spectrum (CDCl$_3$, 270 MHz), δ ppm : 1.45 (9H, singlet); 2.8–3.1 (6H, multiplet); 3.55–3.7 (1H, multiplet); 3.7–4.2 (6H, multiplet); 3.77 (3H, singlet); 6.7–6.95 (5H, multiplet); 7.1–7.3 (3H, multiplet).

45(b)  2-{2-[2-(3-Methoxyphenyl)ethyl]phenoxymethyl}morpholine hydrochloride 2 ml of a 4N solution of hydrogen chloride in dioxane were added to a solution of 0.99 g of 4-t-butoxycarbonyl-2-{2-[2-(3-methoxyphenyl)ethyl]phenoxymethyl}morpholine [prepared as described in step (a) above] in 2 ml of dioxane, and the mixture was allowed to stand at room temperature for 16 hours, after which it was concentrated by distillation under reduced pressure. The resulting residue was dissolved in ethyl acetate, and the solution was allowed to stand at room temperature. The crystals which precipitated were collected by filtration and dried in vacuo, to give 0.42 g (yield 52%) of the title compound as colorless crystals, melting at 110°–112° C.

Nuclear Magnetic Resonance Spectrum (CDCl$_3$, 270 MHz), δ ppm: 2.8–3.0 (4H, multiplet); 3.0–3.2 (2H, multiplet); 3.36 (1H, doublet, J=12.5 Hz); 3.48 (1H, doublet, J=13.2 Hz); 3.76 (3H, singlet); 4.0–4.2 (4H, multiplet); 4.25–4.4 (1H, multiplet); 6.7–7.0 (5H, multiplet); 7.1–7.3 (3H, multiplet).

EXAMPLE 46

2-{2-[2-(3-Methoxyphenyl)ethyl]phenoxymethyl}-4-methylmorpholine hydrochloride

46(a) 2-{2-[2-(3-Methoxyphenyl)ethyl]phenoxymethyl}-4-methylmorpholine

Following a procedure similar to that described in Example 38, 870 mg of 4-t-butoxycarbonyl-2-{2-[2-(3-methoxyphenyl)ethyl]phenoxymethyl}morpholine [prepared as described in Example 45(a)] were reacted with a dispersion of 113 mg of lithium aluminum hydride in 15 ml of tetrahydrofuran. The mixture was then worked up as described in Example 38, and the crude product thus obtained was purified by column chromatography through silica gel, using a 10:1 by volume mixture of methylene chloride and methanol as the eluent, to give 620 mg (yield 94%) of the title compound as a colorless oil.

Nuclear Magnetic Resonance Spectrum (CDCl$_3$, 270 MHz), δ ppm: 2.0–2.3 (2H, multiplet); 2.33 (3H, singlet); 2.65–2.75 (1H, multiplet); 2.8–3.0 (5H, multiplet); 3.7–3.85 (1H, multiplet); 3.78 (3H, singlet); 3.9–4.1 (4H, multiplet); 6.7–6.95 (5H, multiplet); 7.1–7.3 (3H, multiplet).

46(b)  2-{2-[2-(3-Methoxyphenyl)ethyl]phenoxymethyl}-4-methylmorpholine hydrochloride 0.5 ml of a 4N solution of hydrogen chloride in dioxane was added to a solution of 620 mg of 2-{2-[2-(3-methoxyphenyl)ethyl]phenoxymethyl}-1-methylmorpholine [prepared as described in step (a) above] in a suitable amount of ethyl acetate, and the resulting mixture was concentrated by distillation under reduced pressure. The resulting solid residue was recrystallized from ethyl acetate to give 476 mg (yield 69%) of the title compound as colorless crystals, melting at 174°–176° C.

Nuclear Magnetic Resonance Spectrum (CDCl$_3$, 270 MHz), δ ppm: 2.77 (3H, singlet); 2.7–3.1 (6H, multiplet); 3.40 (2H, triplet, J=11.9 Hz); 3.79 (3H, singlet); 4.0–4.2 (3H, multiplet); 4.3–4.5 (1H, multiplet); 4.5–4.65 (1H, multiplet); 6.7–6.9 (4H, multiplet); 6.95 (1H, triplet, J=7.6 Hz); 7.1–7.3 (3H, multiplet).

EXAMPLE 47

2-(2-{2-[2-(3-Methoxyphenyl)ethyl]phenoxy}ethyl)piperidine hydrochloride

47(a)  1-t-Butoxycarbonyl-2-(2-{2-[2-(3-methoxyphenyl)ethyl]phenoxy}ethyl)piperidine Following a procedure similar to that described in Example 36(a), 1.00 g of 2-[2-(3-methoxyphenyl)ethyl]phenol (prepared as described in Preparation 20), 1.51 g of 1-t-butoxycarbonyl-2-(2-hydroxyethyl)piperidine, 1.72 g of triphenylphosphine and 1.14 g of diethyl azodicarboxylate were reacted in 20 ml of methylene chloride. The mixture was then worked up as described in Example 36(a), and the crude product thus obtained was purified by column chromatography through silica gel, using a 4:1 by volume mixture of hexane and ethyl acetate as the eluent, to give 0.630 g (yield 32%) of the title compound as a colorless oil.

Nuclear Magnetic Resonance Spectrum (CDCl$_3$, 270 MHz), δ ppm: 1.46 (9H, singlet); 1.4–2.0 (7H, multiplet); 2.15–2.35 (1H, multiplet); 2.65–3.0 (5H, multiplet); 3.78 (3H, singlet); 3.9–4.2 (3H, multiplet); 4.35–4.45 (1H, multiplet); 6.7–6.9 (5H, multiplet); 7.05–7.3 (3H, multiplet).

47(b)  2-(2-{2-[2-(3-Methoxyphenyl)ethyl]phenoxy}ethyl)piperidine hydrochloride 1 ml of a 4N solution of hydrogen chloride in dioxane was added to a solution of 0.63 g of 1-t-butoxycarbonyl-2-(2-{2-[2-(3-methoxyphenyl)ethyl]phenoxy}ethyl)piperidine [prepared as described in step (a) above] in 1 ml of dioxane, and the resulting solution was allowed to stand at room temperature for 2.5 hours. At the end of this time, it was concentrated by distillation under reduced pressure. The resulting residue was partitioned between ethyl acetate and a saturated aqueous solution of sodium hydrogencarbonate. The ethyl acetate layer was dried over anhydrous magnesium sulfate, and concentrated by distillation under reduced pressure. The resulting residue was dissolved in ethanol, and the solution was adsorbed on a Column packed with CM Sephadex C-25 (H$^+$ type) (Sephadex is a trade mark). The column was washed with ethanol and eluted with a 0.1N solution of hydrogen chloride in ethanol. The eluate was concentrated by evaporation under reduced pressure and dried in vacuo, to give 0.22 g (yield 40%) of the title compound as a colorless oil.

Nuclear Magnetic Resonance Spectrum (CDCl$_3$, 270 MHz), δ ppm: 1.3–2.1 (6H, multiplet); 2.1–2.3 (1H, multiplet); 2.5–2.7 (1H, multiplet); 2.7–3.0 (5H, multiplet); 3.15–3.35 (1H, multiplet); 3.4–3.55 (1H, doublet, J=13.2 Hz); 3.77 (3H, singlet); 4.0–4.25 (2H, multiplet); 6.7–6.95 (5H, multiplet); 7.05–7.3 (3H, multiplet).

Infrared Absorption Spectrum (liquid film), $v_{max}$ cm$^{-1}$: 1601, 1585, 1495, 1455, 1436, 1241

EXAMPLE 48

2-(2-{2-[2-(3-Methoxyphenyl)ethyl]phenoxy}ethyl)-1-methylpiperidine hydrochloride 48(a) 2-(2-{2-[2-(3-Methoxyphenyl)ethyl]phenoxy}ethyl)-1-methylpiperidine Following a procedure similar to that described in Example 38, 1.70 g of 1-t-butoxycarbonyl-2-(2-{2-[2-(3-methoxyphenyl)ethyl]phenoxy}ethyl)piperidine [prepared as described in Example 47(a)] were reacted with a dispersion of 0.294 g of lithium aluminum hydride in 30 ml of tetrahydrofuran. The mixture was then worked up as described in Example 38, and the crude product thus obtained was purified by column chromatography through silica gel, using a 10:1 by volume mixture of methylene chloride and methanol as the eluent, to give 0.730 g (yield 53%) of the title compound as a colorless oil.

Nuclear Magnetic Resonance Spectrum (CDCl$_3$, 270 MHz), δ ppm: 1.2–2.0 (7H, multiplet); 2.05–2.35 (3H, multiplet); 2.34 (3H, singlet); 2.8–3.0 (5H, multiplet); 3.78 (3H, singlet); 4.04 (2H, triplet, J=7.3 Hz); 6.7–6.9 (5H, multiplet); 7.1–7.25 (3H, multiplet).

48(b) 2-(2-{2-[2-(3-Methoxyphenyl)ethyl]phenoxy}ethyl)-1-methylpiperidine hydrochloride 1 ml of a 4N solution of hydrogen chloride in dioxane was added to a solution of 0.730 g of 2-(2-{2-[2-(3-methoxyphenyl)ethyl]phenoxy}ethyl)-1-methylpiperidine [prepared as described in step (a) above] in a suitable amount of ethyl acetate, and the resulting mixture was concentrated by distillation under reduced pressure. The resulting oily residue was dissolved in 15 ml of ethyl acetate, and the solution was allowed to stand at room temperature. The crystals which precipitated were collected by filtration and dried in vacuo, to give 0.561 g (yield 69%) of the title compound as colorless crystals, melting at 115°–117° C.

Nuclear Magnetic Resonance Spectrum (CDCl$_3$, 270 MHz), δ ppm: 1.3–2.2 (5H, multiplet); 2.2–2.45 (2H, multiplet); 2.45–2.7 (2H, multiplet); 2.75 (3H, singlet); 2.8–3.2 (5H, multiplet); 3.4–3.55 (1H, multiplet); 3.78 (3H, singlet); 3.95–4.2 (2H, multiplet); 6.65–6.8 (3H, multiplet); 6.84 (1H, doublet, J=7.9 Hz); 6.93 (1H, triplet, J=7.3 Hz); 7.1–7.3 (3H, multiplet).

EXAMPLE 49

3-{2-[2-(3-Methoxyphenyl)ethyl]phenoxymethyl} piperidine hydrochloride

49(a) 1-t-Butoxycarbonyl-3-{2-[2-(3-methoxyphenyl)ethyl]phenoxymethyl}piperidine Following a procedure similar to that described in Example 40, 0.790 g of 2-[2-(3-methoxyphenyl)ethyl]phenol (prepared as described in Preparation 20), 0.388 g of potassium t-butoxide and 1.28 g of 1-t-butoxycarbonyl-3-(p-toluenesulfonyloxymethyl)piperidine were reacted in 15 ml of dimethylacetamide. The mixture was then worked up as described in Example 40, and the crude product thus obtained was purified by column chromatography through silica gel, using a 4:1 by volume mixture of hexane and ethyl acetate as the eluent, to give 1.09 g (yield 74%) of the title compound as a colorless oil.

Nuclear Magnetic Resonance Spectrum (CDCl$_3$, 270 MHz), δ ppm: 1.1–1.8 (3H, multiplet); 1.43 (9H, multiplet); 1.85–2.15 (2H, multiplet); 2.7–3.0 (6H, multiplet); 3.79 (3H, singlet); 3.85 (2H, doublet, J=5.9 Hz); 3.9–4.25 (2H, multiplet); 6.7–6.95 (5H, multiplet); 7.1–7.3 (3H, multiplet).

49(b) 3-{2-[2-(3-Methoxyphenyl)ethyl]phenoxymethyl]piperidine hydrochloride 240 mg of 1-t-butoxycarbonyl-3-{2-[2-(3-methoxyphenyl)ethyl]phenoxymethyl}piperidine [prepared as described in step (a) above] were dissolved in 4 ml of a 4N solution of hydrogen chloride in dioxane. The solution was allowed to stand at room temperature for 3 hours, after which it was concentrated by evaporation under reduced pressure. The resulting residue was dissolved in ethyl acetate, and the solution was allowed to stand at room temperature. The crystals which precipitated were collected by filtration, to give 183 mg (yield 76%) of the title compound as colorless crystals, melting at 155°–157° C.

Nuclear Magnetic Resonance Spectrum (CDCl$_3$, 270 MHz), δ ppm: 1.4–2.2 (4H, multiplet); 2.45–2.6 (1H, multiplet); 2.7–3.0 (6H, multiplet); 3.4–3.6 (2H, multiplet); 3.76 (3H, singlet); 3.86 (2H, doublet, J=4.6 Hz); 6.65–6.85 (4H, multiplet); 6.89 (1H, triplet, J=7.3 Hz); 7.1–7.3 (3H, multiplet).

EXAMPLE 50

3-{2-[2-(3-Methoxyphenyl)ethyl]phenoxymethyl}-1-methylpiperidine hydrochloride

50(a) 3-{2-[2-(3-Methoxyphenyl)ethyl]phenoxymethyl}-1methylpiperidine

Following a procedure similar to that described in Example 38, 850 mg of 1-t-butoxycarbonyl-3-{2-[2-(3-methoxyphenyl) ethyl]phenoxymethyl}piperidine (prepared as described in Example 49) were reacted with 113 mg of lithium aluminum hydride. The mixture was then worked up as described in Example 38, and the crude product thus obtained was purified by column chromatography through silica gel, using a 10:1 by volume mixture of methylene chloride and methanol as the eluent, to give 520 mg (yield 76%) of the title compound as a solid.

Nuclear Magnetic Resonance Spectrum (CDCl$_3$, 270 MHz), δ ppm: 1.1–1.3 (1H, multiplet); 1.6–2.3 (6H, multiplet); 2.31 (3H, singlet); 2.75–3.0 (5H, multiplet); 3.0–3.1 (1H, multiplet); 3.78 (3H, singlet); 3.8–3.95 (2H, multiplet); 6.7–6.9 (5H, multiplet); 7.1–7.3 (3H, multiplet).

50(b) 3-{2-[2-(3-Methoxyphenyl)ethyl]phenoxymethyl}-1-methylpiperidine hydrochloride 0.5 ml of a 4N solution of hydrogen chloride in dioxane was added to a solution of 520 mg of 3-{2-[2-(3-methoxyphenyl)ethyl]phenoxymethyl}-1-methylpiperidine [prepared as described in step (a) above] in a suitable amount of ethyl acetate, and the resulting mixture was concentrated by distillation under reduced pressure, to produce the hydrochloride as a solid. This solid was dissolved in a small amount of methylene chloride, and then ethyl acetate was added to the resulting solution, which was then allowed to stand at room temperature. The crystals which precipitated were collected by filtration, to give 443 mg (yield 77%) of the title compound as colorless crystals, melting at 191°–193° C.

Nuclear Magnetic Resonance Spectrum (CDCl$_3$, 270 MHz), δ ppm: 1.44–2.1 (3H, multiplet); 2.2–3.0 (8H, multiplet); 2.75 (3H, singlet); 3.4–3.6 (2H, multiplet); 3.79 (3H, singlet); 3.85–4.0 (2H, multiplet); 6.7–6.9 (4H, multiplet); 6.94 (1H, triplet, J=7.6 Hz); 7.1–7.3 (3H, multiplet).

EXAMPLE 51

3-{2-[2-(3-Methoxyphenyl)ethyl]phenoxy}-piperidine hydrochloride

51(a) 1-t-Butoxycarbonyl-3-{2-[2-(3-methoxyphenyl)ethyl]phenoxy}piperidine

Following a procedure similar to that described in Example 36(a), 1.50 g of 2-[2-(3-methoxyphenyl)ethyl]phenol (prepared as described in Preparation 20), 2.64 g of 1-t-butoxycarbonyl-3-hydroxypiperidine, 3.44 g of triphenylphosphine and 2.29 g of diethyl azodicarboxylate were reacted. The mixture was then worked up as described in Example 36(a), and the crude product thus obtained was purified by column chromatography through silica gel, using a 7:1 by volume mixture of hexane and ethyl acetate as the eluent, to give 1.68 g (yield 62%) of the title compound as a colorless oil.

Nuclear Magnetic Resonance Spectrum (CDCl$_3$, 270 MHz), δ ppm: 1.37 (9H, singlet); 1.4–2.2 (4H, multiplet); 2.75–2.95 (4H, multiplet); 3.0–3.8 (4H, multiplet); 3.79 (3H, singlet); 4.2–4.4 (1H, multiplet); 6.7–6.95 (5H, multiplet); 7.05–7.25 (3H, multiplet).

51(b) 3-{2-[2-(3-Methoxyphenyl)ethyl]phenoxy}piperidine hydrochloride 800 mg of 1-t-butoxycarbonyl-3-{2-[2-(3-methoxyphenyl)ethyl]phenoxy}piperidine [prepared as described in step (a) above] were dissolved in 8 ml of a 4N solution of hydrogen chloride in dioxane, and the solution was allowed to stand at room temperature for 2 hours. At the end of this time, the solution was concentrated by evaporation under reduced pressure, the resulting residue was dissolved in ethyl acetate, and the resulting solution was allowed to stand at room temperature. The crystals which precipitated were collected by filtration, to give 300 mg (yield 44%) of the title compound as colorless crystals, melting at 130°–132° C.

Nuclear Magnetic Resonance Spectrum (CDCl$_3$, 270 MHz), δ ppm: 1.6–1.8 (1H, multiplet); 1.9–2.3 (3H, multiplet); 2.8–3.1 (6H, multiplet); 3.25–3.4 (1H, multiplet); 3.55 (1H, doublet of doublets, J=3.3 & 12.6 Hz); 3.77 (3H, singlet); 4.7–4.85 (1H, multiplet); 6.7–6.8 (3H, multiplet); 6.85–7.0 (2H, multiplet); 7.1–7.3 (3H, multiplet).

EXAMPLE 52

3-{2-[2-(3-Methoxyphenyl)ethyl]phenoxy}-1-methylpiperidine hydrochloride

52(a) 3-{2-[2-(3-Methoxyphenyl)ethyl]phenoxy}-1-methylpiperidine

Following a procedure similar to that described in Example 38, 880 mg of 1-t-butoxycarbonyl-3-{2-[2-(3-methoxyphenyl)ethyl]phenoxy}piperidine [prepared as described in Example 51(a)] were reacted with 162 mg of lithium aluminum hydride. The mixture was then worked up as described in Example 38, and the crude product thus obtained was purified by column chromatography through silica gel, using a 10:1 by volume mixture of methylene chloride and methanol as the eluent, to give 360 mg (yield 51%) of the title compound as a colorless oil.

Nuclear Magnetic Resonance Spectrum (CDCl$_3$, 60 MHz) δ ppm: 1.1–2.4 (6H, multiplet); 2.28 (3H, singlet); 2.5–3.3 (6H, multiplet); 3.77 (3H, singlet); 4.1–4.7 (1H, multiplet); 6.6–7.4 (8H, multiplet).

52(b) 3-{2-[2-(3-Methoxyphenyl)ethyl]phenoxy}-1-methylpiperidine hydrochloride 0.4 ml of a 4N solution of hydrogen chloride in dioxane was added to a solution of 360 mg of 3-{2-[2-(3-methoxyphenyl)ethyl]phenoxy}-1-methylpiperidine [prepared as described in step (a) above] in a suitable amount of ethyl acetate, and the resulting solution was concentrated by distillation under reduced pressure. The resulting oily residue was dissolved in ethyl acetate, after which it was allowed to stand at room temperature. The crystals which precipitated were collected by filtration, to give 383 mg (yield 95%) of the title compound as colorless crystals, melting at 158°–160° C.

Nuclear Magnetic Resonance Spectrum (CDCl$_3$, 270 MHz), δ ppm: 1.4–1.65 (1H, multiplet); 1.9–2.1 (1H, multiplet); 2.2–2.6 (3H, multiplet); 2.6–2.8 (1H, multiplet); 2.8–3.0 (4H, multiplet); 2.82 (3H, singlet); 3.4–3.7 (2H, multiplet); 3.78 (3H, singlet); 4.9–5.3 (1H, multiplet); 6.7–6.8 (3H, multiplet); 6.94 (1H, triplet, J=7.3 Hz); 7.0–7.3 (4H, multiplet).

EXAMPLE 53

4-(2-{2-[2-(3-Methoxyphenyl)ethyl]phenoxy}ethyl)piperidine hydrochloride

53(a) 1-t-Butoxycarbonyl-4-(2-{2-[2-(3-methoxyphenyl)ethyl]phenoxy}ethyl)piperidine Following a procedure similar to that described in Example 40(a), 1.20 g of 2-[2-(3-methoxyphenyl) ethyl]phenol (prepared as described in Preparation 20), 2.00 g of 1-t-butoxycarbonyl-4-[2-(p-toluenesulfonyloxy)ethyl]piperidine and 0.590 g of potassium t-butoxide were reacted in 20 ml of dimethylacetamide. The mixture was then worked up as described in Example 40(a), and the crude product thus obtained was purified by column chromatography through silica gel, using a 4:1 by volume mixture of hexane and ethyl acetate as the eluent, to give 2.00 g (yield 86%) of the title compound as a colorless oil.

Nuclear Magnetic Resonance Spectrum (CDCl$_3$, 270 MHz), δ ppm: 1.1–1.3 (2H, multiplet); 1.45 (9H, singlet); 1.6–1.85 (5H, multiplet); 2.68 (2H, triplet, J=12.5 Hz); 2.8–3.0 (4H, multiplet); 3.78 (3H, singlet); 4.0–4.2 (2H, multiplet); 4.18 (2H, triplet, J=5.9 Hz); 6.7–6.9 (5H, multiplet); 7.1–7.3 (3H, multiplet).

53(b) 4-(2-{2-[2-(3-Methoxyphenyl)ethyl]phenoxy}ethyl)piperidine hydrochloride 2.00 g of 1-t-butoxycarbonyl-4-(2-{2-[2-(3-methoxyphenyl)ethyl]phenoxy}ethyl)piperidine [prepared as described in step (a) above] were dissolved in 10 ml of a 4N solution of hydrogen chloride in dioxane, and the solution was allowed to stand at room temperature for 4 hours. At the end of this time, the solvent was removed by distillation under reduced pressure, and the resulting solid residue was dissolved in a small amount of methylene chloride, after which ethyl acetate was added to the solution. The crystals which precipitated were collected by filtration, to give 1.59 g (yield 93%) of the title compound as colorless crystals, melting at 119°–121° C.

Nuclear Magnetic Resonance Spectrum (CDCl$_3$, 270 MHz), δ ppm: 1.6–2.05 (7H, multiplet); 2.7–2.95 (6H, multiplet); 3.47 (2H, doublet, J=12.5 Hz); 3.79 (3H, singlet); 4.00 (2H, triplet, J=5.9 Hz); 6.7–7.0 (5H, multiplet); 7.1–7.3 (3H, multiplet).

EXAMPLE 54

4-(2-{2-[2-(3-Methoxyphenyl)ethyl]phenoxy}ethyl)-1-methylpiperidine hydrochloride Following a procedure similar to that described in Example 38, 2.15 g of 1-t-butoxycarbonyl-4-(2-{2-[2(3-methoxyphenyl)ethyl]phenoxy}ethyl)piperidine [prepared as described in Example 53 (a)] were reacted with 0.371 g of lithium aluminum hydride dispersed in 40 ml of tetrahydrofuran. The mixture was then worked up as described in Example 38, and the crude product thus obtained was purified by column chromatography through silica gel, using a 10:1 by volume mixture of methylene chloride and methanol as the eluent, to give 1.56 g (yield 90%) of 4-(2-{2-[2-(3-methoxyphenyl)ethyl]phenoxy}ethyl)-1-methylpiperidine as an oil.

The whole of this oil was dissolved in a suitable amount of ethyl acetate, and 1.5 ml of a 4N solution of hydrogen chloride in dioxane were added to the resulting solution, which was then concentrated by evaporation under reduced pressure. The resulting oily residue was dissolved in 25 ml of ethyl acetate, and the solution was allowed to stand at room temperature. The crystals which precipitated were collected by filtration, to give 1.06 g (yield 61%) of the title compound as colorless crystals, melting at 97°–99° C.

Nuclear Magnetic Resonance Spectrum (CDCl$_3$, 270 MHz), δ ppm: 1.75–2.2 (7H, multiplet); 2.56 (2H, triplet, J=11.2 Hz); 2.70 (3H, singlet); 2.8–3.0 (4H, multiplet); 3.47 (2H, doublet, J=11.2 Hz); 3.79 (3H, singlet); 4.02 (2H, triplet, J=5.9 Hz); 6.7–7.0 (5H, multiplet); 7.1–7.3 (3H, multiplet).

EXAMPLE 55

4-(2-{2-[2-(3-Hydroxyphenyl)ethyl]phenoxy}ethyl]piperidine hydrochloride

55(a) 1-t-Butoxycarbonyl-4-(2-{2-[2-(3-methoxymethoxyphenyl) ethyl]phenoxy]ethyl)piperidine Following a procedure similar to that described in Example: 40(a), 1.58 g of 2-[2-(3-methoxymethoxyphenyl) ethyl]phenol, 2.34 g of 1-t-butoxycarbonyl-4-[2-(p-toluenesulfonyloxy) ethyl]piperidine and 0.686 g of potassium t-butoxide were reacted in 10 ml of dimethylacetamide. The mixture was then worked up as described in Example 40(a), and the crude product thus obtained was purified by column chromatography through silica gel, using a 4:1 by volume mixture of hexane and ethyl acetate as the eluent, to give 1.96 g (yield 68%) of the title compound as a colorless oil.

Nuclear Magnetic Resonance Spectrum (CDCl$_3$, 270 MHz), δ ppm: 1.1–1.3 (2H, multiplet); 1.45 (9H, singlet); 1.65–1.85 (5H, multiplet); 2.68 (2H, triplet, J=12.5 Hz); 2.8–3.0 (4H, multiplet); 3.48 (3H, singlet); 4.0–4.2 (2H, multiplet); 4.02 (2H, triplet, J=5.9 Hz); 5.15 (2H, singlet); 6.8–6.95 (5H, multiplet); 7.1–7.3 (3H, multiplet).

55(b) 4-(2-{2-[2-(3-Hydroxyphenyl)ethyl]phenoxy}ethyl]piperidine hydrochloride 8 ml of a 4N solution of hydrogen chloride in dioxane were added to a solution of 890 mg of 1-t-butoxycarbonyl-4-(2-{2-[2-(3-methoxymethoxyphenyl)ethyl]phenoxy}ethyl)piperidine [prepared as described in step (a) above] in 8 ml of dioxane, and the resulting mixture was allowed to stand at room temperature. The crystals which precipitated were collected by filtration, washed with ethyl acetate and dried in vacuo, to give 651 mg (yield 95%) of the title compound as colorless needles, melting at 156°–158° C.

Nuclear Magnetic Resonance Spectrum (hexadeuterated dimethyl sulfoxide, 270 MHz) δ ppm : 1,3–1.5 (2H, multiplet); 1.65–1.95 (5H, multiplet); 2.65–2.9 (6H, multiplet); 3.24 (2H, doublet, J=12.5 Hz); 4.02 (2H, triplet, J=5.9 Hz); 6.55–6.7 (3H, multiplet); 6.84 (1H, triplet, J=7.3 Hz); 6.95 (1H, doublet, J=7.9 Hz); 7.06 (1H, triplet, J=7.3 Hz); 7.1–7.2 (2H, multiplet).

EXAMPLE 56

4-(2-{2-[2-(3-Hydroxyphenyl)ethyl]phenoxy}ethyl]-1-methylpiperidine hydrochloride 56(a) 4-(2-{2-[2-(3-Methoxymethoxyphenyl)ethyl]phenoxy}ethyl)-1-methylpiperidine Following a procedure similar to that described in Example 38, 1.40 g of 1-t-butoxycarbonyl-4-(2-{2-[2-(3-methoxymethoxyphenyl) ethyl]phenoxy }ethyl) piperidine [prepared as described in Example 55 (a) ] were reacted with 240 mg of lithium aluminum hydride dispersed in 30 ml of tetrahydrofuran. The mixture was then worked up as described in Example 38, and the crude product thus obtained was purified by column chromatography through silica gel, using a 10:1 by volume mixture of methylene chloride and methanol as the eluent, to give 710 mg of the title compound as a colorless oil.

Nuclear Magnetic Resonance Spectrum (CDCl$_3$, 270 MHz), δ ppm: 1.3–1.9 (7H, multiplet); 1.95–2.1 (2H, multiplet); 2.32 (3H, singlet); 2.75–3.0 (6H, multiplet); 3.48 (3H, singlet); 4.02 (2H, triplet, J=6.3 Hz); 5.16 (2H, singlet); 6.8–6.95 (5H, multiplet); 7.1–7.3 (3H, multiplet).

56(b) 4-(2-{2-[2-(3-Hydroxyphenyl)ethyl]phenoxy}ethyl]-1-methylpiperidine hydrochloride 2.3 ml of a 4N solution of hydrogen chloride in dioxane were added to a solution of 710 mg of 4-(2-{2-[2-(3-methoxymethoxyphenyl)ethyl]phenoxy}ethyl)-1-methylpiperidine [prepared as described in step (a) above] in 2.3 ml of dioxane, and the resulting mixture was allowed to stand at room temperature for 1 hour, after which it was concentrated by evaporation under reduced pressure. The resulting residue was dissolved in a small amount of methylene chloride, and ethyl acetate was added to the solution thus obtained, which was then allowed to stand at room temperature. The crystals which precipitated were collected by filtration and dried in vacuo, to give 294 mg (yield 42%) of the title compound as a crystalline powder, melting at 130°–132° C.

Nuclear Magnetic Resonance Spectrum (CDCl$_3$, 270 MHz), δ ppm: 1.6–2.2 (7H, multiplet); 2.6–2.9 (6H, multiplet); 2.74 (3H, singlet); 3.45 (2H, doublet, J=11.9 Hz); 3.96 (2H, triplet, J=5.0 Hz); 6.62 (1H, doublet, J=7.3 Hz); 6.7–6.85 (2H, multiplet); 6.91 (1H, triplet, J=7.3 Hz); 6.95–7.0 (1H, multiplet); 7.08 (1H, triplet, J=7.3 Hz); 7.1–7.25 (2H, multiplet); 8.05 (1H, broad singlet).

EXAMPLE 57

(S)-2-{2-[2-(3-Methoxyphenyl)ethyl]phenoxymethyl} pyrrolidine hydrochloride

57(a) (S)-1-t-Butoxycarbonyl-2-{2-[2-(3-methoxyphenyl) ethyl]phenoxymethyl}pyrrolidine Following a procedure similar to that described in Example 40(a), 2.00 g of 2-[2-(3-methoxyphenyl)ethyl] phenol (prepared as described in Preparation 20), 3.74 g of (S)-1-t-butoxycarbonyl-2-(p-toluenesulfonyloxymethyl)pyrrolidine and 0.983 g of potassium t-butoxide were reacted in 20 ml of dimethylacetamide. The mixture was then worked up as described in Example 40(a), and the crude product thus obtained was purified by column chromatography through silica gel, using a 4:1 by volume mixture of hexane and ethyl acetate as the eluent, to give 1.65 g (yield 45%) of the title compound as a colorless oil.

Nuclear Magnetic Resonance Spectrum (CDCl$_3$, 270 MHz), δ ppm: 1.47 (9H, singlet); 1.8–2.2 (4H, multiplet); 2.8–3.0(4H, multiplet); 3.3–3.5(2H, multiplet); 3.7–4.3(3H, multiplet); 3.7 (3H, singlet); 6.7–7.0(5H, multiplet); 7.0–7.3 (3H, multiplet).

57(b)  (S)-2-{2-[2-(3-Methoxyphenyl)ethyl] phenoxymethyl}pyrrolidine 5 ml of a 4N solution of hydrogen chloride in dioxane were added to a solution of 1.65 g of (S)-1-t-butoxycarbonyl- 2-{2-[2-(3-methoxyphenyl)ethyl] phenoxymethyl}pyrrolidine [prepared as described in step (a) above] in 5 ml of dioxane, and the resulting mixture was allowed to stand at room temperature for 2.5 hours. At the end of this time, the reaction mixture was concentrated by evaporation under reduced pressure, and the resulting oily residue was purified by column chromatography through silica gel, using a 20:1 by volume mixture of methylene chloride and methanol as the eluent, to give 910 mg (yield 73%) of the title compound as a colorless oil.

Nuclear Magnetic Resonance Spectrum (CDCl$_3$, 270 MHz), δ ppm: 1.7–2.05 (4H, multiplet); 2.8–3.0 (4H, multiplet); 3.05–3.25 (2H, multiplet); 3.65–3.8 (1H, multiplet); 3.76 (3H, singlet); 3.95–4.1 (2H, multiplet); 6.7–6.8 (3H, multiplet); 6.85–6.95 (2H, multiplet); 7.1–7.25 (3H, multiplet).

57(c)  (S)-2-{2-[2-(3-Methoxyphenyl)ethyl] phenoxymethyl}pyrrolidine hydrochloride 0.5 ml of a 4N solution of hydrogen chloride in dioxane was added to a solution of 410 mg of (S)-{2-2-[2-(3-methoxyphenyl)ethyl]phenoxymethyl}pyrrolidine [prepared as described in step (b) above] in a suitable amount of ethyl acetate, and the resulting mixture was freed from the solvent by distillation under reduced pressure. 458 mg (a quantitative yield) of the title compound were obtained as a colorless oil.

$[\alpha]_D^{25}$: +6° (c=1.0, ethanol).

Nuclear Magnetic Resonance Spectrum (CDCl$_3$, 270 MHz), δ ppm: 1.8–2.2 (4H, multiplet); 2.8–3.1 (4H, multiplet); 3.29 (2H, triplet, J=6.6 Hz); 3.75 (3H, singlet); 3.9–4.0 (1H, multiplet); 4.11 (1H, doublet of doublets, J=5.3 & 9.9 Hz); 4.22 (1H, doublet of doublets, J=5.3 & 9.9 Hz); 6.65–6.75 (3H, multiplet); 6.85–6.95 (2H, multiplet); 7.05–7.2 (3H, multiplet).

EXAMPLE 58

(S)-2-{2-[2-(3-Methoxyphenyl)ethyl]phenoxymethyl}-1-methylpyrrolidine hydrochloride 58(a)  (S)-2-{2-[2-(3-Methoxyphenyl)ethyl]phenoxymethyl}-1-methylpyrrolidine 130 mg of potassium carbonate were added to a solution of 500 mg of (S)-2-{2-[2-(3-methoxyphenyl)ethyl] phenoxymethyl}pyrrolidine [prepared as described in Example 57(b)] in 5 ml of dimethylacetamide, and the resulting mixture was stirred at room temperature for 5 minutes, after which 288 mg of methyl iodide were added. The reaction mixture was then stirred at room temperature for 5 minutes, after which it was diluted with ethyl acetate. The diluted solution was then washed with water and with a saturated aqueous solution of sodium chloride, in that order, and dried over anhydrous magnesium sulfate. The solvent was then removed by distillation under reduced pressure, and the resulting residue was purified by column chromatography through silica gel, using a 20:1 by volume mixture of methylene chloride and methanol as the eluent, to give 320 mg (yield 61%) of the title compound as a colorless oil.

Nuclear Magnetic Resonance Spectrum (CDCl$_3$, 270 MHz), δ ppm: 1.6–2.0 (3H, multiplet); 2.0–2.2 (1H, multiplet); 2.34 (1H, quartet, J=8.6 Hz); 2.52 (3H, singlet); 2.65–2.8 (1H, multiplet); 2.8–3.0 (4H, multiplet); 3.05–3.2 (1H, multiplet); 3.79 (3H, singlet); 3.85 (1H, doublet of doublets, J=6.6 &9.2 Hz); 4.07 (1H, doublet of doublets, J=5.3 &9.2Hz); 6.7–6.95 (5H, multiplet); 7.1–7.3 (3H, multiplet).

58(b)  (S)-2-{2-[2-(3-Methoxyphenyl)ethyl]phenoxymethyl}-1-methylpyrrolidine hydrochloride 0.37 ml of a 4N solution of hydrogen chloride in dioxane was added to a solution of (S)-2-{2-[2-(3-methoxyphenyl) ethyl]phenoxymethyl}-1-methylpyrrolidine [prepared as described in step (a) above] in 10 ml of ethyl acetate, and the resulting mixture was allowed to stand at room temperature. The crystals which precipitated were collected by filtration, to give 101 mg (yield 28%) of the title compound as colorless needles, melting at 124°–126° C.

$[\alpha]_D^{25}$: +3.8° (c=1.0, ethanol).

Nuclear Magnetic Resonance Spectrum (hexadeuterated dimethyl sulfoxide, 270 MHz) δ ppm: 1.75–2.2 (3H, multiplet); 2.2–2.4 (1H, multiplet); 275–3.0 (4H, multiplet); 2.95 (3H, singlet); 3.0–3.2 (1H, multiplet); 3.5–3.7 (1H, multiplet); 3.72 (3H, singlet); 3.75–3.95 (1H, multiplet); 4.2–4.45 (2H, multiplet); 6.7–6.85 (3H, multiplet); 6.91 (1H, triplet, J=7.3 Hz); 7.00 (1H, doublet, J=7.9 Hz); 7.15–7.3 (3H, multiplet).

EXAMPLE 59

1-Methyl-2-{2-[2-(2-phenylethyl)phenoxy]ethyl} pyrrolidine hydrochloride

59(a)  1-Methyl-2-{2-[2-(2-phenylethyl) phenoxy] ethyl}pyrrolidine

Following a procedure similar to that described in Example 35(a), 900 mg of 2-(2-phenylethyl)phenol (prepared as described in Preparation 19), 1.02 g of potassium t-butoxide and 836 mg of 2-(2-chloroethyl)-1-methylpyrrolidine hydrochloride were reacted in 10 ml of dimethylacetamide. The mixture was then worked up as described in Example 35(a), and the crude product thus obtained was purified by column chromatography through silica gel, using a 10:1 by volume mixture of methylene chloride and methanol as the eluent, to give 480 mg of the title compound as a colorless oil.

Nuclear Magnetic Resonance Spectrum (CDCl$_3$, 270 MHz), δ ppm: 1.55–2.15 (5H, multiplet); 2.2–2.4 (2H, multiplet); 2.4–3.0 (1H, multiplet); 2.42 (3H, singlet); 2.8–3.0 (4H, multiplet); 3.1–3.25 (1H, multiplet); 3.9–4.2 (2H, multiplet); 6.8–6.95 (2H, multiplet); 7.1–7.35 (7H, multiplet).

59(b)  1-Methyl-2-{2-[2-(2-phenylethyl)phenoxy] ethyl}pyrrolidine hydrochloride

A solution of 480 mg of 1-methyl-2-{2-[2-(2-phenylethyl)phenoxy]ethyl}pyrrolidine [prepared as described in step (a) above] in a suitable amount of ethyl acetate was treated with 0.5 ml of a 4N solution of hydrogen chloride in dioxane, and the resulting mixture was then concentrated by distillation under reduced pressure. The resulting oily residue was dissolved in 10 ml ethyl acetate, and the solution thus obtained was allowed to stand at room temperature. The crystals which precipitated were collected by filtration, to give 130 mg (yield 24%) of the title compound as colorless needles, melting at 154°–156° C.

Nuclear Magnetic Resonance Spectrum (CDCl$_3$, 270 MHz), δ ppm: 1.9–2.15 (2H, multiplet); 2.15–2.4 (2H, multiplet); 2.4–2.6 (2H, multiplet); 2.7–3.0 (5H, multiplet); 2.75 (3H, singlet); 3.2–3.4 (1H, multiplet); 3.8–4.05 (2H, multiplet); 4.15–4.3 (1H, multiplet); 6.8.5 (1H, doublet, J=7.9 Hz); 6.93 (1H, triplet, J=7.6 Hz); 7.1–7.35 (7H, multiplet).

EXAMPLE 60

1-Methyl-2-(2-{2-[2-(3-methylphenyl)ethyl]phenoxy}ethyl]pyrrolidine hydrochloride 60(a)  1-Methyl-2-(2-{2-[2-(3-methylphenyl)ethyl]phenoxy}ethyl)pyrrolidine Following a procedure similar to that described in Example 35(a), 1.00 g of 2-[2-(3-methylphenyl)ethyl]phenol (prepared as described in Preparation 25), 1.05 g of potassium t-butoxide and 0.870 g of 2-(2-chloroethyl)-1-methylpyrrolidine hydrochloride were reacted in 10 ml of dimethylacetamide. The mixture was then worked up as described in Example 35(a), and the crude product thus obtained was purified by column chromatography through silica gel, using a 10:1 by volume mixture of methylene chloride and methanol as the eluent, to give 150 mg (yield 11%) of the title compound as an oil.

Nuclear Magnetic Resonance Spectrum (CDCl$_3$, 270 MHz), δ ppm: 1.6–2.0 (4H, multiplet); 2.0–2.15 (1H, multiplet); 2.2–2.55 (3H, multiplet); 2.33 (3H, singlet); 2.42 (3H, singlet); 2.8–3.0 (4H, multiplet); 3.15–3.25 (1H, multiplet); 3.95–4.2 (2H, multiplet) 6.8–6.95 (2H, multiplet) 7.0–7.1 (3H, multiplet); 7.1–7.25 (3H, multiplet)

60(b)  1-Methyl-2-(2-{2-[2-(3-methylphenyl)ethyl]phenoxy}ethyl]pyrrolidine hydrochloride 0.2 ml of a 4N solution of hydrogen chloride in dioxane was added to a solution of 150 mg of 1-methyl-2-(2-{2-[2-(3-methylphenyl)ethyl]phenoxy}ethyl)pyrrolidine [prepared as described in step (a) above] in a suitable amount of ethyl acetate, to convert it to the hydrochoride, which was recrystallized from ethyl acetate, to give 87 mg (yield 52%) of the title compound as colorless crystals, melting at 128°–130° C.

Nuclear Magnetic Resonance Spectrum (CDCl$_3$, 270 MHz), δ ppm: 1.9–2.15 (2H, multiplet); 2.15–2.4 (2H, multiplet); 2.33 (3H, singlet); 2.4–2.65 (2H, multiplet); 2.7–3.0 (5H, multiplet); 2.75 (3H, singlet); 3.2–3.4 (1H, multiplet); 3.8–4.1 (2H, multiplet); 4.2–4.3 (1H, multiplet); 6.8–7.1 (5H, multiplet); 7.1–7.3 (3H, multiplet).

EXAMPLE 61

2-{2-[2-(2-Phenylethyl)phenoxy]ethyl}piperidine hydrochloride

61(a)  1-t-Butoxycarbonyl-2-(2-[2-(2-phenylethyl)phenoxy]ethyl}piperidine

Following a procedure similar to that described in Example 40(a), 0.930 g of 2-(2-phenylethyl)phenol (prepared as described in Preparation 19), 0.527 g of potassium t-butoxide and 1.66 g of 1-t-butoxycarbonyl-2-[2-(p-toluenesulfonyloxy)ethyl]piperidine were reacted in 20 ml of dimethylacetamide. The mixture was then worked lap as described in Example 40(a), and the crude product thus obtained was purified by column chromatography through silica gel, using a 4:1 by volume mixture of hexane and ethyl acetate as the eluent, to give 1.34 g (yield 75%) of the title compound as a colorless oil.

Nuclear Magnetic Resonance Spectrum (CDCl$_3$, 270 MHz), δ ppm: 1.3–1.8 (6H, multiplet); 1.38 (9H, singlet); 1.8–2.0 (1H, multiplet); 2.15–2.35 (1H, multiplet); 2.7–3.0 (5H, multiplet); 3.9–4.15 (3H, multiplet); 4.4–4.6 (1H, multiplet); 6.75–6.9 (2H, multiplet); 7.05–7.35 (7H, multiplet).

61(b)  2-{2-[2-(2-Phenylethyl)phenoxy]ethyl}piperidine hydrochloride 5 ml of a 4N solution of hydrogen chloride in dioxane were added to a solution of 440 mg of 1-t-butoxycarbonyl-2-{2-[2-(2-phenylethyl)phenoxy]ethyl}piperidine [prepared as described in step (a) above] in 5 ml of dioxane, and the resulting mixture was allowed to stand at room temperature for 2 hours. At the end of this time, the solvent was removed by distillation under reduced pressure, and the resulting solid residue was dissolved in a small amount of methylene chloride; 20 ml of ethyl acetate was then added to the solution thus obtained, after which it was allowed to stand at room temperature. The crystals which precipitated were collected by filtration, to give 214 mg (yield 53%) of the title compound as colorless crystals, melting at 95°–97° C.

Nuclear Magnetic Resonance Spectrum (CDCl$_3$, 270 MHz), δ ppm: 1.3–1.5 (1H, multiplet); 1.7–2.1 (5H, multiplet); 2.15–2.3 (1H, multiplet); 2.5–2.7 (1H, multiplet); 2.7–3.0 (5H, multiplet); 3.2–3.35 (1H, multiplet); 3.45 (1H, doublet, J=12.5 Hz); 4.0–4.2 (2H, multiplet); 6.8–6.9 (2H, multiplet); 7.05–7.35 (7H, multiplet).

EXAMPLE 62

1-Methyl-2-{2-[2-(2-phenylethyl)phenoxy]ethyl}piperidine hydrochloride

62(a)  1-Methyl-2-{2-[2-(2-phenylethyl)phenoxy]ethyl}piperidine

Following a procedure similar to that described Example 38, 1.34 g of 1-t-butoxycarbonyl-2-{2-[2-(2-phenylethyl)phenoxy]ethyl}piperidine [prepared as described in Example 61(a)] were reacted with 0.269 g of lithium aluminum hydride dispersed in 30 ml of tetrahydrofuran. The mixture was then worked up as described in Example 38, and the crude product thus obtained was purified by column chromatography through silica gel, using a 10:1 by volume mixture of methylene chloride and methanol as the eluent, to give 1.12 g (yield 96%) of the title compound as a colorless oil.

Nuclear Magnetic Resonance Spectrum (CDCl$_3$, 270 MHz), δ ppm: 1.2–2.4 (10H, multiplet); 2.35 (3H, singlet); 2.8–3.0 (5H, multiplet); 4.0–4.1 (2H, multiplet); 6.8–6.95 (2H, multiplet); 7.1–7.35 (7H, multiplet).

62(b)  1-Methyl-2-{2-[2-(2-phenylethyl)phenoxy]ethyl}piperidine hydrochloride 0.6 ml of a 4N solution of hydrogen chloride in dioxane was added to a solution of 670 mg of 1-methyl-2-{2-[2-(2-phenylethyl)phenoxy]ethyl}piperidine [prepared as described in step (a) above] in a suitable amount of ethyl acetate, and the resulting mixture was concentrated by distillation under reduced pressure. The resulting solid residue was recrystallized from ethyl acetate, to give 350 mg (yield 47%) of the title compound as colorless crystals, melting at 128°–130° C.

Nuclear Magnetic Resonance Spectrum (CDCl$_3$, 270 MHz), δ ppm: 1.2–2.4 (7H, multiplet); 2.4–2.65 (2H, multiplet); 2.74 (3H, singlet); 2.8–3.2 (5H, multiplet); 3.2–3.6 (1H, multiplet); 3.95–4.2 (2H, multiplet); 6.84 (1H, doublet, J=7.9 Hz); 6.92 (1H, triplet, J=7.3 Hz); 7.1–7.35 (7H, multiplet).

EXAMPLE 63

2-(2-{2-[2-(2-Methoxyphenyl)ethyl]phenoxy}ethyl)-1-methylpyrrolidine hydrochloride 63(a) 2-(2-{2-[2-(2-Methoxyphenyl)ethyl]phenoxy}ethyl)-1-methylpyrrolidine Following a procedure similar to that described in Example 35(a), 1.00 g of 2-[2-(2-methoxyphenyl)ethyl]phenol (prepared as described in Preparation 23), 1.47 g of potassium t-butoxide and 1.61 g of 2-(2-chloroethyl)-1-methylpyrrolidine hydrochloride were reacted in 10 ml of dimethylacetamide. The mixture was then worked up as described in Example 35(a), and the crude product thus obtained was purified by column chromatography through silica gel, using a 10:1 by volume mixture of methylene chloride and methanol as the eluent, to give 300 mg (yield 20%) of the title compound as an oil.

Nuclear Magnetic Resonance Spectrum (CDCl$_3$, 270 MHz), δ ppm: 1.5–1.95 (4H, multiplet); 2.0–2.15 (1H, multiplet); 2.2–2.55 (3H, multiplet); 2.38 (3H, singlet); 2.89 (4H, singlet); 3.1–3.2 (1H, multiplet); 3.82 (3H, singlet); 3.9–4.15 (2H, multiplet); 6.8–6.9 (4H, multiplet); 7.1–7.25 (4H, multiplet).

63(b) 2-(2-{2-[2-(2-Methoxyphenyl)ethyl]phenoxy}ethyl)-1-methylpyrrolidine hydrochloride 0.3 ml of a 4N solution of hydrogen chloride in dioxane was added to a solution of 300 mg of 2-(2-{2-[2-(2-methoxyphenyl)ethyl]phenoxy}ethyl)-1-methylpyrrolidine [prepared as described in step (a) above] in a suitable amount of ethyl acetate, and the resulting mixture was concentrated by distillation under reduced pressure. The resulting solid residue was recrystallized from ethyl acetate, to give 186 mg (yield 56%) of the title compound as colorless needles, melting at 143°–145° C.

Nuclear Magnetic Resonance Spectrum (CDCl$_3$, 270 MHz), δ ppm: 1.7–2.65 (6H, multiplet); 2.65–2.95 (5H, multiplet); 2.74 (3H, singlet); 3.25–3.4 (1H, multiplet); 3.75–3.9 (1H, multiplet); 3.80 (3H, singlet); 3.9–4.05 (1H, multiplet); 4.15–4.3 (1H, multiplet); 6.8–7.0 (4H, multiplet); 7.05–7.3 (4H, multiplet).

EXAMPLE 64

1-Methyl-2-(2-{2-[2-(2-methylphenyl)ethyl]phenoxy}ethyl)pyrrolidine hydrochloride 64(a) 1-Methyl-2-(2-{2-[2-(2-methylphenyl)ethyl]phenoxy}ethyl)pyrrolidine Following a procedure similar to that described in Example 35(a), 1.00 g of 2-[2-(2-methylphenyl)ethyl]phenol (prepared as described in Preparation 24), 1.59 g of potassium t-butoxide and 1.73 g of 2-(2-chloroethyl)-1-methylpyrrolidine hydrochloride were reacted in 10 ml of dimethylacetamide. The mixture was then worked up as described in Example 35(a), and the crude product thus obtained was purified by column chromatography through silica gel, using a 10:1 by volume mixture of methylene chloride and methanol as the eluent, to give 350 mg (yield 23%) of the title compound as a solid.

Nuclear Magnetic Resonance Spectrum (CDCl$_3$, 270 MHz), δ ppm: 1.5–1.9 (4H, multiplet); 1.95–2.5 (4H, multiplet); 2.34 (3H, singlet); 2.37 (3H, singlet); 2.86 (4H, singlet); 3.1–3.2 (1H, multiplet); 3.9–4.2 (2H, multiplet); 6.8–6.95 (2H, multiplet); 7.1–7.25 (6H, multiplet).

64(b) 1-Methyl-2-(2-{2-[2-(2-methylphenyl)ethyl]phenoxy}ethyl)pyrrolidine hydrochloride 0.3 ml of a 4N solution of hydrogen chloride in dioxane was added to a solution of 350 mg of 1-methyl-2-(2-{2-[2-(2-methylphenyl)ethyl]phenoxy}ethyl)pyrrolidine [prepared as described in step (a) above] in a suitable amount of ethyl acetate, and the resulting mixture was concentrated by distillation under reduced pressure. The resulting oily residue was dissolved in 7 ml of ethyl acetate, after which it was allowed to stand at room temperature. The crystals which precipitated were collected by filtration, to give 212 mg (yield 54%) of the title compound as colorless crystals, melting at 163°–165° C.

Nuclear Magnetic Resonance Spectrum (CDCl$_3$, 270 MHz), δ ppm: 1.85–2.6 (6H, multiplet); 2.29 (3H, singlet); 2.6–2.95 (5H, multiplet); 2.7.3 (3H, singlet); 3.2–3.4 (1H, multiplet); 3.8–4.1 (2H, multiplet); 4.2–4.3 (1H, multiplet); 6.86 (1H, doublet, J=7.9 Hz); 6.93 (1H, triplet, J=7.6 Hz); 7.1–7.3 (6H, multiplet).

EXAMPLE 65

(4R)-4-Hydroxy-2-[2-(2-phenylethyl)phenoxymethyl]pyrrolidine hydrochloride

65(a) (4R)-4-Benzyloxy-1-t-butoxycarbonyl-2-[2-(2-phenylethyl)phenoxymethyl]pyrrolidine Following a procedure similar to that described in Example 40(a), 200 mg of 2-(2-phenylethyl)phenol (prepared as described in Preparation 19), 124 mg of potassium t-butoxide and 500 mg of (4R)-4-benzyloxy-1-t-butoxycarbonyl-2-(p-toluenesulfonyloxymethyl)pyrrolidine were reacted in 10 ml of dimethylacetamide. The mixture was then worked up as described in Example 40(a), and the crude product thus obtained was purified by column chromatography through silica gel, using a 4:1 by volume mixture of hexane and ethyl acetate as the eluent, to give 400 mg (yield 81%) of the title compound as a colorless oil.

Nuclear Magnetic Resonance Spectrum (CDCl$_3$, 270 MHz), δ ppm: 1.45 (9H, singlet); 2.15–2.35 (2H, multiplet); 2.75–3.0 (4H, multiplet); 3.4–4.6 (8H, multiplet); 6.8–6.95 (2H, multiplet); 7.05–7.4 (12H, multiplet).

65(b) (4R)-1-t-butoxycarbonyl-4-hydroxy-2-[2-(2-phenylethyl)phenoxymethyl]pyrrolidine A solution of 390 mg of (4R)-4-benzyloxy-1-t-butoxycarbonyl-2-[2-(2-phenylethyl)phenoxymethyl]pyrrolidine [prepared as described in step (a) above] in 25 ml of ethanol was stirred at 60° C. for 5 hours in an atmosphere of hydrogen at atmospheric pressure and in the presence of 100 mg of 5% w/w palladium-on-charcoal. At the end of this time, the catalyst was removed by filtration, and the filtrate was concentrated by distillation under reduced pressure. The resulting residue was purified by column chromatography through silica gel, using a 1:1 by volume mixture of hexane and ethyl acetate as the eluent, to give 310 mg (yield 97%) of the title compound as a colorless oil.

Nuclear Magnetic Resonance Spectrum (CDCl$_3$, 270 MHz), δ ppm: 1.46 (9H, singlet); 2.0–2.4 (2H, multiplet); 2.8–3.0 (4H, multiplet); 3.4–3.7 (2H, multiplet); 4.0–4.6 (4H, multiplet); 6.8–7.0 (2H, multiplet); 7.05–7.35 (7H, multiplet).

65(c) (4R)-4-Hydroxy-2-[2-(2-phenylethyl)phenoxymethyl]pyrrolidine hydrochloride 3 ml of a 4N solution of hydrogen chloride in dioxane were added to a solution of 200 mg of (4R)-1-t-butoxycarbonyl-4-hydroxy-2-[2-(2-phenylethyl)phenoxymethyl]pyrrolidine [prepared as described in step (b) above] in 3 ml of dioxane, and the resulting solution was stirred at room temperature for 2 hours. At the end of this time, the solution was concentrated by distillation under reduced pressure, the resulting residue was dissolved in a small amount of methylene chloride, and ethyl acetate was added to the solution. The resulting mixture was then allowed to stand an room temperature. The crystals which precipitated were collected by filtration, to give 133 mg (yield 79%) of the title compound as colorless crystals, melting at 143°–145° C.

Nuclear Magnetic Resonance Spectrum (CDCl$_3$, 270 MHz), δ ppm: 1.8–2.0 (1H, multiplet); 2.13 (1H, doublet of doublets, J=7.3 & 13.9 Hz); 2.85–3.0 (4H, multiplet); 3.21 (1H, doublet of doublets, J=3.3 & 11.9 Hz); 3.51 (1H, doublet, J=11.9 Hz); 4.01 (1H, doublet of doublets, J=5.3 & 10.6 Hz); 4.10 (1H, doublet of doublets, J=4.0 & 10.6 Hz); 4.2–4.35 (1H, multiplet); 4.4–4.5 (1H, multiplet); 6.75–6.95 (2H, multiplet); 7.9–7.3 (7H, multiplet).

EXAMPLE 66

(4R)-4-Hydroxy-1-methyl-2-[2-(2-phenylethyl)phenoxymethyl]pyrrolidine hydrochloride 66(a) (4R)-4-Hydroxy-1-methyl-2-[2-(2-phenylethyl)phenoxymethyl]pyrrolidine Following a procedure similar to that described in Example 38, 300 mg of (4R)-1-t-butoxycarbonyl-4-hydroxy-2-[2-(2-phenylethyl)phenoxymethyl]pyrrolidine [prepared as described in Example 65(b)] were reacted with 85.9 mg of lithium aluminum hydride dispersed in 30 ml of tetrahydrofuran. The mixture was then worked up as described in Example 38, and the crude product thus obtained was purified by column chromatography through silica gel, using a 10:1 by volume mixture of methylene chloride and methanol as the eluent, to give 150 mg (yield 63%) of the title compound as a colorless oil.

Nuclear Magnetic Resonance Spectrum (CDCl$_3$, 270 MHz), δ ppm: 1.95–2.1 (2H, multiplet); 2.38 (1H, doublet of doublets, J=5.3 & 9.9 Hz); 2.51 (3H, singlet); 2.8–3.0 (4H, multiplet); 3.0–3.15 (1H, multiplet); 3.42 (1H, doublet of doublets, J=5.9 & 10.6 Hz); 3.85 (1H, doublet of doublets, J=5.9 & 9.2 Hz); 4.02 (1H, doublet of doublets, J=5.3 & 9.2 Hz); 4.35–4.5 (1H, multiplet); 6.8–6.95 (2H, multiplet); 7.05–7.35 (7H, multiplet).

66(b) (4R)-4-Hydroxy-1-methyl-2-[2-(2-phenylethyl)phenoxymethyl]pyrrolidine hydrochloride 0.36 ml of a 4N solution of hydrogen chloride in dioxane was added to a solution of 150 mg of (4R)-4-hydroxy-1-methyl-2-[2-(2-phenylethyl)phenoxymethyl]pyrrolidine [prepared as described in step (a) above] in a suitable amount of dioxane, and the resulting mixture was concentrated by distillation under reduced pressure. The resulting solid residue was recrystallized from ethyl acetate, to give 91.6 mg (yield 55%) of the title compound as colorless crystals, melting at 97°–99° C.

Nuclear Magnetic Resonance Spectrum (CDCl$_3$, 270 MHz), δ ppm: 2.1–2.4 (2H, multiplet); 2.7–3.3 (5H, multiplet); 2.89 (3H, singlet); 3.8–4.3 (3H, multiplet); 4.5–4.8 (2H, multiplet); 6.8–7.0 (2H, multiplet); 7.05–7.35 (7H, multiplet);

EXAMPLE 67

(4R)-4-Hydroxy-2-{2-[2-(3-methylphenyl)ethyl]phenoxymethyl]pyrrolidine hydrochloride 67(a) (4R)-4-Benzyloxy-1-t-butoxycarbonyl-2-{2-[2-(3-methylphenyl) ethyl]phenoxymethyl}pyrrolidine Following a procedure similar to that described in Example 40(a), 400 mg of 2-[2-(3-methylphenyl)ethyl]phenol (prepared as described in Preparation 25), 232 mg of potassium t-butoxide and 870 mg of (4R)-4-benzyloxy-1-t-butoxycarbonyl-2-(p-toluenesulfonyloxymethyl)pyrrolidine were reacted in 25 ml of dimethylacetamide. The mixture was then worked up as described in Example 40(a), and the crude product thus obtained was purified by column chromatography through silica gel, using a 4:1 by volume mixture of hexane and ethyl acetate as the eluent, to give 560 mg (yield 59%) of the title compound as a colorless oil.

Nuclear Magnetic Resonance Spectrum (CDCl$_3$, 270 MHz), δ ppm: 1.45 (9H, singlet); 2.15–2.4 (2H, multiplet); 2.31 (3H, singlet); 2.75–3.0 (4H, multiplet); 3.4–4.6 (8H, multiplet); 6.8–7.55 (13H, multiplet).

67(b) (4R)-1-t-Butoxycarbonyl-4-hydroxy-2-{2-[2-(3-methylphenyl) ethyl]phenoxymethyl}pyrrolidine Following a procedure similar to that described in Example 65(b), 550 mg of (4R)-4-benzyloxy-1-t-butoxycarbonyl-2-{2-[2-(3-methylphenyl)ethyl]phenoxymethyl}pyrrolidine [prepared as described in step (a) above] were dissolved in 20 ml of ethanol and hydrogenated in an atmosphere of hydrogen at atmospheric pressure and in the presence of 120 mg of 5% w/w palladium-on-charcoal as a catalyst. The mixture was then worked up as described in Example 65(b), and the crude product thus obtained was purified by column chromatography through silica gel, using a 1:1 by volume mixture of hexane and ethyl acetate as the eluent, to give 370 mg (yield 82%) of the title compound as a colorless oil.

Nuclear Magnetic Resonance Spectrum (CDCl$_3$, 270 MHz), δ ppm: 1.46 (9H, singlet); 2.0–2.4 (2H, multiplet); 2.34 (3H, singlet); 2.75–3.0 (4H, multiplet); 3.4–4.6 (6H, multiplet); 6.8–7.3 (6H, multiplet).

67(c) (4R)-4-Hydroxy-2-{2-[2-(3-methylphenyl)ethyl]phenoxymethyl]pyrrolidine hydrochloride 3 ml of a 4N solution of hydrogen chloride in dioxane were added to a solution of 348 mg of (4R)-1-t-butoxycarbonyl-4-hydroxy-2-{2-[2-(3-methylphenyl)ethyl]phenoxymethyl}pyrrolidine [prepared as described in step (b) above] in 3 ml of dioxane, and the resulting mixture was allowed to stand at room temperature for 3 hours. At the end of this time, the solvent was removed by distillation under reduced pressure, the resulting solid residue was dissolved in methylene chloride, and ethyl acetate was added to the solution, which was then allowed to stand at room temperature. The crystals which precipitated were collected by filtration and dried in vacuo, to give 208 mg (yield 70%) of the title compound as colorless crystals, melting at 141°–143° C.

Nuclear Magnetic Resonance Spectrum (CDCl$_3$, 270 MHz), δ ppm: 1.85–2.05 (1H, multiplet); 2.15 (1H, doublet of doublets, J=6.6 & 13.2 Hz); 2.27 (3H, singlet); 2.7–2.95 (4H, multiplet); 3.18 (1H, doublet of doublets, J=4.0 & 12.5

Hz); 3.49 (1H, doublet, J=12.5 Hz); 4.01 (1H, doublet of doublets, J=4.6 & 10.6 Hz); 4.12 (1H, doublet of doublets, J=4.6 & 10.6 Hz); 4.2–4.35 (1H, multiplet); 4.4–4.5 (1H, multiplet); 6.75–7.2 (8H, multiplet).

EXAMPLE 68

2-[2-{2-[2-(3,5-Dimethoxyphenyl)ethyl]phenoxy}ethyl]-1-methylpyrrolidine hydrochloride 68(a) 2-(2-{2-[2-(3,5-Dimethoxyphenyl)ethyl]phenoxy}ethyl)-1-methylpyrrolidine Following a procedure similar to that described in Example 35(a), 1.00 g of 2-[2-(3,5-dimethoxyphenyl)ethyl]phenol (prepared as described in Preparation 27), 1.30 g of potassium t-butoxide and 1.06 g of 2-(2-chloroethyl)-1-methylpyrrolidine hydrochloride were reacted in 10 ml of dimethylacetamide. The mixture was then worked up as described in Example 35(a), and the crude product thus obtained was purified by column chromatography through silica gel, using a 10:1 by volume mixture of methylene chloride and methanol as the eluent, to give 1.15 g (yield 80%) of the title compound as a colorless oil.

Nuclear Magnetic Resonance Spectrum (CDCl$_3$, 270 MHz), δ ppm: 1.5–2.5 (8H, multiplet); 2.39 (3H, singlet); 2.75–3.0 (4H, multiplet); 3.1–3.2 (1H, multiplet); 3.76 (6H, singlet); 3.95–4.15 (2H, multiplet); 6.3–6.4 (3H, multiplet); 6.8–6.95 (2H, multiplet); 7.1–7.25 (2H, multiplet).

68(b) 2-(2-{2-[2-(3,5-Dimethoxyphenyl)ethyl]phenoxy}ethyl)-1-methylpyrrolidine hydrochloride Using 0.9 ml of a 4N solution of hydrogen chloride in dioxane, 1.15 g of 2-(2-{2-[2-(3,5-dimethoxyphenyl)ethyl]phenoxy}ethyl)-1-methylpyrrolidine [prepared as described in step (a) above] were converted to the hydrochloride, which was recrystallized from ethyl acetate to give 0.657 g (yield 52%) of the title compound as colorless crystals, melting at 99°–101° C.

Nuclear Magnetic Resonance Spectrum (CDCl$_3$, 270 MHz), δ ppm: 1.9–2.6 (6H, multiplet); 2.7–3.0 (5H, multiplet); 2.78 (3H, singlet); 3.35–3.45 (1H, multiplet); 3.76 (6H, singlet); 3.8–4.05 (2H, multiplet); 4.15–4.3 (1H, multiplet); 6.25–6.35 (3H, multiplet); 6.8–7.0 (2H, multiplet); 7.15–7.25 (2H, multiplet).

EXAMPLE 69

2-(2-{2-[2-(4-Ethylphenyl)ethyl]phenoxy}ethyl)piperidine hydrochloride

69(a) 1-t-Butoxycarbonyl-2-(2-{2-[2-(4-ethylphenyl)ethyl]phenoxy}ethyl)piperidine Following a procedure similar to that described in Example 40(a), 1.00 g of 2-[2-(4-ethylphenyl)ethyl]phenol (prepared as described in Preparation 26), 0.496 g of potassium t-butoxide and 1.70 g of 1-t-butoxycarbonyl-2-[2-(p-toluenesulfonyloxy)ethyl]piperidine were reacted in 20 ml of dimethylacetamide. The mixture was then worked up as described in Example 40(a), and the crude product thus obtained was purified by column chromatography through silica gel, using a 4:1 by volume mixture of hexane and ethyl acetate as the eluent, to give 1.92 g (yield 99%) of the title compound as a colorless oil.

Nuclear Magnetic Resonance Spectrum (CDCl$_3$, 270 MHz), δ ppm: 1.23 (3H, triplet, J=7.3 Hz); 1.3–1.8 (6H, multiplet); 1.38 (6H, singlet); 1.8–2.0 (1H, multiplet); 2.15–2.35 (1H, multiplet); 2.63 (2H, quartet, J=7.3 Hz); 2.75–3.0 (5H, multiplet); 3.9–4.15 (3H, multiplet); 4.4–4.6 (1H, multiplet); 6.75–6.9 (2H, multiplet); 7.1–7.25 (6H, multiplet).

69(b) 2-(2-{2-[2-(4-Ethylphenyl)ethyl]phenoxy}-ethyl) piperidine hydrochloride 5 ml of a 4N solution of hydrogen chloride in dioxane were added to a solution of 0.91 g of 1-t-butoxycarbonyl-2-(2-{2-[2-(4-ethylphenyl)ethyl]phenoxy}ethyl)piperidine [prepared as described in step (a) above] in 5 ml of dioxane, and the resulting solution was allowed to stand at room temperature for 1 hour. At the end of this time, the mixture was concentrated by distillation under reduced pressure, and the resulting oily residue was dissolved in a small amount of ethyl acetate. Diethyl ether was added to the solution, which was then allowed to stand at room temperature. The crystals which precipitated were collected by filtration and dried in vacuo, to give 687 mg (yield 88%) of the title compound as colorless crystals, melting at 74°–76° C.

Nuclear Magnetic Resonance Spectrum (CDCl$_3$, 270 MHz), δ ppm: 1.21 (3H, triplet, J=7.6 Hz); 1.3–1.5 (1H, multiplet); 1.7–2.1 (6H, multiplet); 2.15–2.3 (1H, multiplet); 2.61 (2H, quartet, J=7.6 Hz); 2.6–3.0 (5H, multiplet); 3.2–3.35 (1H, multiplet); 3.4–3.55 (1H, multiplet); 4.0–4.2 (2H, multiplet); 6.8–6.95 (2H, multiplet); 7.05–7.2 (6H, multiplet).

EXAMPLE 70

2-(2-{2-[2-(4-Ethylphenyl)ethyl]phenoxy}ethyl)-1-methylpiperidine hydrochloride

70(a) 2-(2-{2-[2-(4-Ethylphenyl)ethyl]phenoxy}ethyl)-1-methylpiperidine

Following a procedure similar to that described in Example 38(a), 1.00 g of 1-t-butoxycarbonyl-2-(2-{2-[2-(4-ethylphenyl)ethyl]phenoxy}ethyl)piperidine [prepared as described in Example 69(a)] were reacted with 0.173 g of lithium aluminum hydride dispersed in 20 ml of tetrahydrofuran. The mixture was then worked up as described in Example 38(a), and the crude product thus obtained was purified by column chromatography through silica gel using a 10:1 by volume mixture of methylene chloride and methanol as the eluent, to give 0.650 g (yield 81%) of the title compound as a colorless oil.

Nuclear Magnetic Resonance Spectrum (CDCl$_3$, 270 MHz), δ ppm: 1.23 (3H, triplet, J=7.6 Hz); 1.2–2.35 (10H, multiplet); 2.38 (3H, singlet); 2.63 (2H, quartet, J=7.6 Hz); 2.8–3.0 (5H, multiplet); 4.0–4.15 (2H, multiplet); 6.8–7.0 (2H, multiplet); 7.1–7.25 (6H, multiplet).

70(b) 2-(2-{2-[2-(4-Ethylphenyl)ethyl]phenoxy}ethyl)-1-methypiperidine hydrochloride 0.6 ml of a 4N solution of hydrogen chloride in dioxane was added to a solution of 0.650 g of 2-(2-{2-[2-(4-ethylphenyl)ethyl]phenoxy}ethyl)-1-methylpiperidine [prepared as described in step (a) above] in a suitable amount of ethyl acetate, and the resulting solution was concentrated by distillation under reduced pressure. The resulting oily residue was dissolved in ethyl acetate, and a small amount of diethyl ether was added to the solution, which was then allowed to stand at room temperature. The crystals which precipitated were collected by filtration and dried in vacuo, to give 0.590 g (yield 82%) of the title compound as colorless crystals, melting at 101°–103° C.

Nuclear Magnetic Resonance Spectrum (CDCl$_3$, 270 MHz), δ ppm: 1.23 (3H, triplet, J=7.6 Hz); 1.25–1.55 (1H, multiplet); 1.6–2.7 (8H, multiplet); 2.63 (2H, quartet, J=7.6 Hz); 2.74 (3H, singlet); 2.8–3.2 (5H, multiplet); 3.3–3.55

(1H, multiplet); 3.95–4.2 (2H, multiplet); 6.8–7.0 (2H, multiplet); 7.05–7.25 (6H, multiplet).

EXAMPLE 71

(S)-2-{2-[2-(3-Methoxyphenyl)ethyl]phenoxymethyl}morpholine hydrochloride

71(a)  (S)-4-t-Butoxycarbonyl-2-{2-[2-(3-methoxyphenyl)ethyl]phenoxymethyl}morpholine Following a procedure similar to that described in Example 40(a), 1.14 g of 2-[2-(3-methoxyphenyl)ethyl]phenol (prepared as described in Preparation 20), 0.560 g of potassium t-butoxide and 1.86 g of (S)-4-t-butoxycarbonyl-2-(p-toluenesulfonyloxymethyl)morpholine were reacted in 25 ml of dimethylacetamide. The mixture was then worked up as described in Example 40(a), and the crude product thus obtained was purified by column chromatography through silica gel, using a 5:1 by volume mixture of hexane and ethyl acetate as the eluent, to give 1.97 g (yield 92%) of the title compound as a colorless oil.

Nuclear Magnetic Resonance Spectrum (CDCl$_3$, 270 MHz), δ ppm: 1.44 (6H, singlet); 2.8–3.1 (6H, multiplet); 3.5–3.7 (1H, multiplet); 3.7–4.2 (6H, multiplet); 3.77 (3H, singlet); 6.7–6.95 (5H, multiplet); 7.1–7.3 (3H, multiplet).

71(b)  (S)-2-{2-[2-(3-Methoxyphenyl)ethyl]phenoxymethyl}morpholine hydrochloride 5 ml of a 4N solution of hydrogen chloride in dioxane were added to a solution of 420 mg of (S)-4-t-butoxycarbonyl-2-{2-[2-(3-methoxyphenyl)ethyl]phenoxymethyl}morpholine [prepared as described in step (a) above] in 5 ml of dioxane, and the resulting solution was allowed to stand at room temperature for 1 hour. At the end of this time, the solution was concentrated by evaporation under reduced pressure, the resulting oily residue was dissolved in 20 ml of ethyl acetate, and the resulting solution was allowed to stand at room temperature. The crystals which precipitated were collected by filtration and dried in vacuo, to give 279 mg (yield 78%) of the title compound as colorless needles, melting at 105°–106° C.

$[\alpha]_D^{25}$+7.3° (c=1.0, water).

Nuclear Magnetic Resonance Spectrum (CDCl$_3$, 270 MHz), δ ppm: 2.75–2.95 (4H, multiplet); 3.0–3.2 (2H, multiplet); 3.35 (1H, doublet, J=12.5 Hz); 3.46 (1H, doublet, J=12.5 Hz); 3.76 (3H, singlet); 3.95–4.2 (4H, multiplet); 4.3–4.4 (1H, multiplet); 6.65–6.95 (5H, multiplet); 7.05–7.3 (3H, multiplet).

EXAMPLE 72

(S)-2-{2-[2-(3-Methoxyphenyl)ethyl]phenoxymethyl}-4-methylmorpholine hydrochloride 72(a)  (S)-2-{2-[2-(3-Methoxylphenyl)ethyl]phenoxymethyl}-4-methylmorpholine Following a procedure similar to that described in Example 38(a), 1.50 g of (S)-4-t-butoxycarbonyl-2-{2-[2-(3-methoxyphenyl)ethyl]phenoxymethyl}morpholine [prepared as described in Example 71(a)] were reacted with 167 mg of lithium aluminum hydride dispersed in 20 ml of tetrahydrofuran. The mixture was then worked up as described in Example 38(a), and the crude product thus obtained was purified by column chromatography through silica gel, using a 20:1 by volume mixture of methylene chloride and methanol as the eluent, to give 1.04 g (yield 87%) of the title compound as a colorless oil.

Nuclear Magnetic Resonance Spectrum (CDCl$_3$, 270 MHz), δ ppm: 2.0–2.25 (2H, multiplet); 2.31 (3H, singlet); 2.65–2.75 (1H, multiplet); 2.8–3.0 (5H, multiplet); 3.7–3.85 (1H, multiplet); 3.77 (3H, singlet); 3.9–4.1 (4H, multiplet); 6.7–6.95 (5H, multiplet); 7.1–7.3 (3H, multiplet).

72(b)  (S)-2-{2-[2-(3-Methoxyphenyl)ethyl]phenoxymethyl}-4-methylmorpholine hydrochloride 1 ml of a 4N solution of hydrogen chloride in dioxane was added to a solution of 1.04 g of (S)-2-{2-[2-(3-methoxyphenyl)ethyl]phenoxymethyl}-4-methylmorpholine [prepared as described in step (a) above] in 20 ml of ethyl acetate, and the resulting mixture was allowed to stand at room temperature. The crystals which precipitated were collected by filtration and dried in vacuo, to give 1.05 g (yield 91%) of the title compound as colorless crystals, melting at 186°–187° C.

$[\alpha]_D^{25}$+5.7° (c=1.0, ethanol).

Nuclear Magnetic Resonance Spectrum (CDCl$_3$, 270 MHz), δ ppm: 2.77 (3H, singlet); 2.7–3.1 (6H, multiplet); 3.41 (2H, triplet, J=10.2 Hz); 3.78 (3H, singlet); 4.0–4.2 (3H, multiplet); 4.3–4.45 (1H, multiplet); 4.5–4.6 (1H, multiplet); 6.7–6.9 (4H, multiplet); 6.94 (1H, triplet, J=7.4 Hz); 7.1–7.3 (3H, multiplet).

EXAMPLE 73

1-Methyl-2-{2-{2-[2-(3,4,5-trimethoxyhenyl)ethyl]phenoxy}ethyl)pyrrolidine hydrochloride 73(a)  1-Methyl-2-(2-{2-[2-(3,4,5-trimethoxyphenyl)ethyl]phenoxy}ethyl)pyrrolidine Following a procedure similar to that described in Example 35(a), 1.00 g of 2-[2-(3,4,5-trimethoxyphenyl)ethyl]phenol (prepared as described in Preparation 28), 1.18 g of potassium t-butoxide and 0.958 g of 2-(2-chloroethyl)-1-methylpyrrolidine hydrochloride were reacted in 10 ml of dimethylacetamide. The mixture was then worked up as described in Example 35(a), and the crude product thus obtained was purified by column chromatography through silica gel, using a 10:1 by volume mixture of methylene chloride and methanol as the eluent, to give 0.900 g (yield 65%) of the title compound as a colorless oil.

Nuclear Magnetic Resonance Spectrum (CDCl$_3$, 270 MHz), δ ppm: 1.6–2.6 (8H, multiplet); 2.46 (3H, singlet); 2.75–3.0 (4H, multiplet); 3.25–3.35 (1H, multiplet); 3.81 (6H, singlet); 3.82 (3H, singlet); 3.9–4.2 (2H, multiplet); 6.35 (2H, singlet); 6.8–6.95 (2H, multiplet); 7.05–7.25 (2H, multiplet).

73(b) 1-Methyl-2-(2-{2-[2-(3,4,5-trimethoxyphenyl)ethyl]phenoxy}ethyl)pyrrolidine hydrochloride 0.84 ml of a 4N solution of hydrogen chloride in dioxane was added to a solution of 0.900 g of 1-methyl-2-(2-{2-[2-(3,4,5-trimethoxyphenyl)ethyl]phenoxy}ethyl)pyrrolidine [prepared as described in step (a) above] in a suitable amount of dioxane, and the resulting solution was freed from the solvent by distillation under reduced pressure. The resulting solid was then dissolved in a small amount of methylene chloride, and ethyl acetate was added to the solution, which was then allowed to stand at room temperature. The crystals which precipitated were collected by filtration and dried in vacuo, to give 0.755 g (yield 77%) of the title compound as colorless crystals, melting at 130°–131° C.

Nuclear Magnetic Resonance Spectrum (CDCl$_3$, 270 MHz), δ ppm: 1.9–2.1 (2H, multiplet); 2.1–2.35 (2H, multiplet); 2.35–2.55 (2H, multiplet); 2.70 (3H, singlet); 2.75–2.95 (5H, multiplet); 3.0–3.1 (1H, multiplet); 3.7–4.0

(2H, multiplet); 3.77 (6H, singlet); 3.81 (3H, singlet); 4.1–4.2 (1H, multiplet); 6.27 (2H, singlet); 6.83 (1H, doublet, J=8.6 Hz); 6.94 (1H, triplet, J=7.9 Hz); 7.1–7.25 (2H, multiplet).

EXAMPLE 74

(R)-2-[2-(2-Phenylethyl)phenoxymethyl]pyrrolidinne hydrochloride ps 74(a)
(R)-1-t-Butoxycarbonyl-2-[2-(2-phenylethyl) phenoxymethyl]pyrrolidine Following a procedure similar to that described in Example 40(a), 1.00 g of 2-(2-phenylethyl)phenol (prepared as described in Preparation 19), 2.89 g of 1-t-butoxycarbonyl-2-(p-toluenesulfonyloxymethyl)pyrrolidine and 0.906 g of potassium t-butoxide were reacted in 10 ml of dimethylacetamide. The mixture was then worked up as described in Example 40(a), and the crude product thus obtained was purified by column chromatography through silica gel, using a 4:1 by volume mixture of hexane and ethyl acetate as the eluent, to give 1.77 g (yield 92%) of the title compound as a colorless oil.

Nuclear Magnetic Resonance Spectrum (CDCl$_3$, 270 MHz), δ ppm: 1.47 (9H, singlet); 1.8–2.2 (4H, multiplet); 2.8–3.0 (4H, multiplet); 3.3–3.5 (2H, multiplet); 3.8–4.3 (3H, multiplet); 6.8–7.0 (2H, multiplet); 7.05–7.35 (7H, multiplet).

74(b) (R)-2-[2-(2-Phenylethyl)phenoxymethyl]pyrrolidine hydrochloride 5 ml of a 4N solution of hydrogen chloride in dioxane were added to a solution of 630 mg of (R)-1-t-butoxycarbonyl-2-[2-(2-phenylethyl)phenoxymethyl]pyrrolidine [prepared as described in step (a) above] in 5 ml of dioxane, and the resulting mixture was allowed to stand at room temperature for 1 hour. At the end of this time, the solvent was removed by distillation under reduced pressure, and the resulting oily residue was cooled, which resulted in its solidification. The solid was triturated in pentane, and the resulting powder was collected by filtration to give 360 mg (yield 68%) of the title compound as a colorless solid, melting 73°–88° C. [α]$_D^{25}$–7.5° (c=3.76, ethanol).

Nuclear Magnetic Resonance Spectrum (hexadeuterated dimethyl sulfoxide, 270 MHz) δ ppm: 1.75–2.1 (3H, multiplet); 2.1–2.25 (1H, multiplet); 2.8–3.0 (4H, multiplet); 3.15–3.3 (2H, multiplet); 3.9–4.05 (1H, multiplet); 4.1–4.3 (2H, multiplet); 6.89 (1H, triplet, J=6.9 Hz); 6.97 (1H, doublet, J=7.3 Hz); 7.1–7.35 (7H, multiplet).

EXAMPLE 75

(R)-1-Methyl-2-[2-(2-phenylethyl)phenoxymethyl] pyrrolidine hydrochloride

75(a) (R)-1-Methyl-2-[2-(2-phenylethyl)phenoxymethyl]pyrrolidine

Following a procedure similar to that described in Example 38(a), 1.14 g of (R)-1-t-butoxycarbonyl-2-[2-(2-phenylethyl)phenoxymethyl]pyrrolidine [prepared as described in Example 74(a)] were reacted with 0.227 g of lithium aluminum hydride dispersed in 10 ml of tetrahydrofuran. The mixture was then worked up as described in Example 38(a), and the crude product thus obtained was purified by column chromatography through silica gel, using a 10:1 by volume mixture of methylene chloride and methanol as the eluent, to give 0.670 g (yield 76%) of the title compound as a colorless oil.

Nuclear Magnetic Resonance Spectrum (CDCl$_3$, 270 MHz), δ ppm: 1.6–1.95 (3H, multiplet); 2.0–2.2 (1H, multiplet); 2.25–2.4 (1H, multiplet); 2.52 (3H, singlet); 2.65–2.8 (1H, multiplet); 2.8–3.0 (4H, multiplet); 3.05–3.2 (1H, multiplet); 3.84 (1H, doublet of doublets, J=6.6 & 9.2 Hz); 4.06 (1H, doublet of doublets, J=5.3 & 9.2 Hz); 6.8–6.9 (2H, multiplet); 7.1–7.35 (7H, multiplet). 75(b) (R)-1-Methyl-2-[2-(2-phenylethyl)phenoxymethyl]pyrrolidine hydrochloride 0.63 ml of a 4N solution of hydrogen chloride in dioxane was added to a solution of 670 mg of (R)-1-methyl-2-[2-(2-phenylethyl)phenoxymethyl]pyrrolidine [prepared as described in step (a) above] in a small amount of dioxane, and the resulting mixture was freed from the solvent by evaporation under reduced pressure. The resulting residue was then dissolved in a small amount of methanol, ethyl acetate was added to the solution, and the resulting mixture was allowed to stand at room temperature. The crystals which precipitated were collected by filtration and dried in vacuo, to give 596 mg (yield 85%) of the title compound as colorless crystals, melting at 211°–212° C. [α]$_D^{25}$–5.6° (c=3 42, methanol)

Nuclear Magnetic Resonance Spectrum (hexadeuterated dimethyl sulfoxide, 270 MHz) δ ppm: 1.8–2.2 (3H, multiplet); 2.2–2.4 (1H, multiplet); 2.8–3.0 (4H, multiplet); 2.94 (3H, singlet); 3.0–3.3 (1H, multiplet); 3.5–3.7 (1H, multiplet); 3.75–3.95 (1H, multiplet); 4.2–4.45 (2H, multiplet); 6.91 (1H, triplet, J=6.9 Hz); 6.99 (1H, doublet, J=7.9 Hz); 7.15–7.35 (7H, multiplet).

EXAMPLE 76

(R)-2-{2-[2-(3-Methoxyphenyl)ethyl] phenoxymethyl}pyrrolidine hydrochloride

76(a) (R)-1-t-Butoxycarbonyl-2-{2-[2-(3-methoxyphenyl) ethyl]phenoxymethyl}pyrrolidine Following a procedure similar to that described in Example 40(a), 1.00 g of 2-[2-(3-methoxyphenyl)ethyl] phenol (prepared as described in Preparation 20), 0.740 g of potassium t-butoxide and 2.33 g of (R)-1-t-butoxycarbonyl-2-(p-toluenesulfonyloxymethyl)pyrrolidine were reacted in 10 ml of dimethylacetamide. The mixture was then worked up as described in Example 40(a), and the crude product thus obtained was purified by column chromatography through silica gel, using a 4:1 by volume mixture of hexane and ethyl acetate as the eluent, to give 1.54 g (yield 85%) of the title compound as a colorless oil.

Nuclear Magnetic Resonance Spectrum (CDCl$_3$, 270 MHz), δ ppm: 1.47 (9H, singlet); 1.8–2.2 (4H, multiplet); 2.8–3.0 (4H, multiplet); 3.3–3.5 (2H, multiplet); 3.7–4.3 (3H, multiplet); 3.78 (3H, singlet); 6.7–7.0 (5H, multiplet); 7.05–7.3 (3H, multiplet).

76(b) (R)-2-{2-[2-(3-Methoxyphenyl)ethyl] phenoxymethyl}pyrrolidine hydrochloride 5 ml of a 4N solution of hydrogen chloride dioxane were added to a solution of 540 mg of (R)-1-t-butoxycarbonyl-2-{2-[2-(3-methoxyphenyl)ethyl] phenoxymethyl}pyrrolidine [prepared as described in step (a) above] in 5 ml of dioxane, and the resulting solution was allowed to stand at room temperature for 1 hour. At the end of this time, the solvent was removed by distillation under reduced pressure, and the resulting residue was dried in vacuo, to give 456 mg (a quantitative yield) of the title compound as a colorless oil.

[α]$_D^{25}$–5.5° (c=2.04, ethanol).

Nuclear Magnetic Resonance Spectrum (CDCl$_3$, 270 MHz), δ ppm: 1.75–2.2 (4H, multiplet); 2.8–3.1 (4H, multiplet); 3.30 (2H, triplet, J=6.6 Hz); 3.75 (3H, singlet); 3.85–4.0 (1H, multiplet); 4.11 (1H, doublet of doublets, J=4.6 & 9.9 Hz); 4.23 (1H, doublet of doublets, J=5.3 & 9.9 Hz); 6.65–6.75 (3H, multiplet); 6.85–6.95 (2H, multiplet); 7.05–7.3 (3H, multiplet).

EXAMPLE 77

(R)-2-{2-[2-(3-Methoxyphenyl)ethyl]phenoxymethyl}-1-methylpyrrolidine hydrochloride 77(a) (R)-2-{2-[2-(3-Methoxyphenyl)ethyl]phenoxymethyl}-1-methylpyrrolidine Following a procedure similar to that described in Example 38(a), 1.00 g of (R)-1-t-butoxycarbonyl-2-{2-[2-(3-methoxyphenyl)ethyl]phenoxymethyl}pyrrolidine [prepared as described in Example 76(a)] was reacted with 0.184 g of lithium aluminum hydride dispersed in 10 ml of tetrahydrofuran. The mixture was then worked up as described in Example 38(a), and the crude product thus obtained was purified by column chromatography through silica gel, using a 20:1 by volume mixture of methylene chloride and methanol as the eluent, to give 0.750 g (yield 95%) of the title compound as a colorless oil.

Nuclear Magnetic Resonance Spectrum (CDCl$_3$, 270 MHz), δ ppm: 1.6–1.95 (3H, multiplet); 2.0–2.2 (1H, multiplet); 2.25–2.4 (1H, multiplet); 2.52 (3H, singlet); 2.65–2.8 (1H, multiplet); 2.8–3.0 (4H, multiplet); 3.05–3.2 (1H, multiplet); 3.79 (3H, singlet); 3.84 (1H, doublet of doublets, J=6.6 & 9.2 Hz); 4.06 (1H, doublet of doublets, J=5.9 & 9.2 Hz); 6.7–6.95 (5H, multiplet); 7.1–7.3 (3H, multiplet).

77(b) (R)-2-{2-[2-(3-Methoxyphenyl)ethyl]phenoxymethyl}-1-methylpyrrolidine hydrochloride 0.7 ml of a 4N solution of hydrogen chloride in dioxane was added to a solution of 750 mg of (R)-2-{2-[2-(3-methoxyphenyl)ethyl]phenoxymethyl}-1-methylpyrrolidine [prepared as described in step (a) above] in a suitable amount of dioxane, and the resulting mixture was concentrated by evaporation under reduced pressure. The resulting oily residue was dissolved in 10 ml of ethyl acetate, and the solution was allowed to stand at room temperature. The crystals which precipitated were collected by filtration and dried in vacuo, to give 686 mg (yield 82%) of the title compound as a colorless powder, melting at 124°–125° C. [α]$_D^{25}$ –4.2° (c=3.45 ethanol).

Nuclear Magnetic Resonance Spectrum (hexadeuterated dimethyl sulfoxide, 270 MHz) δ ppm: 1.75–2.2 (3H, multiplet); 2.2–2.4 (1H, multiplet); 2.75–3.0 (4H, multiplet); 2.94 (3H, singlet); 3.0–3.2 (1H, multiplet); 3.5–3.7 (1H, multiplet); 3.72 (3H, multiplet); 3.75–3.95 (1H, multiplet); 4.2–4.45 (2H, multiplet); 6.7–6.85 (3H, multiplet); 6.92 (1H, triplet, J=7.3 Hz); 7.00 (1H, doublet, J=7.9 Hz); 7.15–7.3 (3H, multiplet).

EXAMPLE 78

2-(2-{2-[4-(3-Methoxyphenyl)butyl]phenoxy}ethyl)-1-methylpyrrolidine hydrochloride 78(a) 2-(2-{2-[4-(3-Methoxyphenyl)butyl]phenoxy}ethyl)-1-methylpyrrolidine 1.48 g of potassium t-butoxide were added to a solution of 1.35 g of 2-[4-(3-methoxyphenyl)butyl]phenol (prepared as described in Preparation 7) in 20 ml of dimethylacetamide, whilst ice-cooling and stirring. 1.45 g of 2-(2-chloroethyl)-1-methylpyrrolidine hydrochoride were then added to the solution, and the mixture was stirred at 55° C. for 2 hours. At the end of this time, the reaction mixture was cooled, 200 ml of ethyl acetate and 100 ml of water were added to the mixture, and the mixture was shaken. The ethyl acetate layer was separated, washed with a saturated aqueous solution of sodium chloride and dried over anhydrous magnesium sulfate. The ethyl acetate layer was then concentrated by distillation under reduced pressure, and the resulting residue was purified by column chromatography through silica gel, using a 10:1 by volume mixture of methylene chloride and methanol as the eluent, to give 0.92 g (yield 48%) of the title compound as an oil.

Nuclear Magnetic Resonance Spectrum (CDCl$_3$, 270 MHz), δ ppm: 1.55–2.5 (12H, multiplet); 2.38 (3H, singlet); 2.55–2.7 (4H, multiplet); 3.05–3.2 (1H, multiplet); 3.79 (3H, singlet); 3.9–4.15 (2H, multiplet); 6.65–6.9 (5H, multiplet); 7.1–7.25 (3H, multiplet).

78(b) 2-(2-{2-[4-(3-Methoxyphenyl)butyl]phenoxy]ethyl)-1-methylpyrrolidine hydrochloride 900 mg of 2-(2-{2-[4-(3-methoxyphenyl)butyl]phenoxy}ethyl)-1-methylpyrrolidine [prepared as described in step (a) above] were dissolved in a small amount of dioxane, and 0.8 ml of a 4N solution of hydrogen chloride in dioxane was added to the resulting solution. The solution was then shaken, after which it was concentrated by distillation under reduced pressure. The concentrate was dissolved in 15 ml of ethyl acetate, and the resulting solution was allowed to stand at room temperature. The crystals which precipitated were collected by filtration and dried in vacuo, to give 343 mg (yield 35%) of the title compound as colorless crystals, melting at 65°–66° C.

Nuclear Magnetic Resonance Spectrum (CDCl$_3$, 270 MHz), δ ppm: 1.5–1.8 (4H, multiplet); 1.85–2.15 (2H, multiplet); 2.15–2.35 (2H, multiplet); 2.35–2.9 (7H, multiplet); 2.74 (3H, singlet); 3.2–3.35 (1H, multiplet); 3.7–4.1 (2H, multiplet); 3.79 (3H, singlet); 4.1–4.3 (1H, multiplet); 6.65–6.8 (3H, multiplet); 6.82 (1H, doublet, J=8.6 Hz); 6.91 (1H, triplet, J=7.6 Hz); 7.1–7.3 (3H, multiplet).

EXAMPLE 79

2-(2-{2-[4-(2-Methoxyphenyl)butyl]phenoxy}ethyl)-1-methylpyrrolidine hydrochloride 79(a) 2-(2-{2-[4-(2-Methoxyphenyl)butyl]phenoxy}ethyl)-1-methylpyrrolidine Following a procedure similar to that described in Example 78(a), 900 mg (yield 36%) of the title compound were obtained as a colorless oil by using 1.74 g of 2-[4-(2-methoxyphenyl)butyl]phenol (prepared as described in Preparation 4), 1.9 g of potassium t-butoxide, 1.87 g of 2-(2-chloroethyl)-1-methylpyrrolidine hydrochloride and 20 ml of dimethylacetamide.

Nuclear Magnetic Resonance Spectrum (CDCl$_3$, 270 MHz), δ ppm: 1.5–1.9 (8H, multiplet); 1.95–2.1 (1H, multiplet); 2.15–2.5 (3H, multiplet); 2.38 (3H, singlet); 2.55–2.7 (4H, multiplet); 3.1–3.2 (1H, multiplet); 3.79 (3H, singlet); 3.9–4.1 (2H, multiplet); 6.75–6.9 (4H, multiplet); 7.1–7.2 (4H, multiplet).

79(b) 2-(2-{2-[4-(2-Methoxyphenyl)butyl]phenoxy}ethyl)-1-methylpyrrolidine hydrochloride Following a procedure similar to that described in Example 78(b), followed by additional recrystallization from ethyl acetate, 530 mg (yield 54%) of the title compound were obtained as a colorless solid, melting at 111°–112° C., by using 900 mg of 2-(2-{2-[4-(2-methoxyphenyl)butyl]phenoxy}ethyl)-1-methylpyrrolidine [prepared as described in step (a) above] and 0.8 ml of a 4N solution of hydrogen chloride in dioxane.

Nuclear Magnetic Resonance Spectrum (CDCl$_3$, 270 MHz), δ ppm: 1.5–1.8 (4H, multiplet); 1.9–2.15 (2H, multiplet); 2.15–2.4 (2H, multiplet); 2.4–2.9 (7H, multiplet); 2.75 (3H, singlet); 3.25–3.5 (1H, multiplet); 3.7–4.05 (2H, multiplet); 3.80 (3H, singlet); 4.15–4.3 (1H, multiplet); 6.8–7.0 (4H, multiplet); 7.05–7.25 (4H, multiplet).

EXAMPLE 80

2-(2-{2-[4-(4-Methoxyphenyl)butyl]phenoxy}ethyl)-1-methylpyrrolidine hydrochloride 80(a)  2-(2-{2-[4-(4-Methoxyphenyl)butyl]phenoxy}ethyl)-1-methylpyrrolidine Following a procedure similar to that described in Example 78(a), 0.830 g (yield 39%) of the title compound was obtained as an oil by using 1.50 g of 2-[4-(4-methoxyphenyl) butyl]phenol (prepared as described in Preparation 12), 1.64 g of potassium t-butoxide, 1.62 g of 2-(2-chloroethyl)-1-methylpyrrolidine hydrochloride and 30 ml of dimethylacetamide.

Nuclear Magnetic Resonance Spectrum (CDCl$_3$, 270 MHz), δ ppm: 1.5–1.95 (8H, multiplet); 1.95–2.15 (1H, multiplet); 2.15–2.5 (3H, multiplet); 2.40 (3H, singlet); 2.5–2.7 (4H, multiplet); 3.1–3.25 (1H, multiplet); 3.78 (3H, singlet); 3.9–4.1 (2H, multiplet); 6.75–6.9 (4H, multiplet); 7.05–7.2 (4H, multiplet).

80(b) 2-(2-{2-[4-(4-Methoxyphenyl)butyl]phenoxy}ethyl)-1-methylpyrrolidine hydrochloride Following a procedure similar to that described in Example 78(b), followed by additional recrystallization from ethyl acetate, 0.275 g (yield 30%) of the title compound were obtained as a colorless solid, melting 91°–92° C., by using 0.830 g of 2-(2-{2-[4-(4-methoxyphenyl)butyl]phenoxy}ethyl)-1-methylpyrrolidine and 0.75 ml of a 4N solution of hydrogen chloride in dioxane.

Nuclear Magnetic Resonance Spectrum (CDCl$_3$, 270 MHz), δ ppm: 1.5–1.75 (4H, multiplet); 1.9–2.15 (2H, multiplet); 2.15–2.4 (2H, multiplet); 2.4–2.7 (6H, multiplet); 2.7–2.9 (1H, multiplet); 2.73 & 2.75 (together 3H, each singlet); 3.2–3.35 (1H, multiplet); 3.78 (3H, singlet); 3.8–4.1 (2H, multiplet); 4.15–4.3 (1H, multiplet); 6.75–6.9 (3H, multiplet); 6.91 (1H, triplet, J=7.6 Hz); 7.0–7.2 (4H, multiplet).

EXAMPLE 81

2-(2-{2-[4-(3,5-Dimethoxyphenyl)butyl]phenoxy}ethyl)-1-methylpyrrolidine hydrochloride 81(a)  2-(2-{2-[4-(3,5-Dimethoxyphenyl)butyl]phenoxy}ethyl)-1- methylpyrrolidine Following a procedure similar to that described in Example 78(a), 1.00 g (yield 40%) of the title compound was obtained as an oil by using 1.80 g of 2-[4-(3,5-dimethoxyphenyl)butyl]phenol (prepared as described in Preparation 9), 1.76 g of potassium t-butoxide, 1.76 g of 2-(2-chloroethyl)-1-methylpyrrolidine hydrochloride and 35 ml of dimethylacetamide.

Nuclear Magnetic Resonance Spectrum (CDCl$_3$, 270 MHz), δ ppm: 1.5–2.5 (12H, multiplet); 2.38 (3H, singlet); 2.5–2.7 (4H, multiplet); 3.1–3.2 (1H, multiplet); 3.77 (6H, singlet); 3.9–4.1 (2H, multiplet); 6.25–6.4 (3H, multiplet); 6.75–6.9 (2H, multiplet); 7.1–7.2 (2H, multiplet).

81(b) 2-(2-{2-[4-(3,5-Dimethoxyphenyl)butyl]phenoxy}ethyl)-1-methylpyrrolidine hydrochloride 1.00 g of 2-(2-{2-[4-(3,5-dimethoxyphenyl)butyl]phenoxy}ethyl)-1-methylpyrrolidine [prepared as described in step (a) above] was dissolved in 10 ml of dioxane, and 0.8 ml of a 4N solution of hydrogen chloride in dioxane was added to the resulting solution. The mixture was stirred and then concentrated by evaporation under reduced pressure. A suitable amount of pentane was added to the concentrate and the mixture was agitated. The upper pentane layer was removed and the resulting oil was dried in vacuo, to give 1.09 g (a quantitative yield) of the title compound, as an oil.

Nuclear Magnetic Resonance Spectrum (CDCl$_3$, 270 MHz), δ ppm: 1.55–1.7 (4H, multiplet); 1.85–2.9 (11H, multiplet); 2.75 & 2.77 (together 3H, each singlet); 3.2–3.4 (1H, multiplet); 3.76 (6H, singlet); 3.8–4.1 (2H, multiplet); 4.15–4.3 (1H, multiplet); 6.30 (3H, singlet); 6.82 (1H, doublet, J=8.6 Hz); 6.91 (1H, triplet, J=7.9 Hz); 7.1–7.25 (2H, multiplet).

Infrared Absorption Spectrum (liquid film), ν$_{max}$ cm$^{-1}$: 1596, 1456, 1239, 1205, 1151.

EXAMPLE 82

3-{2-[4-(3-Methoxyphenyl)butyl]phenoxymethyl}piperidine hydrochloride

82(a) 1-t-Butoxycarbonyl-3-{2-[4-(3-methoxyphenyl)butyl]phenoxymethyl}piperidine 0.965 g of potassium t-butoxide was added to a solution of 1.70 g of 2-[4-(3-methoxyphenyl)butyl]phenol (prepared as described in Preparation 7) in 30 ml of dimethylacetamide, whilst ice-cooling, and the mixture was stirred at the same temperature for 15 minutes. A solution of 3.18 g of 1-t-butoxycarbonyl-3-(p-toluenesulfonyloxymethyl)piperidine in 30 ml of dimethylacetamide was then added dropwise to the solution at the same temperature, and the mixture was stirred at 55° C. for 1.5 hours. At the end of this time, the reaction mixture was cooled, and 200 ml of ethyl acetate and 100 ml of water were added to the mixture, which was then shaken. The ethyl acetate layer was separated, washed twice with a saturated aqueous solution of sodium chloride and dried over anhydrous magnesium sulfate. The ethyl acetate layer was then concentrated by distillation under reduced pressure, and the concentrate was purified by column chromatography through silica gel, using a 3:1 by volume mixture of hexane and ethyl acetate as the eluent, to give 4.54 g (yield 95%) of the title compound as a colorless oil.

Nuclear Magnetic Resonance Spectrum (CDCl$_3$, 270 MHz), δ ppm: 1.3–2.1 (9H, multiplet); 1.45 (9H, singlet); 2.55–2.9 (6H, multiplet); 3.7–4.2 (4H, multiplet); 3.78 (3H, singlet); 6.7–6.9 (5H, multiplet); 7.1–7.25 (3H, multiplet).

82(b) 3-{2-[4-(3-Methoxyphenyl)butyl]phenoxymethyl}piperidine hydrochloride 1.79 g of 1-t-butoxycarbonyl-3-{2-[4-(3-methoxyphenyl)butyl]phenoxymethyl}piperidine [prepared as described in step (a) above] were dissolved in 5 ml of dioxane and 5 ml of a 4N solution of hydrogen chloride in dioxane were added to the solution. The mixture was allowed to stand at room temperature for 2 hours, after which the solvent was removed by distillation under reduced pressure. The resulting residue was dissolved in 20 ml of ethyl acetate, and the solution was allowed to stand at room temperature. The crystals which precipitated were collected by filtration and dried in vacuo, to give 1.31 g (yield 85%) of the title compound as needles, melting at 136°–137° C.

Nuclear Magnetic Resonance Spectrum (CDCl$_3$, 270 MHz), δ ppm: 1.3–2.2 (9H, multiplet); 2.4–2.95 (6H, multiplet); 3.4–3.6 (2H, multiplet); 3.75–4.0 (2H, multiplet); 3.78 (3H, singlet); 6.65–6.85 (4H, multiplet); 6.89 (1H, doublet, J=7.3 Hz); 7.1–7.25 (3H, multiplet).

EXAMPLE 83

3-{2-[4-(3-Methoxyphenyl)butyl]phenoxymethyl}-1-methylpiperidine hydrochloride

83(a) 3-{2-[4-(3-Methoxyphenyl)butyl]phenoxymethyl}-1-methylpiperidine

A solution of 2.70 g of 1-t-butoxycarbonyl-3-{2-[4-(3-methoxyphenyl)butyl]phenoxymethyl}piperidine [prepared as described in Example 82(a)] in 25 ml of tetrahydrofuran was added dropwise to a mixture of 0.450 g of lithium aluminum hydride in 30 ml of tetrahydrofuran, whilst ice-cooling and stirring, and the mixture was stirred at room temperature for 30 minutes and then stirred whilst heating under reflux for 2 hours. At the end of this time, the reaction mixture was cooled, and sodium sulfate decahydrate was added to the mixture to decompose excess lithium aluminium hydride. Insoluble materials were removed by filtration, and the filtrate was concentrated by distillation under reduced pressure. The resulting oil was purified by column chromatography through silica gel, using a 10:1 by volume mixture of methylene chloride and methanol as the eluent, to give 2.10 g (yield 96%) of the title compound as a colorless oil.

Nuclear Magnetic Resonance Spectrum (CDCl$_3$, 270 MHz), δ ppm: 1.5–2.3 (11H, multiplet); 2.30 (3H, singlet); 2.55–2.7 (4H, multiplet); 2.82 (1H, doublet, J=10.6 Hz); 2.9–3.1 (1H, multiplet); 3.79 (3H, singlet); 3.7–3.9 (2H, multiplet); 6.7–6.8 (4H, multiplet); 6.85 (1H, triplet, J=7.3 Hz); 7.1–7.25 (3H, multiplet).

83(b) 3-{2-[4-(3-Methoxyphenyl)butyl]phenoxymethyl}-1-methylpiperidine hydrochloride 2.10 g of 3-{2-[4-(3-methoxyphenyl)butyl]phenoxymethyl}-1-methylpiperidine [prepared as described in step (a) above] were dissolved in 10 ml of dioxane, and 1.7 ml of a 4N solution of hydrogen chloride in dioxane was added to the solution, which was shaken and then concentrated by distillation under reduced pressure to give a solid. The solid was dissolved in a small amount of methanol, and then 50 ml of ethyl acetate were added to the solution. The resulting mixture was then allowed to stand at room temperature. The crystals which precipitated were collected by filtration and dried in vacuo, to give 1.92 g (yield 83%) of the title compound as colorless needles, melting at 141°–142.5° C.

Nuclear Magnetic Resonance Spectrum (CDCl$_3$, 270 MHz), δ ppm: 1.3–2.1 (7H, multiplet); 2.2–3.0 (4H, multiplet); 2.62 (4H, triplet, J=6.6 Hz); 2.74 (3H, singlet); 3.35–3.6 (2H, multiplet); 3.78 (3H, singlet); 3.8–4.0 (2H, multiplet); 6.7–6.85 (4H, multiplet); 6.91 (1H, triplet, J=6.9 Hz); 7.1–7.25 (3H, multiplet).

EXAMPLE 84

2-(2-{2-[4-(3-Methoxyphenyl)butyl]phenoxy}ethyl) piperidine hydrochloride

84(a) 1-t-Butoxycarbonyl-2-(2-{2-[4-(3-methoxyphenyl) butyl]phenoxy}ethyl) piperidine Following a procedure similar to that described in Example 82(a) except that a 5:1 by volume mixture of hexane and ethyl acetate was used as the eluent, 1.99 g (yield 87%) of the title compound were obtained as an oil by using 1.20 g of 2-[4-(3-methoxyphenyl)butyl]phenol (prepared as described in Preparation 7), 0.68 g of potassium t-butoxide, 2.34 g of 1-t-butoxycarbonyl-2-[2-(p-toluenesulfonyloxy)ethyl]piperidine and 20 ml of dimethylacetamide.

Nuclear Magnetic Resonance Spectrum (CDCl$_3$, 270 MHz), δ ppm: 1.3–1.8 (10H, multiplet); 1.39 (9H, singlet); 1.8–2.0 (1H, multiplet); 2.1–2.3 (1H, multiplet); 2.5–2.7 (4H, multiplet); 2.7–2.95 (1H, multiplet); 3.79 (3H, singlet); 3.8–4.1 (3H, multiplet); 4.35–4.55 (1H, multiplet); 6.7–6.9 (5H, multiplet); 7.05–7.25 (3H, multiplet).

84(b) 2-(2-{2-[4-(3-Methoxyphenyl)butyl]phenoxy}ethyl) piperidine hydrochloride 400 mg of 1-t-butoxycarbonyl-2-(2-{2-[4-(3-methoxyphenyl)butyl]phenoxy}ethyl)piperidine [prepared as described in step (a) above] were dissolved in 2 ml of dioxane, and 2 ml of a 4N solution of hydrogen chloride in dioxane were added to the solution, which was then allowed to stand at room temperature for 30 minutes. At the end of this time, the solution was concentrated by distillation under reduced pressure, and the resulting oil was dissolved in diethyl ether and allowed to stand at room temperature. The crystals which precipitated were collected by filtration and dried in vacuo, to give 276 mg (yield 80%) of the title compound as a colorless solid, melting at 76°–79° C.

Nuclear Magnetic Resonance Spectrum (CDCl$_3$, 270 MHz), δ ppm: 1.2–2.1 (9H, multiplet); 2.1–3.0 (7H, multiplet); 3.1–3.3 (1H, multiplet); 3.35–3.6 (1H, multiplet); 3.77 (3H, singlet ); 3.8–4.2 (3H, multiplet); 6.55–6.9 (5H, multiplet); 7.05–7.3 (3H, multiplet).

EXAMPLE 85

2-(2-{2-[4-(3-Methoxyphenyl)butyl]phenoxy}ethyl)-1-methylpiperidine citrate

85(a) 2-(2-{2-[4-(3-Methoxyphenyl)butyl]phenoxy}ethyl)-1-methylpiperidine

Following a procedure similar to that described in Example 83(a), 1.10 g (yield 89%) of the title compound were obtained as an oil by using 1.50 g of 1-t-butoxycarbonyl-2-(2-{2-[4-(3-methoxyphenyl)butyl]phenoxy}ethyl) piperidine [prepared as described in Example 84(a)], 0.245 g of lithium aluminum hydride and 30 m l of tetrahydrofuran.

Nuclear Magnetic Resonance Spectrum (CDCl$_3$, 270 MHz), δ ppm: 1.2–2.3 (14H, multiplet); 2.35 (3H, singlet); 2.55–2.7 (4H, multiplet); 2.85–3.0 (1H, multiplet); 3.79 (3H, singlet); 3.9–4.1 (2H, multiplet); 6.65–6.9 (5H, multiplet); 7.05–7.25 (3H, multiplet).

85(b) 2-(2-{2-[4-(3-Methoxyphenyl)butyl]phenoxy}ethyl)-1-methylpiperidine citrate 1.05 g of 2-(2-{2-[4-(3-methoxyphenyl)butyl]phenoxy}ethyl)-1-methylpiperidine [prepared as described in step (a) above]and 0.58 g of citric acid monohydrate were dissolved in 10 ml of ethanol, and the resulting solution was concentrated by evaporation under reduced pressure. The resulting oil was dissolved in 20 ml of ethyl acetate, and the solution was allowed to stand at room temperature. The crystals which precipitated were collected by filtration and dried in vacuo, to give 1.20 g (yield 76%) of the title compound as a colorless solid, melting at 77°–79° C.

Nuclear Magnetic Resonance Spectrum (hexadeuterated dimethyl sulfoxide, 270 MHz), δ ppm: 1.2–2.3 (12H, multiplet); 2.5–3.7 (11H, multiplet); 2.69 (3H, singlet); 3.71 (3H, singlet); 3.9–4.1 (2H, multiplet); 6.7–6.8 (3H, multiplet); 6.86 (1H, triplet, J=7.3 Hz); 6.92 (1H, doublet, J=7.9 Hz); 7.1–7.3 (3H, multiplet).

EXAMPLE 86

N,N-Dimethyl-3-[2-(3-phenylpropyl)phenoxy] propylamine hydrochloride

86(a) N,N-Dimethyl-3-[2-(3-phenylpropyl)phenoxy]propylamine 134 mg of 3-(N,N-dimethylamino)propanol and 342 mg of triphenyl phosphine were added to a solution of 230 mg of 2-(3-phenylpropyl)phenol (prepared as described in Preparation 29) in 10 ml of methylene chloride, and the mixture was cooled with ice and stirred. 227 mg of diethyl azodicarboxylate were then added dropwise to the solution, and the mixture was stirred at room temperature for 5 hours. At the end of this time, the solvent was removed by distillation under reduced pressure, and ethyl acetate and water were added to the residue and shaken. The ethyl acetate layer was separated and dried over anhydrous magnesium sulfate. The solvent was then removed by distillation under reduced pressure, and the resulting residue was purified by column chromatography through silica gel, using a 10:1 by volume mixture of methylene chloride and methanol as the eluent, to give 115 mg (yield 36%) of the title compound as a colorless oil.

Nuclear Magnetic Resonance Spectrum (60 MHz, CDCl$_3$), δ ppm: 1.6–3.0 (10H, multiplet); 2.23 (6H, singlet); 4.00 (2H, triplet, J=6 Hz); 6.7–7.4 (9H, multiplet).

86(b) N,N-Dimethyl-3-[2-(3-phenylpropyl)phenoxy]propylamine hydrochloride 100 mg of N,N-dimethyl-3-[2-(3-phenylpropyl)phenoxy] propylamine were dissolved in 2 ml of dioxane, and 0.1 ml of a 4N solution of hydrogen chloride in dioxane was added to the solution. The mixture was then concentrated by distillation under reduced pressure, and the resulting oil was dissolved in a small amount of ethyl acetate and allowed to stand at room temperature. The crystals which precipitated were collected by filtration and dried in vacuo, to give 53.9 mg (yield 48%) of the title compound as needles, melting at 147°–149° C.

Nuclear Magnetic Resonance Spectrum (CDCl$_3$, 270 MHz), δ ppm: 1.8–2.0 (2H, multiplet); 2.3–2.45 (2H, multiplet); 2.6–2.8 (4H, multiplet); 2.76 (6H, singlet); 3.0–3.2 (2H, multiplet); 4.06 (2H, triplet, J=5.6 Hz); 6.80 (1H, doublet, J=7.9 Hz); 6.92 (1H, triplet, J=7.3 Hz); 7.1–7.35 (7H, multiplet).

EXAMPLE 87

3-(N,N-Dimethylamino)-1-[2-(3-phenylpropyl) phenoxy]-2-propanol hydrochloride

87(a) 2-[2-(3-Phenylpropyl)phenoxymethyl]oxirane

Following a procedure similar to that described in Example 26(a), except that a 10:1 by volume mixture of hexane and ethyl acetate was used as the eluent, 0.450 g (yield 34%) of the title compound was obtained as a colorless oil by using 1.05 g of 2-(3-phenylpropyl)phenol (prepared as described in Preparation 29), 0.44 g of glycidol, 1.56 g of triphenyl phosphine, 20 ml of methylene chloride and 1.03 g of diethyl azodicarboxylate.

Nuclear Magnetic Resonance Spectrum (CDCl$_3$, 270 MHz), δ ppm: 1.85–2.05 (2H, multiplet); 2.6–3.0 (6H, multiplet); 3.3–3.45 (1H, multiplet); 3.98 (1H, doublet of doublets, J=5.3 & 11.2 Hz); 4.15–4.3 (1H, multiplet); 6.82 (1H, doublet, J=8.6 Hz); 6.90 (1H, triplet, J=7.3 Hz); 7.1–7.3 (7H, multiplet).

87(b) 3-(N,N-Dimethylamino)-1-[2-(3-phenylpropyl)phenoxy]-2-propanol 3 ml of 50% by volume aqueous dimethylamine were added to a solution of 0.45 g of 2-[2-(3-phenylpropyl)phenoxymethyl]oxirane [prepared as described in step (a) above] in 10 ml of tetrahydrofuran, and the mixture was stirred at room temperature for one day. At the end of this time, the solvent was removed by distillation under reduced pressure, and the resulting residue was purified by column chromatography through silica gel, using a 20:1 by volume mixture of methylene chloride and methanol as the eluent, to give 0.31 g (yield 59%) of the title compound as a colorless oil.

Nuclear Magnetic Resonance Spectrum (CDCl$_3$, 270 MHz), δ ppm: 1.85–2.0 (2H, multiplet); 2.32 (6H, singlet); 2.41 (1H, doublet of doublets, J=4.0 & 12.5 Hz); 2.54 (1H, doublet of doublets, J=9.2 & 12.5 Hz); 2.6.7 (4H, triplet, J=7.6 Hz); 3.9–4.1 (3H, multiplet); 6.8–6.95 (2H, multiplet); 7.1–7.35 (7H, multiplet).

87(c) 3-(N,N-Dimethylamino)-1-[2-(3-phenylpropyl)phenoxy]-2-propanol hydrochloride 0.30 g of 3-(N,N-dimethylamino)-1-[2-(3-phenylpropyl)phenoxy]-2-propanol [prepared as described in step (b) above] was dissolved in a small amount of ethyl acetate, and 0.48 ml of a 4N solution of hydrogen chloride in dioxane was added to the solution, which was then concentrated by distillation under reduced pressure. Pentane was added to the resulting concentrate, and the mixture was shaken and then concentrated by distillation under reduced pressure. This operation was repeated twice and the resulting oil was then dried in vacuo, to give 0.41 g (a quantitative yield) of the title compound as a colorless oil.

Nuclear Magnetic Resonance Spectrum (CDCl$_3$, 270 MHz), δ ppm: 1.8–2.0 (2H, multiplet); 2.55–2.75 (4H, multiplet); 2.86 (6H, singlet); 3.1–3.3 (2H, multiplet); 3.92 (1H, doublet of doublets, J=7.8 & 9.3 Hz); 4.14 (1H, doublet of doublets, 4.4 & 9.3 Hz); 4.45–4.6 (1H, multiplet); 6.82 (1H, doublet, J=7.8 Hz); 6.93 (1H, triplet, J=7.3 Hz); 7.1–7.35 (5H, multiplet).

Infrared Absorption Spectrum (CHCl$_3$), $v_{max}$ cm$^{-1}$: 1660, 1585, 1495, 1470, 1450, 1235, 1050.

EXAMPLE 88

3-(N,N-Dimethylamino)-1-[2-(5-phenylpentyl) phenoxy]-2-propanol hydrochloride

88(a) 2-[2-(5-Phenylpentyl)phenoxymethyl]oxirane

Following a procedure similar to that described in Example 26(a), except that a 5:1 by volume mixture of hexane and ethyl acetate was used as the eluent, 0.484 g (yield 49%) of the title compound was obtained as a colorless oil by using 0.800 g of 2-(5-phenylpentyl)phenol (prepared as described in Preparation 31), 0.370 g of glycidol, 1.31 g of triphenylphosphine, 12 ml of methylene chloride and 0.874 g of diethyl azodicarboxylate.

Nuclear Magnetic Resonance Spectrum (CDCl$_3$, 270 MHz), δ ppm: 1.3–1.8 (6H, multiplet); 2.55–2.7 (4H, multiplet); 2.76 (1H, doublet of doublets, J=2.6 & 5.3 Hz); 2.88 (1H, doublet of doublets, J=4.0 & 5.3 Hz); 3.3–3.4 (1H, multiplet); 3.98 (1H, doublet of doublets, J=5.3 & 11.2 Hz); 4.21 (1H, doublet of doublets, J=2.6 & 11.2 Hz); 6.81 (1H, doublet, J=7.9 Hz); 6.90 (1H, triplet, J=7.9 Hz); 7.1–7.35 (7H, multiplet).

88(b) 3-(N,N-Dimethylamino)-1-[2-(5-phenylpentyl)phenoxy]-2-propanol 0.7 ml of 50% by volume aqueous dimethylamine was added to a solution of 0.208 g of 2-[2-(5-phenylpentyl)phenoxymethyl]oxirane [prepared as described in step (a) above] in 9 ml of tetrahydrofuran, and the mixture was stirred at room temperature for one day. At the end of this time, the solvent was removed by distillation under reduced pressure, and the resulting residue was purified by column chromatography through silica gel, using a 20:1 by volume mixture of methylene chloride and methanol as the eluent, to give 0.230 g (yield 96%) of the title compound as a colorless oil.

Nuclear Magnetic Resonance Spectrum (CDCl$_3$, 270 MHz), δ ppm: 1.35–1.5 (2H, multiplet); 1.55–1.75 (4H, multiplet); 2.31 (6H, singlet); 2.43 (1H, doublet of doublets, J=4.0 & 12.6 Hz); 2.5–2.7 (5H, multiplet); 3.9–4.15 (3H, multiplet); 6.8–6.95 (2H, multiplet); 7.1–7.4 (7H, multiplet).

88(c) 3-(N,N-Dimethylamino)-1-[2-(5-phenylpentyl)phenoxy]-2-propanol hydrochloride 0.225 g of 3-(N,N-dimethylamino)-1-[2-(5-phenylpentyl)phenoxy]-2-propanol [prepared as described in step (b) above] was dissolved in a small amount of ethyl acetate, and 0.25 ml of a 4N solution of hydrogen chloride in dioxane was added to the solution. The mixture was then concentrated by distillation under reduced pressure. Pentane was added to the resulting concentrate, and the mixture was shaken and then the upper pentane layer was removed. The operation was repeated twice and the resulting oil was dried in vacuo, to give 0.235 g (yield 94%) of the title compound as a colorless oil.

Nuclear Magnetic Resonance Spectrum (CDCl$_3$, 270 MHz), δ ppm: 1.3–1.5 (2H, multiplet); 1.5–1.7 (4H, multiplet); 2.5–2.65 (4H, multiplet); 2.89 (6H, singlet); 3.15–3.4 (2H, multiplet); 3.92 (1H, doublet of doublets, J=7.9 & 9.2 Hz); 4.16 (1H, doublet of doublets, J=4.6 & 9.2 Hz); 4.5–4.65 (1H, multiplet); 6.82 (1H, doublet, J=7.9 Hz); 6.90 (1H, triplet, J=7.6 Hz); 7.1–7.4 (7H, multiplet).

Infrared Absorption Spectrum (CHCl$_3$), ν$_{max}$ cm$^{-1}$: 1600, 1585, 1490, 1470, 1450, 1235, 1110, 1040.

EXAMPLE 89

3-(N,N-Dimethylamino)-1-[2-(6-phenylhexyl)phenoxy]-2-propanol hydrochloride

89(a) 2-[2-(6-Phenylhexyl)phenoxymethyl]oxirane

Following a procedure similar to that described in Example 26(a), except that a 5:1 by volume mixture of hexane and ethyl acetate was used as the eluent, 1.58 g (yield 43%) of the title compound were obtained as a colorless oil by using 3.00 g of 2-(6-phenylhexyl)phenol (prepared as described in preparation 32), 1.31 g of glycidol, 4.64 g of triphenylphosphine, 30 ml of methylene chloride and 4.65 g of diethyl azodicarboxylate.

Nuclear Magnetic Resonance Spectrum (CDCl$_3$, 270 MHz), δ ppm: 1.3–1.7 (8H, multiplet); 2.5–2.7 (4H, multiplet); 2.7–2.8 (1H, multiplet); 2.85–2.95 (1H, multiplet); 3.3–3.4 (1H, multiplet); 3.98 (1H, doublet of doublets, J=5.3 & 11.2 Hz); 4.21 (1H, doublet of doublets, J=3.3 & 11.2 Hz); 6.81 (1H, doublet, J=7.9 Hz); 6.90 (1H, triplet, J=7.3 Hz); 7.1–7.3 (7H, multiplet).

89(b) 3-(N,N-Dimethylamino)-1-[2-(6-phenylhexyl)phenoxy]-2-propanol 0.7 ml of 50% by volume aqueous dimethylamine were added to a solution of 0.200 g of 2-[2-(6-phenylhexyl)phenoxymethyl]oxirane [prepared as described in step (a) above] in 7 ml of tetrahydrofuran, and the mixture was stirred at room temperature for one day. At the end of this time, the solvent was removed by distillation under reduced pressure, and the resulting residue was purified by column chromatography through silica gel, using a 15:1 by volume mixture of methylene chloride and methanol as the eluent, to give 0.227 g (yield 99%) of the title compound as a colorless oil.

Nuclear Magnetic Resonance Spectrum (CDCl$_3$, 270 MHz), δ ppm: 1.2–1.7 (8H, multiplet); 2.32 (6H, singlet); 2.44 (1H, doublet of doublets, J=3.6 & 12.2 Hz); 2.5–2.7 (5H, multiplet); 3.9–4.15 (3H, multiplet); 6.8–6.95 (2H, multiplet); 7.1–7.35 (7H, multiplet).

89(c) 3-(N,N-Dimethylamino)-1-[2-(6-phenylhexyl)phenoxy]-2-propanol hydrochloride 0.226 g of 3-(N,N-dimethylamino)-1-[2-(6-phenylhexyl)phenoxy]-2-propanol [prepared as described in step (b) above] was dissolved in a small amount of ethyl acetate, and 0.25 ml of a 4N solution of hydrogen chloride in dioxane was added to the solution. The resulting mixture was then concentrated by distillation under reduced pressure. Pentane was added to the resulting concentrate, and the mixture was shaken and then concentrated by distillation under reduced pressure. This operation was repeated twice, and the resulting oil was dried in vacuo, to give 0.237 g (a quantitative yield) of the title compound as a colorless oil.

Nuclear Magnetic Resonance Spectrum (CDCl$_3$+D$_2$O, 270 MHz), δ ppm: 1.3–1.7 (8H, multiplet); 2.5–2.65 (4H, multiplet); 2.90 (6H, singlet); 3.15–3.4 (2H, multiplet); 3.94 (1H, doublet of doublets, J=7.8 & 9.3 Hz); 4.15 (1H, doublet of doublets, J=4.4 & 9.3 Hz); 4.5–4.65 (1H, multiplet); 6.82 (1H, doublet, J=7.8 Hz); 6.90 (1H, triplet, J=7.3 Hz); 7.1–7.4 (7H, multiplet).

Infrared Absorption Spectrum (liquid film), ν$_{max}$ cm$^{-1}$: 1600, 1580, 1490, 1445, 1285, 1240, 1175, 1110, 1045.

EXAMPLE 90

3-(N,N-Dimethylamino)-1-[2-(7-phenylheptyl)phenoxy]-2-propanol hydrochloride

90(a) 2-[2-(7-Phenylheptyl)phenoxymethyl]oxirane

Following a procedure similar to that described in Example 26(a), except that a 5:1 by volume mixture of hexane and ethyl acetate was used as the eluent, 0.41 g of a crude compound containing the title compound was obtained as an oil by using 0.400 g of 2-(7-phenylheptyl)phenol (prepared as described in Preparation 30), 0.330 g of glycidol, 1.17 g of triphenylphosphine, 15 ml of methylene chloride and 0.779 g of diethyl azodicarboxylate. The compound was used in the next step without further purification.

90(b) 3-(N,N-Dimethylamino)-1-[2-(7-phenylheptyl)phenoxy]-2-propanol 1.0 ml of 50% by volume aqueous dimethylamine was added to a solution of 0.41 g of the crude compound containing 2-[2-(7-phenylheptyl)phenoxymethyl]oxirane [prepared as described in step (a) above]in 6 ml of tetrahydrofuran, and the mixture was stirred at room temperature for one day. At the end of this time, the solvent was removed by distillation under reduced pressure, and the resulting residue was purified by column chromatography through silica gel, using a 19:1 by volume mixture of methylene chloride and methanol as the eluent, to give 0.32 g (yield 69%) of the title compound as a colorless oil.

Nuclear Magnetic Resonance Spectrum (CDCl$_3$, 270 MHz), δ ppm: 1.2–1.4 (6H, multiplet); 1.5–1.7 (4H, multiplet); 2.34 (6H, singlet); 2.46 (1H, doublet of doublets, J=3.6 & 12.2 Hz); 3.6 & 12.2 Hz); 2.5–2.7 (5H, multiplet); 3.9–4.2 (3H, multiplet); 6.8–6.95 (2H, multiplet); 7.1–7.35 (7H, multiplet).

90(c) 3-(N,N-Dimethylamino)-1-[2-(7-phenylheptyl)phenoxy]-2-propanol hydrochloride 0.31 g of 3-(N,N-dimethylamino)-1-[2-(7-phenylheptyl) phenoxy]-2-propanol [prepared as described in step (b) above] was dissolved in 10 ml of ethyl acetate, and 0.33 ml of a 4N solution of hydrogen chloride in dioxane was added to the solution, whilst ice-cooling and stirring. The resulting mixture was stirred at room temperature for a few minutes, after which it was concentrated by distillation under reduced pressure. Pentane was added to the resulting concentrate, and the mixture was shaken and then concentrated by distillation under reduced pressure. This operation was repeated twice, and then the resulting oil was dried in vacuo, to give 0.34 g (a quantitative yield) of the title compound as a colorless oil.

Nuclear Magnetic Resonance Spectrum (CDCl$_3$, 270 MHz), δ ppm: 1.2–1.4 (6H, multiplet); 1.45–1.7 (4H, multiplet); 2.45–2.65 (4H, multiplet); 2.93 (6H, singlet); 3.2–3.4 (2H, multiplet); 3.93 (1H, doublet of doublets, J=7.9 & 9.2 Hz); 4.16 (1H, doublet of doublets, J=4.0 & 9.2 Hz); 4.45–4.7 (1H, multiplet); 6.82 (1H, doublet, J=7.9 Hz); 6.91 (1H, triplet, J=7.6 Hz); 7.1–7.35 (7H, multiplet).

Infrared Absorption Spectrum (liquid film), ν$_{max}$ cm$^{-1}$: 1600, 1585, 1490, 1450, 1285, 1240, 1180, 1115, 1045.

EXAMPLE 91

1-Methyl-2-{2-[2-(5-phenylpentyl)phenoxy]ethyl} pyrrolidine hydrochloride

91(a) 1-Methyl-2-{2-[2-(5-phenylpentyl)phenoxy] ethyl}pyrrolidine

Following a procedure similar to that described in Example 5(a), except that a 20:1 by volume mixture of methylene chloride and methanol was used as the eluent, 130 mg yield 19%) of the title compound were obtained as a yellow oil by using 480 mg of 2-(5-phenylpentyl)phenol (prepared as described in Preparation 31), 387 mg of 2-(2-hydroxyethyl)-1-methylpyrrolidine, 786 mg of triphenylphosphine, 10 ml of methylene chloride and 520 mg of diethyl azodicarboxylate.

Nuclear Magnetic Resonance Spectrum (CDCl$_3$, 270 MHz), δ ppm: 1.35–1.5 (2H, multiplet); 1.55–2.0 (8H, multiplet); 2.0–2.5 (4H, multiplet); 2.42 (3H, singlet); 2.64 (4H, triplet, J=7.6 Hz); 3.1–3.3 (1H, multiplet); 3.9–4.2 (2H, multiplet); 6.8–6.95 (2H, multiplet); 7.1–7.4 (7H, multiplet).

91(b) 1-Methyl-2-{2-[2-(5-phenylpentyl)phenoxy] ethyl}pyrrolidine hydrochloride 125 mg of 1-methyl-2-{2-[2-(5-phenylpentyl)phenoxy] ethyl}pyrrolidine [prepared as described in step (a) above] were dissolved in 3 ml of dioxane, and 0.13 ml of a 4N solution of hydrogen chloride in dioxane was added to the solution. The resulting mixture was then shaken and concentrated by distillation under reduced pressure. Pentane was added to the resulting concentrate, and the mixture was agitated and then concentrated by distillation under reduced pressure. This operation was repeated twice, and then he resulting oil was dried in vacuo, to give 0.138 g (a quantitative yield) of the title compound as a colorless oil.

Nuclear Magnetic Resonance Spectrum (CDC$_3$+D$_2$O 270 MHz), δ ppm : 1.3–1.5 (2H, multiplet); 1.5–1.75 (4H, multiplet); 1.8–2.15 (2H, multiplet); 2.15–2.4 (2H, multiplet); 2.4–2.7 (7H, multiplet); 2.71 (3H, singlet); 3.2–3.5 (1H, multiplet); 3.8–4.1 (2H, multiplet); 4.15–4.3 (1H, multiplet); 6.82 (1H, doublet, J=8.3 Hz); 6.91 (1H, triplet, J=7.3 Hz); 7.1–7.4 (7H, multiplet).

Infrared Absorption Spectrum (CH$_3$Cl), ν$_{max}$ cm$^{-1}$: 1600, 1585, 1495, 1450, 1230.

EXAMPLE 92

2-(2-{2-[2-(3-Chlorophenyl)ethyl]phenoxy}ethyl)-1-methylpyrrolidine hydrochloride 92(a) 2-(2-{2-[2-(3-Chlorophenyl)ethyl]phenoxy}ethyl)-1-methylpyrrolidine 1.06 g of potassium t-butoxide were added to a solution of 1.00 g of 2-[2-(3-chlorophenyl)ethyl]phenol (prepared as described in Preparation 44) in 20 ml of dimethylacetamide, whilst cooling by ice and sodium chloride and stirring. 0.949 g of 2-(2-chloroethyl)-1-methylpyrrolidine hydrochoride was then added to the solution, and the mixture was stirred at 50° C. for 3 hours. At the end of this time, the reaction mixture was cooled, and 100 ml of ethyl acetate and 50 ml of water were added to the mixture, which was then shaken. The ethyl acetate layer was separated, washed twice with a saturated aqueous solution of sodium chloride and dried over anhydrous magnesium sulfate. The ethyl acetate layer was then concentrated by distillation under reduced pressure, and the concentrate was purified by column chromatography through silica gel, using a 20:1 by volume mixture of methylene chloride and methanol as the eluent, to give 0.770 g (yield 52%) of the title compound as a colorless oil.

Nuclear Magnetic Resonance Spectrum (CDCl$_3$, 270 MHz), δ ppm: 1.55–1.95 (4H, multiplet); 1.95–2.15 (1H, multiplet); 2.2–2.5 (3H, multiplet); 2.42 (3H, singlet); 2.75–3.0 (4H, multiplet); 3.1–3.25 (1H, multiplet); 3.9–4.15 (2H, multiplet); 6.8–6.95 (2H, multiplet); 7.0–7.3 (6H, multiplet).

92(b) 2-(2-{2-[2-(3-Chlorophenyl)ethyl]phenoxy}ethyl)-1-methylpyrrolidine hydrochloride 0.752 g of 2-(2-{2-[2-(3-chlorophenyl)ethyl] phenoxy}ethyl)-1-methylpyrrolidine [prepared as described in step (a) above] was dissolved in 15 ml of ethyl acetate, and 0.6 ml of a 4N solution of hydrogen chloride in dioxane was added to the resulting solution. The mixture was then concentrated by distillation under reduced pressure. The concentrate was dissolved in 20 ml of ethyl acetate and the solution was allowed to stand at room temperature. The crystals which precipitated were collected by filtration and dried in vacuo, to give 0.530 g (yield 64%) of the title compound as colorless crystals, melting at 119°–121° C.

Nuclear Magnetic Resonance Spectrum (CDCl$_3$, 270 MHz), δ ppm: 1.95–2.2 (2H, multiplet); 2.2–2.4 (2H, multiplet); 2.4–2.6 (2H, multiplet); 2.7–3.0 (5H, multiplet); 2.79 (3H, singlet); 3.15–3.4 (1H, multiplet); 3.8–4.1 (2H, multiplet); 4.15–4.3 (1H, multiplet); 6.84 (1H, doublet, J=7.9 Hz); 6.93 (1H, triplet, J=7.9 Hz); 6.95–7.05 (1H, multiplet); 7.1–7.3 (5H, multiplet).

EXAMPLE 93

2-(2-{2-[2-(2-Chlorophenyl)ethyl]phenoxy}ethyl)-1-methylpyrrolidine hydrochloride 93(a) 2-(2-{2-[2-(2-Chlorophenyl)ethyl]phenoxy}ethyl)-1-methylpyrrolidine Following a procedure similar to that described in Example 92(a), 0.410 g (yield 29%) of the title compound was obtained as a colorless solid by using 0.950 g of 2-[2-(2-chlorophenyl)ethyl]phenol (prepared as described in Preparation 45), 1.15 g of potassium t-butoxide, 1.13 g of 2-(2-chloroethyl)-1-methylpyrrolidine hydrochoride and 20 ml of dimethylacetamide.

Nuclear Magnetic Resonance Spectrum (CDCl$_3$, 270 MHz), δ ppm: 1.6–2.0 (4H, multiplet); 2.0–2.15 (1H, multiplet); 2.2–2.4 (2H, multiplet); 2.4–2.6 (1H, multiplet); 2.44 (3H, singlet); 2.85–3.05 (4H, multiplet); 3.15–3.3 (1H, multiplet); 3.9–4.1 (2H, multiplet); 6.8–6.95 (2H, multiplet); 7.1–7.2 (5H, multiplet); 7.3–7.4 (1H, multiplet).

93(b) 2-(2-(2-[2-(2-Chlorophenyl)ethyl]phenoxy}ethyl)-1-methylpyrrolidine hydrochloride 0.410 g of 2-(2-{2-[2-(2-chlorophenyl)ethyl]phenoxy}ethyl)-1-methylpyrrolidine [prepared as described in step (a) above] was dissolved in 5 ml of methylene chloride, and 0.35 ml of a 4N solution of hydrogen chloride in dioxane was added to the solution. The resulting mixture was concentrated by distillation under reduced pressure. The resulting solid was dissolved in a small amount of methylene chloride, and 30 ml of ethyl acetate was added to the solution, which was then allowed to stand at room temperature. The crystals which precipitated were collected by filtration and dried in vacuo, to give 0.408 g (yield 90%) of the title compound as colorless crystals, melting at 187°–188° C.

Nuclear Magnetic Resonance Spectrum (CDCl$_3$, 270 MHz), δ ppm: 1.9–2.15 (2H, multiplet); 2.15–2.4 (2H, multiplet); 2.4–2.6 (2H, multiplet); 2.7–3.1 (5H, multiplet); 2.78 (3H, singlet); 3.3–3.5 (1H, multiplet); 3.8–4.0 (2H, multiplet); 4.1–4.2 (1H, multiplet); 6.82 (1H, doublet, J=7.9 Hz); 6.94 (1H, triplet, J=7.6 Hz); 7.05–7.25 (5H, multiplet); 7.3–7.4 (1H, multiplet).

EXAMPLE 94

2-(2-{2-[2-(4-Chlorophenyl)ethyl]phenoxy}ethyl)-1-methylpyrrolidine hydrochloride 94(a) 2-(2-{2-[2-(4-Chlorophenyl)ethyl]phenoxy}ethyl)-1-methylpyrrolidine Following a procedure similar to that described in Example 92(a), 0.450 g (yield 30%) of the title compound was obtained as a colorless oil by using 1.00 g of 2-[2-(4-chlorophenyl)ethyl]phenol (prepared as described in Preparation 46), 1.21 g of potassium t-butoxide, 1.19 g of 2-(2-chloroethyl)-1-methylpyrrolidine hydrochoride and 20 ml of dimethylacetamide.

Nuclear Magnetic Resonance Spectrum (CDCl$_3$, 270 MHz), δ ppm: 1.6–2.7 (8H, multiplet); 2.47 (3H, singlet); 2.86 (4H, singlet); 3.2–3.35 (1H, multiplet); 3.9–4.15 (2H, multiplet); 6.8–6.95 (2H, multiplet); 7.0–7.3 (6H, multiplet).

94(b) 2-(2-{2-[2-(4-Chlorophenyl)ethyl]phenoxy}ethyl)-1-methylpyrrolidine hydrochloride 0.450 g of 2-(2-{2-[2-(4-chlorophenyl)ethyl]phenoxy}ethyl)-1-methylpyrrolidine [prepared as described in step (a) above] was dissolved in a small amount of dioxane, and 0.36 ml of a 4N solution of hydrogen chloride in dioxane was added to the solution. The mixture was then concentrated by distillation under reduced pressure. The concentrate was dissolved in 15 ml of ethyl acetate and allowed to stand at room temperature. The crystals which precipitated were collected by filtration and dried in vacuo, to give 0.350 g (yield 70%) of the title compound as colorless crystals, melting at 145°–146° C.

Nuclear Magnetic Resonance Spectrum (CDCl$_3$, 270 MHz), δ ppm: 1.9–2.15 (2H, multiplet); 2.2–2.4 (2H, multiplet); 2.4–2.65 (2H, multiplet); 2.7–3.0 (1H, multiplet); 2.77 (3H, singlet); 2.86 (4H, singlet); 3.15–3.3 (1H, multiplet); 3.8–4.1 (2H, multiplet); 4.1–4.25 (1H, multiplet); 6.82 (1H, doublet, J=8.6 Hz); 6.92 (1H, triplet, J=7.6 Hz); 7.0–7.15 (3H, multiplet); 7.15–7.3 (3H, multiplet).

EXAMPLE 95

2-(2-{2-[2-(3-Fluorophenyl)ethyl]phenoxy}ethyl)-1-methylpyrrolidine hydrochloride 95(a) 2-(2-{2-[2-(3-Fluorophenyl)ethyl]phenoxy}ethyl)-1-methylpyrrolidine Following a procedure similar to that described in Example 92(a), 0.940 g (yield 62%) of the title compound was obtained as a colorless oil by using 1.00 g of 2-[2-(3-fluorophenyl)ethyl]phenol (prepared as described in Preparation 48), 1.14 g of potassium t-butoxide, 1.02 g of 2-(2-chloroethyl)-1-methylpyrrolidine hydrochoride and 20 ml of dimethylacetamide.

Nuclear Magnetic Resonance Spectrum (CDCl$_3$, 270 MHz), δ ppm: 1.6–2.0 (4H, multiplet); 2.0–2.1 (1H, multiplet); 2.2–2.4 (2H, multiplet); 2.4–2.6 (1H, multiplet); 2.44 (3H, singlet); 2.8–3.0 (4H, multiplet); 3.15–3.3 (1H, multiplet); 3.9–4.2 (2H, multiplet); 6.8–7.0 (5H, multiplet); 7.05–7.3 (3H, multiplet).

95(b) 2-(2-{2-[2-(3-Fluorophenyl)ethyl]phenoxy}ethyl)-1-methylpyrrolidine hydrochloride 0.923 g of 2-(2-{2-[2-(3-fluorophenyl)ethyl]phenoxy}ethyl)-1-methylpyrrolidine [prepared as described in step (a) above] was dissolved in 15 ml of ethyl acetate, and 0.8 ml of a 4N solution of hydrogen chloride in dioxane was added to the solution. The mixture was then concentrated by distillation under reduced pressure. The concentrate was dissolved in 25 ml of ethyl acetate, and the solution was allowed to stand at room temperature. The crystals which precipitated were collected by filtration and dried in vacuo, to give 0.585 g (yield 56%) of the title compound as colorless crystals, melting at 135°–136° C.

Nuclear Magnetic Resonance Spectrum (CDCl$_3$, 270 MHz), δ ppm: 1.9–2.2 (2H, multiplet); 2.2–2.4 (2H, multiplet); 2.4–2.65 (2H, multiplet); 2.7–3.0 (1H, multiplet); 2.78 (3H, singlet); 2.88 (4H, singlet); 3.2–3.4 (1H, multiplet); 3.2–4.1 (2H, multiplet); 4.15–4.3 (1H, multiplet); 6.8–7.0 (5H, multiplet); 7.1–7.3 (3H, multiplet).

EXAMPLE 96

2-(2-{2-[2-(4-Fluorophenyl)ethyl]phenoxy}ethyl)-1-methylpyrrolidine hydrochloride 96(a) 2-(2-{2-[2-(4-Fluorophenyl)ethyl]phenoxy}ethyl)-1-methylpyrrolidine Following a procedure similar to that described in Example 92(a), 0.560 g (yield 37%) of the title compound was obtained as a colorless oil by using 1.00 g of 2-[2-(4-fluorophenyl)ethyl]phenol (prepared as described in Preparation 49), 1.30 g of potassium t-butoxide, 1.27 g of 2-(2-chloroethyl)-1-methylpyrrolidine hydrochoride and 20 ml of dimethylacetamide.

Nuclear Magnetic Resonance Spectrum (CDCl$_3$, 270 MHz), δ ppm: 1.55–1.95 (4H, multiplet); 1.95–2.15 (1H, multiplet); 2.15–2.5 (3H, multiplet); 2.40 (3H, singlet); 2.75–2.95 (4H, multiplet); 3.1–3.2 (1H, multiplet); 3.9–4.15 (2H, multiplet); 6.8–7.0 (4H, multiplet); 7.05–7.25 (4H, multiplet).

96(b) 2-(2-{2-[2-(4-Fluorophenyl)ethyl]phenoxy}ethyl)-1-methylpyrrolidine hydrochloride 0.560 g of 2-(2-{2-[2-(4-fluorophenyl)ethyl]phenoxy}ethyl)-1-methylpyrrolidine [prepared as described in step (a) above] was dissolved in 10 ml of ethyl acetate, and 0.5 ml of a 4N solution of hydrogen chloride in dioxane was added to the solution. The resulting mixture was then concentrated by distillation under reduced pressure, and the concentrate was dissolved in 15 ml of ethyl acetate and allowed to stand at room temperature. The crystals which precipitated were collected by filtration and dried in vacuo, to give 0.484 g (yield 78%) of the title compound as colorless crystals, melting at 114°–115° C.

Nuclear Magnetic Resonance Spectrum (CDCl$_3$, 270 MHz), δ ppm: 1.9–2.2 (2H, multiplet); 2.2–2.4 (2H, multiplet); 2.4–2.65 (2H, multiplet); 2.7–3.0 (1H, multiplet); 2.78 (3H, singlet); 2.86 (4H, singlet); 3.15–3.35 (1H, multiplet); 3.8–4.1 (2H, multiplet); 4.15–4.3 (1H, multiplet); 6.8–7.0 (4H, multiplet); 7.0–7.2 (4H, multiplet).

EXAMPLE 97

2-(2-{2-[2-(2-Fluorophenyl)ethyl]phenoxy}ethyl)-1-methylpyrrolidine hydrochloride 97(a) 2-(2-{2-[2-(2-Fluorophenyl)ethyl]phenoxy}ethyl)-1-methylpyrrolidine Following a procedure similar to that described in Example 92(a), 0.316 g (yield 21%) of the title compound was obtained as a colorless oil by using 1.00 g of 2-[2-(2-fluorophenyl)ethyl]phenol (prepared as described in Preparation 47), 1.30 g of potassium t-butoxide, 1.26 g of 2-(2-chloroethyl)-1-methylpyrrolidine hydrochoride and 20 ml of dimethylacetamide.

Magnetic Resonance Spectrum (CDCl$_3$, 270 MHz), δ ppm: 1.6–2.6 (7H, multiplet); 2.54 (3H, singlet); 2.6–2.9 (1H, multiplet); 2.90 (4H, singlet); 3.3–3.45 (1H, multiplet); 3.9–4.2 (2H, multiplet); 6.8–6.95 (2H, multiplet); 6.95–7.1 (2H, multiplet); 7.1–7.25 (4H, multiplet).

97(b) 2-(2-{2-[2-(2-Fluorophenyl)ethyl]phenoxy}-ethyl)-1-methylpyrrolidine hydrochloride 0.311 g of 2-(2-{2-[2-(2-fluorophenyl)ethyl]phenoxy}ethyl)-1-methylpyrrolidine [prepared as described in step (a) above] was dissolved in 10 ml of ethyl acetate, and 0.36 ml of a 4N solution of hydrogen chloride in dioxane was added to the solution. The mixture was then allowed to stand at room temperature, and the crystals which precipitated were collected by filtration and dried in vacuo, to give 0.290 g (yield 84%) of the title compound as colorless crystals, melting at 178°–180° C.

Nuclear Magnetic Resonance Spectrum (CDCl$_3$, 270 MHz), δ ppm: 1.9–2.2 (2H, multiplet); 2.2–2.7 (4H, multiplet); 2.7–3.0 (1H, multiplet); 2.84 (3H, singlet); 2.87 (4H, singlet); 3.4–3.65 (1H, multiplet); 3.8–4.1 (2H, multiplet); 4.2–4.3 (1H, multiplet); 6.8–7.3 (8H, multiplet).

EXAMPLE 98

2-(2-{2-[2-(3-Bromophenyl)ethyl]phenoxy}ethyl)-1-methylpyrrolidine hydrochloride 98(a) 2-(2-{2-[2-(3-Bromophenyl)ethyl]phenoxy}ethyl)-1-methylpyrrolidine Following a procedure similar to that described in Example 92(a), 0,450 g (yield 32%) of the title compound was obtained as a colorless oil by using 1.00 g of 2-[2-(3-bromophenyl)ethyl]phenol (prepared as described in Preparation 50), 1.01 g of potassium t-butoxide, 0.996 g of 2-(2-chloroethyl)-1-methylpyrrolidine hydrochoride and 20 ml of dimethylacetamide, Nuclear Magnetic Resonance Spectrum (CDCl$_3$, 270 MHz), δ ppm: 1.6–2.0 (4H, multiplet); 2.0–2.6 (4H, multiplet); 2.44 (3H, singlet); 2.8–2.95 (4H, multiplet); 3.15–3.3 (1H, multiplet); 3.9–4.15 (2H, multiplet); 6.8–6.95 (2H, multiplet); 7.1–7.4 (6H, multiplet).

95(b) 2-(2-{2-[2-(3-Bromophenyl)ethyl]phenoxy}ethyl)-1-methylpyrrolidine hydrochloride 0.450 g of 2-(2-{2-[2-(3-bromophenyl)ethyl]phenoxy}ethyl)-1-methylpyrrolidine [prepared as described in step (a) above] was dissolved in a small amount of dioxane, and 0.4 ml of a 4N solution of hydrogen chloride in dioxane was added to the solution. The mixture was then concentrated by distillation under reduced pressure. The concentrate was dissolved in 15 ml of ethyl acetate and allowed to stand at room temperature. The crystals which precipitated were collected by filtration and dried in vacuo, to give 0.394 g (yield 80%) of the title compound as colorless crystals, melting at 127°–129° C.

Nuclear Magnetic Resonance Spectrum (CDCl$_3$, 720 MHz), δ ppm: 1.9–2.2 (2H, multiplet); 2.2–2.4 (2H, multiplet); 2.4–2.7 (2H, multiplet); 2.75–3.1 (5H, multiplet); 2.79 (3H, singlet); 3.2–3.4 (1H, multiplet); 3.8–4.1 (2H, multiplet); 4.15–4.3 (1H, multiplet); 6.85 (1H, doublet, J=7.9 Hz); 6.93 (1H, triplet, J=7.3 Hz); 7.05 (1H, triplet, J=7.3 Hz); 7.1–7.4 (5H, multiplet).

EXAMPLE 99

2-(2-{2-[2-(3-Ethoxyphenyl)ethyl]phenoxy}ethyl)-1-methylpyrrolidine hydrochloride 99(a) 2-(2-{2-[2-(3-Ethoxyphenyl)ethyl]phenoxy}ethyl)-1-methylpyrrolidine Following a procedure similar to that described in Example 92(a), 0.900 g (yield 35%) of the title compound was obtained as a colorless oil by using 1.78 g of 2-[2-(3-ethoxyphenyl)ethyl]phenol (prepared as described in Preparation 33), 2.06 g of potassium t-butoxide, 2.03 g of 2-(2-chloroethyl)-1-methylpyrrolidine hydrochoride and 40 ml of dimethylacetamide.

Nuclear Magnetic Resonance Spectrum (CDCl$_3$, 270 MHz), δ ppm: 1.40 (3H, triplet, J=7.3 Hz); 1.6–2.0 (4H, multiplet); 2.0–2.15 (1H, multiplet); 2.2–2.4 (2H, multiplet); 2.4–2.6 (1H, multiplet); 2.45 (3H, singlet); 2.75–3.0 (4H, multiplet); 3.15–3.3 (1H, multiplet); 3.9–4.2 (2H, multiplet); 4.00 (2H, quartet, J=7.3 Hz); 6.7–7.0 (5H, multiplet); 7.05–7.25 (3H, multiplet).

99(b) 2-(2-{2-[2-(3-Ethoxyphenyl)ethyl]phenoxy}ethyl)-1-methylpyrrolidine hydrochloride 0.891 g of 2-(2-{2-[2-(3-ethoxyphenyl)ethyl]phenoxy}ethyl)-1-methylpyrrolidine [prepared as described in step (a) above] was dissolved in a small amount of ethyl acetate, and 0.76 ml of a 4N solution of hydrogen chloride in dioxane was added to the solution. The mixture was then concentrated by distillation under reduced pressure, and the concentrate was dissolved in 25 ml of ethyl acetate and allowed to stand at room temperature. The crystals which precipitated were collected by filtration and dried in vacuo, to give 0.518 g (yield 53%) of the title compound as colorless crystals, melting at 120°–121° C.

Nuclear Magnetic Resonance Spectrum (CDCl$_3$, 270 MHz), δ ppm : 1.39 (3H, triplet, J=7.3 Hz); 1.9–2.15 (2H, multiplet); 2.15–2.4 (2H, multiplet); 2.4–2.65 (2H, multiplet); 2.7–3.0 (5H, multiplet); 2.78 (3H, singlet); 3.2–3.4 (1H, multiplet); 3.8–4.1 (2H, multiplet); 4.00 (2H, quartet, J=7.3

Hz); 4.1–4.2 (1H, multiplet); 6.65–6.8 (3H, multiplet); 6.84 (1H, doublet, J=7.9 Hz); 6.93 (1H, triplet, J=7.9 Hz); 7.1–7.25 (3H, multiplet).

EXAMPLE 100

2-(2-{2-[2-(2-Ethoxyphenyl)ethyl]phenoxy}ethyl)-1-methylpyrrolidine hydrochloride 100(a) 2-(2-{2-[2-(2-Ethoxyphenyl)ethyl]phenoxy}ethyl)-1-methylpyrrolidine Following a procedure similar to that described in Example 92 (a), 0.636 g (yield 40%) of the title compound was obtained as a colorless oil by using 1.10 g of 2-[2-(2-ethoxyphenyl) ethyl]phenol (prepared as described in Preparation 34), 1.27 g of potassium t-butoxide, 1.26 g of 2-(2-chloroethyl)-1-methylpyrrolidine hydrochoride and 15 ml of dimethylacetamide.

Nuclear Magnetic Resonance Spectrum (CDCl$_3$, 270 MHz), δ ppm: 1.42 (3H, triplet, J=7.2 Hz); 1.55–2.0 (4H, multiplet); 2.0–2.15 (1H, multiplet); 2.2–2.55 (3H, multiplet); 2.40 (3H, singlet); 2.90 (4H, singlet); 3.1–3.25 (1H, multiplet); 3.9–4.15 (2H, multiplet); 4.02 (2H, quartet, J=7.2 Hz); 6.8–6.95 (4H, multiplet); 7.1–7.25 (4H, multiplet).

100(b) 2-(2-{2-[2-(2-Ethoxyphenyl)ethyl]phenoxy}ethyl)-1-methylpyrrolidine hydrochloride 0.600 g of 2-(2-{2-[2-(2-ethoxyphenyl)ethyl]phenoxy}ethyl)-1-methylpyrrolidine [prepared as described in step (a) above] was dissolved in a small amount of ethyl acetate, and 0.41 ml of a 4N solution of hydrogen chloride in dioxane was added to the solution. The mixture was then concentrated by distillation under reduced pressure. The resulting solid was dissolved in a small amount of methanol, and 30 ml of ethyl acetate were added to the solution, which was then allowed to stand at room temperature. The crystals which precipitated were collected by filtration and dried in vacuo, to give 0.420 g (yield 63%) of the title compound as colorless crystals, melting at 148°–150° C.

Nuclear Magnetic Resonance Spectrum (CDCl$_3$, 270 MHz), δ ppm: 1.40 (3H, triplet, J=7.3 Hz); 1.9–2.15 (2H, multiplet); 2.15–2.4 (2H, multiplet); 2.4–2.65 (2H, multiplet); 2.65–3.0 (5H, multiplet); 2.71 (3H, singlet); 3.2–3.4 (1H, multiplet); 3.8–4.1 (2H, multiplet); 4.02 (2H, quartet, J=7.3 Hz); 4.15–4.3 (1H, multiplet); 6.8–7.0 (4H, multiplet); 7.05–7.25 (4H, multiplet).

EXAMPLE 101

2-(2-{2-[2-(4-Ethoxyphenyl)ethyl]phenoxy}ethyl)-1-methylpyrrolidine hydrochloride 101(a) 2-(2-{2-[2-(4-Ethoxyphenyl)ethyl]phenoxy}ethyl)-1-methylpyrrolidine Following a procedure similar to that described in Example 92(a), 1.00 g (yield 69%) of the title compound was obtained as a colorless oil by using 1.00 g of 2-[2-(4-ethoxyphenyl)ethyl]phenol (prepared as described in Preparation 35), 1.16 g of potassium t-butoxide, 1.14 g of 2-(2-chloroethyl)-1-methylpyrrolidine hydrochoride and 15 ml of dimethylacetamide.

Nuclear Magnetic Resonance Spectrum (CDCl$_3$, 270 MHz), δ ppm: 1.40 (3H, triplet, J=7.2 Hz); 1.55 1.95 (4H, multiplet); 1.95–2.15 (1H, multiplet); 2.15–2.5 (3H, multiplet); 2.40 (3H, singlet); 2.75–2.95 (4H, multiplet); 3.1–3.25 (1H, multiplet); 3.9–4.15 (2H, multiplet); 4.00 (2H, quartet, J=7.2 Hz); 6.75–6.9 (4H, multiplet); 7.05–7.2 (4H, multiplet).

101(b) 2-(2-{2-[2-(4-Ethoxyphenyl)ethyl]phenoxy}ethyl)-1-methylpyrrolidine hydrochloride 1.00 g of 2-(2-{2-[2-(4-ethoxyphenyl)ethyl]phenoxy}ethyl)-1-methylpyrrolidine [prepared as described in step (a) above] was dissolved in 10 m l of ethyl acetate, and 0.8 ml of a 4N solution of hydrogen chloride in dioxane was added to the solution. The mixture was then concentrated by distillation under reduced pressure. The resulting solid was dissolved in a small amount of methanol, and 30 ml of ethyl acetate were added to the solution, which was then allowed to stand at room temperature. The crystals which precipitated were collected by filtration and dried in vacuo, to give 0.810 g (yield 73%) of the title compound as colorless crystals, melting at 131°–132° C.

Nuclear Magnetic Resonance Spectrum (CDCl$_3$, 270 MHz), δ ppm: 1.40 (3H, triplet, J=7.2 Hz); 1.9–2.15 (2H, multiplet); 2.15–2.4 (2H, multiplet); 2.4–2.65 (2H, multiplet); 2.7–3.0 (5H, multiplet); 2.76 (3H, singlet); 3.2–3.4 (1H, multiplet); 3.8–4.1 (2H, multiplet); 4.01 (2H, quartet, J=7.2 Hz); 4.15–4.3 (1H, multiplet); 6.75–6.9 (3H, multiplet); 6.92 (1H, triplet, J=7.3 Hz); 7.04 (2H, doublet, J=8.6 Hz); 7.1–7.25 (2H, multiplet).

EXAMPLE 102

(R)-2-[2-(2-Phenylethyl)phenoxymethyl]morpholine hydrochloride

102(a) (R)-4-t-Butoxycarbonyl-2-[2-(2-phenylethyl)phenoxymethyl]morpholine

Following a procedure similar to that described in Example 40(a), except that a 5:1 by volume mixture of hexane and ethyl acetate was used as the eluent, 1.96 g (yield 98%) of the title compound were obtained as a colorless oil by using 1.00 g of 2-(2-phenylethyl)phenol (prepared as described in Preparation 19), 2.33 g of (R)-4-t-butoxycarbonyl-2-(p-toluenesulfonyloxymethyl)morpholine, 0.743 g of potassium t-butoxide and 20 ml of dimethylacetamide.

Nuclear Magnetic Resonance Spectrum (CDCl$_3$, 270 MHz), δ ppm: 1.45 (9H, singlet); 2.8–3.1 (6H, multiplet); 3.5–3.7 (1H, multiplet); 3.75–4.2 (6H, multiplet); 6.8–6.95 (2H, multiplet); 7.1–7.3 (7H, multiplet).

102(b) (R)-2-[2-(2-Phenylethyl)phenoxymethyl]morpholine hydrochloride 0.930 g of (R)-4-t-butoxycarbonyl-2-[2-(2-phenylethyl)phenoxymethyl]morpholine [prepared as described in step (a) above] was dissolved in 5 ml of dioxane, and 5 ml of a 4N solution of hydrogen chloride in dioxane was added to the solution, which was then allowed to stand at room temperature for 1 hour. At the end of this time, the mixture was concentrated by distillation under reduced pressure, and the resulting oil was dissolved in 25 ml of ethyl acetate and allowed to stand at room temperature. The crystals which precipitated were collected by filtration and dried in vacuo, to give 0.692 g (yield 89%) of the title compound as colorless crystals, melting at 150°–151° C.

[α]$_D$ −7.94° (c=1.0, H$_2$O).

Nuclear Magnetic Resonance Spectrum (CDCl$_3$, 270 MHz), δ ppm: 2.8–3.0 (4H, multiplet); 3.0–3.2 (2H, multiplet); 3.33 (1H, doublet, J=12.5 Hz); 3.45 (1H, doublet, J=12.5 Hz); 3.9–4.2 (4H, multiplet); 4.25–4.4 (1H, multiplet); 6.79 (1H, doublet, J=7.9 Hz); 6.91 (1H, triplet, J=7.9 Hz); 7.1–7.4 (7H, multiplet).

EXAMPLE 103

(R)-4-Methyl-2-[2-(2-phenylethyl)phenoxymethyl] morpholine hydrochloride

103(a) (R)-4-Methyl-2-[2-(2-phenylmethyl)phenoxymethyl]morpholine

Following a procedure similar to that described in Example 38(a), 0.800 g (yield 99%) of the title compound was obtained as a colorless oil by using 1.03 g of (R)-4-t-butoxycarbonyl-2-[2-(2-phenylethyl)phenoxymethyl]morpholine [prepared as described in Example 102(a)], 0.196 g of lithium aluminum hydride and 20 ml of tetrahydrofuran.

Nuclear Magnetic Resonance Spectrum (CDCl$_3$, 270 MHz), δ ppm: 2.2–2.4 (2H, multiplet); 2.44 (3H, singlet); 2.8–3.0 (5H, multiplet); 3.08 (1H, doublet, J=11.2 Hz); 3.8–4.2 (5H, multiplet); 6.8–6.95 (2H, multiplet); 7.1–7.35 (7H, multiplet).

103(b) (R)-4-Methyl-2-[2-(2-phenylethyl)phenoxymethyl]morpholine hydrochloride 0.800 g of (R)-4-methyl-2-[2-(2-phenylethyl)phenoxymethyl]morpholine [prepared as described in step (a) above] was dissolved in 10 ml of dioxane, and 0.8 ml of a 4N solution of hydrogen chloride in dioxane was added to the solution. The mixture was then concentrated by distillation under reduced pressure. The resulting oil was dissolved in 15 ml of ethyl acetate and allowed to stand at room temperature. The crystals which precipitated were collected by filtration and dried in vacuo, to give 0.541 g (yield 61%) of the title compound as colorless crystals, melting at 123°–125° C.

[α]$_D$ –5.08° (c=1.3, ethanol).

Nuclear Magnetic Resonance Spectrum (CDCl$_3$, 270 MHz), δ ppm: 2.7–3.0 (6H, multiplet); 2.73 (3H, singlet); 3.40 (2H, triplet, J=11.9 Hz); 4.0–4.2 (3H, multiplet); 4.37 (1H, triplet, J=11.9 Hz); 4.5–4.6 (1H, multiplet); 6.83 (1H, doublet, J=7.9 Hz); 6.94 (1H, triplet, J=7.9 Hz); 7.1–7.3 (7H, multiplet).

EXAMPLE 104

(S)-2-[2-(2-Phenylethyl)phenoxymethyl]morpholine hydrochloride

104(a) (S)-4-t-Butoxycarbonyl-2-[2-(2-phenylethyl)phenoxymethyl]morpholine

Following a procedure similar to that described in Example 40(a), except that a 5:1 by volume mixture of hexane and ethyl acetate was used as the eluent, 1.23 g (yield 99%) of the title compound was obtained as a colorless oil by using 0.620 g of 2-(2-phenylethyl)phenol (prepared as described in Preparation 19), 1.51 g of (S)-4-t-butoxycarbonyl-2-(p-toluenesulfonyloxymethyl)morpholine, 0.460 g of potassium t-butoxide and 16 ml of dimethylacetamide.

Nuclear Magnetic Resonance Spectrum (CDCl$_3$, 270 MHz), δ ppm: 1.45 (9H, singlet); 2.8–3.1 (6H, multiplet); 3.5–3.7 (1H, multiplet); 3.75–4.2 (6H, multiplet); 6.8–6.95 (2H, multiplet); 7.1–7.3 (7H, multiplet).

104(b) (S)-2-[2-(2-phenylethyl)phenoxymethyl]morpholine hydrochloride 0.500 g of (S)-4-t-butoxycarbonyl-2-[2-(2-phenylethyl)phenoxymethyl]morpholine [prepared as described in step (a) above] was dissolved in 2 ml of dioxane, and 4 ml of a 4N solution of hydrogen chloride in dioxane was added to the solution, which was then allowed to stand at room temperature for 1 hour. At the end of this time, the mixture was concentrated by distillation under reduced pressure. The resulting oil was dissolved in 15 ml of ethyl acetate and allowed to stand at room temperature. The crystals which precipitated were collected by filtration and dried in vacuo, to give 0.345 g (yield 82%) of the title compound as colorless crystals, melting at 143°–145° C.

[α]$_D$ +7.25° (c=1.49, H$_2$O)

Nuclear Magnetic Resonance Spectrum (CDCl$_3$, 270 MHz), δ ppm: 2.8–3.0 (4H, multiplet); 3.0–3.2 (2H, multiplet); 3.33 (1H, doublet, J=12.5 Hz); 3.45 (1H, doublet, J=12.5 Hz); 3.9–4.2 (4H, multiplet); 4.25–4.4 (1H, multiplet); 6.79 (1H, triplet, J=7.9 Hz); 6.91 (1H, triplet, J=7.9 Hz); 7.1–7.4 (7H, multiplet).

EXAMPLE 105

(S)-4-Methyl-2-[2-(2-phenylethyl)phenoxymethyl] morpholine hydrochloride

105(a) (S)-4-Methyl-2-[2-(2-phenylethyl)phenoxymethyl]morpholine

Following a procedure similar to that described in Example 38(a), 0.560 g (yield 99%) of the title compound was obtained as a colorless oil by using 0.720 g of (S)-4-t-butoxycarbonyl-2-[2-(2-phenylethyl)phenoxymethyl]morpholine [prepared as described in Example 104(a)], 0.142 g of lithium aluminum hydride and 15 ml of tetrahydrofuran.

Nuclear Magnetic Resonance Spectrum (CDCl$_3$, 270 MHz), δ ppm: 2.2–2.4 (2H, multiplet); 2.44 (3H, singlet); 2.8–3.0 (5H, multiplet); 3.08 (1H, doublet, J=11.2 Hz); 3.8–4.2 (5H, multiplet); 6.8–6.95 (2H, multiplet); 7.1–7.35 (7H, multiplet).

105(b) (S)-4-Methyl-2-[2-(2-phenylethyl)phenoxymethyl]morpholine hydrochloride 0.560 g of (S)-4-methyl-2-[2-(2-phenylethyl)phenoxymethyl]morpholine [prepared as described in step (a) above] was dissolved in 5 ml of dioxane, and 0.56 ml of a 4N solution of hydrogen chloride in dioxane was added to the solution. The mixture was then concentrated by distillation under reduced pressure, and the resulting oil was dissolved in 10 ml of ethyl acetate and allowed to stand at room temperature. The crystals which precipitated were collected by filtration and dried in vacuo, to give 0.448 g (yield 72%) of the title compound as colorless crystals, melting at 125°–127° C.

[α]$_D$ +5.29° (c=1.36, ethanol).

Nuclear Magnetic Resonance Spectrum (CDCl$_3$, 270 MHz), δ ppm: 2.7–3.0 (6H, multiplet); 2.73 (3H, singlet); 3.40 (2H, triplet, J=11.9 Hz); 4.0–4.2 (3H, multiplet); 4.38 (1H, triplet, J=11.9 Hz); 4.5–4.6 (1H, multiplet); 6.83 (1H, doublet, J=7.9 Hz); 6.94 (1H, triplet, J=7.9 Hz); 7.1–7.3 (7H, multiplet).

EXAMPLE 106

2-(2-{2-[2-(4-Methoxyphenyl)ethyl]-phenoxy}ethyl)-1-methylpyrrolidine hydrochloride 106(a) 2-(2-{2-[2-(4-Methoxyphenyl)ethyl]phenoxy}ethyl)-1-methylpyrrolidine Following a procedure similar to that described in Example 92(a), 0.602 g (yield 40%) of the title compound was obtained as a colorless oil by using 1.00 g of 2-[2-(4-methoxyphenyl)ethyl]phenol (prepared as described in Preparation 36), 1.23 g of potassium t-butoxide, 1.61 g of 2-(2-chloroethyl)-1-methylpyrrolidine hydrochoride and 20 ml of dimethylacetamide.

Nuclear Magnetic Resonance Spectrum (CDCl$_3$, 270 MHz), δ ppm: 1.5–2.7 (8H, multiplet); 2.65 (3H, singlet); 2.75–3.0 (4H, multiplet); 3.5–3.7 (1H, multiplet); 3.83 (3H, singlet); 3.95–4.1 (1H, multiplet); 4.15–4.25 (1H, multiplet); 6.8–7.0 (4H, multiplet); 7.1–7.3 (4H, multiplet).

106(b) 2-(2-{2-[2-(4-Methoxyphenyl)ethyl]phenoxy}ethyl)-1-methylpyrrolidine hydrochloride 0.602 g of 2-(2-{2-[2-(4-methoxyphenyl)ethyl]phenoxy}ethyl)-1-methylpyrrolidine [prepared as described in step (a) above] was dissolved in a small amount of dioxane, and 0.66 ml of a 4N solution of hydrogen chloride in dioxane was added to the solution. The mixture was then concentrated by distillation under reduced pressure, and the resulting oil was dissolved in 15 ml of ethyl acetate and allowed to stand at room temperature. The crystals which precipitated were collected by filtration and dried in vacuo, to give 0.331 g (yield 50%) of the title compound as colorless crystals, melting at 136°–138° C.

Nuclear Magnetic Resonance Spectrum ($CDCl_3+D_2O$, 270 MHz), δ ppm: 1.9–2.15 (2H, multiplet); 2.15–2.4 (2H, multiplet); 2.4–2.6 (2H, multiplet); 2.7–2.95 (5H, multiplet); 2.78 (3H, singlet); 3.2–3.35 (1H, multiplet); 3.79 (3H, singlet); 3.8–4.1 (2H, multiplet); 4.15–4.3 (1H, multiplet); 6.8–6.9 (3H, multiplet); 6.92 (1H, triplet, J=7.6 Hz); 7.0–7.25 (4H, multiplet).

EXAMPLE 107

2-(2-{2-[2-(4-Methylphenyl)ethyl]phenoxy}ethyl)-1-methylpyrrolidine hydrochloride 107(a) 2-(2-{2-[2-(4-Methylphenyl)ethyl]phenoxy}ethyl)-1-methylpyrroridine Following a procedure similar to that described in Example 92(a), 0.813 g (yield 53%) of the title compound was obtained as a colorless oil by using 1.00 g of 2-[2-(4-methylphenyl)ethyl]phenol (prepared as described in Preparation 37), 1.32 g of potassium t-butoxide, 1.30 g of 2-(2-chloroethyl)-1-methylpyrrolidine hydrochoride and 20 ml of dimethylacetamide.

Nuclear Magnetic Resonance Spectrum ($CDCl_3$, 270 MHz), δ ppm: 1.6–2.0 (4H, multiplet); 2.0–2.2 (1H, multiplet); 2.2–2.4 (2H, multiplet); 2.32 (3H, singlet); 2.45–2.65 (1H, multiplet); 2.46 (3H, singlet); 2.75–2.95 (4H, multiplet); 3.2–3.35 (1H, multiplet); 3.9–4.3 (2H, multiplet); 6.8–6.95 (2H, multiplet); 7.05–7.25 (6H, multiplet).

107(b) 2-(2-{2-[2-(4-Methylphenyl)ethyl]phenoxy}ethyl)-1-methylpyrrolidine hydrochloride 0.813 g of 2-(2-{2-[2-(4-methylphenyl)ethyl]phenoxy}ethyl)-1-methylpyrrolidine [prepared as described in step (a) above] was dissolved in 5 ml of dioxane, and 0.95 ml of a 4N solution of hydrogen chloride in dioxane was added to the solution. The mixture was then concentrated by distillation under reduced pressure, and the resulting oil was dissolved in 5 ml of ethyl acetate and allowed to stand at room temperature. The crystals which precipitated were collected by filtration and dried in vacuo, to give 0.740 g (yield 82%) of the title compound as colorless crystals, melting at 137°–138° C.

Nuclear Magnetic Resonance Spectrum ($CDCl_3$, 270 MHz), δ ppm: 1.9–2.15 (2H, multiplet); 2.15–2.4 (2H, multiplet); 2.33 (3H, singlet); 2.4–2.65 (2H, multiplet); 2.7–3.0 (5H, multiplet); 2.75 (3H, singlet); 3.2–3.4 (1H, multiplet); 3.8–4.1 (2H, multiplet); 4.2–4.3 (1H, multiplet); 6.85 (1H, doublet, J=7.9 Hz); 6.93 (1H, triplet, J=6.9 Hz); 7.0–7.3 (6H, multiplet).

EXAMPLE 108

2-(2-{2-[2-(2-Cyanophenyl)ethyl]phenoxy}ethyl)-1-methylpyrrolidine hydrochloride 108(a) 2-(2-{2-[2-(2-Cyanophenyl)ethyl]phenoxy}ethyl)-1-methylpyrrolidine Following a procedure similar to that described in Example 92(a), 0.201 g (yield 13%) of the title compound was obtained as a colorless oil by using 1.00 g of 2-[2-(2-cyanophenyl)ethyl]phenol (prepared as described in Preparation 40), 1.26 g of potassium t-butoxide, 1.24 g of 2-(2-chloroethyl)-1-methylpyrrolidine hydrochoride and 20 ml of dimethylacetamide.

Nuclear Magnetic Resonance Spectrum ($CDCl_3$, 270 MHz), δ ppm: 1.55–1.95 (4H, multiplet); 1.95–2.2 (1H, multiplet); 2.2–2.35 (2H, multiplet); 2.35–2.55 (1H, multiplet); 2.43 (3H, singlet); 2.9–3.3 (5H, multiplet); 3.95–4.15 (2H, multiplet); 6.8–6.9 (2H, multiplet); 7.05–7.35 (4H, multiplet); 7.47 (1H, triplet, J=7.6 Hz); 7.60 (1H, doublet, J=8.6 Hz).

108(b) 2-(2-{2-[2-(2-Cyanophenyl)ethyl]phenoxy}ethyl)-1-methylpyrrolidine hydrochloride 0.201 g of 2-(2-{2-[2-(2-cyanophenyl)ethyl]phenoxy}ethyl)-1-methylpyrrolidine [prepared as described in step (a) above] was dissolved in a small amount of dioxane, and 0.25 ml of a 4N solution of hydrogen chloride in dioxane was added to the solution. The mixture was then concentrated by distillation under reduced pressure, and the resulting oil was dissolved in 10 ml of ethyl acetate and allowed to stand at room temperature. The crystals which precipitated were collected by filtration and dried in vacuo, to give 0.170 g (yield 76%) of the title compound as colorless crystals, melting at 172°–173° C.

Nuclear Magnetic Resonance Spectrum ($CDCl_3$, 270 MHz), δ ppm: 1.95–2.2 (2H, multiplet); 2.2–2.7 (4H, multiplet); 2.75–3.2 (5H, multiplet); 2.88 (3H, singlet); 3.55–3.8 (1H, multiplet); 3.8–4.1 (2H, multiplet); 4.15–4.3 (1H, multiplet); 6.85 (1H, doublet, J=7.9 Hz); 6.92 (1H, triplet, J=7.6 Hz); 7.1–7.4 (4H, multiplet); 7.52 (1H, triplet, J=7.6 Hz); 7.61 (1H, doublet, J=7.9 Hz).

EXAMPLE 109

2-(2-{2-[2-(3-Cyanophenyl)ethyl]phenoxy}ethyl)-1-methylpyrrolidine hydrochloride 109(a) 2-(2-{2-[2-(3-Cyanophenyl)ethyl]phenoxy}ethyl)-1-methylpyrrolidine Following a procedure similar to that described in Example 92(a), 0.510 g (yield 34%) of the title compound was obtained as a colorless oil by using 1.00 g of 2-[2-(3-cyanophenyl)ethyl]phenol (prepared as described in Preparation 41), 1.26 g of potassium t-butoxide, 1.24 g of 2-(2-chloroethyl)-1-methylpyrrolidine hydrochoride and 20 ml of dimethylacetamide.

Nuclear Magnetic Resonance Spectrum ($CDCl_3$, 270 MHz), δ ppm: 1.55–1.95 (4H, multiplet); 1.95–2.15 (1H, multiplet); 2.15–2.5 (3H, multiplet); 2.40 (3H, singlet); 2.91 (4H, singlet); 3.1–3.2 (1H, multiplet); 3.95–4.15 (2H, multiplet); 6.8–6.9 (2H, multiplet); 7.04 (1H, doublet, J=5.9 Hz); 7.19 (1H, triplet, J=7.2 Hz); 7.25–7.55 (4H, multiplet).

109(b) 2-(2-{2-[2-(3-Cyanophenyl)ethyl]phenoxy}ethyl)-1-methylpyrrolidine hydrochloride 0.50 g of 2-(2-{2-[2-(3-cyanophenyl)ethyl]phenoxy}ethyl)-1-methylpyrrolidine [prepared as described in step (a) above] was dissolved in a small amount of dioxane, and 0.56 ml of a 4N solution of hydrogen chloride in dioxane was added to the solution. The mixture was then concentrated by distillation under reduced pressure, and the resulting oil was dissolved in 20 ml of ethyl acetate and allowed to stand at room temperature. The crystals which precipitated were collected by filtration and dried in vacuo, to give 0.406 g (yield 72%) of the title compound as colorless crystals, melting at 101°–102° C.

Nuclear Magnetic Resonance Spectrum (CDCl$_3$, 270 MHz), δ ppm: 1.95–2.2 (2H, multiplet); 2.2–2.45 (2H, multiplet); 2.45–2.65 (2H, multiplet); 2.8–3.0 (1H, multiplet); 2.83 (3H, singlet); 2.90 (4H, singlet); 3.2–3.4 (1H, multiplet); 3.85–4.1 (2H, multiplet); 4.15–4.3 (1H, multiplet); 6.85 (1H, doublet, J=7.9 Hz); 6.91 (1H, triplet, J=7.3 Hz); 7.06 (1H, doublet, J=7.3 Hz); 7.21 (1H, triplet, J=7.9 Hz); 7.3–7.45 (3H, multiplet); 7.50 (1H, doublet, J=6.9 Hz).

EXAMPLE 110

2-(2-{2-[2-(4-Cyanophenyl)ethyl]phenoxy}ethyl)-1-methylpyrrolidine hydrochloride 110(a) 2-(2-{2-[2-(4-Cyanophenyl)ethyl]phenoxy}ethyl)-1-methylpyrrolidine Following a procedure similar to that described in Example 92(a), 0.310 g (yield 21%) of the title compound was obtained as a colorless oil by using 1.00 g of 2-[2-(4-cyanophenyl)ethyl]phenol (prepared as described in Preparation 42), 1.26 g of potassium t-butoxide, 1.24 g of 2-(2-chloroethyl)-1-methylpyrrolidine hydrochoride and 20 ml of dimethylacetamide.

Nuclear Magnetic Resonance Spectrum (CDCl$_3$, 270 MHz), δ ppm: 1.55–1.95 (4H, multiplet); 1.95–2.15 (1H, multiplet); 2.2–2.5 (3H, multiplet); 2.42 (3H, singlet); 2.8–3.05 (4H, multiplet); 3.15–3.3 (1H, multiplet); 3.9–4.15 (2H, multiplet); 6.8–6.9 (2H, multiplet); 7.03 (1H, triplet, J=5.9 Hz); 7.19 (1H, doublet, J=7.9 Hz); 7.25 (2H, doublet, J=7.9 Hz); 7.55 (2H, doublet, J=7.9 Hz).

110(b) 2-(2-{2-[2-(4-Cyanophenyl)ethyl]phenoxy}ethyl)-1-methylpyrrolidine hydrochloride 0.300 g of 2-(2-{2-[2-(4-cyanophenyl)ethyl]phenoxy}ethyl)-1-methylpyrrolidine [prepared as described in step (a) above] was dissolved in a small amount of dioxane, and 0.25 ml of a 4N solution of hydrogen chloride in dioxane was added to the solution. The mixture was then concentrated by distillation under reduced pressure, and the resulting oil was dissolved in 10 ml of ethyl acetate and allowed to stand at room temperature. The crystals which precipitated were collected by filtration and dried in vacuo, to give 0.170 g (yield 49%) of the title compound as colorless crystals, melting at 137.5°–139° C.

Nuclear Magnetic Resonance Spectrum (CDCl$_3$, 270 MHz), δ ppm: 1.95–2.2 (2H, multiplet); 2.2–2.45 (2H, multiplet); 2.45–2.65 (2H, multiplet); 2.75–3.1 (5H, multiplet); 2.81 (3H, singlet); 3.15–3.35 (1H, multiplet); 3.8–4.1 (2H, multiplet); 4.15–4.3 (1H, multiplet); 6.8–7.0 (2H, multiplet); 7.02 (1H, triplet, J=7.3 Hz); 7.15–7.3 (3H, multiplet); 7.56 (2H, doublet, J=7.9 Hz).

EXAMPLE 111

2-(2-{2-[2-(2-Hydroxyphenyl)ethyl]phenoxy}ethyl)-1-methylpyrrolidine hydrochloride 111(a) 2-(2-{2-[2-(2-Methoxymethoxyphenyl)ethyl]phenoxy}ethyl)-1-methylpyrrolidine Following a procedure similar to that described in Example 92(a), 0.660 g (yield 46%) of the title compound was obtained as a colorless oil by using 1.00 g of 2-[2-(2-methoxymethoxyphenyl) ethyl]phenol (prepared as described in Preparation 38), 1.09 g of potassium t-butoxide, 1.07 g of 2-(2-chloroethyl)-1-methylpyrrolidine hydrochoride and 20 ml of dimethylacetamide.

Nuclear Magnetic Resonance Spectrum (CDCl$_3$, 270 MHz), δ ppm: 1.6–2.0 (4H, multiplet); 2.0–2.2 (1H, multiplet); 2.2–2.4 (2H, multiplet); 2.46 (3H, singlet); 2.45–2.65 (1H, multiplet); 2.91 (4H, singlet); 3.2–3.35 (1H, multiplet); 3.48 (3H, singlet); 3.9–4.2 (2H, multiplet); 5.12 (2H, singlet); 6.8–7.0 (3H, multiplet); 7.05–7.2 (5H, multiplet).

111(b) 2-(2-{2-[2-(2-Hydroxyphenyl)ethyl]phenoxy}ethyl)-1-methylpyrrolidine hydrochloride 0.660 g of 2-(2-{2-[2-(2-methoxymethoxyphenyl)ethyl]phenoxy}ethyl)-1-methylpyrrolidine [prepared as described in step (a) above] was dissolved in 5 ml of dioxane, and 5 ml of a 4N solution of hydrogen chloride in dioxane was added to the solution. The mixture was then allowed to stand at room temperature for 30 minutes, after which it was concentrated by distillation under reduced pressure. The resulting colorless solid was dissolved in a small amount of a mixture of methylene chloride and methanol, and about 30 ml of ethyl acetate were added to the solution, which was then allowed to stand at room temperature. The crystals which precipitated were collected by filtration and dried in vacuo, to give 0.555 g (yield 86%) of the title compound as colorless crystals, melting at 168.5°–171° C.

Nuclear Magnetic Resonance Spectrum (hexadeuterated dimethyl sulfoxide, 270 MHz), δ ppm: 1.7–2.5 (6H, multiplet); 2.65–2.9 (4H, multiplet); 2.79 (3H, singlet); 2.9–3.15 (1H, multiplet); 3.3–3.65 (2H, multiplet); 3.9–4.2 (2H, multiplet); 6.69 (1H, triplet, J=7.3 Hz); 6.8–7.2 (7H, multiplet).

EXAMPLE 112

2-(2-{2-[2-(4-Hydrophenyl)ethyl]phenoxy}ethyl)-1-methylpyrrolidine hydrochloride 112(a) 2-(2-{2-[2-(4-Methoxymethoxyphenyl)ethyl]phenoxy}ethyl)-1-methylpyrrolidine Following a procedure similar to that described in Example 92(a), 0.411 g (yield 26%) of the title compound was obtained as a colorless oil by using 1.10 g of 2-[2-(4-methoxymethoxyphenyl)ethyl]phenol (prepared as described in Preparation 39), 1.20 g of potassium t-butoxide, 1.18 g of 2-(2-chloroethyl)-1-methylpyrrolidine hydrochoride and 20 ml of dimethylacetamide.

Nuclear Magnetic Resonance Spectrum (CDCl$_3$, 270 MHz), δ ppm: 1.7–2.2 (5H, multiplet); 2.25–2.5 (2H, multiplet); 2.54 (3H, singlet); 2.6–2.95 (5H, multiplet); 3.35–3.5 (1H, multiplet); 3.48 (3H, singlet); 3.95–4.05 (1H, multiplet); 4.05–4.2 (1H, multiplet); 5.15 (2H, singlet); 6.8–7.0 (4H, multiplet); 7.05–7.25 (4H, multiplet).

112(b) 2-(2-{2-[2-(4-Hydroxyphenyl)ethyl]phenoxy}ethyl)-1-methylpyrrolidine hydrochloride 0.400 g of 2-(2-{2-[2-(4-methoxymethoxyphenyl)ethyl]phenoxy}ethyl)-1-methylpyrrolidine [prepared as described in step (a) above] was dissolved in 5 ml of dioxane, and 5 ml of a 4N solution of hydrogen chloride in dioxane was added to the solution. The mixture was then allowed to stand at room temperature for 30 minutes, after which it was concentrated by distillation under reduced pressure. The resulting colorless solid was dissolved in a small amount of methanol, and about 50 ml of ethyl acetate were added to the solution, which was then allowed to stand at room temperature. The crystals which precipitated were collected by filtration and dried in vacuo, to give 0.219 g (yield 56%) of the title compound as colorless crystals, melting at 132°–133.5° C.

Nuclear Magnetic Resonance Spectrum (hexadeuterated dimethyl sulfoxide, 270 MHz), δ ppm: 1.7–2.5 (6H, multiplet); 2.6–2.9 (4H, multiplet); 2.80 (3H, singlet); 2.95–3.15

(1H, multiplet); 3.25–3.45 (1H, multiplet); 3.45–3.65 (1H, multiplet); 3.95–4.15 (2H, multiplet); 6.67 (2H, doublet, J=8.6 Hz); 6.86 (1H, triplet, J=6.9 Hz); 6.9–7.05 (3H, multiplet); 7.1–7.25 (2H, multiplet).

EXAMPLE 113

(S)-2-(2-{2-[2-(3-Methoxyphenyl)ethyl]phenoxy}ethyl)-1-methylpyrrolidine hydrochloride 113(a) (S)-1-Ethoxycarbonyl-2-(2-{2-[2-(3-methoxyphenyl) ethyl]phenoxy}ethyl)pyrrolidine Following a procedure similar to that described in Example 40(a), 1.08 g (yield 89%) of the title compound was obtained as a colorless oil by using 0.700 g of 2-[2-(3-methoxyphenyl)ethyl]phenol (prepared as described in Preparation 20), 1.15 g of (S)-1-ethoxycarbonyl- 2-[2-(p-toluenesulfonyloxy)ethyl]pyrrolidine, 0.378 g of potassium t-butoxide and 20 ml of dimethylacetamide.

Nuclear Magnetic Resonance Spectrum (CDCl$_3$, 270 MHz), δ ppm: 1.1–1.35 (3H, multiplet); 1.75–2.1 (5H, multiplet); 2.1–2.45 (1H, multiplet); 2.8–3.0 (4H, multiplet); 3.3–3.55 (2H, multiplet); 3.88 (3H, singlet); 3.95–4.2 (5H, multiplet); 6.7–6.95 (5H, multiplet); 7.05–7.25 (3H, multiplet).

113(b) (S)-2-(2-{2-[2-(3-Methoxyphenyl)ethyl]phenoxy}ethyl)-1-methylpyrrolidine

Following a procedure similar to that described in Example 38(a), 0.852 g (yield 94%) of the title compound was obtained as a colorless oil by using 1.06 g of (S)-1-ethoxycarbonyl-2-(2-{2-[2-(3-methoxyphenyl)ethyl]phenoxy}ethyl) pyrrolidine [prepared as described in step (a) above], 0.303 g of lithium aluminum hydride and 40 ml of tetrahydrofuran.

Nuclear Magnetic Resonance Spectrum (CDCl$_3$, 270 MHz), δ ppm: 1.55–2.0 (4H, multiplet); 2.0–2.15 (1H, multiplet); 2.2–2.4 (2H, multiplet); 2.4–2.6 (1H, multiplet); 2.43 (3H, singlet); 2.8–3.0 (4H, multiplet); 3.15–3.3 (1H, multiplet); 3.78 (3H, singlet); 3.9–4.15 (2H, multiplet); 6.7–6.95 (5H, multiplet); 7.1–7.3 (3H, multiplet).

113(c) (S)-2-(2-{2-[2-(3-Methoxyphenyl)ethyl]phenoxy}ethyl)-1-methylpyrrolidine hydrochloride 0.829 g of (S)-2-(2-{2-[2-(3-methoxyphenyl)ethyl]phenoxy}ethyl)-1-methylpyrrolidine was dissolved in 10 ml of dioxane, and 1.83 ml of a 4N solution of hydrogen chloride in dioxane was added to the solution, which was then concentrated by distillation under reduced pressure. The resulting oil was dissolved in 15 ml of ethyl acetate, and the solution was allowed to stand at room temperature. The crystals which precipitated were collected by filtration and dried in vacuo, to give 0.741 g (yield 81%) of the title compound as colorless crystals, melting at 133°–135° C.

[α]$_D$–18.4° (c=1.29, methanol).

Nuclear Magnetic Resonance Spectrum (CDCl$_3$, 270 MHz), δ ppm: 1.9–2.15 (2H, multiplet); 2.15–2.4 (2H, multiplet); 2.4–2.6 (2H, multiplet); 2.7–3.0 (5H, multiplet); 2.76 (3H, singlet); 3.2–3.4 (1H, multiplet); 3.78 (3H, singlet); 3.8–4.05 (2H, multiplet); 4.15–4.3 (1H, multiplet); 6.65–6.8 (3H, multiplet); 6.84 (1H, doublet, J=7.9 Hz); 6.93 (1H, triplet, J=7.9 Hz); 7.1–7.3 (3H, multiplet).

EXAMPLE 114

(R)-2-(2-{2-[2-(3-Methoxyphenyl)ethyl]phenoxy}ethyl)-1-methylpyrrolidine hydrochloride 114(a) (R)-1-Ethoxycarbonyl-2-(2-{2-[2-(3-methoxyphenyl) ethyl]phenoxy}ethyl)pyrrolidine Following a procedure similar to that described in Example 40(a), 0.475 g (yield 86%) of the title compound was obtained as a colorless oil by using 0.320 g of 2-[2-(3-methoxyphenyl) ethyl]phenol (prepared as described in Preparation 20), 0.526 g of (R)-1-ethoxycarbonyl-2-[2-(p-toluenesulfonyloxy) ethyl]pyrrolidine, 0.173 g of potassium t-butoxide and 15 ml of dimethylacetamide.

Nuclear Magnetic Resonance Spectrum (CDCl$_3$, 270 MHz), δ ppm: 1.1–1.35 (3H, multiplet); 1.75–2.1 (5H, multiplet); 2.1–2.45 (1H, multiplet); 2.8–3.0 (4H, multiplet); 3.3–3.55 (2H, multiplet); 3.78 (3H, singlet); 3.95–4.2 (5H, multiplet); 6.7–6.95 (5H, multiplet); 7.05–7.25 (3H, multiplet).

114(b) (R)-2-(2-{2-[2-(3-Methoxyphenyl)ethyl]phenoxy}ethyl)-1-methylpyrrolidine

Following a procedure similar to that described in Example 38(a), 0.392 g (yield 99%) of the title compound was obtained as a colorless oil by using 0.460 g of (R)-1-ethoxycarbonyl-2-(2-{2-[2-(3-methoxyphenyl)ethyl] phenoxy}ethyl)pyrrolidine [prepared as described in step (a) above], 0.132 g of lithium aluminum hydride and 20 ml of tetrahydrofuran.

Nuclear Magnetic Resonance Spectrum (CDCl$_3$, 270 MHz), δ ppm: 1.55–2.0 (4H, multiplet); 2.0–2.15 (1H, multiplet); 2.2–2.4 (2H, multiplet); 2.4–2.6 (1H, multiplet); 2.42 (3H, singlet); 2.8–3.0 (4H, multiplet); 3.15–3.3 (1H, multiplet); 3.78 (3H, singlet); 3.9–4.15 (2H, multiplet); 6.7–6.95 (5H, multiplet); 7.1.–7.3 (3H, multiplet).

114(c) (R)-2-(2-{2-[2-(3-Methoxyphenyl)ethyl]phenoxy}ethyl)-1-methylpyrrolidine hydrochloride 0.392 g of (R)-2-(2-{2-[2-(3-methoxyphenyl)ethyl]phenoxy}ethyl)-1-methylpyrrolidine was dissolved in 7 ml of dioxane, and 0.87 ml of a 4N solution of hydrogen chloride in dioxane was added to the solution, which was then concentrated by distillation under reduced pressure. The resulting oil was dissolved in 10 ml of ethyl acetate, and the solution was allowed to stand at room temperature. The crystals which precipitated were collected by filtration and dried in vacuo, to give 0.272 g (yield 67%) of the title compound as colorless crystals, melting at 133°–136° C.

[α]$_D$+18.8° (c=1.08, methanol).

Nuclear Magnetic Resonance Spectrum (CDCl$_3$, 270 MHz), δ ppm: 1.9–2.15 (2H, multiplet); 2.15–2.4 (2H, multiplet); 2.4–2.6 (2H, multiplet); 2.7–3.0 (5H, multiplet); 2.77 (3H, singlet); 3.2–3.4 (1H, multiplet); 3.77 (3H, singlet); 3.8–4.05 (2H, multiplet); 4.15–4.3 (1H, multiplet); 6.65–6.8 (3H, multiplet); 6.84 (1H, doublet, J=7.9 Hz); 6.93 (1H, triplet, J=7.3 Hz); 7.1–7.3 (3H, multiplet).

EXAMPLE 115

(S)-2-(2-{2-[2-(3,5-Dimethoxyphenyl)ethyl]phenoxy}ethyl)-1-methylpyrrolidine hydrochloride 115(a) (S)-1-Ethoxycarbonyl-2-(2-{2-[2-(3,5-dimethoxyphenyl) ethyl]phenoxy}ethyl)pyrrolidine Following a procedure similar to that described in Example 40(a), except that a 5:1 by volume mixture of hexane and ethyl acetate was used as the eluent, 0.723 g (yield 93%) of the title compound was obtained as a colorless oil by using 0.450 g of 2-[2-(3,5-dimethoxyphenyl) ethyl]phenol (prepared as described in Preparation 27), 0.773 g of (S)-1-ethoxycarbonyl-2-[2-(p-toluenesulfonyloxy) ethyl]pyrrolidine, 0.254 g of potassium t-butoxide and 20 ml of dimethylacetamide.

Nuclear Magnetic Resonance Spectrum (CDCl$_3$, 270 MHz), δ ppm: 1.1–1.35 (3H, multiplet); 1.75–2.1 (5H, multiplet); 2.1–2.45 (1H, multiplet); 2.75–3.0 (4H, multiplet); 3.3–3.55 (2H, multiplet); 3.76 (6H, singlet); 3.95–4.2 (5H, multiplet); 6.3–6.4 (3H, multiplet); 6.8–6.9 (2H, multiplet); 7.05–7.25 (2H, multiplet).

115(b)   (S)-2-(2-{2-[2-(3,5-Dimethoxyphenyl)ethyl]phenoxy}ethyl)-1-methylpyrrolidine Following a procedure similar to that described in Example 38(a), 0.565 g (yield 93%) of the title compound was obtained as a colorless oil by using 0.704 g of (S)-1-ethoxycarbonyl-2-(2-{2-[2-(3,5-dimethoxyphenyl)ethyl]phenoxy}ethyl)pyrrolidine [prepared as described in step (a) above], 0.187 g of lithium aluminum hydride and 35 ml of tetrahydrofuran.

Nuclear Magnetic Resonance Spectrum (CDCl$_3$, 270 MHz), δ ppm: 1.6–2.0 (4H, multiplet); 2.0–2.2 (1H, multiplet); 2.2–2.4 (2H, multiplet); 2.4–2.65 (1H, multiplet); 2.46 (3H, singlet); 2.75–2.95 (4H, multiplet); 3.2–3.35 (1H, multiplet); 3.76 (6H, singlet); 3.9–4.2 (2H, multiplet); 6.3–6.4 (3H, multiplet); 6.8–6.95 (2H, multiplet); 7.05–7.25 (2H, multiplet).

115(c)   (S)-2-(2-{2-[2-(3,5-Dimethoxyphenyl)ethyl]phenoxy}ethyl)-1-methylpyrrolidine hydrochloride 0.545 g of (S)-2-(2-{2-[2-(3,5-dimethoxyphenyl)ethyl]phenoxy}ethyl)-1-methylpyrrolidine [prepared as described in step (b) above] was dissolved in 8 ml of dioxane, and 1.11 ml of a 4N solution of hydrogen chloride in dioxane was added to the solution, which was then concentrated by distillation under reduced pressure. The resulting oil was dissolved in 10 ml of ethyl acetate, and the solution was allowed to stand at room temperature. The crystals which precipitated were collected by filtration and dried in vacuo, to give 0.361 g (yield 60%) of the title compound as colorless crystals, melting at 125°–126° C.

[α]$_D$ –19.0° (c=1.15, methanol).

Nuclear Magnetic Resonance Spectrum (CDCl$_3$, 270 MHz), δ ppm: 1.9–2.15 (2H, multiplet); 2.15–2.4 (2H, multiplet); 2.4–2.65 (2H, multiplet); 2.7–3.0 (5H, multiplet); 2.78 (3H, singlet); 3.2–3.4 (1H, multiplet); 3.76 (6H, singlet); 3.8–4.05 (2H, multiplet); 4.15–4.3 (1H, multiplet); 6.25–6.35 (3H, multiplet); 6.84 (1H, doublet, J=8.6 Hz); 6.94 (1H, triplet, J=7.3 Hz); 7.15–7.25 (2H, multiplet).

EXAMPLE 116

(S)-2-(2-{2-[2-(3-Difluoromethoxyphenyl)ethyl]phenoxy}ethyl)-1-methylpyrrolidine hydrochloride 116(a)   (S)-1-Ethoxycarbonyl-2-(2-{2-[2-(3-difluoromethoxyphenyl) ethyl]phenoxy}ethyl)pyrrolidine Following a procedure similar to that described in Example 40(a), 0.865 g (yield 99%) of the title compound was obtained as a colorless oil by using 0.529 g of 2-[2-(3-difluoromethoxyphenyl)ethyl]phenol (prepared as described in Preparation 43), 0.683 g of (S)-1-ethoxycarbonyl- 2-[2-(p-toluenesulfonyloxy)ethyl]pyrrolidine, 0.225 g of potassium t-butoxide and 10 ml of dimethylacetamide.

Nuclear Magnetic Resonance Spectrum (CDCl$_3$, 270 MHz), δ ppm: 1.1–1.35 (3H, multiplet); 1.75–2.1 (5H, multiplet); 2.1–2.45 (1H, multiplet); 2.90 (4H, singlet); 3.3–3.55 (2H, multiplet); 3.9–4.2 (5H, multiplet); 6.47 (1H, triplet, J=74.6 Hz); 6.8–7.0 (4H, multiplet); 7.0–7.1 (2H, multiplet); 7.1–7.3 (2H, multiplet).

116(b)   (S)-2-(2-{2-[2-(3-Difluoromethoxyphenyl)ethyl]phenol}ethyl)-1-methylpyrrolidine Following a procedure similar to that described in Example 38(a), 0.690 g (yield 94%) of the title compound was obtained as a colorless oil by using 0.850 g of (S)-1-ethoxycarbonyl-2-(2-{2-[2-(3-difluoromethoxyphenyl)ethyl]phenoxy}ethyl)pyrrolidine [prepared as described in step (a) above], 0.175 g of lithium aluminum hydride and 10 ml of tetrahydrofuran.

Nuclear Magnetic Resonance Spectrum (CDCl$_3$, 270 MHz), δ ppm: 1.55–1.95 (4H, multiplet); 1.95–2.15 (1H, multiplet); 2.15–2.45 (2H, multiplet); 2.40 (3H, singlet); 2.5–2.75 (1H, multiplet); 2.8–3.0 (4H, multiplet); 3.1–3.3 (1H, multiplet); 3.9–4.15 (2H, multiplet); 6.45 (1H, triplet, J=74.2 Hz); 6.8–7.0 (4H, multiplet); 7.0–7.1 (2H, multiplet); 7.15–7.3 (2H, multiplet).

116(c)   (S)-2-(2-{2-[2-(3-Difluoromethoxyphenyl)ethyl]phenoxy}ethyl)-1-methylpyrrolidine hydrochloride 0.690 g of (S)-2-(2-{2-[2-(3-difluoromethoxyphenyl)ethyl]phenoxy}ethyl)-1-methylpyrrolidine [prepared as described in step (b) above] was dissolved in 5 ml of dioxane, and 0.55 ml of a 4N solution of hydrogen chloride in dioxane was added to the solution, which was then concentrated by distillation under reduced pressure. The resulting oil was dissolved in 15 ml of ethyl acetate, and the solution was allowed to stand at room temperature. The crystals which precipitated were collected by filtration and dried in vacuo, to give 0.375 g (yield 50%) of the title compound as colorless crystals, melting at 119°–120° C.

[α]$_D$ –16.4° (c=2.38, methanol).

Nuclear Magnetic Resonance Spectrum (CDCl$_3$, 270 MHz), δ ppm: 1.95–2.15 (2H, multiplet); 2.15 2.4 (2H, multiplet); 2.4–2.65 (2H, multiplet); 2.75–3.0 (5H, multiplet); 2.79 (3H, singlet); 3.2–3.4 (1H, multiplet); 3.8–4.1 (2H, multiplet); 4.15–4.3 (1H, multiplet); 6.49 (1H, triplet, J=73.9 Hz); 6.75–7.05 (5H, multiplet); 7.1–7.35 (3H, multiplet).

EXAMPLE 117

(2R,4R)-4-Hydroxy-2-(2-{2-[2-(3-methoxyphenyl)ethyl]phenoxy}ethyl)-1-methylpyrrolidine hydrochloride 117(a)   (2R,4R)-4-Benzyloxy-1-ethoxycarbonyl-2-(2-{2-[2-(3-methoxyphenyl)ethyl]phenoxy}ethyl)pyrrolidine Following a procedure similar to that described in Example 40(a), 0.880 g (yield 80%) of the title compound was obtained as a colorless oil by using 0.500 g of 2-[2-(3-methoxyphenyl)ethyl]phenol (prepared as described in Preparation 20), 1.19 g of (2R,4R)-4-benzyloxy-1-ethoxycarbonyl-2-[2-(p-toluenesulfonyloxy)ethyl]pyrrolidine, 0.270 g of potassium t-butoxide and 20 ml of dimethylacetamide.

Nuclear Magnetic Resonance Spectrum (CDCl$_3$, 270 MHz), δ ppm: 1.1–1.35 (3H, multiplet); 1.75–2.1 (2H, multiplet); 2.2–2.6 (2H, multiplet); 2.8–3.0 (4H, multiplet); 3.43 (1H, doublet of doublets, J=4.6 & 11.9 Hz); 3.55–4.3 (7H, multiplet); 3.75 (3H, singlet); 4.45 (2H, singlet); 6.65–6.9 (5H, multiplet); 7.05–7.4 (8H, multiplet).

117(b)   (2R,4R)-1-Ethoxycarbonyl-4-hydroxy-2-(2-{-2-[2-(3-methoxyphenyl)ethyl]phenoxy}ethyl)-1-methylpyrrolidine A mixture of 0.853 g of (2R,4R)-4-benzyloxy-1-ethoxycarbonyl-2-(2-{2-[2-(3-methoxyphenyl)ethyl]phenoxy}ethyl)pyrrolidine [prepared as described in step (a) above], and 85 mg of 5% w/w palladium-on-carbon in 6 ml of ethanol was stirred under an atmosphere of hydrogen at 60° C. for 7 hours. At the end of this time, the mixture was cooled, and the catalyst was removed by filtration. The filtrate was concentrated by distillation under reduced pressure, and the resulting oil was purified by column chromatography through silica gel, using a 1:1 by volume mixture of hexane and ethyl acetate as the eluent, to give 0.650 g (yield 93%) of the title compound as a colorless oil.

Nuclear Magnetic Resonance Spectrum (CDCl$_3$, 270 MHz), δ ppm: 1.1–1.35 (3H, multiplet); 1.7–2.3 (3H, multiplet); 2.3–2.6 (1H, multiplet); 2.8–3.0 (4H, multiplet); 3.46 (1H, doublet of doublets, J=4.6 & 11.9 Hz); 3.5–3.8 (1H, multiplet); 3.78 (3H, singlet); 3.95–4.3 (5H, multiplet); 4.35–4.5 (1H, multiplet); 6.7–6.95 (5H, multiplet); 7.1–7.3 (3H, multiplet).

117(c) (2R,4R)-4-Hydroxy-2-(2-{2-[2-(3-methoxyphenyl)ethyl]phenoxy}ethyl)-1-methylpyrrolidine Following a procedure similar to that described in Example 38(a), 0.523 g (yield 95%) of the title compound was obtained as a colorless oil by using 0.640 g of (2R,4R)-1-ethoxycarbonyl-4-hydroxy-2-(2-{2-[2-(3-methoxyphenyl) ethyl]phenoxy}ethyl)pyrrolidine [prepared as described in step (b) above], 0.176 g of lithium aluminum hydride and 30 ml of tetrahydrofuran.

Nuclear Magnetic Resonance Spectrum (CDCl$_3$, 270 MHz), δ ppm: 1.7–2.5 (5H, multiplet); 2.48 (3H, singlet); 2.8–3.0 (5H, multiplet); 3.59 (1H, doublet of doublets, J=5.9 & 10.6 Hz); 3.78 (3H, singlet); 3.9–4.2 (2H, multiplet); 4.4–4.5 (1H, multiplet); 6.7–7.0 (5H, multiplet); 7.1–7.3 (3H, multiplet).

117(d) (2R,4R)-4-Hydroxy-2-(2-{2-[2-(3-methoxyphenyl)ethyl]phenoxy}ethyl)-1-methylpyrrolidine hydrochloride 0.520 g of (2R,4R)-4-hydroxy-2-(2-{2-[2-(3-methoxyphenyl)ethyl]phenoxy}ethyl)-1-methylpyrrolidine [prepared as described in step (c) above] was dissolved in 5 ml of dioxane, and 1.1 ml of a 4N solution of hydrogen chloride in dioxane was added to the solution, which was then concentrated by distillation under reduced pressure. The resulting oil was dissolved in 2 ml of methylene chloride, and 40 ml of ethyl acetate were added to the solution, which was then allowed to stand at room temperature. The crystals which precipitated were collected by filtration and dried in vacuo, to give 0.420 g (yield 73%) of the title compound as colorless crystals, melting at 100°–102° C.

[α]$_D$ –12.2° (c=1.06 methanol).

Nuclear Magnetic Resonance Spectrum (CDCl$_3$+D$_2$O, 400 MHz), δ ppm: 2.0–2.2 (1H, multiplet); 2.3–2.65 (3H, multiplet); 2.75–3.1 (5H, multiplet); 2.88 (3H, singlet); 3.77 (3H, singlet); 3.8–4.3 (4H, multiplet); 4.55–4.7 (1H, multiplet); 6.7–6.8 (3H, multiplet); 6.83 (1H, doublet, J=8.1 Hz); 6.92 (1H, triplet, J=7.3 Hz); 7.1–7.3 (3H, multiplet).

EXAMPLE 118

(2R,4R)-2-(2-{2-[2-(3,5-Dimethoxyphenyl)ethyl]phenoxy}ethyl)-4-hydroxy-1-methylpyrrolidine hydrochloride 118(a) (2R,4R)-4-Benzyloxy-1-ethoxycarbonyl-2-(2-{2-[2-(3,5-dimethoxyphenyl)ethyl]phenoxy}ethyl)pyrrolidine Following a procedure similar to that described in Example 40(a), 0.980 g (yield 78%) of the title compound was obtained as a colorless oil by using 0.605 g of 2-[2-(3,5-dimethoxyphenyl)ethyl]phenol (prepared as described in Preparation 27), 1.15 g of (2R,4R)-4-benzyloxy-1-ethoxycarbonyl-2-[2-(p-toluenesulfonyloxy)ethyl]pyrrolidine, 0.289 g of potassium t-butoxide and 20 ml of dimethylacetamide.

Nuclear Magnetic Resonance Spectrum (CDCl$_3$, 270 MHz), δ ppm: 1.1–1.3 (3H, multiplet); 1.75–2.1 (2H, multiplet); 2.2–2.55 (2H, multiplet); 2.75–3.0 (4H, multiplet); 3.43 (1H, doublet of doublets, J=4.6 & 11.9 Hz); 3.55–4.3 (7H, multiplet); 3.74 (6H, singlet); 4.45 (2H, singlet); 6.25–6.4 (3H, multiplet); 6.75–6.95 (2H, multiplet); 7.05–7.4 (7H, multiplet).

118(b) (2R,4R)-1-Ethoxycarbonyl-4-hydroxy-2-(2-{2-[2-(3,5-dimethoxyphenyl)ethyl]phenoxy}ethyl)pyrrolidine A solution of 0.951 g of (2R,4R)-4-benzyloxy-1-ethoxycarbonyl-2-(2-{2-[2-(3,5-dimethoxyphenyl)ethyl]phenoxy}ethyl)pyrrolidine and 95 mg of 5% w/w palladium-on-carbon in 6 ml of ethanol was stirred under an atmosphere of hydrogen at 60° C. for 9 hours. At the end of this time, the mixture was cooled, and the catalyst was removed by filtration. The filtrate was then concentrated by distillation under reduced pressure. The resulting oil was purified by column chromatography through silica gel, using a 1:2 by volume mixture of hexane and ethyl acetate as the eluent, to give 0.717 g (yield 91%) of (2R,4R)-1-ethoxycarbonyl-4-hydroxy-2-(2-{2-[2-(3,5-dimethoxyphenyl)ethyl]phenoxy}ethyl)pyrrolidine as a colorless oil.

Nuclear Magnetic Resonance Spectrum (CDCl$_3$, 270 MHz), δ ppm: 1.1–1.3 (3H, multiplet); 1.75–2.3 (3H, multiplet) 2.3–2.65 (1H, multiplet) 2.75–3.0 (4H, multiplet) 3.46 (1H, doublet of doublets, J=4.6 & 11.9 Hz); 3.5–3.8 (1H, multiplet); 3.77 (6H, singlet); 3.95–4.3 (3H, multiplet); 4.12 (2H, quartet, J=7.3 Hz); 4.35–4.5 (1H, multiplet); 6.25–6.4 (3H, multiplet); 6.83 (1H, doublet, J=8.6 Hz); 6.89 (1H, doublet, J=6.6 Hz); 7.1–7.25 (2H, multiplet).

118(c) (2R,4R)-4-Hydroxy-2-(2-{2-[2-(3,5-dimethoxyphenyl) ethyl]phenoxy}ethyl)-1-methylpyrrolidine Following a procedure similar to that described in Example 38(a), 0.547 g (yield 91%) of the title compound was obtained as a colorless oil by using 0.693 g of (2R,4R)-1-ethoxycarbonyl-4-hydroxy-2-(2-{2-[2-(3,5-dimethoxyphenyl) ethyl]phenoxy}ethyl)pyrrolidine [prepared as described in step (b) above], 0.178 g of lithium aluminum hydride and 30 ml of tetrahydrofuran.

Nuclear Magnetic Resonance Spectrum (CDCl$_3$, 270 MHz) δ ppm: 1.75–2.5 (5H, multiplet); 2.51 (3H, singlet); 2.75–3.1 (5H, multiplet); 3.62 (1H, doublet of doublets, J=5.9 & 10.6 Hz); 3.77 (6H, singlet); 3.9–4.2 (2H, multiplet); 4.4–4.55 (1H, multiplet); 6.3–6.4 (3H, multiplet); 6.84 (1H, doublet, J=7.9 Hz); 6.91 (1H, doublet, J=7.3 Hz); 7.1–7.25 (2H, multiplet).

118(d) (2R,4R)-2-(2-{2-[2-(3,5-Dimethoxyphenyl)ethyl]phenoxy]ethyl]-4-hydroxy-1-methylpyrrolidine hydrochloride 0.535 g of (2R,4R)-4-hydroxy-2-(2-{2-[2-(3,5-dimethoxyphenyl)ethyl]phenoxy}ethyl)-1-methylpyrrolidine [prepared as described in step (c) above] was dissolved in 5 ml of dioxane, and 1.04 ml of a 4N solution of hydrogen chloride in dioxane was added to the solution, which was then concentrated by distillation under reduced pressure. The resulting oil was dissolved in 2 ml of methylene chloride, and 40 ml of ethyl acetate were added to the solution, which was then allowed to stand at room temperature. The crystals which precipitated were collected by filtration and dried in vacuo, to give 0.501 g (yield 84%) of the title compound as colorless crystals, melting at 134°–136° C.

[α]$_D$ –121° (c=1.15, methanol).

Nuclear Magnetic Resonance Spectrum (CDCl$_3$+D$_2$O, 400 MHz), δ ppm: 2.0–2.2 (1H, multiplet); 2.3–2.65 (3H, multiplet); 2.7–3.1 (5H, multiplet); 2.89 (3H, singlet); 3.76 (6H, singlet); 3.8–4.3 (4H, multiplet); 4.55–4.65 (1H, multiplet); 6.25–6.4 (3H, multiplet); 6.83 (1H, doublet, J=8.0 Hz); 6.92 (1H, triplet, J=7.3 Hz); 7.1–7.3 (2H, multiplet).

EXAMPLE 119

(S)-2-(3-{2-[2-(3,5-Dimethoxyphenyl)ethyl]phenoxy}propyl]-1-methylpyrrolidine hydrochloride 119(a) (S)-1-Ethoxycarbonyl-2-(3-{2-[2-(3,5-dimethoxyphenyl) ethyl]phenoxy}propyl)pyrrolidine Following a procedure similar to that described in Example 40(a), 1.68 g (yield 98%) of the title compound were obtained as a colorless oil by using 1.00 g of 2-[2-(3,5-dimethoxyphenyl)ethyl]phenol (prepared as described in Preparation 27), 1.51 g of (S)-1-ethoxycarbonyl-2-[3-(p-toluenesulfonyloxy)propyl]pyrrolidine, 0.478 g of potassium t-butoxide and 17 ml of dimethylacetamide.

Nuclear Magnetic Resonance Spectrum (CDCl$_3$, 270 MHz), δ ppm: 1.15–1.3 (3H, multiplet); 1.5–2.1 (8H, multiplet); 2.75–3.0 (4H, multiplet); 3.25–3.6 (2H, multiplet); 3.76 (6H, singlet); 3.8–4.2 (5H, multiplet); 6.25–6.4 (3H, multiplet); 6.8–6.95 (2H, multiplet); 7.05–7.25 (2H, multiplet).

119(b) (S)-2-(3-{2-[2-(3,5-Dimethoxyphenyl)ethyl]phenoxy}propyl)-1-methylpyrrolidine Following a procedure similar to that described in Example 38(a), 1.22 g (yield 86%) of the title compound was obtained as a colorless oil by using 1.63 g of (S)-1-ethoxycarbonyl-2-(3-{2-[2-(3,5-dimethoxyphenyl)ethyl]phenoxy}propyl)pyrrolidine [prepared as described in step (a) above], 0.419 g of lithium aluminum hydride and 35 ml of tetrahydrofuran.

Nuclear Magnetic Resonance Spectrum (CDCl$_3$, 270 MHz), δ ppm: 1.4–2.3 (8H, multiplet); 2.35 (3H, singlet); 2.4–2.65 (2H, multiplet); 2.75–3.0 (4H, multiplet); 3.1–3.25 (1H, multiplet); 3.76 (6H, singlet); 3.9–4.1 (2H, multiplet); 6.25–6.4 (3H, multiplet); 6.8–6.95 (2H, multiplet); 7.05–7.25 (2H, multiplet).

119(c) (S)-2-(3-{2-[2-(3,5-Dimethoxyphenyl)ethyl]phenoxy}propyl]-1-methylpyrrolidine hydrochloride 1.19 g of (S)-2-(3-{2-[2-(3,5-dimethoxyphenyl)ethyl]phenoxy}propyl)-1-methylpyrrolidine [prepared as described in step (b) above] were dissolved in 8 ml of dioxane, and 2.33 ml of a 4N solution of hydrogen chloride in dioxane was added to the solution, which was then concentrated by distillation under reduced pressure. The resulting oil was dissolved in 20 ml of ethyl acetate, and about 4 ml of diethyl ether were added to the solution, which was then allowed to stand at room temperature. The crystals which precipitated were collected by filtration and dried in vacuo, to give 0.536 g (yield 41%) of the title compound as colorless crystals, melting at 101°–102° C.

[α]$_D$19.7° (c=0.94, methanol).

Nuclear Magnetic Resonance Spectrum (CDCl$_3$, 270 MHz), δ ppm: 1.75–2.4 (8H, multiplet); 2.7–3.0 (5H, multiplet); 2.72 (3H, singlet); 3.0–3.2 (1H, multiplet); 3.77 (6H, singlet); 3.8–4.15 (3H, multiplet); 6.25–6.4 (3H, multiplet); 6.82 (1H, doublet, J–7.9 Hz); 6.91 (1H, triplet, J=7.3 Hz); 7.1–7.25 (2H, multiplet).

EXAMPLE 120

(S)-3-{2-[2-(3-Methoxyphenyl)ethyl]phenoxymethyl}piperidine hydrochloride

120(a) (S)-1-t-Butoxycarbonyl-3-{2-[2-(3-methoxyphenyl) ethyl]phenoxymethyl}piperidine 0.295 g of a 50% w/w dispersion of sodium hydride in mineral oil was added to a solution of 1.55 g of 2-[2-(3-methoxyphenyl)ethyl]phenol (prepared as described in Preparation 21) in 60 ml of dimethylacetamide, whilst ice-cooling and stirring, and the mixture was stirred at the same temperature for 15 minutes. 2.50 g of (S)-1-t-butoxycarbonyl-3-(p-toluenesulfonyloxymethyl)piperidine were then added to the mixture, whilst ice-cooling, and the mixture was stirred at the same temperature for 30 minutes and then at room temperature for 6 hours. At the end of this time, 250 ml of ethyl acetate and 150 ml of water were added to the reaction mixture, and the ethyl acetate layer was separated. The aqueous layer was extracted with 50 ml of ethyl acetate once, and the ethyl acetate layer and the extract were combined, washed with a saturated aqueous solution of sodium chloride twice, dried over anhydrous magnesium sulfate and concentrated by distillation under reduced pressure. The concentrate was purified by column chromatography through silica gel, using a 5:1 by volume mixture of hexane and ethyl acetate as the eluent, to give 2.78 g (yield 96%) of the title compound as a colorless oil.

Nuclear Magnetic Resonance Spectrum (CDCl$_3$, 270 MHz), δ ppm: 1.4–1.8 (3H, multiplet); 1.42 (9H, singlet); 1.85–2.15 (2H, multiplet); 2.75–3.0 (6H, multiplet); 3.78 (3H, singlet); 3.8–4.25 (4H, multiplet); 6.7–6.9 (5H, multiplet); 7.1–7.25 (3H, multiplet).

1.20(b) (S)-3-{2-[2-(3-Methoxyphenyl)ethyl]phenoxymethyl}piperidine hydrochloride 1.00 g of (S)-1-t-butoxycarbonyl-3-{2-[2-(3-methoxyphenyl)ethyl]phenoxymethyl}piperidine [prepared as described in step (a) above] was dissolved in 10 ml of dioxane, and 10 ml of a 4N solution of hydrogen chloride in dioxane was added to the solution, which was then allowed to stand at room temperature for 1 hour and then concentrated by distillation under reduced pressure. The resulting solid was dissolved in a small amount of methylene chloride, and 50 ml of ethyl acetate were added to the solution, which was then allowed to stand at room temperature. The crystals which precipitated were collected by filtration and dried in vacuo, to give 0.638 g (yield 80%) of the title compound as colorless crystals, melting at 150°–152° C.

[α]$_D$–7.46° (c=2.44, methanol).

Nuclear Magnetic Resonance Spectrum (CDCl$_3$, 270 MHz), δ ppm: 1.4–1.7 (1H, multiplet); 1.85–2.15 (3H, multiplet); 2.45–2.65 (1H, multiplet); 2.7–3.0 (6H, multiplet); 3.4–3.6 (2H, multiplet); 3.76 (3H, singlet); 3.8–3.95 (2H, multiplet); 6.65–6.85 (4H, multiplet); 6.89 (1H, doublet, J=7.3 Hz); 7.05–7.3 (3H, multiplet).

EXAMPLE 121

(S)-3-{2-[2-(3-Methoxyphenyl)ethyl]phenoxymethyl}-1-methylpiperidine hydrochloride 121(a) (S)-3-{2-[2-(3-Methoxyphenyl)ethyl]phenoxymethyl}-1-methylpiperidine Following a procedure similar to that described in Example 38(a), except that a 9:1 by volume mixture of methylene chloride and methanol was used as the eluent, 1.82 g (yield 97%) of the title compound was obtained as a colorless oil by using 2.35 g of (S)-1-t-butoxycarbonyl-3-{2-[2-(3-methoxyphenyl)ethyl]phenoxymethyl}pyrrolidine, 0.210 g of lithium aluminum hydride and 40 ml of tetrahydrofuran.

Nuclear Magnetic Resonance Spectrum (CDCl$_3$, 270 MHz), δ ppm: 1.05–1.3 (1H, multiplet); 1.6–2.3 (6H, multiplet); 2.28 (3H, singlet); 2.7–3.1 (6H, multiplet); 3.75–3.9

(2H, multiplet); 3.78 (3H, singlet); 6.7–6.9 (5H, multiplet); 7.1–7.3 (3H, multiplet).

121(b)  (S)-3-{2-[2-(3-Methoxyphenyl)ethyl]phenoxymethyl}-1-methylpiperidine hydrochloride 1.80 g of (S)-3-{2-[2-(3-methoxyphenyl)ethyl]phenoxymethyl}-1-methylpiperidine [prepared as described in step (a) above], was dissolved in 10 ml of dioxane, and 1.5 ml of a 4N solution of hydrogen chloride in dioxane was added to the solution, which was then concentrated by distillation under reduced pressure. The resulting oil was dissolved in 25 ml of ethyl acetate, and the solution was allowed to stand at room temperature. The crystals which precipitated were collected by filtration and dried in vacuo, to give 1.18 g (yield 59%) of the title compound as colorless crystals, melting at 206°–207° C.

$[\alpha]_D$ –4.48° (c=2.1, methanol).

Nuclear Magnetic Resonance Spectrum (CDCl$_3$, 270 MHz), δ ppm: 1.5–1.75 (1H, multiplet); 1.85–2.05 (2H, multiplet); 2.25–2.7 (2H, multiplet); 2.7–3.0 (6H, multiplet); 2.74 (3H, singlet); 3.4–3.6 (2H, multiplet); 3.78 (3H, singlet); 3.85–4.0 (2H, multiplet); 6.7–6.85 (4H, multiplet); 6.93 (1H, doublet, J=7.2 Hz); 7.1–7.3 (3H, multiplet).

EXAMPLE 122

(R)-3-{2-[2-(3-Methoxyphenyl)ethyl]phenoxymethyl}-1-methylpiperidine hydrochloride 122(a)  (R)-1-t-Butoxycarbonyl-3-{2-[2-(3-methoxyphenyl) ethyl]phenoxymethyl}piperidine Following a procedure similar to that described in Example 36(a), except that a 10:1 by volume mixture of hexane and ethyl acetate was used as the eluent, 0.64 g (yield 69%) of the title compound was obtained as a colorless oil by using 0.53 g of 2-[2-(3-methoxyphenyl)ethyl]phenol (prepared as described in Preparation 20), 0.50 g of (R)-1-t-butoxycarbonyl-3-hydroxymethylpiperidine, 0.67 g of triphenylphosphine, 0.45 g of diethyl azodicarboxylate and 15 ml of methylene chloride.

Nuclear Magnetic Resonance Spectrum (CDCl$_3$, 270 MHz), δ ppm: 1.4–1.8 (3H, multiplet); 1.42 (9H, singlet); 1.85–2.15 (2H, multiplet); 2.75–3.0 (6H, multiplet); 3.78 (3H, singlet); 3.84 (2H, doublet, J=5.9 Hz); 3.85–4.25 (2H, multiplet); 6.7–6.9 (5H, multiplet); 7.1–7.25 (3H, multiplet).

122(b)  (R)-3-{2-[2-(3-Methoxyphenyl)ethyl]phenoxymethyl}-1-methylpiperidine

Following a procedure similar to that described in Example 38(a), 0.430 g (yield 86%) of the title compound was obtained as a colorless oil by using 0.63 g of (R)-1-t-butoxycarbonyl-3-{2-[2-(3-methoxyphenyl)ethyl] phenoxymethyl}piperidine, 0.060 g of lithium aluminum hydride and 12 ml of tetrahydrofuran.

Nuclear Magnetic Resonance Spectrum (CDCl$_3$, 270 MHz), δ ppm: 1.05–1.3 (1H, multiplet); 1.55–2.3 (6H, multiplet); 2.31 (3H, singlet); 2.65–3.1 (6H, multiplet); 3.75–3.95 (2H, multiplet); 3.78 (3H, singlet); 6.7–6.9 (5H, multiplet); 7.1–7.3 (3H, multiplet).

122(c)  (R)-3-{2-[2-(3-Methoxyphenyl)ethyl]phenoxymethyl}-1-methylpiperidine hydrochloride 0.43 g of (R)-3-{2-[2-(3-methoxyphenyl)ethyl]phenoxymethyl}-1-methylpiperidine [prepared as described in step (b) above] was dissolved in 1 ml of dioxane, and 0.38 ml of a 4N solution of hydrogen chloride in dioxane was added to the solution, which was then concentrated by distillation under reduced pressure. The resulting oil was dissolved in 10 ml of ethyl acetate, and the solution was allowed to stand at room temperature. The crystals which precipitated were collected by filtration and dried in vacuo, to give 0.39 g (yield 82%) of the title compound as colorless crystals, melting at 190°–193° C.

$[\alpha]_D$ +4.56° (c=2.41, methanol).

Nuclear Magnetic Resonance Spectrum (CDCl$_3$, 270 MHz), δ ppm: 1.5–1.75 (1H, multiplet); 1.85–2.05 (2H, multiplet); 2.25–2.7 (2H, multiplet); 2.7–3.0 (6H, multiplet); 2.74 (3H, singlet); 3.4–3.6 (2H, multiplet); 3.78 (3H, singlet); 3.85–4.0 (2H, multiplet); 6.7–6.85 (4H, multiplet); 6.93 (1H, doublet, J=7.3 Hz); 7.1–7.3 (3H, multiplet).

EXAMPLE 123

3-{2-[2-(3-Difluoromethoxyphenyl)ethyl] phenoxymethyl}piperidine hydrochloride

123(a)  1-t-Butoxycarbonyl-3-{2-[2-(3-difluoromethoxyphenyl) ethyl]phenoxymethyl}piperidine Following a procedure similar to that described in Example 40(a), 1.55 g (yield 84%) of the title compound was obtained as a colorless oil by using 1.05 g of 2-[2-(3-difluoromethoxyphenyl)ethyl]phenol (prepared as described in Preparation 43), 1.47 g of 1-t-butoxycarbonyl-3-(p-toluenesulfonyloxymethyl)piperidine, 0.45 g of potassium t-butoxide and 20 ml of dimethylacetamide.

Nuclear Magnetic Resonance Spectrum (CDCl$_3$, 270 MHz), δ ppm: 1.35–1.8 (3H, multiplet); 1.42 (9H, singlet); 1.85–2.15 (2H, multiplet); 2.7–3.0 (6H, multiplet); 3.75–4.3 (4H, multiplet); 6.46 (1H, triplet, J=74.6 Hz); 6.8–7.0 (4H, multiplet); 7.0–7.1 (2H, multiplet); 7.1–7.3 (2H, multiplet).

123(b)  3-{2-[2-(3-Difluoromethoxyphenyl)ethyl] phenoxymethyl}piperidine hydrochloride 0.858 g of 1-t-butoxycarbonyl-3-{2-[2-(3-difluoromethoxyphenyl) ethyl]phenoxymethyl}piperidine [prepared as described in step (a) above] was dissolved in 8 ml of dioxane. 8 ml of a 4N solution of hydrogen chloride in dioxane was then added to the solution, whilst ice-cooling, and the solution was allowed to stand at room temperature for 1 hour. At the end of this time, it was concentrated by distillation under reduced pressure, and the resulting oil was dissolved in 50 ml of ethyl acetate. The solution was allowed to stand at room temperature, and the crystals which precipitated were collected by filtration and dried in vacuo, to give 0.680 g (yield 92%) of the title compound as colorless crystals, melting at 153°–154° C.

Nuclear Magnetic Resonance Spectrum (CDCl$_3$, 270 MHz), δ ppm: 1.4–1.65 (1H, multiplet); 1.85–2.2 (3H, multiplet); 2.45–2.65 (1H, multiplet); 2.7–3.0 (6H, multiplet); 2.87 (4H, singlet); 3.4–3.6 (2H, multiplet); 3.8–3.95 (2H, multiplet); 6.49 (1H, triplet, J=73.9 Hz); 6.75–7.35 (8H, multiplet).

EXAMPLE 124

3-{2-[2-(3-Difluoromethoxyphenyl)ethyl] phenoxymethyl}-1-methylpiperidine hydrochloride 124(a)  3-{2-[2-(3-Difluoromethoxyphenyl)ethyl]phenoxymethyl}-1-methylpiperidine Following a procedure similar to that described in Example 38(a), 0.56 g (a quantitative yield) of the title compound was obtained as a colorless oil by using 0.69 g of 1-t-butoxycarbonyl-3-{2-[2-(3-difluoromethoxyphenyl) ethyl]phenoxymethyl}piperidine [prepared as described in Example 123(a)], 0.053 g of lithium aluminum hydride and 10 ml of tetrahydrofuran.

Nuclear Magnetic Resonance Spectrum (CDCl$_3$, 270 MHz), δ ppm: 1.05–1.3 (1H, multiplet); 1.6–2.1 (5H, multiplet); 2.1–2.35 (1H, multiplet); 2.30 (3H, singlet); 2.75–3.1 (6H, multiplet); 3.75–3.95 (2H, multiplet); 6.46 (1H, triplet, J=74.6 Hz); 6.8–7.0 (4H, multiplet); 7.0–7.1 (2H, multiplet); 7.1–7.3 (2H, multiplet).

124(b) 3-{2-[2-(3-Difluoromethoxyphenyl)ethyl]phenoxymethyl}-1-methylpiperidine hydrochloride 0.56 g of 3-{2-[2-(3-difluoromethoxyphenyl)ethyl]phenoxymethyl}-1-methylpiperidine [prepared as described in step (a) above] was dissolved in 5 ml of dioxane, and 0.45 ml of a 4N solution of hydrogen chloride in dioxane was added to the solution, which was then concentrated by distillation under reduced pressure. The resulting solid was dissolved in a small amount of methanol, and about 50 ml of ethyl acetate were added to the solution, which was then allowed to stand at room temperature for one hour. The crystals which precipitated were collected by filtration and dried in vacuo, to give 0.43 g (yield 70%) of the title compound as colorless crystals, melting at 174°–175° C.

Nuclear Magnetic Resonance Spectrum (CDCl$_3$, 270 MHz), δ ppm: 1.45–1.7 (1H, multiplet); 1.85–2.05 (2H, multiplet); 2.3–3.0 (4H, multiplet); 2.76 (3H, singlet); 2.89 (4H, singlet); 3.4–3.6 (2H, multiplet); 3.8–4.05 (2H, multiplet); 6.51 (1H, triplet, J=73.9 Hz); 6.75–7.35 (8H, multiplet).

PREPARATION 1

2-Benzyloxybenzyltriphenylphosphonium chloride 151 g of potassium t-butoxide were added, whilst ice-cooling and stirring, to a solution of 152 g of salicyl alcohol in 600 ml of dimethylformamide, and the resulting mixture was stirred at room temperature for 30 minutes; 160 ml of benzyl bromide were then added dropwise to the mixture. The reaction mixture was then stirred at a temperature of from 30° to 40° C. for 2 hours, after which it was partitioned between ethyl acetate and water. The organic layer was washed twice, each time with a saturated aqueous solution of sodium chloride, dried over anhydrous magnesium sulfate, and concentrated by evaporation under reduced pressure. The oily residue thus obtained was subjected to column chromatography through silica gel, using a 5:1 by volume mixture of hexane and ethyl acetate as the eluent, to give 228.5 g (yield 87%) of 2-benzyloxybenzyl alcohol as a colorless oil.

The whole of the 2-benzyloxybenzyl alcohol thus obtained was dissolved in 500 ml of tetrahydrofuran, and 85 ml of thionyl chloride were added dropwise, whilst ice-cooling, to the resulting solution. The reaction mixture was then allowed to stand overnight at room temperature, after which it was concentrated by evaporation under reduced pressure to give a dark colored oil. This product was dissolved in toluene, and the solution was decolorized by treating it with silica gel for chromatography followed by filtration. The filtrate was concentrated by evaporation under reduced pressure to give 2-benzyloxybenzyl chloride as a yellow oil, which was used in the following reaction without further purification.

The whole of this yellow oil was dissolved in 500 ml of toluene, and 420 g of triphenylphosphine were added to the resulting solution. The mixture was then heated under reflux for 3 hours. In the course of heating, white insoluble materials gradually appeared in the reaction mixture. After the mixture had been cooled, the deposited materials were collected by filtration and dried in vacuo, to give 539.9 g (yield 96%) of the title compound as a colorless solid.

Nuclear Magnetic Resonance Spectrum (CDCl$_3$, 60 MHz) δ ppm: 4.46 (2H, singlet); 5.28 (2H, doublet, J=14.0 Hz); 6.5–8.0 (24H, multiplet).

PREPARATION 2

2-Methoxymethxybenzoyltriphenyltriphenylphosphonium chloride

2(a) 2-Methoxymethoxybenzyl chloride 16.4 ml of carbon tetrachloride, followed by 44.5 g of triphenylphosphine were added, whilst ice-cooling, to a solution of 23.8 g of 2-methoxymethoxybenzyl alcohol in 240 ml of tetrahydrofuran, and the resulting mixture was heated under reflux for 5 hours. At the end of this time, the mixture was cooled, insoluble materials were filtered off and the filtrate was concentrated by evaporation under reduced pressure. The resulting residue was purified by column chromatography through silica gel, using a 9:1 by volume mixture of hexane and ethyl acetate as the eluent, to give 15.5 g (yield 57%) of the title compound as a colorless liquid.

Nuclear Magnetic Resonance Spectrum (CDCl$_3$, 270 MHz), δ ppm: 3.51 (3H, singlet); 4.68 (2H, singlet); 5.26 (2H, singlet); 6.9–7.4 (4H, multiplet).

2(b) 2-Methoxymethoxybenzyltriphenylphosphonium chloride 32 g of triphenylphosphine were added to a solution of 15.0 g of 2-methoxymethoxybenzyl chloride [prepared as described in step (a) above] in 150 ml of toluene, and the resulting mixture was heated under reflux for 14 hours. At the end of this time, the reaction mixture was cooled, and the resulting precipitates were collected by filtration, washed with toluene and dried in vacuo, to give 21.3 g (yield 59%) of the title compound as a colorless solid.

Nuclear Magnetic Resonance Spectrum (hexadeuterated dimethyl sulfoxide, 270 MHz), δ ppm: 3.12 (3H, singlet); 4.65 (2H, singlet); 4.98 (2H, doublet, J=15.2 Hz); 6.84 (1H, triplet, J=7.3 Hz); 6.9–7.1 (2H, multiplet); 7.2–7.35 (1H, multiplet); 7.7–8.0 (15H, multiplet).

PREPARATION 3

2-(4-Phenylbutyl)phenol 5.28 g of cinnamaldehyde and 19.8 g of 2-benzyloxybenzyltriphenylphosphonium chloride (prepared as described in Preparation 1) were dissolved, with heating, in 200 ml of acetonitrile, and then 6 g of 1,8-diazabicyclo[5,4,0]undec-7-ene were added dropwise to the solution. The resulting mixture was then heated under reflux for 3 hours. At the end of this time, the solvent was removed by distillation under reduced pressure, and the resulting residue was partitioned between ethyl acetate and water. The organic layer was dried over anhydrous magnesium sulfate, and concentrated by evaporation under reduced pressure. The oily residue thus obtained was again dissolved in 200 ml of ethyl acetate, with heating, and 50 ml of hexane was added to the solution, after which deposited insoluble materials were filtered off. The filtrate was concentrated by evaporation under reduced pressure, and the resulting residue was purified by column chromatography through silica gel, using a 9:1 by volume mixture of hexane and ethyl acetate as the eluent, to give 12.2 g (yield 97.7%) of 1-(2-benzyloxyphenyl)-4-phenylbutadiene as a colorless oil.

The whole of this 1-(2-benzyloxyphenyl)-4-phenylbutadiene was mixed with 300 ml of ethanol, and the mixture was stirred at 60° C. for 5 hours in an atmosphere of hydrogen and in the presence of 1 g of 5% w/w palladium-on-charcoal. At the end of this time, the catalyst was removed by filtration, and the filtrate was concentrated by evaporation under reduced pressure. The resulting residue was purified by column chromatography through silica gel, using a 8:1 by volume mixture of hexane and ethyl acetate as the eluent, to give 8.34 g (yield 94.4%) of the title compound as a colorless solid.

Nuclear Magnetic Resonance Spectrum (CDCl$_3$, 60 MHz), δ ppm: 1.6–1.9 (4H, multiplet); 2.4–2.9 (4H, multiplet); 4.64 (1H, singlet); 6.5–7.5 (9H, multiplet).

PREPARATION 4

2-[4-(2-Methoxyphenyl)butyl]phenol

A solution of 980 mg of ethyl 2-methoxycinnamate in 15 ml of tetrahydrofuran was added dropwise to a dispersion of 290 mg of lithium aluminum hydride and 10 ml of tetrahydrofuran, whilst ice-cooling. After the addition was complete, the reaction mixture was stirred at room temperature for 1.5 hours, and then sufficient sodium sulfate decahydrate was slowly added, whilst ice-cooling, to the mixture in order to decompose any excess of the hydride. Insoluble materials were filtered off, and the filtrate was concentrated by distillation under reduced pressure. The resulting residue was purified by column chromatography through silica gel, using a 3:1 by volume mixture of hexane and ethyl acetate as the eluent, to give 640 mg of 3-(2-methoxyphenyl)propanol as a colorless oil.

Meanwhile, a solution of 760 mg of dimethyl sulfoxide in 2 ml of methylene chloride was added dropwise to a solution of 740 mg of oxalyl chloride in 12 ml of methylene chloride at −60° C., with stirring, and the mixture was stirred at the same temperature for 10 minutes. At the end of this time, a solution of 640 mg of 3-(2-methoxyphenyl)propanol (prepared as described above) in 3 ml of methylene chloride was added dropwise to the mixture, and the mixture was stirred for a further 10 minutes. 1.96 g of triethylamine were then slowly added dropwise to the mixture at the same temperature. The cooling bath was removed, and the reaction mixture was stirred at room temperature for 30 minutes and then mixed with water. The methylene chloride layer was separated, dried over anhydrous magesium sulfate, and concentrated by evaporation under reduced pressure. The oily residue thus obtained was purified by column chromatography through silica gel, using a 5:1 by volume mixture of hexane and ethyl acetate as the eluent, to give 540 mg of 3-(2-methoxyphenyl)propanal as a colorless oil.

Nuclear Magnetic Resonance Spectrum (CDCl$_3$, 270 MHz), δ ppm: 2.72 (2H, triplet, J=7.3 Hz); 2.95 (2H, triplet, J=7.3 Hz); 3.82 (3H, singlet); 6.8–6.95 (2H, multiplet); 7.1–7.3 (2H, multiplet); 9.80 (1H, singlet).

Following a procedure similar to that described in the first part of Preparation 3, the whole of the 3-(2-methoxyphenyl)propanal prepared as described above, 1.65 g of 2-benzyloxybenzyltriphenylphosphonium chloride (prepared as described in Preparation 1) and 1.01 g of 1,8-diazabicyclo[5,4,0]undec-7-ene were reacted in 30 ml of acetonitrile. The crude product, extracted as described in Preparation 3, was purified by column chromatography through silica gel, using a 9:1 by volume mixture of hexane and ethyl acetate as the eluent, to give 0.98 g of benzyl 2-[4-(2-methoxyphenyl)-1-butenyl]phenyl ether as a colorless oil.

Following a procedure similar to that described in the latter part of Preparation 3, the whole of the benzyl 2-[4-(2-methoxyphenyl)-1-butenyl]phenyl ether prepared as described above was dissolved in 50 ml of ethanol and hydrogenated at 50° C. in an atmosphere of hydrogen at atmospheric pressure and in the presence of 100 mg of 5% w/w palladium-on-charcoal for 6 hours. The crude product thus obtained was purified by column chromatography through silica gel, using 10:1 by volume mixture of hexane and ethyl acetate as the eluent, to give 0.44 g (yield 60%) of the title compound as a colorless oil.

Nuclear Magnetic Resonance Spectrum (CDCl$_3$, 270 MHz), δ ppm: 1.6–1.75 (4H, multiplet); 2.55–2.7 (4H, multiplet); 3.80 (3H, singlet); 4.75 (1H, singlet); 6.7–7.3 (8H, multiplet).

PREPARATION 5

2-[4-(3-Methoxymethoxyphenyl)butyl]phenol 11.2 g of potassium t-butoxide were added, whilst ice-cooling and stirring, to a solution of 12.0 g of 3-hydroxybenzaldehyde in 100 ml of dimethylacetamide, and, about ten minutes later, 8.05 g of methoxymethyl chloride were added dropwise to the resulting mixture. The reaction mixture was then stirred at room temperature for 1 hour, after which it was partitioned between ethyl acetate and water. The organic layer was concentrated by distillation under reduced pressure, and the residue was purified by column chromatography through silica gel, using a 5:1 by volume mixture of hexane and ethyl acetate as the eluent, to give 11.1 g (yield 68%) of 3-methoxymethoxybenzaldehyde as a colorless oil. 10 g of this colorless oil were dissolved in 100 ml of acetonitrile, and 18.3 g of (triphenylphosphoranylidene)acetaldehyde were added to the solution. The resulting mixture was then heated under reflux for 5 hours. At the end of this time, the solvent was removed by distillation under reduced pressure, and the residue was mixed with a mixture of ethyl acetate and hexane in a proportion of about 2:1 by volume. The mixture was stirred and the resulting precipitates were filtered off. The filtrate was concentrated by distillation under reduced pressure, and the residue was purified by column chromatography through silica gel, using a 3:1 by volume mixture of hexane and ethyl acetate as the eluent, to give 7.16 g (yield 62%) of 3-(3-methoxymethoxyphenyl)-2-propenal as a colorless oil.

Following a procedure similar to that described in the first part of Preparation 3, 7.00 g of 3-(3-methoxymethoxyphenyl)-2-propenal and 18 g of 2-benzyloxybenzyltriphenylphosphonium chloride (prepared as described in Preparation 1) were dissolved in 200 ml of acetonitrile, with heating, and 5.54 g of 1,8-diazabicyclo[5,4,0]undec-7-ene were added to the mixture and reacted. The crude product, extracted as described in Preparation 3, was purified as described in Preparation 3, to give 12.0 g of 1-(2-benzyloxyphenyl)-4-(3-methoxymethoxyphenyl)butadiene as a colorless oil.

The whole of this colorless oil was dissolved in 250 ml of ethanol, and the resulting solution was stirred for 5 hours at 50° C. in an atmosphere of hydrogen at atmospheric pressure and in the presence of 500 mg of 5% w/w palladium-on-charcoal. At the end of this time, the catalyst was removed by filtration, and the filtrate was concentrated by distillation under reduced pressure. The resulting residue was purified by column chromatography through silica gel, using a 3:1 by volume mixture of hexane and ethyl acetate as the eluent, to give 8.46 g (yield 91%) of the title compound as a colorless oil.

Nuclear Magnetic Resonance Spectrum (CDCl$_3$, 270 MHz), δ ppm: 1.6–1.75 (4H, multiplet); 2.55–2.7 (4H, multiplet); 3.49 (3H, singlet); 4.73 (1H, singlet); 5.17 (2H, singlet); 6.74 (1H, doublet, J=7.9 Hz); 6.8–6.95 (4H, multiplet); 7.05–7.25 (3H, multiplet).

PREPARATIONS 6 to 12

The following phenol derivatives were synthesized in a similar manner to those described in Preparations 3 and 4.

PREPARATION 6

2-[4-(4-Methylphenyl)butyl]phenol

Nuclear Magnetic Resonance Spectrum (CDCl$_3$, 270 MHz), δ ppm: 1.6–1.8 (4H, multiplet); 2.31 (3H, singlet); 2.55–2.7 (4H, multiplet); 4.64 (1H, singlet); 6.74 (1H, doublet, J=7.3 Hz); 6.85 (1H, triplet, J=7.6 Hz); 7.05–7.11 (6H, multiplet).

PREPARATION 7

2-[4-(3-Methoxyphenyl)butyl]phenol

Nuclear Magnetic Resonance Spectrum (CDCl$_3$, 270 MHz), δ ppm: 1.6–1.8 (4H, multiplet); 2.63 (4H, triplet, J=6.9 Hz); 3.79 (3H, singlet); 4.72 (1H, singlet); 6.65–6.8 (4H, multiplet); 6.85 (1H, triplet, J=7.9 Hz); 7.0–7.25 (3H, multiplet).

PREPARATION 8

2-[4-(4-Isopropylphenyl)butyl]phenol

Nuclear Magnetic Resonance Spectrum (CDCl$_3$, 270 MHz), δ ppm: 1.24 (6H, doublet, J=7.3 Hz); 1.65–1.8 (4H, multiplet); 2.55–2.7 (4H, multiplet); 2.8–3.0 (1H, multiplet); 4.65 (1H, singlet); 6.74 (1H, doublet, J=7.9 Hz); 6.85 (1H, triplet, J=7.6 Hz); 7.0–7.2 (6H, multiplet).

PREPARATION 9

2-[4-(3,5-Dimethoxyphenyl)butyl]phenol

Nuclear Magnetic Resonance Spectrum (CDCl$_3$, 60 MHz) δ ppm: 1.6–1.9 (4H, multiplet); 2.4–2.8 (4H, multiplet); 3.77 (6H, singlet); 4.70 (1H, singlet); 6.33 (3H, singlet); 6.6–7.3 (4H, multiplet).

PREPARATION 10

2-[4-(3-Methylphenyl)butyl]phenol

Nuclear Magnetic Resonance Spectrum (CDCl$_3$, 270 MHz), δ ppm: 1.6–1.8 (4H, multiplet); 2.32 (3H, singlet); 2.5–2.7 (4H, multiplet); 4.60 (1H, singlet); 6.74 (1H, doublet, J=6.6 Hz); 6.86 (1H, triplet, J=7.3 Hz); 6.9–7.4 (6H, multiplet).

PREPARATION 11

2-[4-(2-Cyanophenyl)butyl]phenol

Nuclear Magnetic Resonance Spectrum (CDCl$_3$, 60 MHz) δ ppm: 1.5–2.0 (4H, multiplet); 2.4–3.0 (4H, multiplet); 5.20 (1H, broad singlet); 6.5–7.7 (8H, multiplet).

PREPARATION 12

2-[4-(4-Methoxyphenyl)butyl]phenol

Nuclear Magnetic Resonance Spectrum (CDCl$_3$, 270 MHz), δ ppm: 1.55–1.75 (4H, multiplet); 2.5–2.7 (4H, multiplet); 3.78 (3H, singlet); 4.73 (1H, singlet); 6.7–6.9 (4H, multiplet); 7.0–7.2 (4H, multiplet).

PREPARATION 13

2-(3-Methyl-4-phenylbutyl)phenol

Following a procedure similar to that described in the first part of Preparation 3, 1.32 g of α-methylcinnamaldehyde, 4.47 g of 2-benzyloxybenzyltriphenylphosphonium chloride (prepared as described in Preparation 1) and 1.37 g of 1,8-diazabicyclo[5,4,0]-undec-7-ene were reacted in acetonitrile. The crude product thus obtained was purified as described in the first part of Preparation 3, to give 2.66 g (yield 90%) of 1-(2-benzyloxyphenyl)-3-methyl-4-phenylbutadiene as a colorless oil.

Then, following a procedure similar to that described in the latter part of Preparation 3, the whole of this 1-(2-benzyloxyphenyl)-3-methyl-4-phenylbutadiene was hydrogenated, to give 1.87 g (yield 95%) of the title compound as a colorless oil.

Nuclear Magnetic Resonance Spectrum (CDCl$_3$, 270 MHz), δ ppm: 0.94 (3H, doublet, J=6.6 Hz); 1.4–1.9 (3H, multiplet); 2.43 (1H, doublet of doublets, J=7.9 & 13.2 Hz); 2.5–2.8 (3H, multiplet); 4.57 (1H, singlet); 6.74 (1H, doublet, J=7.9 Hz); 6.86 (1H, triplet, J=7.9 Hz); 7.05–7.35 (7H, multiplet).

PREPARATION 14

2-[4-(2-Benzyloxyphenyl)-1-buten-1-yl]phenol

Following a procedure similar to that described in the first part of Preparation 3, 2.51 g of 3-(2-benzyloxyphenyl)propanal, 5.6 g of 2-methoxymethoxybenzylphosphonium chloride (prepared as described in Preparation 2) and 1.91 g of 1,8-diazabicyclo[5,4,0]-undec-7-ene were reacted in 50 ml of acetonitrile. The crude product, extracted as described in the first part of Preparation 3, was purified by column chromatography through silica gel, using a 10:1 by volume mixture of hexane and ethyl acetate as the eluent, to give 2.52 g (yield 64%) of 1-(2-methoxymethoxyphenyl)-4-(2-benzyloxyphenyl)-1-butene as a colorless oil.

The whole of this colorless oil was dissolved in 20 ml of methylene chloride. 5 ml of a 4N solution of hydrogen chloride in dioxane were then added to the solution, and the resulting mixture was allowed to stand at room temperature for 30 minutes, after which it was concentrated by distillation under reduced pressure. The oily residue thus obtained was purified by column chromatography through silica gel, using a 5:1 by volume mixture of hexane and ethyl acetate as the eluent, to give 1.60 g (yield 72%) of the title compound as a colorless oil.

Nuclear Magnetic Resonance Spectrum (CDCl$_3$, 270 MHz; cis-trans mixture) δ ppm: 2.5–2.9 (4H, multiplet); 4.82 & 4.91 (together 1H, each singlet); 5.00 & 5.10 (together 2H, each singlet); 5.9–7.5 (15H, multiplet).

PREPARATION 15

2-[4-(2-Naphthyl)butyl]phenol

A solution of 3.00 g of 2-naphthaldehyde and 6.69 g of ethoxycarbonylmethylenetriphenylphosphorane in 100 ml of acetonitrile was heated under reflux for 1 hour, after which the reaction mixture was concentrated by evaporation under reduced pressure. The resulting residue was purified by column chromatography through silica gel, using 4:1 by volume mixture of hexane and ethyl acetate as the eluent, to give 4.32 g (yield 99%) of ethyl 3-(2-naphthyl)-2-propenoate as a colorless solid.

4.29 g of this ethyl 3-(2-naphthyl)-2-propenoate were dissolved in 60 ml of ethanol. The solution was stirred at room temperature for 3 hours in an atmosphere of hydrogen at atmospheric pressure and in the presence of 500 mg of 5% w/w palladium-on-charcoal. At the end of this time, the catalyst was removed by filtration, and the filtrate was concentrated by distillation under reduced pressure. The resulting residue was purified by column chromatography through silica gel, using a 5:1 by volume mixture of hexane and ethyl acetate as the eluent, to give 4.04 g (yield 93%) of ethyl 3-(2-naphthyl)propionate as a colorless oil.

Following a procedure similar to that described in the first part of Preparation 4, the whole of this ethyl 3-(2-naphthyl)propionate was reacted with 668 mg of lithium aluminum hydride in tetrahydrofuran at room temperature for 1.5 hours. At the end of this time, the reaction mixture was worked up and purified as described in the first part of Preparation 4, to give 3.29 g of 3-(2-naphthyl)propanol as a colorless oil.

Then, following a procedure similar to that described in the second part of Preparation 4, the whole of this 3-(2-naphthyl)propanol was reacted with 2.06 g of dimethyl sulfoxide, 3.35 g of oxalyl chloride and 7.34 ml of triethylamine in 45 ml of methylene chloride. The reaction mixture was worked up and purified as described in the second part of Preparation 4, to give 1.74 g (yield 53%) of 3-(2-naphthyl)propanal as a colorless oil.

Nuclear Magnetic Resonance Spectrum (CDCl$_3$, 270 MHz), δ ppm: 2.86 (2H, triplet, J=7.9 Hz); 3.12 (2H, triplet, J=7.9 Hz); 7.2–7.9 (7H, multiplet); 9.85 (1H, singlet).

Following a procedure similar to that described in the first part of Preparation 3, 1.73 g of 3-(2-naphthyl)propanal prepared as described above, 4.65 g of 2-benzyloxybenzyltriphenylphosphonium chloride (prepared as described in Preparation 1) and 2.15 g of 1,8-diazabicyclo[5,4,0]undec-7-ene were reacted in 200 ml of acetonitrile. The reaction mixture was worked up and purified as described in the first part of Preparation 3, to obtain 2.83 g (yield 82%) of 4-(2-naphthyl)-1-(2-benzyloxyphenyl)-1-butene as a colorless oil.

The whole of this 4-(2-naphthyl)-1-(2-benzyloxyphenyl)-1-butene was catalytically reduced in a similar manner to that described above in the second part of this Preparation, to give 2.60 g of 4-(2-naphthyl)-1-(2-benzyloxyphenyl)butane as an oil.

The whole of this 4-(2-naphthyl)-1-(2-benzyloxyphenyl)butane was dissolved in 20 ml of methylene chloride, and 9.5 ml of a 1M solution of boron tribromide in methylene chloride were added, whilst ice-cooling and stirring, to the solution. The resulting mixture was then stirred at the same temperature for 1 hour. At the end of this time, the reaction mixture was diluted with methylene chloride, washed with water, dried over anhydrous sodium sulfate, and concentrated by evaporation under reduced pressure. The resulting residue was purified by column chromatography through silica gel, using a 4:1 by volume mixture of hexane and ethyl acetate as the eluent, to give 1.56 g (yield 78%) of the title compound as colorless solid.

Nuclear Magnetic Resonance Spectrum (CDCl$_3$, 270 MHz), δ ppm: 1.6–1.9 (4H, multiplet); 2.65 (2H, triplet, J=7.6 Hz); 2.81 (2H, triplet, J=6.9 Hz); 4.64 (1H, singlet); 6.73 (1H, doublet, J=7.9 Hz); 6.85 (1H, triplet, J=7.9 Hz); 7.0–7.9 (9H, multiplet).

PREPARATION 16

2-[4-(1-Naphthyl)butyl]phenol

Following a procedure similar to that described in Preparation 15, but using 3.0 g of 1-naphthaldehyde and 6.69 g of carboethoxymethylenetriphenylphosphorane, 0.88 g of the title compound was obtained as a colorless solid.

Nuclear Magnetic Resonance Spectrum (CDCl$_3$, 270 MHz), δ ppm: 1.7–1.9 (4H, multiplet); 2.68 (2H, triplet, J=7.3 Hz); 3.12 (2H, triplet, J=7.3 Hz); 4.73 (1H, singlet); 6.76 (1H, doublet, J=6.6 Hz); 6.87 (1H, triplet, J=7.3 Hz); 7.0–7.6 (6H, multiplet); 7.71 (1H, doublet, J=7.9 Hz); 7.8–7.95 (1H, multiplet); 8.0–8.1 (1H, multiplet).

PREPARATION 17

2-[4-(3-Chlorophenyl)butyl]phenol

A solution of 3.00 g of 3-chlorobenzaldehyde and 6.49 g of (triphenylphosphoranylidene)acetaldehyde in 100 ml of acetonitrile was heated under reflux for 5 hours. At the end of this time, the reaction mixture was concentrated by evaporation under reduced pressure, and the resulting residue was purified by column chromatography through silica gel, using a 4:1 by volume mixture of hexane and ethyl acetate as the eluent, to give 2.11 g (yield 59%) of 3-(3-chlorophenyl)-2-propenal as a solid.

Following a procedure similar to that described in the first part of Preparation 3, the whole of this 3-(3-chlorophenyl)-2-propenal was reacted with 6.9 g of 2-benzyloxybenzyltriphenylphosphonium chloride (prepared as described in Preparation 1) and 2.89 g of 1,8-diazabicyclo[5,4,0]undec-7-ene in 100 ml of acetonitrile. The crude product, extracted as described in the first part of Preparation 3, was purified as described in the first part of Preparation 3, to give 4.13 g (yield 94%) of 1-(2-benzyloxyphenyl)-4-(3-chlorophenyl)butadiene as an oil.

3.50 g of this 1-(2-benzyloxyphenyl)-4-(3-chlorophenyl)butadiene were dissolved in 125 ml of a 4:1 by volume mixture of tetrahydrofuran and ethanol. The resulting solution was stirred for 4 hours in an atmosphere of hydrogen at atmospheric pressure and in the presence of 100 mg of 5% w/w palladium-on-charcoal, whilst ice-cooling. At the end of this time, the catalyst was removed by filtration, and the filtrate was concentrated by evaporation under reduced pressure. The resulting residue was then purified by column chromatography through silica gel, using a 4:1 by volume mixture of hexane and ethyl acetate as the eluent, to give 3.06 g (yield 86%) of 1-(2-benzyloxyphenyl)-4-(3-chlorophenyl)butane as a colorless oil.

Following a procedure similar to that described in the final part of Preparation 15, a solution of 3.04 g of this 1-(2-benzyloxyphenyl)-4-(3-chlorophenyl)butane in 18 ml of methylene chloride was treated with 8.67 ml of a 1M solution of boron tribromide in methylene chloride to eliminate the benzyl group. The resulting crude product was purified by column chromatography through silica gel, using a 4:1 by volume mixture of hexane and ethyl acetate as the eluent, to give 1.82 g (yield 80%) of the title compound as a colorless oil.

Nuclear Magnetic Resonance Spectrum (CDCl$_3$, 270 MHz), δ ppm: 1.55–1.8 (4H, multiplet); 2.55–2.75 (4H, multiplet); 4.64 (1H, singlet); 6.74 (1H, doublet, J=7.9 Hz); 6.86 (1H, triplet, J=7.6 Hz); 7.0–7.3 (6H, multiplet).

PREPARATION 18

2-[4-(2-Chlorophenyl)butyl]phenol

Following a procedure similar to that described in the first part of Preparation 17, 3.00 g of 2-chlorobenzaldehyde and 7.5 g of (triphenylphosphoranylidene)acetaldehyde were reacted in 100 ml of acetonitrile. The crude product thus obtained was purified by column chromatography through silica gel, using a 4:1 by volume mixture of hexane and ethyl acetate as the eluent, to give 2.44 g (yield 68%) of 3-(2-chlorophenyl)-2-propenal as a solid.

Then, following a procedure similar to that described in the first part of Preparation 3, the whole of this 3-(2-chlorophenyl)-2-propenal was reacted with 7.97 g of 2-benzyloxybenzyltriphenylphosphonium chloride (prepared as described in Preparation 1) and 3.35 g of 1,8-diazabicyclo[5,4,0]undec-7-ene. The resulting crude product was purified as described in the first part of Preparation 3, to give 4.57 g (yield 90%) of 1-(2-benzyloxyphenyl)-4-(2-chlorophenyl)butadiene as an oil.

Following a procedure similar to that described in the latter part of Preparation 3, 4.53 g of this 1-(2-benzyloxyphenyl)-4-(2-chlorophenyl)butadiene were dissolved in a 4:1 by volume mixture of tetrahydrofuran and ethanol and were hydrogenated, whilst ice-cooling. The reaction mixture was then worked up as described in the latter part of Preparation 3, to give 2.86 g (yield 62%) of 1-(2-benzyloxyphenyl)-4-(2-chlorophenyl)butane.

Finally, following a procedure similar to that described in the final part of Preparation 15, the whole of this 1-(2-benzyloxyphenyl)-4-(2-chlorophenyl)butane was dissolved in 18 ml of methylene chloride and debenzylated by means of 8.15 ml of a 1M solution of boron tribromide in methylene chloride. The crude product thus obtained was purified by column chromatography through silica gel, using a 4:1 by volume mixture of hexane and ethyl acetate as the eluent, to give 2.0 g (yield 94%) of the title compound as a colorless solid.

Nuclear Magnetic Resonance Spectrum (CDCl$_3$, 270 MHz), δ ppm: 1.55–1.8 (4H, multiplet); 2.5–2.9 (4H, multiplet); 4.66 (1H, singlet); 6.75 (1H, doublet, J=8.6 Hz); 6.86 (1H, triplet, J=7.3 Hz); 7.0–7.4 (6H, multiplet).

PREPARATION 19

2-(2-Phenylethyl)phenol 5.09 g of benzaldehyde and 26.1 g of 2-benzyloxybenzyltriphenylphosphonium chloride (prepared as described in Preparation 1) were dissolved in 100 ml of acetonitrile, with heating. 8.04 g of 1,8-diazabicyclo[5.4.0]undec-7-ene were then added dropwise to the solution at 80° C., whilst stirring, and the resulting mixture was stirred at the same temperature for 40 minutes. At the end of this time, the solvent was removed by distillation under reduced pressure, and the resulting residue was partitioned between ethyl acetate and water. The organic layer was concentrated by distillation under reduced pressure, and 100 ml of a 2:1 by volume mixture of hexane and ethyl acetate were added to the resulting residue, and the mixture was agitated. Insoluble materials were filtered off, and the filtrate was concentrated by distillation under reduced pressure. The resulting residue was purified by column chromatography through silica gel, using a 30:1 by volume mixture of hexane and ethyl acetate as the eluent, to give 10.4 g (yield 76%) of 2-benzyloxystilbene.

The whole of this 2-benzyloxystilbene was dissolved in 300 ml of ethanol, and the resulting solution was stirred at 60° C. for 3.5 hours in an atmosphere of hydrogen at atmospheric pressure and in the presence of 1.00 g of 5% w/w palladium-on-charcoal. The catalyst was removed by filtration, and the filtrate was concentrated by distillation under reduced pressure. The resulting residue was then purified by column chromatography through silica gel, using a 4:1 by volume mixture of hexane and ethyl acetate as the eluent, to give 6.41 g (yield 89%) of the title compound as a colorless solid.

Nuclear Magnetic Resonance Spectrum (CDCl$_3$, 270 MHz), δ ppm: 2.92 (4H, singlet); 4.64 (1H, singlet); 6.74 (1H, doublet, J=7.9 Hz); 6.86 (1H, triplet, J=7.3 Hz); 7.0–7.4 (7H, multiplet).

PREPARATIONS 20 TO 28

Following a procedure similar to that described in Preparation 19, the following phenol derivatives were synthesized using the corresponding aldehyde and 2-benzyloxybenzyltriphenylphosphonium chloride (prepared as described in Preparation 1).

PREPARATION 20

2-[2-(3-Methoxyphenyl)ethyl]phenol

Nuclear Magnetic Resonance Spectrum (CDCl$_3$, 270 MHz), δ ppm: 2.91 (4H, singlet); 3.79 (3H, singlet); 4.65 (1H, singlet); 6.7–6.95 (5H, multiplet); 7.05–7.3 (3H, multiplet).

PREPARATION 21

2-[2-(3-Methoxymethoxyphenyl)ethyl]phenol

Nuclear Magnetic Resonance Spectrum (CDCl$_3$, 270 MHz), δ ppm: 2.90 (4H, singlet); 3.47 (3H, singlet); 4.78 (1H, singlet); 5.15 (2H, singlet); 6.73 (1H, doublet, J=7.9 Hz); 6.8–6.95 (4H, multiplet); 7.0–7.3 (3H, multiplet).

PREPARATION 22

2-[2-(3,4-Dimethoxyphenyl)ethyl]phenol

Nuclear Magnetic Resonance Spectrum (CDCl$_3$, 270 MHz), δ ppm: 2.8–3.0 (4H, multiplet); 3.81 (3H, singlet); 3.86 (3H, singlet); 4.71 (1H, singlet); 6.6–6.9 (5H, multiplet); 7.05–7.15 (2H, multiplet).

PREPARATION 23

2-[2-(2-Methoxyphenyl)ethyl]phenol

Nuclear Magnetic Resonance Spectrum (CDCl$_3$, 270 MHz), δ ppm: 2.7–2.9 (4H, multiplet); 3.94 (3H, singlet); 6.25 (1H, singlet); 6.7–7.0 (4H, multiplet); 7.05–7.3 (4H, multiplet).

PREPARATION 24

2-[2-(2-Methylphenyl)ethyl]phenol

Nuclear Magnetic Resonance Spectrum (CDCl$_3$, 270 MHz), δ ppm: 2.31 (3H, singlet); 2.8–3.0 (4H, multiplet); 4.70 (1H, singlet); 6.74 (1H, doublet, J=7.9 Hz); 6.87 (1H, triplet, J=7.6 Hz); 7.0–7.2 (6H, multiplet).

PREPARATION 25

2-[2-(3-Methylphenyl)ethyl]phenol

Nuclear Magnetic Resonance Spectrum (CDCl$_3$, 270 MHz), δ ppm: 2.33 (3H, singlet); 2.89 (4H, singlet); 4.63 (1H, singlet); 6.75 (1H, doublet, J=7.9 Hz); 6.87 (1H, triplet, J=7.9 Hz); 7.0–7.25 (6H, multiplet).

PREPARATION 26

2-[2-(4-Ethylphenyl)ethyl]phenol

Nuclear Magnetic Resonance Spectrum (CDCl$_3$, 270 MHz), δ ppm: 1.23 (3H, triplet, J=7.6 Hz); 2.63 (2H, quartet, J=7.6 Hz); 2.89 (4H, singlet); 4.64 (1H, singlet); 6.75 (1H, doublet, J=7.9 Hz); 6.87 (1H, triplet, J=7.6 Hz); 7.05–7.2 (6H, multiplet).

PREPARATION 27

2-[2-(3,5-Dimethoxyphenyl)ethyl]phenol

Nuclear Magnetic Resonance Spectrum (CDCl$_3$, 270 MHz), δ ppm: 2.8–3.0 (4H, multiplet); 3.75 (6H, singlet); 4.78 (1H, singlet); 6.3–6.4 (3H, multiplet); 6.74 (1H, doublet, J=8.6 Hz); 6.86 (1H, triplet, J=8.6 Hz); 7.05–7.2 (2H, multiplet).

PREPARATION 28

2-[2-(3,4,5-Trimethoxyphenyl)ethyl]phenol

Nuclear Magnetic Resonance Spectrum (CDCl$_3$, 270 MHz, δ ppm: 2.8–3.0 (4H, multiplet); 3.81 (6H, singlet); 3.83 (3H, singlet); 4.76 (1H, singlet); 6.38 (2H, singlet); 6.75 (1H, doublet, J=9.9 Hz); 6.86 (1H, triplet, J=6.9 Hz); 7.05–7.15 (2H, multiplet).

PREPARATION 29

2-(3-Phenylpropyl)phenol

Following a procedure similar to that described in the first part of Preparation 3, except that a 8:1 by volume mixture of hexane and ethyl acetate was used as the eluent, 0.390 g of benzyl 2-(3-phenyl-1-propenyl)phenyl ether was obtained by using 0.480 g of phenylacetaldehyde, 1.98 g of 2-benzyloxybenzyl triphenylphosphonium chloride, 20 ml of acetonitrile and 0.609 g of 1,8-diazabicyclo[5.4.0]undec-7-ene.

The whole of this benzyl 2-(3-phenyl-1-propenyl)phenyl ether was treated with hydrogen in the presence of 100 mg of 5% w/w palladium-on-carbon in 40 ml of ethanol at room temperature for 3 hours. At the end of this time, insoluble materials were removed by filtration, and the filtrate was concentrated by distillation under reduced pressure, to give 0.230 g (yield 83%) of the title compound as a colorless oil.

Nuclear Magnetic Resonance Spectrum (CDCl$_3$, 60 MHz), δ ppm: 1.6–2.2 (2H, multiplet); 2.4–3.0 (4H, multiplet); 4.3–5.2 (1H, broad); 6.6–7.4 (9H, multiplet).

PREPARATION 30

2-(7-Phenylheptyl)phenol

Following a procedure similar to that described in the first part of Preparation 3, 1.92 g of 1-benzyloxy-6-phenyl-3,5-hexadiene were obtained as a colorless oil by using 1.32 g of cinnamaldehyde, 4.91 g of 3-benzyloxypropyl triphenylphosphonium bromide, 25 ml of acetonitrile and 1.6 g of 1,8-diazabicyclo[5.4.0]undec-7-ene.

The whole of this 1-benzyloxy-6-phenyl-3,5-hexadiene was then treated with hydrogen in the presence of 250 mg of 5% w/w palladium-on-carbon in 40 ml ethanol at room temperature for 15 hours, the catalyst was removed by filtration and the filtrate was concentrated by distillation under reduced pressure. The resulting residue was purified by column chromatography through silica gel, using a 2:1 by volume mixture of hexane and ethyl acetate as the eluent, to give 1.14 g (yield 88%) of 6-phenylhexanol as an oil.

A procedure similar to that described in the second step of Preparation 4 was then repeated, except that a 5:1 by volume mixture of hexane and ethyl acetate was used as the eluent, to give 1.08 g of 6-phenylhexanal as an oil from 1.14 g of the 6-phenylhexanol (prepared as described above), 0.893 g of oxalyl chloride, 1.10 g of dimethyl sulfoxide, 3.24 g of triethylamine and 18 ml of methylene chloride.

Following a procedure similar to that described in the first step of Preparation 3, 2.00 g of benzyl 2-(7-phenyl-1-heptenyl)phenyl ether were obtained by using 1.08 g of the 6-phenylhexanal (prepared as described above), 3.34 g of 2-benzyloxybenzyltriphenylphosphonium chloride (prepared as described in Preparation 1), 30 ml of acetonitrile and 1.03 g of 1,8-diazabicyclo[5.4.0]undec-7-ene.

The whole of this benzyl 2-(7-phenyl-1-heptenyl)phenyl ether was then treated with hydrogen in the presence of 200 mg of 5% w/w palladium-on-carbon in 250 ml of ethanol at 50° C. for 5 hours at atmospheric pressure. At the end of this time, insoluble materials were removed by filtration, and the filtrate was concentrated by distillation under reduced pressure. The resulting residue was purified by column chromatography through silica gel, using a 5:1 by volume mixture of hexane and ethyl acetate as the eluent, to give 1.03 g (yield 69%) of the title compound as a colorless oil.

Nuclear Magnetic Resonance Spectrum (CDCl$_3$, 60 MHz), δ ppm: 1.2–2.0 (10H, multiplet); 2.3–2.9 (4H, multiplet); 4.56 (1H, singlet); 6.5–7.4 (9H, multiplet).

PREPARATION 31

2-(5-Phenylpentyl)phenol

Following a procedure similar to that described in the second step of Preparation 4, 4-phenylbutanal was prepared in a 62% yield from 4-phenylbutanol.

A procedure similar to that described in the first step of Preparation 3 was then repeated, except that the whole of this 4-phenylbutanal was treated to give benzyl 2-(5-phenyl-1-pentenyl)phenyl ether in a 67% yield, and this was hydrogenated, as described in the last step of Preparation 31, to give the title compound in a 70% yield.

Nuclear Magnetic Resonance Spectrum (CDCl$_3$, 270 MHz), δ ppm: 1.35–1.5 (2H, multiplet); 1.5–1.75 (4H, multiplet); 2.55–2.7 (4H, multiplet); 4.73 (1H, singlet); 6.75 (1H, doublet, J=7.9 Hz); 6.86 (1H, triplet, J=6.9 Hz); 7.05–7.35 (7H, multiplet).

PREPARATION 32

2-(6-Phenylhexyl)phenol

Following a procedure similar to that described in the second step of Preparation 4, 5-phenylpentanal was prepared in a 77% yield from 5-phenylpentanol.

A procedure similar to that described in the first step of Preparation 3 was repeated, except that 5-phenylpentanal was treated to give benzyl 2-(6-phenyl-1-hexenyl)phenyl ether in a 67% yield, and this was then hydrogenated, as described in the last step of Preparation 31, to give the title compound in a 80% yield.

Nuclear Magnetic Resonance Spectrum (CDCl$_3$, 270 MHz), δ ppm: 1.3–1.5 (4H, multiplet); 1.5–1.7 (4H, multiplet); 2.5–2.7 (4H, multiplet); 4.66 (1H, singlet); 6.74 (1H, doublet, J=7.9 Hz); 6.86 (1H, triplet, J=6.9 Hz); 7.05–7.4 (7H, multiplet).

PREPARATIONS 33 TO 43

Following a procedure similar to that described in Preparation 19, the following phenols were prepared from the corresponding aldehyde and 2-benzyloxybenzyl triphenylphosphonium chloride.

PREPARATION 33

2-[2-(3-Ethoxyphenyl)ethyl]phenol

Nuclear Magnetic Resonance Spectrum (CDCl$_3$, 270 MHz), δ ppm: 1.39 (3H, triplet, J=7.3 Hz); 2.89 (4H, singlet); 4.00 (2H, quartet, J=7.3 Hz); 4.65 (1H, singlet); 6.7–6.9 (5H, multiplet); 7.05–7.25 (3H, multiplet).

PREPARATION 34

2-[2-(2-Ethoxyphenyl)ethyl]phenol

Nuclear Magnetic Resonance Spectrum (CDCl$_3$, 270 MHz), δ ppm: 1.52 (3H, triplet, J=6.9 Hz); 2.82 (4H, singlet); 4.18 (2H, quartet, J=6.9 Hz); 5.90 (1H, singlet); 6.8–7.0 (4H, multiplet); 7.1–7.3 (4H, multiplet).

PREPARATION 35

2-[2-(4-Ethoxyphenyl)ethyl]phenol

Nuclear Magnetic Resonance Spectrum (CDCl$_3$, 270 MHz), δ ppm: 1.40 (3H, triplet, J=7.2 Hz); 2.87 (4H, singlet); 4.01 (2H, quartet, J=7.2 Hz); 4.57 (1H, singlet); 6.7–6.9 (4H, multiplet); 7.05–7.15 (4H, multiplet).

REPARATION 36

2-[2-(4- Methoxyphenyl)ethyl]phenol.

Nuclear Magnetic Resonance Spectrum (CDCl$_3$, 270 MHz), δ ppm: 2.87 (4H, singlet); 3.79 (3H, singlet); 4.58 (1H, singlet); 6.75 (1H, doublet, J=7.9 Hz); 6.8–6.9 (3H, multiplet); 7.05–7.15 (4H, multiplet).

PREPARATION 37

2-[2-(4 -Methylphenyl)ethyl]phenol

Nuclear Magnetic Resonance Spectrum (CDCl$_3$, 270 MHz), δ ppm: 2.32 (3H, singlet); 2.88 (4H, singlet); 4.57 (1H, singlet); 6.75 (1H, doublet, J=7.9 Hz); 6.86 (1H, triplet, J=6.9 Hz); 7.0–7.2 (6H, multiplet).

PREPARATION 38

2-[2-(2-Methoxymethoxyphenyl)ethyl]phenol

Nuclear Magnetic Resonance Spectrum (CDCl$_3$, 270 MHz), δ ppm: 2.75–2.95 (4H, multiplet); 3.53 (3H, singlet); 5.30 (2H, singlet); 5.95 (1H, singlet); 6.8–7.05 (3H, multiplet); 7.1–7.3 (4H, multiplet).

PREPARATION 39

2-[2-(4-Methoxymethoxyphenyl)ethyl]phenol

Nuclear Magnetic Resonance Spectrum (CDCl$_3$, 270 MHz), δ ppm: 2.87 (4H, singlet); 3.48 (3H, multiplet); 4.68 (1H, singlet); 5.15 (2H, singlet); 6.74 (1H, doublet, J=7.9 Hz); 6.85 (1H, triplet, J=6.9 Hz); 6.9–7.0 (2H, multiplet); 7.05–7.15 (4H, multiplet).

PREPARATION 40

2-[2-(2-Cyanophenyl)ethyl]phenol

Nuclear Magnetic Resonance Spectrum (CDCl$_3$, 270 MHz), δ ppm: 2.9–3.2 (4H, multiplet); 4.99 (1H, singlet); 6.76 (1H, doublet, J=7.9 Hz); 6.83 (1H, triplet, J=7.3 Hz); 7.04 (1H, doublet, J=7.3 Hz); 7.10 (1H, triplet, J=7.9 Hz); 7.2–7.35 (2H, multiplet); 7.49 (1H, triplet, J=7.3 Hz); 7.61 (1H, doublet, J=7.9 Hz).

PREPARATION 41

2-[2-(3-Cyanophenyl)ethyl]phenol

Nuclear Magnetic Resonance Spectrum (CDCl$_3$, 270 MHz), δ ppm: 2.75–3.1 (4H, multiplet); 4.87 (1H, singlet); 6.74 (1H, doublet, J=7.9 Hz); 6.84 (1H, triplet, J=7.3 Hz); 7.01 (1H, doublet, J=7.3 Hz); 7.09 (1H, triplet, J=7.9 Hz); 7.3–7.55 (4H, multiplet).

PREPARATION 42

2-[2-(4-Cyanophenyl)ethyl]phenol

Nuclear Magnetic Resonance Spectrum (CDCl$_3$, 270 MHz), δ ppm: 2.85–3.1 (4H, multiplet); 4.81 (1H, singlet); 6.74 (1H, doublet, J=7.9 Hz); 6.84 (1H, triplet, J=7.3 Hz); 7.01 (1H, doublet, J=7.3 Hz); 7.09 (1H, triplet, J=7.9 Hz); 7.27 (2H, doublet, J=8.6 Hz); 7.55 (2H, doublet, J=8.6 Hz).

PREPARATION 43

2-[2-(3-Difluoromethoxyphenyl)ethyl]phenol

Nuclear Magnetic Resonance Spectrum (CDCl$_3$, 270 MHz), δ ppm: 2.91 (4H, singlet); 4.90 (1H, singlet); 6.44 (1H, triplet, J=74.6 Hz); 6.7–7.2 (6H, multiplet); 7.25 (1H, triplet, J=7.6 Hz).

PREPARATION 44

2-[2-(3-Chlorophenyl)ethyl]phenol

Following a procedure similar to that described in Preparation 19, except that a 9:1 by volume mixture of hexane and ethyl acetate was used as the eluent, 28.8 g (yield 90%) of 2-benzyloxy-3'-chlorostilbene were obtained by using 14.0 g of 3-chlorobenzaldehyde, 59.4 g of 2-benzyloxybenzyltriphenylphosphonium chloride, 300 ml of acetonitrile and 18.0 g of 1,8-diazabicyclo[5.4.0]undec-7-ene.

5.4 g of this 2-benzyloxy-3'-chlorostilbene were treated with hydrogen in the presence of 300 mg of tris(triphenylphosphine)rhodium (I) chloride in a mixture of 60 ml of benzene and 40 ml ethanol at room temperature for one day. At the end of this time, aqueous sodium hydrogensulfite containing a small amount of sodium metabisulfite was added to the reaction mixture and allowed to react. Insoluble materials were removed by filtration. Ethyl acetate was added to the filtrate, and the mixture was washed once with water and twice with a saturated aqueous solution of sodium chloride. It was then dried over anhydrous sodium sulfate and concentrated by evaporation under reduced pressure. The resulting residue was purified by column chromatography through silica gel, using a 20:1 by volume mixture of hexane and ethyl acetate as the eluent, to give 5.35 g (yield 98%) of benzyl 2-[2-(3-chlorophenyl)ethyl]phenyl ether.

The whole of this benzyl 2-[2-(3-chlorophenyl)ethyl]phenyl ether was dissolved in 50 ml of methylene chloride, and 17 ml of a 1M solution of boron tribromide in methylene chloride were added to the solution, whilst ice-cooling. The mixture was then allowed to stand at room temperature for 2 hours. At the end of this time, the solvent was removed by distillation under reduced pressure, and the resulting residue was purified by column chromatography through silica gel, using a 10:1 by volume mixture of hexane and ethyl acetate as the eluent, to give 3.80 g (yield 99%) of the title compound as a solid.

Nuclear Magnetic Resonance Spectrum (CDCl$_3$, 2.70 MHz), δ ppm: 2.89 (4H, singlet); 4.5–4.9 (1H, broad); 6.74 (1H, doublet, J=7.9 Hz); 6.86 (1H, triplet, J=7.9 Hz); 7.0–7.3 (6H, multiplet).

PREPARATIONS 45 TO 50

Following a procedure similar to that described in Preparation 44, the following phenols were prepared from the corresponding aldehyde and 2-benzyloxybenzyltriphenylphosphonium chloride.

PREPARATION 45

2-[2-(2-Chlorophenyl)ethyl]phenol

Nuclear Magnetic Resonance Spectrum (CDCl$_3$, 270 MHz), δ ppm: 2.85–3.1 (4H, multiplet); 4.77 (1H, singlet); 6.78 (1H, doublet, J=7.9 Hz); 6.87 (1H, triplet, J=7.6 Hz); 7.1–7.3 (5H, multiplet); 7.3–7.4 (1H, multiplet).

PREPARATION 46

2-[2-(4-Chlorophenyl)ethyl]phenol

Nuclear Magnetic Resonance Spectrum (CDCl$_3$, 270 MHz), δ ppm: 2.89 (4H, singlet); 4.61 (1H, singlet); 6.74 (1H, doublet, J=7.9 Hz); 6.85 (1H, triplet, J=7.3 Hz); 7.0–7.15 (4H, multiplet); 7.2–7.3 (2H, multiplet).

PREPARATION 42

2-[2-(2-Fluorophenyl)ethyl]phenol

Nuclear Magnetic Resonance Spectrum (CDCl$_3$, 270 MHz), δ ppm: 2.85–3.05 (4H, multiplet); 4.72 (1H, singlet); 6.77 (1H, doublet, J=7.9 Hz); 6.86 (1H, triplet, J=7.3 Hz); 7.0–7.25 (6H, multiplet).

PREPARATION 48

2-[2-(3-Fluorophenyl)ethyl]phenol

Nuclear Magnetic Resonance Spectrum (CDCl$_3$, 270 MHz), δ ppm: 2.91 (4H, singlet); 4.65 (1H, singlet); 6.7–7.3 (8H, multiplet).

PREPARATION 49

2-[2-(4-Fluorophenyl)ethyl]phenol

Nuclear Magnetic Resonance Spectrum (CDCl$_3$, 270 MHz), δ ppm: 2.89 (4H, singlet); 4.61 (1H, singlet); 6.74 (1H, doublet, J=8.6 Hz); 6.8–7.3 (7H, multiplet).

PREPARATION 50

2-[2-(3-Bromophenyl)ethyl]phenol

Nuclear Magnetic Resonance Spectrum (CDCl$_3$, 270 MHz), δ ppm: 2.89 (4H, singlet); 4.67 (1H, singlet); 6.74 (1H, doublet, J=7.9 Hz); 6.86 (1H, triplet, J=7.3 Hz); 7.0–7.2 (4H, multiplet); 7.3–7.4 (2H, multiplet).

We claim:
1. A compound of formula

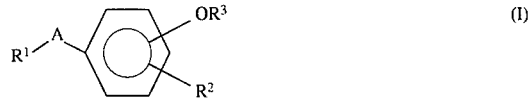 (I)

wherein:

$R^1$ represents an aryl group;

$R^2$ represents a hydrogen atom, a methyl group, an ethyl group, a fluorine atom or a chlorine atom;

$R^3$ represents a group of formula —B—NR$^4$R$^5$,
where $R^4$ and $R^5$ are independently selected from the group consisting of hydrogen atoms, alkyl groups and substituted alkyl groups or $R^4$ and $R^5$, together with the nitrogen atom to which they are attached, represent a heterocyclic group having from 3 to 6 ring atoms, and B represents an alkylene group having from 2 to 6 carbon atoms or a group of formula —CH$_2$CH(OR$^6$)CH$_2$—, where $R^6$ represents a hydrogen atom, an alkanoyl group, a substituted alkanoyl group or an arylcarbonyl group, or a group of formula —D—R$^7$, where D represents a carbon-carbon single bond or an alkylene group having from 1 to 4 carbon atoms and $R^7$ represents a heterocyclic group having 5 or 6 ring atoms bonded to D via a carbon atom in the heterocyclic group;

A represents an alkylene group having from 2 to 8 carbon atoms;

or a pharmaceutically acceptable salt or an alkyl ester or an aralkyl ester thereof wherein the alkyl ester has 1–6 carbon atoms and the aralkyl ester has 1–4 carbon atoms in the alkyl part and the aryl part has 6 to 10 ring atoms and is unsubstituted or contains a substituent selected from the group consisting of substituent β, defined below;

PROVIDED THAT, where A represents an ethylene group, $R^3$ represents a group of formula —D—$R^7$;

said alkyl, substituted alkyl and alkoxy groups have from 1 to 6 carbon atoms;

said substituted alkyl groups are substituted by one of substituents ζ, defined below;

said substituents ζ are selected from the group consisting of hydroxy groups, dialkylamino groups in which the or each alkyl part has from 1 to 6 carbon atoms and aryl groups which have from 6 to 10 ring carbon atoms and which are unsubstituted or are substituted by one, two or three substituents selected from the group consisting of substituents β, defined below;

said alkanoyl and substituted alkanoyl groups have 1 to 6 carbon atoms, and, in the case of the substituted groups are substituted by one carboxy group;

aryl groups have from 6 to 10 ring carbon atoms and are unsubstituted or are substituted by one, two or three substituents selected from the group consisting of substituents α defined below;

the aryl parts of said arylcarbonyl groups have from 6 to 10 ring carbon atoms and are unsubstituted or are substituted by one, two or three substituents selected from the group consisting of substituents β, defined below;

said substituents α are selected from the group consisting of alkyl groups having from 1 to 6 carbon atoms,
alkenyl groups having from 2 to 6 carbon atoms,
alkynyl groups having from 2 to 6 carbon atoms,
hydroxy groups,
alkoxy groups having from 1 to 6 carbon atoms,
haloalkoxy groups having from 1 to 6 carbon atoms,
halogen atoms,
cyano groups,
carbamoyl groups,
mono- and di- alkylcarbamoyl groups in which the or each alkyl part has from 1 to 6 carbon atoms, and aryl groups which have from 6 to 10 ring carbon atoms and which are unsubstituted or are substituted by one, two or three substituents selected from the group consisting of substituents β;

said substituents β are selected from the group consisting of alkyl groups having from 1 to 6 carbon atoms,
alkoxy groups having from 1 to 6 carbon atoms, and
halogen atoms, said heterocyclic groups have one to four heterto-atoms selected from the group consisting of nitrogen, oxygen and sulfur heterto-atoms and are unsubstituted or substituted; in the case of substituents on a nitrogen atom, said substituents are selected from the group consisting of substituents γ; in the case of substituents on a carbon atom of the heterocyclic group represented by $R^4$ and $R^5$ together, said substituents are selected from the group consisting of substituents δ; in the case of substituents on a carbon atom of the heterocyclic group represented by $R^7$, said substituents are selected from the group consisting of substituents ε;

said substituents γ are selected from the group consisting of alkyl groups having from 1 to 6 carbon atoms and aryl groups which have from 6 to 10 ring carbon atoms and which are unsubstituted or are substituted by one, two or three substituents selected from the group consisting of substituents β;

said substituents δ are selected from the group consisting of:
alkyl groups having from 1 to 6 carbon atoms; hydroxy groups; and
aryl groups which have from 6 to 10 ring carbon atoms and which are unsubstituted or are substituted by one, two or three substituents selected from the group consisting of substituents β;

said substituents β are selected from the group consisting of:
alkyl groups having from 1 to 6 carbon atoms;
alkenyl groups having from 2 to 6 carbon atoms;
alkynyl groups having from 2 to 6 carbon atoms;
hydroxy groups;
alkoxy groups having from 1 to 6 carbon atoms;
alkoxycarbonyloxy groups having from 2 to 7 carbon atoms;
alkanoyloxy groups which have from 1 to 20 carbon atoms;
substituted alkanoyloxy groups which have from 2 to 5 carbon atoms and which are substituted by
one carboxy group;
carbamoyloxy groups;
mono- and di- alkylcarbamoyloxy groups in which the or each alkyl part has from 1 co 6 carbon atoms; halogen atoms;
cyano groups; and
aryl groups which have from 6 to 10 ring carbon atoms and which are unsubstituted or are substituted by one, two or three substituents selected from the group consisting of substituents β.

2. The compound of claim 1, wherein: $R^1$ represents a phenyl or naphthyl group which is unsubstituted or is substituted by at least one substituent selected from the group consisting of alkyl groups having from 1 to 4 carbon atoms,
hydroxy groups,
alkoxy groups having from 1 to 4 carbon atoms,
haloalkoxy groups having from 1 to 4 carbon atoms,
halogen atoms,
cyano groups, and
carbamoyl groups.

3. The compound of claim 1 wherein $R^2$ represents a hydrogen atom, a methyl group or an ethyl group.

4. The compound of claim 1, wherein the group represented by —$OR^3$ is present at the 2-position of the benzene ring (relative to the position of attachment of the group represented by A taken to be the 1-position).

5. The compound of claim 1, wherein $R^3$ represents
a group of formula —B—$NR^4R^5$,
where $R^4$ and $R^5$ are independently selected from the group consisting of hydrogen atoms, alkyl groups having from 1 to 4 carbon atoms, substituted alkyl groups having from 1 to 4 carbon atoms and substituted by at least one phenyl group, and substituted alkyl groups having from 2 to 4 carbon atoms and substituted by at least one substituent selected from the group consisting of hydroxy groups and dialkylamino groups in which each alkyl part is a methyl or ethyl group, or $R^4$ and $R^5$, together with the nitrogen atom to which they are attached, represent a heterocyclic group selected from the group consisting of the 1-pyrrolidinyl, 1-piperidyl, 4-morpholinyl, 4-thiomorpholinyl, 1-piperazinyl, 1-imidazolyl, 1-pyrazolyl and 1-triazolyl groups, any of which is substituted or unsubstituted, said substituted heterocyclic groups being substituted on at least one of a carbon atom and a nitrogen atom, the substituents being, in the case of substituents on a carbon atom, selected from the group consisting of alkyl groups having from 1 to 4 carbon atoms, hydroxy groups and phenyl groups which are unsubstituted or which have at least one substituent selected from the group consisting of methyl groups, methoxy groups, fluorine atoms and chlorine atoms, and B represents an alkylene group having from 2 to 4 carbon atoms or a group of formula —$CH_2CH(OR^6)CH_2$—, where $R^6$ represents a hydrogen atom, an alkanoyl group having from 2 to 4 carbon atoms, a substituted alkanoyl group having 2 or 3 carbon atoms and substituted by a carboxy group, or a benzoyl group which is unsubstituted or is substituted by at least one substituent selected from the group consisting of methyl groups, methoxy groups, fluorine atoms and chlorine atoms.

6. The compound of claim 1, wherein $R^3$ represents a group of formula —D—$R^7$, where D represents a carbon-carbon single bond or an alkylene group having from 1 to 3 carbon atoms and $R^7$ represents a heterocyclic group having 5 or 6 ring atoms bonded to D via a carbon atom in the heterocyclic group, said heterocyclic group being selected from the group consisting of pyrrolidinyl groups, piperidyl groups, morpholinyl groups, thiomorpholinyl groups and piperazinyl groups which are unsubstituted or are substituted on at least one of a carbon atom and a nitrogen atom by at least one substituent selected from the group consisting of in the case of substituents on a carbon atom, alkyl groups having from 1 to 4 carbon atoms, hydroxy groups, alkoxy groups having from 1 to 4 carbon atoms, alkoxycarbonyloxy groups having from 2 to 5 carbon atoms, alkanoyloxy groups having from 2 to 20 carbon atoms, carboxy-substituted alkanoyloxy groups having 3 or 4 carbon atoms in the alkanoyl part, carbamoyloxy groups, mono- and di- alkylcarbamoyloxy groups in which the or each alkyl part is a methyl or ethyl group, fluorine atoms and chlorine atoms, in the case of substituents on a nitrogen atom, alkyl groups having from 1 to 4 carbon atoms, and phenyl groups which are unsubstituted or which have at least one substituent selected from the group consisting of methyl groups, methoxy groups, fluorine atoms and chlorine atoms.

7. The compound of claim 4, wherein $R^3$ represents a group of formula —B—$NR^4R^5$, where $R^4$ and $R^5$ are independently selected from the group consisting of hydrogen atoms, alkyl groups having from 1 to 4 carbon atoms, substituted alkyl groups having from 1 to 4 carbon atoms and substituted by at least one phenyl group, and substituted alkyl groups having from 2 to 4 carbon atoms and substituted by at least one substituent selected from the group consisting of hydroxy groups and dialkylamino groups in which each alkyl part is a methyl or ethyl group, or $R^4$ and $R^5$, together with the nitrogen atom to which they are attached, represent a heterocyclic group selected from the group consisting of the 1-pyrrolidinyl, 1-piperidyl, 4-morpholinyl, 4-thiomorpholinyl, 1-piperazinyl, 1-imidazolyl, 1-pyrazolyl and 1-triazolyl groups, any of which is substituted or unsubstituted, said substituted heterocyclic groups being substituted on at least one of a carbon atom and a nitrogen atom, the substituents being, in the case of substituents on a carbon atom, selected from the group consisting of alkyl groups having from 1 to 4 carbon atoms, hydroxy groups and phenyl groups which are unsubstituted or which have at least one substituent selected from the group consisting of methyl groups, methoxy groups, fluorine atoms and chlorine atoms, and B represents an alkylene group having from 2 to 4 carbon atoms or a group of formula —$CH_2CH(OR^6)CH_2$—, where $R^6$ represents a hydrogen atom, an alkanoyl group having from 2 to 4 carbon atoms, a substituted alkanoyl group having 2 or 3 carbon atoms and substituted by a carboxy group, or a benzoyl group which is unsubstituted or is substituted by at least one substituent selected from the group consisting of methyl groups, methoxy groups, fluorine atoms and chlorine atoms.

8. The compound of claim 4, wherein $R^3$ represents a group of formula —D—$R^7$ where D represents a carbon-carbon single bond or an alkylene group having from 1 to 3 carbon atoms and $R^7$ represents a heterocyclic group having 5 or 6 ring atoms bonded to D via a carbon atom in the heterocyclic group, said heterocyclic group being selected from the group consisting of pyrrolidinyl groups, piperidyl groups, morpholinyl groups, thiomorpholinyl groups and piperazinyl groups which are unsubstituted or are substituted on at least one of a carbon atom and a nitrogen atom by at least one substituent selected from the group consisting of in the case of substituents on a carbon atom, alkyl groups having from 1 to 4 carbon atoms, hydroxy groups, alkoxy groups having from 1 to 4 carbon atoms, alkoxycarbonyloxy groups having from 2 to 5 carbon atoms, alkanoyloxy groups having from 2 to 20 carbon atoms, carboxy-substituted alkanoyloxy groups having 3 or 4 carbon atoms in the alkanoyl part, carbamoyloxy groups, mono- and di- alkylcarbamoyloxy groups in which the or each alkyl part is a methyl or ethyl group, fluorine atoms and chlorine atoms, in the case of substituents on a nitrogen atom, alkyl groups having from 1 to 4 carbon atoms, and phenyl groups which are unsubstituted or which have at least one substituent selected from the group consisting of methyl groups, methoxy groups, fluorine atoms and chlorine atoms.

9. The compound of claim 1, wherein A represents an alkylene group having from 2 to 7 carbon atoms.

10. The compound of claim 1, wherein:

$R^1$ represents a phenyl or naphthyl group which is unsubstituted or is substituted by at least one substituent selected from the group consisting of
alkyl groups having from 1 to 4 carbon atoms,
hydroxy groups,
alkoxy groups having from 1 to 4 carbon atoms, haloalkoxy groups having from 1 to 4 carbon atoms, halogen atoms, cyano groups, and carbamoyl groups;

$R^2$ represents a hydrogen atom, a methyl group, or an ethyl group;

the group represented by —$OR^3$ is present at the 2-position of the benzene ring (relative to the position of attachment of the group represented by A taken to be the 1-position);

$R^3$ represents a group of formula —B—$NR^4R^5$, where $R^4$ and $R^5$ are independently selected from the group consisting of hydrogen atoms, alkyl groups having from 1 to 4 carbon atoms, substituted alkyl groups having from 1 to 4 carbon atoms and substituted by at least one phenyl group, and substituted alkyl groups having from 2 to 4 carbon atoms and substituted by at least one substituent selected from the group consisting of hydroxy groups and dialkylamino groups in which each alkyl part is a methyl or ethyl group, or $R^4$ and $R^5$ together with the nitrogen atom to which they are attached, represent a heterocyclic group selected from the group consisting of the 1-pyrrolidinyl, 1-piperidyl, 4-morpholinyl, 4-thiomorpholinyl, 1-piperazinyl, 1-imidazolyl, 1-pyrazolyl and 1-triazolyl groups, any of which is substituted or unsubstituted, said substituted heterocyclic groups being substituted on at least one of a carbon atom and a nitrogen atom, the substituents being, in the case of substituents on a carbon atom, selected from the group consisting of alkyl groups having from 1 to 4 carbon atoms, hydroxy groups and phenyl groups which are unsubstituted or which have at least one substituent selected from the group consisting of methyl groups, methoxy groups, fluorine atoms and chlorine atoms, and B represents an alkylene group having from 2 to 4 carbon atoms or a group of formula —$CH_2CH(OR^6)CH_2$—, where $R^6$ represents a hydrogen atom, an alkanoyl group having from 2 to 4 carbon atoms, a substituted alkanoyl group having 2 or 3 carbon atoms and substituted by a carboxy group, or a benzoyl group which is unsubstituted or is substituted by at least one substituent selected from the group consisting of methyl groups, methoxy groups, fluorine atoms and chlorine atoms, or a group of formula —D—$R^7$, where D represents a carbon-carbon single bond or an alkylene group having from 1 to 3 carbon atoms and $R^7$ represents a heterocyclic group having 5 or 6 ring atoms bonded to D via a carbon atom in the heterocyclic group, said heterocyclic group being selected from the group consisting of pyrrolidinyl groups, piperidyl groups, morpholinyl groups, thiomorpholinyl groups and piperazinyl groups which are unsubstituted or are substituted on at least one of a carbon atom and a nitrogen atom by at least one substituent selected from the group consisting of in the case of substituents on a carbon atom, alkyl groups having from 1 to 4 carbon atoms, hydroxy groups, alkoxy groups having from 1 to 4 carbon atoms, alkoxycarbonyloxy groups having from 2 to 5 carbon atoms, alkanoyloxy groups having from 2 to 20 carbon atoms, carboxy-substituted alkanoyloxy groups having 3 or 4 carbon atoms in the alkanoyl part, carbamoyloxy groups, mono- and di- alkyl- carbamoyloxy groups in which the or each alkyl part is a methyl or ethyl group, fluorine atoms and chlorine atoms, in the case of substituents on a nitrogen atom, alkyl groups having from 1 to 4 carbon atoms, and phenyl groups which are unsubstituted or which have at least one substituent selected from the group consisting of methyl groups, methoxy groups, fluorine atoms and chlorine atoms;

A represents an alkylene group having from 2 to 7 carbon atoms.

11. The compound of claim 1, wherein:

$R^1$ represents a phenyl group which is unsubstituted or is substituted by at least one substituent selected from the group consisting of methyl groups, ethyl groups, fluoromethoxy groups, difluoromethoxy groups, 2-fluoroethoxy groups, hydroxy groups, methoxy groups, ethoxy groups, fluorine atoms, chlorine atoms, bromine atoms and cyano groups;

$R^2$ represents a hydrogen atom;

the group represented by —$OR^3$ is present at the 2-position of the benzene ring (relative to the position of attachment of the group represented by A taken to be the 1-position);

$R^3$ represents a group of formula —B—$NR^4R^5$, where $R^4$ and $R^5$ are independently selected from the group consisting of hydrogen atoms, alkyl groups having from 1 to 4 carbon atoms, benzyl groups, phenethyl groups, 2-hydroxyethyl groups, 3-hydroxypropyl groups, 2-(N,N-dimethyl-amino)ethyl groups and 2-(N,N-dimethylamino)propyl groups, or $R^4$ and $R^5$, together with the nitrogen atom to which they are attached, represent a 1-pyrrolidinyl group, a 1-piperidyl group, a 4-hydroxy-1-piperidyl group, a 4-morpholinyl group, a 4-methyl-1-piperazinyl group, a 4-ethyl-1-piperazinyl group, a 4-phenyl-1-piperazinyl group, a 1-imidazolyl group or a 1-triazolyl group, and B represents an alkylene group having 2 or 3 carbon atoms or a group of formula —$CH_2CH(OR^6)CH_2$—, where $R^6$ represents a hydrogen atom, an alkanoyl group having 2 or 3 carbon atoms, or a substituted alkanoyl group having 3 or 4 carbon atoms and substituted by a carboxy group, or a group of formula —D—$R^7$, where D represents a carbon-carbon single bond or an alkylene group having 1 or 2 carbon atoms and $R^7$ represents a heterocyclic group having 5 or 6 ring atoms bonded to D via a carbon atom in the heterocyclic group, said heterocyclic group being selected from the group consisting of pyrrolidinyl groups, piperidyl groups, morpholinyl groups and thiomorpholinyl groups which are unsubstituted or are substituted on at least one of a carbon atom and a nitrogen atom by at least one substituent selected from the group consisting of in the case of substituents on a carbon atom, alkyl groups having from 1 to 4 carbon atoms, hydroxy groups, alkoxy groups having from 1 to 4 carbon atoms, alkoxycarbonyloxy groups having from 2 to 5 carbon atoms, alkanoyloxy groups having 2 or 3 carbon atoms, alkanoyloxy groups having from 12 to 20 carbon atoms, carboxy-substituted alkanoyloxy groups having 3 or 4 carbon atoms in the alkanoyl part, carbamoyloxy groups, and mono- and di- alkyl- carbamoyloxy groups in which the or each alkyl part is a methyl or ethyl group, in the case of substituents on a nitrogen atom, alkyl groups having from 1 to 4 carbon atoms;

A represents an alkylene group having from 2 to 5 carbon atoms.

12. The compound of claim 1, wherein:

$R^1$ represents a phenyl group which is unsubstituted or is substituted by at least one substituent selected from the group consisting of methyl groups, ethyl groups, fluoromethoxy groups, difluoromethoxy groups, 2-fluoroethoxy groups, hydroxy groups, methoxy groups, ethoxy groups, fluorine atoms, chlorine atoms, bromine atoms and cyano groups;

$R^2$ represents a hydrogen atom;

the group represented by —$OR^3$ is present at the 2-position of the benzene ring (relative to the position of attachment of the group represented by A taken to be the 1-position);

$R^3$ represents a group of formula —B—$NR^4R^5$,
where $R^4$ and $R^5$ are independently selected from the group consisting of hydrogen atoms, methyl groups, ethyl groups, benzyl groups and 2-hydroxyethyl groups, or $R^4$ and $R^5$ together with the nitrogen atom to which they are attached, represent a 1-pyrrolidinyl group, a 1-piperidyl group, a 4-hydroxy-1-piperidyl group, a 4-morpholinyl group, a 4-methyl-1-piperazinyl group, a 4-phenyl-1-piperazinyl group or a 1-imidazolyl group, and B represents an alkylene group having 2 or 3 carbon atoms or a group of formula —$CH_2CH(OR^6)CH_2$—, where $R^6$ represents a hydrogen atom, an acetyl group, a succinyl group or a glutaryl group, or a group of formula —D—$R^7$, where D represents a carbon-carbon single bond or an alkylene group having 1 or 2 carbon atoms and $R^7$ represents a heterocyclic group having 5 or 6 ring atoms bonded to D via a carbon atom in the heterocyclic group, said heterocyclic group being selected from the group consisting of pyrrolidinyl groups, piperidyl groups, morpholinyl groups and thiomorpholinyl groups which are unsubstituted or are substituted on at least one of a carbon atom and a nitrogen atom by at least one substituent selected from the group consisting of in the case of substituents on a carbon atom, methyl groups, ethyl groups, hydroxy groups, methoxy groups, ethoxy groups, ethoxycarbonyloxy groups, isopropoxycarbonyloxy groups, t-butoxycarbonyloxy groups, alkanoyloxy groups having 2 or 3 carbon atoms, alkanoyloxy groups having from 14 to 20 carbon atoms, carboxy-substituted alkanoyloxy groups having 3 or 4 carbon atoms in the alkanoyl part, carbamoyloxy groups, and mono- and di- alkyl- carbamoyloxy groups in which the or each alkyl part is a methyl or ethyl group, in the case of substituents on a nitrogen atom, methyl groups and ethyl groups;

A represents an alkylene group having from 2 to 4 carbon atoms.

13. The compound of claim 1, wherein:

$R^1$ represents a phenyl group which is unsubstituted or is substituted by at least one substituent selected from the group consisting of methyl groups, hydroxy groups, methoxy groups, ethoxy groups, fluoromethoxy groups, difluoromethoxy groups, fluorine atoms, chlorine atoms, bromine atoms and cyano groups;

$R^2$ represents a hydrogen atom;

the group represented by —$OR^3$ is present at the 2-position of the benzene ring (relative to the position of attachment of the group represented by A taken to be the 1-position);

$R^3$ represents a group of formula —B—$NR^4R^5$,
where $R^4$ and $R^5$ are independently selected from the group consisting of methyl groups, ethyl groups and 2-hydroxyethyl groups, or $R^4$ and $R^5$, together with the nitrogen atom to which they are attached, represent a 1-pyrrolidinyl group, a 1-piperidyl group, a 4-hydroxy-1-piperidyl group or a 4-morpholinyl group, and B represents an alkylene group having 2 or 3 carbon atoms or a group of formula —$CH_2CH(OR^6)CH_2$—, where $R^6$ represents a hydrogen atom, an acetyl group, a succinyl group or a glutaryl group, or a group of formula —D—$R^7$ where D represents a carbon-carbon single bond or an alkylene group having 1 or 2 carbon atoms and $R^7$ represents a heterocyclic group bonded to D via a carbon atom in the heterocyclic group, said heterocyclic group being selected from the group consisting of pyrrolidinyl groups, 1-methylpyrrolidinyl groups, 4-hydroxy-1-methylpyrrolidinyl groups, 4-ethoxycarbonyloxy-1-methylpyrrolidinyl groups, 4-isopropoxycarbonyloxy-1-methylpyrrolidinyl groups, 4-t-butoxycarbonyloxy-1-methylpyrrolidinyl groups, 4-palmitoyloxy-1-methylpyrrolidinyl groups, 4-stearoyloxy-1-methylpyrrolidinyl groups, piperidyl groups, 1-methylpiperidyl groups, morpholinyl groups and thiomorpholinyl groups;

A represents an ethylene group or a tetramethylene group.

14. The compound of claim 1, wherein:

$R^1$ represents a phenyl group which is unsubstituted or is substituted by at least one substituent selected from the group consisting of methyl groups, hydroxy groups, methoxy groups, ethoxy groups, difluoromethoxy groups, fluorine atoms, chlorine atoms, bromine atoms and cyano groups;

$R^2$ represents a hydrogen atom;

the group represented by —$OR^3$ is present at the 2-position of the benzene ring (relative to the position of attachment of the group represented by A taken to be the 1-position);

$R^3$ represents a group of formula —D—$R^7$ where D represents a carbon-carbon single bond or an alkylene group having 1 or 2 carbon atoms and $R^7$ represents a heterocyclic group bonded to D via a carbon atom in the heterocyclic group, said heterocyclic group being selected from the group consisting of pyrrolidinyl groups, 1-methylpyrrolidinyl groups, 4-hydroxy-1-methylpyrrolidinyl groups, piperidyl groups, 1-methylpiperidyl groups, morpholinyl groups and thiomorpholinyl groups;

A represents an ethylene group.

15. The compound of claim 1, wherein:

$R^1$ represents a phenyl group which is unsubstituted or is substituted by at least one substituent selected from the group consisting of methyl groups, ethyl groups, hydroxy groups, methoxy groups, ethoxy groups, fluoromethoxy groups, difluoromethoxy groups, 2-fluoroethoxy groups, fluorine atoms, chlorine atoms, bromine atoms and cyano groups;

$R^2$ represents a hydrogen atom;

the group represented by $-OR^3$ is present at the 2-position of the benzene ring (relative to the position of attachment of the group represented by A taken to be the 1-position);

$R^3$ represents a group of formula $-B-NR^4R^5$, where $R^4$ and $R^5$ are independently selected from the group consisting of hydrogen atoms, alkyl groups having from 1 to 4 carbon atoms, benzyl groups, phenethyl groups, 2-hydroxyethyl groups, 3-hydroxypropyl groups, 2-(N,N-dimethylamino)ethyl groups and 3-(N,N-dimethylamino)propyl groups, or $R^4$ and $R^5$, together with the nitrogen atom to which they are attached, represent a 1-pyrrolidinyl group, a 1-piperidyl group, a 4-hydroxy-1-piperidyl group, a 4-morpholinyl group, a 4-methyl-1-piperazinyl group, a 4-ethyl-1-piperazinyl group, a 4-phenyl-1-piperazinyl group, a 1-imidazolyl group or a 1-triazolyl group, and B represents an alkylene group having 2 or 3 carbon atoms or a group of formula $-CH_2CH(OR^6)CH_2 13$, where $R^6$ represents a hydrogen atom, an alkanoyl group having 2 or 3 carbon atoms, or a substituted alkanoyl group having 3 or 4 carbon atoms and substituted by a carboxy group, or a group of formula $-D-R^7$, where D represents a carbon-carbon single bond or an alkylene group having 1 or 2 carbon atoms and $R^7$ represents a heterocyclic group bonded to D via a carbon atom in the heterocyclic group, said heterocyclic group being selected from the group consisting of pyrrolidinyl groups, piperidyl groups, morpholinyl groups and thiomorpholinyl groups which are unsubstituted or are substituted on at least one of a carbon atom and a nitrogen atom by at least one substituent selected from the group consisting of in the case of substituents on a carbon atom, alkyl groups having from 1 to 4 carbon atoms, hydroxy groups, alkoxy groups having from 1 to 4 carbon atoms, alkoxycarbonyloxy groups having from 2 to 5 carbon atoms, alkanoyloxy groups having 2 or 3 carbon atoms, alkanoyloxy groups having from 12 to 20 carbon atoms, carboxy-substituted alkanoyloxy groups having 3 or 4 carbon atoms in the alkanoyl part, carbamoyloxy groups, and mono- and di- alkylcarbamoyloxy groups in which the or each alkyl part is a methyl or ethyl group, in the case of substituents on a nitrogen atom, alkyl groups having from 1 to 4 carbon atoms;

A represents an alkylene group having from 2 to 7 carbon atoms.

16. The compound of claim 1, wherein:

$R^1$ represents a phenyl group which is unsubstituted or is substituted by at least one substituent selected from the group consisting of methyl groups, ethyl groups, hydroxy groups, methoxy groups, ethoxy groups, fluoromethoxy groups, difluoromethoxy groups, fluorine atoms, chlorine atoms, bromine atoms and cyano groups;

$R^2$ represents a hydrogen atom;

the group represented by $-OR^3$ is present at the 2-position of the benzene ring (relative to the position of attachment of the group represented by A taken to be the 1-position);

$R^3$ represents a group of formula $-B-NR^4R^5$, where $R^4$ and $R^5$ are independently selected from the group consisting of hydrogen atoms, methyl groups, ethyl groups, benzyl groups and 2-hydroxyethyl groups, or $R^4$ and $R^5$, together with the nitrogen atom to which they are attached, represent a 1-pyrrolidinyl group, a 1-piperidyl group, a 4-hydroxy-1-piperidyl group, a 4-morpholinyl group, a 4-methyl-1-piperazinyl group, a 4-phenyl-1-piperazinyl group or a 1-imidazolyl group, and B represents an alkylene group having 2 or 3 carbon atoms or a group of formula $-CH_2CH(OR^6)CH_2-$, where $R^6$ represents a hydrogen atom, an acetyl group, a succinyl group or a glutaryl group, or a group of formula $-D-R^7$, where D represents a carbon-carbon single bond or an alkylene group having 1 or 2 carbon atoms and $R^7$ represents a heterocyclic group bonded to D via a carbon atom in the heterocyclic group, said heterocyclic group being selected from the group consisting of pyrrolidinyl groups, piperidyl groups, morpholinyl groups and thiomorpholinyl groups which are unsubstituted or are substituted on at least one of a carbon atom and a nitrogen atom by at least one substituent selected from the group consisting of in the case of substituents on a carbon atom, methyl groups, ethyl groups, hydroxy groups, methoxy groups, ethoxy groups, ethoxycarbonyloxy groups, isopropoxycarbonyloxy groups, t-butoxycarbonyloxy groups, alkanoyloxy groups having 2 or 3 carbon atoms, alkanoyloxy groups having from 14 to 20 carbon atoms, carboxy-substituted alkanoyloxy groups having 3 or 4 carbon atoms in the alkanoyl part, carbamoyloxy groups, and mono- and di- alkylcarbamoyloxy groups in which the or each alkyl part is a methyl or ethyl group, in the case of substituents on a nitrogen atom, methyl groups and ethyl groups;

A represents an alkylene group having from 2 to 5 carbon atoms.

17. The compound of claim 1, wherein:

$R^1$ represents a phenyl group which is unsubstituted or is substituted by at least one substituent selected from the group consisting of methyl groups, ethyl groups, hydroxy groups, methoxy groups, ethoxy groups, difluoromethoxy groups, fluorine atoms, chlorine atoms, bromine atoms and cyano groups;

$R^2$ represents a hydrogen atom;

the group represented by $-OR^3$ is present at the 2-position of the benzene ring (relative to the position of attachment of the group represented by A taken to be the 1-position);

$R^3$ represents a group of formula $-B-NR^4R^5$, where $R^4$ and $R^5$ are independently selected from the group consisting of hydrogen atoms, methyl groups, ethyl groups and 2-hydroxyethyl groups, or $R^4$ and $R^5$, together with the nitrogen atom to which they are attached, represent a 1-pyrrolidinyl group, a 1-piperidyl group, a 4-hydroxy-1-piperidyl group or a 4-morpholinyl group, and B represents an alkylene group having 2 or 3 carbon atoms or a group of formula —CH$_2$CH(OR$^6$)CH$_2$—, where R$^6$ represents a hydrogen atom, an acetyl group, a succinyl group or a glutaryl group, or a group of formula —D—R$^7$, where D represents a carbon-carbon single bond or an alkylene group having 1 or 2 carbon atoms and R$^7$ represents a heterocyclic group bonded to D via a carbon atom in the heterocyclic group, said heterocyclic group being selected from the group consisting of pyrrolidinyl groups, 1-methylpyrrolidinyl groups, 4-hydroxy-1-methylpyrrolidinyl groups, piperidyl groups, 1-methylpiperidyl groups, morpholinyl groups and 4-methylmorpholinyl groups;

A represents an alkylene group having from 2 to 5 carbon atoms.

18. The compound of claim 1, wherein:

R$^1$ represents a phenyl group which is unsubstituted or is substituted by at least one substituent selected from the group consisting of methyl groups, hydroxy groups, methoxy groups, ethoxy groups, difluoromethoxy groups, fluorine atoms, chlorine atoms, bromine atoms and cyano groups;

R$^2$ represents a hydrogen atom; the group represented by —OR$^3$ is present at the 2-position of the benzene ring (relative to the position of attachment of the group represented by A taken to be the 1-position);

R$^3$ represents a group of formula —D—R$^7$, where D represents a carbon-carbon single bond or an alkylene group having 1 or 2 carbon atoms and R$^7$ represents a heterocyclic group bonded to D via a carbon atom in the heterocyclic group, said heterocyclic group being selected from the group consisting of pyrrolidinyl groups, 1-methylpyrrolidinyl groups, 4-hydroxy-1-methylpyrrolidinyl groups, piperidyl groups, 1-methylpiperidyl groups, morpholinyl groups and 4-methylmorpholinyl groups;

A represents a tetramethylene group or a pentamethylene group.

19. The compound of claim 1, selected from the group consisting of 3-dimethylamino-1-[2-(4-phenylbutyl)phenoxy]-2-propanol and pharmaceutically acceptable salts thereof.

20. The compound of claim 1, selected from the group consisting of 1-methyl-2-{2-[2-(4-phenylbutyl)phenoxy]ethyl}pyrrolidine and pharmaceutically acceptable salts thereof.

21. The compound of claim 1, selected from the group consisting of 1-methyl-2-(2-{2-[4-(3-methoxyphenyl)butyl]phenoxy}ethyl)pyrrolidine and pharmaceutically acceptable salts thereof.

22. The compound of claim 1, selected from the group consisting of 1-methyl-2-{2-[2-(2-phenylethyl)phenoxy]ethyl}pyrrolidine and pharmaceutically acceptable salts thereof.

23. The compound of claim 1, selected from the group consisting of 4-hydroxy-1-methyl-2-{2-[2-(2-phenylethyl)phenoxy]ethyl}pyrrolidine and pharmaceutically acceptable salts thereof.

24. The compound of claim 1, selected from the group consisting of 1-methyl-2-(2-{2-[2-(3-methoxyphenyl)ethyl]phenoxy}ethyl)pyrrolidine and pharmaceutically acceptable salts thereof.

25. The compound of claim 1, selected from the group consisting of 2-(2-{2-[2-(3,5-dimethoxyphenyl)ethyl]phenoxy}ethyl)-1-methylpyrrolidine and pharmaceutically acceptable salts thereof.

26. The compound of claim 1, selected from the group consisting of 2-(2-{2-[2-(3-fluorophenyl)ethyl]phenoxy}ethyl)-1-methylpyrrolidine and pharmaceutically acceptable salts thereof.

27. The compound of claim 1, selected from the group consisting of 2-(2-{2-[2-(3-bromophenyl)ethyl]phenoxy}ethyl)-1-methylpyrrolidine and pharmaceutically acceptable salts thereof.

28. The compound of claim 1, selected from the group consisting of 4-hydroxy-1-methyl-2-(2-{2-[2-(3-methoxyphenyl)ethyl]phenoxy}ethyl)pyrrolidine and pharmaceutically acceptable salts thereof.

29. The compound of claim 1, selected from the group consisting of 2-(2-{2-[2-(3-fluorophenyl)ethyl]phenoxy}ethyl)-4-hydroxy-1-methylpyrrolidine and pharmaceutically acceptable salts thereof.

30. The compound of claim 1, selected from the group consisting of 2-(2-{2-[2-(3-difluoromethoxyphenyl)ethyl]phenoxy}ethyl)-1-methylpyrrolidine and pharmaceutically acceptable salts thereof.

31. The compound of claim 1, selected from the group consisting of 2-(2-{2-[2-(3-difluoromethoxyphenyl)ethyl]phenoxy}ethyl)-4-hydroxy-1-methylpyrrolidine and pharmaceutically acceptable salts thereof.

32. The compound of claim 1, selected from the group consisting of 2-(2-{2-[2-(3,5-dimethoxyphenyl)ethyl]phenoxy}ethyl)-4-hydroxy-1-methylpyrrolidine and pharmaceutically acceptable salts thereof.

33. The compound of claim 1, selected from the group consisting of 1-methyl-2-(2-{2-[2-(3-methoxyphenyl)ethyl]phenoxy}ethyl)-4-succinyloxypyrrolidine and pharmaceutically acceptable salts thereof.

34. The compound of claim 1, selected from the group consisting of 2-(2-{2-[2-(3,5-dimethoxyphenyl)ethyl]phenoxy}ethyl)-4-succinyloxy-1-methylpyrrolidine and pharmaceutically acceptable salts thereof.

35. The compound of claim 1, selected from the group consisting of 2-(2-{2-[2-(3-bromophenyl)ethyl]phenoxy}ethyl)-4-hydroxy-1-methylpyrrolidine and pharmaceutically acceptable salts thereof, and 36. The compound of claim 1, selected from the group consisting of 2-(2-{2-[2-(2-difluoromethoxyphenyl)ethyl]phenoxy}ethyl)-4-succinyloxy-1-methylpyrrolidine and pharmaceutically acceptable salts thereof.

37. The compound of claim 1, selected from the group consisting of N,N-dimethyl-3-[2-(4-phenylbutyl)phenoxy]propylamine and pharmaceutically acceptable salts thereof.

38. The compound of claim 1, selected from the group consisting of 1-methyl-3-[2-(4-phenylbutyl)phenoxymethyl]piperidine and pharmaceutically acceptable salts thereof.

39. The compound of claim 1, selected from the group consisting of N,N-dimethyl-3-{2-[4-(3-methoxyphenyl)butyl]phenoxy}propylamine and pharmaceutically acceptable salts thereof.

40. The compound of claim 1, selected from the group consisting of 1-methyl-3-{2-[4-(3-methoxyphenyl)butyl]phenoxymethyl}piperidine and pharmaceutically acceptable salts thereof.

41. The compound of claim 1, selected from the group consisting of N,N-dimethyl-3-{2-[4-(2-methoxyphenyl)butyl]phenoxy}propylamine and pharmaceutically acceptable salts thereof.

42. The compound of claim 1, selected from the group consisting of 1-methyl-2-(2-{2-[4-(2-methoxyphenyl)butyl]phenoxy}ethyl)pyrrolidine and pharmaceutically acceptable salts thereof.

43. The compound of claim 1, selected from the group consisting of 2-(2-{2-[4-(3,5-dimethoxyphenyl)butyl]phenoxy}ethyl)-1-methylpyrrolidine and pharmaceutically acceptable salts thereof.

44. The compound of claim 1, selected from the group consisting of 3-{2-[4-(3,5-dimethoxyphenyl)butyl]phenoxymethyl}-1-methylpiperidine and pharmaceutically acceptable salts thereof.

45. The compound of claim 1, selected from the group consisting of 1-methyl-3-{2-[4-(2-methoxyphenyl)butyl]phenoxymethyl}piperidine and pharmaceutically acceptable salts thereof.

46. The compound of claim 1, selected from the group consisting of 1-methyl-2-{2-[2-(5-phenylpentyl)phenoxy]ethyl}pyrrolidine and pharmaceutically acceptable salts thereof.

47. The compound of claim 1, selected from the group consisting of 1-methyl-3-[2-(5-phenylpentyl)phenoxymethyl]piperidine and pharmaceutically acceptable salts thereof.

48. The compound of claim 1, selected from the group consisting of 1-methyl-3-{2-[5-(3-methoxyphenyl)pentyl]phenoxymethyl}piperidine and pharmaceutically acceptable salts thereof.

49. The compound of claim 1, selected from the group consisting of 1-methyl-3-[2-(6-phenylhexyl)phenoxymethyl]piperidine and pharmaceutically acceptable salts thereof.

50. The compound of claim 1, selected from the group consisting of 1-methyl-3-{2-[6-(3-methoxyphenyl)hexyl]phenoxymethyl}piperidine and pharmaceutically acceptable salts thereof, and 51. The compound of claim 1, selected from the group consisting of 3-{2-[5-(3,5-dimethoxyphenyl)pentyl]phenoxymethyl}-1-methylpiperidine and pharmaceutically acceptable salts thereof.

52. A pharmaceutical composition comprising a compound of formula (I) or a pharmaceutically acceptable salt or ester thereof, as claimed in claim 1, in admixture with a pharmaceutically acceptable carrier or diluent.

53. The composition of claim 52, wherein:

$R^1$ represents a phenyl or naphthyl group which is unsubstituted or is substituted by at least one substituent selected from the group consisting of
   alkyl groups having from 1 to 4 carbon atoms,
   hydroxy groups,
   alkoxy groups having from 1 to 4 carbon atoms,
   haloalkoxy groups having from 1 to 4 carbon atoms,
   halogen atoms,
   cyano groups, and
   carbamoyl groups;

$R^2$ represents a hydrogen atom, a methyl group or an ethyl group;

the group represented by —$OR^3$ is present at the 2-position of the benzene ring (relative to the position of attachment of the group represented by A taken to be the 1-position);

$R^3$ represents
   a group of formula —B—$NR^4R^5$,
      where $R^4$ and $R^5$ are independently selected from the group consisting of hydrogen atoms, alkyl groups having from 1 to 4 carbon atoms, substituted alkyl groups having from 1 to 4 carbon atoms and substituted by at least one phenyl group, and substituted alkyl groups having from 2 to 4 carbon atoms and substituted by at least one substituent selected from the group consisting of hydroxy groups and dialkylamino groups in which each alkyl part is a methyl or ethyl group, or $R^4$ and $R^5$, together with the nitrogen atom to which they are attached, represent a heterocyclic group selected from the group consisting of the 1-pyrrolidinyl, 1-piperidyl, 4-morpholinyl, 4-thiomorpholinyl, 1-piperazinyl, 1-imidazolyl, 1-pyrazolyl and 1-triazolyl groups, any of which is substituted or unsubstituted, said substituted heterocyclic groups being substituted on at least one of a carbon atom and a nitrogen atom, the substituents being, in the case of substituents on a carbon atom, selected from the group consisting of
      alkyl groups having from 1 to 4 carbon atoms, hydroxy groups and phenyl groups which are unsubstituted or which have at least one substituent selected from the group consisting of methyl groups, methoxy groups, fluorine atoms and chlorine atoms, and B represents an alkylene group having from 2 to 4 carbon atoms or a group of formula —$CH_2CH(OR^6)CH_2$—, where $R^6$ represents a hydrogen atom, an alkanoyl group having from 2 to 4 carbon atoms, a substituted alkanoyl group having 2 or 3 carbon atoms and substituted by a carboxy group, or a benzoyl group which is unsubstituted or is substituted by at least one substituent selected from the group consisting of methyl groups, methoxy groups, fluorine atoms and chlorine atoms, or a group of formula —D—$R^7$, where D represents a carbon-carbon single bond or an alkylene group having from 1 to 3 carbon atoms and $R^7$ represents a heterocyclic group having 5 or 6 ring atoms bonded to D via a carbon atom in the heterocyclic group, said heterocyclic group being selected from the group consisting of pyrrolidinyl groups, piperidyl groups, morpholinyl groups, thiomorpholinyl groups and piperazinyl groups which are unsubstituted or are substituted on at least one of a carbon atom and a nitrogen atom by at least one substituent selected from the group consisting of
   in the case of substituents on a carbon atom, alkyl groups having from 1 to 4 carbon atoms, hydroxy groups, alkoxy groups having from 1 to 4 carbon atoms, alkoxycarbonyloxy groups having from 2 to 5 carbon atoms, alkanoyloxy groups having from 2 to 20 carbon atoms, carboxy-substituted alkanoyloxy groups having 3 or 4 carbon atoms in the alkanoyl part, carbamoyloxy groups, mono- and di- alkyl- carbamoyloxy groups in which the or each alkyl part is a methyl or ethyl group, fluorine atoms and chlorine atoms, in the case of substituents on a nitrogen atom, alkyl groups having from 1 to 4 carbon atoms, and phenyl groups which are unsubstituted or which have at least one substituent selected from the group consisting of methyl groups, methoxy groups, fluorine atoms and chlorine atoms;

A represents an alkylene group having from 2 to 7 carbon atoms.

54. The composition of claim 52, wherein:

$R^1$ represents a phenyl group which is unsubstituted or is substituted by at least one substituent selected from the group consisting of methyl groups, ethyl groups, fluoromethoxy groups, difluoromethoxy groups, 2-fluoroethoxy groups, hydroxy groups, methoxy groups, ethoxy groups, fluorine atoms, chlorine atoms, bromine atoms and cyano groups;

$R^2$ represents a hydrogen atom;

the group represented by —$OR^3$ is present at the 2-position of the benzene ring (relative to the position of attachment of the group represented by A taken to be the 1-position);

$R^3$ represents
a group of formula —B—$NR^4R^5$,
where $R^4$ and $R^5$ are independently selected from the group consisting of hydrogen atoms, alkyl groups having from 1 to 4 carbon atoms, benzyl groups, phenethyl groups, 2-hydroxyethyl groups, 3-hydroxypropyl groups, 2-(N,N-dimethylamino)ethyl groups and 2-(N,N-dimethylamino)propyl groups, or $R^4$ and $R^5$, together with the nitrogen atom to which they are attached, represent a 1-pyrrolidinyl group, a 1-piperidyl group, a 4-hydroxy-1-piperidyl group, a 4-morpholinyl group, a 4-methyl-1-piperazinyl group, a 4-ethyl-1-piperazinyl group, a 4-phenyl-1-piperazinyl group, a 1-imidazolyl group or a 1-triazolyl group, and B represents an alkylene group having 2 or 3 carbon atoms or a group of formula —$CH_2CH(OR^6)CH_2$—, where $R^6$ represents a hydrogen atom, an alkanoyl group having 2 or 3 carbon atoms, or a substituted alkanoyl group having 3 or 4 carbon atoms and substituted by a carboxy group, or a group of formula —D—$R^7$ where D represents a carbon-carbon single bond or an alkylene group having 1 or 2 carbon atoms and $R^7$ represents a heterocyclic group having 5 or 6 ring atoms bonded to D via a carbon atom in the heterocyclic group, said heterocyclic group being selected from the group consisting of pyrrolidinyl groups, piperidyl groups, morpholinyl groups and thiomorpholinyl groups which are unsubstituted or are substituted on at least one of a carbon atom and a nitrogen atom by at least one substituent selected from the group consisting of in the case of substituents on a carbon atom, alkyl groups having from 1 to 4 carbon atoms, hydroxy groups, alkoxy groups having from 1 to 4 carbon atoms, alkoxycarbonyloxy groups having from 2 to 5 carbon atoms, alkanoyloxy groups having 2 or 3 carbon atoms, alkanoyloxy groups having from 12 to 20 carbon atoms, carboxy-substituted alkanoyloxy groups having 3 or 4 carbon atoms in the alkanoyl part, carbamoyloxy groups, and mono- and di- alkyl- carbamoyloxy groups in which the or each alkyl part is a methyl or ethyl group, in the case of substituents on a nitrogen atom, alkyl groups having from 1 to 4 carbon atoms;

A represents an alkylene group having from 2 to 5 carbon atoms.

55. The composition of claim 52, wherein:

$R^1$ represents a phenyl group which is unsubstituted or is substituted by at least one substituent selected from the group consisting of methyl groups, ethyl groups, fluoromethoxy groups, difluoromethoxy groups, 2-fluoroethoxy groups, hydroxy groups, methoxy groups, ethoxy groups, fluorine atoms, chlorine atoms, bromine atoms and cyano groups;

$R^2$ represents a hydrogen atom; the group represented by —$OR^3$ is present at the 2-position of the benzene ring (relative to the position of attachment of the group represented by A taken to be the 1-position);

$R^3$ represents
a group of formula —B—$NR^4R^5$,
where $R^4$ and $R^5$ are independently selected from the group consisting of hydrogen atoms, methyl groups, ethyl groups, benzyl groups and 2-hydroxyethyl groups, or $R^4$ and $R^5$ together with the nitrogen atom to which they are attached, represent a 1-pyrrolidinyl group, a 1-piperidyl group, a 4-hydroxy-1-piperidyl group, a 4-morpholinyl group, a 4-methyl-1-piperazinyl group, a 4-phenyl-1-piperazinyl group or a 1-imidazolyl group, and B represents an alkylene group having 2 or 3 carbon atoms or a group of formula —$CH_2CH(OR^6)CH_2$—, where $R^6$ represents a hydrogen atom, an acetyl group, a succinyl group or a glutaryl group, or a group of formula —D—$R^7$ where D represents a carbon-carbon single bond or an alkylene group having 1 or 2 carbon atoms and $R^7$ represents a heterocyclic group having 5 or 6 ring atoms bonded to D via a carbon atom in the heterocyclic group, said heterocyclic group being selected from the group consisting of pyrrolidinyl groups, piperidyl groups, morpholinyl groups and thiomorpholinyl groups which are unsubstituted or are substituted on at least one of a carbon atom and a nitrogen atom by at least one substituent selected from the group consisting of in the case of substituents on a carbon atom, methyl groups, ethyl groups, hydroxy groups, methoxy groups, ethoxy groups, ethoxycarbonyloxy groups, isopropoxycarbonyloxy groups, t-butoxycarbonyloxy groups, alkanoyloxy groups having 2 or 3 carbon atoms, alkanoyloxy groups having from 14 to 20 carbon atoms, carboxy-substituted alkanoyloxy groups having 3 or 4 carbon atoms in the alkanoyl part, carbamoyloxy groups, and mono- and di- alkyl- carbamoyloxy groups in which the or each alkyl part is a methyl or ethyl group, in the case of substituents on a nitrogen atom, methyl groups and ethyl groups;

A represents an alkylene group having from 2 to 4 carbon atoms.

56. The composition of claim 52, wherein:

$R^1$ represents a phenyl group which is unsubstituted or is substituted by at least one substituent selected from the group consisting of methyl groups, hydroxy groups, methoxy groups, ethoxy groups, fluoromethoxy groups, difluoromethoxy groups, fluorine atoms, chlorine atoms, bromine atoms and cyano groups;

$R^2$ represents a hydrogen atom;

the group represented by —$OR^3$ is present at the 2-position of the benzene ring (relative to the position of attachment of the group represented by A taken to be the 1-position);

$R^3$ represents
a group of formula —B—$NR^4R^5$,
where $R^4$ and $R^5$ are independently selected from the group consisting of methyl groups, ethyl groups and 2-hydroxyethyl groups, or $R^4$ and $R^5$, together with the nitrogen atom to which they are attached, represent a 1-pyrrolidinyl group, a 1-piperidyl group, a 4-hydroxy-1-piperidyl group or a 4-morpholinyl group, and B represents an alkylene group having 2 or 3 carbon atoms or a group of formula —$CH_2CH(OR^6)CH_2$—, where $R^6$ represents a hydrogen atom, an acetyl group, a succinyl group or a glutaryl group, or a group of formula —D—$R^7$ where D represents a carbon-carbon single bond or an alkylene group having 1 or 2 carbon atoms and $R^7$ represents a heterocyclic group bonded to D via a carbon atom in the heterocyclic group, said heterocyclic group being selected from the group consisting of pyrrolidinyl groups, 1-methylpyrrolidinyl groups, 4-hydroxy-1-methylpyrrolidinyl groups, 4-ethoxycarbonyloxy-1-methylpyrrolidinyl groups, 4-isopropoxycarbonyloxy-1-methylpyrrolidinyl groups, 4-t-butoxycarbonyloxy-1-methylpyrrolidinyl groups, 4-palmitoyloxy-1-methylpyrrolidinyl groups, 4-stearoyloxy-1-methylpyrrolidinyl groups, piperidyl groups, 1-methylpiperidyl groups, morpholinyl groups and thiomorpholinyl groups;

A represents an ethylene group or a tetramethylene group.

57. The composition of claim 52, wherein:

$R^1$ represents a phenyl group which is unsubstituted or is substituted by at least one substituent selected from the group consisting of methyl groups, hydroxy groups, methoxy groups, ethoxy groups, difluoromethoxy groups, fluorine atoms, chlorine atoms, bromine atoms and cyano groups;

$R^2$ represents a hydrogen atom;

the group represented by —$OR^3$ is present at the 2-position of the benzene ring (relative to the position of attachment of the group represented by A taken to be the 1-position);

$R^3$ represents a group of formula —D—$R^7$, where D represents a carbon-carbon single bond or an alkylene group having 1 or 2 carbon atoms and $R^7$ represents a heterocyclic group bonded to D via a carbon atom in the heterocyclic group, said heterocyclic group being selected from the group consisting of pyrrolidinyl groups, 1-methylpyrrolidinyl groups, 4-hydroxy-1-methylpyrrolidinyl groups, piperidyl groups, 1-methylpiperidyl groups, morpholinyl groups and thiomorpholinyl groups;

A represents an ethylene group.

58. The composition of claim 52, wherein:

$R^1$ represents a phenyl group which is unsubstituted or is substituted by at least one substituent selected from the group consisting of methyl groups, ethyl groups, hydroxy groups, methoxy groups, ethoxy groups, fluoromethoxy groups, difluoromethoxy groups, 2-fluoroethoxy groups, fluorine atoms, chlorine atoms, bromine atoms and cyano groups;

$R^2$ represents a hydrogen atom;

the group represented by —$OR^3$ is present at the 2-position of the benzene ring (relative to the position of attachment of the group represented by A taken to be the 1-position);

$R^3$ represents a group of formula —B—$NR^4R^5$,
  where $R^4$ and $R^5$ are independently selected from the group consisting of hydrogen atoms, alkyl groups having from 1 to 4 carbon atoms, benzyl groups, phenethyl groups, 2-hydroxyethyl groups, 3-hydroxypropyl groups, 2-(N,N-dimethylamino)ethyl groups and 3-(N,N-dimethylamino)propyl groups, or $R^4$ and $R^5$, together with the nitrogen atom to which they are attached, represent a 1-pyrrolidinyl group, a 1-piperidyl group, a 4-hydroxy-1-piperidyl group, a 4-morpholinyl group, a 4-methyl-1-piperazinyl group, a 4-ethyl-1-piperazinyl group, a 4-phenyl-1-piperazinyl group, a 1-imidazolyl group or a 1-triazolyl group, and B represents an alkylene group having 2 or 3 carbon atoms or a group of formula —$CH_2CH(OR^6)CH_2$—, where $R^6$ represents a hydrogen atom, an alkanoyl group having 2 or 3 carbon atoms, or a substituted alkanoyl group having 3 or 4 carbon atoms and substituted by a carboxy group, or a group of formula —D—$R^7$, where D represents a carbon-carbon single bond or an alkylene group having 1 or 2 carbon atoms and R represents a heterocyclic group bonded to D via a carbon atom in the heterocyclic group, said heterocyclic group being selected from the group consisting of pyrrolidinyl groups, piperidyl groups, morpholinyl groups and thiomorpholinyl groups which are unsubstituted or are substituted on at least one of a carbon atom and a nitrogen atom by at least one substituent selected from the group consisting of in the case of substituents on a carbon atom, alkyl groups having from 1 to 4 carbon atoms, hydroxy groups, alkoxy groups having from 1 to 4 carbon atoms, alkoxycarbonyloxy groups having from 2 to 5 carbon atoms, alkanoyloxy groups having 2 or 3 carbon atoms, alkanoyloxy groups having from 12 to 20 carbon atoms, carboxy-substituted alkanoyloxy groups having 3 or 4 carbon atoms in the alkanoyl part, carbamoyloxy groups, and mono- and di- alkylcarbamoyloxy groups in which the or each alkyl part is a methyl or ethyl group, in the case of substituents on a nitrogen atom, alkyl groups having from 1 to 4 carbon atoms;

A represents an alkylene group having from 2 to 7 carbon atoms.

59. The composition of claim 52, wherein:

$R^1$ represents a phenyl group which is unsubstituted or is substituted by at least one substituent selected from the group consisting of methyl groups, ethyl groups, hydroxy groups, methoxy groups, ethoxy groups, fluoromethoxy groups, difluoromethoxy groups, fluorine atoms, chlorine atoms, bromine atoms and cyano groups;

$R^2$ represents a hydrogen atom;

the group represented by —$OR^3$ is present at the 2-position of the benzene ring (relative to the position of attachment of the group represented by A taken to be the 1-position);

$R^3$ represents a group of formula —B—$NR^4R^5$,
  where $R^4$ and $R^5$ are independently selected from the group consisting of hydrogen atoms, methyl groups, ethyl groups, benzyl groups and 2-hydroxyethyl groups, or $R^4$ and $R^5$, together with the nitrogen atom to which they are attached, represent a 1-pyrrolidinyl group, a 1-piperidyl group, a 4-hydroxy-1-piperidyl group, a 4-morpholinyl group, a 4-methyl-1-piperazinyl group, a 4-phenyl-1-piperazinyl group or a 1-imidazolyl group, and B represents an alkylene group having 2 or 3 carbon atoms or a group of formula —CH$_2$CH(OR$^6$)CH$_2$—, where R$^6$ represents a hydrogen atom, an acetyl group, a succinyl group or a glutaryl group, or a group of formula —D—R$^7$ where D represents a carbon-carbon single bond or an alkylene group having 1 or 2 carbon atoms and R$^7$ represents a heterocyclic group bonded to D via a carbon atom in the heterocyclic group, said heterocyclic group being selected from the group consisting of pyrrolidinyl groups, piperidyl groups, morpholinyl groups and thiomorpholinyl groups which are unsubstituted or are substituted on at least one of a carbon atom and a nitrogen atom by at least one substituent selected from the group consisting of in the case of substituents on a carbon atom, methyl groups, ethyl groups, hydroxy groups, methoxy groups, ethoxy groups, ethoxycarbonyloxy groups, isopropoxycarbonyloxy groups, t-butoxycarbonyloxy groups, alkanoyloxy groups having 2 or 3 carbon atoms, alkanoyloxy groups having from 14 to 20 carbon atoms, carboxy-substituted alkanoyloxy groups having 3 or 4 carbon atoms in the alkanoyl part, carbamoyloxy groups, and mono- and di- alkylcarbamoyloxy groups in which the or each alkyl part is a methyl or ethyl group, in the case of substituents on a nitrogen atom, methyl groups and ethyl groups;

A represents an alkylene group having from 2 to 5 carbon atoms.

60. The composition of claim 52, wherein:

R$^1$ represents a phenyl group which is unsubstituted or is substituted by at least one substituent selected from the group consisting of methyl groups, ethyl groups, hydroxy groups, methoxy groups, ethoxy groups, difluoromethoxy groups, fluorine atoms, chlorine atoms, bromine atoms and cyano groups;

R$^2$ represents a hydrogen atom;

the group represented by —OR$^3$ is present at the 2-position of the benzene ring (relative to the position of attachment of the group represented by A taken to be the 1-position);

R$^3$ represents
a group of formula —B—NR$^4$R$^5$,
where R$^4$ and R$^5$ are independently selected from the group consisting of hydrogen atoms, methyl groups, ethyl groups and 2-hydroxyethyl groups, or R$^4$ and R$^5$, together with the nitrogen atom to which they are attached, represent a 1-pyrrolidinyl group, a 1-piperidyl group, a 4-hydroxy-1-piperidyl group or a 4-morpholinyl group, and B represents an alkylene group having 2 or 3 carbon atoms or a group of formula —CH$_2$CH(OR$^6$)CH$_2$—, where R$^6$ represents a hydrogen atom, an acetyl group, a succinyl group or a glutaryl group, or a group of formula —D—R$^7$, where D represents a carbon-carbon single bond or an alkylene group having 1 or 2 carbon atoms and R$^7$ represents a heterocyclic group bonded to D via a carbon atom in the heterocyclic group, said heterocyclic group being selected from the group consisting of pyrrolidinyl groups, 1-methylpyrrolidinyl groups, 4-hydroxy-1-methylpyrrolidinyl groups, piperidyl groups, 1-methylpiperidyl groups, morpholinyl groups and 4-methylmorpholinyl groups;

A represents an alkylene group having from 2 to 5 carbon atoms.

61. The composition of claim 52, wherein:

R$^1$ represents a phenyl group which is unsubstituted or is substituted by at least one substituent selected from the group consisting of methyl groups, hydroxy groups, methoxy groups, ethoxy groups, difluoromethoxy groups, fluorine atoms, chlorine atoms, bromine atoms and cyano groups;

R$^2$ represents a hydrogen atom;

the group represented by —OR$^3$ is present at the 2-position of the benzene ring (relative to the position of attachment of the group represented by A taken to be the 1-position);

R$^3$ represents a group of formula —D—R$^7$ where D represents a carbon-carbon single bond or an alkylene group having 1 or 2 carbon atoms and R$^7$ represents a heterocyclic group bonded to D via a carbon atom in the heterocyclic group, said heterocyclic group being selected from the group consisting of pyrrolidinyl groups, 1-methylpyrrolidinyl groups, 4-hydroxy-1-methylpyrrolidinyl groups, piperidyl groups, 1-methylpiperidyl groups, morpholinyl groups and 4-methylmorpholinyl groups;

A represents a tetramethylene group or a pentamethylene group.

62. The composition of claim 52, wherein said compound is selected from the group consisting of:

3-Dimethylamino-1-[2-(4-phenylbutyl)phenoxy]-2-propanol;

1-Methyl-2-{2-[2-(4-phenylbutyl)phenoxy]ethyl}pyrrolidine;

1-Methyl-2-(2-{2-[4-(3-methoxyphenyl)butyl]phenoxy}ethyl)pyrrolidine;

1-Methyl-2-{2-[2-(2-phenylethyl)phenoxy]ethyl}pyrrolidine;

4-Hydroxy-1-methyl-2-{2-[2-(2-phenylethyl)phenoxy]ethyl}pyrrolidine;

1-Methyl-2-(2-{2-[2-(3-methoxyphenyl)ethyl]phenoxy}ethyl)pyrrolidine;

2-(2-{2-[2-(3,5-Dimethoxyphenyl)ethyl]phenoxy}ethyl)-1-methylpyrrolidine;

2-(2-{2-[2-(3-Fluorophenyl)ethyl]phenoxy}ethyl)-1-methylpyrrolidine;

2-(2-{2-[2-(3-Bromophenyl)ethyl]phenoxy}ethyl)-1methylpyrrolidine;

4-Hydroxy-1-methyl-2-(2-{2-[2-(3-methoxyphenyl)ethyl]phenoxy}ethyl)pyrrolidine;

2-(2-{2-[2-(3-Fluorophenyl)ethyl]phenoxy}ethyl)-4-hydroxy-1-methylpyrrolidine;

2-(2-{2-[2-(3-Difluoromethoxyphenyl)ethyl]phenoxy}-ethyl)-1-methylpyrrolidine;

2-(2-{2-[2-(3-Difluoromethoxyphenyl)ethyl]phenoxy}ethyl]phenoxy}ethyl)-4-hydroxy-1-methylpyrrolidine;

2-(2-{2-[2-(3,5-Dimethoxylphenyl)ethyl]phenoxy}ethyl)-4-hydroxy-1-methylpyrrolidine;

1-Methyl-2-(2-{2-[2-(3-methoxyphenyl)ethyl]phenoxy}ethyl)-4-succinyloxypyrrolidine;

2-(2-{2-[2-(3,5-Dimethoxyphenyl)ethyl]phenoxy}ethyl)-4-succinyloxy-1-methylpyrrolidine;

2-(2-{2-[2-(3-Bromophenyl)ethyl]phenoxy}ethyl)-4-hydroxy-1-methylpyrrolidine; and 2-(2-{2-[2-(2-Difluoromethoxyphenyl)ethyl]phenoxy}ethyl)-4-succinyloxy-1-methylpyrrolidine;

N,N-Dimethyl-3-[2-(4-phenylbutyl)phenoxy]propylamine;

1-Methyl-3-[2-(4-phenylbutyl)phenoxymethyl]piperidine;

N,N-Dimethyl-3-{2-[4-(3-methoxyphenyl)butyl]phenoxy}propylamine;

1-Methyl-3-{2-[4-(3-methoxyphenyl)butyl]phenoxymethyl}piperidine;

N,N-Dimethyl-3-{2-[4-(2-methoxyphenyl)butyl]phenoxy}propylamine;

-Methyl-2-(2-{2-[4-(2-methoxyphenyl)butyl]phenoxy}ethyl)pyrrolidine;

2-(2-{2-[4-(3,5-Dimethoxyphenyl)butyl]phenoxy}ethyl)-1-methylpyrrolidine;

3-{2-[4-(3,5-Dimethoxyphenyl)butyl]phenoxymethyl}-1-methylpiperidine;

1-Methyl-3-{2-[4-(2-methoxyphenyl)butyl]phenoxymethyl}piperidine;

1-Methyl-2-{2-[2-(5-phenylpentyl)phenoxy]ethyl}pyrrolidine;

1-Methyl-3-[2-(5-phenylpentyl)phenoxymethyl]piperidine;

1-Methyl-3-{2-[5-(3-methoxyphenyl)pentyl]phenoxymethyl}piperidine;

1-Methyl-3-[2-(6-phenylhexyl)phenoxymethyl]piperidine;

1-Methyl-3-{2-[6-(3-methoxyphenyl)hexyl]phenoxymethyl}piperidine; and

3-{2-[5-(3,5-Dimethoxyphenyl)pentyl]phenoxymethyl}-1-methylpiperidine;

and pharmaceutically acceptable salts and esters thereof.

63. A method for the treatment or prophylaxis of circulatory diseases in a mammal, by the administration to said mammal of an effective amount of an active compound, wherein the active compound is at least one compound of formula (I) or a pharmaceutically acceptable salt or ester thereof, as claimed in claim 1.

64. The method of claim 63, wherein:

$R^1$ represents a phenyl or naphthyl group which is unsubstituted or is substituted by at least one substituent selected from the group consisting of
alkyl groups having from 1 to 4 carbon atoms,
hydroxy groups,
alkoxy groups having from 1 to 4 carbon atoms,
haloalkoxy groups having from 1 to 4 carbon atoms,
halogen atoms,
cyano groups, and
carbamoyl groups;

$R^2$ represents a hydrogen atom, a methyl group, or an ethyl group;

the group represented by —$OR^3$ is present at the 2-position of the benzene ring (relative to the position of attachment of the group represented by A taken to be the 1-position);

$R^3$ represents
a group of formula —B—$NR^4R^5$,
where $R^4$ and $R^5$ are independently selected from the group consisting of hydrogen atoms, alkyl groups having from 1 to 4 carbon atoms, substituted alkyl groups having from 1 to 4 carbon atoms and substituted by at least one phenyl group, and substituted alkyl groups having from 2 to 4 carbon atoms and substituted by at least one substituent selected from the group consisting of hydroxy groups and dialkylamino groups in which each alkyl part is a methyl or ethyl group, or $R^4$ and $R^5$, together with the nitrogen atom to which they are attached, represent a heterocyclic group selected from the group consisting of the 1-pyrrolidinyl, 1-piperidyl, 4-morpholinyl, 4-thiomorpholinyl, 1-piperazinyl, 1-imidazolyl, 1-pyrazolyl and 1-triazolyl groups, any of which is substituted or unsubstituted, said substituted heterocyclic groups being substituted on at least one of a carbon atom and a nitrogen atom, the substituents being, in the case of substituents on a carbon atom, selected from the group consisting of
alkyl groups having from 1 to 4 carbon atoms, hydroxy groups and phenyl groups which are unsubstituted or which have at least one substituent selected from the group consisting of methyl groups, methoxy groups, fluorine atoms and chlorine atoms, and B represents an alkylene group having from 2 to 4 carbon atoms or a group of formula —$CH_2CH(OR^6)CH_2$—, where $R^6$ represents a hydrogen atom, an alkanoyl group having from 2 to 4 carbon atoms, a substituted alkanoyl group having 2 or 3 carbon atoms and substituted by a carboxy group, or a benzoyl group which is unsubstituted or is substituted by at least one substituent selected from the group consisting of methyl groups, methoxy groups, fluorine atoms and chlorine atoms, or a group of formula —D—$R^7$, where D represents a carbon-carbon single bond or an alkylene group having from 1 to 3 carbon atoms and $R^7$ represents a heterocyclic group having 5 or 6 ring atoms bonded to D via a carbon atom in the heterocyclic group, said heterocyclic group being selected from the group consisting of pyrrolidinyl groups, piperidyl groups, morpholinyl groups, thiomorpholinyl groups and piperazinyl groups which are unsubstituted or are substituted on at least one of a carbon atom and a nitrogen atom by at least one substituent selected from the group consisting of
in the case of substituents on a carbon atom, alkyl groups having from 1 to 4 carbon atoms, hydroxy groups, alkoxy groups having from 1 to 4 carbon atoms, alkoxycarbonyloxy groups having from 2 to 5 carbon atoms, alkanoyloxy groups having from 2 to 20 carbon atoms, carboxy-substituted alkanoyloxy groups having 3 or 4 carbon atoms in the alkanoyl part, carbamoyloxy groups, mono- and di- alkyl- carbamoyloxy groups in which the or each alkyl part is a methyl or ethyl group, fluorine atoms and chlorine atoms, in the case of substituents on a nitrogen atom, alkyl groups having from 1 to 4 carbon atoms, and phenyl groups which are unsubstituted or which have at least one substituent selected from the group consisting of methyl groups, methoxy groups, fluorine atoms and chlorine atoms;

A represents an alkylene group having from 2 to 7 carbon atoms.

65. The method of claim 63, wherein:

$R^1$ represents a phenyl group which is unsubstituted or is substituted by at least one substituent selected from the group consisting of methyl groups, ethyl groups, fluoromethoxy groups, difluoromethoxy groups, 2-fluoroethoxy groups, hydroxy groups, methoxy groups, ethoxy groups, fluorine atoms, chlorine atoms, bromine atoms and cyano groups;

$R^2$ represents a hydrogen atom;

the group represented by —$OR^3$ is present at the 2-position of the benzene ring (relative to the position of attachment of the group represented by A taken to be the 1-position);

$R^3$ represents
a group of formula —B—$NR^4R^5$,
where $R^4$ and $R^5$ are independently selected from the group consisting of hydrogen atoms, alkyl groups having from 1 to 4 carbon atoms, benzyl groups, phenethyl groups, 2-hydroxyethyl groups, 3-hydroxypropyl groups, 2-(N,N-dimethylamino) ethyl groups and 2-(N,N-dimethylamino)propyl groups, or $R^4$ and $R^5$, together with the nitrogen atom to which they are attached, represent a 1-pyrrolidinyl group, a 1-piperidyl group, a 4-hydroxy-1-piperidyl group, a 4-morpholinyl group, a 4-methyl-1-piperazinyl group, a 4-ethyl-1-piperazinyl group, a 4-phenyl-1-piperazinyl group, a 1-imidazolyl group or a 1-triazolyl group, and B represents an alkylene group having 2 or 3 carbon atoms or a group of formula —$CH_2CH(OR^6)CH_2$—, where $R^6$ represents a hydrogen atom, an alkanoyl group having 2 or 3 carbon atoms, or a substituted alkanoyl group having 3 or 4 carbon atoms and substituted by a carboxy group, or a group of formula —D—$R^7$, where D represents a carbon-carbon single bond or an alkylene group having 1 or 2 carbon atoms and $R^7$ represents a heterocyclic group having 5 or 6 ring atoms bonded to D via a carbon atom in the heterocyclic group, said heterocyclic group being selected from the group consisting of pyrrolidinyl groups, piperidyl groups, morpholinyl groups and thiomorpholinyl groups which are unsubstituted or are substituted on at least one of a carbon atom and a nitrogen atom by at least one substituent selected from the group consisting of in the case of substituents on a carbon atom, alkyl groups having from 1 to 4 carbon atoms, hydroxy groups, alkoxy groups having from 1 to 4 carbon atoms, alkoxycarbonyloxy groups having from 2 to 5 carbon atoms, alkanoyloxy groups having 2 or 3 carbon atoms, alkanoyloxy groups having from 12 to 20 carbon atoms, carboxy-substituted alkanoyloxy groups having 3 or 4 carbon atoms in the alkanoyl part, carbamoyloxy groups, and mono- and di- alkyl- carbamoyloxy groups in which the or each alkyl part is a methyl or ethyl group, in the case of substituents on a nitrogen atom, alkyl groups having from 1 to 4 carbon atoms;

A represents an alkylene group having from 2 to 5 carbon atoms.

66. The method of claim 63, wherein:

$R^1$ represents a phenyl group which is unsubstituted or is substituted by at least one substituent selected from the group consisting of methyl groups, ethyl groups, fluoromethoxy groups, difluoromethoxy groups, 2-fluoroethoxy groups, hydroxy groups, methoxy groups, ethoxy groups, fluorine atoms, chlorine atoms, bromine atoms and cyano groups;

$R^2$ represents a hydrogen atom;

the group represented by —$OR^3$ is present at the 2-position of the benzene ring (relative to the position of attachment of the group represented by A taken to be the 1-position);

$R^3$ represents
a group of formula —B-$NR^4R^5$,
where $R^4$ and $R^5$ are independently selected from the group consisting of hydrogen atoms, methyl groups, ethyl groups, benzyl groups and 2-hydroxyethyl groups, or $R^4$ and $R^5$, together with the nitrogen atom to which they are attached, represent a 1-pyrrolidinyl group, a 1-piperidyl group, a 4-hydroxy-1-piperidyl group, a 4-morpholinyl group, a 4-methyl-1-piperazinyl group, a 4-phenyl-1-piperazinyl group or a 1-imidazolyl group, and B represents an alkylene group having 2 or 3 carbon atoms or a group of formula —$CH_2CH(OR^6)CH_2$—, where $R^6$ represents a hydrogen atom, an acetyl group, a succinyl group or a glutaryl group, or a group of formula —D—$R^7$, where D represents a carbon-carbon single bond or an alkylene group having 1 or 2 carbon atoms and $R^7$ represents a heterocyclic group having 5 or 6 ring atoms bonded to D via a carbon atom in the heterocyclic group, said heterocyclic group being selected from the group consisting of pyrrolidinyl groups, piperidyl groups, morpholinyl groups and thiomorpholinyl groups which are unsubstituted or are substituted on at least one of a carbon atom and a nitrogen atom by at least one substituent selected from the group consisting of in the case of substituents on a carbon atom, methyl groups, ethyl groups, hydroxy groups, methoxy groups, ethoxy groups, ethoxycarbonyloxy groups, isopropoxycarbonyloxy groups, t-butoxycabonyloxy groups, alkanoyloxy groups having 2 or 3 carbon atoms, alkanoyloxy groups having from 14 to 20 carbon atoms, carboxy-substituted alkanoyloxy groups having 3 or 4 carbon atoms in the alkanoyl part, carbamoyloxy groups, and mono- and di- alkyl- carbamoyloxy groups in which the or each alkyl part is a methyl or ethyl group, in the case of substituents on a nitrogen atom, methyl groups and ethyl groups;

A represents an alkylene group having from 2 to 4 carbon atoms.

67. The method of claim 63, wherein:

$R^1$ represents a phenyl group which is unsubstituted or is substituted by at least one substituent selected from the group consisting of methyl groups, hydroxy groups, methoxy groups, ethoxy groups, fluoromethoxy groups, difluoromethoxy groups, fluorine atoms, chlorine atoms, bromine atoms and cyano groups;

$R^2$ represents a hydrogen atom;

the group represented by —$OR^3$ is present at the 2-position of the benzene ring (relative to the position of attachment of the group represented by A taken to be the 1-position);

$R^3$ represents
a group of formula —B—$NR^4R^5$,
where $R^4$ and $R^5$ are independently selected from the group consisting of methyl groups, ethyl groups and 2-hydroxyethyl groups, or $R^4$ and $R^5$, together with the nitrogen atom to which they are attached, represent a 1-pyrrolidinyl group, a 1-piperidyl group, a 4-hydroxy-1-piperidyl group or a 4-morpholinyl group, and B represents an alkylene group having 2 or 3 carbon atoms or a group of formula —$CH_2CH(OR^6)CH_2$—, where $R^6$ represents a hydrogen atom, an acetyl group, a succinyl group or a glutaryl group, or a group of formula —D—$R^7$ where D represents a carbon-carbon single bond or an alkylene group having 1 or 2 carbon atoms and $R^7$ represents a heterocyclic group bonded to D via a carbon atom in the heterocyclic group, said heterocyclic group being selected from the group consisting of pyrrolidinyl groups, 1-methylpyrrolidinyl groups, 4-hydroxy-1-methylpyrrolidinyl groups, 4-ethoxycarbonyloxy-1-methylpyrrolidinyl groups, 4-isopropoxycarbonyloxy-1-methylpyrrolidinyl groups, 4-t-butoxycarbonyloxy-1-methylpyrrolidinyl groups, 4-palmitoyloxy-1-methylpyrrolidinyl groups, 4-stearoyloxy-1-methylpyrrolidinyl groups, piperidyl groups, 1-methylpiperidyl groups, morpholinyl groups and thiomorpholinyl groups;

A represents an ethylene group or a tetramethylene group.

68. The method of claim 63, wherein:

$R^1$ represents a phenyl group which is unsubstituted or is substituted by at least one substituent selected from the group consisting of methyl groups, hydroxy groups, methoxy groups, ethoxy groups, difluoromethoxy groups, fluorine atoms, chlorine atoms, bromine atoms and cyano groups;

$R^2$ represents a hydrogen atom;

the group represented by —$OR^3$ is present at the 2-position of the benzene ring (relative to the position of attachment of the group represented by A taken to be the 1-position);

$R^3$ represents a group of formula —D—$R^7$, where D represents a carbon-carbon single bond or an alkylene group having 1 or 2 carbon atoms and $R^7$ represents a heterocyclic group bonded to D via a carbon atom in the heterocyclic group, said heterocyclic group being selected from the group consisting of pyrrolidinyl groups, 1-methylpyrrolidinyl groups, 4-hydroxy-1-methylpyrrolidinyl groups, piperidyl groups, 1-methylpiperidyl groups, morpholinyl groups and thiomorpholinyl groups;

A represents an ethylene group.

69. The method of claim 63, wherein said compound is selected from the group consisting of:

3-Dimethylamino-1-[2-(4-phenylbutyl)phenoxy]-2-propanol;

1-Methyl-2-{2-[2-(4-phenylbutyl)phenoxy]ethyl}pyrrolidine;

1-Methyl-2-(2-{2-[4-(3-methoxyphenyl)butyl]phenoxy}ethyl)pyrrolidine;

1-Methyl-2-{2-[2-(2-phenylethyl)phenoxy]ethyl}pyrrolidine;

4-Hydroxy-1-methyl-2-{2-[2-(2-phenylethyl)phenoxy]ethyl}pyrrolidine;

1-Methyl-2-(2-{2-[2-(3-methoxyphenyl)ethyl]phenoxy}ethyl)pyrrolidine;

2-(2-{2-[2-(3,5-Dimethoxyphenyl)ethyl]phenoxy}ethyl)-1-methylpyrrolidine;

2-(2-{2-[2-(3-Fluorophenyl)ethyl]phenoxy}ethyl)-1-methylpyrrolidine;

2-(2-{2-[2-(3-Bromophenyl)ethyl]phenoxy}ethyl)-1-methylpyrrolidine;

4-Hydroxy-1-methyl-2-(2-{2-[2-(3-methoxyphenyl)ethyl]phenoxy}ethyl)pyrrolidine;

2-(2-{2-[2-(3-Fluorophenyl)ethyl]phenoxy}ethyl)-4-hydroxy-1-methylpyrrolidine;

2-(2-{2-[2-(3-Difluoromethoxyphenyl)ethyl]phenoxy}ethyl)-1-methylpyrrolidine;

2-(2-{2-[2-(3-Difluoromethoxyphenyl)ethyl]phenoxy}ethyl)-4-hydroxy-1-methylpyrrolidine;

2-(2-{2-[2-(3,5-Dimethoxyphenyl)ethyl]phenoxy}ethyl)-4-hydroxy-1-methylpyrrolidine;

1-Methyl-2-(2-{2-[2-(3-methoxyphenyl)ethyl]phenoxy}ethyl)-4-succinyloxypyrrolidine;

2-(2-{2-[2-(3,5-Dimethoxyphenyl)ethyl]phenoxy}ethyl)-4-succinyloxy-1-methylpyrrolidine;

2-(2-{2-[2-(3-Bromophenyl)ethyl]phenoxy}ethyl)-4-hydroxy-1-methylpyrrolidine; and 2-(2-{2-[2-(2-Difluoromethoxyphenyl)ethyl]phenoxy}ethyl)-4-succinyloxy-1-methylpyrrolidine;

and pharmaceutically acceptable salts and esters thereof.

70. A method for the treatment or prophylaxis of psychosis in a mammal, by the administration to said mammal of an effective amount of an active compound, wherein the active compound is at least one compound of formula (I) or a pharmaceutically acceptable salt or ester thereof.

71. The method of claim 70, wherein:

$R^1$ represents a phenyl group which is unsubstituted or is substituted by at least one substituent selected from the group consisting of methyl groups, ethyl groups, hydroxy groups, methoxy groups, ethoxy groups, fluoromethoxy groups, difluoromethoxy groups, 2-fluoroethoxy groups, fluorine atoms, chlorine atoms, bromine atoms and cyano groups;

$R^2$ represents a hydrogen atom;

the group represented by —$OR^3$ is present at the 2-position of the benzene ring (relative to the position of attachment of the group represented by A taken to be the 1-position);

$R^3$ represents a group of formula —B—$NR^4R^5$,
where $R^4$ and $R^5$ are independently selected from the group consisting of hydrogen atoms, alkyl groups having from 1 to 4 carbon atoms, benzyl groups, phenethyl groups, 2-hydroxyethyl groups, 3-hydroxypropyl groups, 2-(N,N-dimethylamino)ethyl groups and 3-(N,N-dimethylamino)propyl groups, or $R^4$ and $R^5$, together with the nitrogen atom to which they are attached, represent a 1-pyrrolidinyl group, a 1-piperidyl group, a 4-hydroxy-1-piperidyl group, a 4-morpholinyl group, a 4-methyl-1-piperazinyl group, a 4-ethyl-1-piperazinyl group, a 4-phenyl-1-piperazinyl group, a 1-imidazolyl group or a 1-triazolyl group, and B represents an alkylene group having 2 or 3 carbon atoms or a group of formula —$CH_2CH(OR^6)CH_2$—, where $R^6$ represents a hydrogen atom, an alkanoyl group having 2 or 3 carbon atoms, or a substituted alkanoyl group having 3 or 4 carbon atoms and substituted by a carboxy group, or a group of formula —D—$R^7$, where D represents a carbon-carbon single bond or an alkylene group having 1 or 2 carbon atoms and $R^7$ represents a heterocyclic group bonded to D via a carbon atom in the heterocyclic group, said heterocyclic group being selected from the group consisting of pyrrolidinyl groups, piperidyl groups, morpholinyl groups and thiomorpholinyl groups which are unsubstituted or are substituted on at least one of a carbon atom and a nitrogen atom by at least one substituent selected from the group consisting of in the case of substituents on a carbon atom, alkyl groups having from 1 to 4 carbon atoms, hydroxy groups, alkoxy groups having from 1 to 4 carbon atoms, alkoxycarbonyloxy groups having from 2 to 5 carbon atoms, alkanoyloxy groups having 2 or 3 carbon atoms, alkanoyloxy groups having from 12 to 20 carbon atoms, carboxy-substituted alkanoyloxy groups having 3 or 4 carbon atoms in the alkanoyl part, carbamoyloxy groups, and mono- and di- alkylcarbamoyloxy groups in which the or each alkyl part is a methyl or ethyl group, in the case of substituents on a nitrogen atom, alkyl groups having from 1 to 4 carbon atoms;

A represents an alkylene group having from 2 to 7 carbon atoms.

72. The method of claim 70, wherein:

$R^1$ represents a phenyl group which is unsubstituted or is substituted by at least one substituent selected from the group consisting of methyl groups, ethyl groups, hydroxy groups, methoxy groups, ethoxy groups, fluoromethoxy groups, difluoromethoxy groups, fluorine atoms, chlorine atoms, bromine atoms and cyano groups;

$R^2$ represents a hydrogen atom;

the group represented by —$OR^3$ is present at the 2-position of the benzene ring (relative to the position of attachment of the group represented by A taken to be the 1-position);

$R^3$ represents a group of formula —B—$NR^4R^5$,
where $R^4$ and $R^5$ are independently selected from the group consisting of hydrogen atoms, methyl groups, ethyl groups, benzyl groups and 2-hydroxyethyl groups, or $R^4$ and $R^5$, together with the nitrogen atom to which they are attached, represent a 1-pyrrolidinyl group, a 1-piperidyl group, a 4-hydroxy-1-piperidyl group, a 4-morpholinyl group, a 4-methyl-1-piperazinyl group, a 4-phenyl-1-piperazinyl group or a 1-imidazolyl group, and B represents an alkylene group having 2 or 3 carbon atoms or a group of formula —$CH_2CH(OR^6)CH_2$—, where $R^6$ represents a hydrogen atom, an acetyl group, a succinyl group or a glutaryl group, or a group of formula —D—$R^7$, where D represents a carbon-carbon single bond or an alkylene group having 1 or 2 carbon atoms and $R^7$ represents a heterocyclic group bonded to D via a carbon atom in the heterocyclic group, said heterocyclic group being selected from the group consisting of pyrrolidinyl groups, piperidyl groups, morpholinyl groups and thiomorpholinyl groups which are unsubstituted or are substituted on at least one of a carbon atom and a nitrogen atom by at least one substituent selected from the group consisting of in the case of substituents on a carbon atom, methyl groups, ethyl groups, hydroxy groups, methoxy groups, ethoxy groups, ethoxycarbonyloxy groups, isopropoxycarbonyloxy groups, t-butoxycarbonyloxy groups, alkanoyloxy groups having 2 or 3 carbon atoms, alkanoyloxy groups having from 14 to 20 carbon atoms, carboxy-substituted alkanoyloxy groups having 3 or 4 carbon atoms in the alkanoyl part, carbamoyloxy groups, and mono- and di- alkylcarbamoyloxy groups in which the or each alkyl part is a methyl or ethyl group, in the case of substituents on a nitrogen atom, methyl groups and ethyl groups;

A represents an alkylene group having from 2 to 5 carbon atoms.

73. The method of claim 70, wherein:

$R^1$ represents a phenyl group which is unsubstituted or is substituted by at least one substituent selected from the group consisting of methyl groups, ethyl groups, hydroxy groups, methoxy groups, ethoxy groups, difluoromethoxy groups, fluorine atoms, chlorine atoms, bromine atoms and cyano groups;

$R^2$ represents a hydrogen atom;

the group represented by —$OR^3$ is present at the 2-position of the benzene ring (relative to the position of attachment of the group represented by A taken to be the 1-position);

$R^3$ represents a group of formula —B—$NR^4R^5$,
where $R^4$ and $R^5$ are independently selected from the group consisting of hydrogen atoms, methyl groups, ethyl groups and 2-hydroxyethyl groups, or $R^4$ and $R^5$, together with the nitrogen atom to which they are attached, represent a 1-pyrrolidinyl group, a 1-piperidyl group, a 4-hydroxy-1-piperidyl group or a 4-morpholinyl group, and B represents an alkylene group having 2 or 3 carbon atoms or a group of formula —$CH_2CH(OR^6)CH_2$—, where $R^6$ represents a hydrogen atom, an acetyl group, a succinyl group or a glutaryl group, or a group of formula —D—$R^7$, where D represents a carbon-carbon single bond or an alkylene group having 1 or 2 carbon atoms and $R^7$ represents a heterocyclic group bonded to D via a carbon atom in the heterocyclic group, said heterocyclic group being selected from the group consisting of pyrrolidinyl groups, 1-methylpyrrolidinyl groups, 4-hydroxy-1-methylpyrrolidinyl groups, piperidyl groups, 1-methylpiperidyl groups, morpholinyl groups and 4-methylmorpholinyl groups;

A represents an alkylene group having from 2 to 5 carbon atoms.

74. The method of claim 70, wherein:

$R^1$ represents a phenyl group which is unsubstituted or is substituted by at least one substituent selected from the group consisting of methyl groups, hydroxy groups, methoxy groups, ethoxy groups, difluoromethoxy groups, fluorine atoms, chlorine atoms, bromine atoms and cyano groups;

$R^2$ represents a hydrogen atom;

the group represented by —$OR^3$ is present at the 2-position of the benzene ring (relative to the position of attachment of the group represented by A taken to be the 1-position);

$R^3$ represents a group of formula 'D—$R^7$, where D represents a carbon-carbon single bond or an alkylene group having 1 or 2 carbon atoms and $R^7$ represents a heterocyclic group bonded to D via a carbon atom in the heterocyclic group, said heterocyclic group being selected from the group consisting of pyrrolidinyl groups, 1-methylpyrrolidinyl groups, 4-hydroxy-1-methylpyrrolidinyl groups, piperidyl groups, 1-methylpiperidyl groups, morpholinyl groups and 4-methylmorpholinyl groups;

A represents a tetramethylene group or a pentamethylene group.

75. The method of claim 70, wherein said compound is selected from the group consisting of:

N,N-Dimethyl-3-[2-(4-phenylbutyl)phenoxy]propylamine;

1-Methyl-2-{2-[2-(4-phenylbutyl)phenoxy]ethyl}pyrrolidine;

1-Methyl-3-[2-(4-phenylbutyl)phenoxymethyl]piperidine;

N,N-Dimethyl-3-{2-[4-(3-methoxyphenyl)butyl]phenoxy}propylamine;

1-Methyl-3-{2-[4-(3-methoxyphenyl)butyl]phenoxymethyl}piperidine;

N,N-Dimethyl-3-{2-[4-(2-methoxyphenyl)butyl]phenoxy}propylamine;

1-Methyl-2-(2-{2-[4-(2-methoxyphenyl)butyl]phenoxy}ethyl)pyrrolidine;

2-(2-{2-[4-(3,5-Dimethoxyphenyl)butyl]phenoxy}ethyl)-1-methylpyrrolidine;

3-{2-[4-(3,5-Dimethoxyphenyl)butyl]phenoxymethyl}-1-methylpiperidine;

1-Methyl-3-{2-[4-(2-methoxyphenyl)butyl]phenoxymethyl}piperidine;

1-Methyl-2-{2-[2-(5-phenylpentyl)phenoxy]ethyl}pyrrolidine;

1-Methyl-3-[2-(5-phenylpentyl)phenoxymethyl]piperidine;

1-Methyl-3-{2-[5-(3-methoxyphenyl)pentyl]phenoxymethyl}piperidine;

1-Methyl-3-[2-(6-phenylhexyl)phenoxymethyl]piperidine;

1-Methyl-3-{2-[6-(3-methoxyphenyl)hexyl]phenoxymethyl}piperidine; and

3-{2-[5-(3,5-Dimethoxyphenyl)pentyl]phenoxymethyl}-1-methylpiperidine;

and pharmaceutically acceptable salts and esters thereof.

* * * * *

UNITED STATES PATENT AND TRADEMARK OFFICE
CERTIFICATE OF CORRECTION

PATENT NO. : 5,556,864
DATED : September 17, 1996
INVENTOR(S) : FUJIMOTO et al

It is certified that error appears in the above-identified patent and that said Letters Patent is hereby corrected as shown below:

Column 207, line 35 (Claim 50): after "thereof" delete ", and" and insert -- . --.

Signed and Sealed this

Sixth Day of June, 2000

Attest:

Attesting Officer

Q. TODD DICKINSON

Director of Patents and Trademarks